United States Patent
Li et al.

(10) Patent No.: US 11,708,385 B2
(45) Date of Patent: *Jul. 25, 2023

(54) METAL-ASSISTED DELAYED FLUORESCENT EMITTERS EMPLOYING PYRIDO-PYRROLO-ACRIDINE AND ANALOGUES

(71) Applicant: Arizona Board of Regents on behalf of Arizona State University, Scottsdale, AZ (US)

(72) Inventors: Jian Li, Tempe, AZ (US); Yunlong Ji, Mesa, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/481,179

(22) PCT Filed: Jan. 26, 2018

(86) PCT No.: PCT/US2018/015506
§ 371 (c)(1),
(2) Date: Jul. 26, 2019

(87) PCT Pub. No.: WO2018/140765
PCT Pub. Date: Aug. 2, 2018

(65) Prior Publication Data
US 2019/0389893 A1 Dec. 26, 2019

Related U.S. Application Data

(60) Provisional application No. 62/451,574, filed on Jan. 27, 2017.

(51) Int. Cl.
*C07F 15/00* (2006.01)
*H10K 85/30* (2023.01)

(52) U.S. Cl.
CPC ........ *C07F 15/0086* (2013.01); *C07F 15/006* (2013.01); *H10K 85/346* (2023.02)

(58) Field of Classification Search
CPC .................. C07F 15/0086; H01L 51/0087
See application file for complete search history.

(56) References Cited

U.S. PATENT DOCUMENTS

| | | |
|---|---|---|
| 4,769,292 A | 9/1988 | Tang |
| 5,451,674 A | 9/1995 | Silver |
| 5,641,878 A | 6/1997 | Dandliker |
| 5,707,745 A | 1/1998 | Forrest |
| 5,844,363 A | 12/1998 | Gu |
| 6,200,695 B1 | 3/2001 | Arai |
| 6,303,238 B1 | 10/2001 | Thompson |
| 6,780,528 B2 | 8/2004 | Tsuboyama |
| 7,002,013 B1 | 2/2006 | Chi |
| 7,037,599 B2 | 5/2006 | Culligan |
| 7,064,228 B1 | 6/2006 | Yu |
| 7,268,485 B2 | 9/2007 | Tyan |
| 7,279,704 B2 | 10/2007 | Walters |
| 7,332,232 B2 | 2/2008 | Ma |
| 7,442,797 B2 | 10/2008 | Itoh |
| 7,501,190 B2 | 3/2009 | Ise |
| 7,635,792 B1 | 12/2009 | Cella |
| 7,655,322 B2 | 2/2010 | Forrest |
| 7,854,513 B2 | 12/2010 | Quach |
| 7,947,383 B2 | 5/2011 | Ise |
| 8,106,199 B2 | 1/2012 | Jabbour |
| 8,133,597 B2 | 3/2012 | Yasukawa |
| 8,389,725 B2 | 3/2013 | Li |
| 8,617,723 B2 | 12/2013 | Stoessel |
| 8,669,364 B2 | 3/2014 | Li |
| 8,778,509 B2 | 7/2014 | Yasukawa |
| 8,816,080 B2 | 8/2014 | Li |
| 8,846,940 B2 | 9/2014 | Li |
| 8,871,361 B2 | 10/2014 | Xia |
| 8,927,713 B2 | 1/2015 | Li |
| 8,933,622 B2 | 1/2015 | Kawami |
| 8,946,417 B2 | 2/2015 | Jian |
| 8,987,451 B2 | 3/2015 | Tsai |
| 9,059,412 B2 | 6/2015 | Zeng |
| 9,076,974 B2 | 7/2015 | Li |
| 9,082,989 B2 | 7/2015 | Li |
| 9,203,039 B2 | 12/2015 | Li |

(Continued)

FOREIGN PATENT DOCUMENTS

| | | |
|---|---|---|
| CN | 1680366 A | 10/2005 |
| CN | 1777663 | 5/2006 |

(Continued)

OTHER PUBLICATIONS

Murakami; JP 2007324309, English machine translation from EPO, dated Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Wong. Challenges in organometallic research—Great opportunity for solar cells and OLEDs. Journal of Organometallic Chemistry 2009, vol. 694, pp. 2644-2647.

(Continued)

*Primary Examiner* — David K O'Dell
(74) *Attorney, Agent, or Firm* — Riverside Law LLP

(57) ABSTRACT

Metal-assisted delayed fluorescent (MADF) emitters including cyclic tetradentate platinum (II) and palladium (II) complexes employing 8H-pyrido[3',2':4,5]-pyrrolo[3,2,1-de]acridine and its analogues. These complexes provide improved color purity and enhanced operational stability and are suitable for luminescent labels, emitters for organic light emitting diodes (OLEDs), and lighting applications.

5 Claims, 3 Drawing Sheets

(56) References Cited

U.S. PATENT DOCUMENTS

| | | |
|---|---|---|
| 9,221,857 B2 | 12/2015 | Li |
| 9,224,963 B2 | 12/2015 | Li |
| 9,238,668 B2 | 1/2016 | Li |
| 9,312,502 B2 | 4/2016 | Li |
| 9,312,505 B2 | 4/2016 | Brooks |
| 9,318,725 B2 | 4/2016 | Li |
| 9,324,957 B2 | 4/2016 | Li |
| 9,382,273 B2 | 7/2016 | Li |
| 9,385,329 B2 | 7/2016 | Li |
| 9,425,415 B2 | 8/2016 | Li |
| 9,461,254 B2 | 10/2016 | Tsai |
| 9,493,698 B2 | 11/2016 | Beers |
| 9,502,671 B2 | 11/2016 | Jian |
| 9,550,801 B2 | 1/2017 | Li |
| 9,598,449 B2 | 3/2017 | Li |
| 9,617,291 B2 | 4/2017 | Li |
| 9,666,822 B2 | 5/2017 | Forrest |
| 9,673,409 B2 | 6/2017 | Li |
| 9,698,359 B2 | 7/2017 | Li |
| 9,711,739 B2 | 7/2017 | Li |
| 9,711,741 B2 | 7/2017 | Li |
| 9,711,742 B2 | 7/2017 | Li |
| 9,735,397 B2 | 8/2017 | Riegel |
| 9,755,163 B2 | 9/2017 | Li |
| 9,818,959 B2 | 11/2017 | Li |
| 9,865,825 B2 | 1/2018 | Li |
| 9,879,039 B2 | 1/2018 | Li |
| 9,882,150 B2 | 1/2018 | Li |
| 9,899,614 B2 | 2/2018 | Li |
| 9,920,242 B2 | 3/2018 | Li |
| 9,923,155 B2 | 3/2018 | Li |
| 9,941,479 B2 | 4/2018 | Li |
| 9,947,881 B2 | 4/2018 | Li |
| 9,985,224 B2 | 5/2018 | Li |
| 10,020,455 B2 | 7/2018 | Li |
| 10,033,003 B2 | 7/2018 | Li |
| 10,056,564 B2 | 8/2018 | Li |
| 10,056,567 B2 | 8/2018 | Li |
| 10,158,091 B2 | 12/2018 | Li |
| 10,177,323 B2 | 1/2019 | Li |
| 10,211,411 B2 | 2/2019 | Li |
| 10,211,414 B2 | 2/2019 | Li |
| 10,263,197 B2 | 4/2019 | Li |
| 10,294,417 B2 | 5/2019 | Li |
| 10,392,387 B2 | 8/2019 | Li |
| 10,411,202 B2 | 9/2019 | Li |
| 10,414,785 B2 | 9/2019 | Li |
| 10,516,117 B2 | 12/2019 | Li |
| 10,566,553 B2 | 2/2020 | Li |
| 10,566,554 B2 | 2/2020 | Li |
| 10,836,785 B2 * | 11/2020 | Li ................ H01L 51/0085 |
| 2001/0019782 A1 | 9/2001 | Igarashi |
| 2002/0068190 A1 | 6/2002 | Tsuboyama |
| 2003/0062519 A1 | 4/2003 | Yamazaki |
| 2003/0180574 A1 | 9/2003 | Huang |
| 2003/0186077 A1 | 10/2003 | Chen |
| 2004/0230061 A1 | 11/2004 | Seo |
| 2005/0037232 A1 | 2/2005 | Tyan |
| 2005/0139810 A1 | 6/2005 | Kuehl |
| 2005/0170207 A1 | 8/2005 | Ma |
| 2005/0260446 A1 | 11/2005 | MacKenzie |
| 2006/0024522 A1 | 2/2006 | Thompson |
| 2006/0032528 A1 | 2/2006 | Wang |
| 2006/0066228 A1 | 3/2006 | Antoniadis |
| 2006/0073359 A1 | 4/2006 | Ise |
| 2006/0094875 A1 | 5/2006 | Itoh |
| 2006/0127696 A1 | 6/2006 | Stossel |
| 2006/0182992 A1 | 8/2006 | Nii |
| 2006/0202197 A1 | 9/2006 | Nakayama |
| 2006/0210831 A1 | 9/2006 | Sano |
| 2006/0255721 A1 | 11/2006 | Igarashi |
| 2006/0263635 A1 | 11/2006 | Ise |
| 2006/0286406 A1 | 12/2006 | Igarashi |
| 2007/0057630 A1 | 3/2007 | Nishita |
| 2007/0059551 A1 | 3/2007 | Yamazaki |
| 2007/0082284 A1 | 4/2007 | Stoessel |
| 2007/0103060 A1 | 5/2007 | Itoh |
| 2007/0160905 A1 | 7/2007 | Morishita |
| 2007/0252140 A1 | 11/2007 | Limmert |
| 2008/0001530 A1 | 1/2008 | Ise |
| 2008/0036373 A1 | 2/2008 | Itoh |
| 2008/0054799 A1 | 3/2008 | Satou |
| 2008/0079358 A1 | 4/2008 | Satou |
| 2008/0102310 A1 | 5/2008 | Thompson |
| 2008/0111476 A1 | 5/2008 | Choi |
| 2008/0241518 A1 | 10/2008 | Satou |
| 2008/0241589 A1 | 10/2008 | Fukunaga |
| 2008/0269491 A1 | 10/2008 | Jabbour |
| 2008/0315187 A1 | 12/2008 | Bazan |
| 2009/0026936 A1 | 1/2009 | Satou |
| 2009/0026939 A1 | 1/2009 | Kinoshita |
| 2009/0032989 A1 | 2/2009 | Karim |
| 2009/0039768 A1 | 2/2009 | Igarashi |
| 2009/0079340 A1 | 3/2009 | Kinoshita |
| 2009/0126796 A1 | 5/2009 | Yang |
| 2009/0128008 A1 | 5/2009 | Ise |
| 2009/0136779 A1 | 5/2009 | Cheng |
| 2009/0153045 A1 | 6/2009 | Kinoshita |
| 2009/0167167 A1 | 7/2009 | Aoyama |
| 2009/0205713 A1 | 8/2009 | Mitra |
| 2009/0218561 A1 | 9/2009 | Kitamura |
| 2009/0261721 A1 | 10/2009 | Murakami |
| 2009/0267500 A1 | 10/2009 | Kinoshita |
| 2010/0000606 A1 | 1/2010 | Thompson |
| 2010/0013386 A1 | 1/2010 | Thompson |
| 2010/0043876 A1 | 2/2010 | Tuttle |
| 2010/0093119 A1 | 4/2010 | Shimizu |
| 2010/0127246 A1 | 5/2010 | Nakayama |
| 2010/0141127 A1 | 6/2010 | Xia |
| 2010/0147386 A1 | 6/2010 | Benson-Smith |
| 2010/0171111 A1 | 7/2010 | Takada |
| 2010/0171418 A1 | 7/2010 | Kinoshita |
| 2010/0200051 A1 | 8/2010 | Triani |
| 2010/0204467 A1 | 8/2010 | Lamarque |
| 2010/0270540 A1 | 10/2010 | Chung |
| 2010/0288362 A1 | 11/2010 | Hatwar |
| 2010/0297522 A1 | 11/2010 | Creeth |
| 2010/0301315 A1 | 12/2010 | Masui |
| 2010/0307594 A1 | 12/2010 | Zhu |
| 2011/0028723 A1 | 2/2011 | Li |
| 2011/0049496 A1 | 3/2011 | Fukuzaki |
| 2011/0062858 A1 | 3/2011 | Yersin |
| 2011/0132440 A1 | 6/2011 | Sivarajan |
| 2011/0217544 A1 | 9/2011 | Young |
| 2011/0227058 A1 | 9/2011 | Masui |
| 2011/0301351 A1 | 12/2011 | Li |
| 2012/0024383 A1 | 2/2012 | Kaiho |
| 2012/0025588 A1 | 2/2012 | Humbert |
| 2012/0039323 A1 | 2/2012 | Hirano |
| 2012/0095232 A1 | 4/2012 | Li |
| 2012/0108806 A1 | 5/2012 | Li |
| 2012/0146012 A1 | 6/2012 | Limmert |
| 2012/0181528 A1 | 7/2012 | Takada |
| 2012/0199823 A1 | 8/2012 | Molt |
| 2012/0202997 A1 | 8/2012 | Parham |
| 2012/0204960 A1 | 8/2012 | Kato |
| 2012/0215001 A1 | 8/2012 | Li |
| 2012/0223634 A1 | 9/2012 | Xia |
| 2012/0264938 A1 | 10/2012 | Li |
| 2012/0273736 A1 | 11/2012 | James |
| 2012/0302753 A1 | 11/2012 | Li |
| 2013/0048963 A1 | 2/2013 | Beers |
| 2013/0082245 A1 | 4/2013 | Kottas |
| 2013/0137870 A1 | 5/2013 | Li |
| 2013/0168656 A1 | 7/2013 | Tsai |
| 2013/0172561 A1 | 7/2013 | Tsai |
| 2013/0200340 A1 | 8/2013 | Otsu |
| 2013/0203996 A1 | 8/2013 | Li |
| 2013/0237706 A1 | 9/2013 | Li |
| 2013/0341600 A1 | 12/2013 | Lin |
| 2014/0014922 A1 | 1/2014 | Lin |
| 2014/0014931 A1 | 1/2014 | Riegel |
| 2014/0027733 A1 | 1/2014 | Zeng |
| 2014/0042475 A1 | 2/2014 | Park |

(56) References Cited

U.S. PATENT DOCUMENTS

| | | |
|---|---|---|
| 2014/0066628 A1 | 3/2014 | Li |
| 2014/0073798 A1 | 3/2014 | Li |
| 2014/0084261 A1 | 3/2014 | Brooks |
| 2014/0114072 A1 | 4/2014 | Li |
| 2014/0147996 A1 | 5/2014 | Vogt |
| 2014/0148594 A1 | 5/2014 | Li |
| 2014/0191206 A1 | 7/2014 | Cho |
| 2014/0203248 A1 | 7/2014 | Zhou |
| 2014/0249310 A1 | 9/2014 | Li |
| 2014/0326960 A1 | 11/2014 | Kim |
| 2014/0330019 A1 | 11/2014 | Li |
| 2014/0364605 A1 | 12/2014 | Li |
| 2015/0008419 A1 | 1/2015 | Li |
| 2015/0018558 A1 | 1/2015 | Li |
| 2015/0028323 A1 | 1/2015 | Xia |
| 2015/0060804 A1 | 3/2015 | Kanitz |
| 2015/0069334 A1 | 3/2015 | Xia |
| 2015/0105556 A1 | 4/2015 | Li |
| 2015/0123047 A1 | 5/2015 | Maltenberger |
| 2015/0162552 A1 | 6/2015 | Li |
| 2015/0194616 A1 | 7/2015 | Li |
| 2015/0207086 A1 | 7/2015 | Li |
| 2015/0228914 A1 | 8/2015 | Li |
| 2015/0274762 A1 | 10/2015 | Li |
| 2015/0287938 A1 | 10/2015 | Li |
| 2015/0311456 A1 | 10/2015 | Li |
| 2015/0318500 A1 | 11/2015 | Li |
| 2015/0349279 A1 | 12/2015 | Li |
| 2015/0380666 A1 | 12/2015 | Szigethy |
| 2016/0028028 A1 | 1/2016 | Li |
| 2016/0028029 A1 | 1/2016 | Li |
| 2016/0043331 A1 | 2/2016 | Li |
| 2016/0072082 A1 | 3/2016 | Brooks |
| 2016/0133861 A1 | 5/2016 | Li |
| 2016/0133862 A1 | 5/2016 | Li |
| 2016/0181529 A1 | 6/2016 | Tsai |
| 2016/0194344 A1 | 7/2016 | Li |
| 2016/0197285 A1 | 7/2016 | Zeng |
| 2016/0197291 A1 | 7/2016 | Li |
| 2016/0204358 A1 | 7/2016 | Stoessel |
| 2016/0285015 A1 | 9/2016 | Li |
| 2016/0359120 A1 | 12/2016 | Li |
| 2016/0359125 A1* | 12/2016 | Li ............... C09K 11/06 |
| 2017/0005278 A1 | 1/2017 | Li |
| 2017/0012224 A1 | 1/2017 | Li |
| 2017/0040555 A1 | 2/2017 | Li |
| 2017/0047533 A1 | 2/2017 | Li |
| 2017/0066792 A1 | 3/2017 | Li |
| 2017/0069855 A1 | 3/2017 | Li |
| 2017/0077420 A1 | 3/2017 | Li |
| 2017/0125708 A1 | 5/2017 | Li |
| 2017/0267923 A1 | 9/2017 | Li |
| 2017/0271611 A1 | 9/2017 | Li |
| 2017/0301871 A1 | 10/2017 | Li |
| 2017/0305881 A1 | 10/2017 | Li |
| 2017/0309943 A1 | 10/2017 | Angell |
| 2017/0331056 A1 | 11/2017 | Li |
| 2017/0342098 A1 | 11/2017 | Li |
| 2017/0373260 A1 | 12/2017 | Li |
| 2018/0006246 A1 | 1/2018 | Li |
| 2018/0013096 A1 | 1/2018 | Hamada |
| 2018/0037812 A1 | 2/2018 | Pegington |
| 2018/0052366 A1 | 2/2018 | Hao |
| 2018/0053904 A1 | 2/2018 | Li |
| 2018/0062084 A1 | 3/2018 | Watabe |
| 2018/0130960 A1 | 5/2018 | Li |
| 2018/0138428 A1 | 5/2018 | Li |
| 2018/0148464 A1 | 5/2018 | Li |
| 2018/0159051 A1 | 6/2018 | Li |
| 2018/0166655 A1 | 6/2018 | Li |
| 2018/0175329 A1 | 6/2018 | Li |
| 2018/0194790 A1 | 7/2018 | Li |
| 2018/0198081 A1 | 7/2018 | Zeng |
| 2018/0219161 A1 | 8/2018 | Li |
| 2018/0226592 A1 | 8/2018 | Li |
| 2018/0226593 A1 | 8/2018 | Li |
| 2018/0277777 A1 | 9/2018 | Li |
| 2018/0301641 A1 | 10/2018 | Li |
| 2018/0312750 A1 | 11/2018 | Li |
| 2018/0331307 A1 | 11/2018 | Li |
| 2018/0334459 A1 | 11/2018 | Li |
| 2018/0337345 A1 | 11/2018 | Li |
| 2018/0337349 A1 | 11/2018 | Li |
| 2018/0337350 A1 | 11/2018 | Li |
| 2018/0353771 A1 | 12/2018 | Kim |
| 2019/0013485 A1 | 1/2019 | Li |
| 2019/0058137 A1 | 2/2019 | Ko |
| 2019/0067602 A1 | 2/2019 | Li |
| 2019/0109288 A1 | 4/2019 | Li |
| 2019/0119312 A1 | 4/2019 | Chen |
| 2019/0157352 A1 | 5/2019 | Li |
| 2019/0194536 A1 | 6/2019 | Li |
| 2019/0221757 A1 | 7/2019 | Tarran |
| 2019/0259963 A1 | 8/2019 | Jian |
| 2019/0276485 A1 | 9/2019 | Li |
| 2019/0312217 A1 | 10/2019 | Li |
| 2019/0367546 A1 | 12/2019 | Li |
| 2019/0389893 A1 | 12/2019 | Li |
| 2020/0006678 A1 | 1/2020 | Li |
| 2020/0055885 A1 | 2/2020 | Tarran |
| 2020/0071330 A1 | 3/2020 | Li |
| 2020/0075868 A1 | 3/2020 | Li |
| 2020/0119288 A1* | 4/2020 | Li ............... H01L 51/0087 |
| 2020/0119289 A1 | 4/2020 | Lin |
| 2020/0140471 A1 | 5/2020 | Chen |
| 2020/0152891 A1 | 5/2020 | Li |
| 2020/0239505 A1 | 7/2020 | Li |
| 2020/0243776 A1 | 7/2020 | Li |
| 2021/0024559 A1* | 1/2021 | Li ............... C07F 15/006 |
| 2021/0292351 A1 | 9/2021 | MacInnis |

FOREIGN PATENT DOCUMENTS

| | | | |
|---|---|---|---|
| CN | 1894267 | | 1/2007 |
| CN | 1894269 A | | 1/2007 |
| CN | 101142223 A | | 3/2008 |
| CN | 101667626 | | 3/2010 |
| CN | 102449108 A | | 5/2012 |
| CN | 102892860 A | | 1/2013 |
| CN | 102971396 A | | 3/2013 |
| CN | 103102372 | | 5/2013 |
| CN | 104232076 A | | 12/2014 |
| CN | 104377231 | | 2/2015 |
| CN | 104576934 | | 4/2015 |
| CN | 104693243 A | | 6/2015 |
| CN | 105367605 A | | 3/2016 |
| CN | 105418591 A | | 3/2016 |
| CN | 106783922 | | 5/2017 |
| EP | 1617493 | | 1/2006 |
| EP | 1808052 A1 | | 7/2007 |
| EP | 1874893 A1 | | 1/2008 |
| EP | 1874894 A1 | | 1/2008 |
| EP | 1919928 A1 | | 5/2008 |
| EP | 1968131 | | 9/2008 |
| EP | 2020694 | | 2/2009 |
| EP | 2036907 A1 | | 3/2009 |
| EP | 2096690 | | 9/2009 |
| EP | 2112213 A2 | | 10/2009 |
| EP | 2417217 A2 | | 2/2012 |
| EP | 2684932 | | 1/2014 |
| EP | 2711999 A2 * | 3/2014 | ......... H01L 51/0072 |
| EP | 2711999 A2 | | 3/2014 |
| EP | 3032293 | | 6/2016 |
| JP | 2002010505 | | 1/2002 |
| JP | 2002105055 | | 4/2002 |
| JP | 2003342284 | | 12/2003 |
| JP | 2005031073 | | 2/2005 |
| JP | 2005267557 | | 9/2005 |
| JP | 2005310733 A | | 11/2005 |
| JP | 2006047240 A | | 2/2006 |
| JP | 2006232784 A | | 9/2006 |
| JP | 2006242080 | | 9/2006 |
| JP | 2006242081 A | | 9/2006 |
| JP | 2006256999 A | | 9/2006 |

(56) References Cited

FOREIGN PATENT DOCUMENTS

| | | |
|---|---|---|
| JP | 2006257238 A | 9/2006 |
| JP | 2006261623 A | 9/2006 |
| JP | 2006290988 A | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007031678 | 2/2007 |
| JP | 2007042875 A | 2/2007 |
| JP | 2007051243 A | 3/2007 |
| JP | 2007053132 A | 3/2007 |
| JP | 2007066581 | 3/2007 |
| JP | 2007073620 A | 3/2007 |
| JP | 2007073845 A | 3/2007 |
| JP | 2007073900 A | 3/2007 |
| JP | 2007080593 | 3/2007 |
| JP | 2007080677 A | 3/2007 |
| JP | 2007088105 | 4/2007 |
| JP | 2007088164 A | 4/2007 |
| JP | 2007096259 A | 4/2007 |
| JP | 2007099765 A | 4/2007 |
| JP | 2007110067 | 4/2007 |
| JP | 2007110102 A | 4/2007 |
| JP | 2007519614 | 7/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 | 5/2008 |
| JP | 2008109103 A | 5/2008 |
| JP | 2008116343 A | 5/2008 |
| JP | 2008117545 A | 5/2008 |
| JP | 2008160087 A | 7/2008 |
| JP | 2008198801 A | 8/2008 |
| JP | 2008270729 A | 11/2008 |
| JP | 2008270736 | 11/2008 |
| JP | 2008310220 A | 12/2008 |
| JP | 2009016184 A | 1/2009 |
| JP | 2009016579 | 1/2009 |
| JP | 2009032977 A | 2/2009 |
| JP | 2009032988 A | 2/2009 |
| JP | 2009059997 | 3/2009 |
| JP | 2009076509 | 4/2009 |
| JP | 2009161524 A | 7/2009 |
| JP | 2009247171 | 10/2009 |
| JP | 2009266943 A | 11/2009 |
| JP | 2009267171 A | 11/2009 |
| JP | 2009267244 A | 11/2009 |
| JP | 2009272339 A | 11/2009 |
| JP | 2009283891 A | 12/2009 |
| JP | 1460952 | 5/2010 |
| JP | 2010135689 A | 6/2010 |
| JP | 2010171205 A | 8/2010 |
| JP | 2011071452 A | 4/2011 |
| JP | 2012074444 A | 4/2012 |
| JP | 2012079895 A | 4/2012 |
| JP | 2012079898 A | 4/2012 |
| JP | 5604505 | 9/2012 |
| JP | 2012522843 | 9/2012 |
| JP | 2012207231 A | 10/2012 |
| JP | 2012222255 A | 11/2012 |
| JP | 2012231135 A | 11/2012 |
| JP | 2013023500 A | 2/2013 |
| JP | 2013048256 A | 3/2013 |
| JP | 2013053149 A | 3/2013 |
| JP | 2013525436 | 6/2013 |
| JP | 2014019701 A | 2/2014 |
| JP | 2014058504 A | 4/2014 |
| JP | 2014520096 | 8/2014 |
| JP | 2012709899 | 11/2014 |
| JP | 2014221807 A | 11/2014 |
| JP | 2014239225 A | 12/2014 |
| JP | 2015081257 A | 4/2015 |
| KR | 20060011537 | 2/2006 |
| KR | 20060015371 | 2/2006 |
| KR | 20060115371 | 11/2006 |
| KR | 20070061830 | 6/2007 |
| KR | 20070112465 | 11/2007 |
| KR | 20130043460 | 4/2013 |
| KR | 101338250 | 12/2013 |
| KR | 20140052501 | 5/2014 |
| TW | 200701835 | 1/2007 |
| TW | 201249851 | 12/2012 |
| TW | 201307365 A | 2/2013 |
| TW | 201710277 | 3/2017 |
| WO | 0070655 A2 | 11/2000 |
| WO | 2000070655 | 11/2000 |
| WO | 2004003108 | 1/2004 |
| WO | 2004070655 | 8/2004 |
| WO | 2004085450 | 10/2004 |
| WO | 2004108857 | 12/2004 |
| WO | 2005042444 A2 | 5/2005 |
| WO | 2005042550 A1 | 5/2005 |
| WO | 2005113704 | 12/2005 |
| WO | 2006033440 A1 | 3/2006 |
| WO | 2006067074 | 6/2006 |
| WO | 2006081780 | 8/2006 |
| WO | 2006098505 A1 | 9/2006 |
| WO | 2006113106 | 10/2006 |
| WO | 2006115299 A1 | 11/2006 |
| WO | 2006115301 | 11/2006 |
| WO | 2007034985 A1 | 3/2007 |
| WO | 2007069498 A1 | 6/2007 |
| WO | 2008054578 | 5/2008 |
| WO | 2008066192 A1 | 6/2008 |
| WO | 2008066195 A1 | 6/2008 |
| WO | 2008066196 A1 | 6/2008 |
| WO | 2008101842 A1 | 8/2008 |
| WO | 2008117889 | 10/2008 |
| WO | 2008123540 | 10/2008 |
| WO | 2008131932 A1 | 11/2008 |
| WO | 2009003455 | 1/2009 |
| WO | 2009008277 | 1/2009 |
| WO | 2009011327 | 1/2009 |
| WO | 2009017211 A1 | 2/2009 |
| WO | 2009023667 | 2/2009 |
| WO | 2009086209 | 7/2009 |
| WO | 2009111299 | 9/2009 |
| WO | 2010007098 A1 | 1/2010 |
| WO | 2010056669 | 5/2010 |
| WO | 2010093176 | 8/2010 |
| WO | 2010105141 | 9/2010 |
| WO | 2010118026 | 10/2010 |
| WO | 2011064335 A1 | 6/2011 |
| WO | 2011070989 A1 | 6/2011 |
| WO | 2011089163 | 7/2011 |
| WO | 2011137429 | 11/2011 |
| WO | 2011137431 | 11/2011 |
| WO | 2012074909 | 6/2012 |
| WO | 2012112853 | 8/2012 |
| WO | 2012116231 | 8/2012 |
| WO | 2012142387 | 10/2012 |
| WO | 2012162488 | 11/2012 |
| WO | 2012163471 A1 | 12/2012 |
| WO | 2013130483 | 9/2013 |
| WO | 2014009310 | 1/2014 |
| WO | 2014016611 | 1/2014 |
| WO | 2014031977 | 2/2014 |
| WO | 2014047616 | 3/2014 |
| WO | 2014109814 | 7/2014 |
| WO | 2014208271 | 12/2014 |
| WO | 2015027060 | 2/2015 |
| WO | 2015131158 | 9/2015 |
| WO | 2016025921 | 2/2016 |
| WO | 2016029137 | 2/2016 |
| WO | 2016029186 | 2/2016 |
| WO | 2016088354 A1 | 6/2016 |
| WO | 2016197019 | 12/2016 |
| WO | 2017117935 | 7/2017 |
| WO | 2018071697 | 4/2018 |
| WO | 2018140765 | 8/2018 |
| WO | 2019079505 | 4/2019 |

(56) References Cited

FOREIGN PATENT DOCUMENTS

| WO | 2019079508 | 4/2019 |
|---|---|---|
| WO | 2019079509 | 4/2019 |
| WO | 2019236541 | 12/2019 |
| WO | 2020018476 | 1/2020 |

OTHER PUBLICATIONS

JP2009267244, English Translation from EPO, Nov. 2009, 80 pages.
JP2010135689, English translation from EPO, dated Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6, Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Vanessa Wood et al., "Colloidal quantum dot light-emitting devices," Nano Reviews 1, Jul. 2010, pp. 5202.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al. "Confinement of triplet energy on phosphorescent molecules for highly-efficient organic blue-light-emitting devices" Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices", Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al. "High-Triplet-Energy Dendrons: Enhancing the Luminescence of Deep Blue Phosphorescent Indium(III) Complexes" J. Am. Chem. Soc.,vol. 131, 2009, pp. 16681-16688.
Jan Kalinowski et al.,"Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al. "Photophysical Properties and OLEO Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Letters 12, Apr. 2, 2012, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O/\N/\C/\N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O/\N/\C/\N ligands: high efficiency OLEDs with excellent efficiency stability," Chem. Commun., 2013, vol. 49, pp. 1497-1499.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Pui Keong Chow et al., "Strongly Phosphorescent Palladium(II) Complexes of Tetradentate Ligands with Mixed Oxygen, Carbon, and Nitrogen Donor Atoms: Photophysics, Photochemistry, and Applications," Angew. Chem. Int. Ed. 2013, 52, 11775-11779.
Pui-Keong Chow et al., "Highly luminescent palladium(II) complexes with sub-millisecond blue to green phosphorescent excited states. Photocatalysis and highly efficient PSF-OLEDs," Chem. Sci., 2016, 7, 6083-6098.
Guijie Li et al., "Modifying Emission Spectral Bandwidth of Phosphorescent Platinum(II) Complexes Through Synthetic Control," Inorg. Chem. 2017, 56, 8244-8256.
Tyler Fleetham et al., "Efficient Red-Emitting Platinum Complex with Long Operational Stability," ACS Appl. Mater. Interfaces 2015, 7, 16240-16246.
Supporting Information: Xiao-Chun Hang et al., "Highly Efficient Blue-Emitting Cyclometalated Platinum(II) Complexes by Judicious Molecular Design," Wiley-VCH 2013, 7 pages.
Russell J. Holmes et al., "Blue and Near-UV Phosphorescence from Iridium Complexes with Cyclometalated Pyrazolyl or N-Heterocyclic Carbene Ligands," Inorganic Chemistry, 2005, vol. 44, No. 22, pp. 7995-8003.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Zhi-Qiang Zhu et.al., "Harvesting All Electrogenerated Excitons through Metal Assisted Delayed Fluorescent Materials," Adv. Mater. 27 (2015) 2533-2537.

(56) References Cited

OTHER PUBLICATIONS

Zhi-Qiang Zhu et. al., "Efficient Cyclometalated Platinum(II) Complex with Superior Operational Stability," Adv. Mater. 29 (2017) 1605002, pp. 1-5.

Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligands," Helvetica Chimica Acta, vol. 71, Issue 5, Aug. 10, 1988, pp. 1053-1059.

Adachi, C. et al., "High-efficiency organic electrophosphorescent devices with tris(2-phenylpyridine)iridium doped into electron-transporting materials", Applied Physics Letters, Aug. 2000, vol. 77, No. 6, pp. 904-906 <DOI:10.1063/1.1306639>.

Baldo et al., "Very high-efficiency green organic light-emitting devices based on electrophosphorescence," Appl. Phys. Lett., vol. 75, No. 3, 4-6 (1999).

Baldo et al., Very High-Efficiency Green Organic Light-Emitting Devices Based on Electrophosphorescence, Appl Phys Lett, 75(3):4-6 (1999).

Baldo, M. et al., "Excitonic singlet-triplet ratio in a semiconducting organic thin film", Physical Review B, Nov. 1999, vol. 60, No. 20, pp. 14422-14428 <DOI:10.1103/PhysRevB.60.14422>.

Baldo, M. et al., "High-efficiency fluorescent organic light-emitting devices using a phosphorescent sensitizer", Nature, Feb. 2000, vol. 403, pp. 750-753.

Berson et al. (2007). "Poly(3-hexylthiophene) fibers for photovoltaic applications," Adv. Funct. Mat., 17, 1377-84.

Bouman et al. (1994). "Chiroptical properties of regioregular chiral polythiophenes," Mol. Cryst. Liq. Cryst., 256, 439-48.

Bronner; Dalton Trans., 2010, 39, 180-184. DOI: 10.1039/b908424j (Year: 2010).

Brooks, J. et al., "Synthesis and Characterization of Phosphorescent Cyclometalated Platinum Complexes", Inorganic Chemistry, May 2002, vol. 41, No. 12, pp. 3055-3066 <DOI:10.1021/ic0255508>.

Brown, A. et al., "Optical spectroscopy of triplet excitons and charged excitations in poly(p-phenylenevinylene) light-emitting diodes", Chemical Physics Letters, Jul. 1993, vol. 210, No. 1-3, pp. 61-66 <DOI:10.1016/0009-2614(93)89100-V>.

Burroughes, J. et al., "Light-emitting diodes based on conjugated polymers", Nature, Oct. 1990, vol. 347, pp. 539-541.

Campbell et al. (2008). "Low-temperature control of nanoscale morphology for high performance polymer photovoltaics," Nano Lett., 8, 3942-47.

Chen, F. et al., "High-performance polymer light-emitting diodes doped with a red phosphorescent iridium complex", Applied Physics Letters, Apr. 2002 [available online Mar. 2002], vol. 80, No. 13, pp. 2308-2310 <10.1063/1.1462862>.

Chen, X., et al., "Fluorescent Chemosensors Based on Spiroring-Opening of Xanthenes and Related Derivatives", Chemical Reviews, 2012 [available online Oct. 2011], vol. 112, No. 3, pp. 1910-1956 <DOI:10.1021/cr200201z>.

Chew, S. et al: Photoluminescence and electroluminescence of a new blue-emitting homoleptic iridium complex. Applied Phys. Letters; vol. 88, pp. 093510-1-093510-3, 2006.

Chow; Angew. Chem. Int. Ed. 2013, 52, 11775-11779. DOI: 10.1002/anie.201305590 (Year: 2013).

Christoph Ulbricht et al., "Synthesis and Characterization of Oxetane-Functionalized Phosphorescent Ir(III)-Complexes", Macromol. Chem. Phys. 2009, 210, pp. 531-541.

Coakley et al. (2004). "Conjugated polymer photovoltaic cells," Chem. Mater., 16, 4533-4542.

Colombo, M. et al., "Synthesis and high-resolution optical spectroscopy of bis[2-(2-thienyl)pyridinato-C3,N'](2,2'-bipyridine)iridium(III)", Inorganic Chemistry, Jul. 1993, vol. 32, No. 14, pp. 3081-3087 <DOI:10.1021/ic00066a019>.

D.F. O'Brien et al., "Improved energy transfer in electrophosphorescent devices," Appl. Phys. Lett., vol. 74, No. 3, Jan. 18, 1999, pp. 442-444.

D'Andrade, B. et al., "Operational stability of electrophosphorescent devices containing p and n doped transport layers ", Applied Physics Letters, Nov. 2003, vol. 83, No. 19, pp. 3858-3860 <DOI:10.1063/1.1624473>.

Dan Wang et al., "Carbazole and arylamine functionalized iridium complexes for efficient electro-phosphorescent light-emitting diodes", Inorganica Chimica Acta 370 (2011) pp. 340-345.

Dorwald, Side Reactions in Organic Synthesis 2005, Wiley:VCH Weinheim Preface, pp. 1-15 & Chapter 1, pp. 279-308.

Dsouza, R., et al., "Fluorescent Dyes and Their Supramolecular Host/Guest Complexes with Macrocycles in Agueous Solution", Oct. 2011, vol. 111, No. 12, pp. 7941-7980 <DOI:10.1021/cr200213s>.

Finikova, M.A. et al., New Selective Synthesis of Substituted Tetrabenzoporphyris, Doklady Chemistry, 2003, vol. 391, No. 4-6, pp. 222-224.

Galanin et al. Synthesis and Properties of meso-Phenyl-Substituted Tetrabenzoazaporphines Magnesium Complexes. Russian Journal of Organic Chemistry (Translation of Zhurnal Organicheskoi Khimii) (2002), 38(8), 1200-1203.

Gong et al., Highly Selective Complexation of Metal Ions by the Self-Tuning Tetraazacalixpyridine macrocycles, Tetrahedron, 65(1): 87-92 (2009).

Gottumukkala,V. et al., Synthesis, cellular uptake and animal toxicity of a tetra carboranylphenyl N-tetrabenzoporphyr in, Bioorganic &Medicinal Chemistry, 2006, vol. 14, pp. 1871-1879.

Hansen (1969). "The universality of the solubility parameter," I & EC Product Research and Development, 8, 2-11.

Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, 1, pp. 755-757.

Holmes, R. et al., "Efficient, deep-blue organic electrophosphorescence by guest charge trapping", Applied Physics Letters, Nov. 2003 [available online Oct. 2003], vol. 83, No. 18, pp. 3818-3820 <DOI:10.1063/1.1624639>.

Huaijun Tang et al., "Novel yellow phosphorescent iridium complexes containing a carbazoleeoxadiazole unit used in polymeric light-emitting diodes", Dyes and Pigments 91 (2011) pp. 413-421.

Imre et al. (1996). "Liquid-liquid demixing ffrom solutions of polystyrene. 1. A review. 2. Improved correlation with solvent properties," J. Phys. Chem. Ref. Data, 25, 637-61.

Ivaylo Ivanov et al., "Comparison of the INDO band structures of polyacetylene, polythiophene, polyfuran, and polypyrrole," Synthetic Metals, vol. 116, Issues 1-3, Jan. 1, 2001, pp. 111-114.

Jack W. Levell et al., "Carbazole/iridium dendrimer side-chain phosphorescent copolymers for efficient light emitting devices", New J. Chem., 2012, vol. 36, pp. 407-413.

Jeong et al. (2010). "Improved efficiency of bulk heterojunction poly (3-hexylthiophene):[6,6]-phenyl-C61-butyric acid methyl ester photovoltaic devices using discotic liquid crystal additives," Appl. Phys. Lett.. 96, 183305. (3 pages).

Kim et al (2009). "Altering the thermodynamics of phase separation in inverted bulk-heterojunction organic solar cells," Adv. Mater., 21, 3110-15.

Kim et al. (2005). "Device annealing effect in organic solar cells with blends of regioregular poly (3-hexylthiophene) and soluble fullerene," Appl. Phys. Lett. 86, 063502. (3 pages).

Kroon et al. (2008). "Small bandgap olymers for organic solar cells," Polymer Reviews, 48, 531-82.

Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.

Kwon-Hyeon Kim et al., "Crystal Organic Light-Emitting Diodes with Perfectly Oriented Non-Doped Pt-Based Emitting Layer", Adv. Mater. 2016, 28, pp. 2526-2532.

Kwong, R. et al., "High operational stability of electrophosphorescent devices", Applied Physics Letters, Jul. 2002 [available online Jun. 2002], vol. 81, No. 1, pp. 162-164 <DOI:10.1063/1.1489503>.

(56) References Cited

OTHER PUBLICATIONS

Lamansky, S. et al., "Cyclometalated Ir complexes in polymer organic light-emitting devices", Journal of Applied Physics, Aug. 2002 [available online Jul. 2002], vol. 92, No. 3, pp. 1570-1575 <10.1063/1.1491587>.

Lamansky, S. et al., "Synthesis and Characterization of Phosphorescent Cyclometalated Iridium Complexes", Inorganic Chemistry, Mar. 2001, vol. 40, No. 7, pp. 1704-1711 <DOI:10.1021/ic0008969>.

Lee et al. (2008). "Processing additives for inproved efficiency from bulk heterojunction solar cells," J. Am. Chem. Soc, 130, 3619-23.

Li et al. (2005). "Investigation of annealing effects and film thickness dependence of polymer solar cells based on poly (3-hexylthiophene)," J. Appl. Phys., 98, 043704. (5 pages).

Li et al. (2007). "Solvent annealing effect in polymer solar cells based on poly(3-hexylthiophene) and methanofullerenes," Adv. Funct. Mater, 17, 1636-44.

Li, J. et al., "Synthesis and characterization of cyclometalated Ir(III) complexes with pyrazolyl ancillary ligands", Polyhedron, Jan. 2004, vol. 23, No. 2-3, pp. 419-428 <DOI:10.1016/j.poly.2003.11.028>.

Li, J., et al., "Synthetic Control of Excited-State Properties in Cyclometalated Ir(III) Complexes Using Ancillary Ligands", Inorganic Chemistry, Feb. 2005, vol. 44, No. 6, pp. 1713-1727 <DOI:10.1021/ic048599h>.

Liang, et al. (2010). "For the bright future-bulk heterojunction polymer solar cells with power conversion efficiency of 7.4%," Adv. Mater. 22, E135-38.

Markham, J. et al., "High-efficiency green phosphorescence from spin-coated single-layer dendrimer light-emitting diodes ", Applied Physics Lettersm Apr. 2002, vol. 80, vol. 15, pp. 2645-2647 <DOI:10.1063/1.1469218>.

Matthew J. Jurow et al., "Understanding and predicting the orientation of heteroleptic phosphors in organic light-emitting materials", Nature Materials, vol. 15, Jan. 2016, pp. 85-93.

Galanin et al., meso-Phenyltetrabenzoazaporphyrins and their zinc complexes. Synthesis and spectral properties, Russian Journal of General Chemistry (2005), 75(4), 651-655.

Michl, J., "Relationship of bonding to electronic spectra", Accounts of Chemical Research, May 1990, vol. 23, No. 5, pp. 127-128 <DOI:10.1021/ar00173a001>.

Miller, R. et al., "Polysilane high polymers", Chemical Reviews, Sep. 1989, vol. 89, No. 6, pp. 1359-1410 <DOI:10.1021/cr00096a006>.

Morana et al. (2007). "Organic field-effect devices as tool to characterize the bipolar transport in polymer-fullerene blends: the case of P3HT-PCBM," Adv. Funct. Mat., 17, 3274-83.

Moule et al. (2008). "Controlling morphology in Polymer-Fullerene mixtures," Adv. Mater., 20, 240-45.

Nazeeruddin, M. et al., "Highly Phosphorescence Iridium Complexes and Their Application in Organic Light-Emitting Devices", Journal of the American Chemical Society, Jun. 2003, vol. 125, No. 29, pp. 8790-8797 <DOI:10.1021/ja021413y>.

Nillson et al. (2007). "Morphology and phase segregation of spin-casted films of polyfluorene/PCBM Blends," Macromolecules, 40, 8291-8301.

Olynick et al. (2009). "The link between nanoscale feature development in a negative resist and the Hansen solubility sphere," Journal of Polymer Science: Part B: Polymer Physics, 47, 2091-2105.

Peet et al. (2007). "Efficiency enhancement in low-bandgap polymer solar cells by processing with alkane dithiols," Nature Materials, 6, 497-500.

Pivrikas et al. (2008). "Substituting the postproduction treatment for bulk-heterojunction solar cells using chemical additives," Organic Electronics, 9, 775-82.

Rui Zhu et al., "Color tuning based on a six-membered chelated iridium (III) complex with aza-aromatic ligand,", Chemistry Letters, vol. 34, No. 12, 2005, pp. 1668-1669.

Sajoto, T. et al., "Temperature Dependence of Blue Phosphorescent Cyclometalated Ir(III) Complexes", Journal of the American Chemical Society, Jun. 2009, vol. 131, No. 28, pp. 9813-9822 <DOI:10.1021/ja903317w>.

Saricifci et al. (1993). "Semiconducting polymerbuckminsterfullerene heterojunctions: diodes photodiodes, and photovoltaic cells," Appl. Phys. Lett., 62, 585-87.

Saunders et al. (2008). "Nanoparticle-polymer photovoltaic cells," Advances in Colloid and Interface Science, 138, 1-23.

Shin et al. (2010). "Abrupt morphology change upon thermal annealing in Poly(3-hexathiophene)/soluble fullerene blend films for polymer solar cells," Adv. Funct. Mater., 20, 748-54.

Strouse, G. et al., "Optical Spectroscopy of Single Crystal [Re(bpy)(CO)4](PF6): Mixing between Charge Transfer and Ligand Centered Excited States", Inorganic Chemistry, Oct. 1995, vol. 34, No. 22, pp. 5578-5587 <DOI:10.1021/ic00126a031>.

Sylvia Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.

Tang, C. et al., "Organic electroluminescent diodes", Applied Physics Letters, Jul. 1987, vol. 51, No. 12, pp. 913-915 <DOI:10.1063/1.98799>.

Tsuoboyama, A. et al., "Homoleptic Cyclometalated Iridium Complexes with Highly Efficient Red Phosphorescence and Application to Organic Light-Emitting Diode", Journal of the American Chemical Society, Sep. 2003, vol. 125, No. 42, pp. 12971-12979 <DOI:10.1021/ja034732d>.

Turro, N., "Modern Molecular Photochemistry" (Sausalito, California, University Science Books, 1991), p. 48.

U.S. Appl. No. 16/668,010, filed Oct. 30, 2019.

U.S. Appl. No. 16/739,480, filed Jan. 10, 2020.

V. Adamovich et al., "High efficiency single dopant white electrophosphorescent light emitting diodes", New J. Chem, vol. 26, pp. 1171-1178. 2002.

V. Thamilarasan et al., "Green-emitting phosphorescent iridium(III) complex: Structural, photophysical and electrochemical properties," Inorganica Chimica Acta, vol. 408, 2013, pp. 240-245.

Wang et al. (2010). "The development of nanoscale morphology in polymer: fullerene photovoltaic blends during solvent casting," Soft Matter, 6, 4128-4134.

Wang et al., C(aryl)-C(alkyl) bond formation from Cu(Cl04)2-mediated oxidative cross coupling reaction between arenes and alkyllithium reagents through structurally well-defined Ar—Cu(III) intermediates, Chem Commun, 48: 9418-9420 (2012).

Williams, E. et al., "Excimer Based White Phosphorescent Organic Light Emitting Diodes with Nearly 100 % Internal Quantum Efficiency", Advanced Materials, Jan. 2007, vol. 19, No. 2, pp. 197-202 <DOI:10.1002/adma.200602174>.

Williams, E. et al., "Organic light-emitting diodes having exclusive near-infrared electrophosphorescence", Applied Physics Letters, Aug. 2006, vol. 89, No. 8, pp. 083506-1-083506-3 <DOI:10.1063/1.2335275>.

Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.

Yakubov, L.A. et al., Synthesis and Properties of Zinc Complexes of mesoHexadecyloxy-Substituted Tetrabenzoporphyrin and Tetrabenzoazaporphyrins, Russian Journal of Organic Chemistry, 2008, vol. 44, No. 5, pp. 755-760.

Yang et al. (2005). "Nanoscale morphology of high-performance polymer solar cells," Nano Lett., 5, 579-83.

Yang, X. et al., "Efficient Blue and White Emitting Electrophosphorescent Devices Based on Platinum(II) [1,3 Difluoro 4,6 di(2 pyridinyl)benzene] Chloride", Advanced Materials, Jun. 2008, vol. 20, No. 12, pp. 2405-2409 <DOI:10.1002/adma.200702940>.

Yao et al. (2008). "Effect of solvent mixture on nanoscale phase separation in polymer solar cells," Adv. Funct. Mater.,18, 1783-89.

(56) References Cited

OTHER PUBLICATIONS

Yao et al., Cu(Cl04)2-Mediated Arene C—H Bond Halogenations of Azacalixaromatics Using Alkali Metal Halides as Halogen Sources, The Journal of Organic Chemistry, 77(7): 3336-3340 (2012).
Yu et al. (1995). "Polymer Photovoltaic Cells: Enhanced efficiencies via a network of internal donor-acceptor heterojunctions," Science, 270, 1789-91.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Z Xu et al., "Synthesis and properties of iridium complexes based 1,3,4-oxadiazoles derivatives", Tetrahedron 64 (2008) pp. 1860-1867.
Zhu, W. et al., "Highly efficient electrophosphorescent devices based on conjugated polymers doped with iridium complexes", Applied Physics Letters, Mar. 2002, vol. 80, No. 12, pp. 2045-2047 <DOI:10.1063/1.1461418>.
U.S. Appl. No. 61/719,077.
Fuchs, C. et al., "Enhanced light emission from top-emitting organic light-emitting diodes by optimizing surface plasmon polariton losses", arXiv, submitted Mar. 2015, 11 pages, arXiv:1503.01309.
Fuchs, C. et al., "Enhanced light emission from top-emitting organic light-emitting diodes by optimizing surface plasmon polariton losses", Physical Review B, Dec. 2015, vol. 92, No. 24, pp. 245306-1-245306-10 <DOI:10.1103/PhysRevB.92.245306>.
Gather, M. et al., "Recent advances in light outcoupling from white organic light-emitting diodes," Journal of Photonics for Energy, May 2015, vol. 5, No. 1, 057607-1-057607-20 <DOI:10.1117/1.JPE.5.057607>.
Graf, A. et al., "Correlating the transition dipole moment orientation of phosphorescent emitter molecules in OLEDs with basic material properties", Journal of Materials Chemistry C, Oct. 2014, vol. 2, No. 48, pp. 10298-10304 <DOI:10.1039/c4tc00997e>.
Hatakeyama, T. et al., "Ultrapure Blue Thermally Activated Delayed Fluorescence Molecules: Efficient HOMO-LUMO Separation by the Multiple Resonance Effect", Advanced Materials, Apr. 2016, vol. 28, No. 14, pp. 2777-2781, <DOI:10.1002/adma.201505491>.
Kim, HY. et al., "Crystal Organic Light-Emitting Diodes with Perfectly Oriented Non-Doped Pt-Based Emitting Layer", Advanced Functional Materials, Feb. 2016, vol. 28, No. 13, pp. 2526-2532 <DOI:10.1002/adma.201504451>.
Kim, J.J., "Setting up the new efficiency limit of OLEDs; Abstract" [online], Electrical Engineering-Princeton University, Aug. 2014 [retrieved on Aug. 24, 2016], retrieved from the internet: <URL:http://ee.princeton.edu/events/setting-new-efficiency-limit-oled> 2 pages.

Kim, SY. et al., "Organic Light-Emitting Diodes with 30% External Quantum Efficiency Based on a Horizontally Oriented Emitter", Advanced Functional Materials, Mar. 2013, vol. 23, No. 31, pp. 3896-3900 <DOI:10.1002/adfm.201300104 >.
Lampe, T. et al., "Dependence of Phosphorescent Emitter Orientation on Deposition Technique in Doped Organic Films", Chemistry of Materials, Jan. 2016, vol. 28, pp. 712-715 <DOI:10.1021/acs.chemmater.5b04607>.
Li, J., "Efficient and Stable OLEDs Employing Square Planar Metal Complexes and Inorganic Nanoparticles", in DOE SSL R&D Workshop (Raleigh, North Carolina, 2016), Feb. 2016, 15 pages.
Lin, TA et al., "Sky-Blue Organic Light Emitting Diode with 37% External Quantum Efficiency Using Thermally Activated Delayed Fluorescence from Spiroacridine-Triazine Hybrid", Advanced Materials, Aug. 2016, vol. 28, No. 32, pp. 6876-6983 <DOI:10.1002/adma.201601675>.
Sakai, Y. et al., "Simple model-free estimation of orientation order parameters of vacuum-deposited and spin-coated amorphous films used in organic light-emitting diodes", Applied Physics Express, Aug. 2015, vol. 8, No. 9, pp. 096601-1-096601-4 <DOI:10.7567/APEX.8.096601>.
Senes, A. et al., "Transition dipole moment orientation in films of solution processed fluorescent oligomers: investigating the influence of molecular anisotropy", Journal of Materials Chemistry C, Jun. 2016, vol. 4, No. 26, pp. 6302-6308 <DOI:10.1039/c5tc03481g>.
U.S. Appl. No. 61/692,937.
Results from SciFinder Compound Search on Dec. 8, 2016. (17 pages).
U.S. Appl. No. 16/668,010, filed Oct. 30, 2019, has not yet published. Inventor: Li et al.
U.S. Appl. No. 16/739,480, filed Jan. 10, 2020, has not yet published. Inventors: Li et al.
U.S. Appl. No. 16/751,561, filed Jan. 24, 2020, has not yet published. Inventor: Li.
U.S. Appl. No. 16/751,586, filed Jan. 24, 2020, has not yet published. Inventor: Li et al.
Claim set of the U.S. Appl. No. 62/444,973, filed Jan. 11, 2017, Lichang Zeng, 36 pages. (Year: 2017).
Korean Office Action (with English translation) for App. No. KR10-2015-0104260, dated Jan. 12, 2022, 12 pages.
Machine-translated English version of JP 2012/074444 A, Sekine Noboru, Apr. 12, 2012 (Year: 2012) 75 pages.
Tyler Fleetham, "Phosphorescent Pt(II) and Pd(II) Complexes for Efficient, High-Color-Quality, and Stable OLEDs", Material Science and Engineering, Arizona State University (Year: 2016).
JP4460952 machine translation downloaded from Google patents Dec. 30, 2022.

\* cited by examiner

METAL-ASSISTED DELAYED FLUORESCENT EMITTERS EMPLOYING PYRIDO-PYRROLO-ACRIDINE AND ANALOGUES

CROSS-REFERENCE TO RELATED APPLICATIONS

The present application is a 35 U.S.C. § 371 national stage patent application of International Patent Application No. PCT/US2018/015506, filed Jan. 26, 2018, which claims priority under 35 U.S.C. § 119(e) to U.S. Provisional Patent Application Ser. No. 62/451,574, filed Jan. 27, 2017, all of which are incorporated herein by reference in their entireties.

STATEMENT REGARDING FEDERALLY SPONSORED RESEARCH OR DEVELOPMENT

This invention was made with government support under DE-EE0007090 awarded by the Department of Energy. The government has certain rights in the invention.

TECHNICAL FIELD

This invention relates to metal-assisted delayed fluorescent (MADF) emitters including cyclic tetradentate platinum (II) and palladium (II) complexes employing 8H-pyrido [3',2':4,5]-pyrrolo[3,2,1-de]acridine and its analogues.

BACKGROUND

Compounds capable of absorbing and/or emitting light can be suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in organic light emitting diodes (OLEDs), lighting, and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is greater than that of the red and green phosphors, which suggests that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

Metal-assisted delayed fluorescent emitters represented by General Formulas I-IV are disclosed.

General Formula I

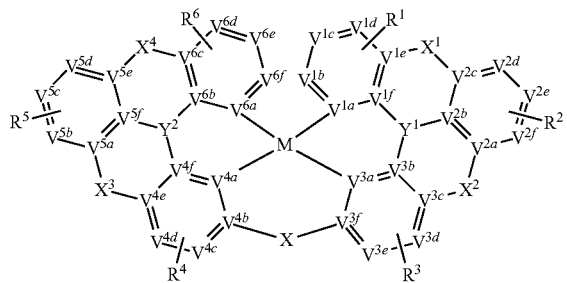

General Formula II

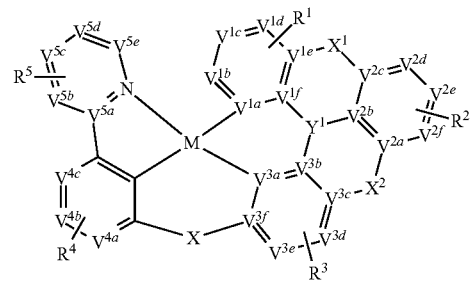

General Formula III

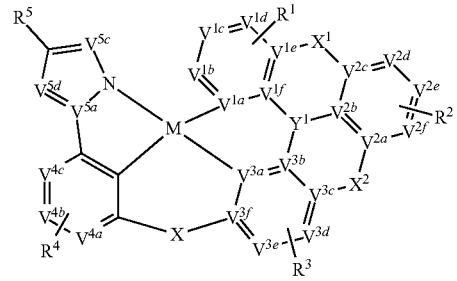

General Formula IV

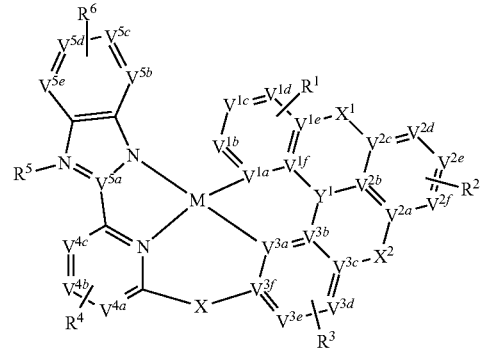

In General Formulas I-IV:

M is Pt (II) or Pd (II);

each of $V^{1a}$-$V^{1f}$, $V^{2a}$-$V^{2f}$, $V^{3a}$-$V^{3f}$, $V^{4a}$-$V^{4f}$, $V^{5a}$-$V^{5f}$, and $V^{6a}$-$V^{6f}$, if present, is independently N, C, P, O, S or Si;

each of X, $X^1$, $X^2$, $X^3$, and $X^4$ is independently present or absent, and each X, $X^1$, $X^2$, $X^3$, and $X^4$ present independently represents a single bond, $CR^7R^8$, C=O, $SiR^7R^8$, GeR⁷R⁸, NR⁷, PR⁷, PR⁷R⁸, R⁷P=O, AsR⁷, R⁷As=O, O, S, S=O, SO₂, Se, Se=O, SeO₂, BR⁷, BR⁷R⁸, AlR⁷, AlR⁷R⁸, R⁷Bi=O, or BiR⁷;

each of Y¹ and Y², if present, is independently CR, SiR, GeR, N, NR, P, P=O, As, As=O, B, BR, Al, AlR, Bi=O, or Bi; and each of R, R¹, R², R³, R⁴, R⁵, R⁶, R⁷, and R⁸ is independently absent or present as a single substituent or multiple substituents, valency permitting, and each R, R¹, R², R³, R⁴, R⁵, R⁶, R⁷, and R⁸ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

The complexes of General Formulas I-IV provide improved color purity and enhanced operational stability, and reduce or eliminate potential strong intermolecular interactions. These complexes are suitable for luminescent labels, emitters for organic light emitting diodes (OLEDs), and lighting applications.

The details of one or more implementations of the subject matter described in this specification are set forth in the accompanying drawings and the description below. Other features, aspects, and advantages of the subject matter will become apparent from the description, the drawings, and the claims.

DETAILED DESCRIPTION

Figure 1:
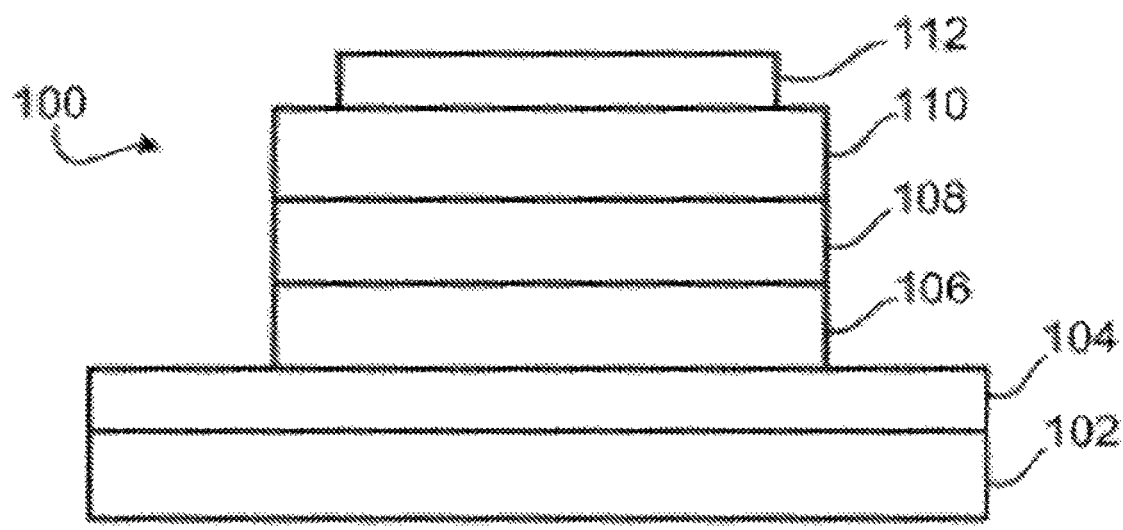
FIG. 1 depicts a cross section of an exemplary organic light emitting diode (OLED).

Metal-assisted delayed fluorescent emitters represented by General Formulas I-IV are disclosed.

General Formula I

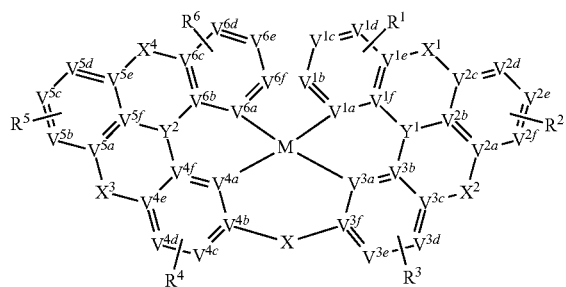

General Formula II

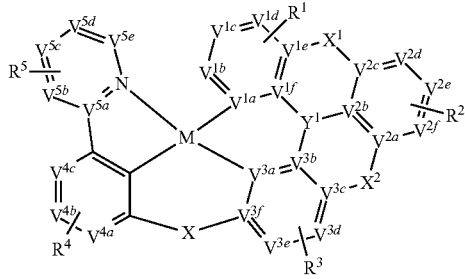

General Formula III

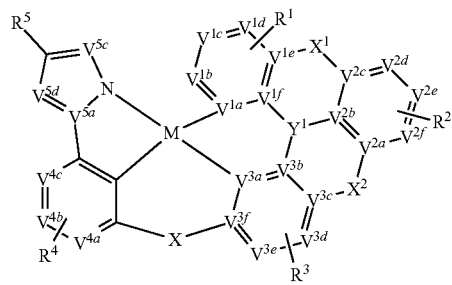

General Formula IV

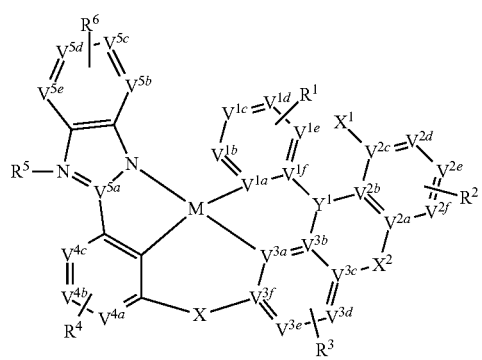

In General Formulas I-IV:
M is Pt (II) or Pd (II);
each of $V^{1a}$-$V^{1f}$, $V^{2a}$-$V^{2f}$, $V^{3a}$-$V^{3f}$, $V^{4a}$-$V^{4f}$, $V^{5a}$-$V^{5f}$, and $V^{6a}$-$V^{6f}$, if present, is independently N, C, P, O, S or Si;
each of X, X¹, X², X³, and X⁴ is independently present or absent, and each X, X¹, X², X³, and X⁴ present independently represents a single bond, CR⁷R⁸, C=O, SiR⁷R⁸, GeR⁷R⁸, NR⁷, PR⁷, PR⁷R⁸, R⁷P=O, AsR⁷, R⁷As=O, O, S, S=O, SO₂, Se, Se=O, SeO₂, BR⁷, BR⁷R⁸, AlR⁷, AlR⁷R⁸, R⁷Bi=O, or BiR⁷;

each of Y¹ and Y², if present, is independently CR, SiR, GeR, N, NR, P, P=O, As, As=O, B, BR, Al, AlR, Bi=O, or Bi; and each of R, R¹, R², R³, R⁴, R⁵, R⁶, R⁷, and R⁸ is independently absent or present as a single substituent or multiple substituents, valency permitting, and each R, R¹, R², R³, R⁴, R⁵, R⁶, R⁷, and R⁸ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Examples of complexes of General Formulas I-IV include the following structures, where each of $R^9$, $R^{10}$, $R^{11}$, and $R^{12}$, if present, independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

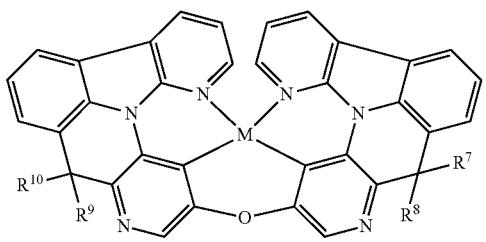

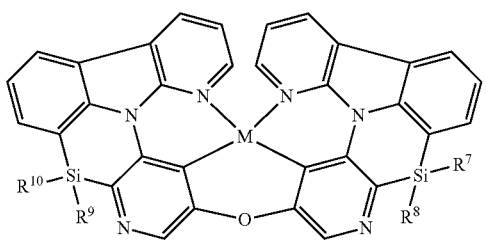

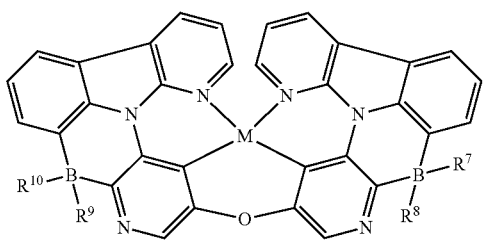

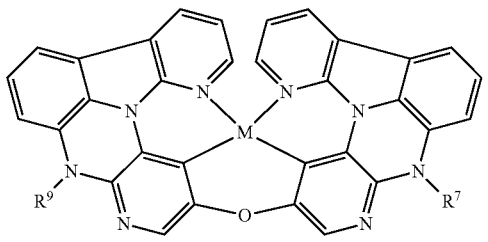

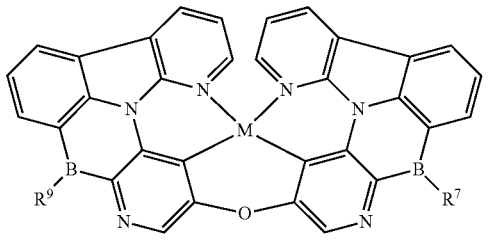

-continued

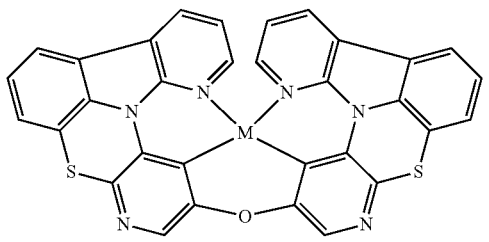

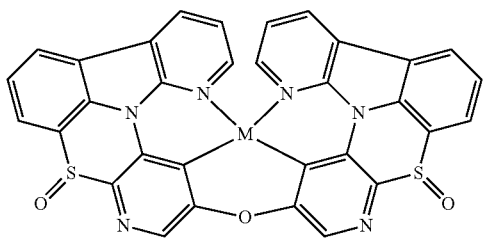

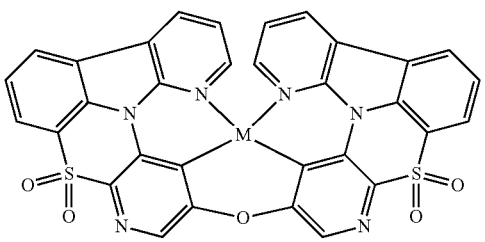

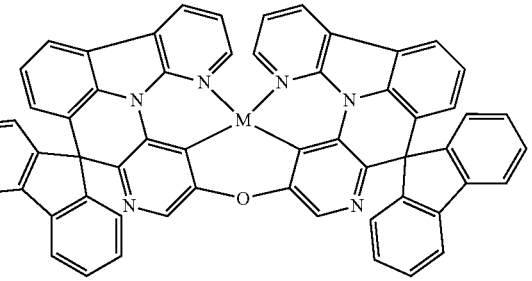

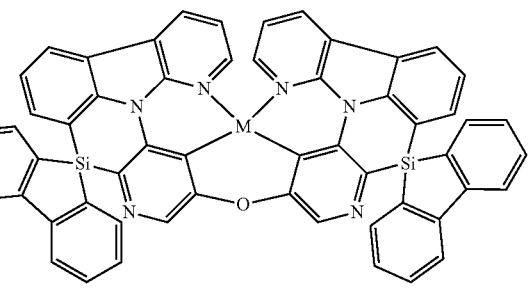

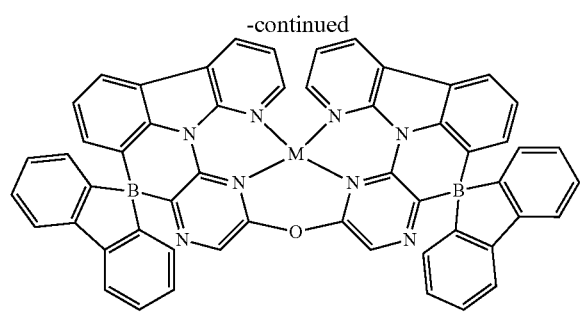
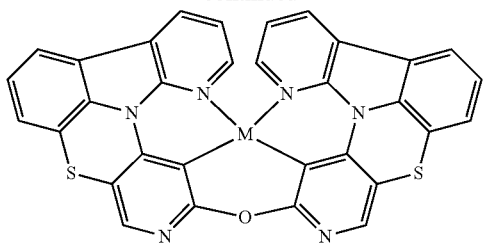
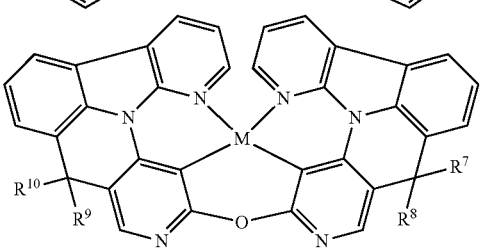
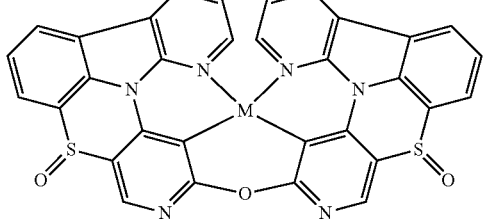
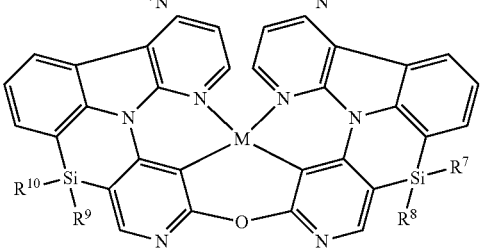
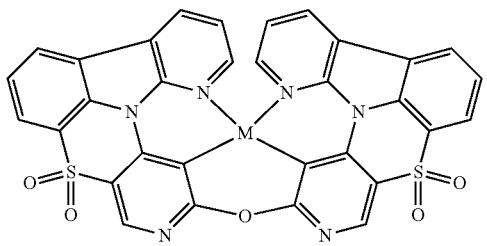
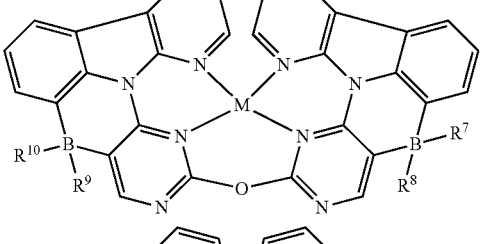
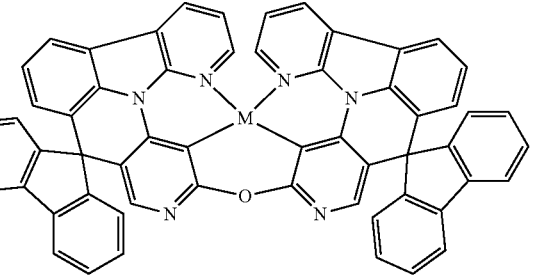
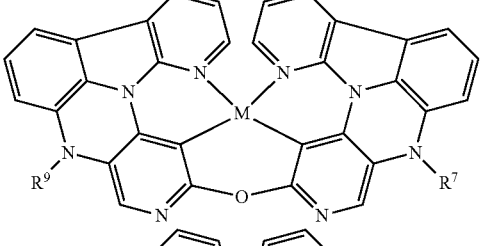
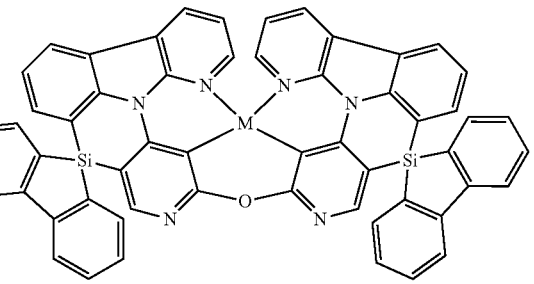
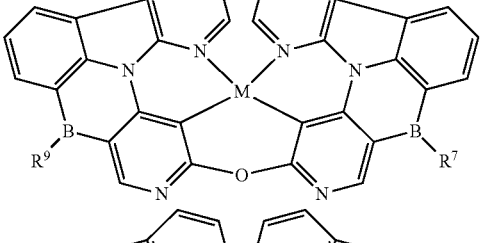
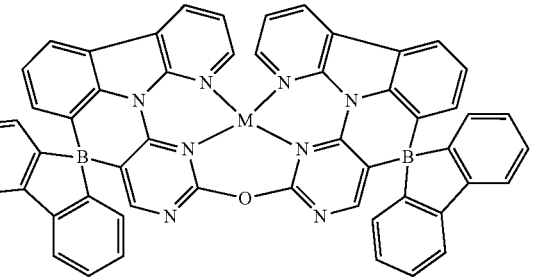

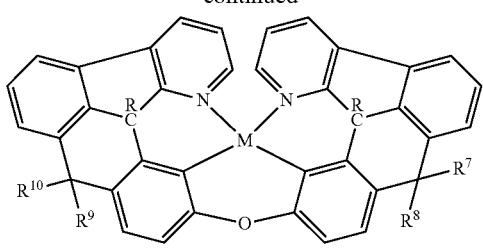
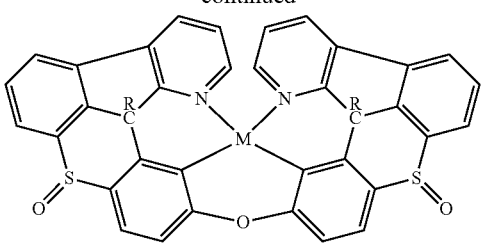
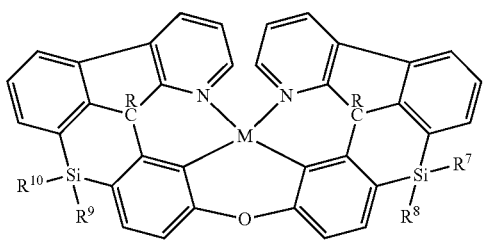
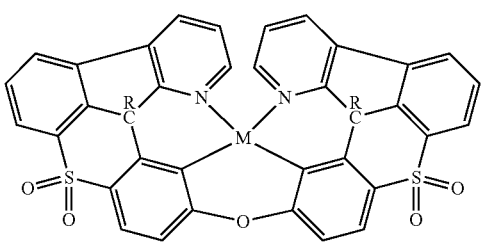
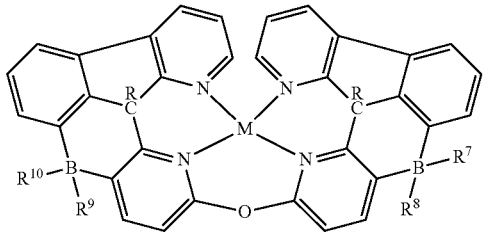

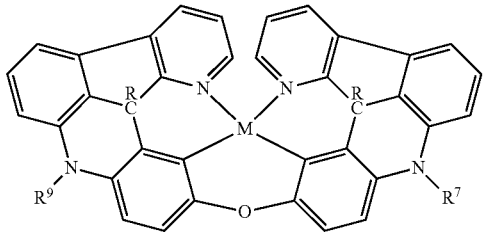

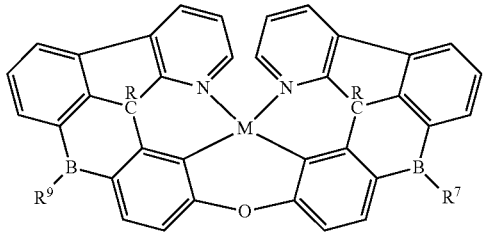
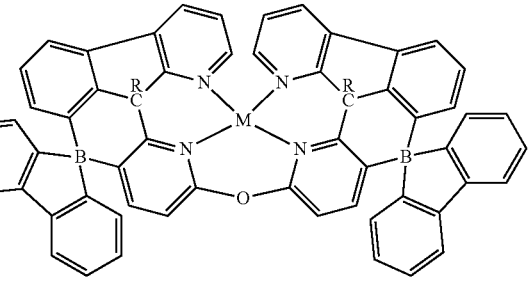
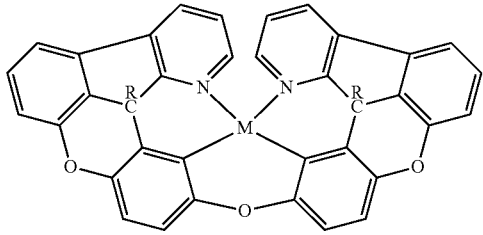
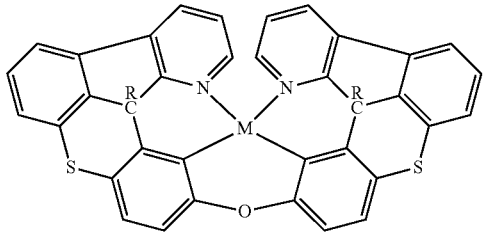
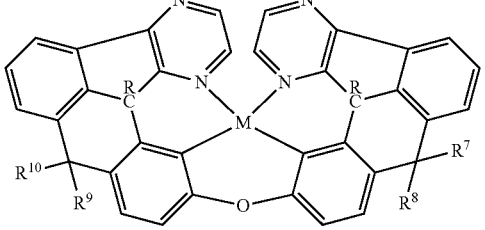

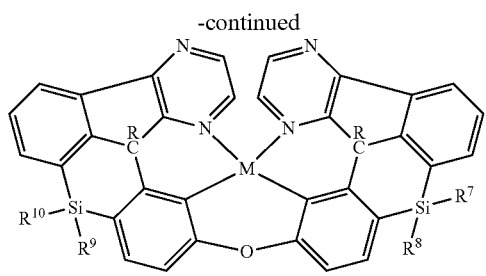
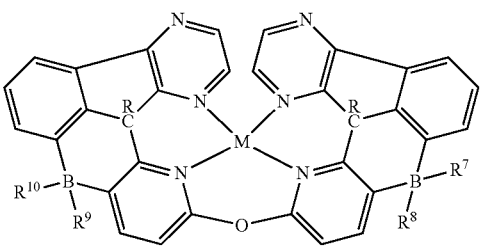
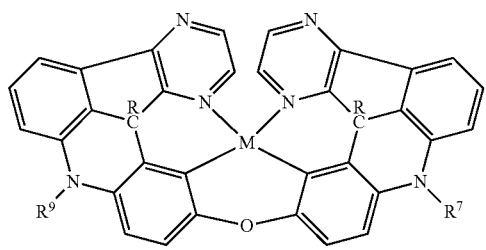
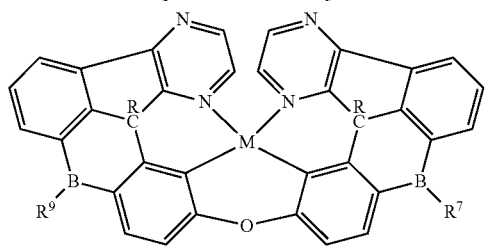
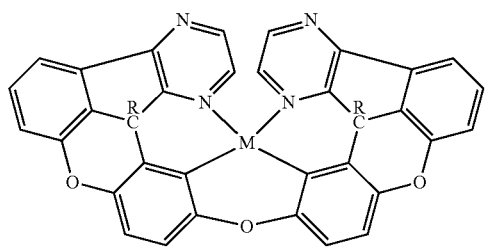
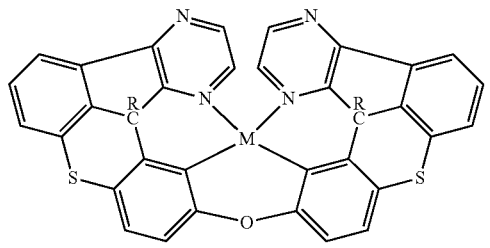
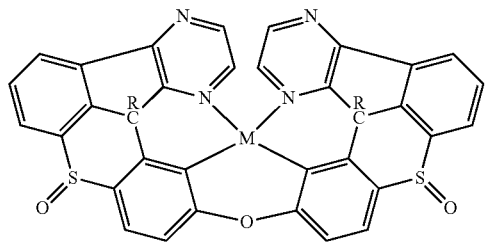
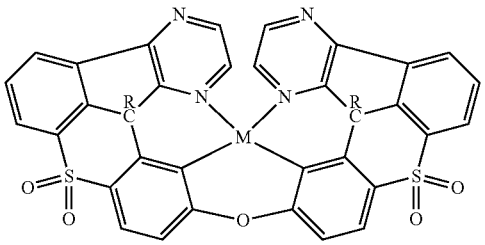
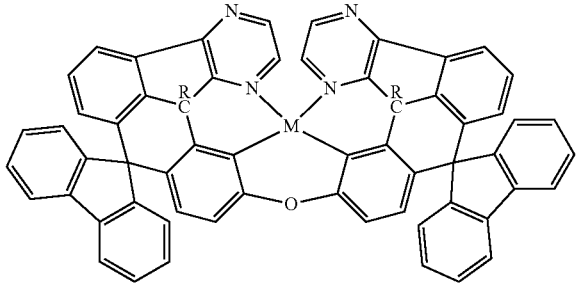
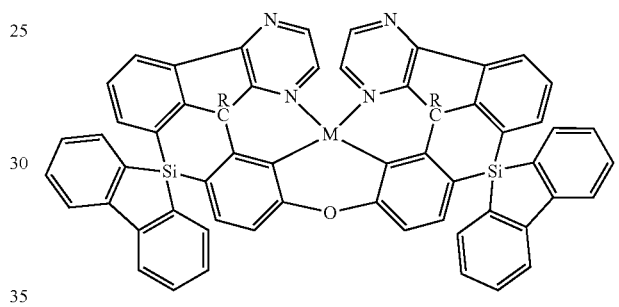
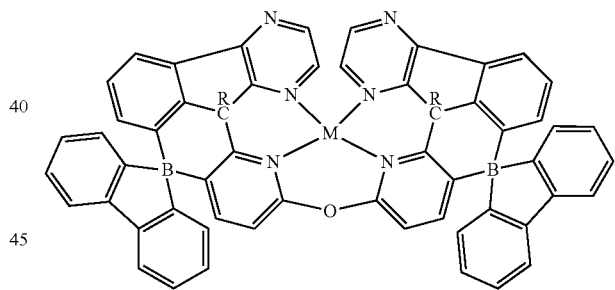
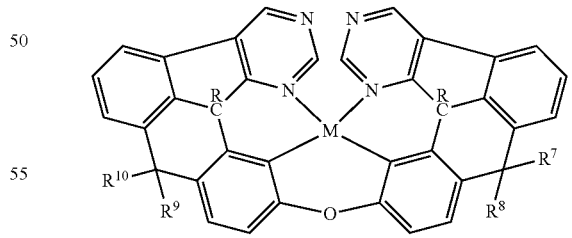
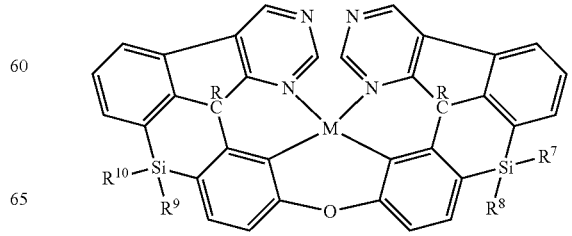

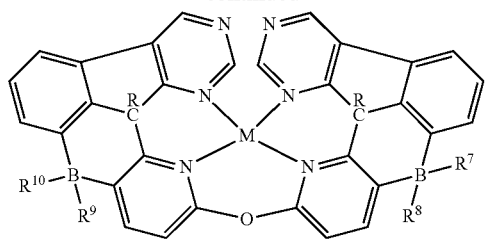
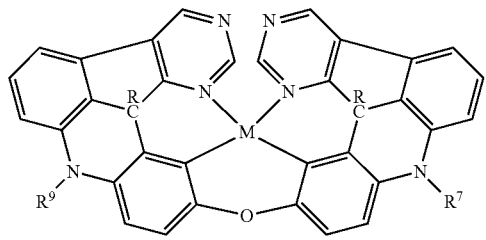
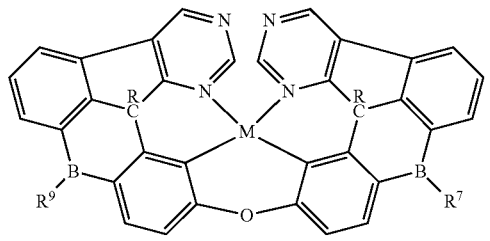
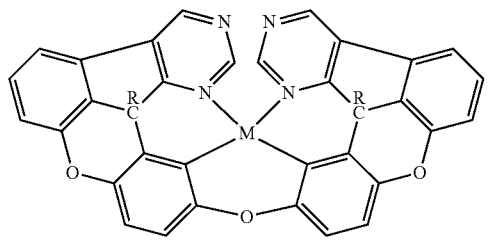
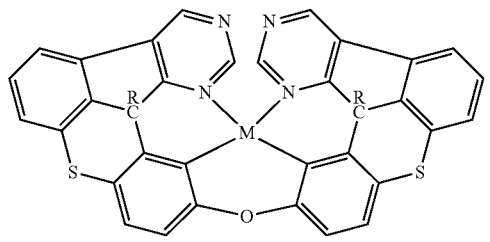
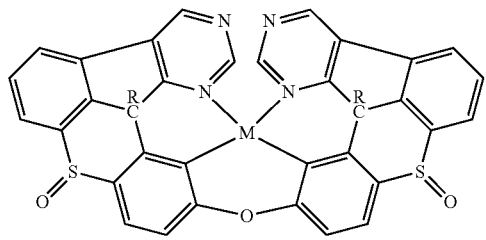
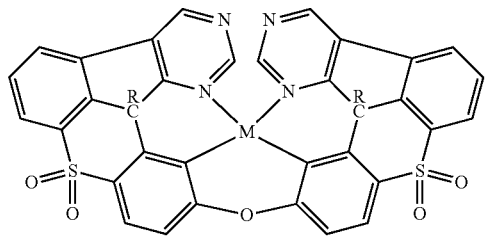
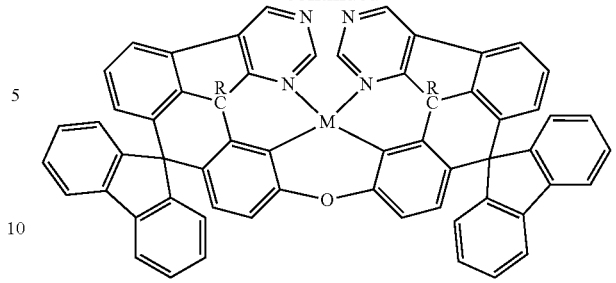
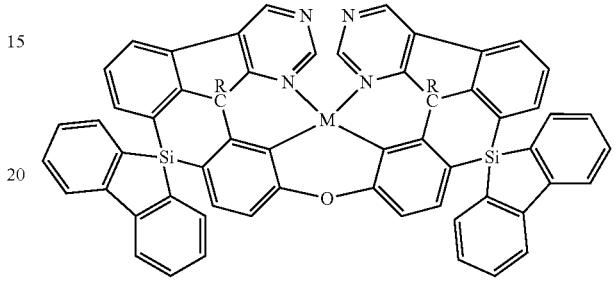
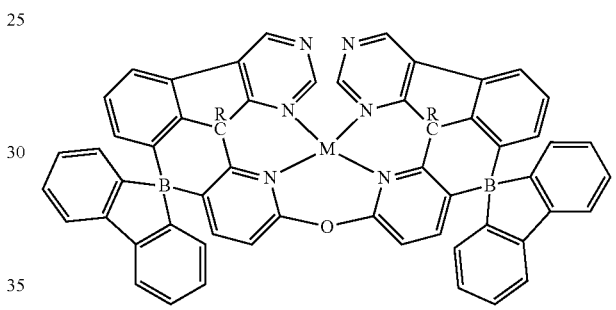

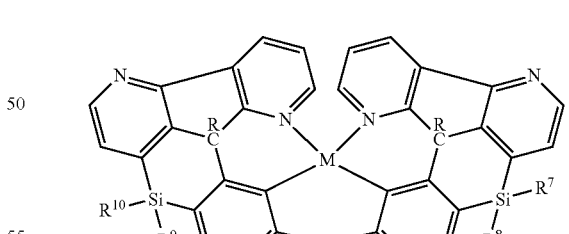
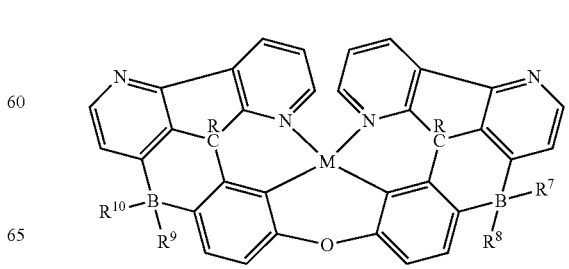

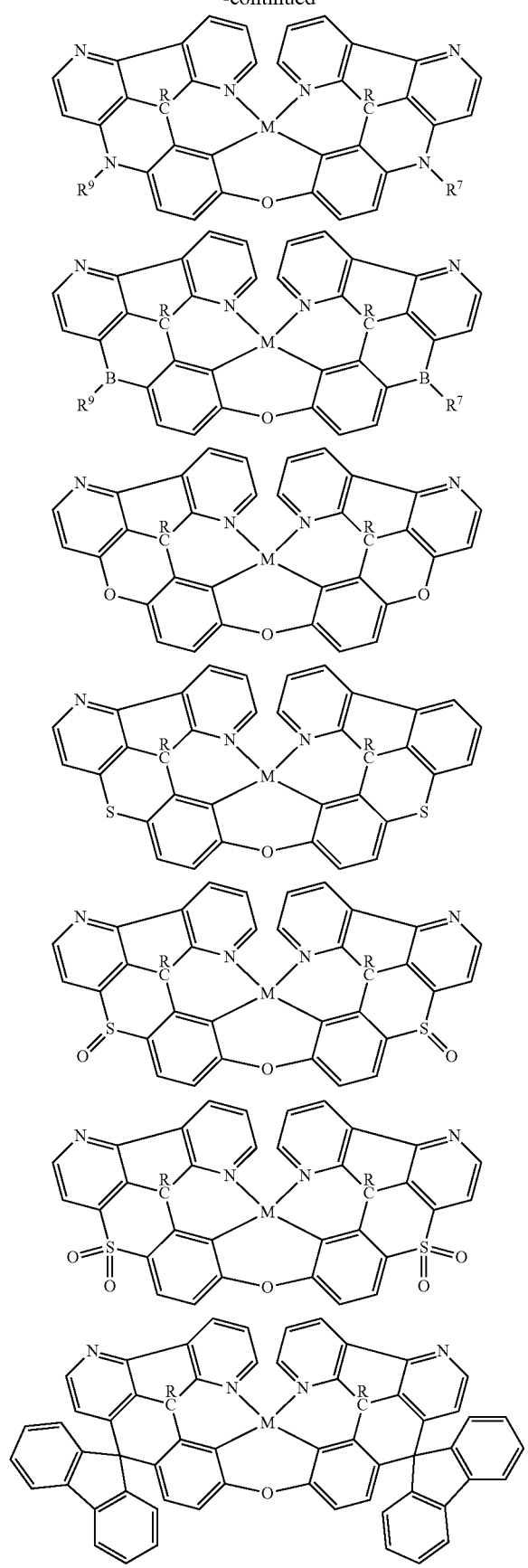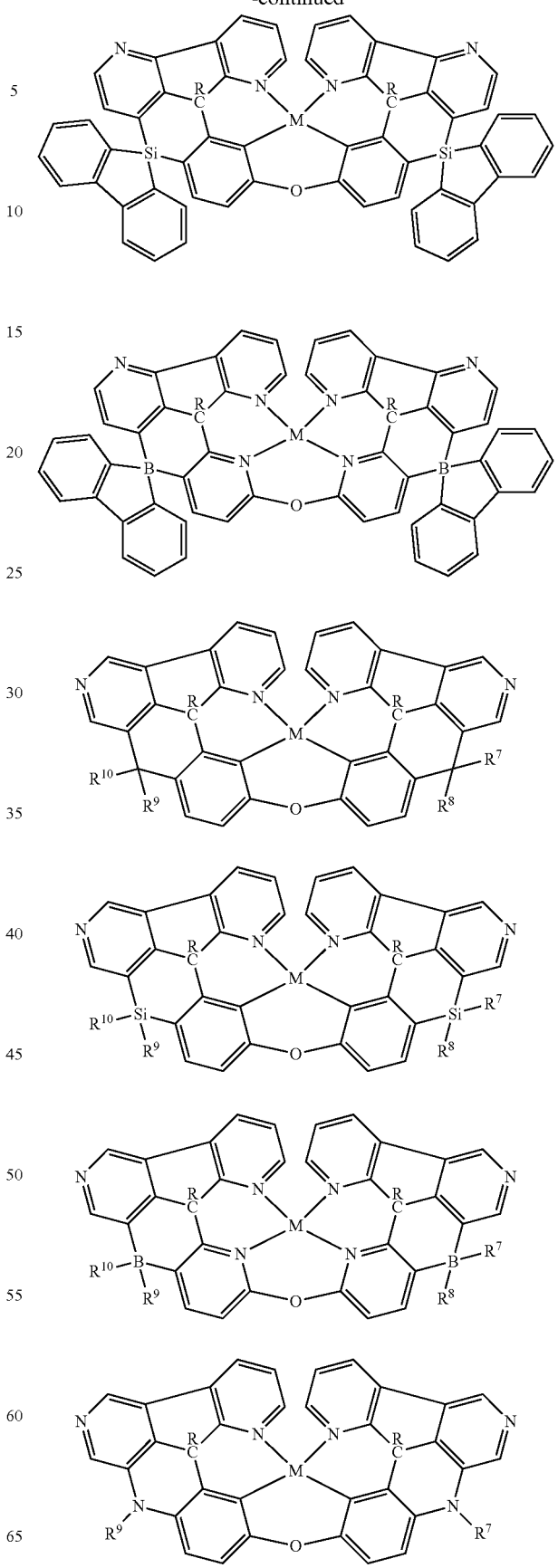

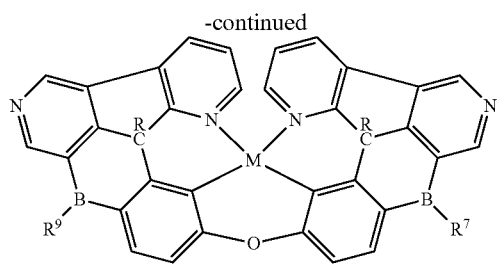
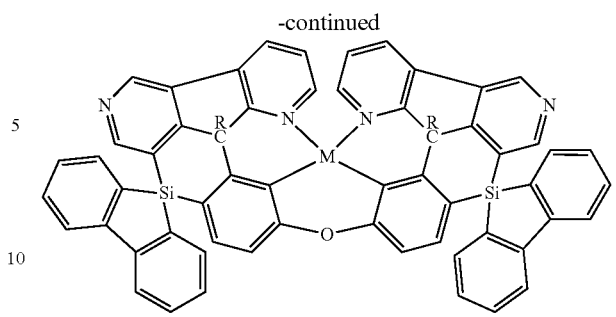
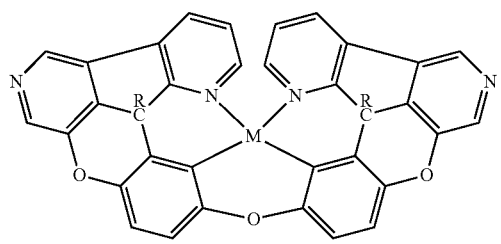
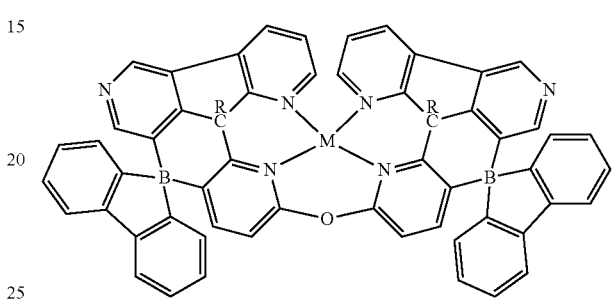
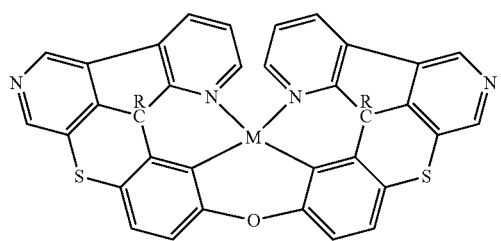
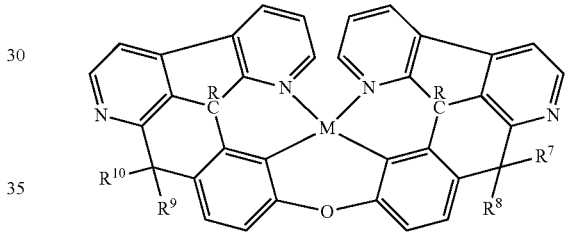
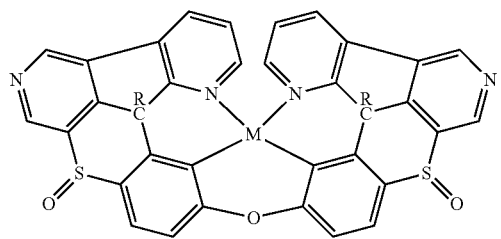
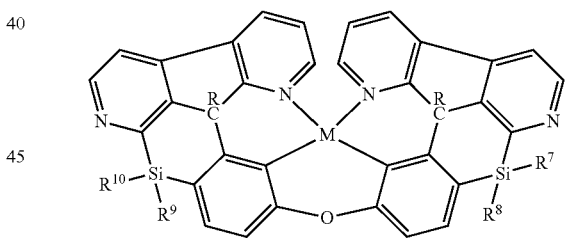
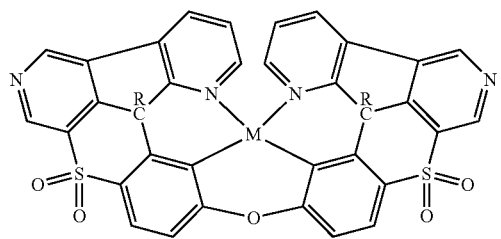
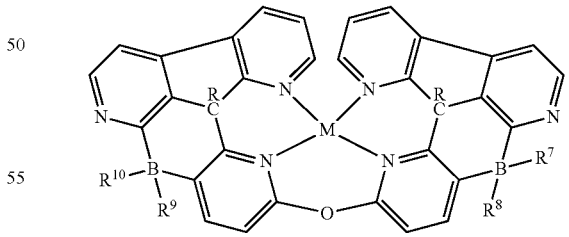
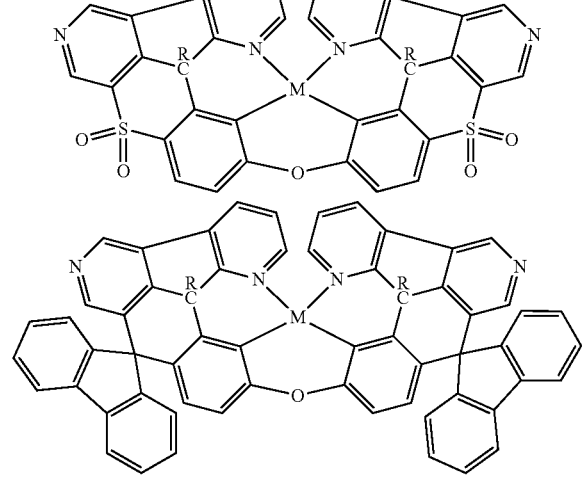
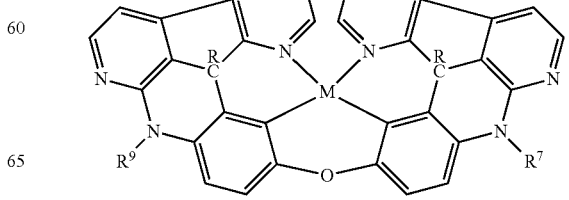

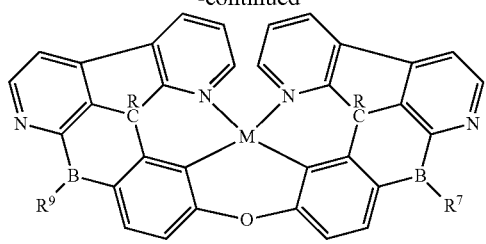
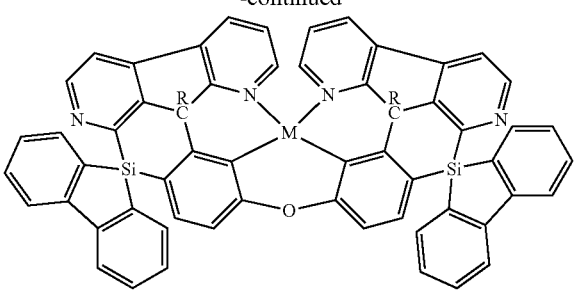
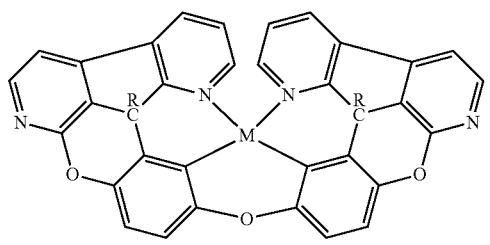
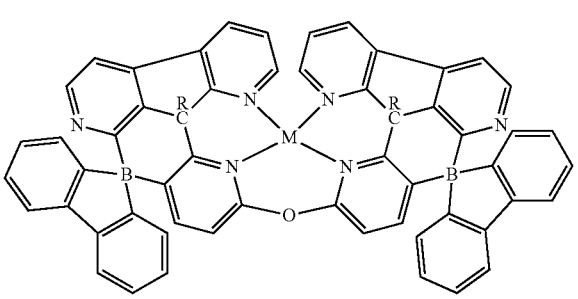

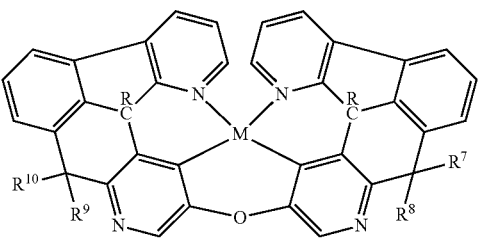
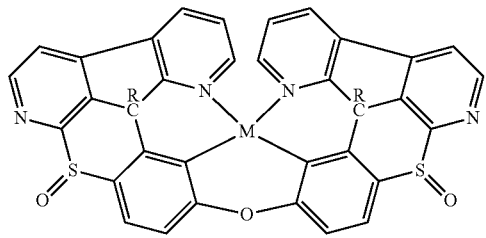
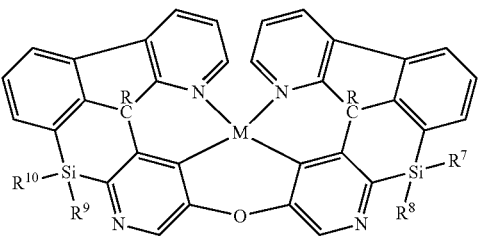
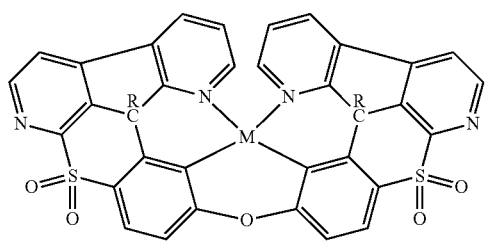
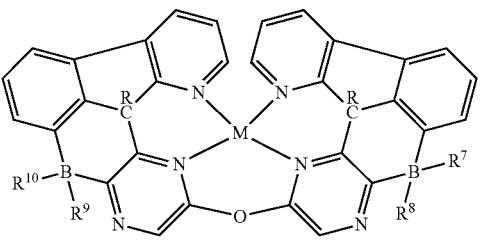
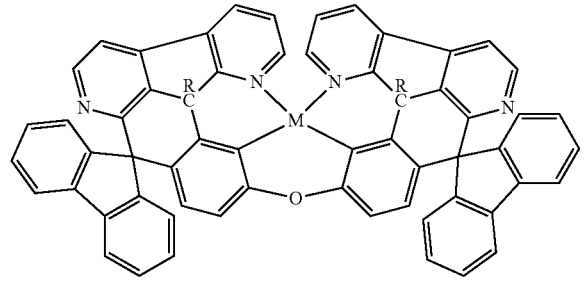
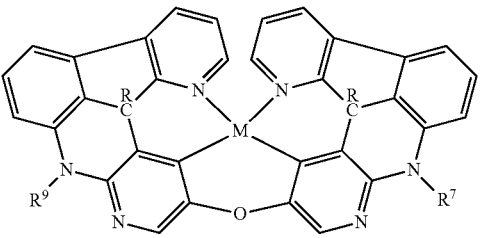

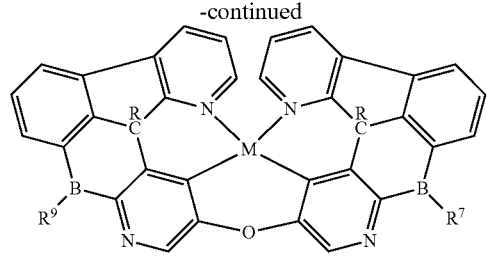
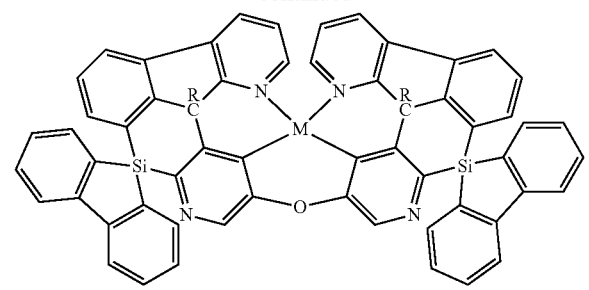
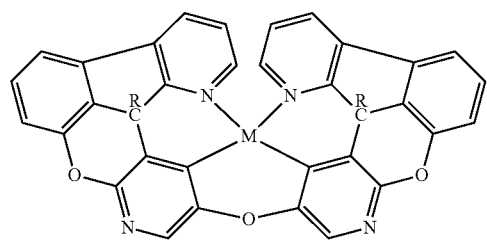
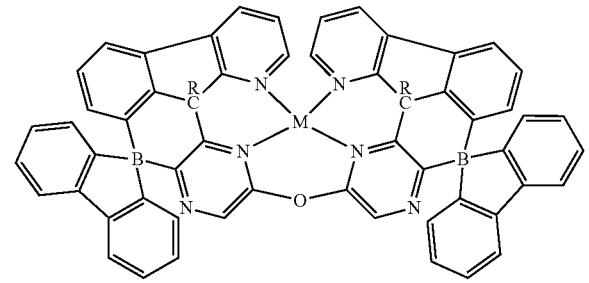
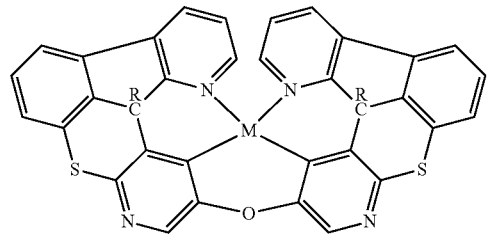
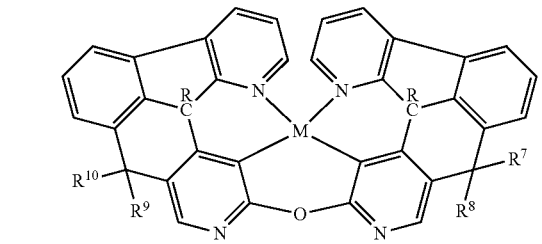
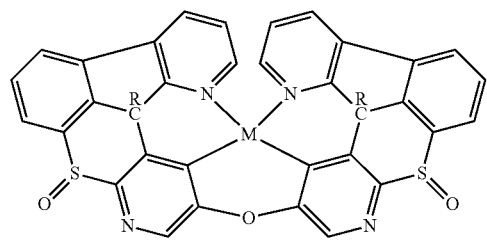
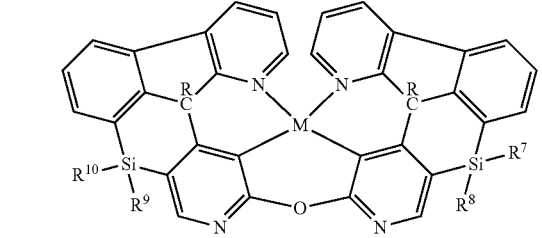
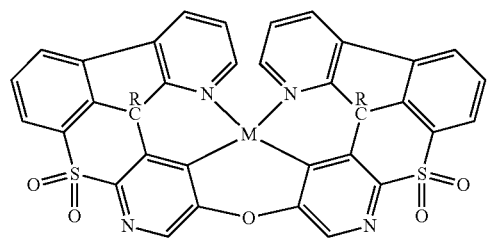
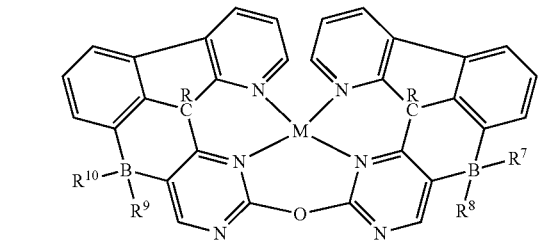
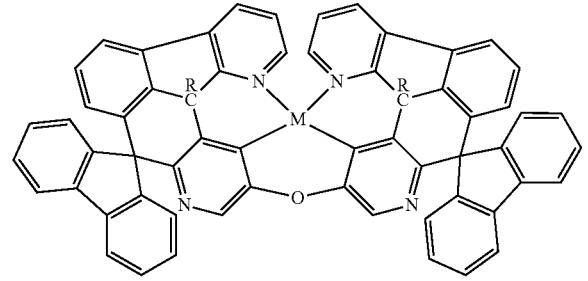
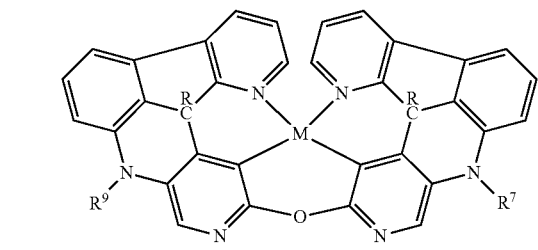

-continued
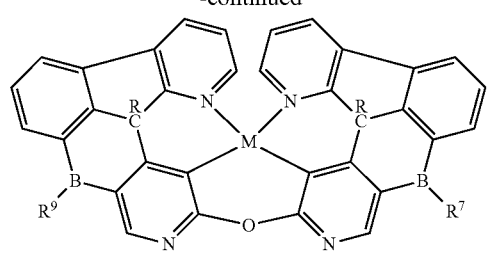
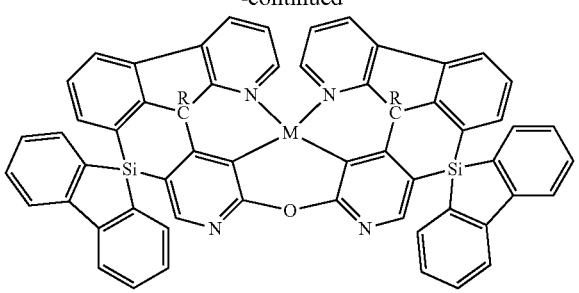
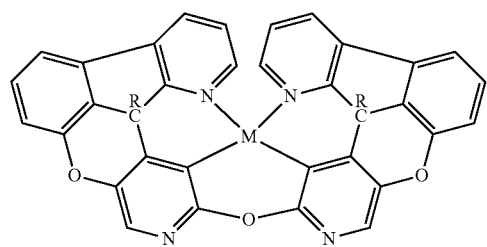
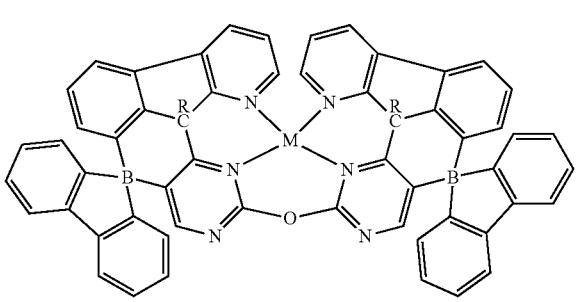
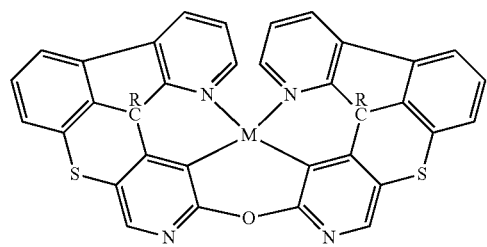
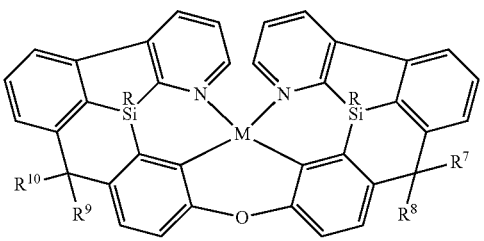
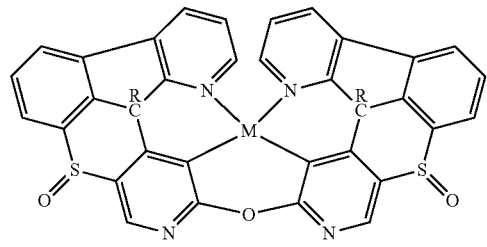
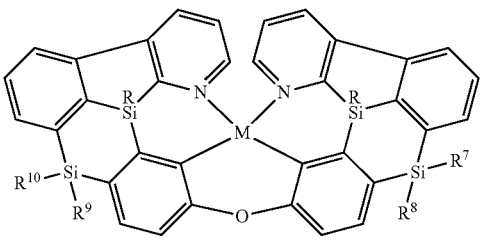
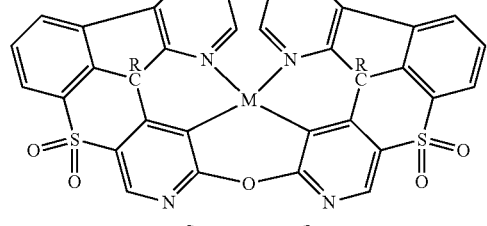
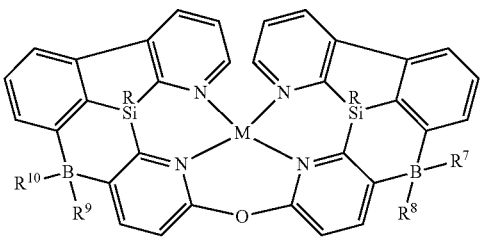
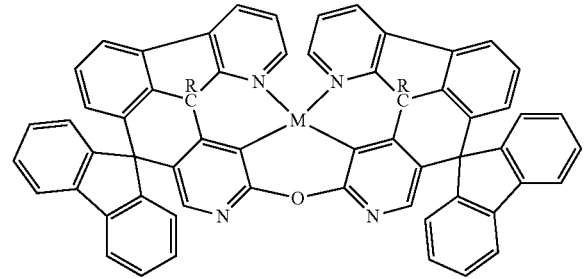
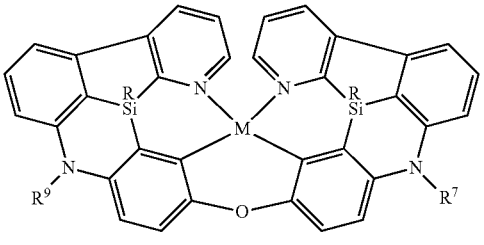

25
-continued
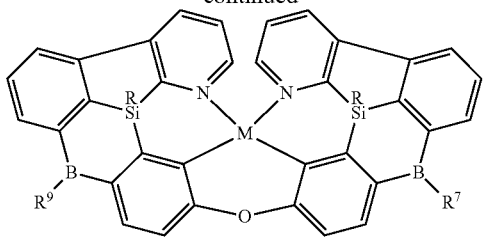
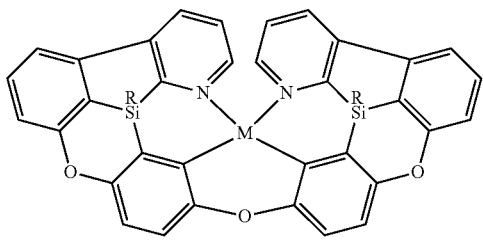
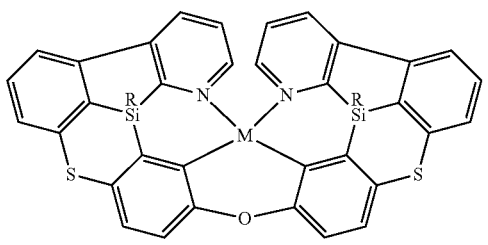
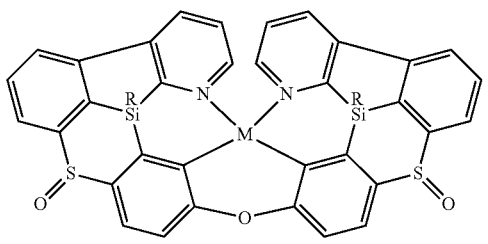
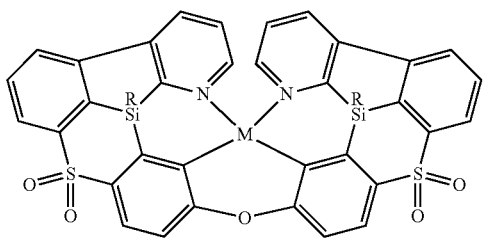
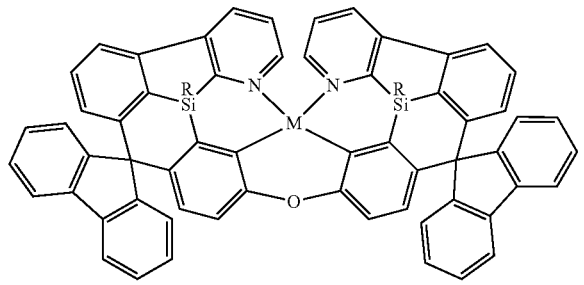
26
-continued
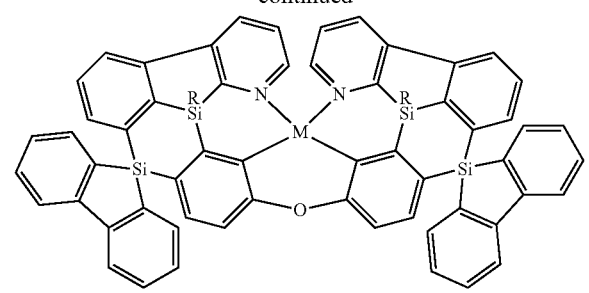
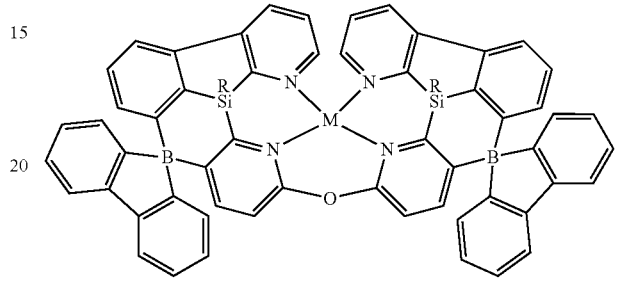
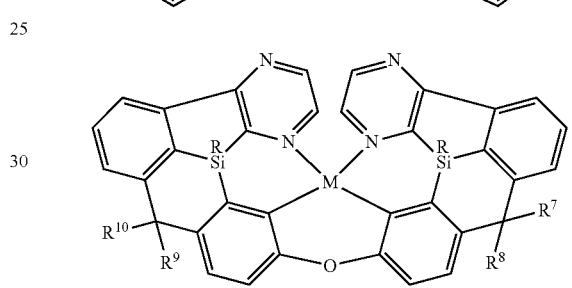
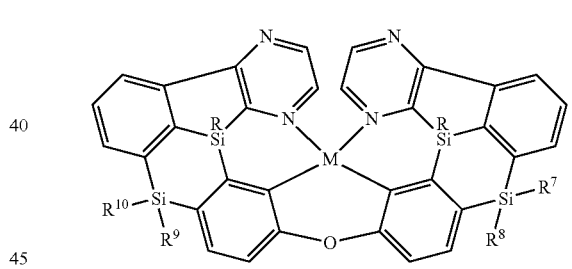
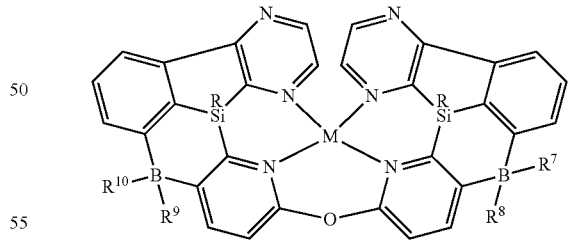
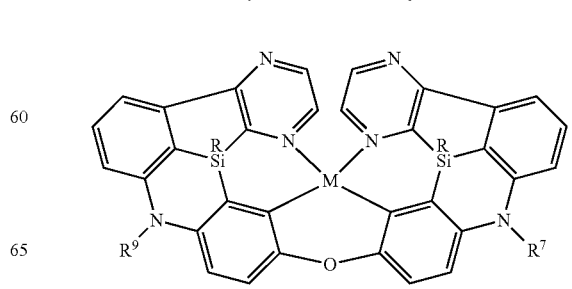

27
-continued
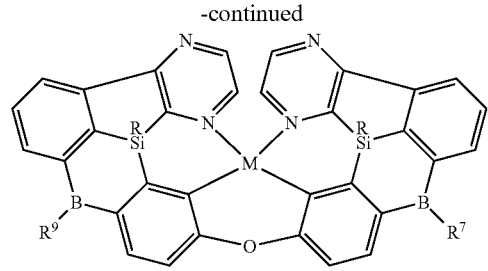
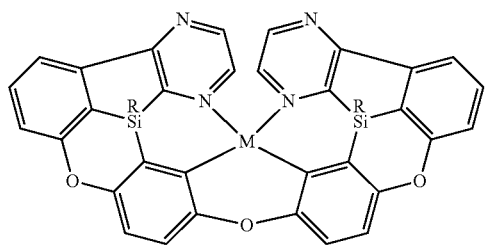
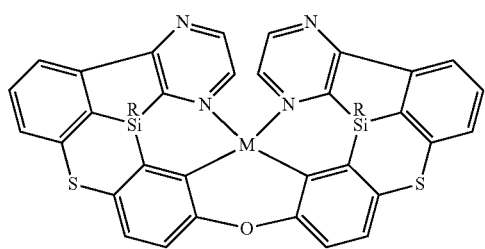
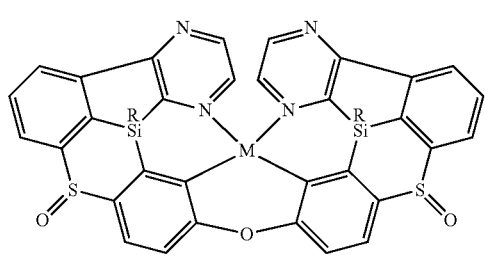
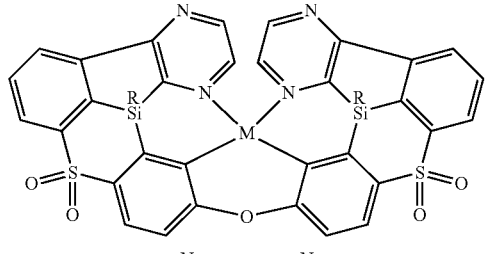
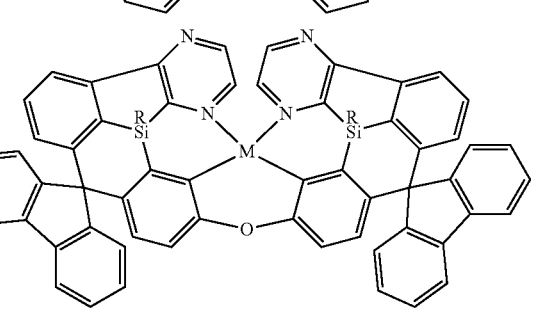
28
-continued
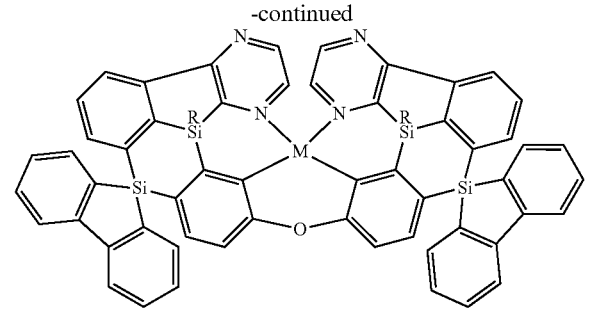
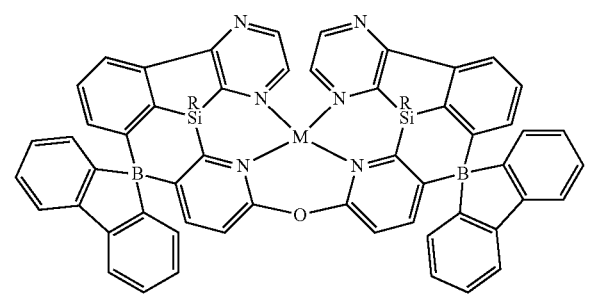
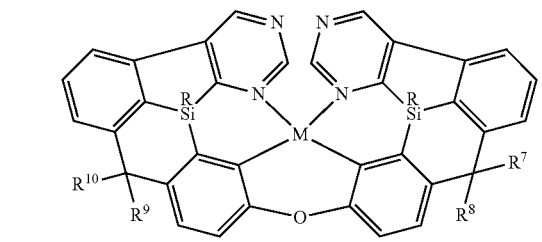
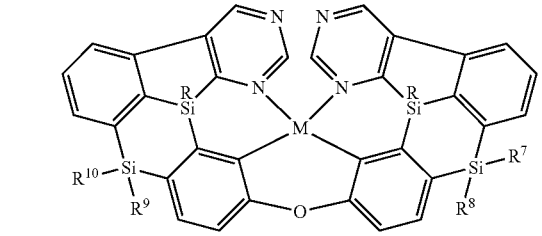
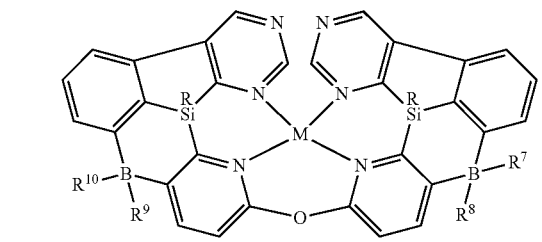
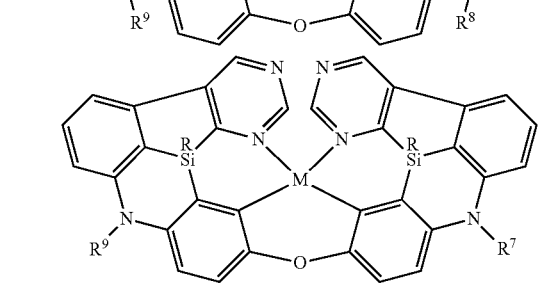
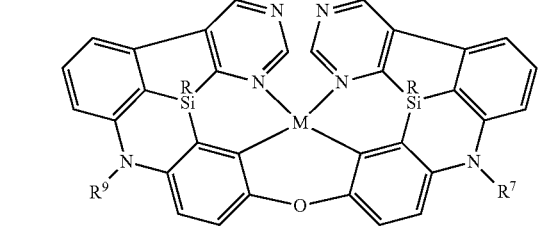

-continued
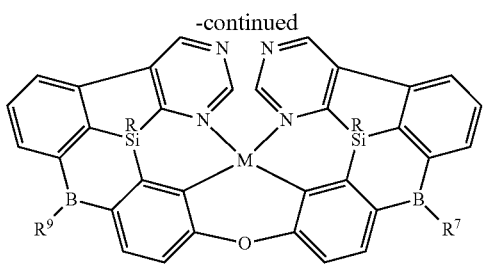
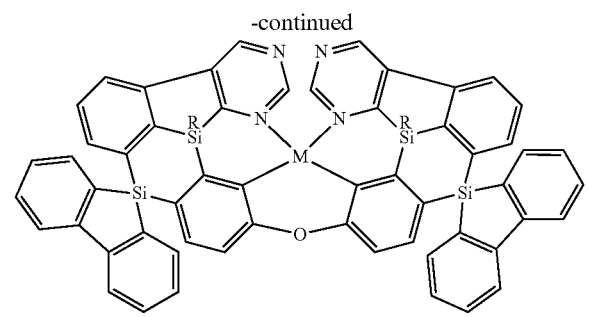
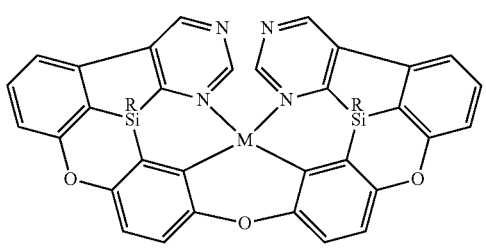
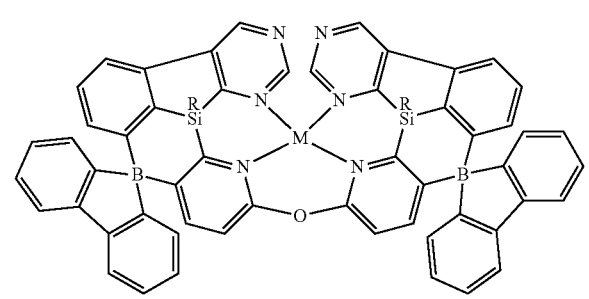
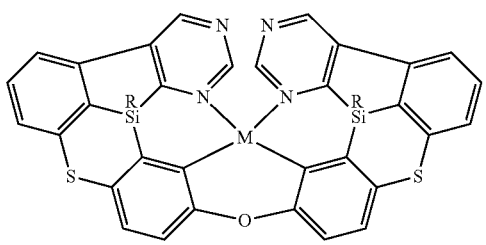
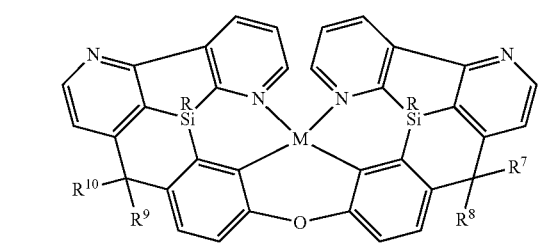
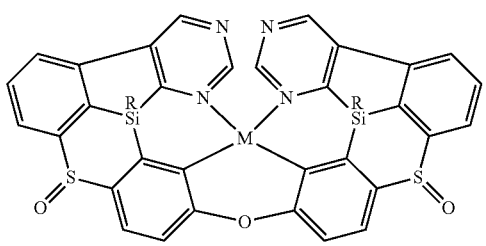
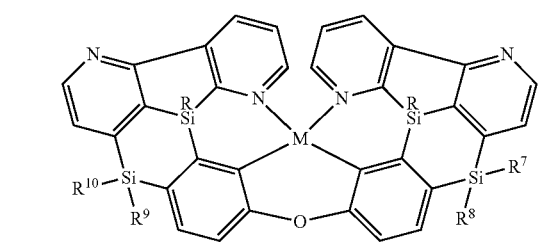
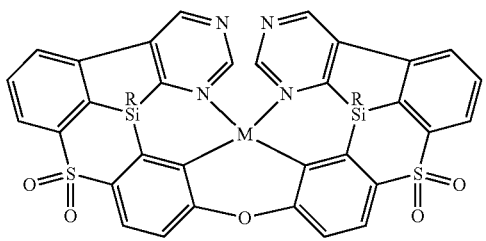
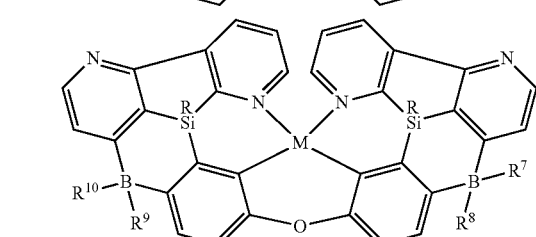
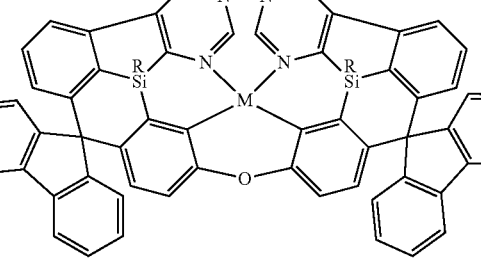
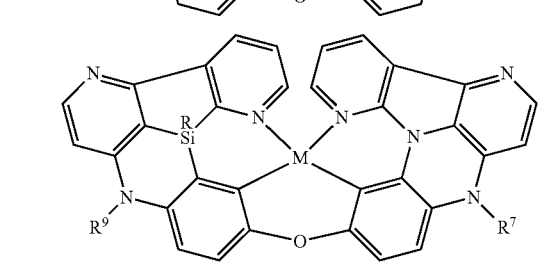

31
-continued
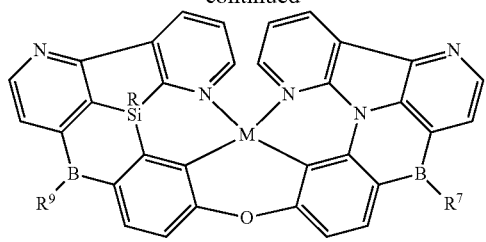
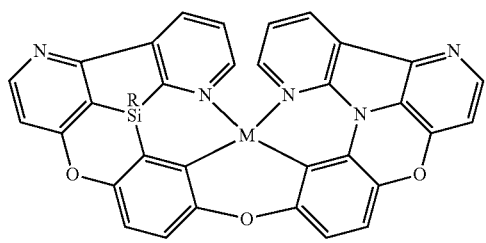
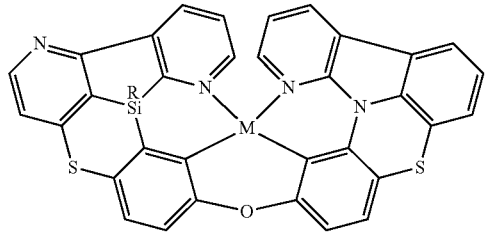
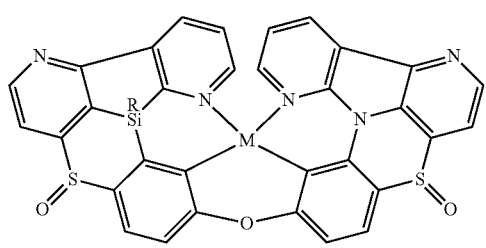
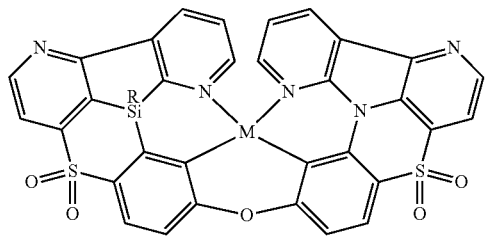
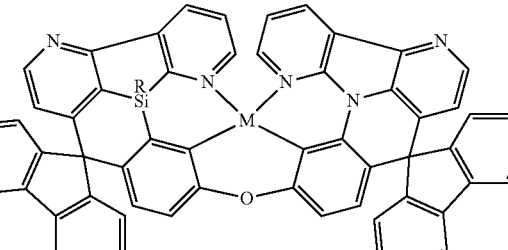
32
-continued
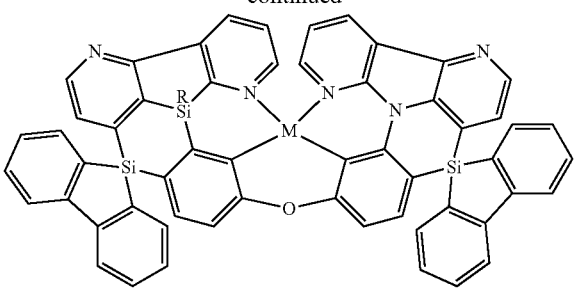
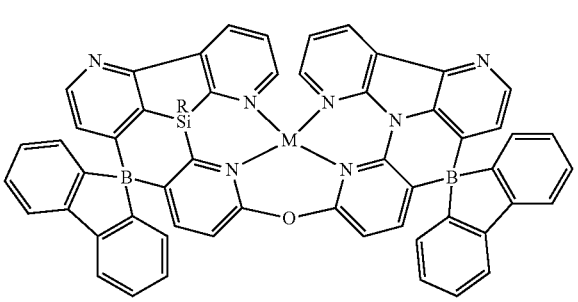
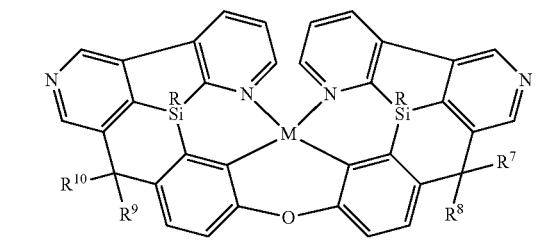
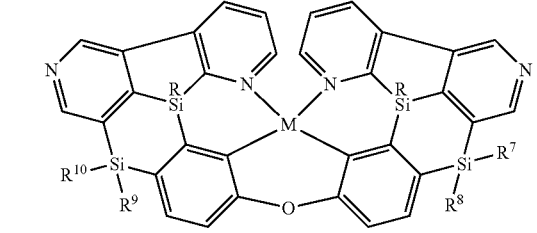
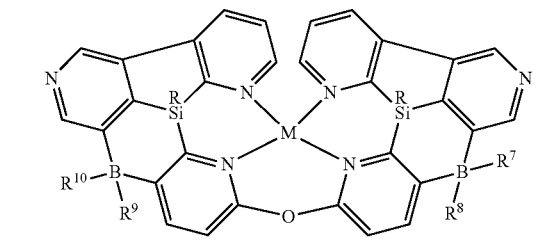
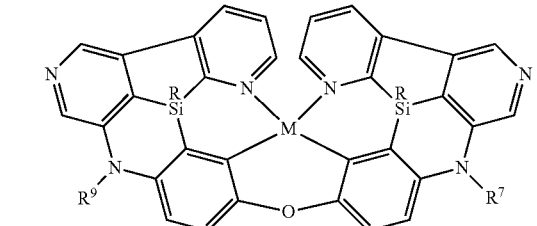

33
-continued
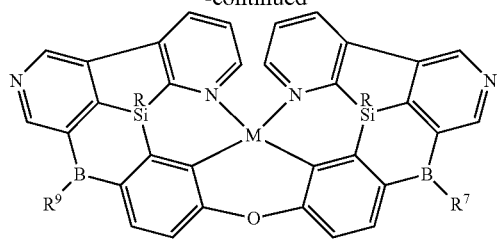
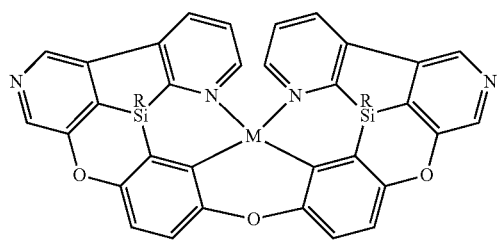
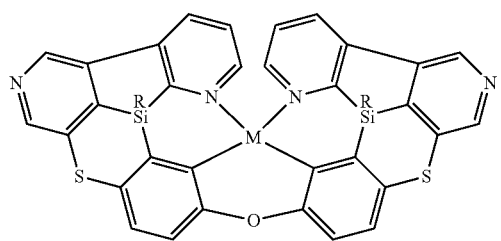
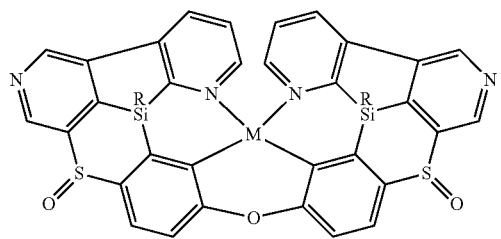
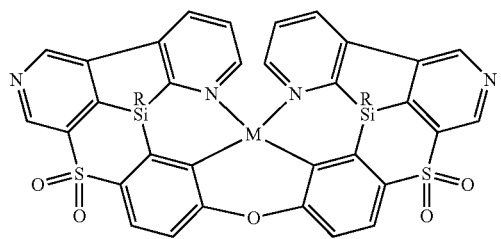
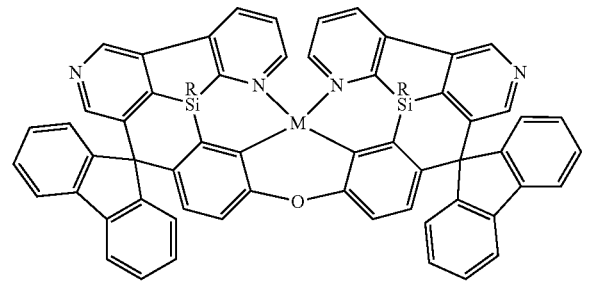
34
-continued
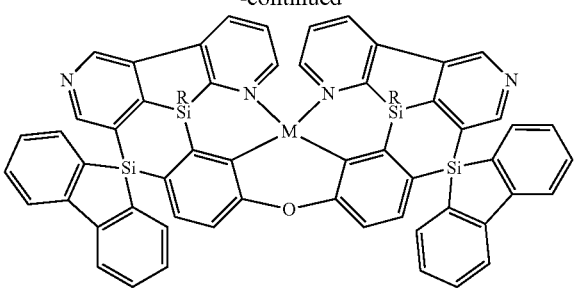
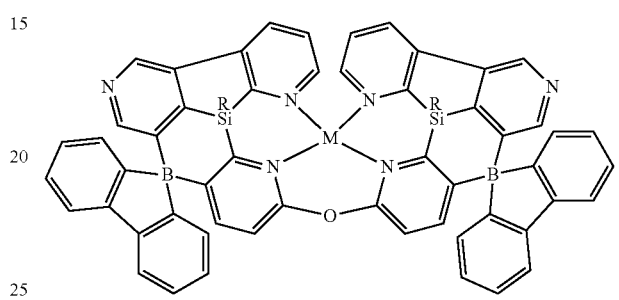
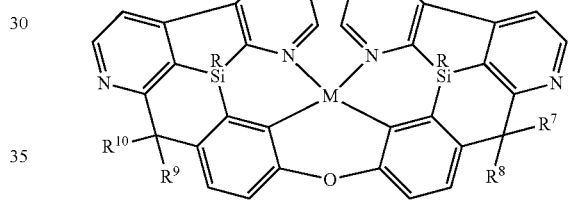
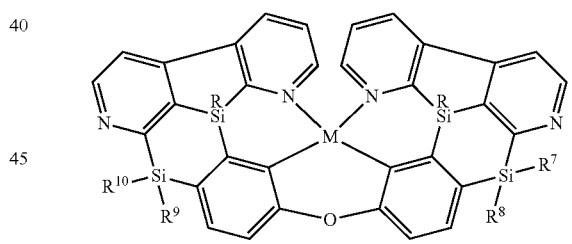
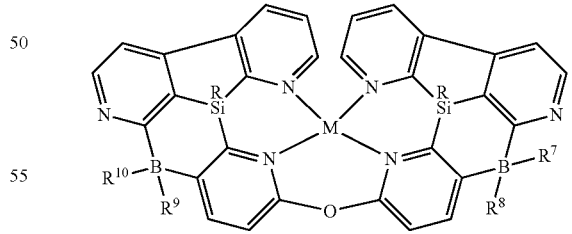
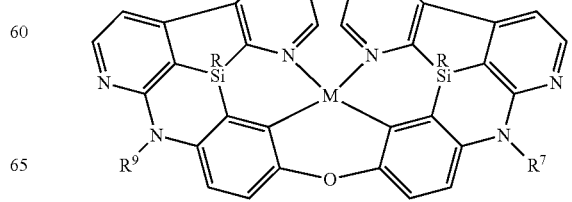

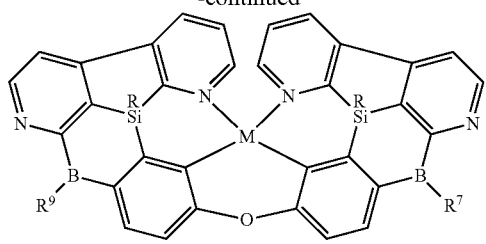
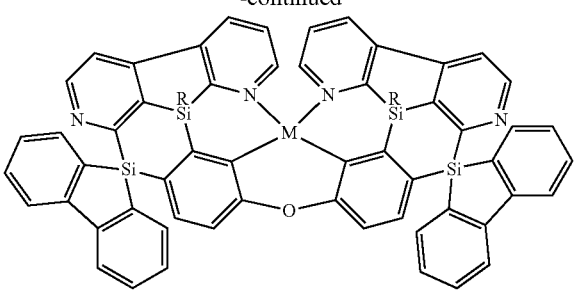
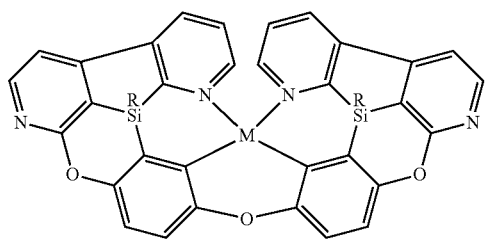
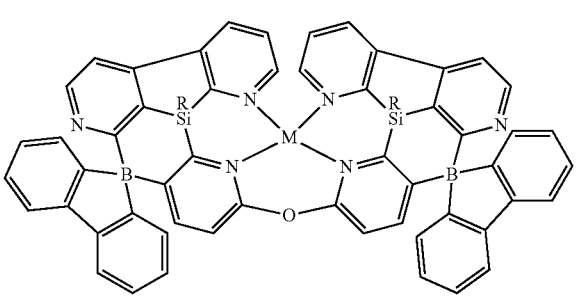
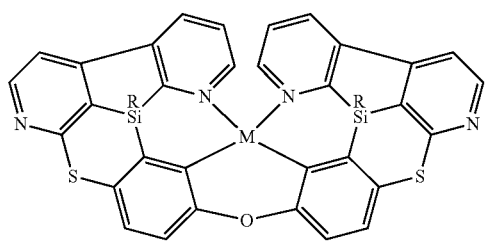
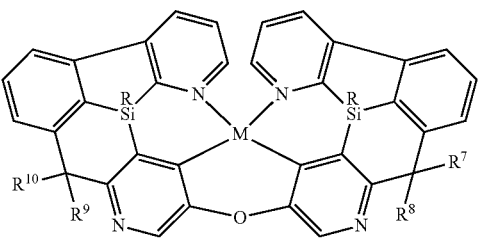
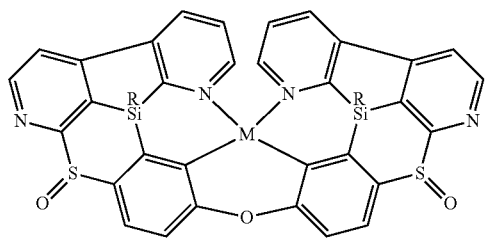
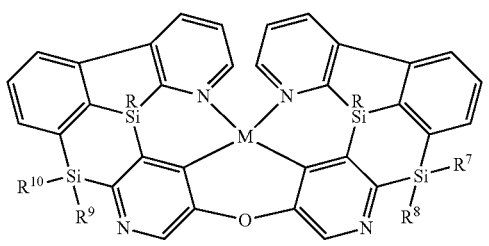
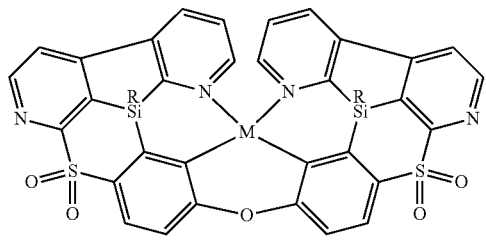
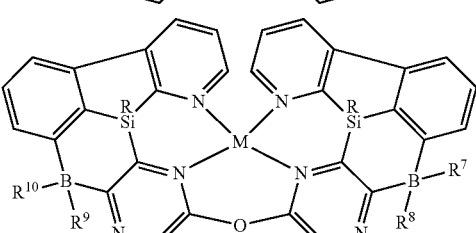
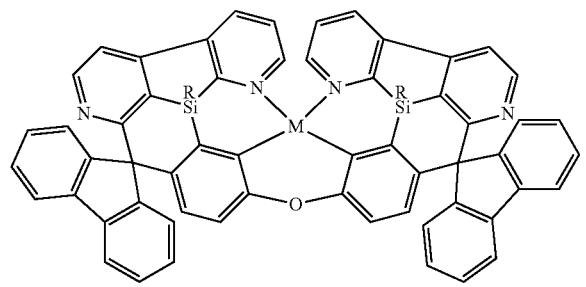
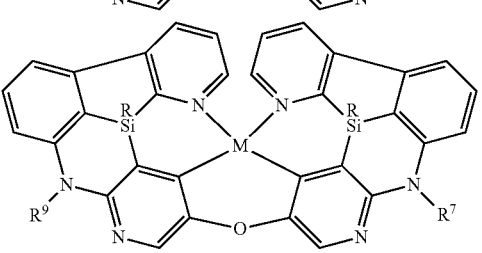

37
-continued
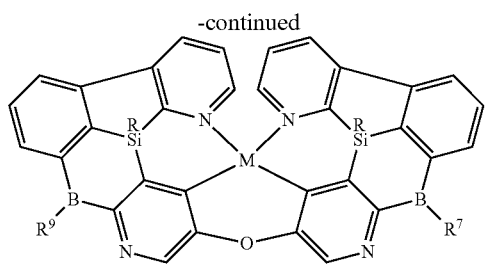
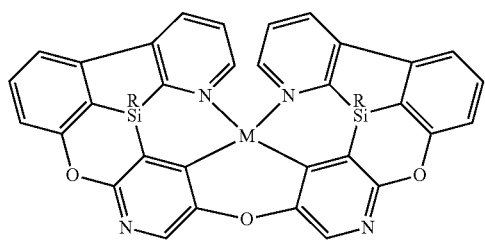
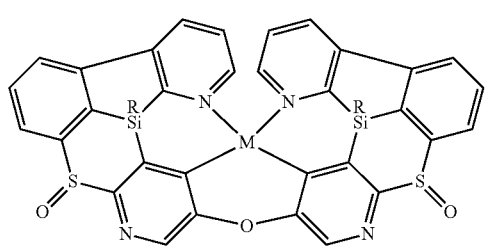
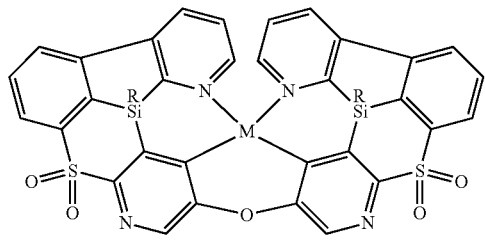
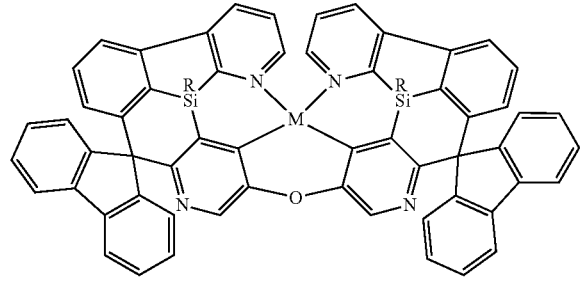
38
-continued
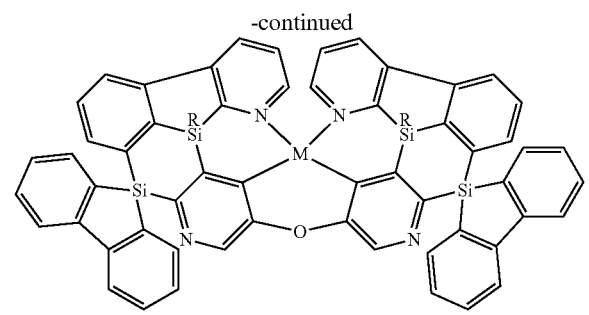
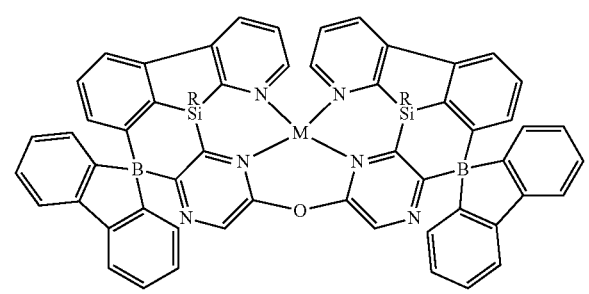
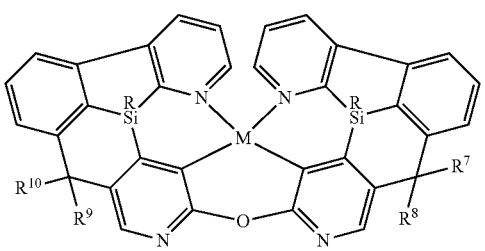
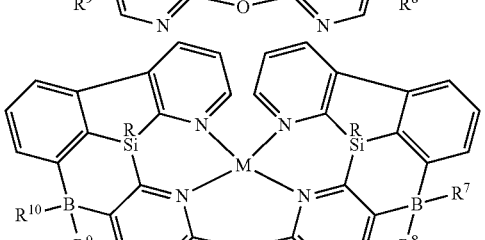
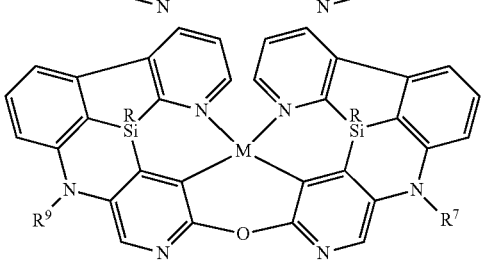

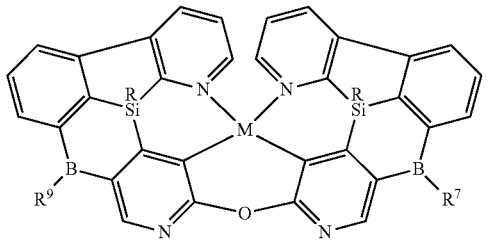
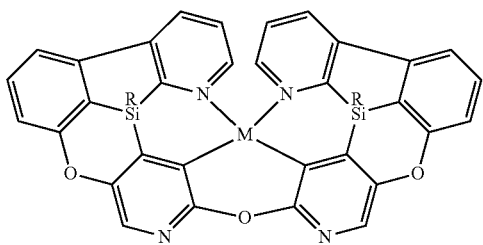
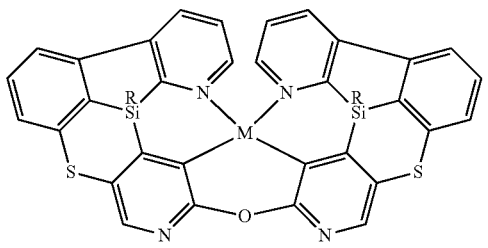
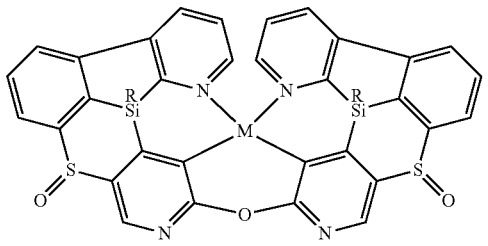
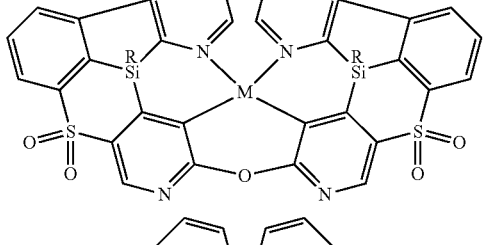
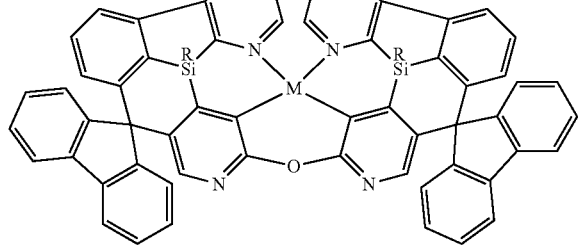
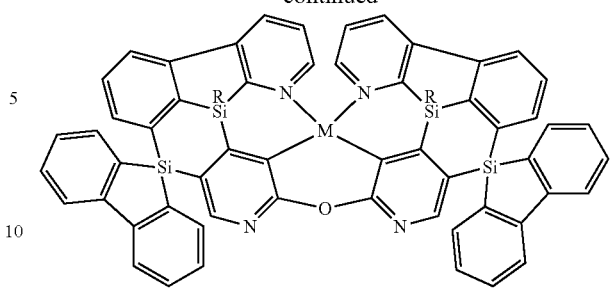
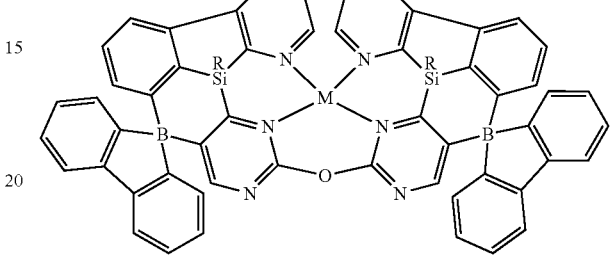
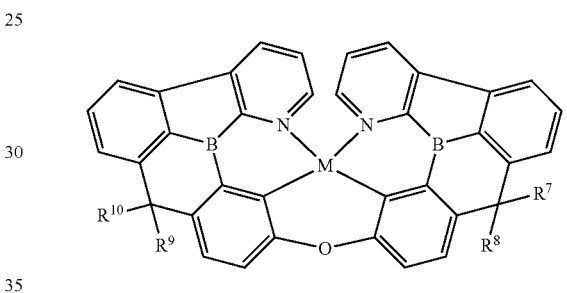
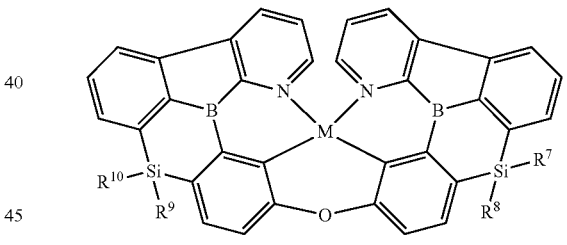
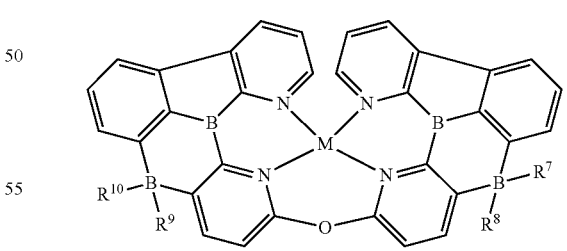
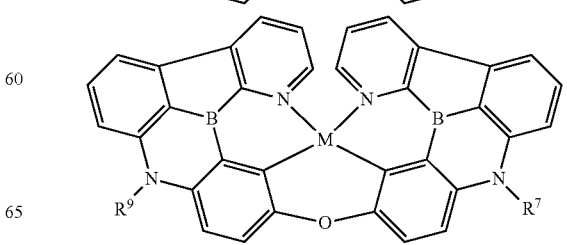

-continued
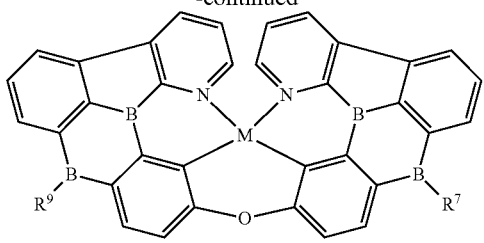
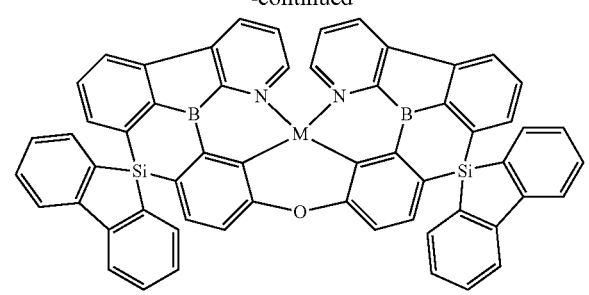
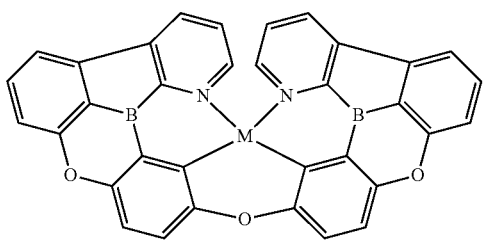
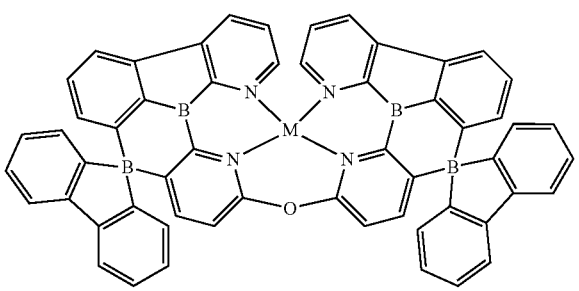
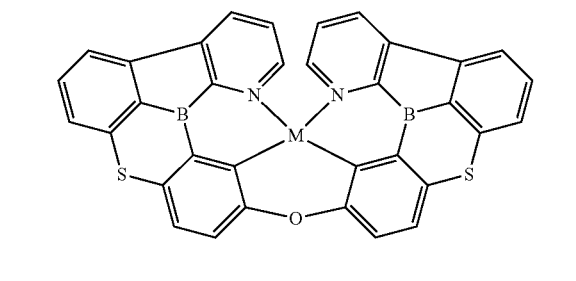
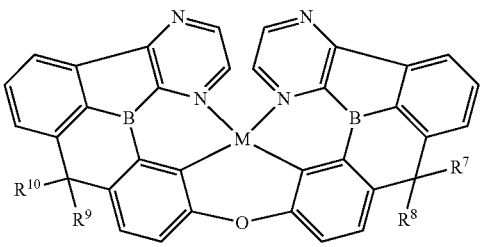
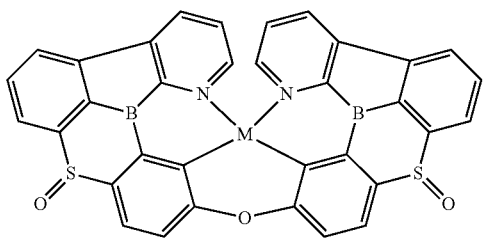
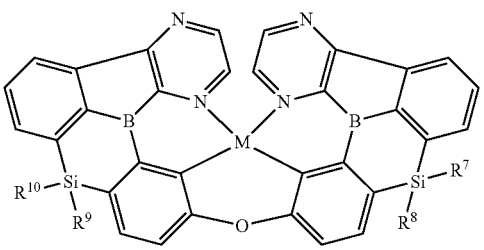
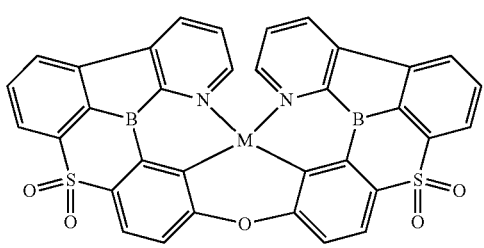
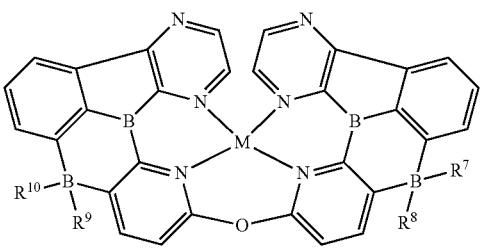
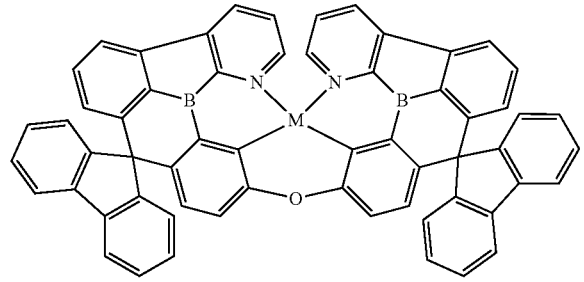
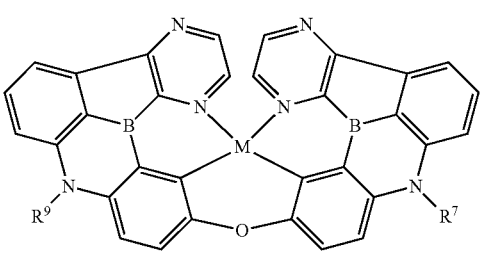

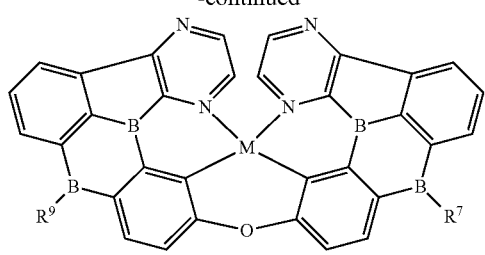
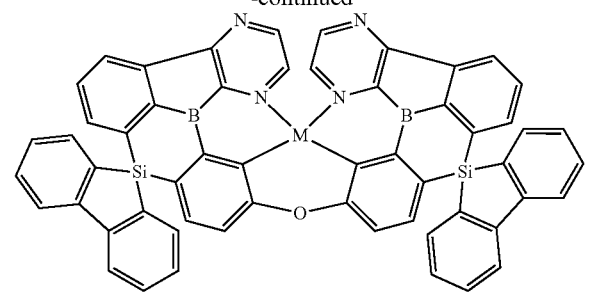
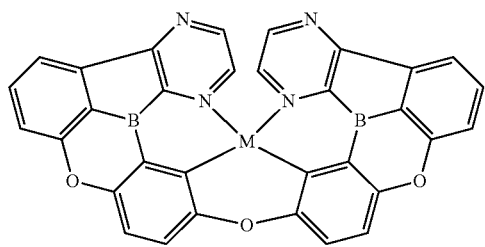
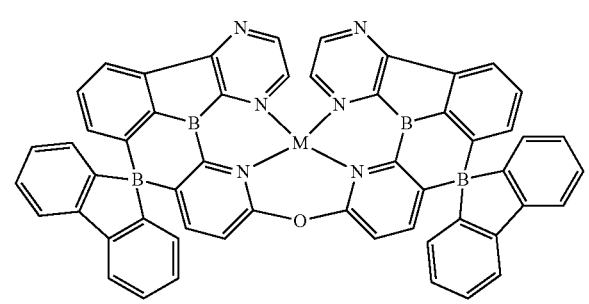
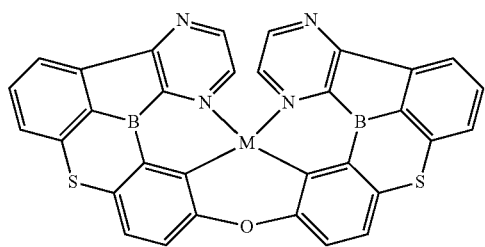
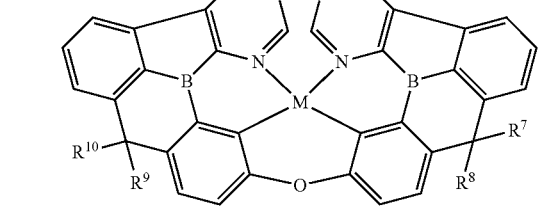
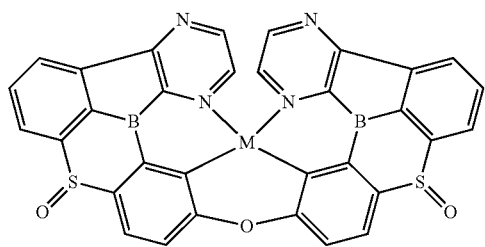
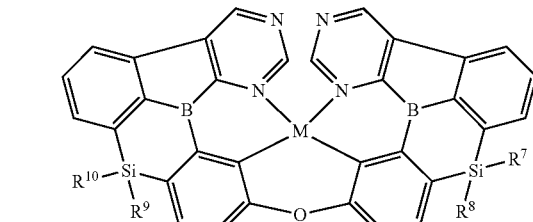
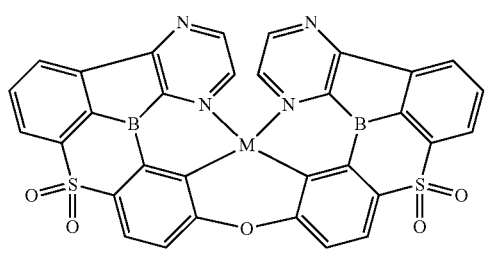
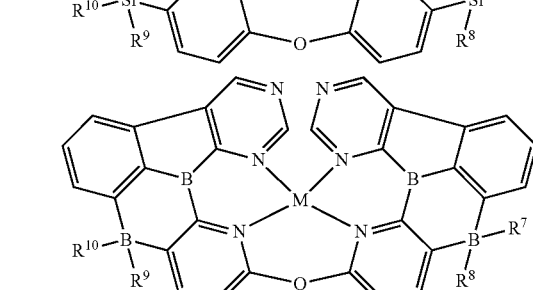
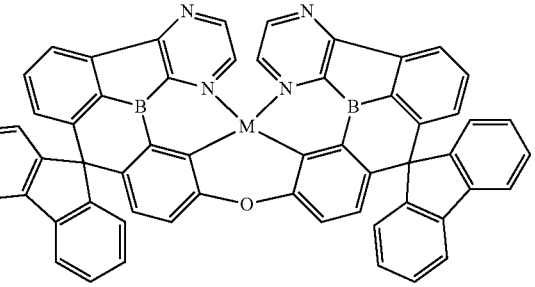
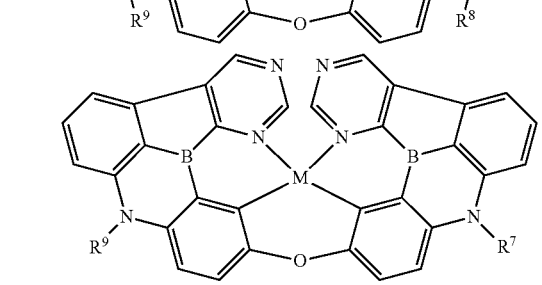

-continued
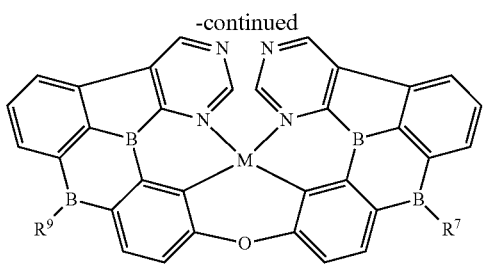
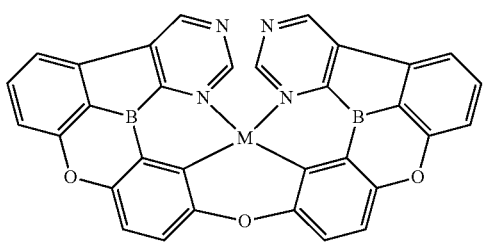
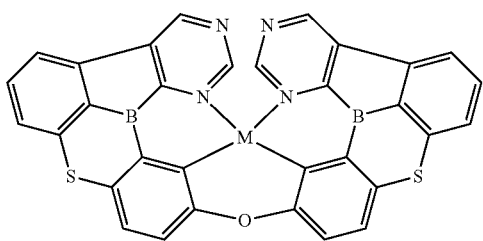
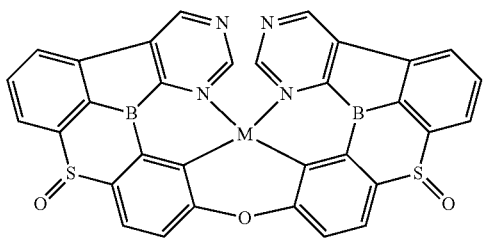
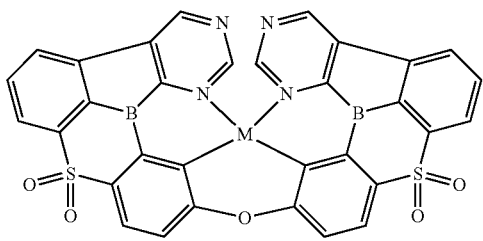
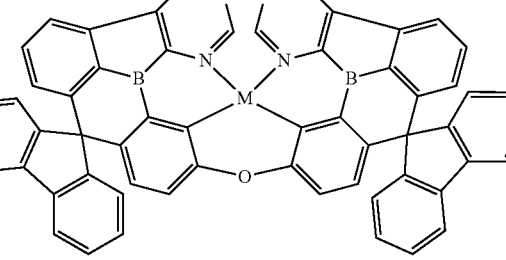
-continued
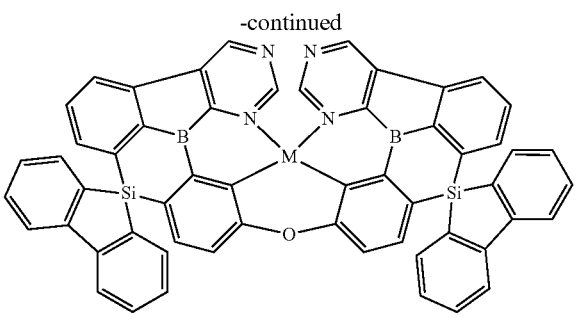
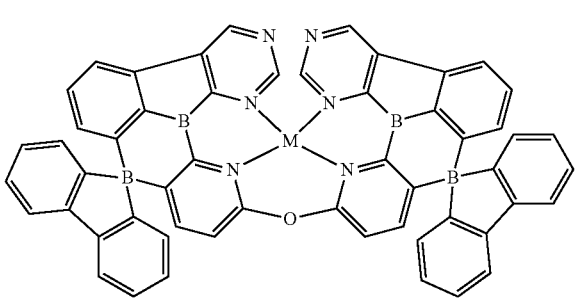
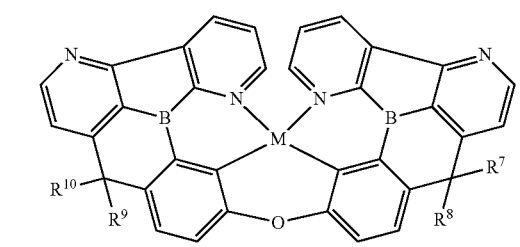
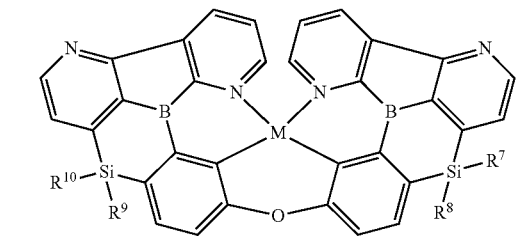
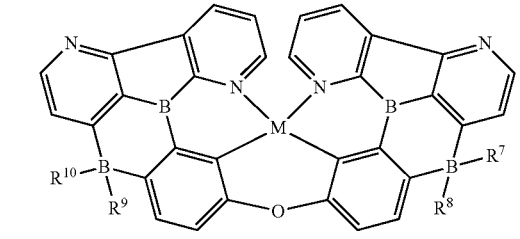
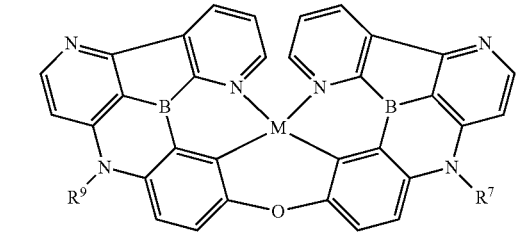

-continued
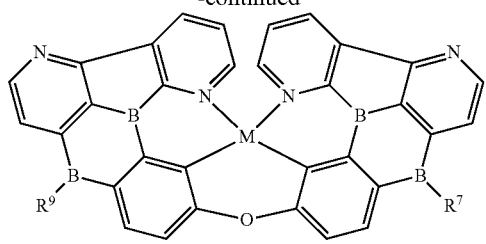
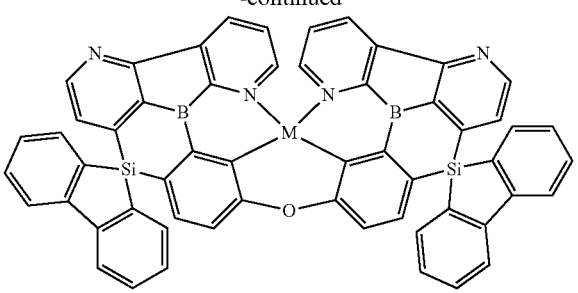
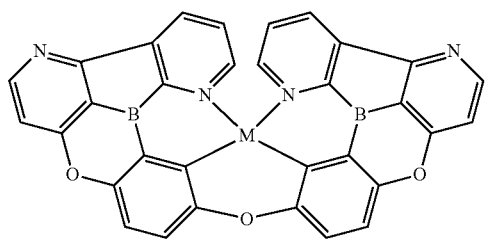
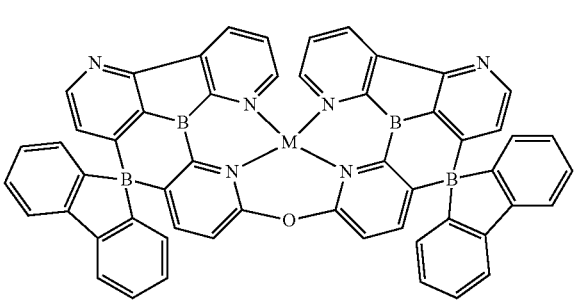

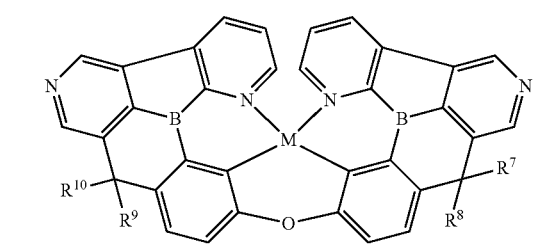
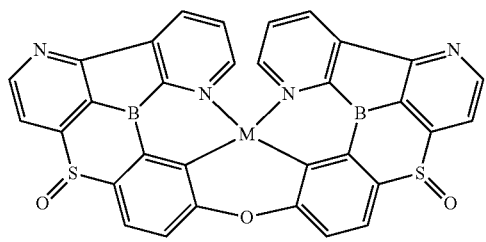
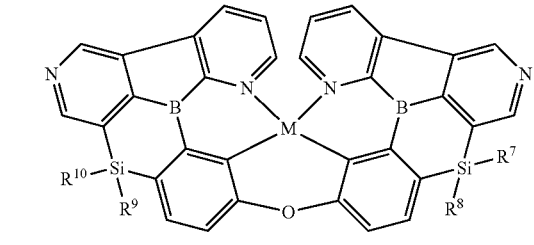
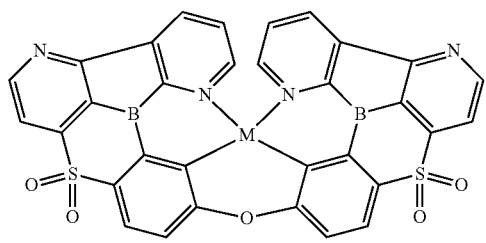
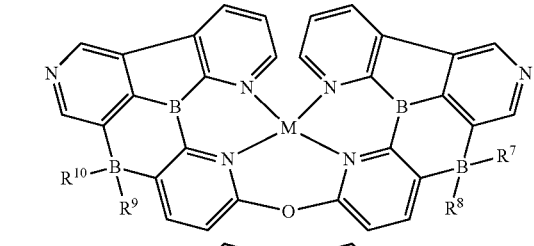
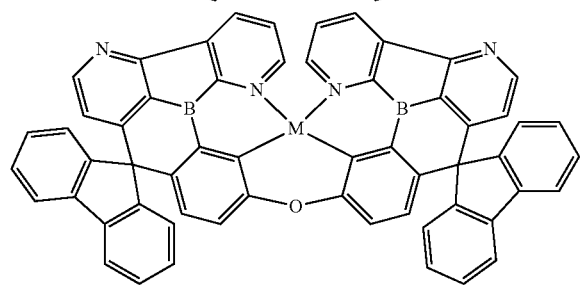
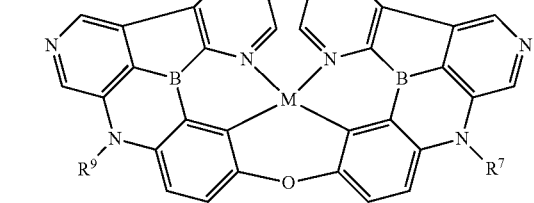

-continued
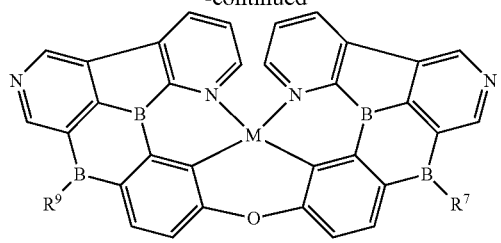
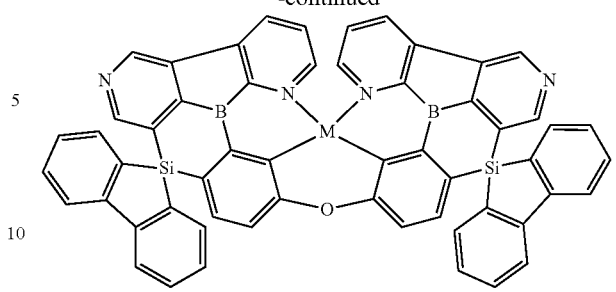
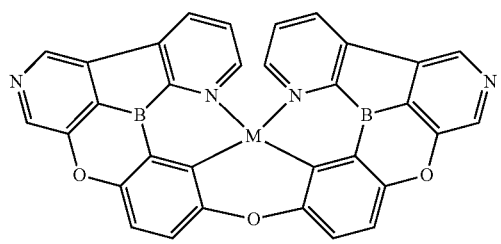
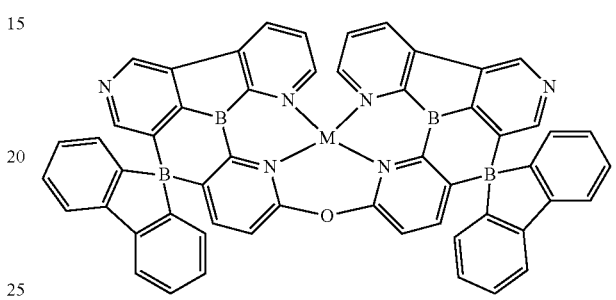
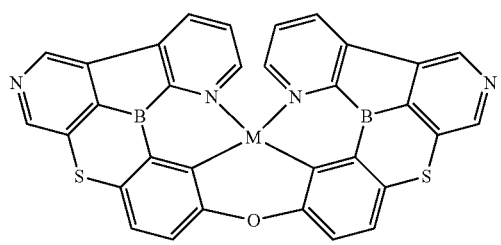
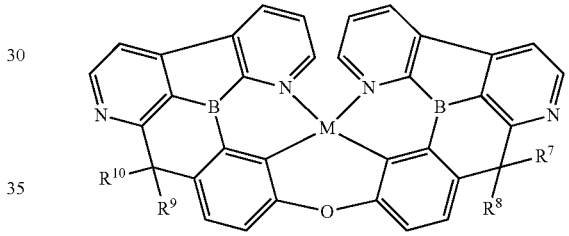
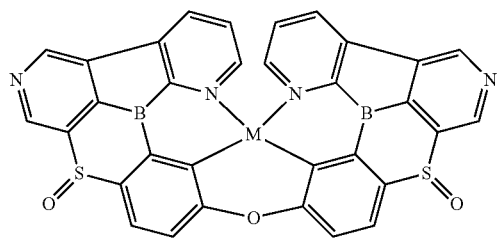
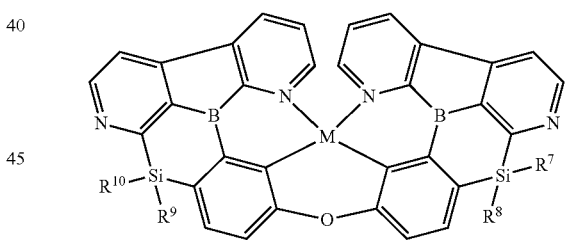
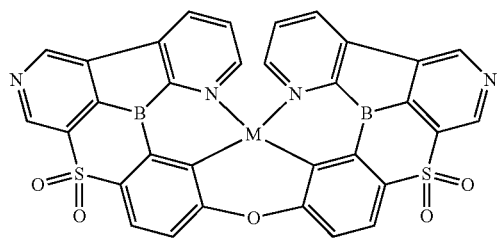
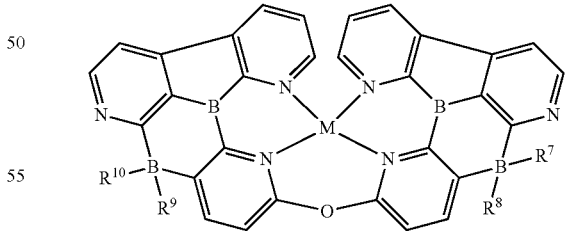
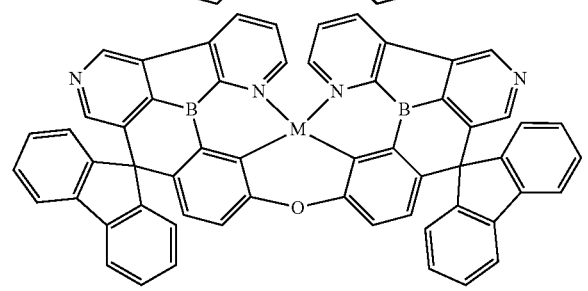
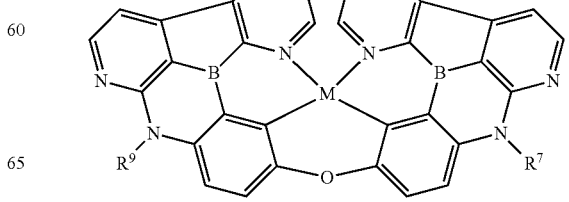

51
-continued
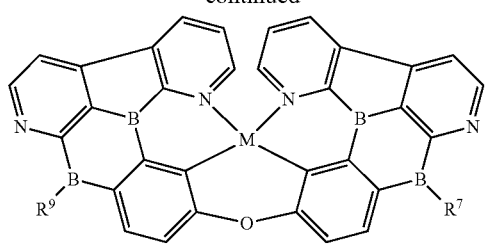
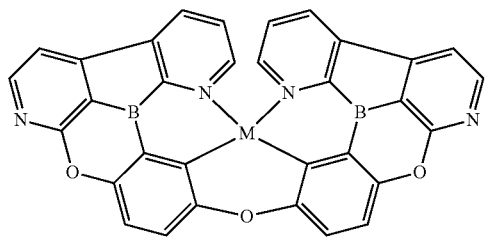
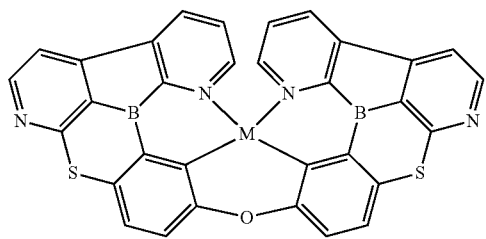
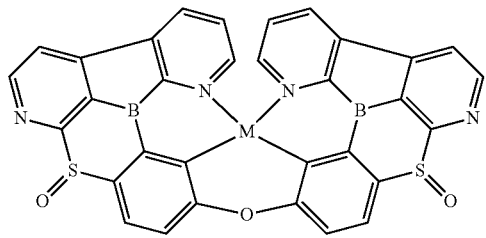
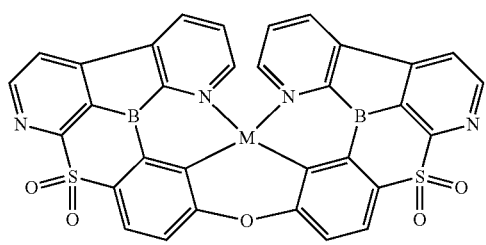
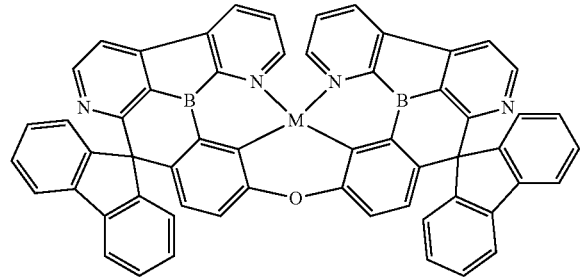
52
-continued
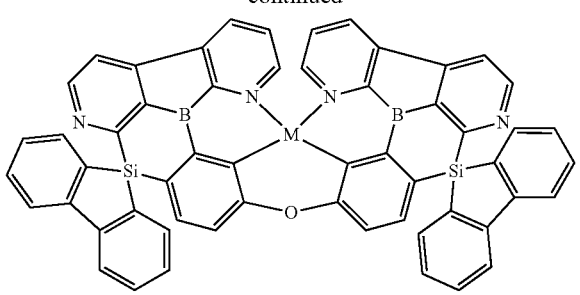
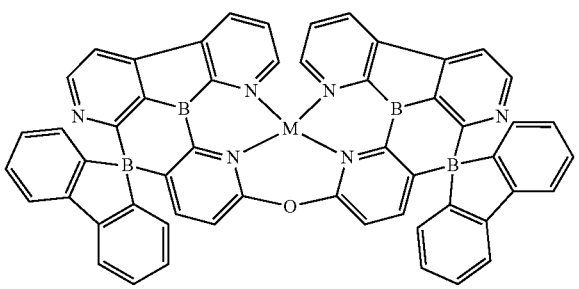
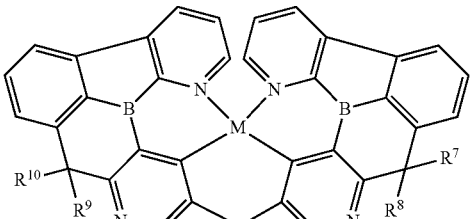
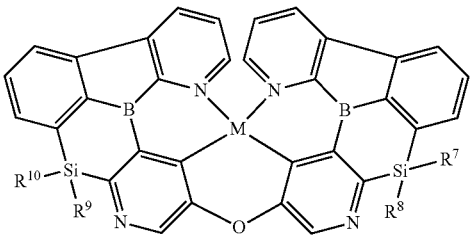
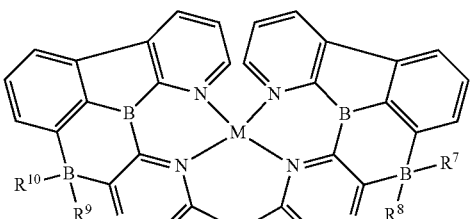
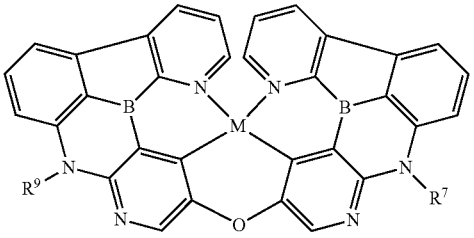

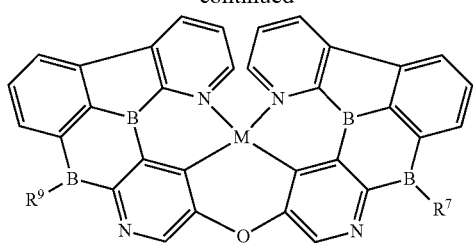
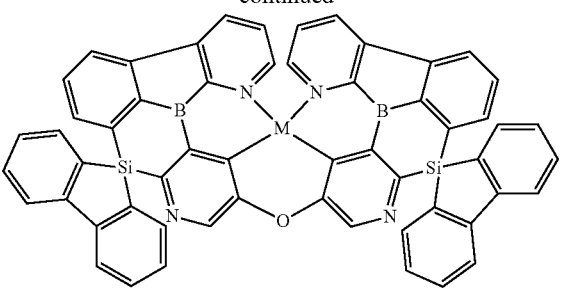
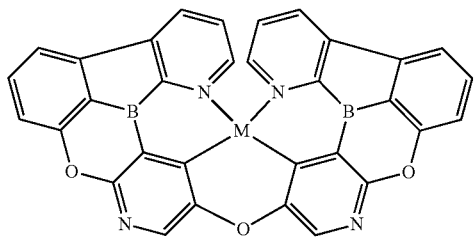
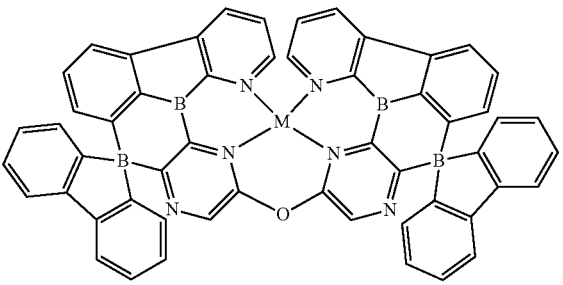
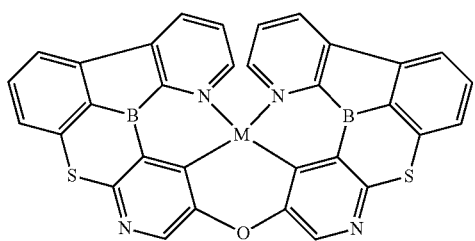
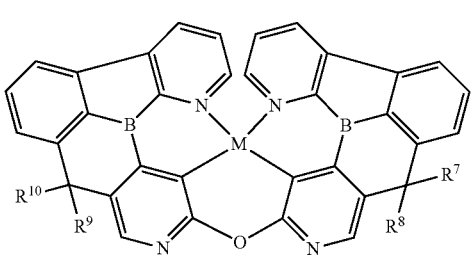
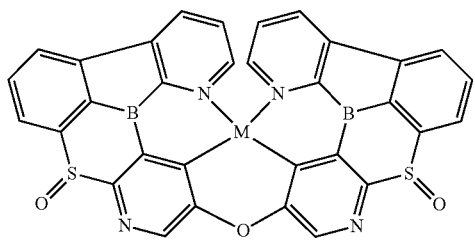
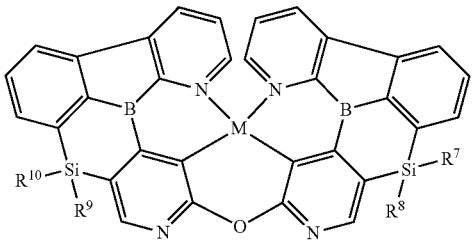
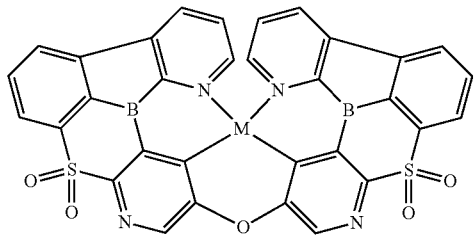
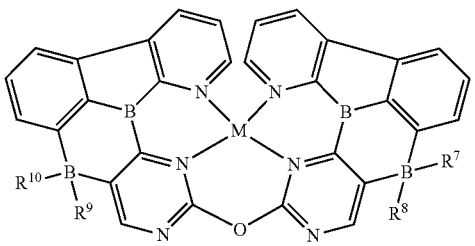
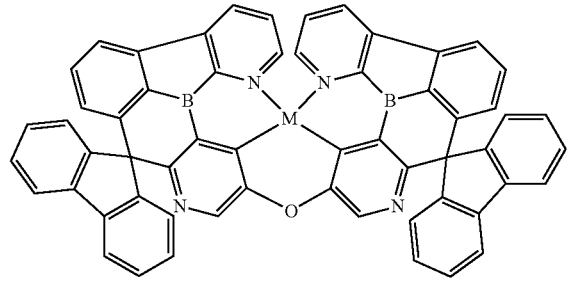
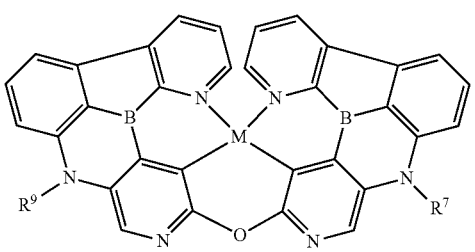

-continued
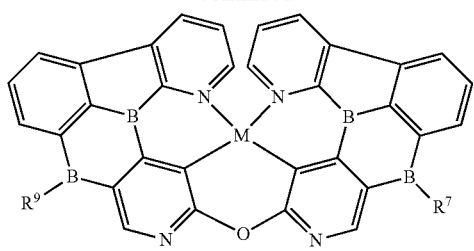
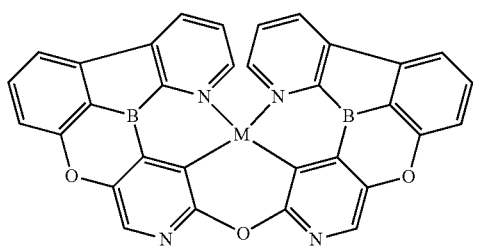
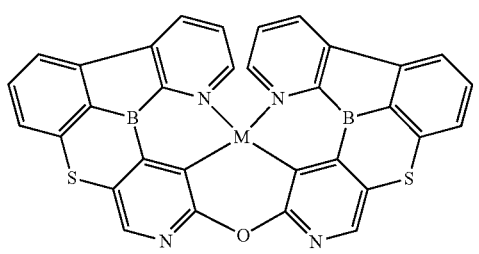
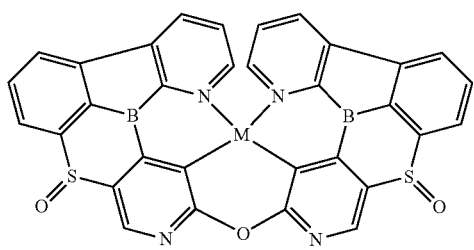
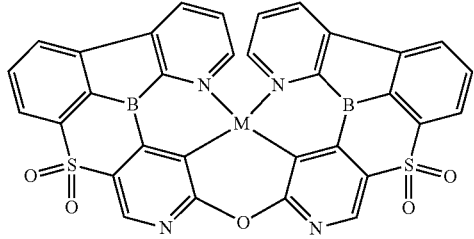
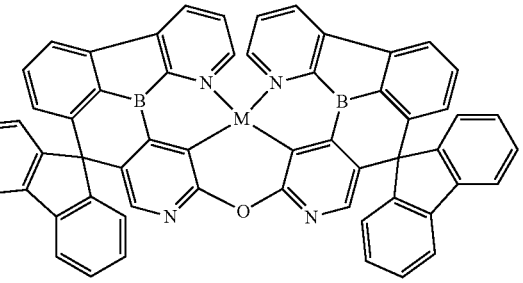
-continued
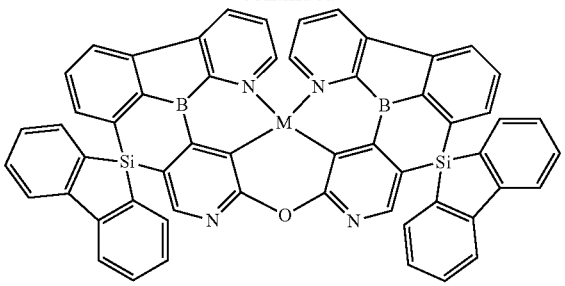
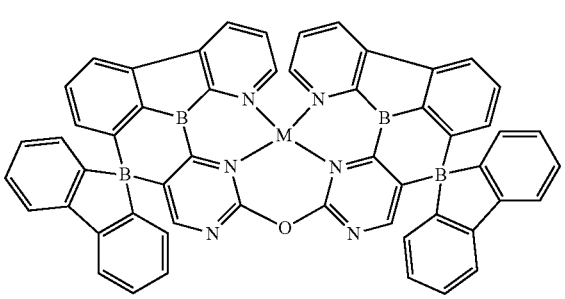
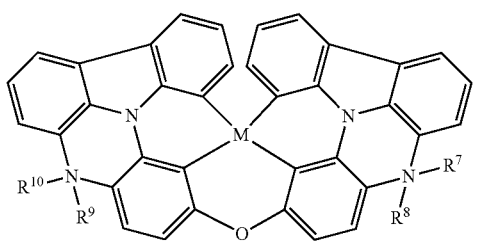
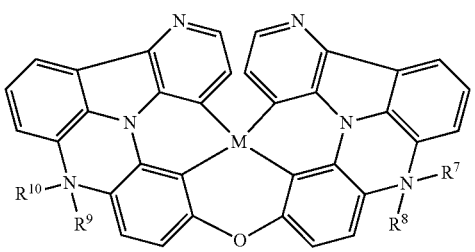

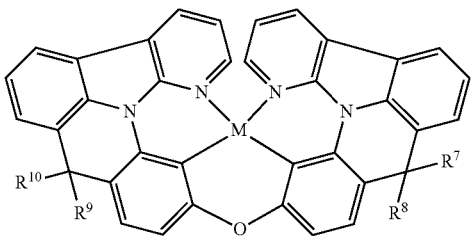

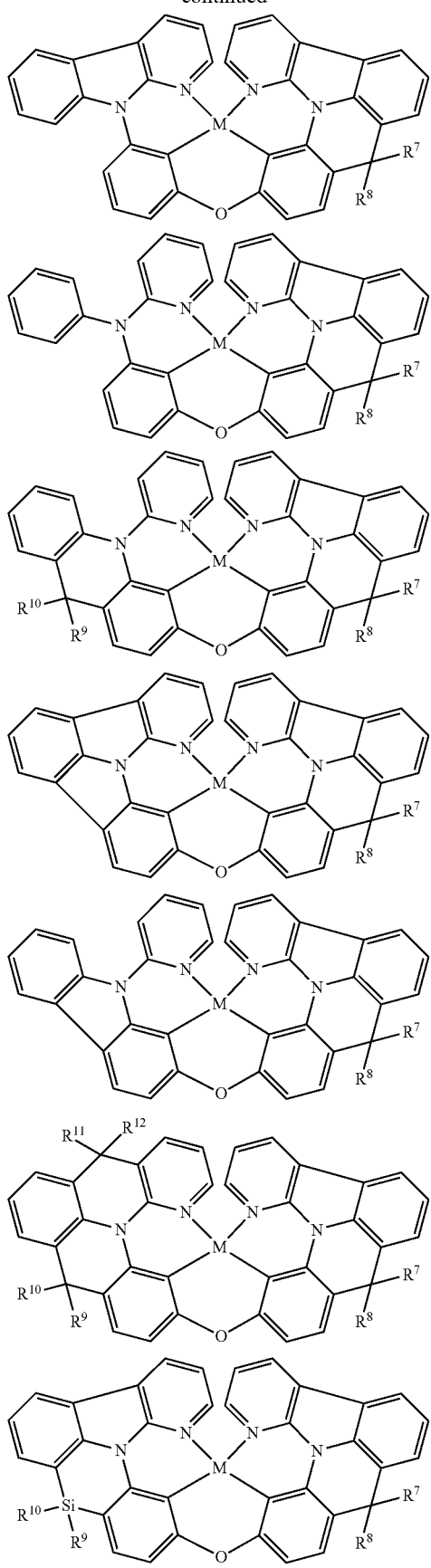
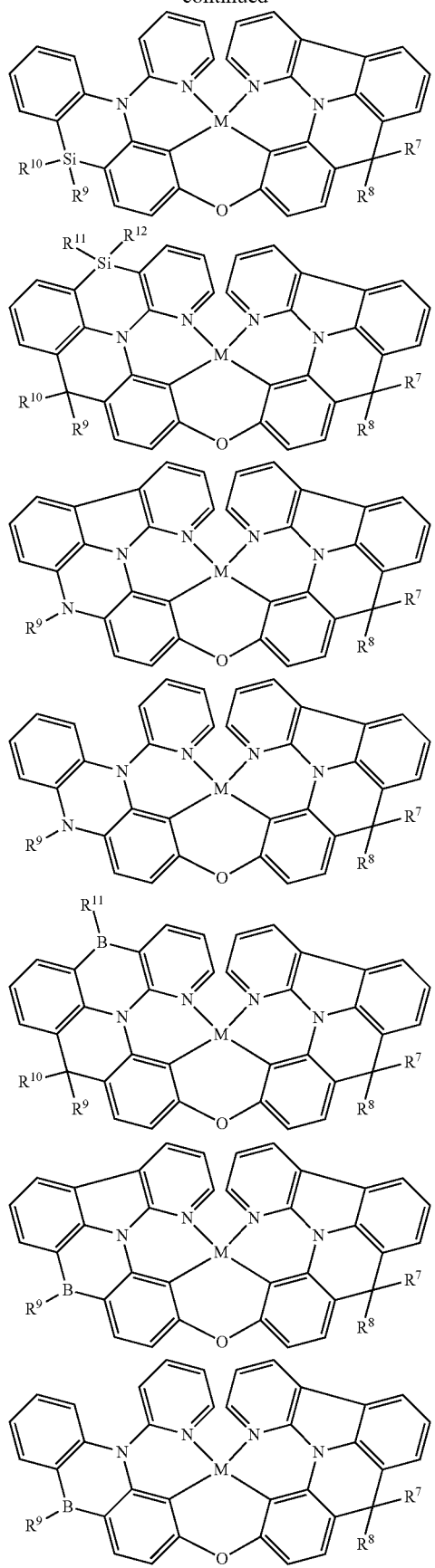

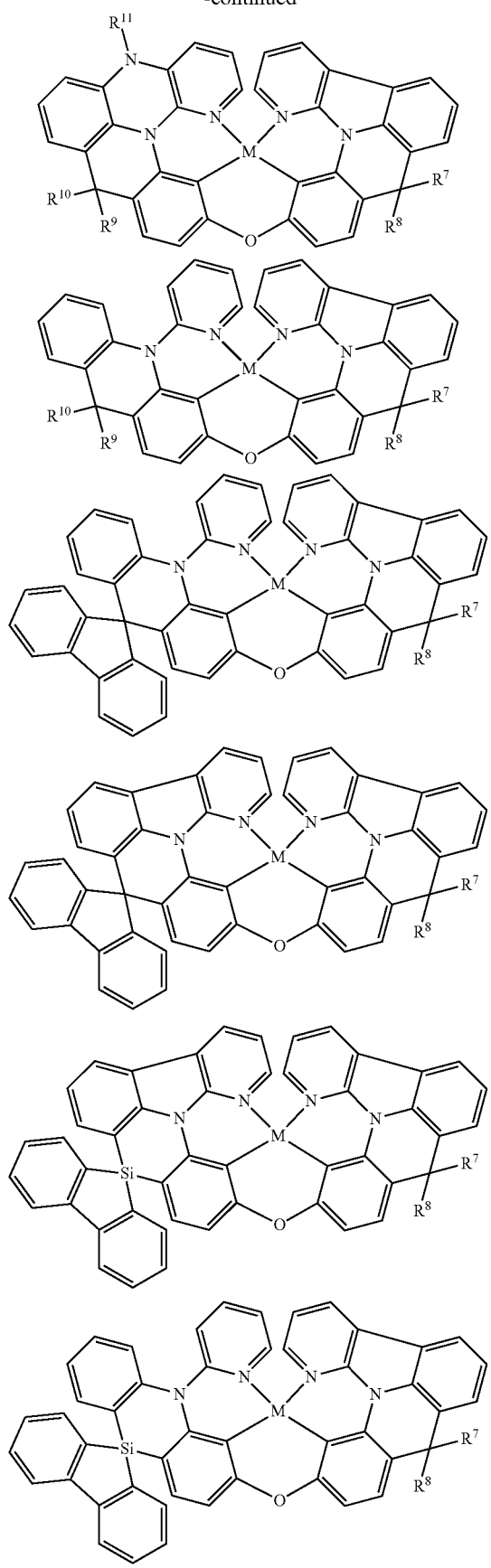
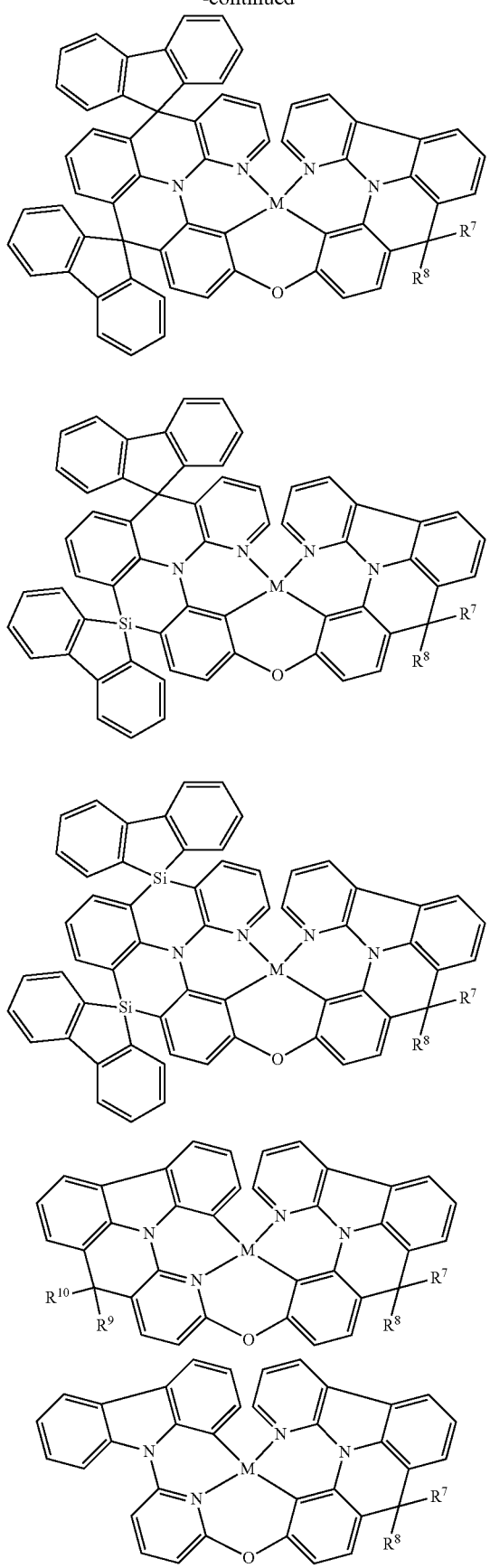

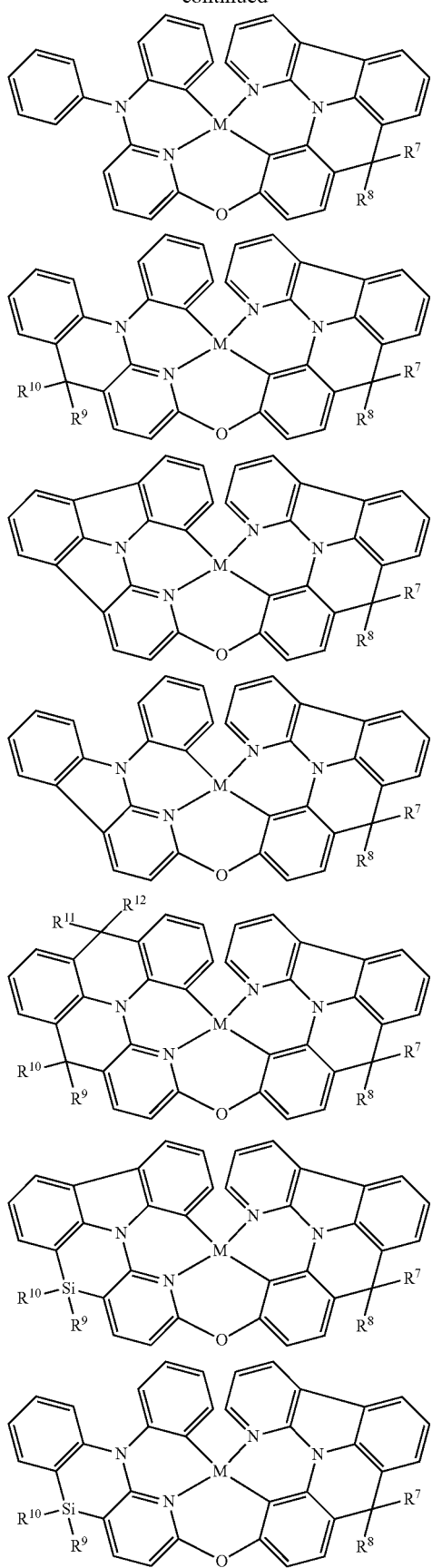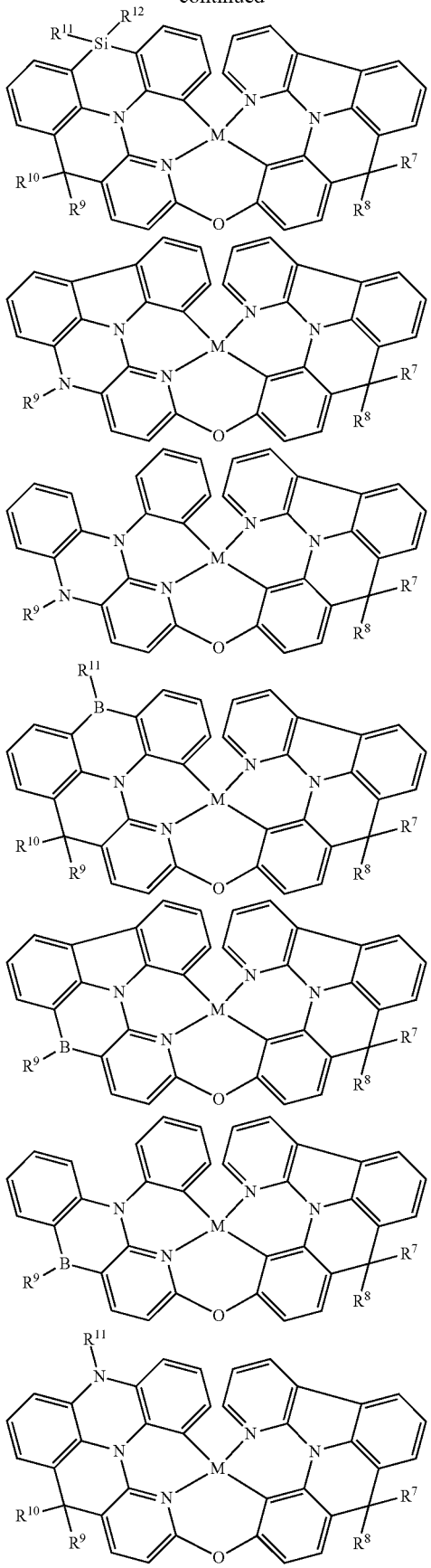

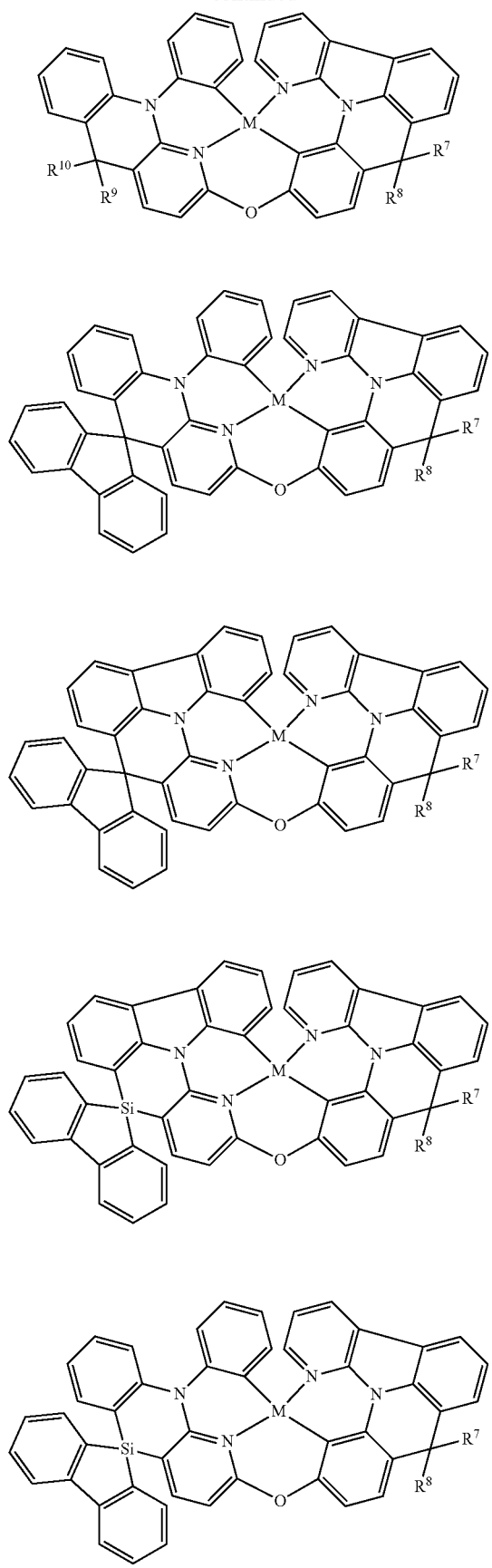
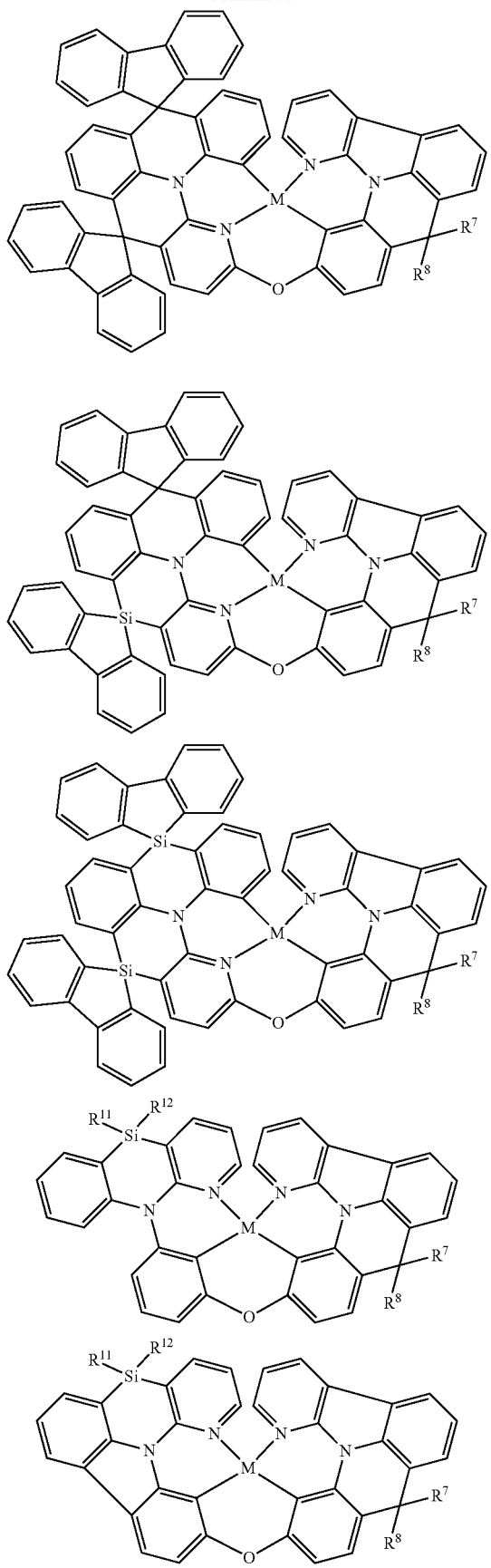

-continued
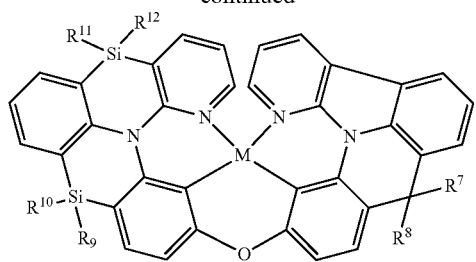
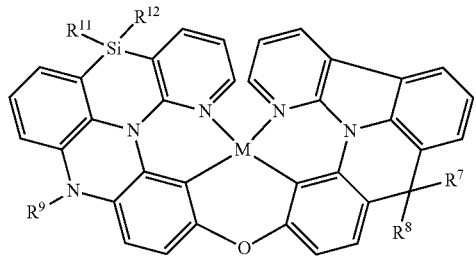
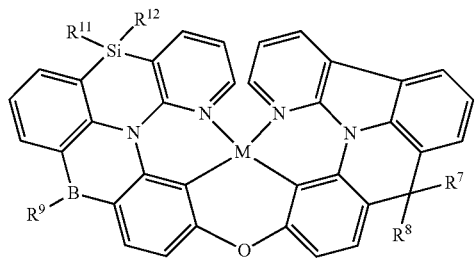
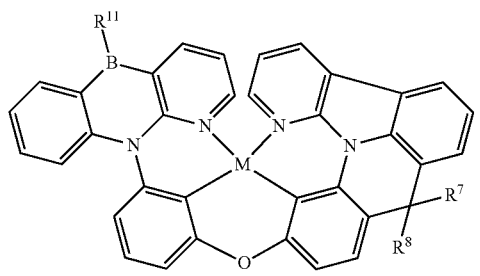
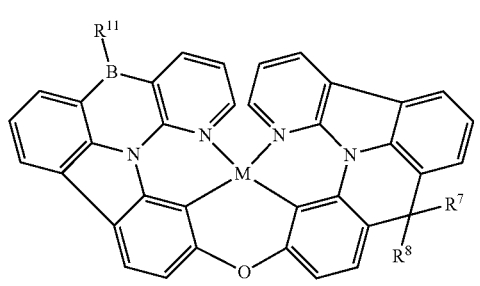
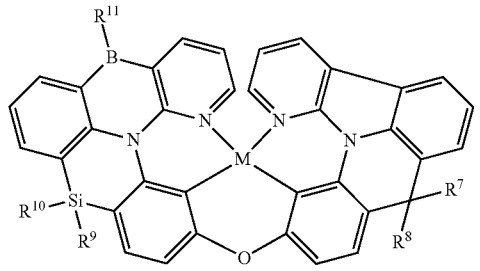
-continued
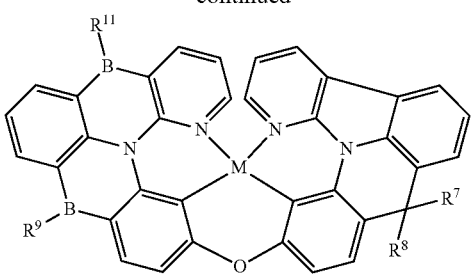
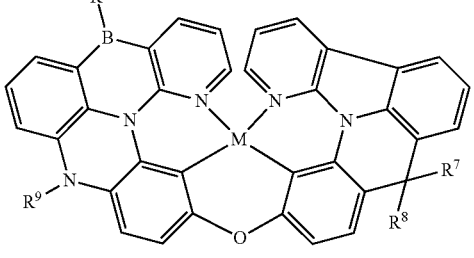
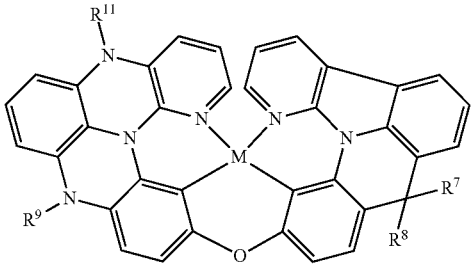
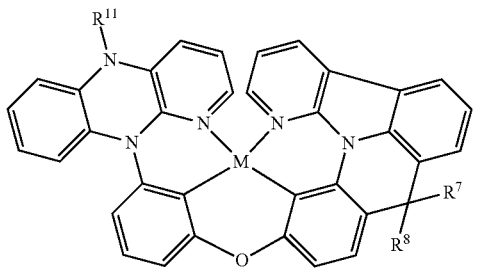
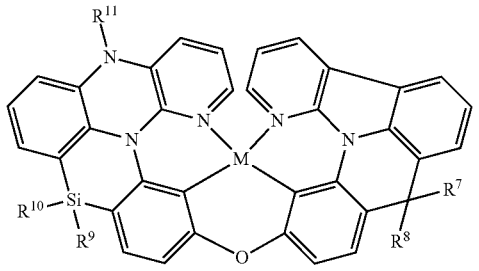

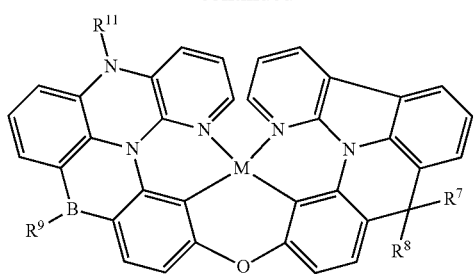
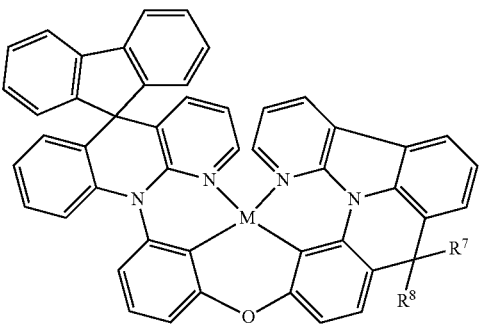
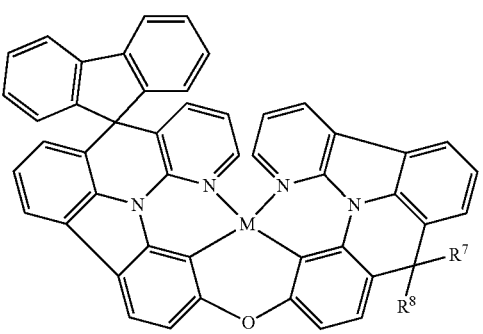
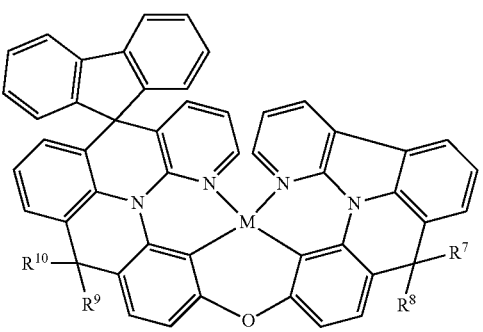
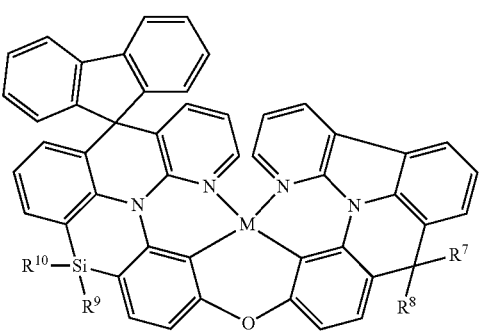
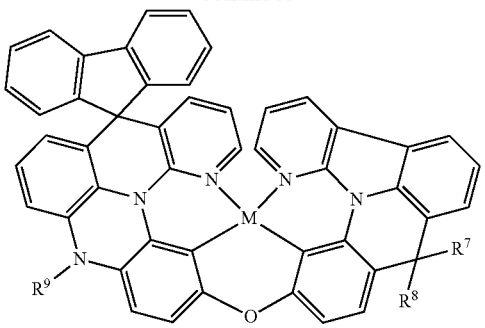
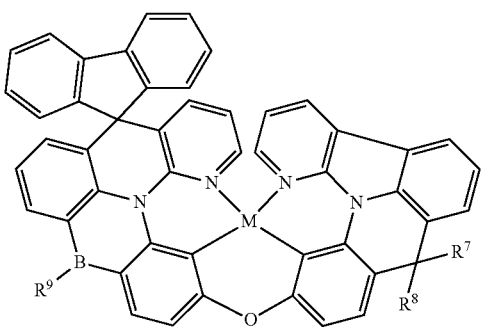
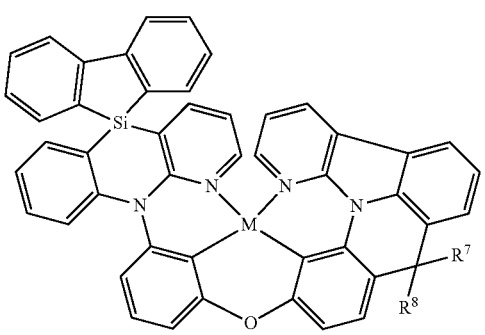
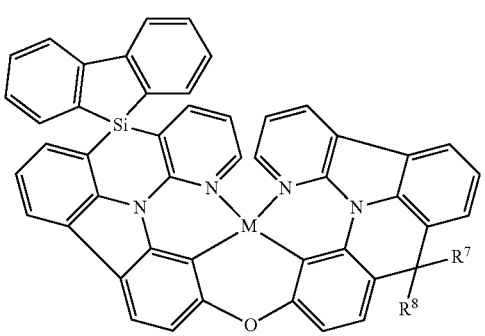
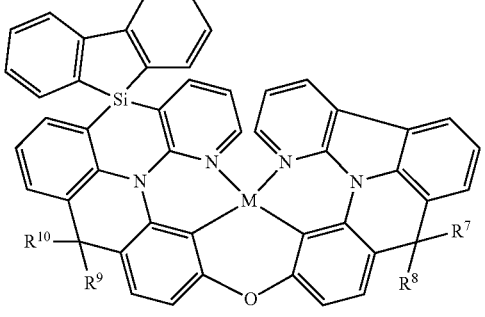

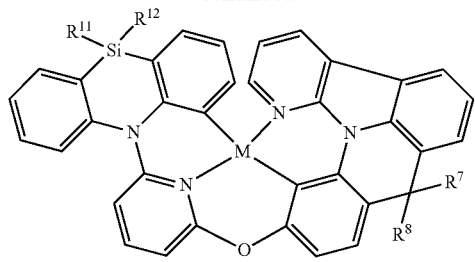
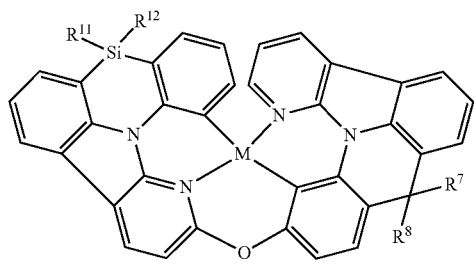
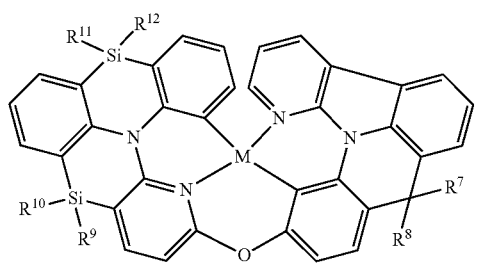
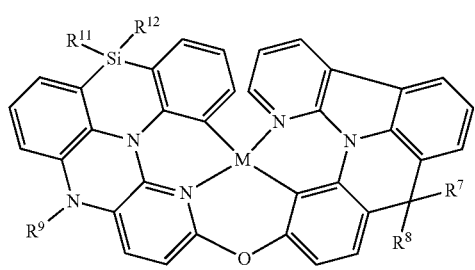
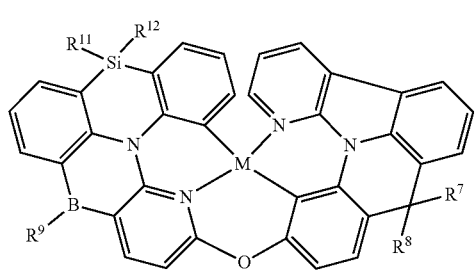
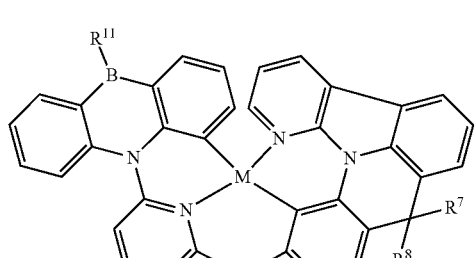
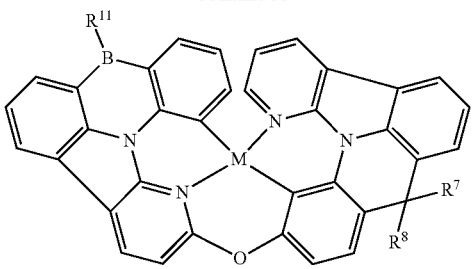
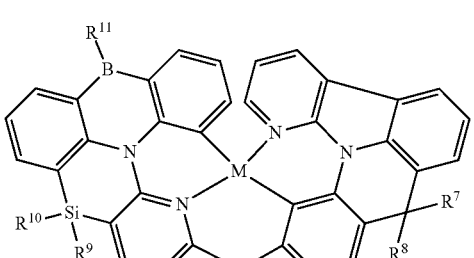
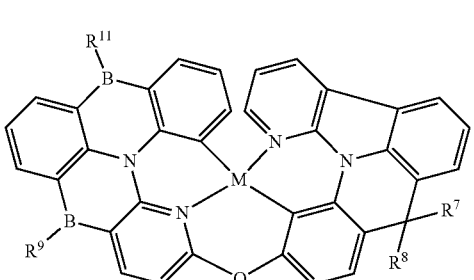
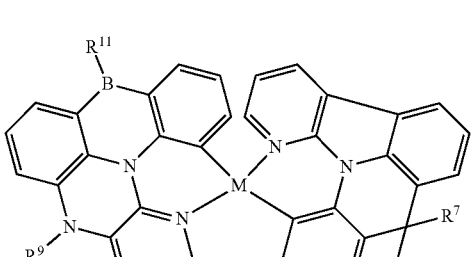
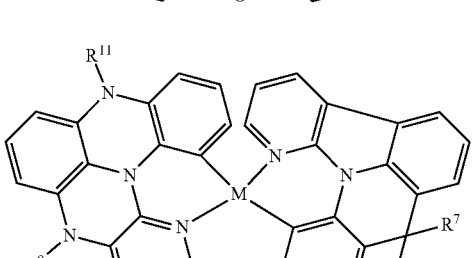
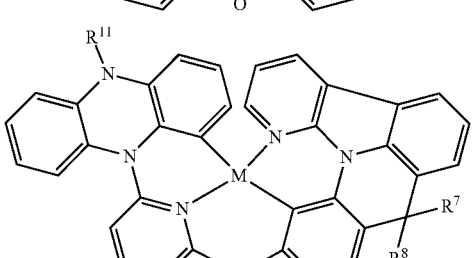

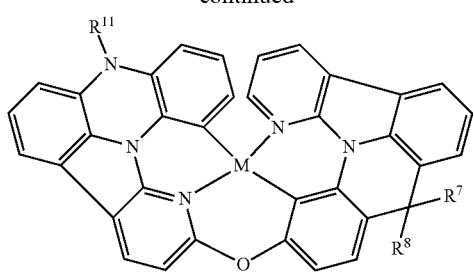

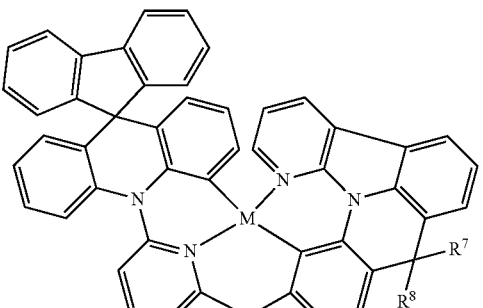
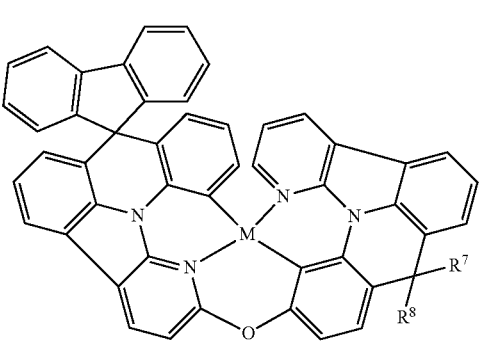
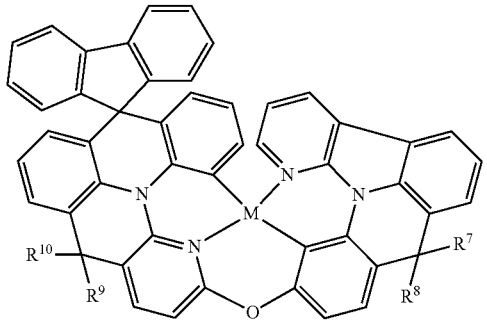
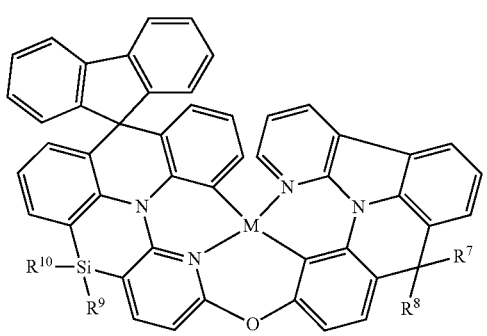
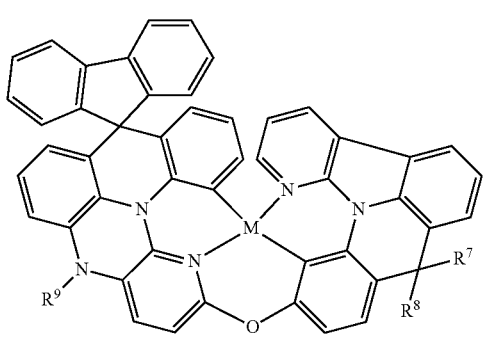
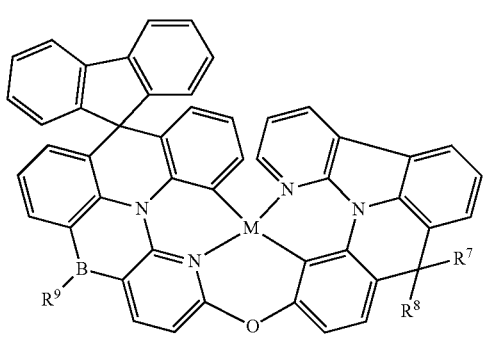
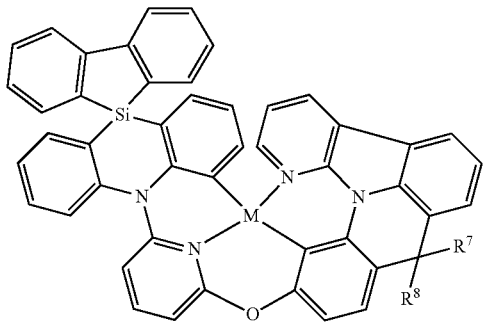

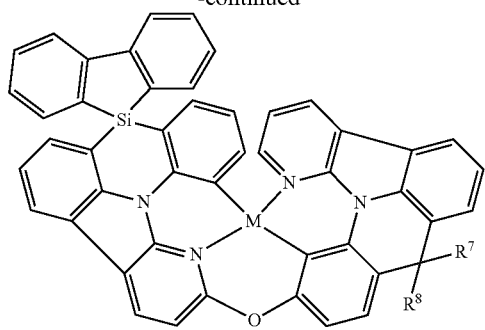
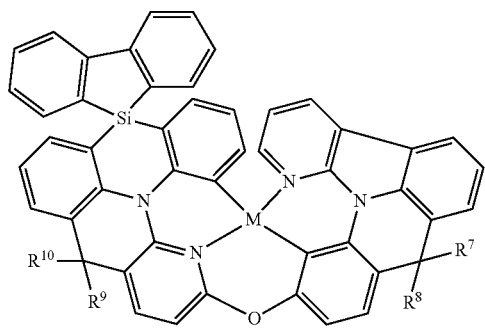
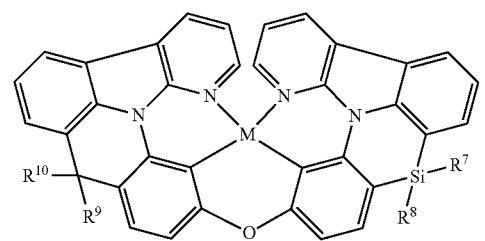
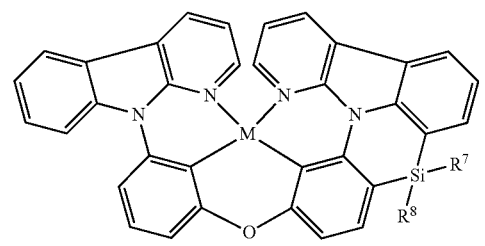
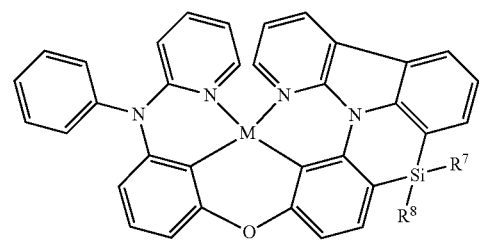
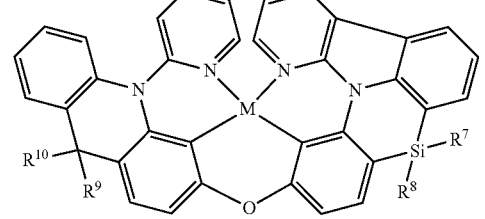
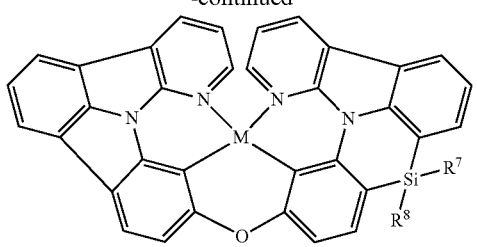
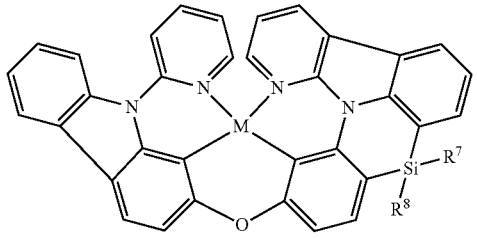
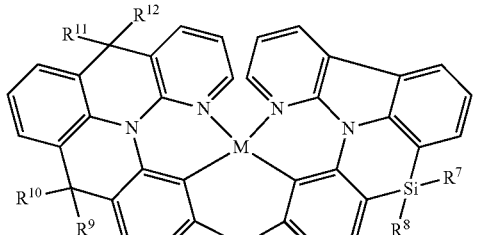
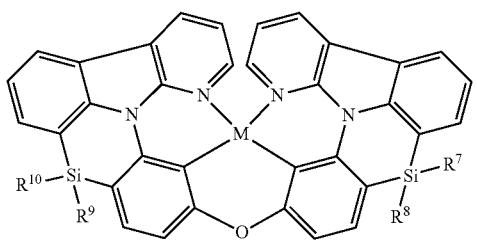
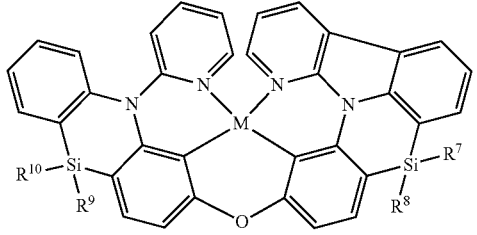
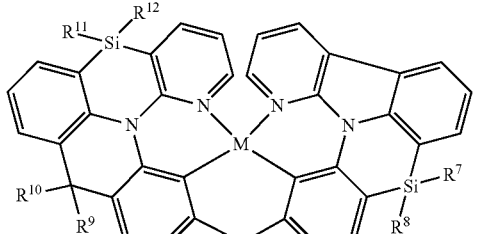
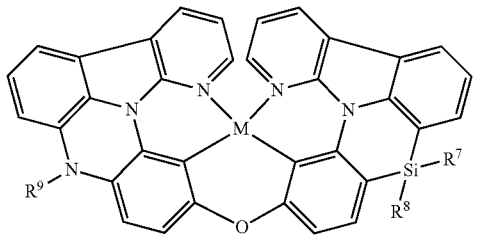

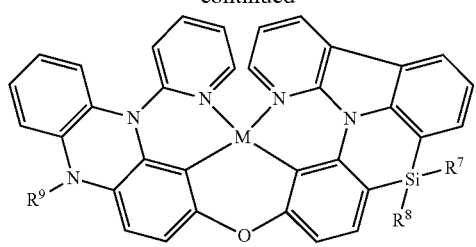
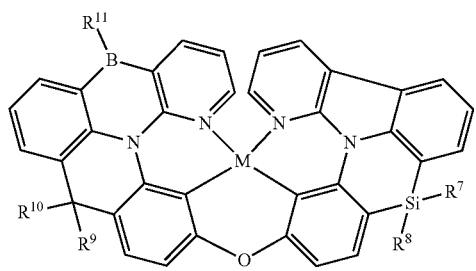
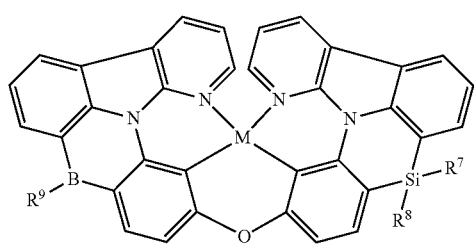
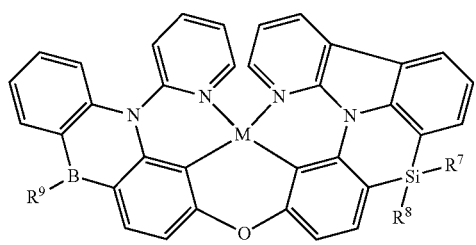
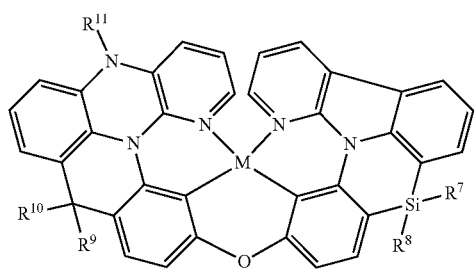
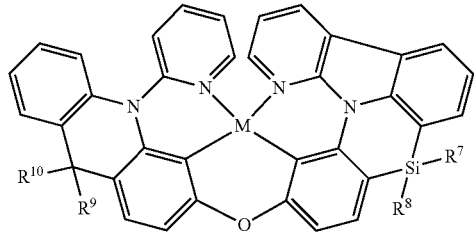
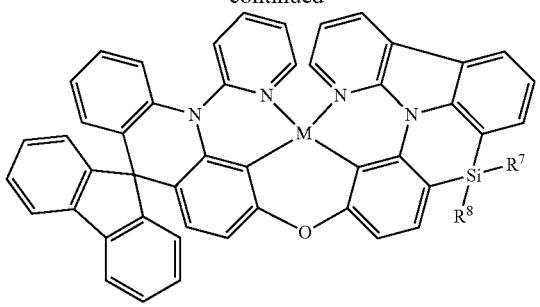
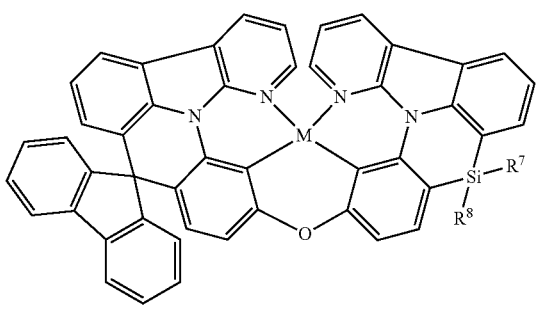
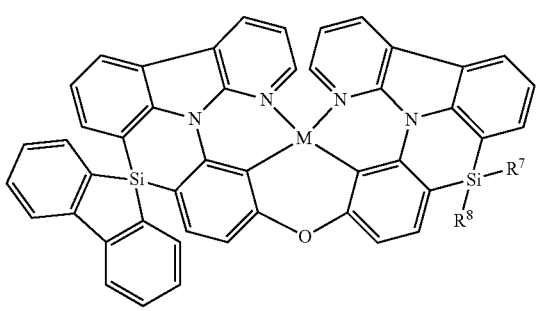
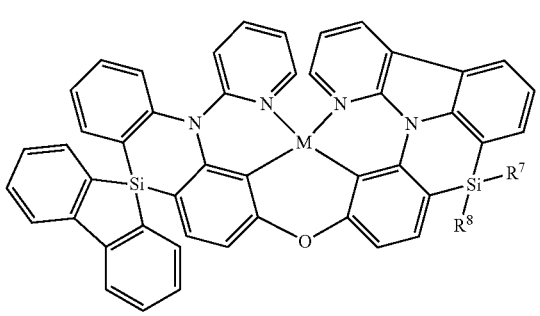
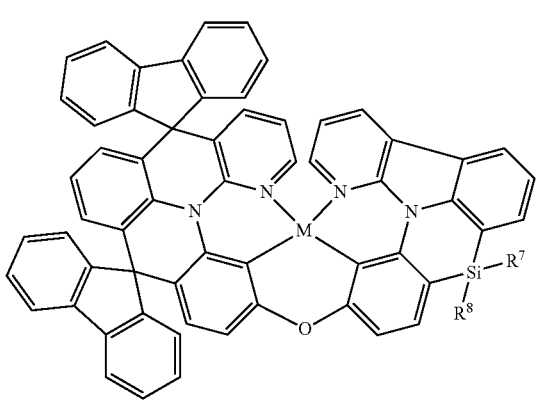

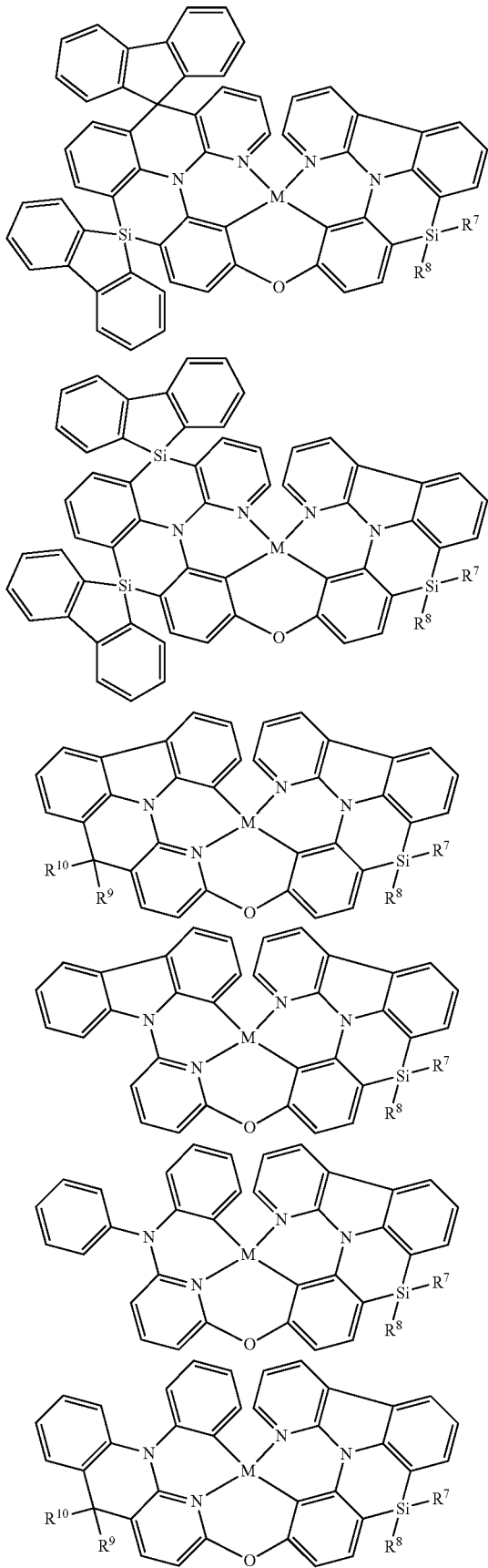
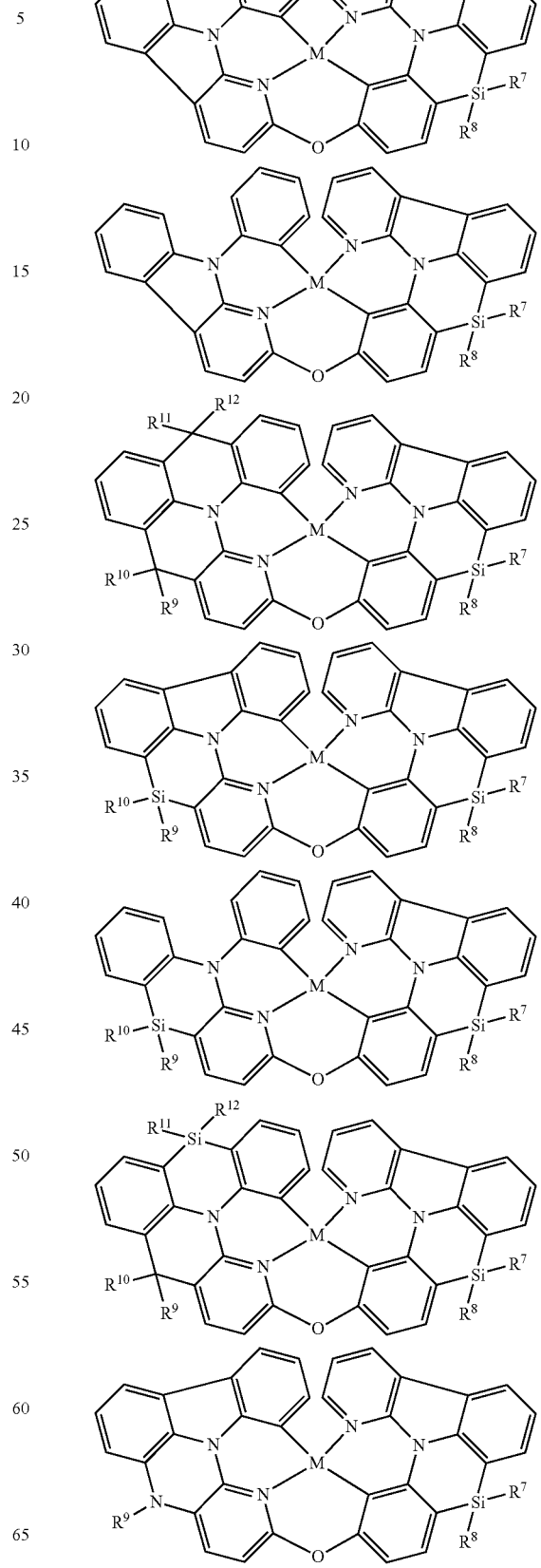

-continued
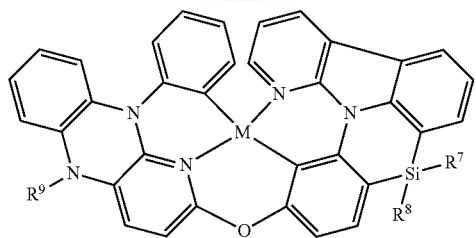
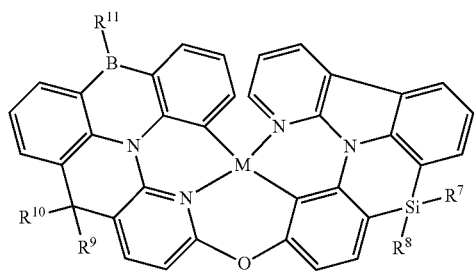
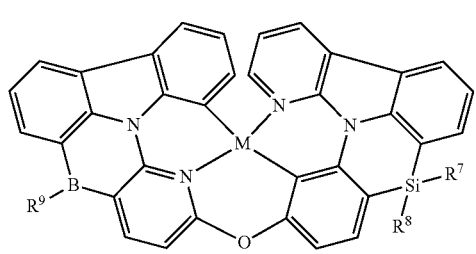
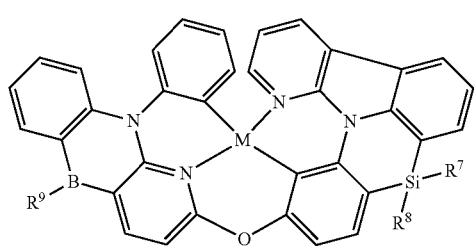
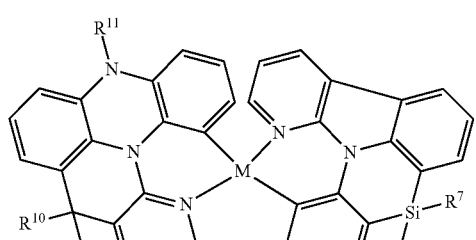
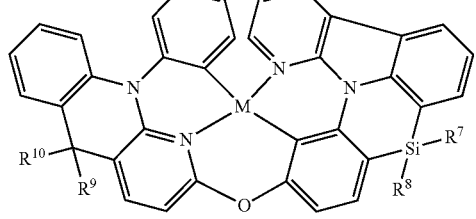
-continued
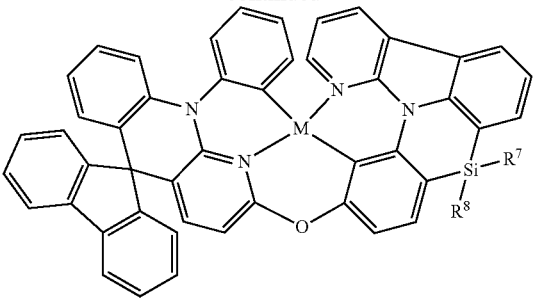
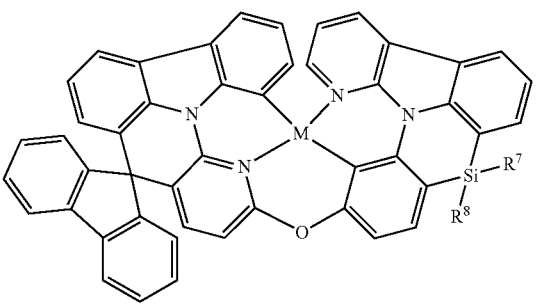
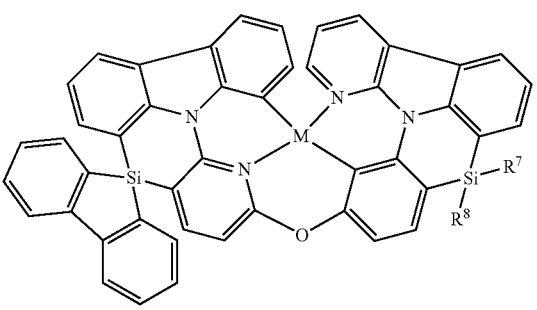
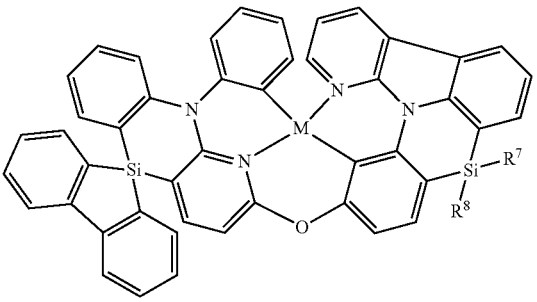
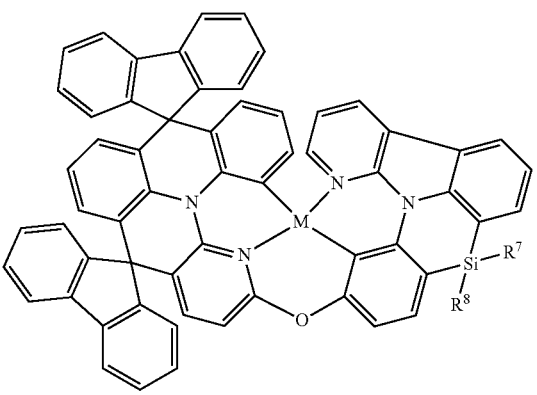

81
-continued
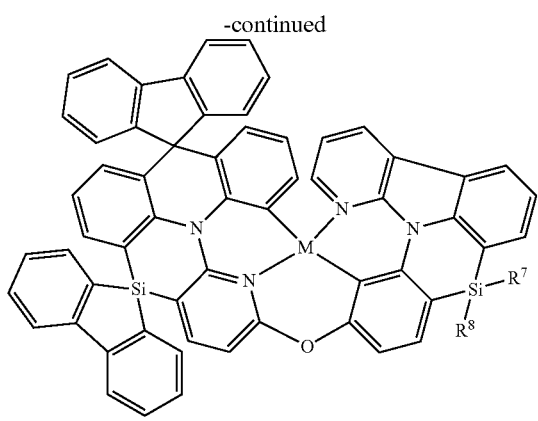
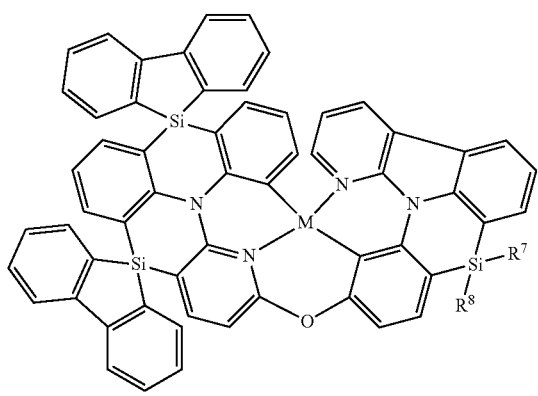
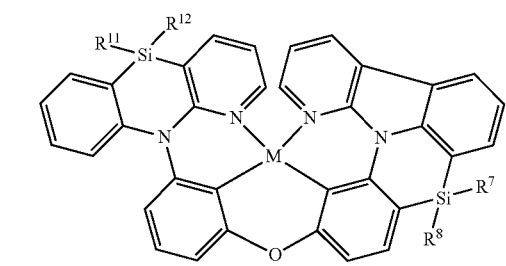
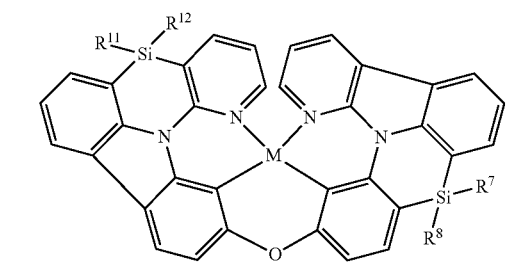
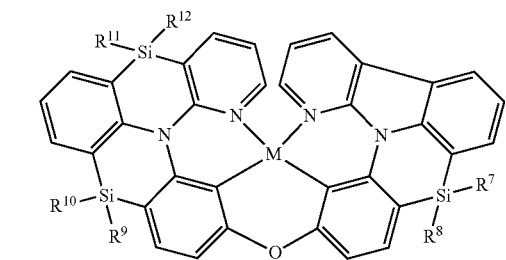
82
-continued
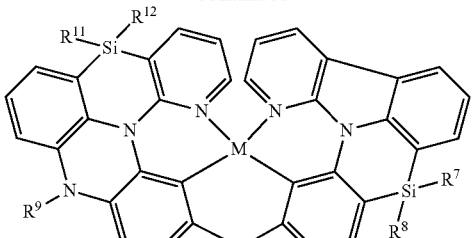
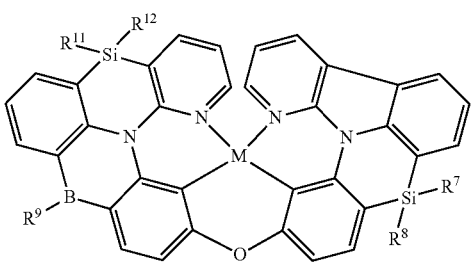
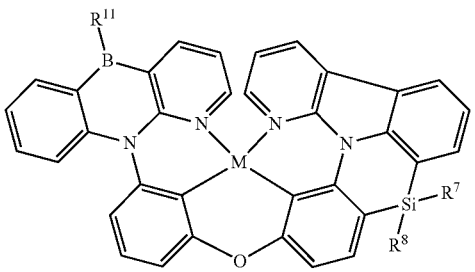
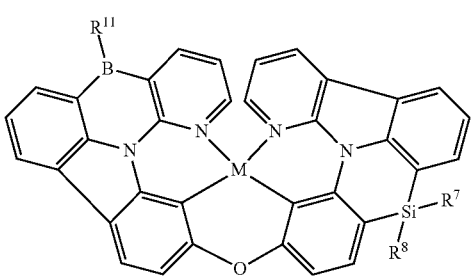
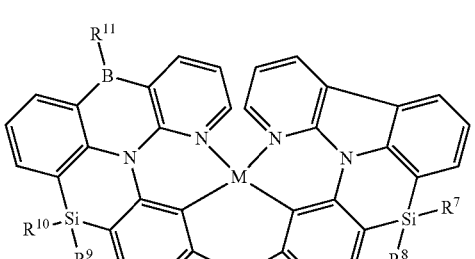

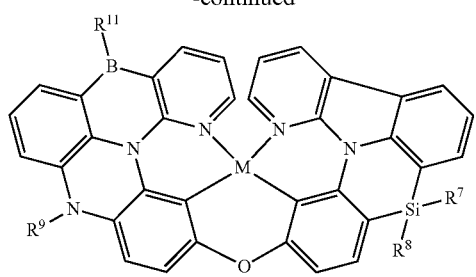
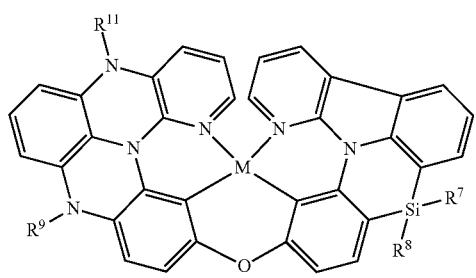
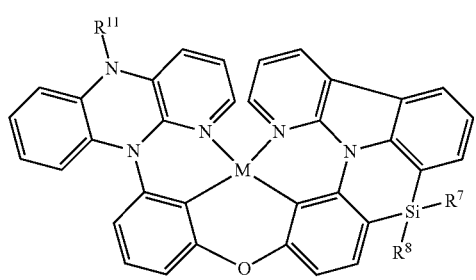
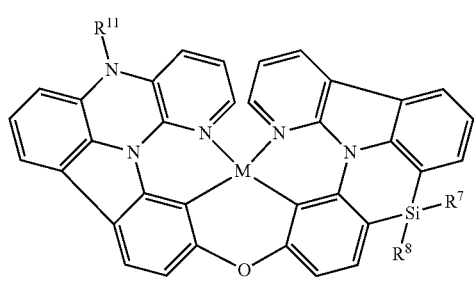
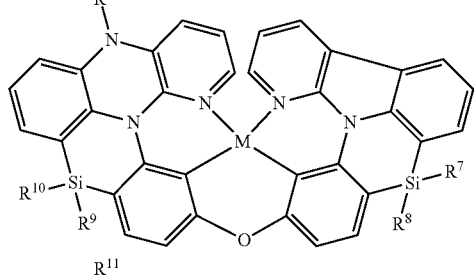
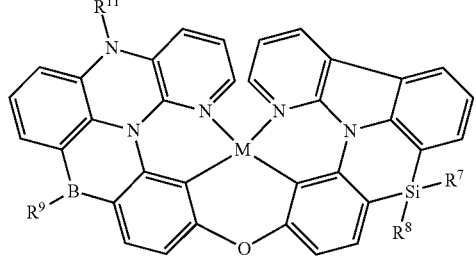
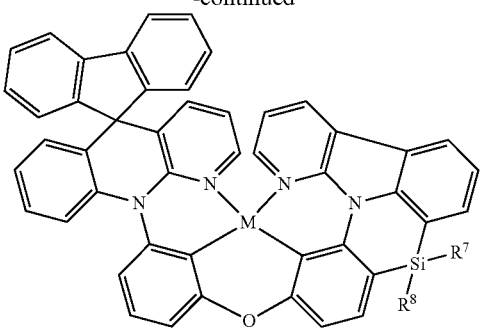
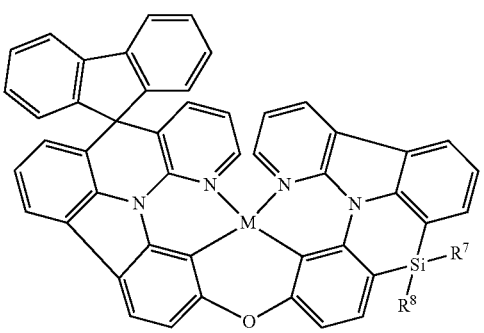
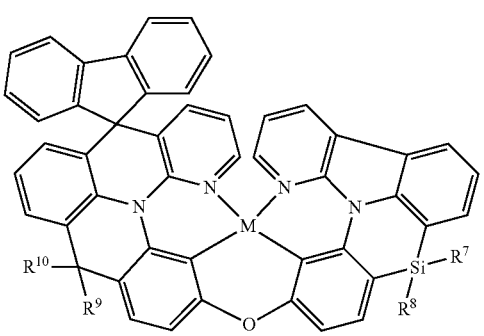
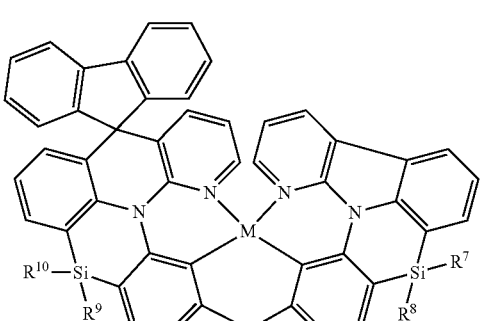
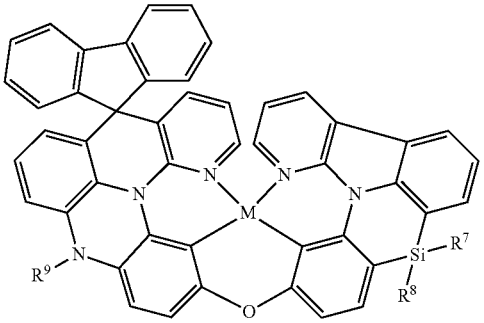

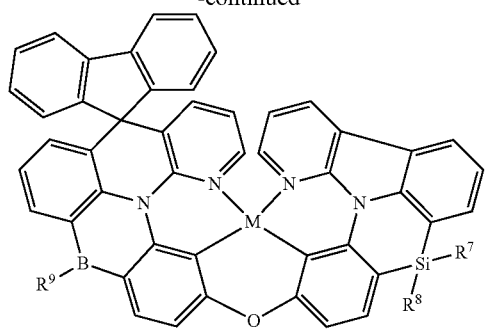
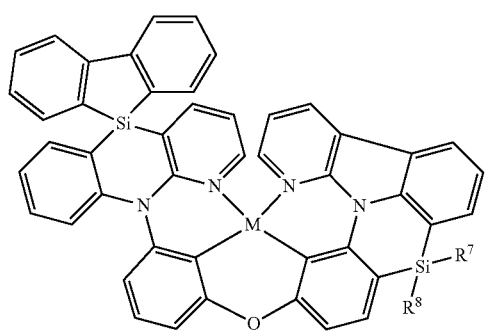
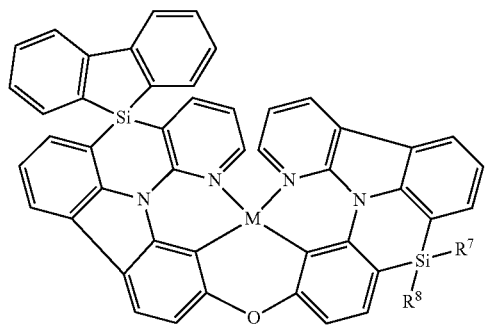
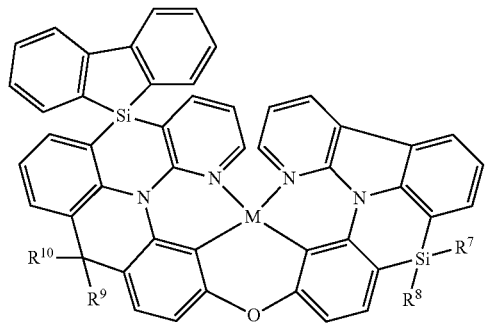
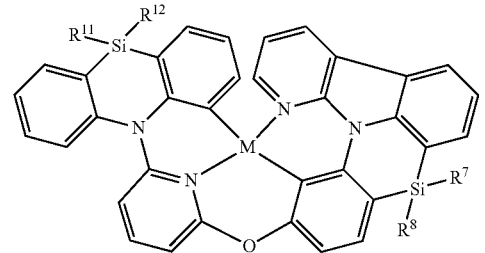
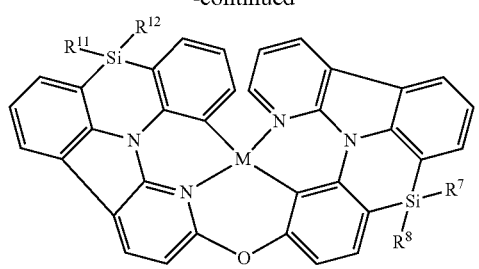
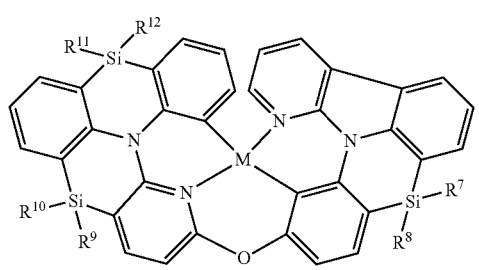
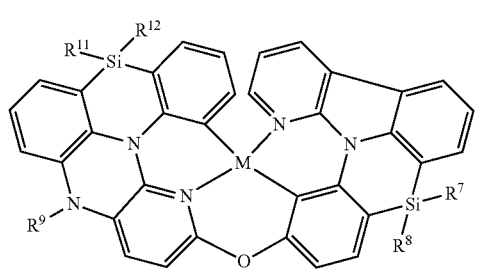
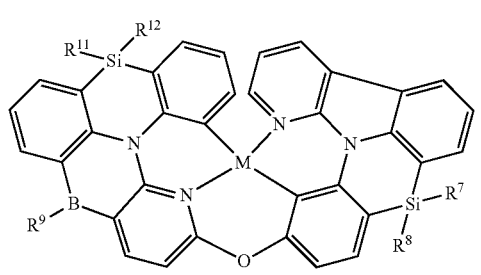
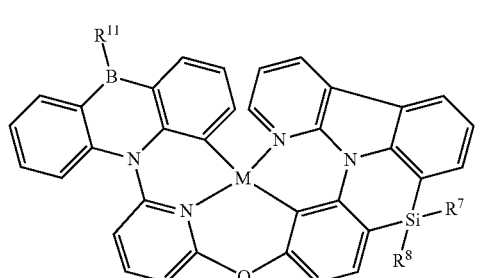
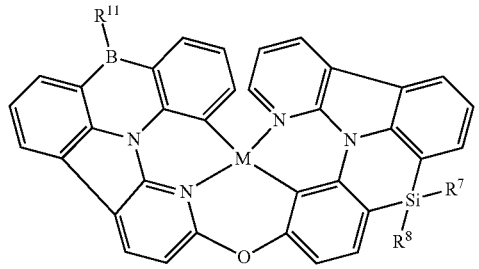

-continued
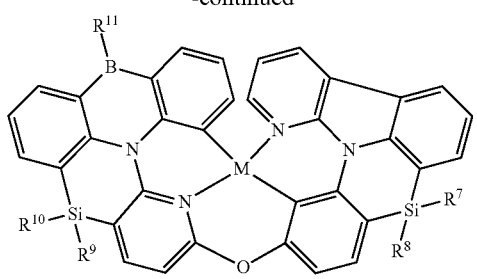
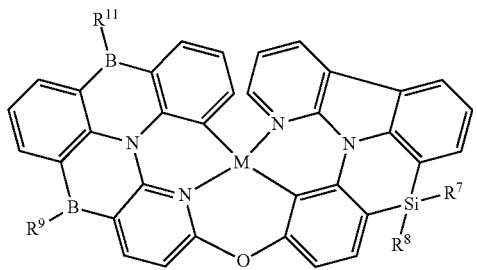
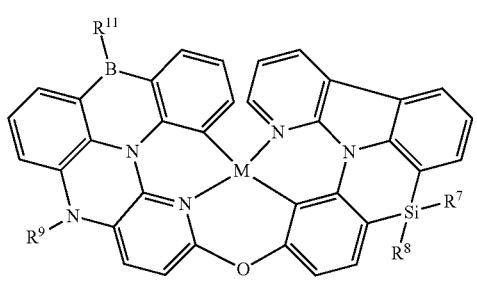
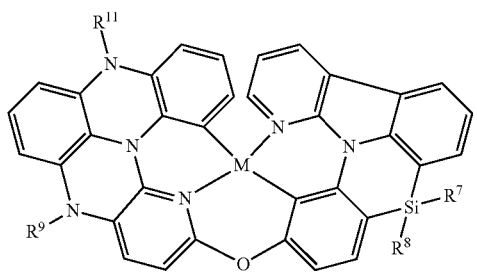
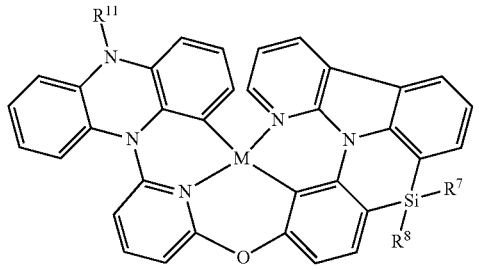
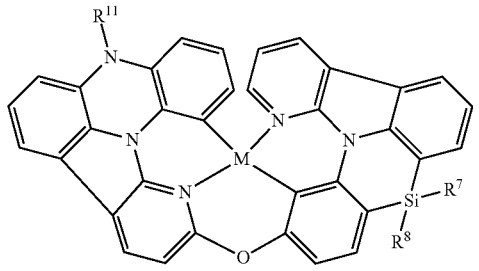
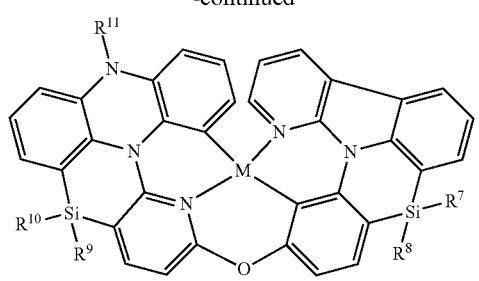
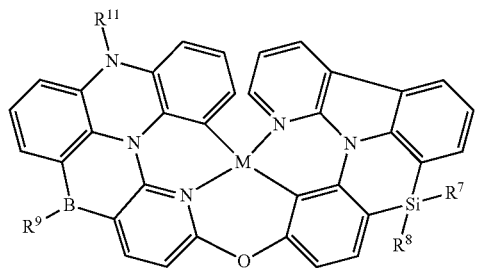
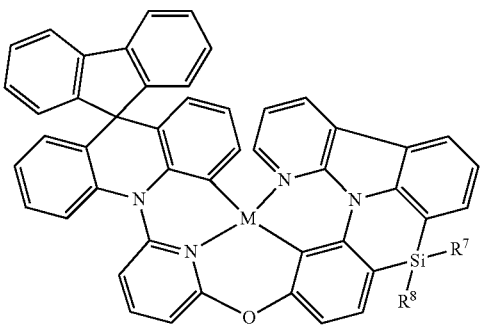
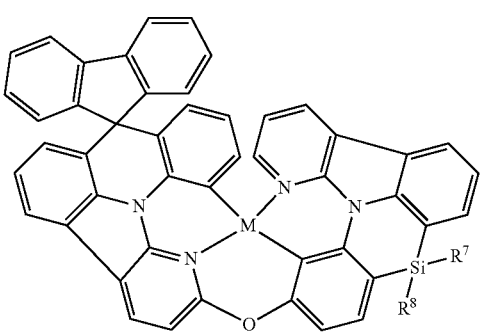
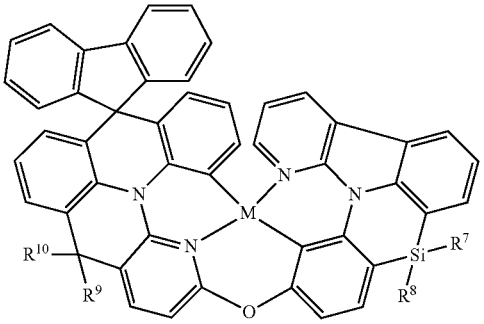

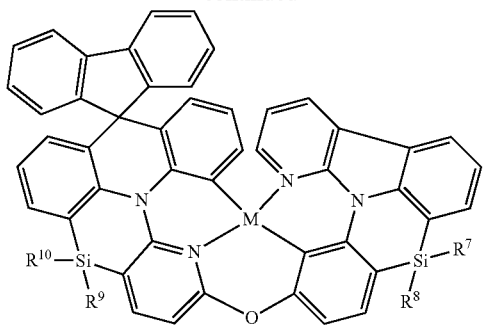
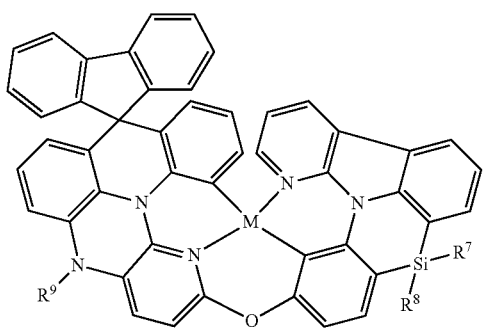
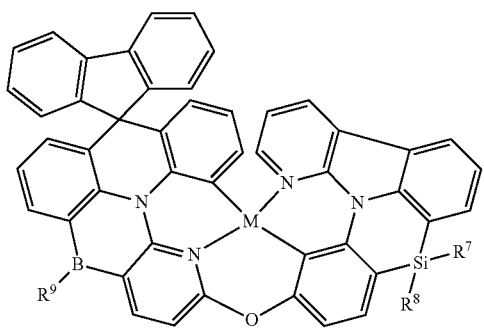
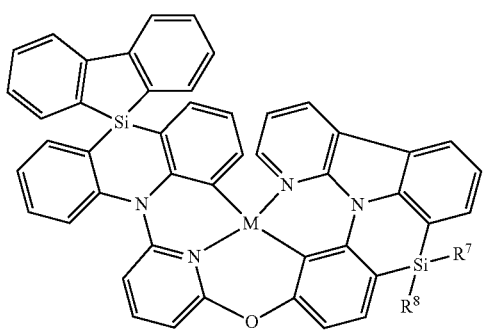
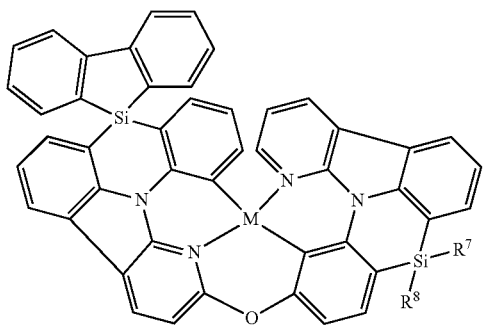
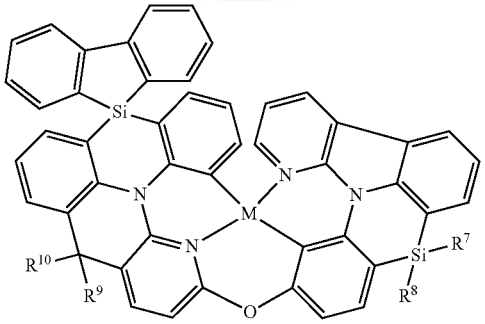
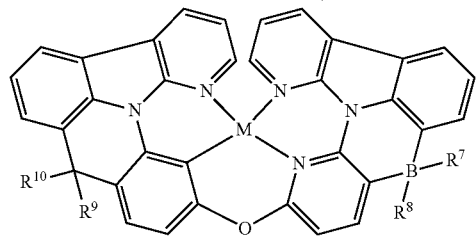
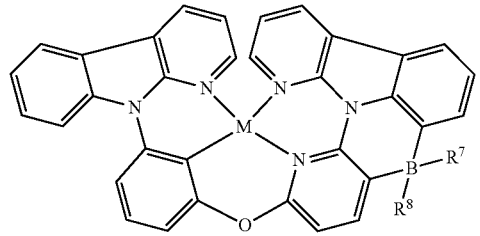
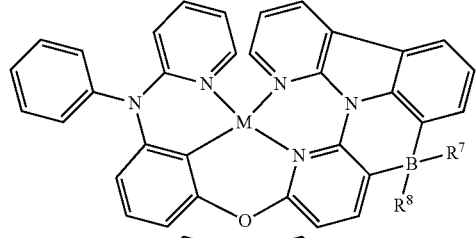
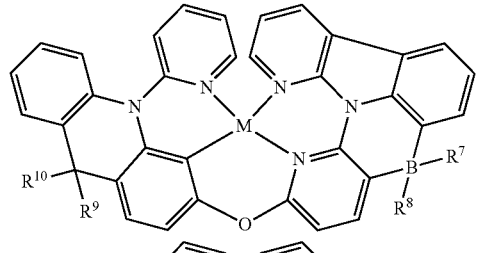
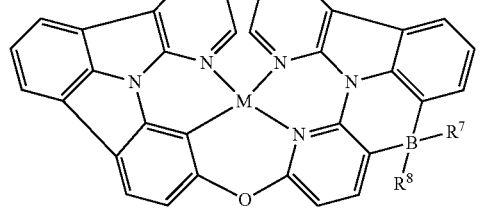
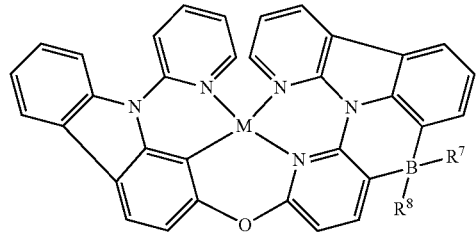

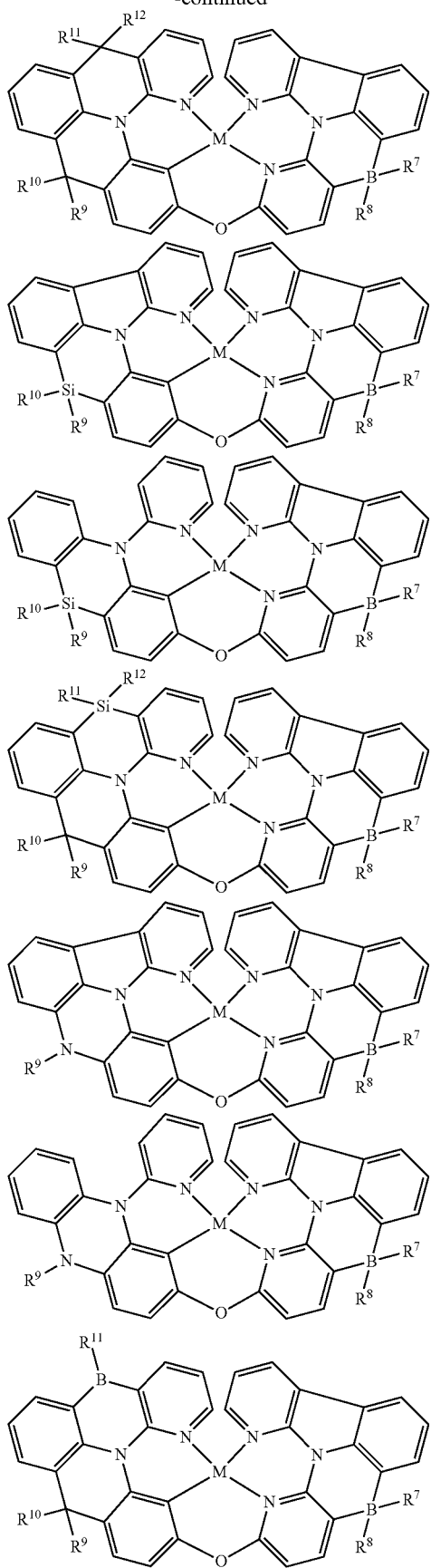
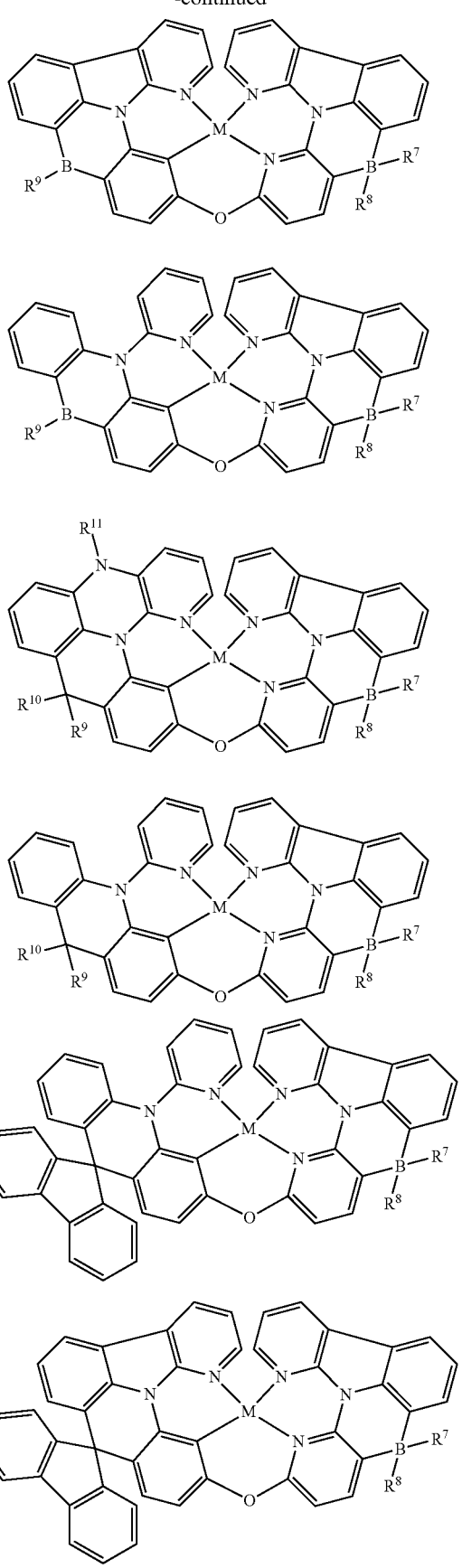

93
-continued
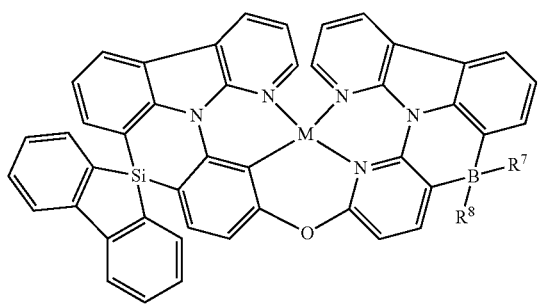
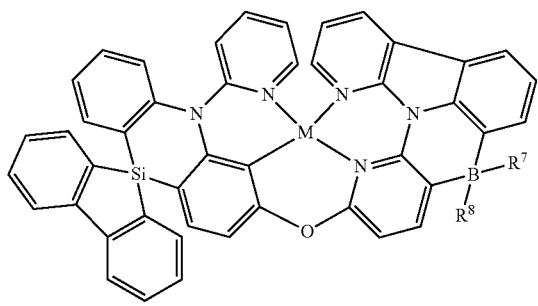
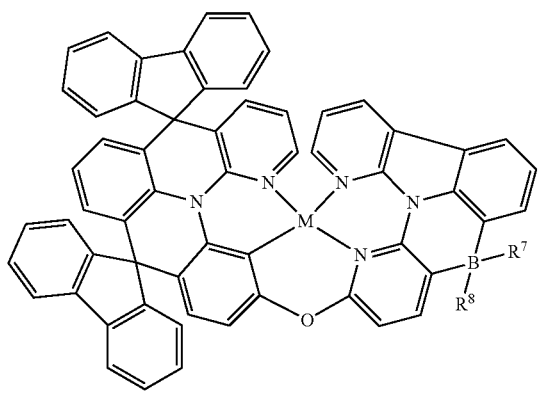
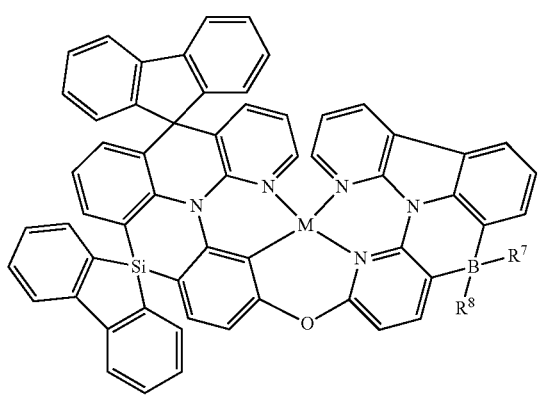
94
-continued
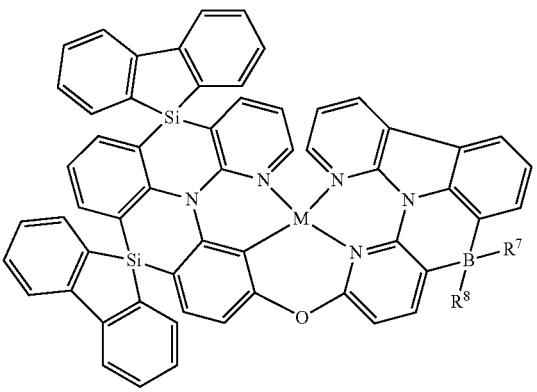
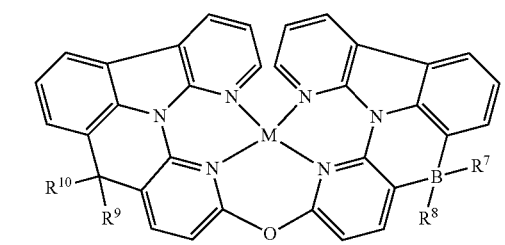
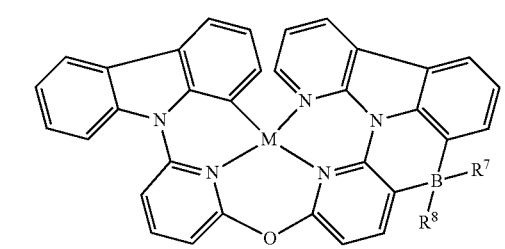
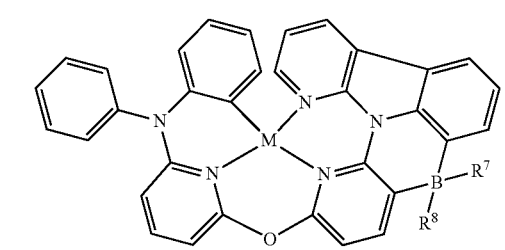
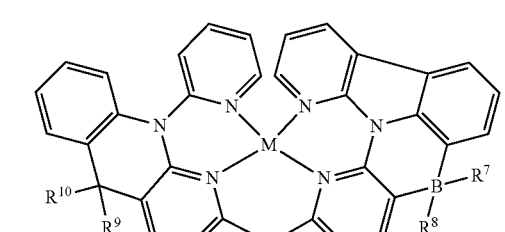
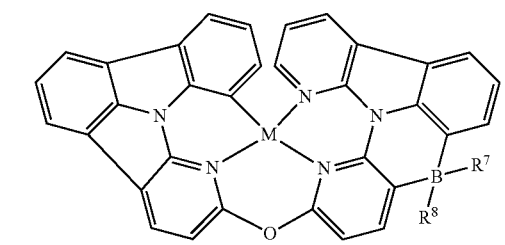

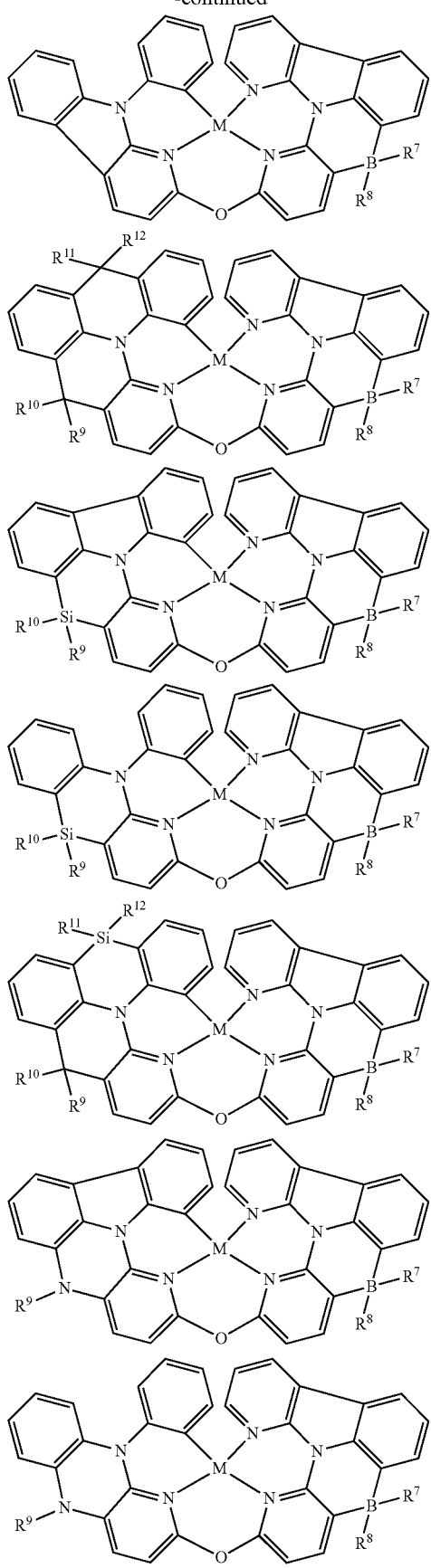
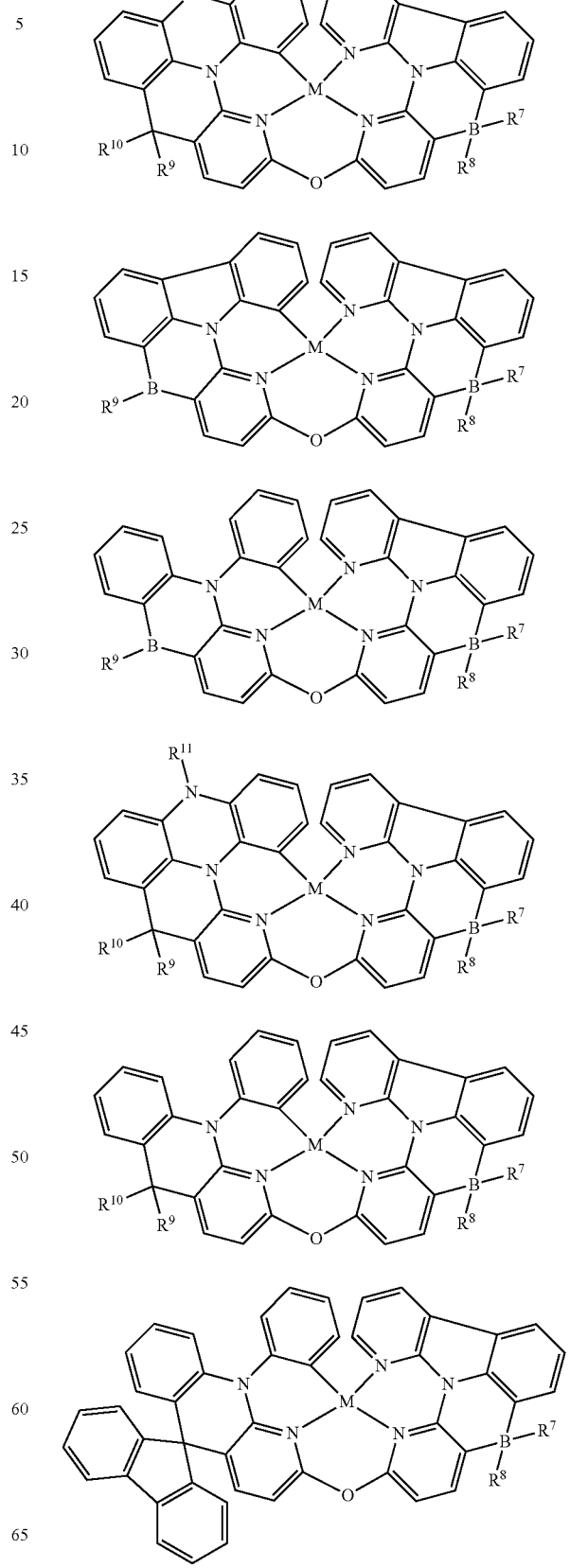

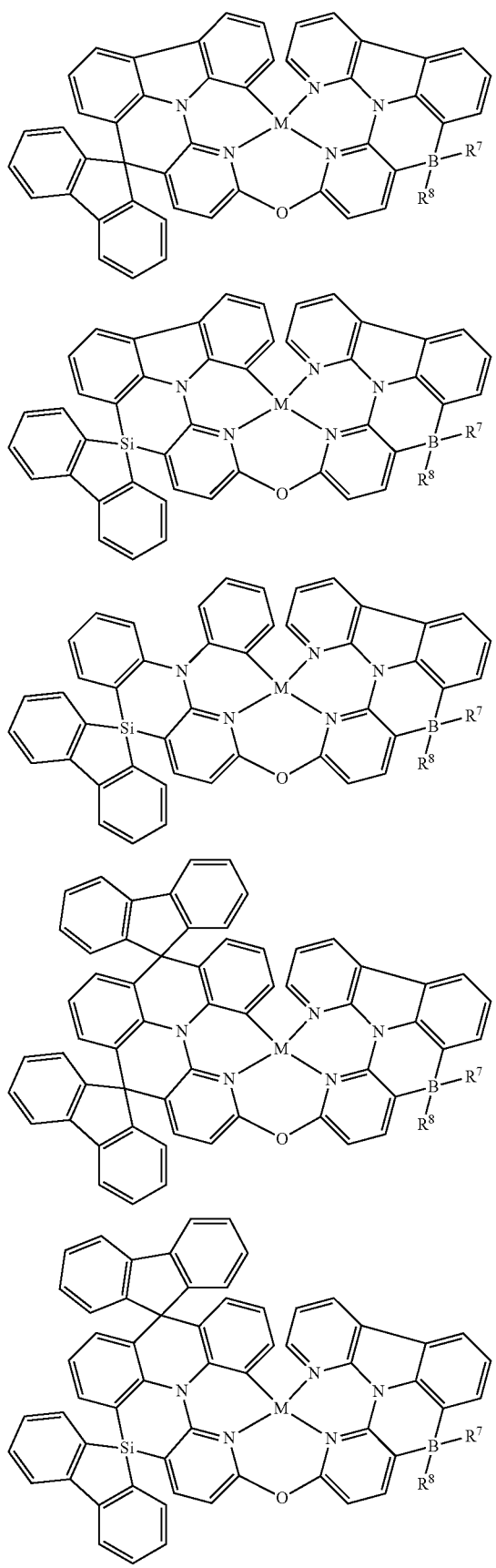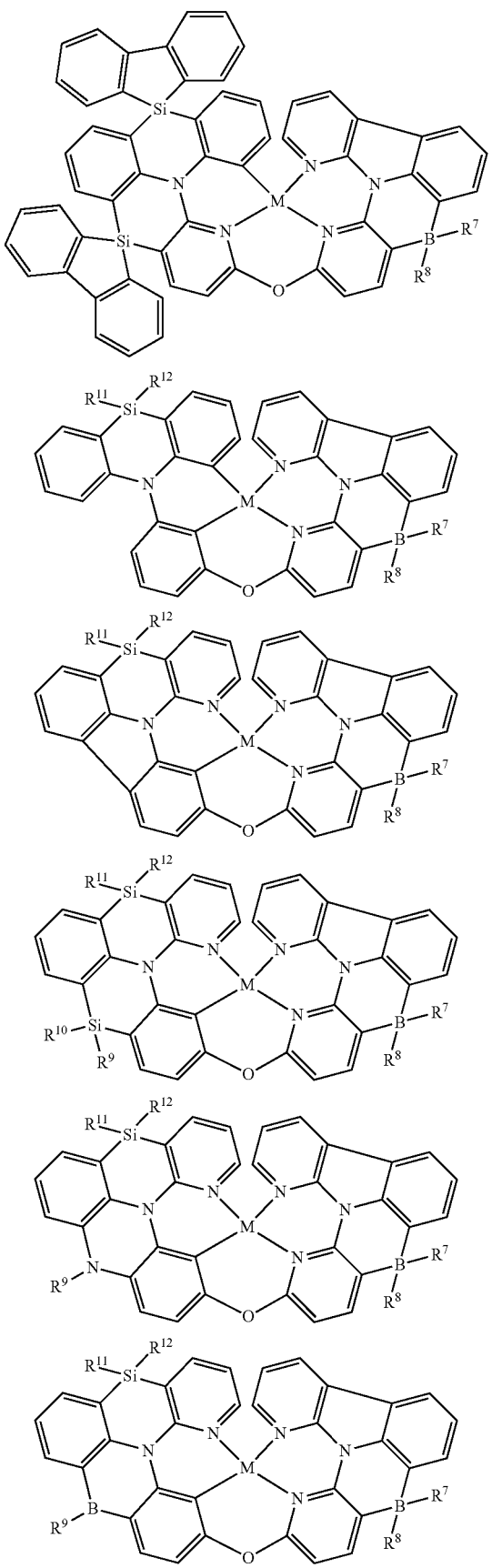

99
-continued
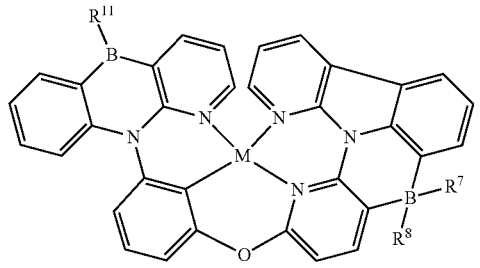
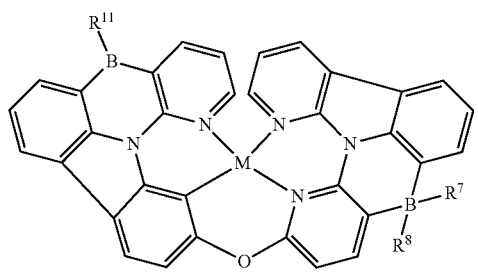
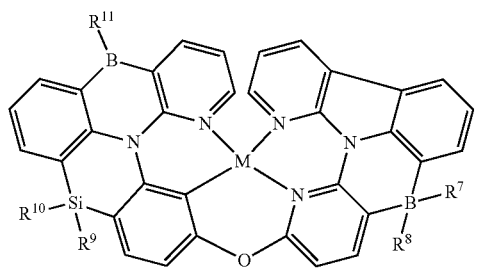
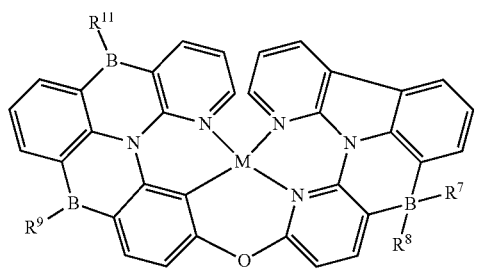
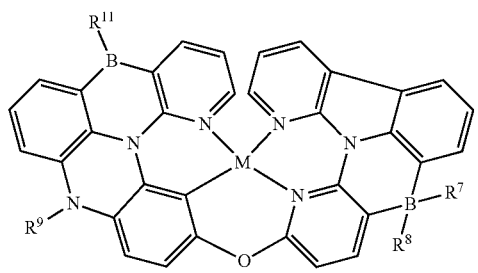
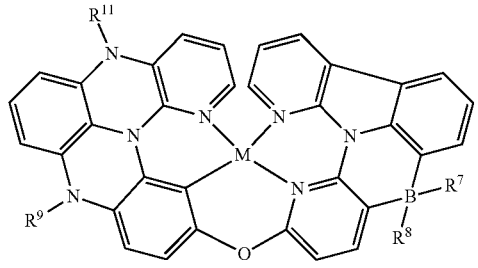
100
-continued
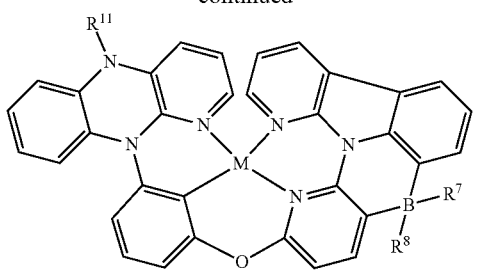
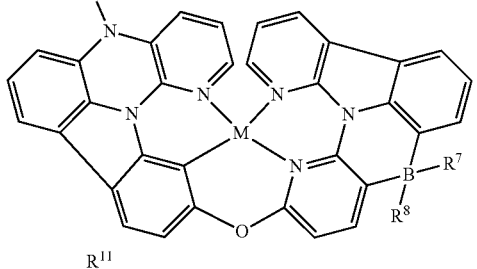
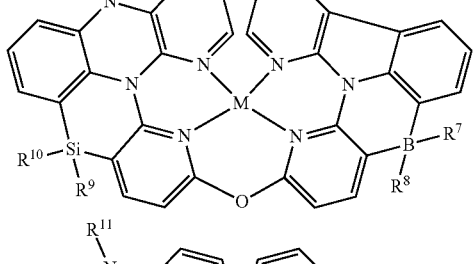
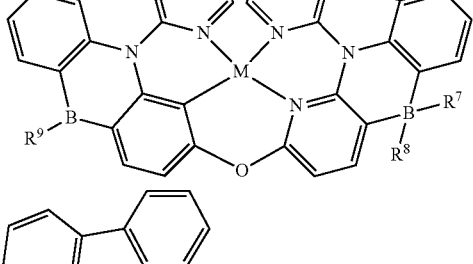
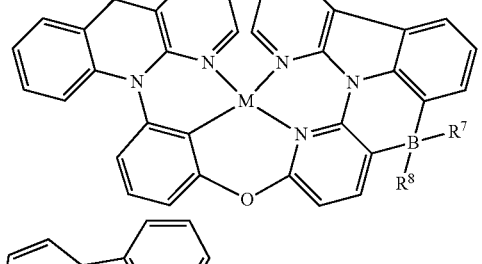
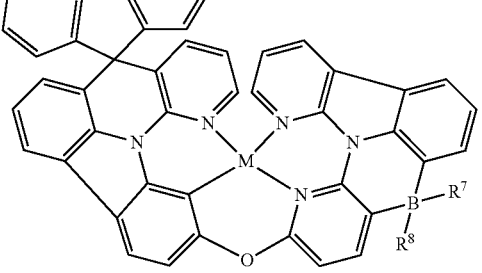

101
-continued

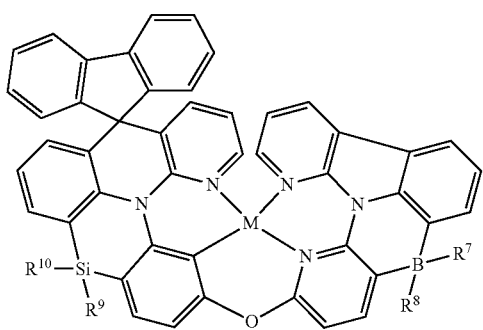
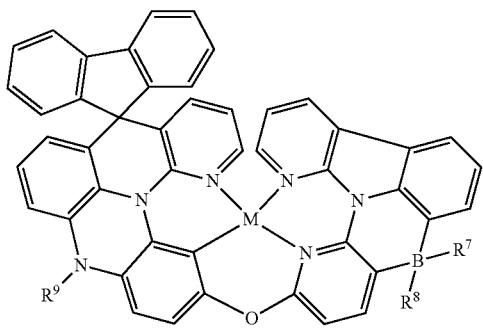
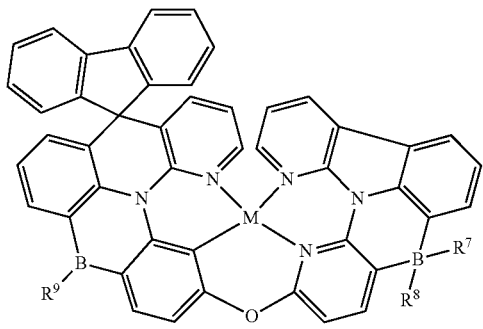
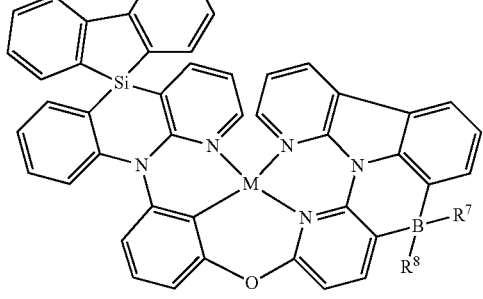
102
-continued
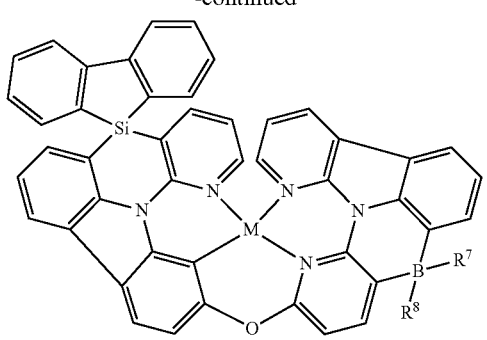
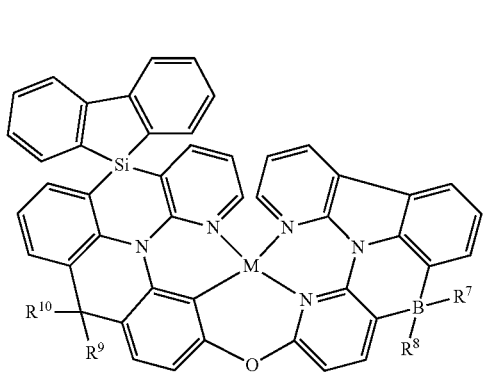
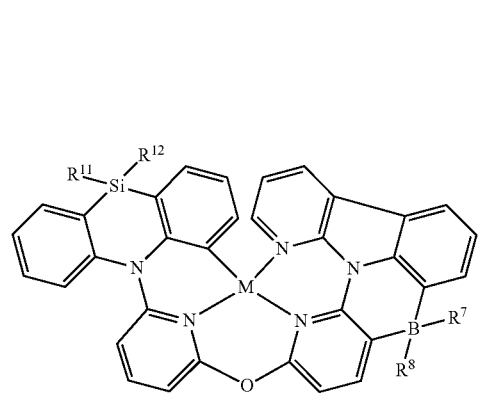
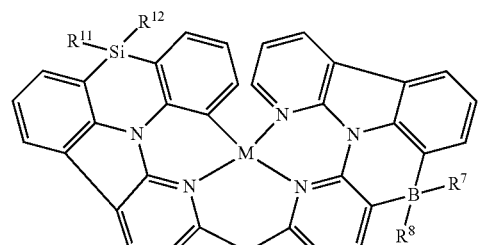
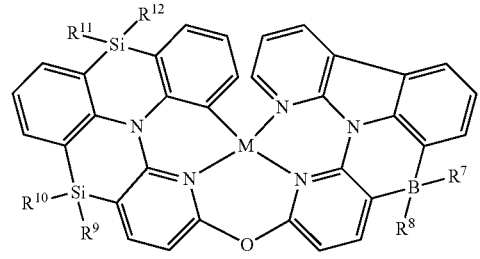

103
-continued
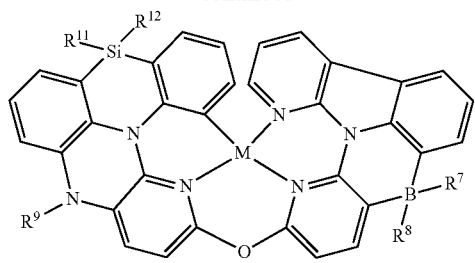
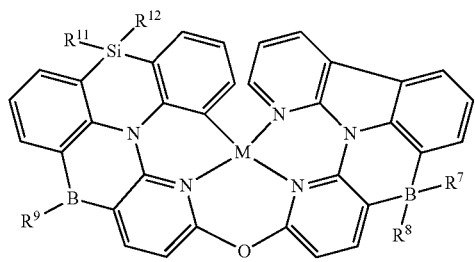
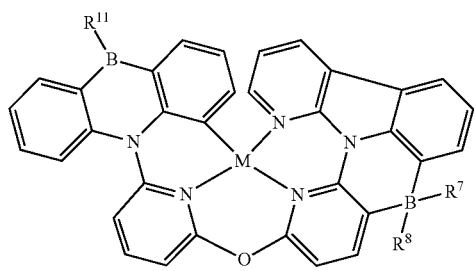
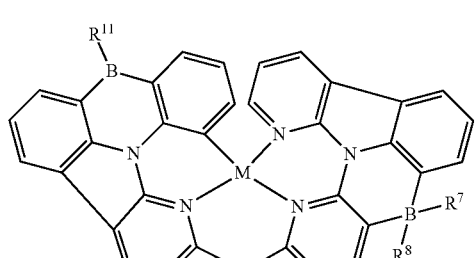
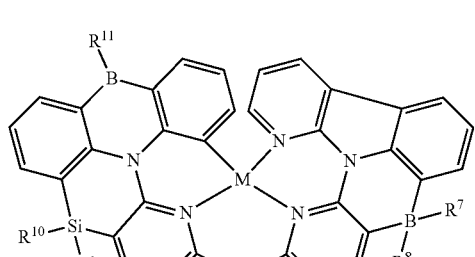
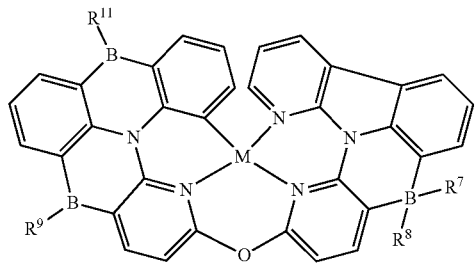
104
-continued
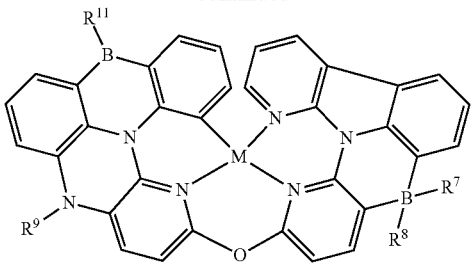
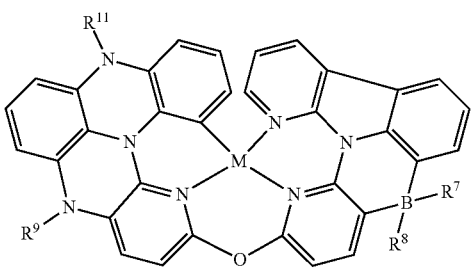
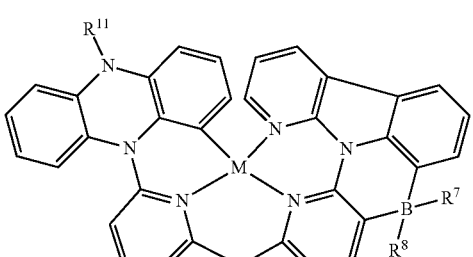
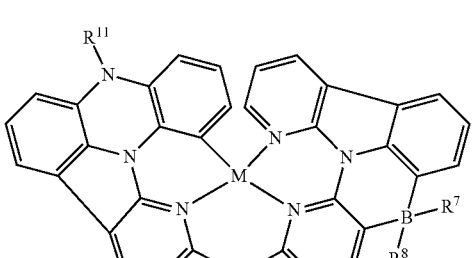
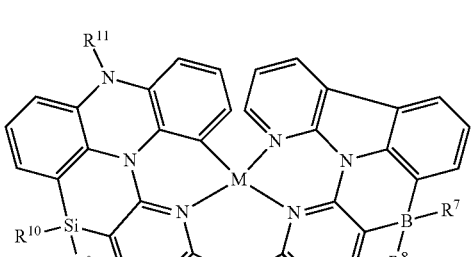
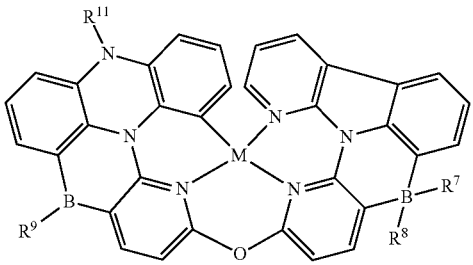

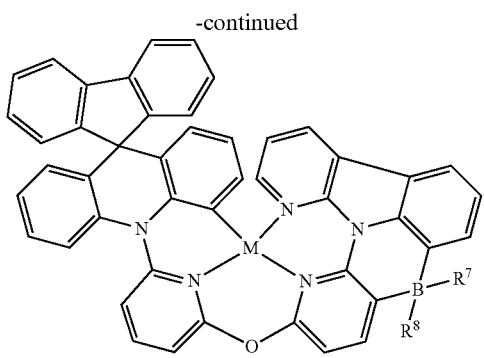
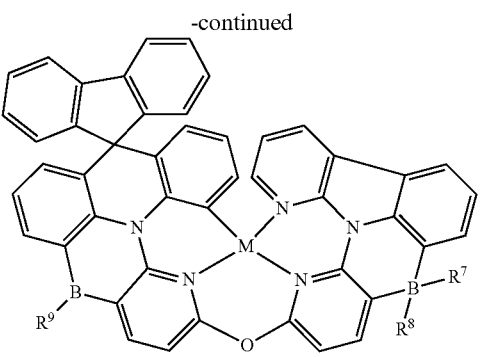
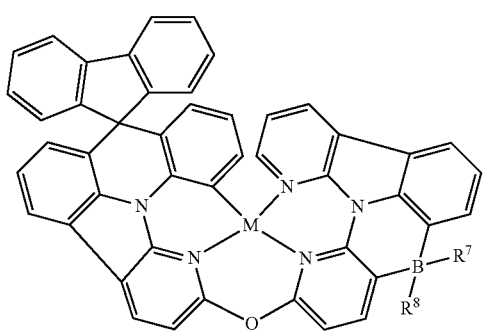
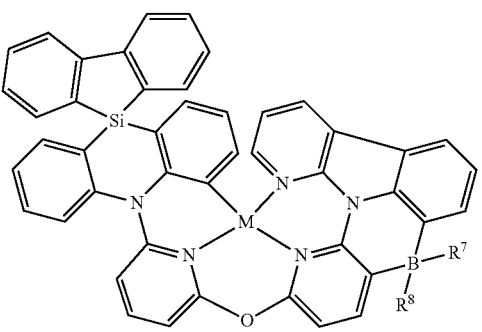
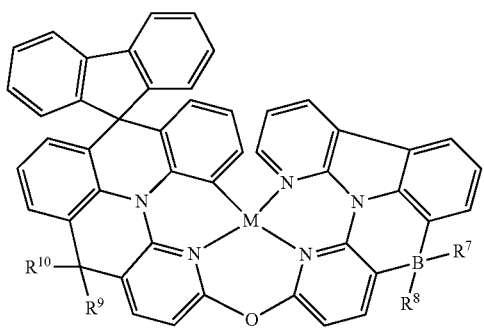
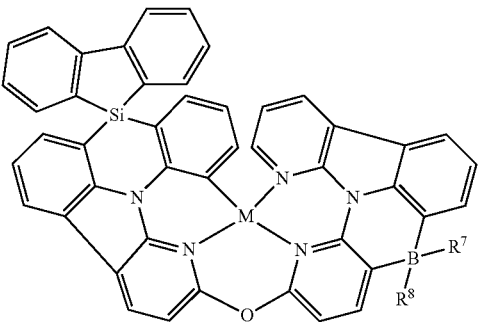
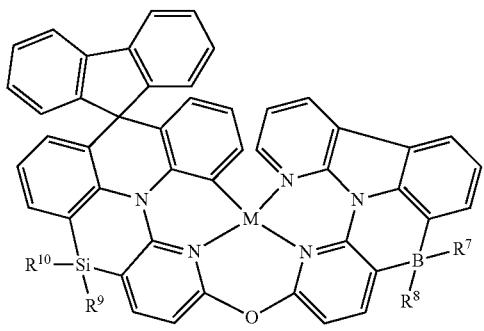
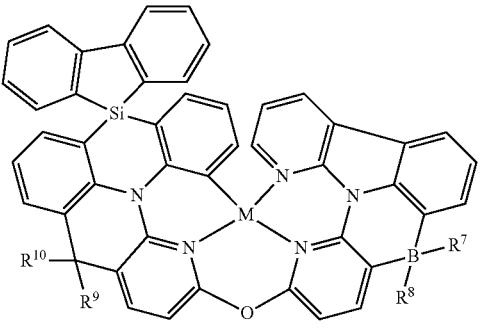
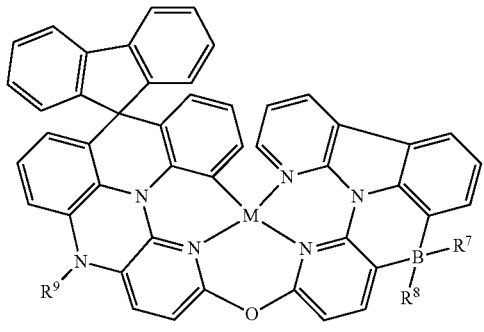

107
-continued
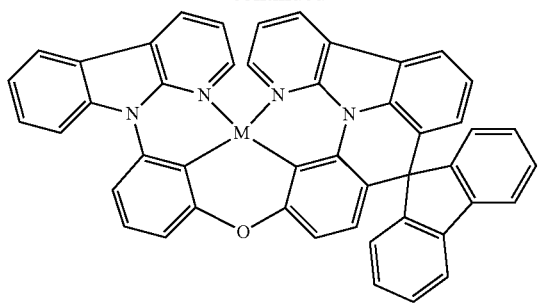
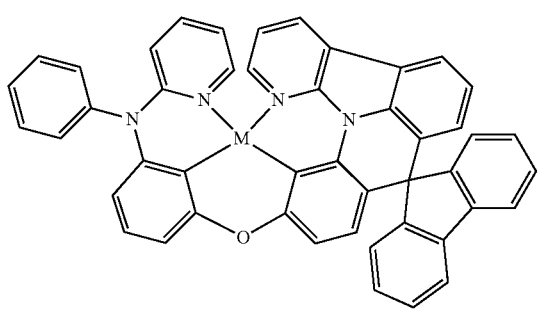
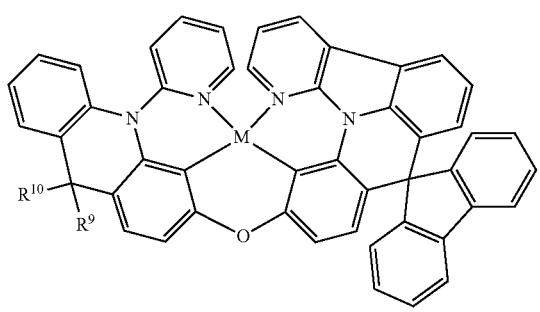
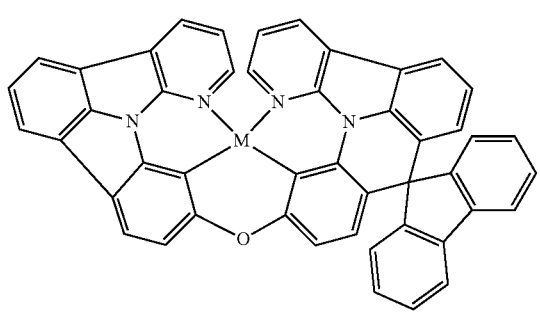
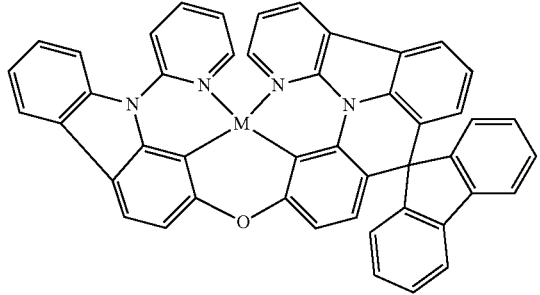
108
-continued
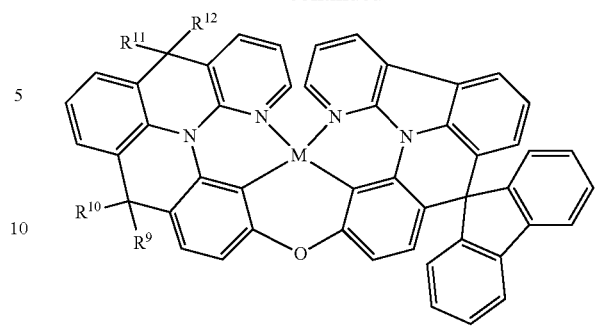
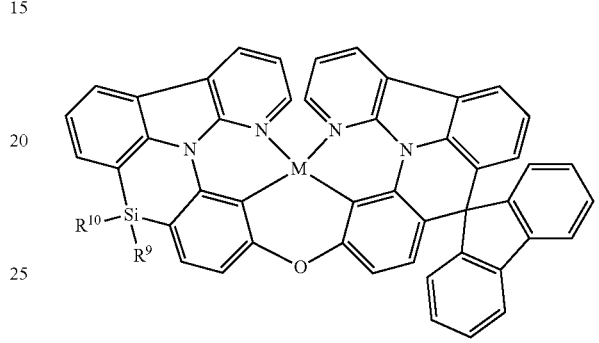
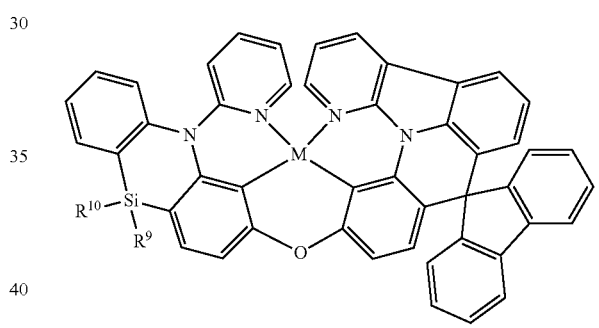
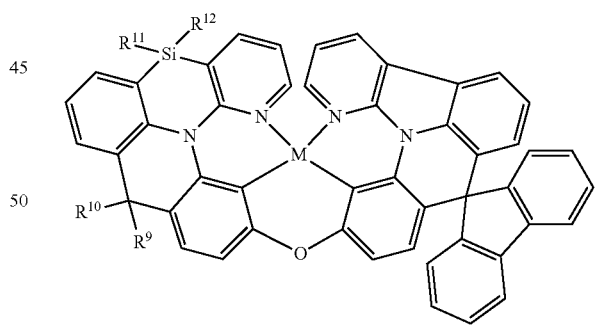
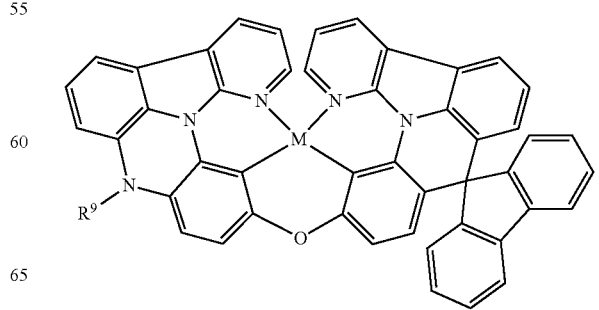

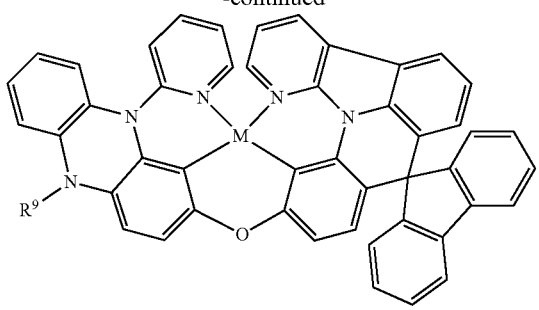
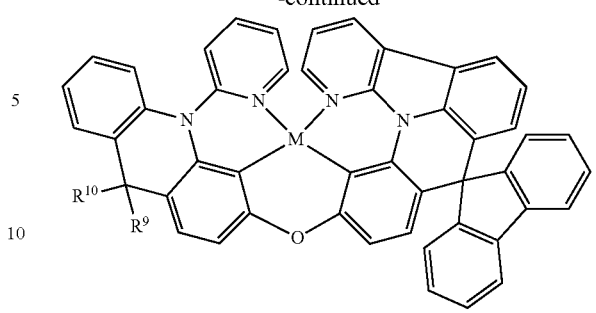
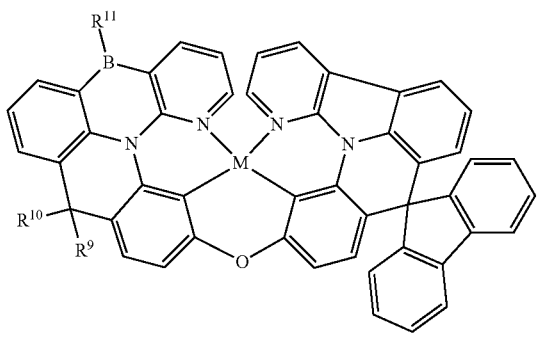
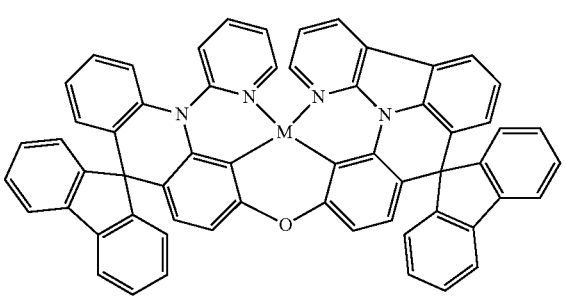
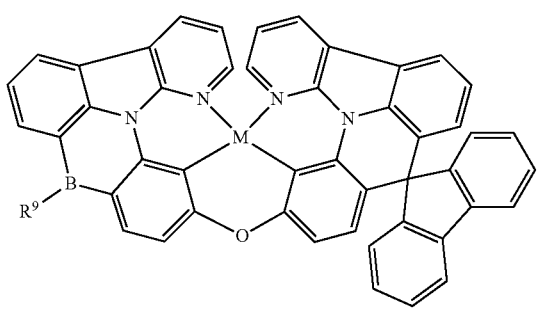
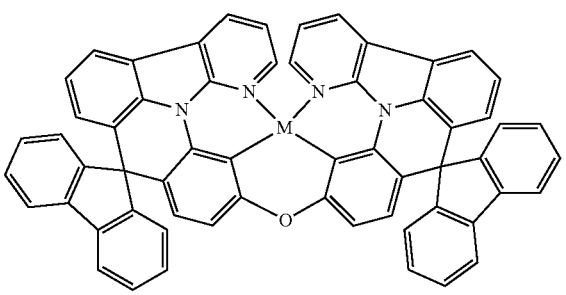
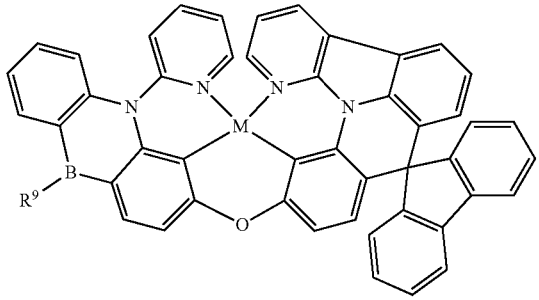
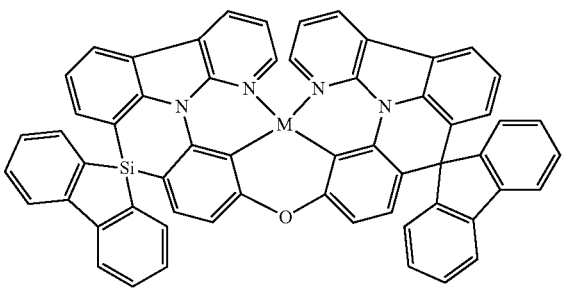
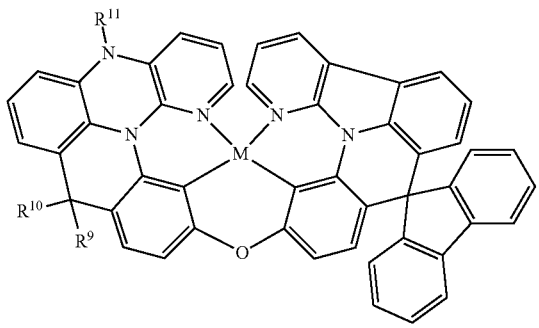
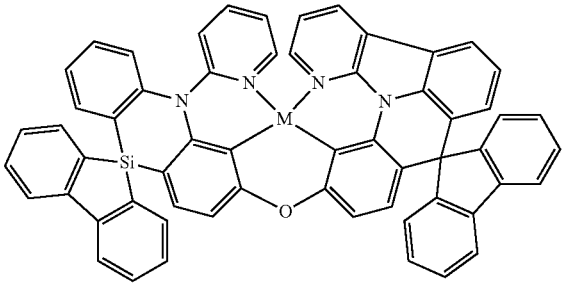

111
-continued
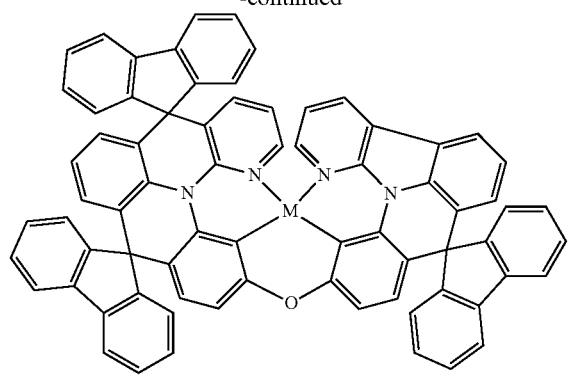
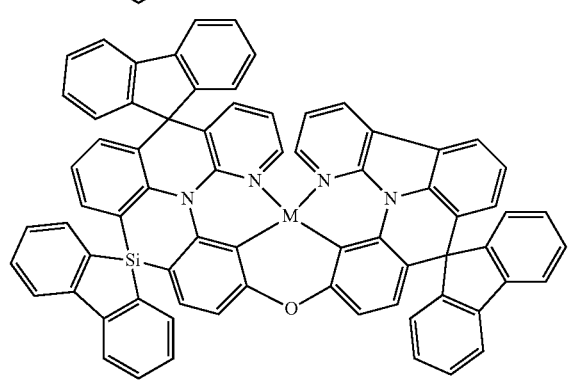
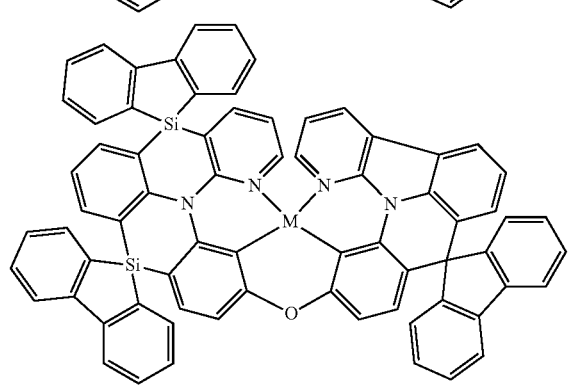
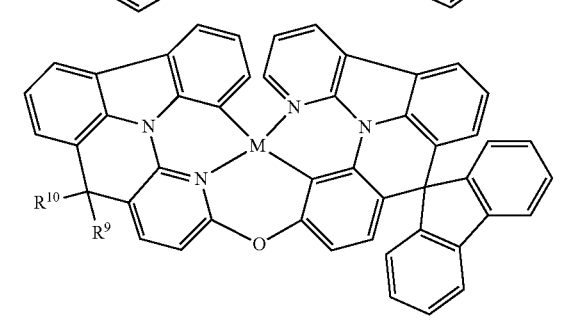
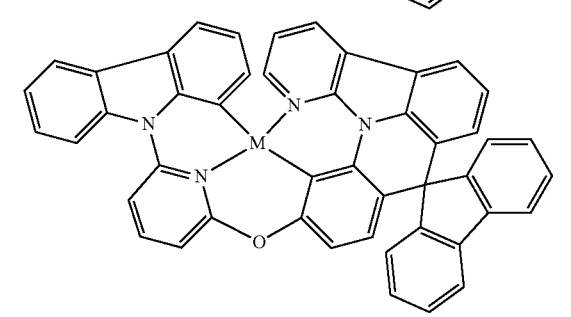
112
-continued
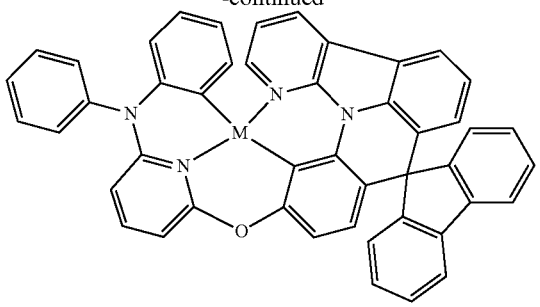
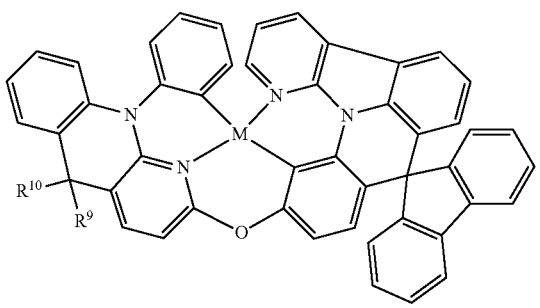
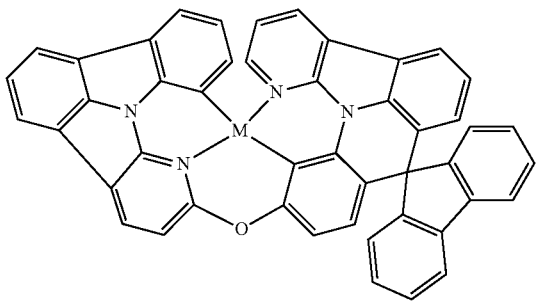
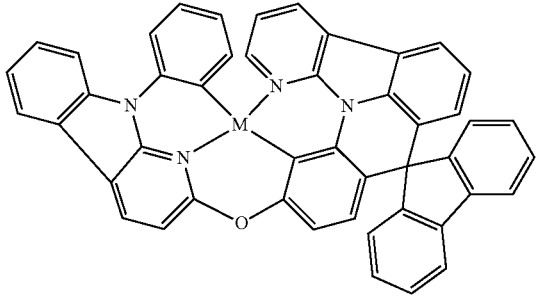
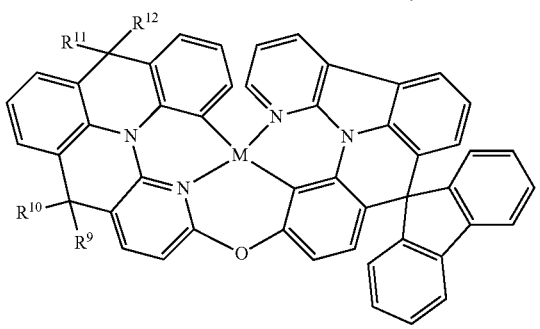

113
-continued
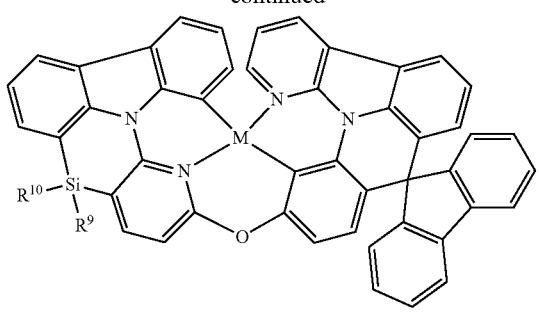
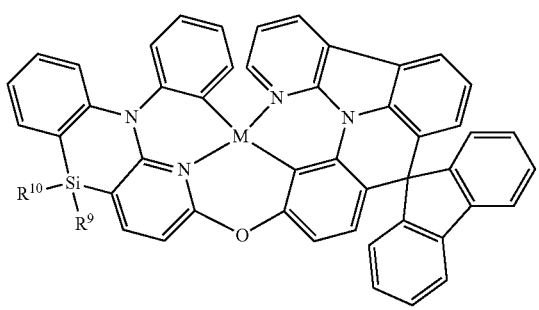
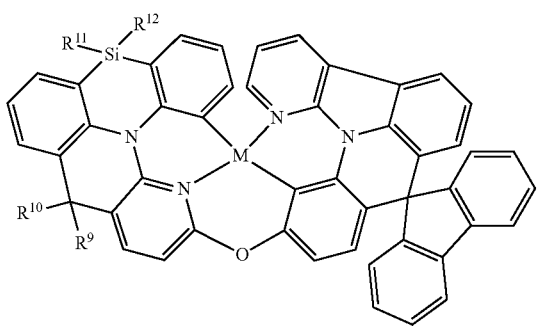
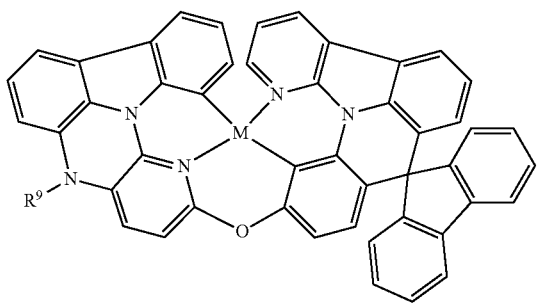
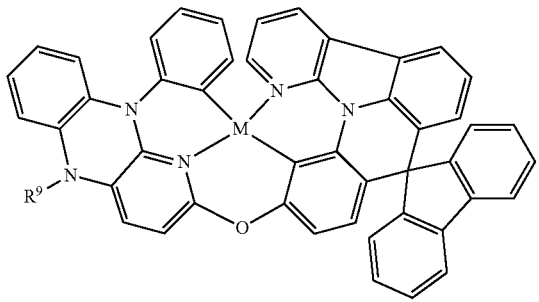
114
-continued
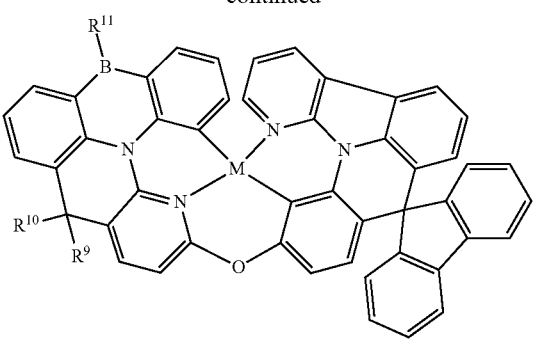
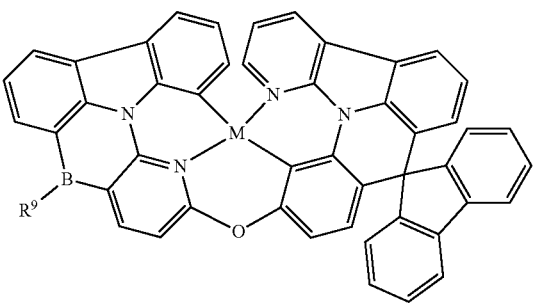
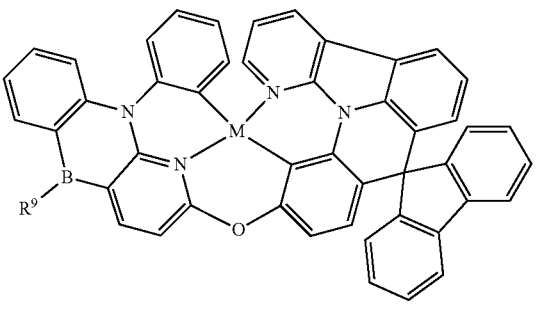
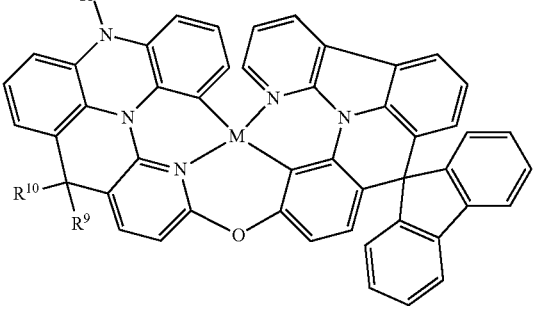
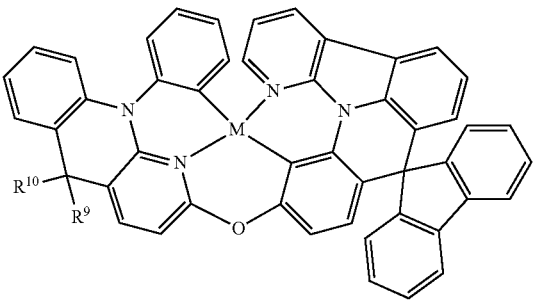

115
-continued
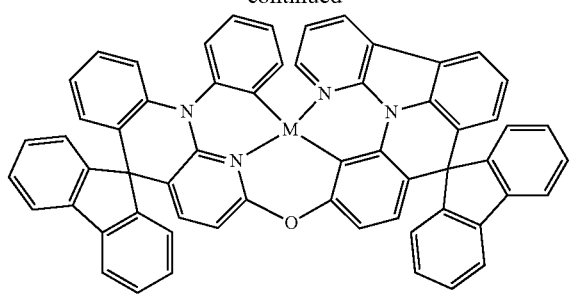
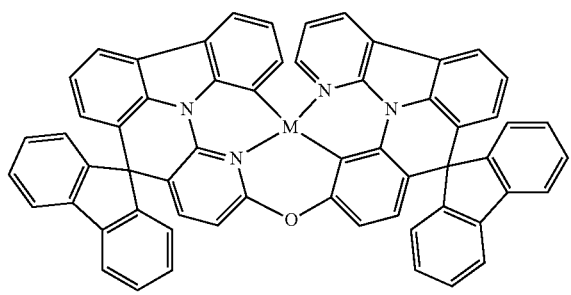
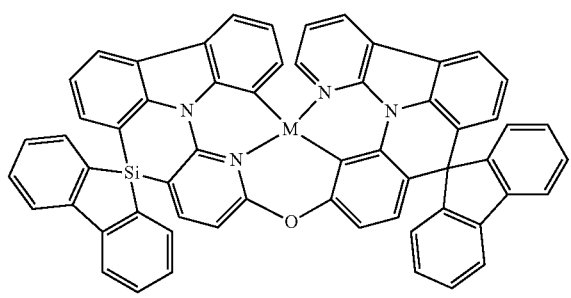
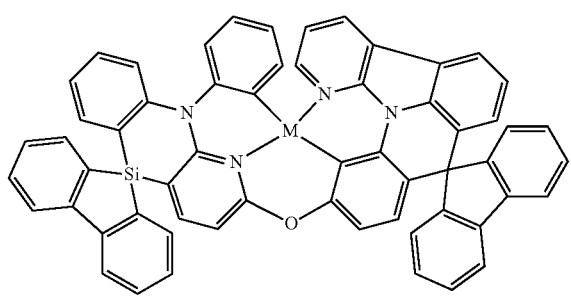
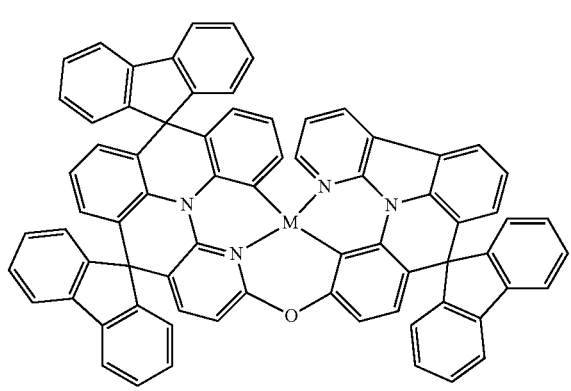
116
-continued
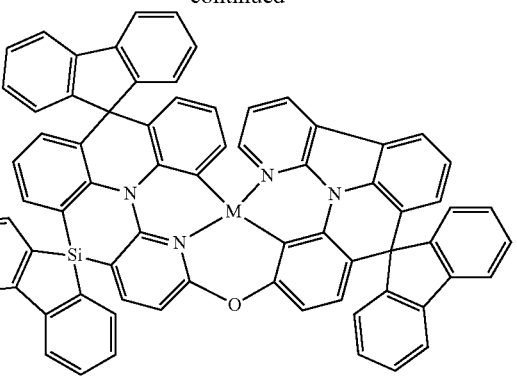
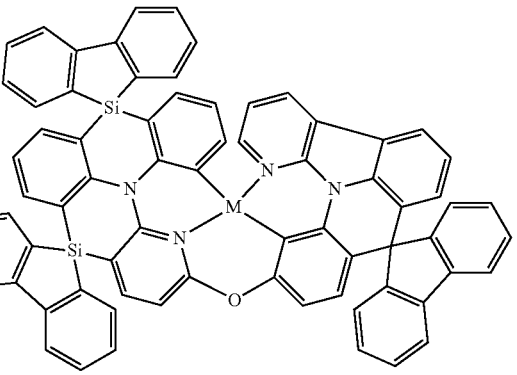
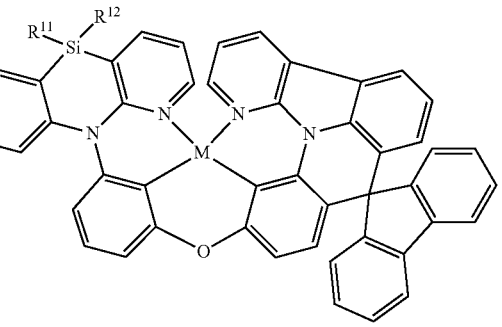

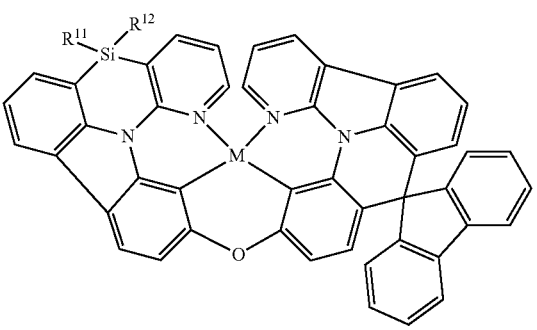

-continued
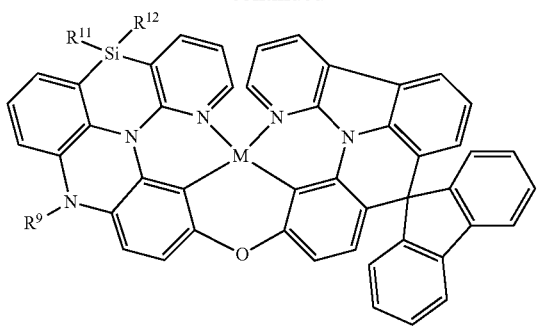
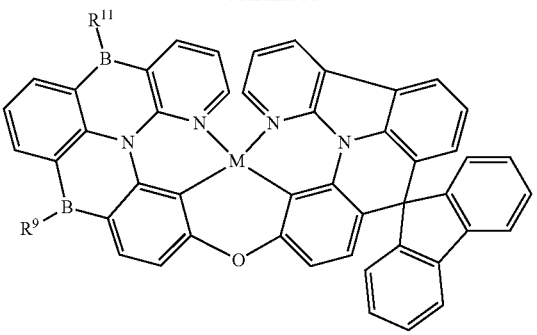
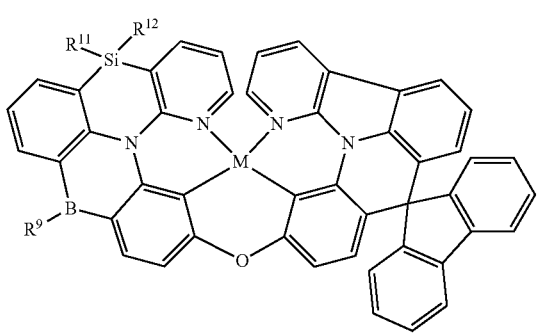
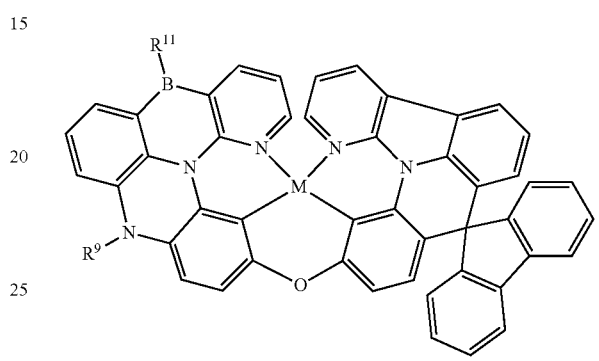
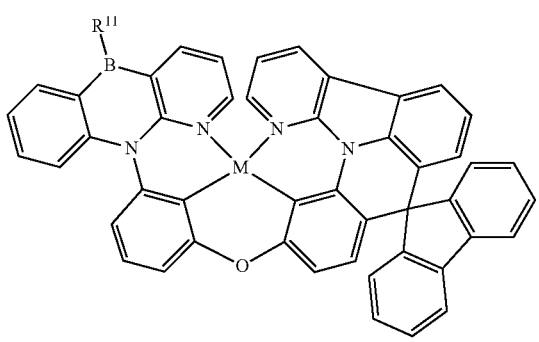
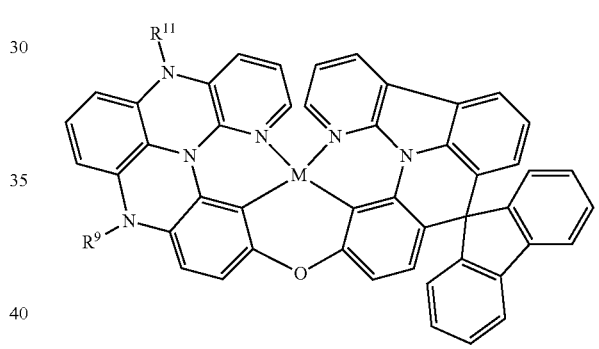
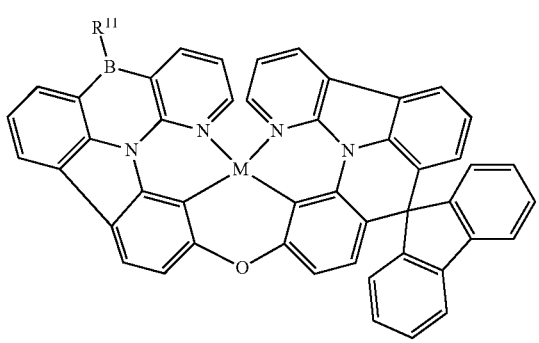
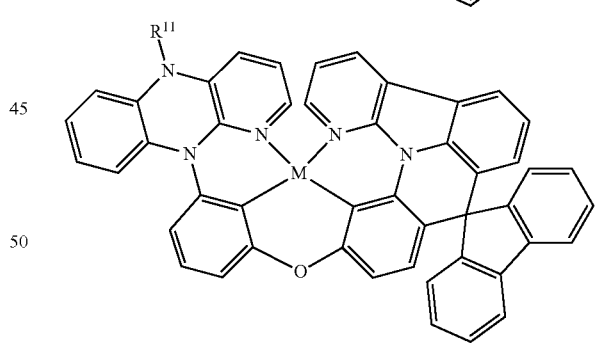
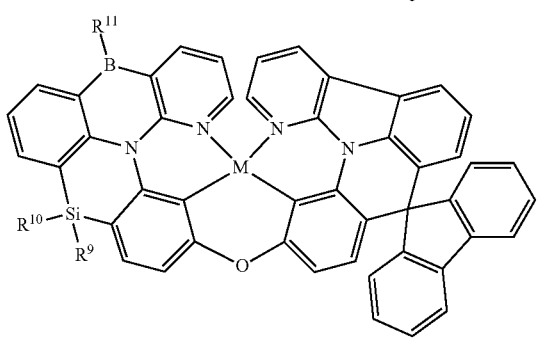
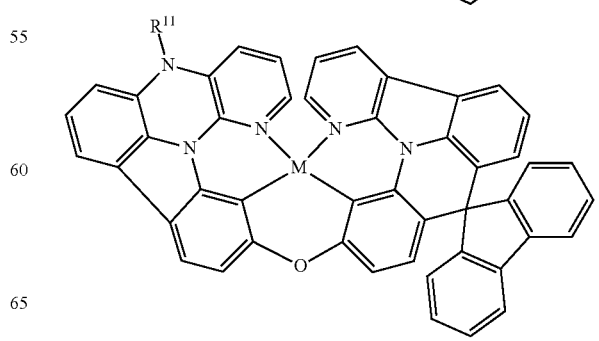

-continued
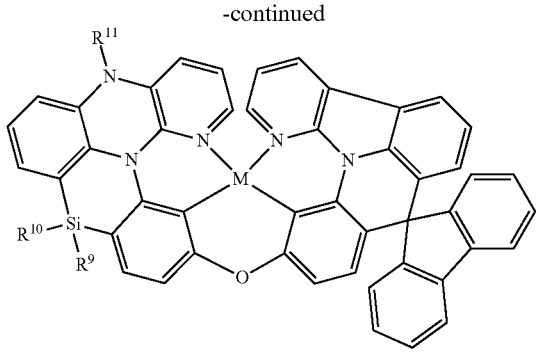
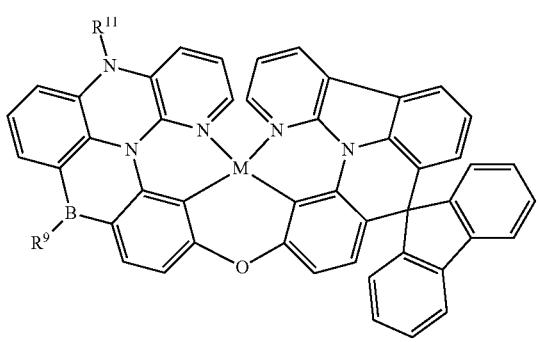
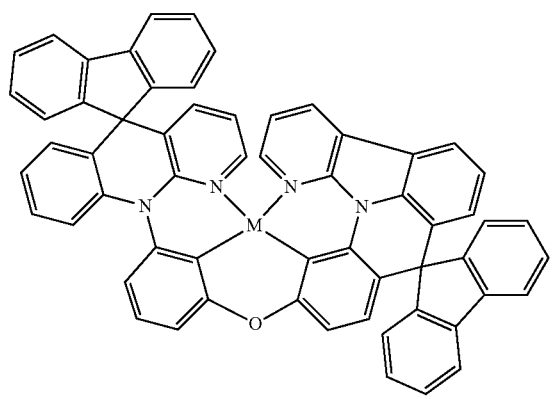
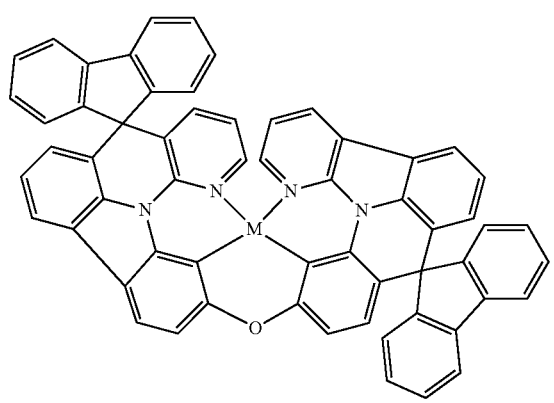
-continued
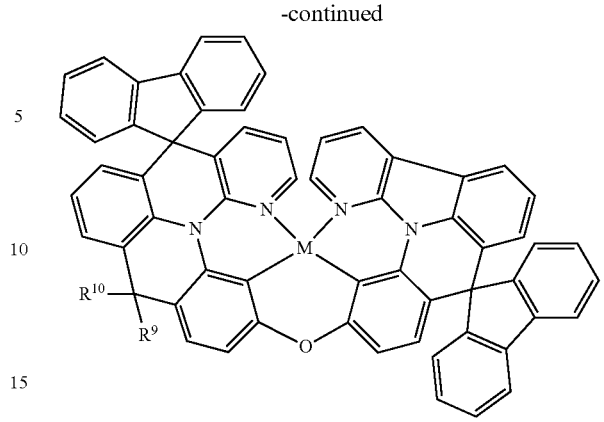
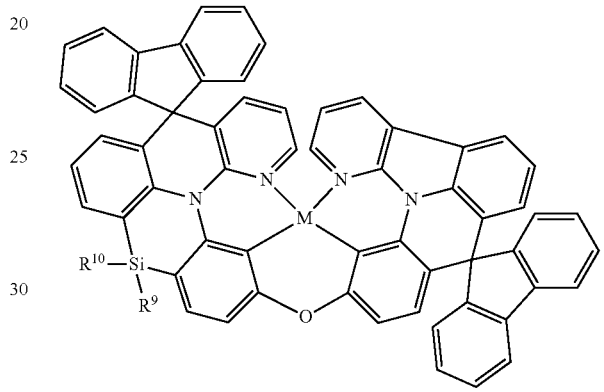
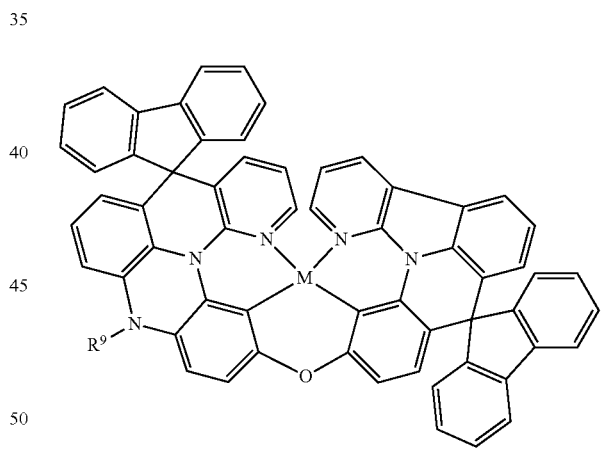
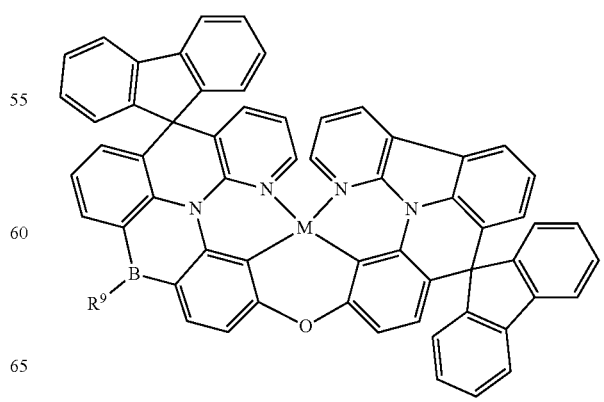

121
-continued
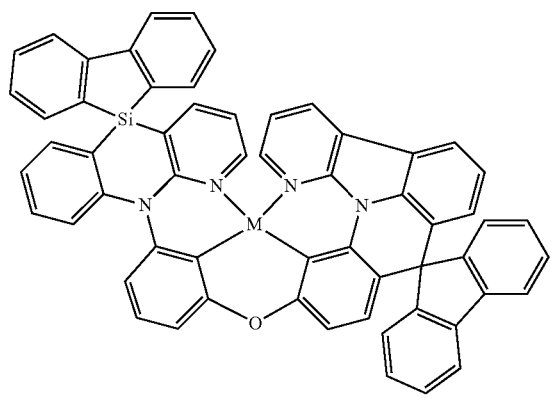
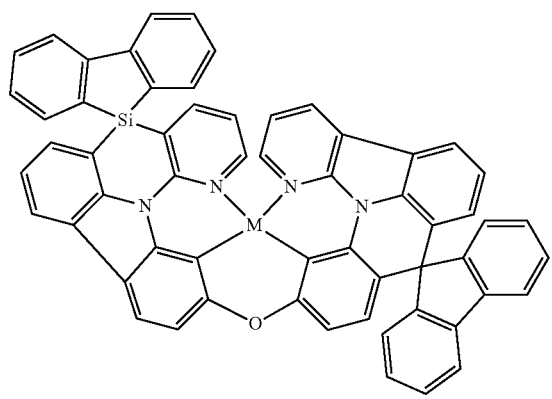
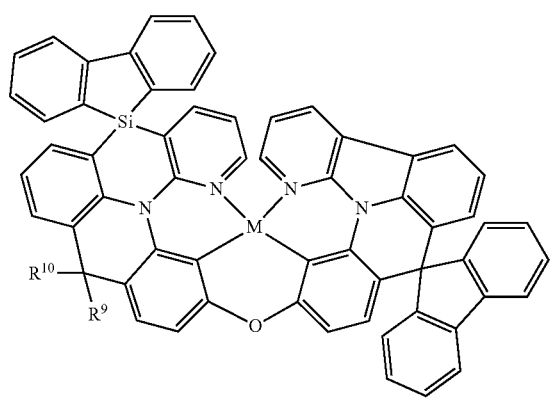
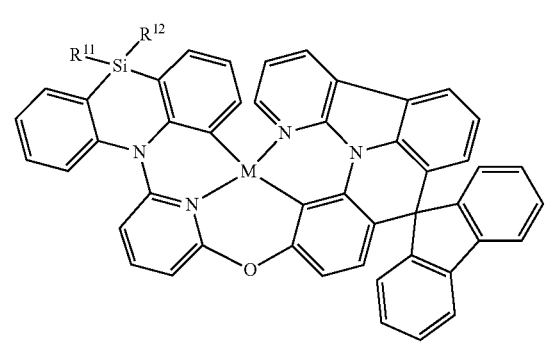
122
-continued
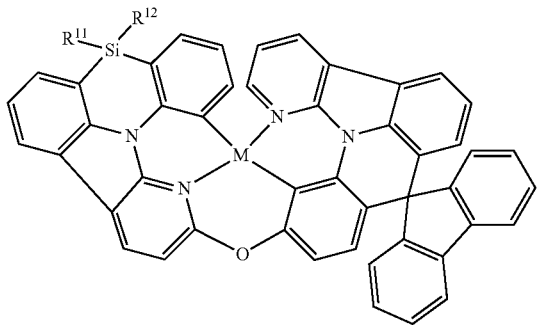
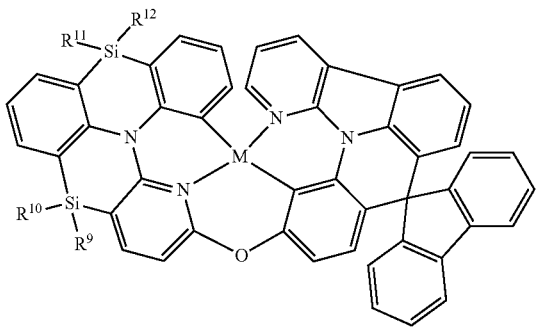
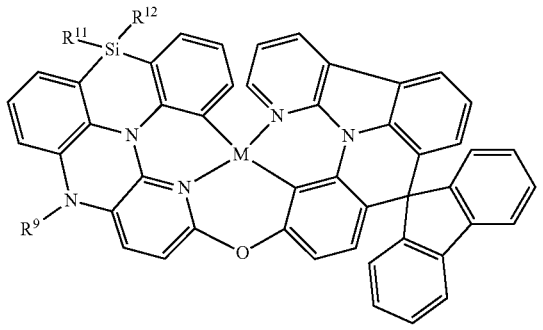
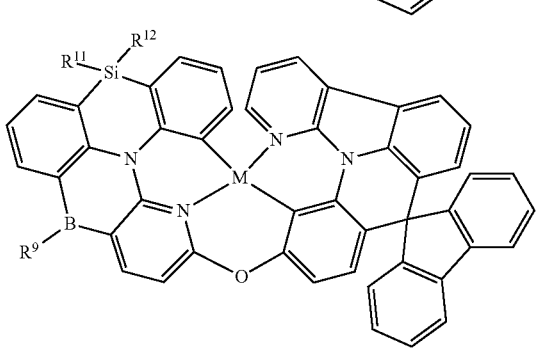
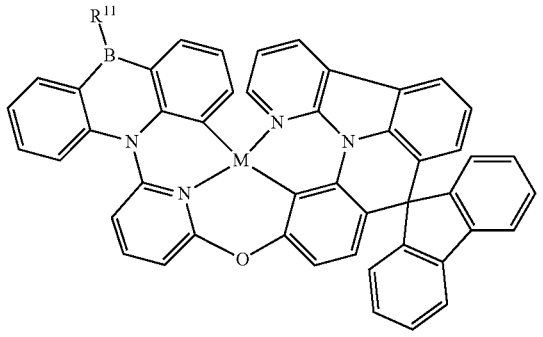

123
-continued
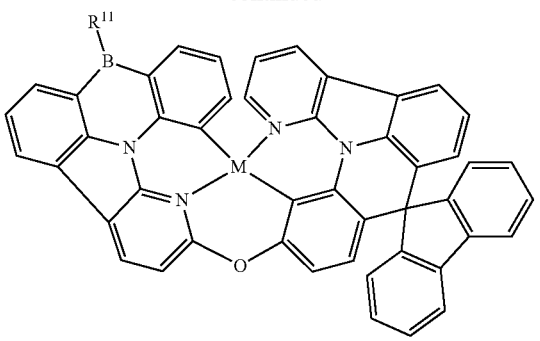
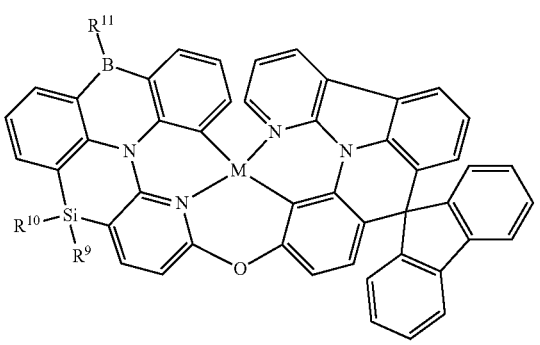
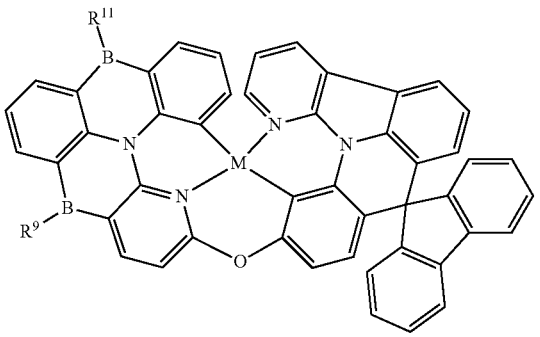
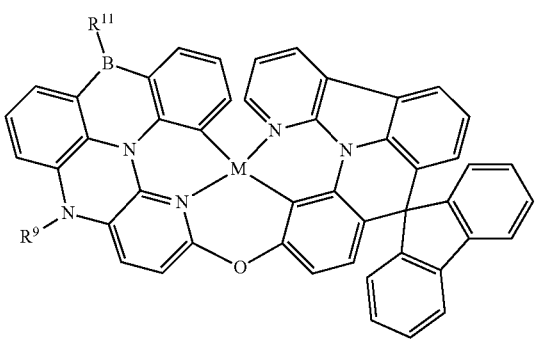
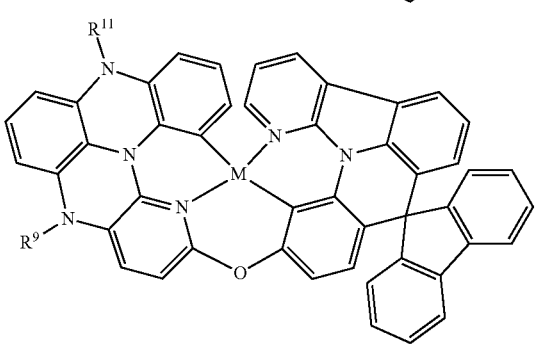
124
-continued
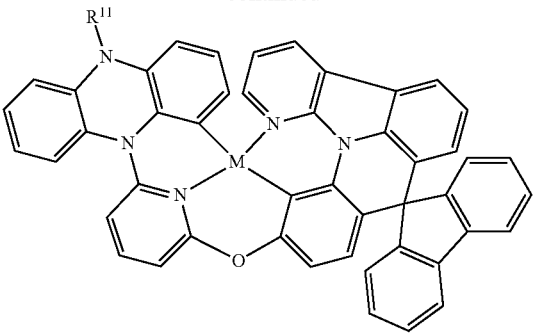
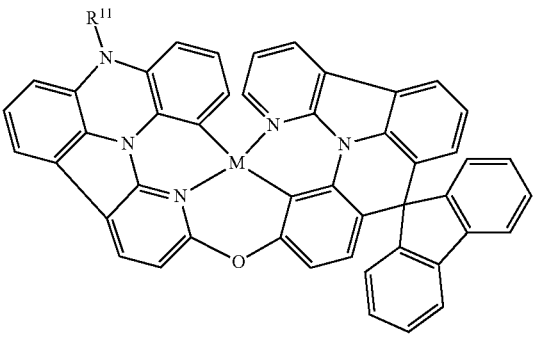
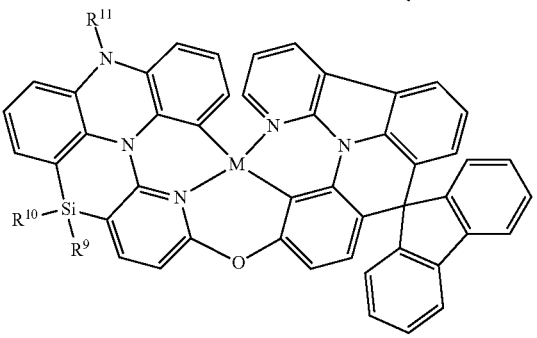
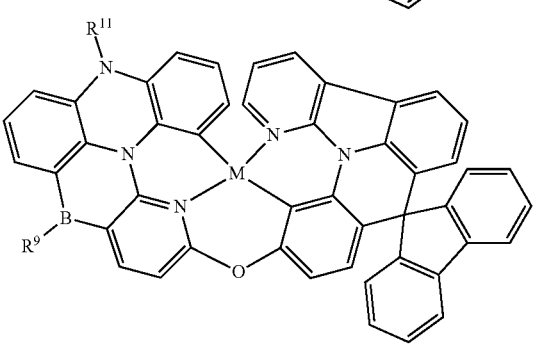
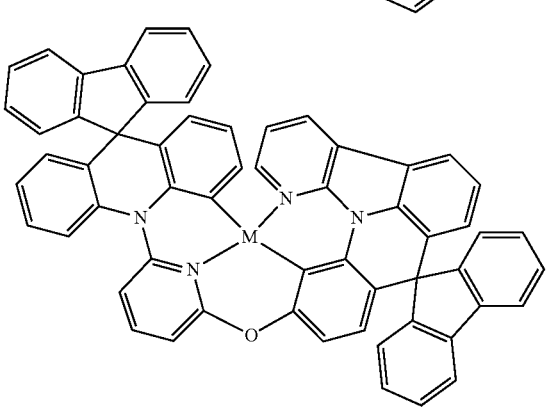

125
-continued
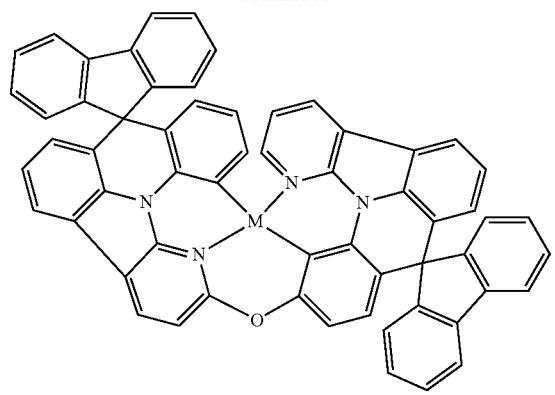
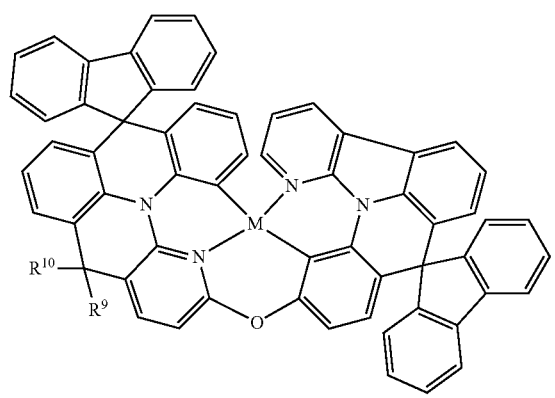
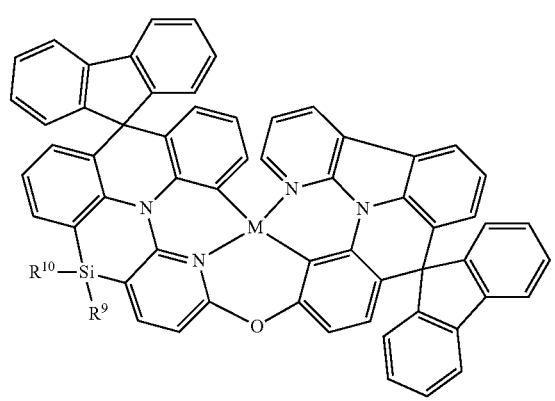
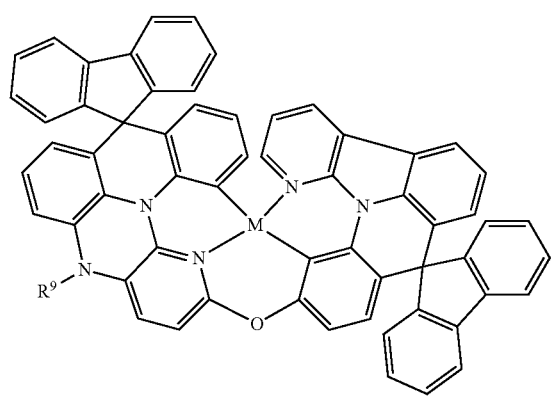
126
-continued
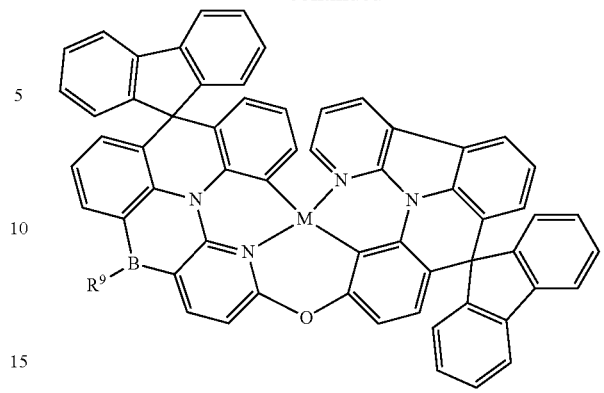
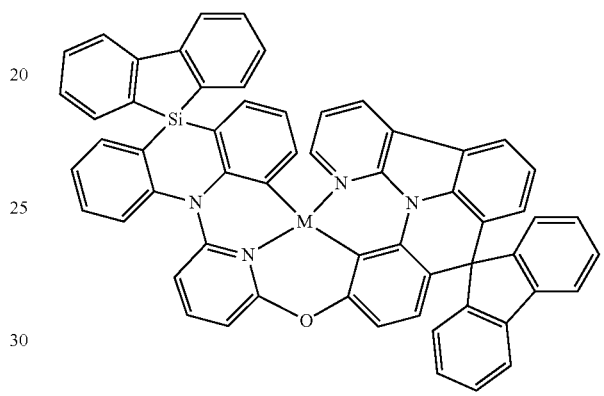
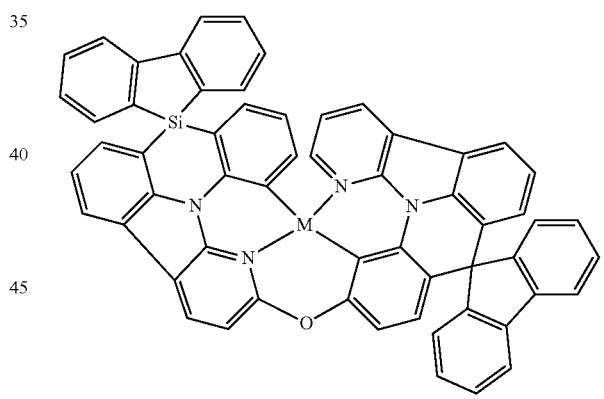
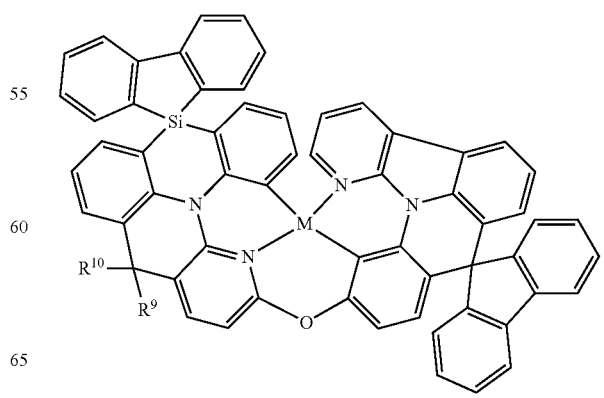

127
-continued
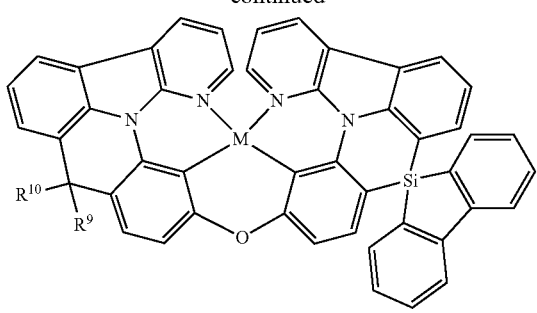
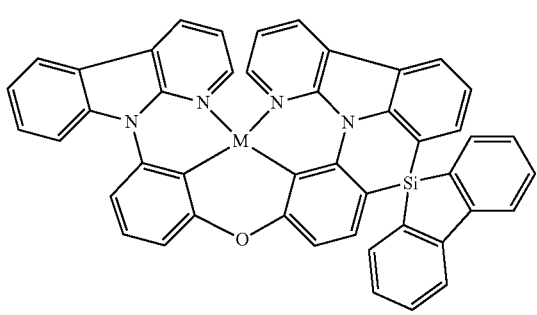
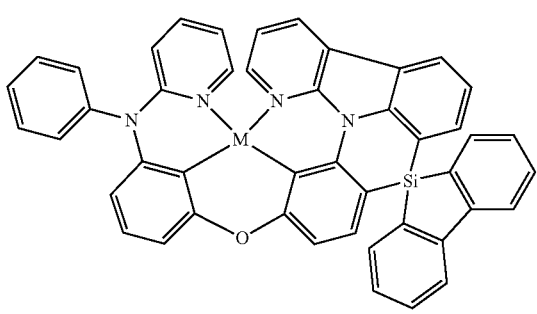
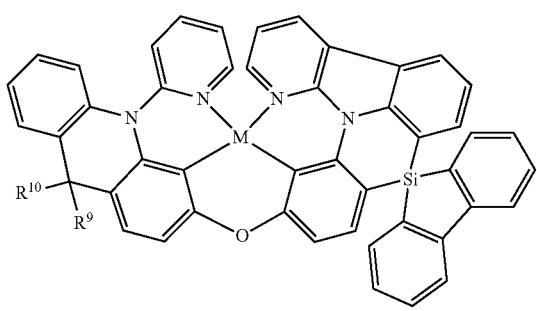
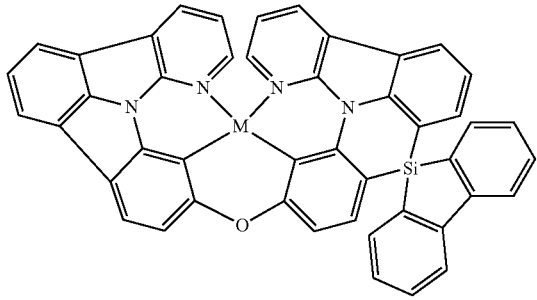
128
-continued
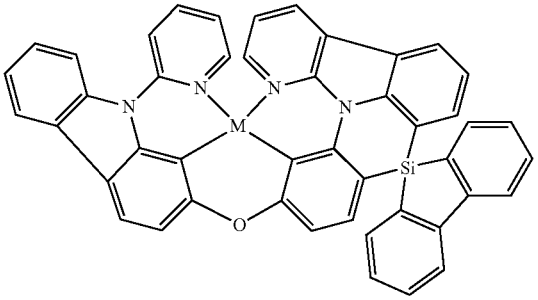
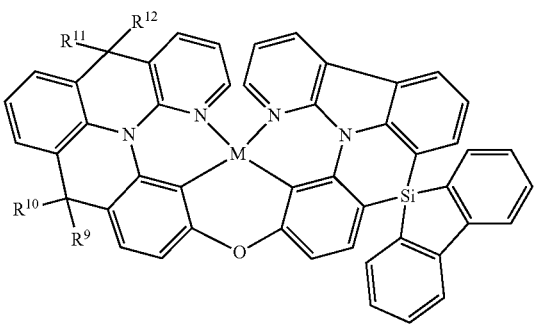
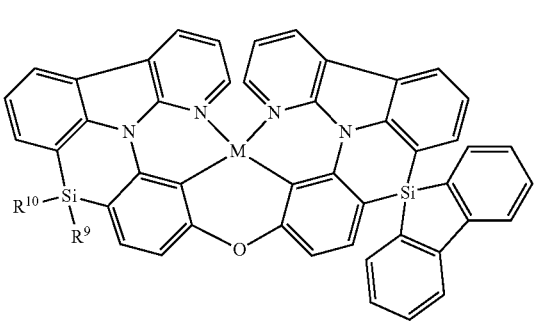
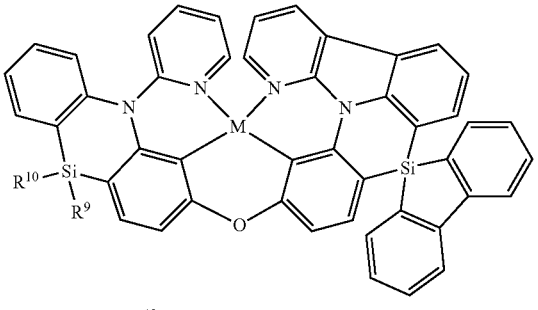
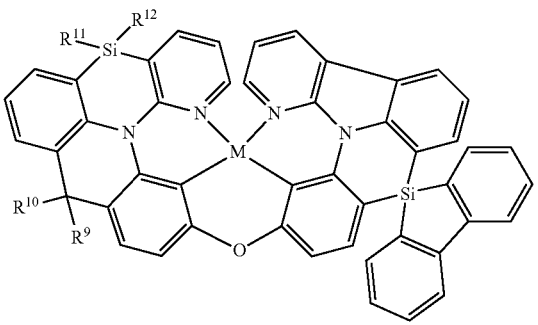

129
-continued
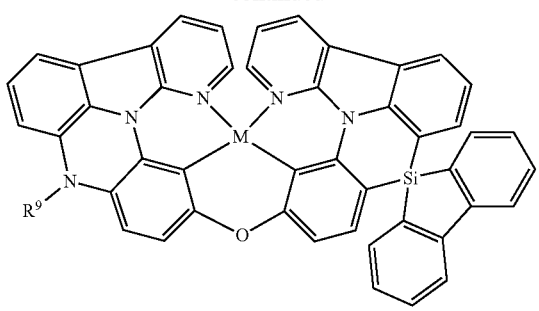
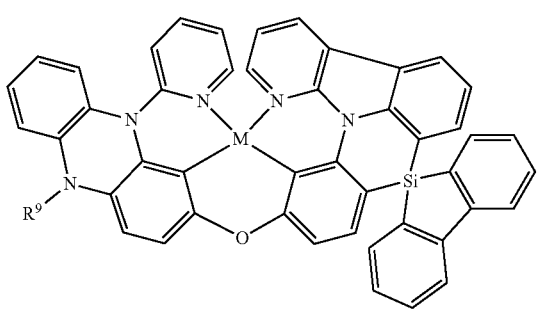
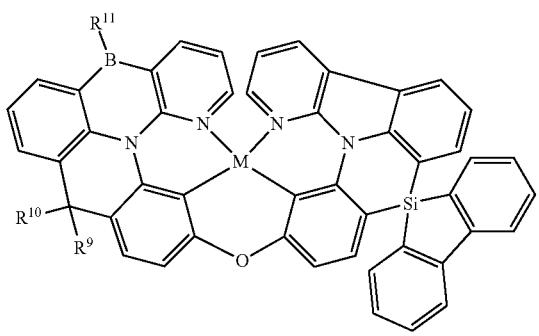
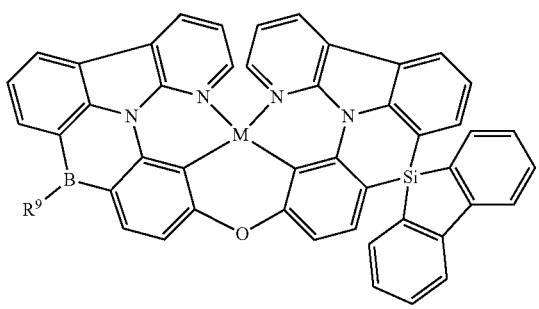
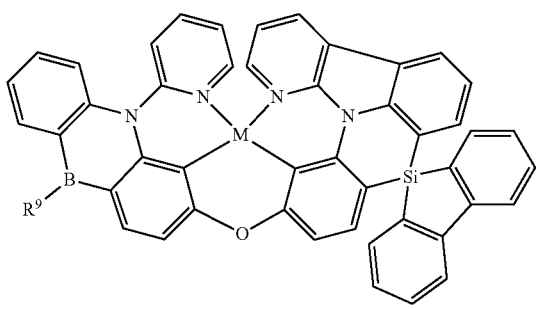
130
-continued
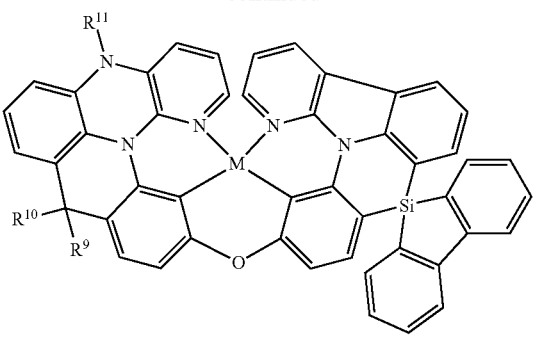
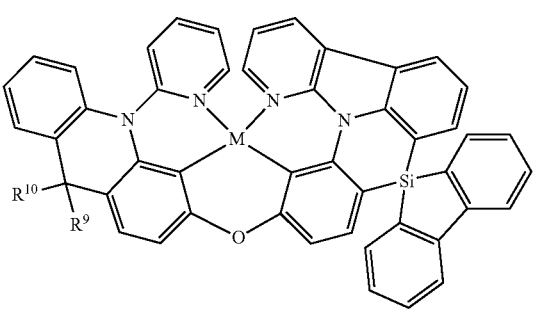
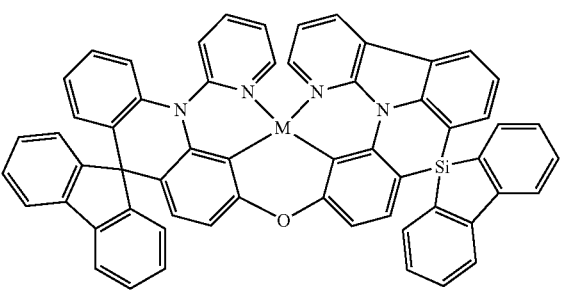
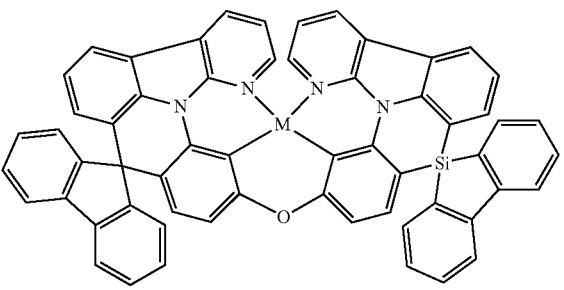
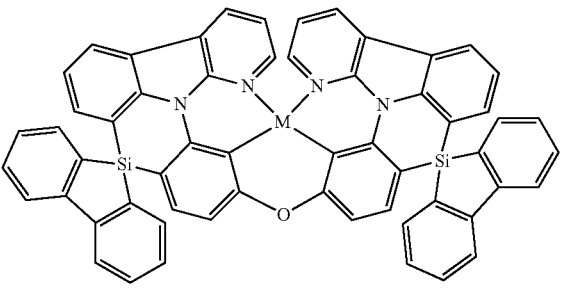

131
-continued
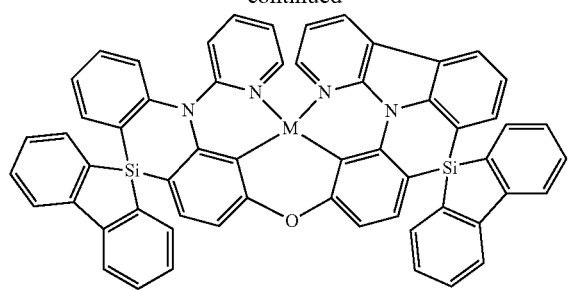
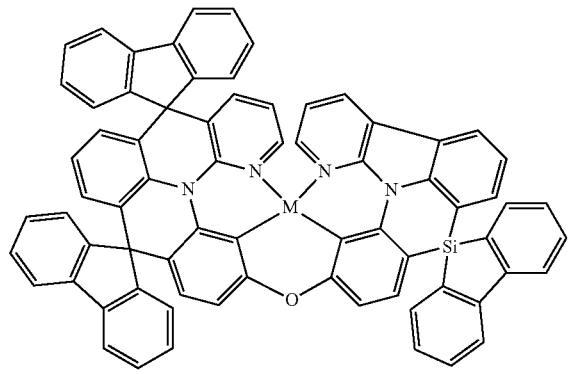
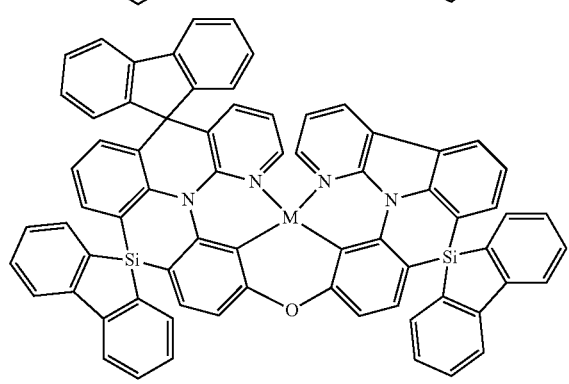
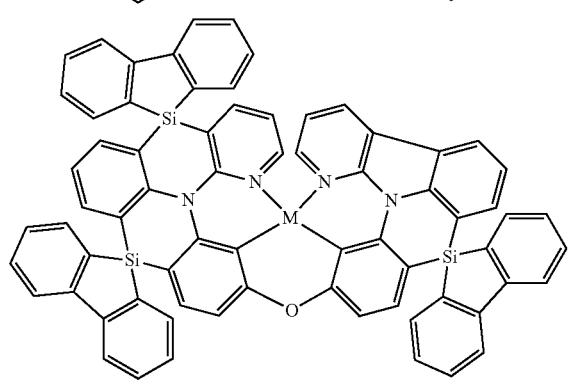
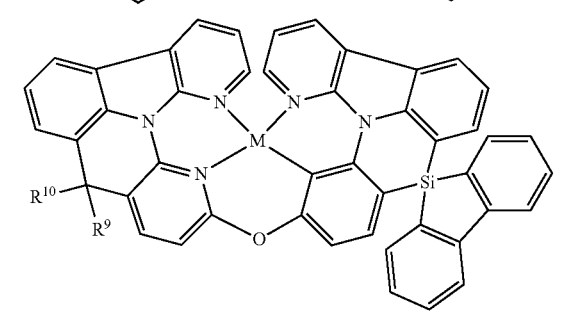
132
-continued
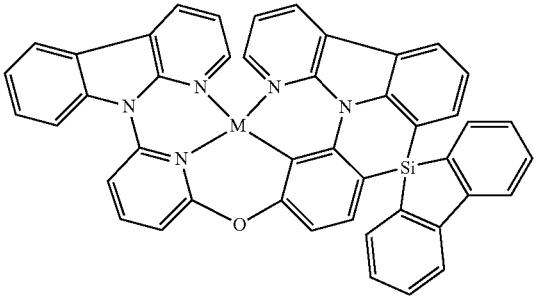
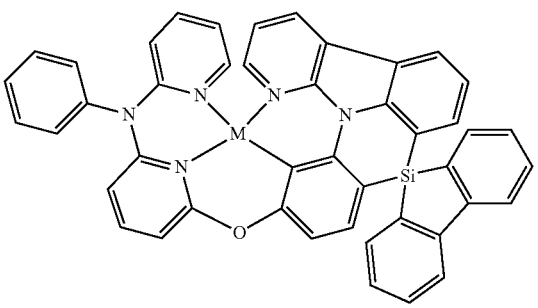
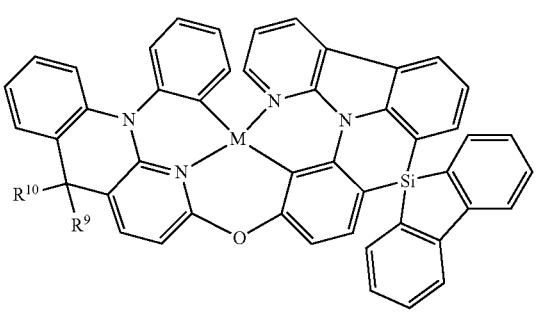
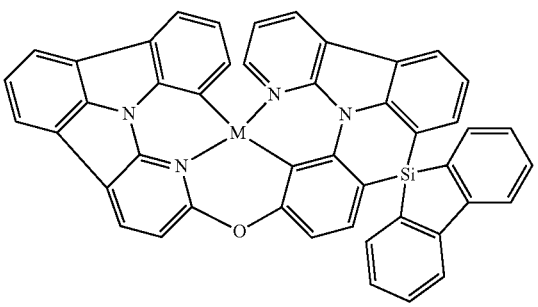
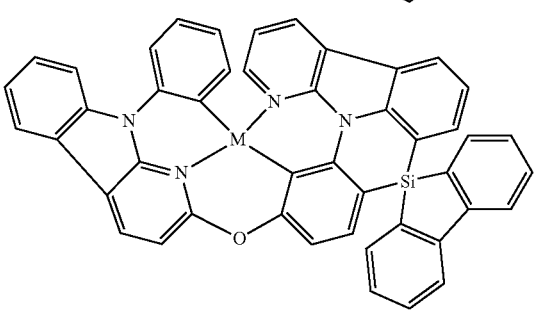

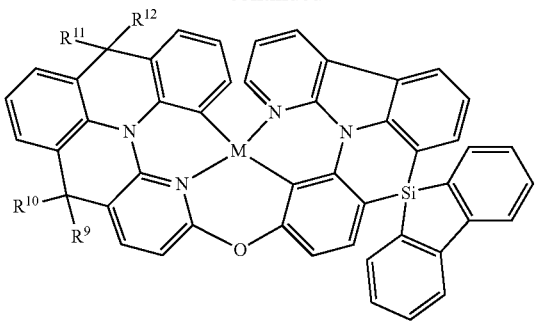
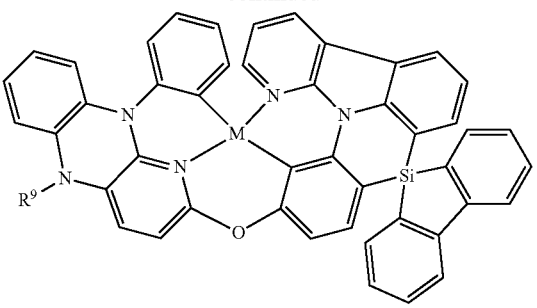
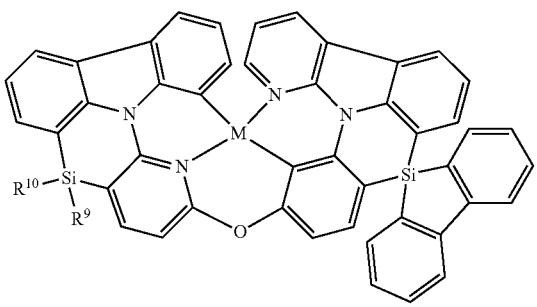
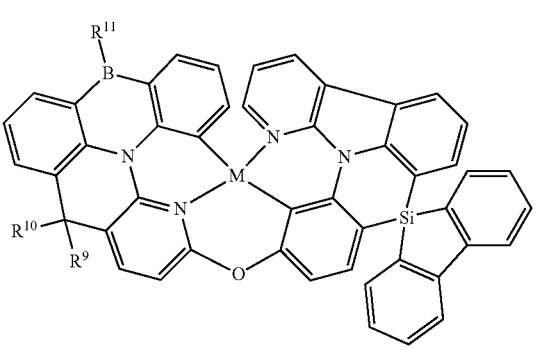
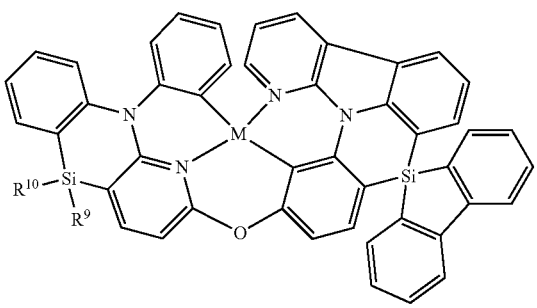
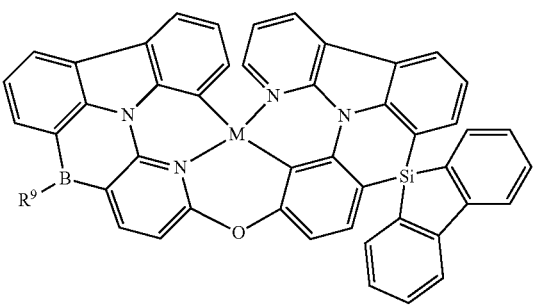
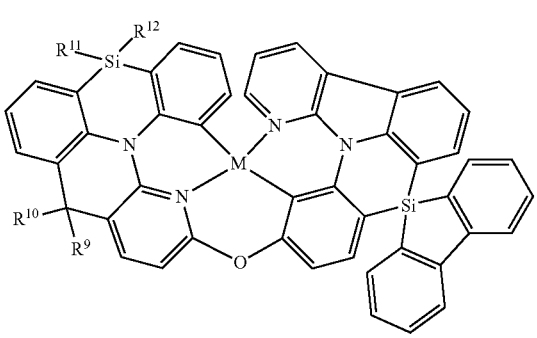
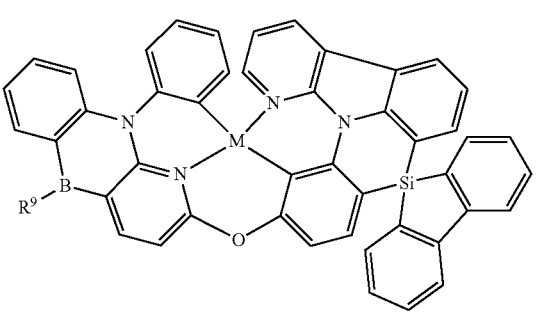
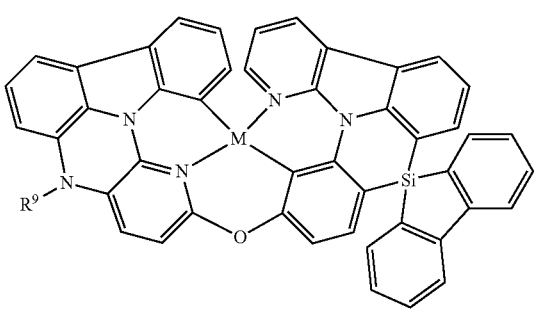
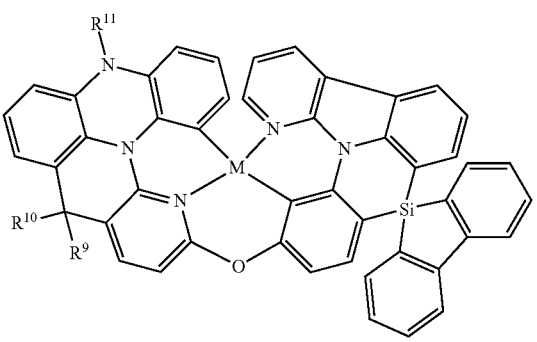

135
-continued
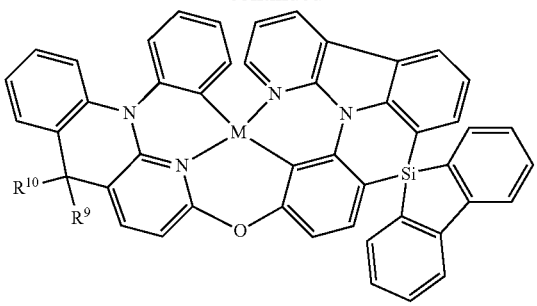
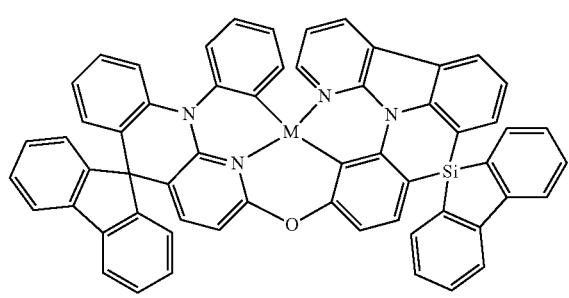
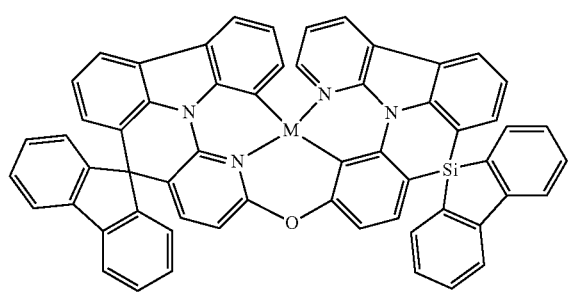
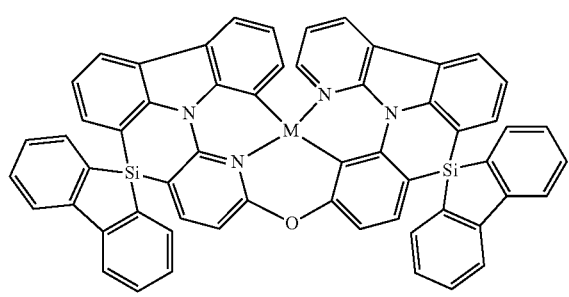
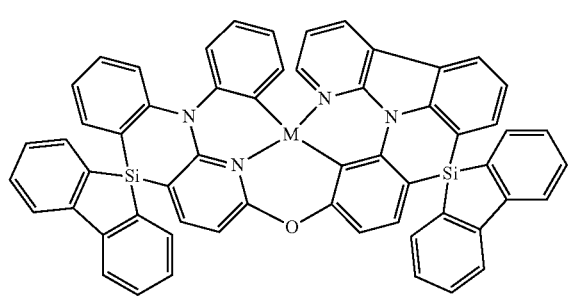
136
-continued
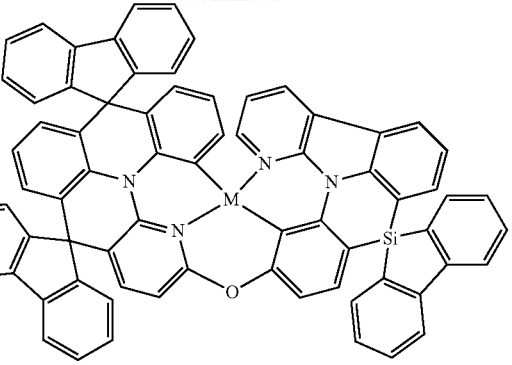
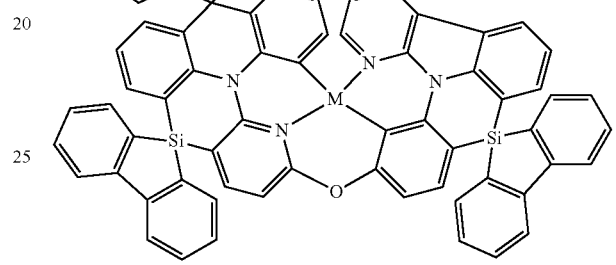
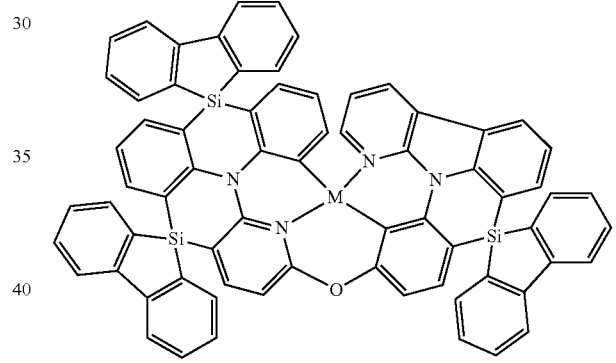
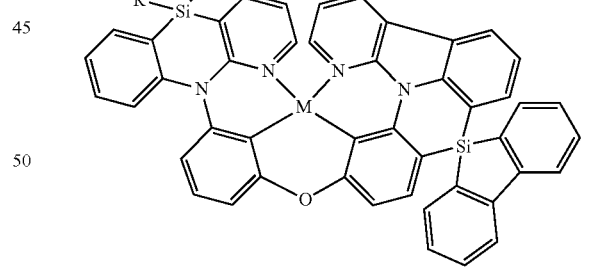
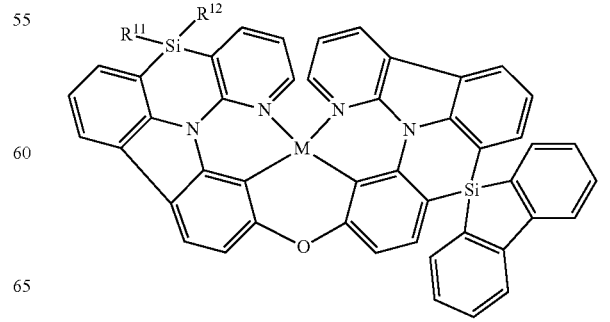

137
-continued
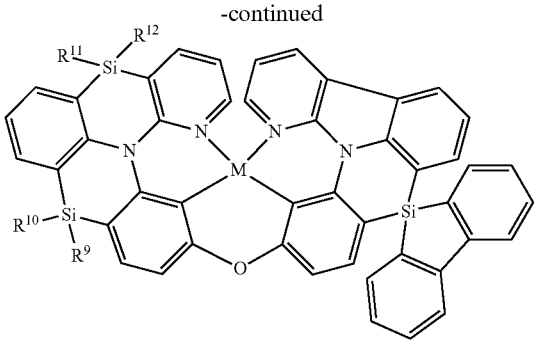
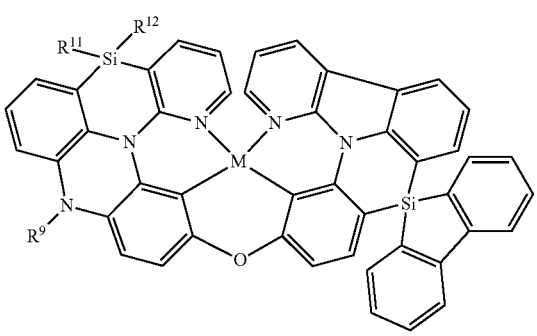
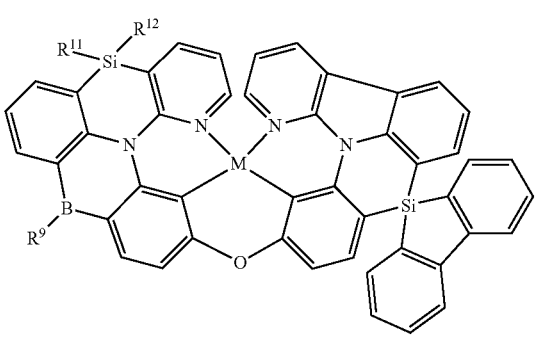
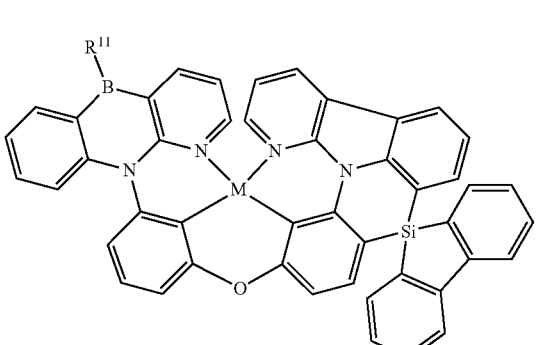
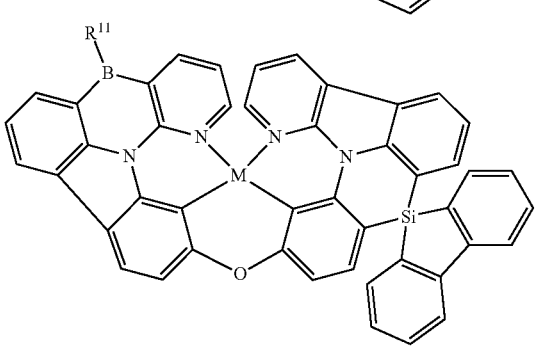
138
-continued
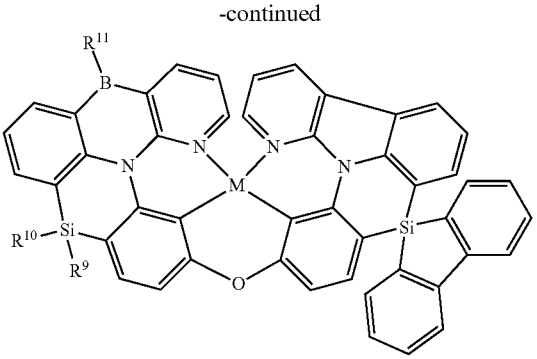
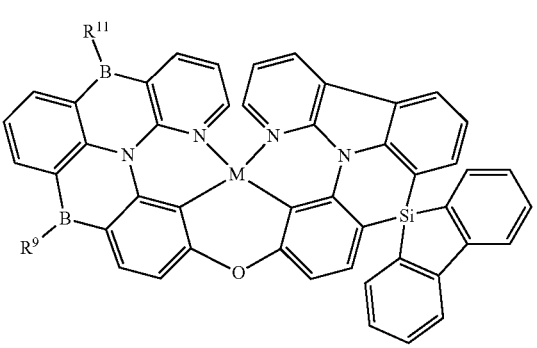
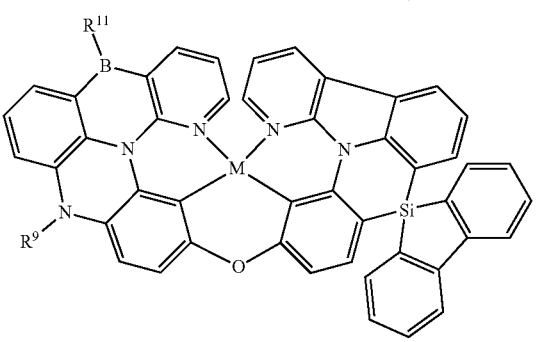
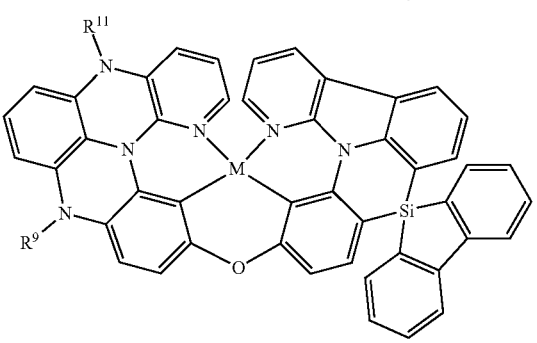
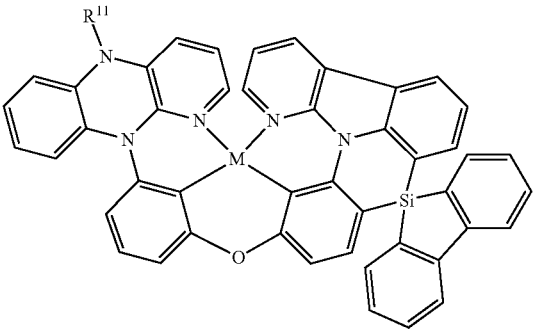

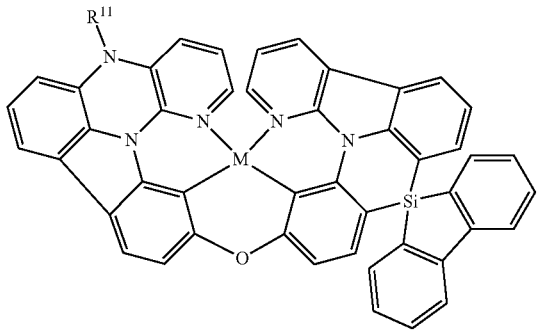
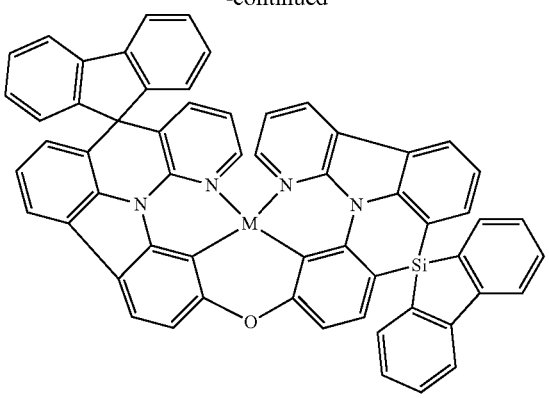
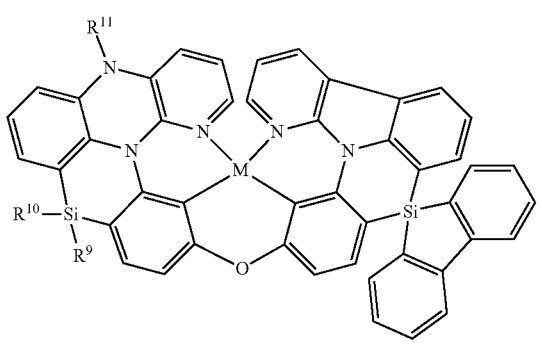
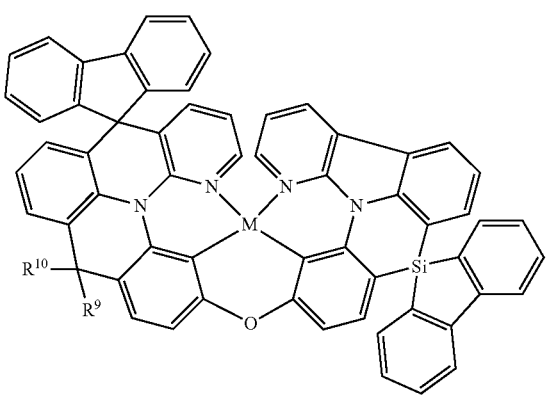
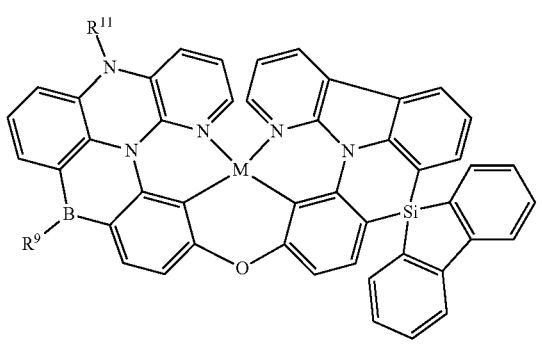
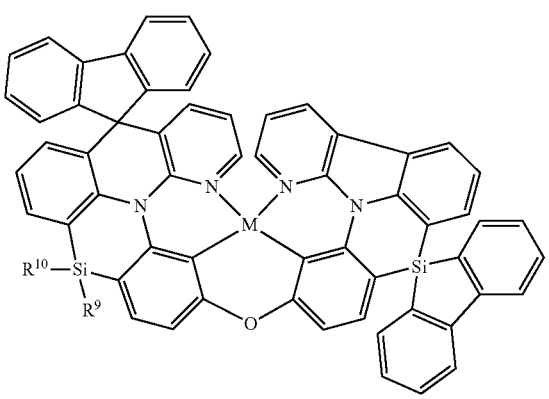
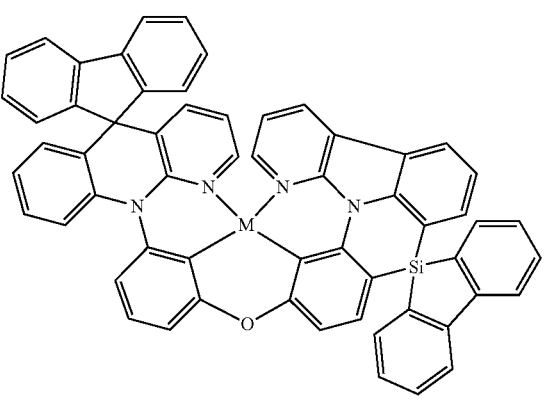
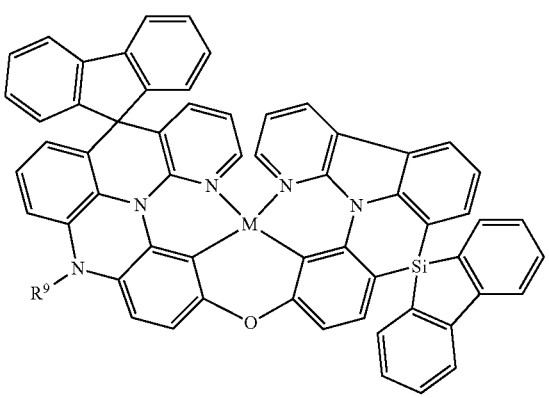

141
-continued
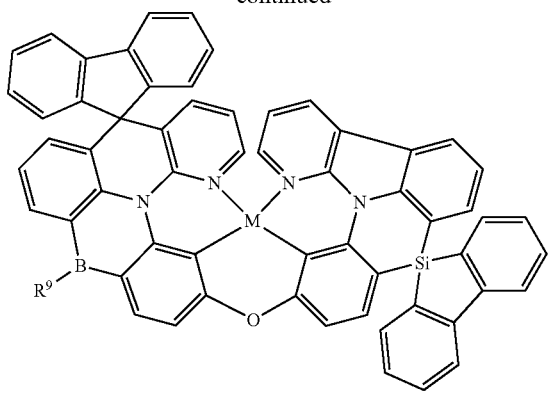
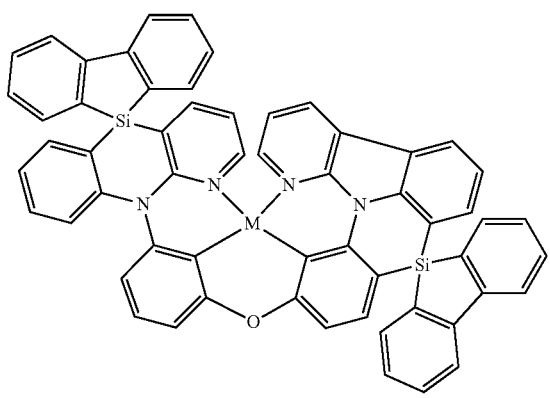
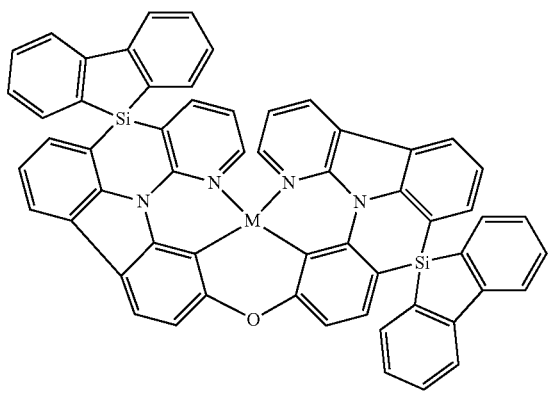
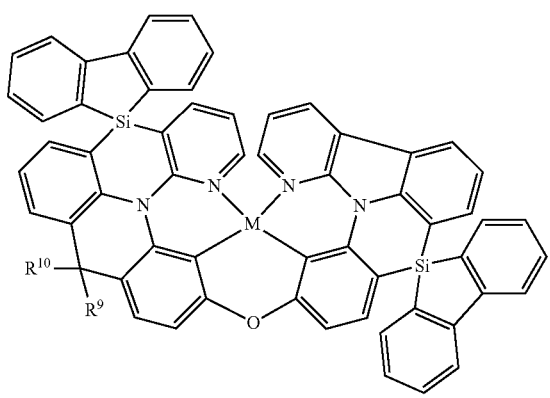
142
-continued
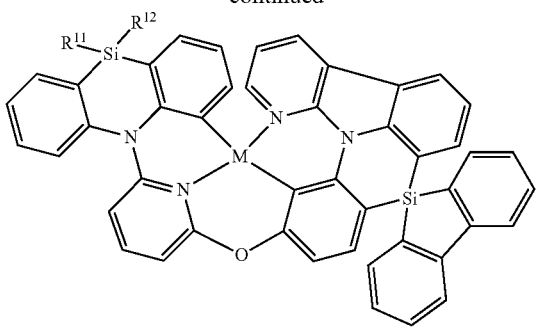
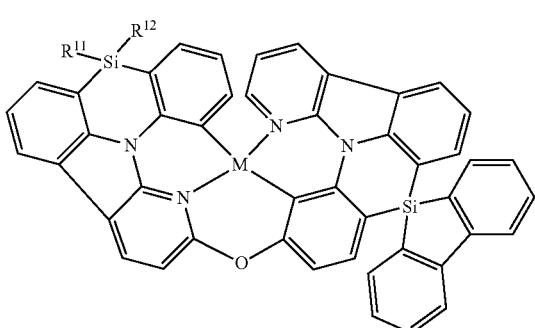
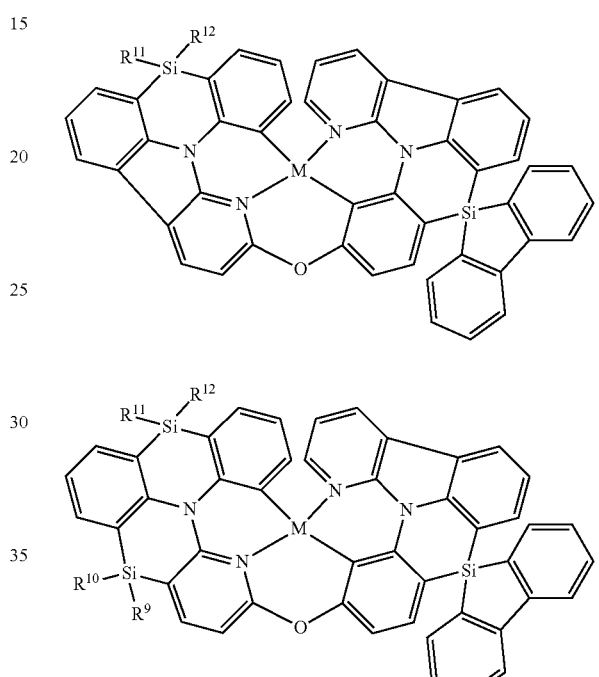

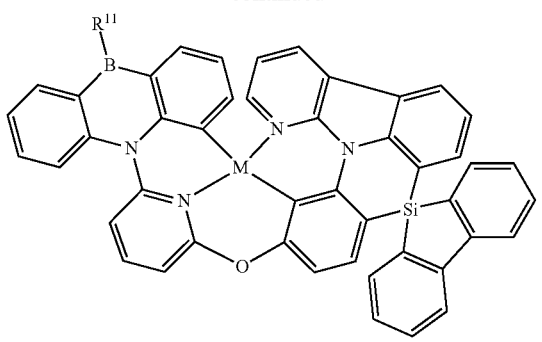
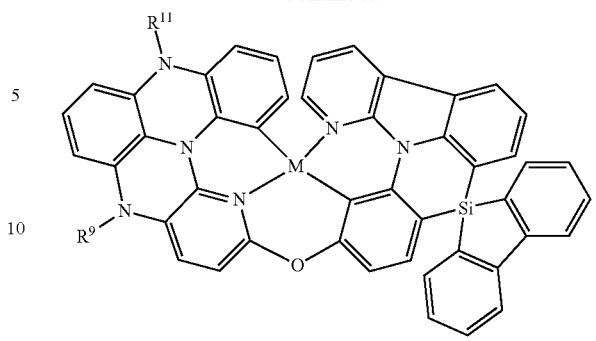
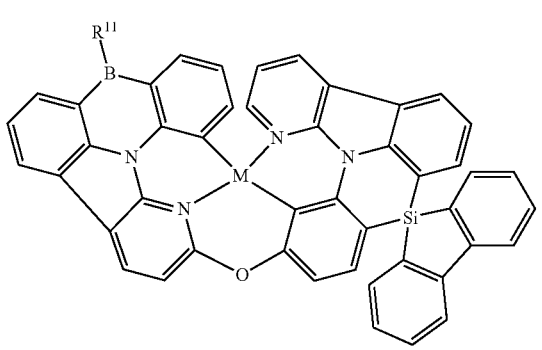
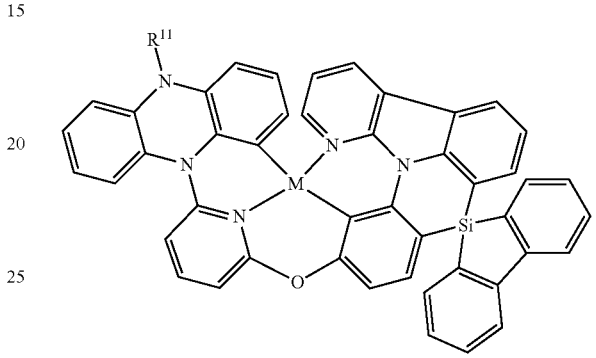
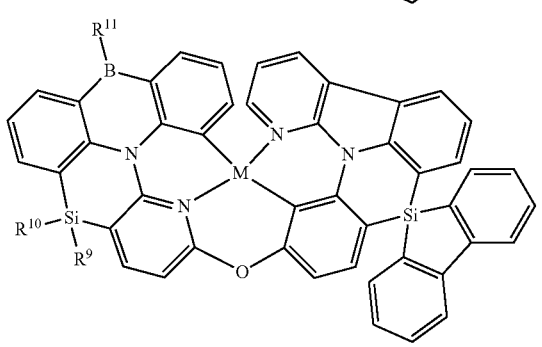
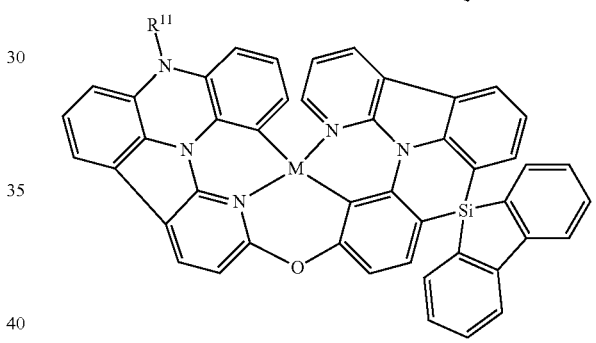
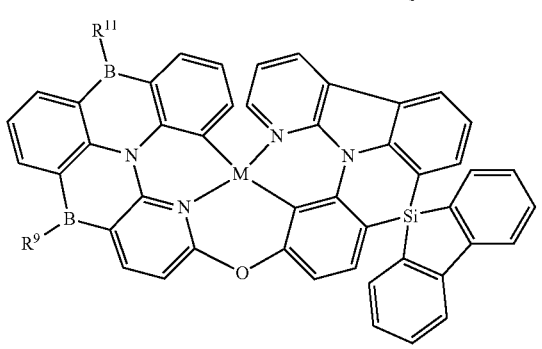
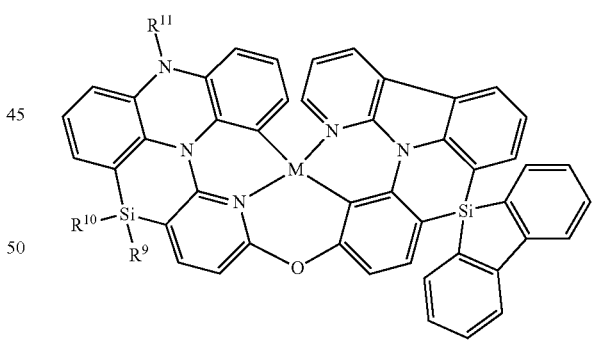
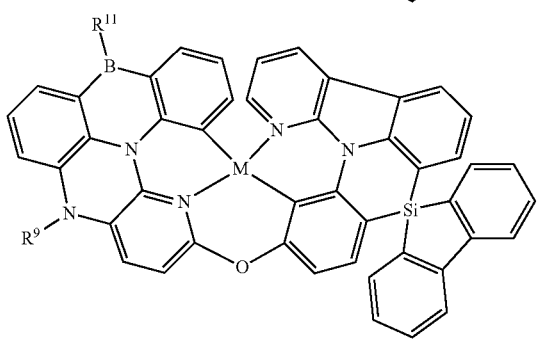
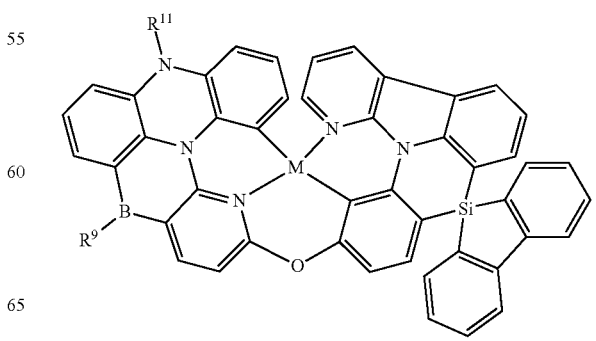

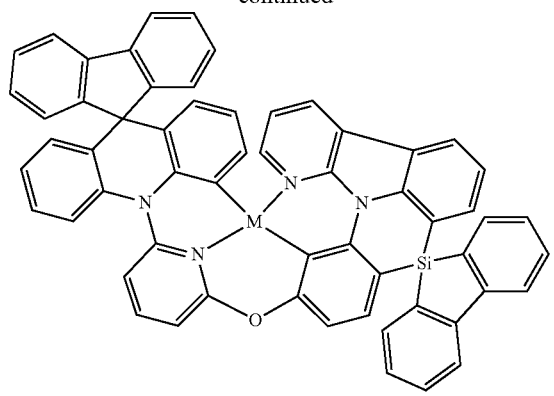
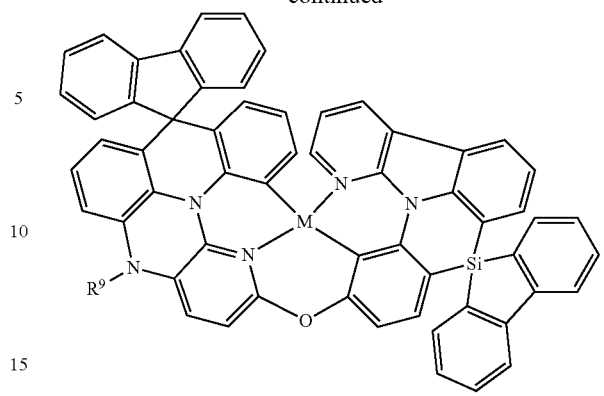
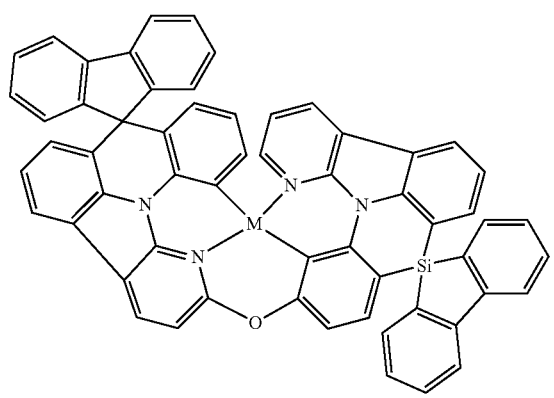
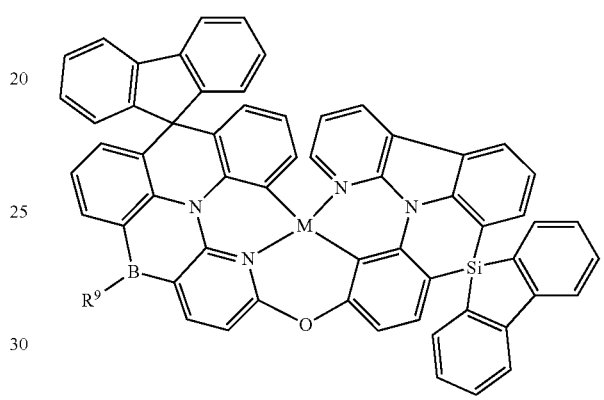
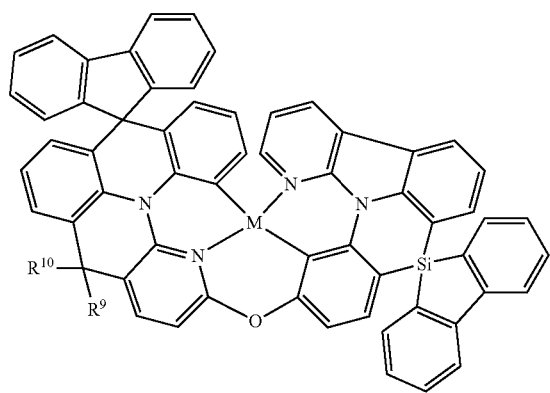
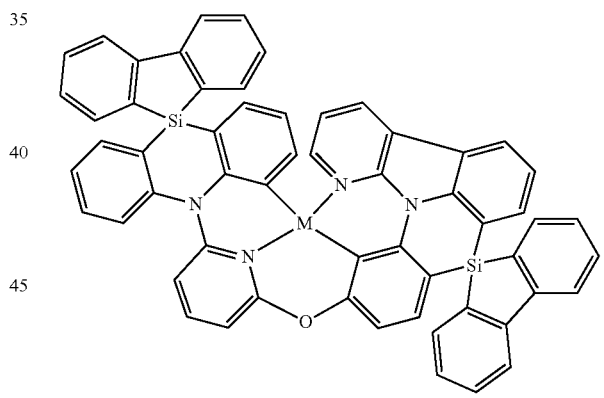
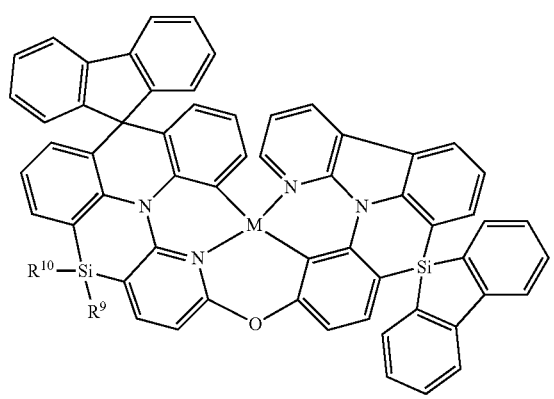
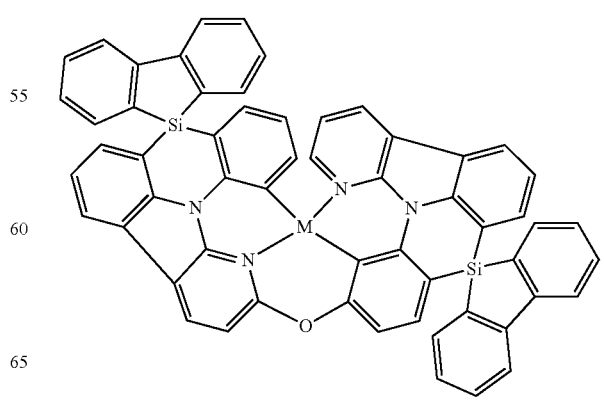

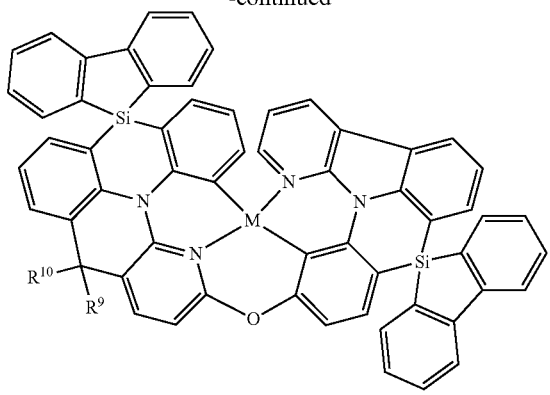
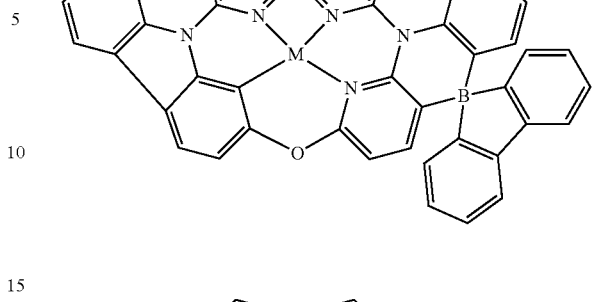
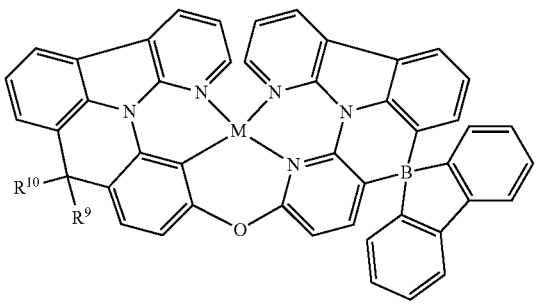
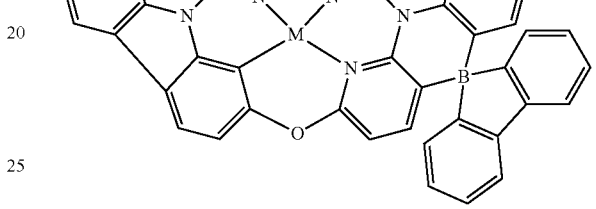
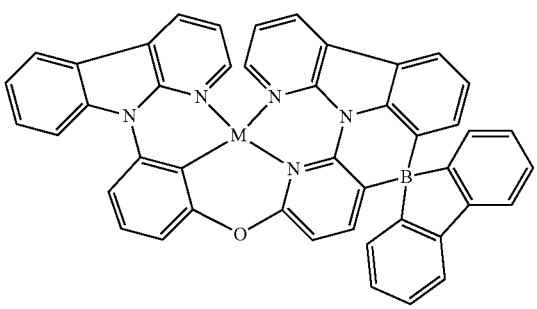
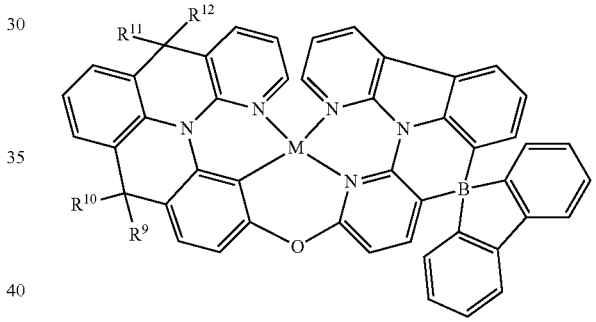
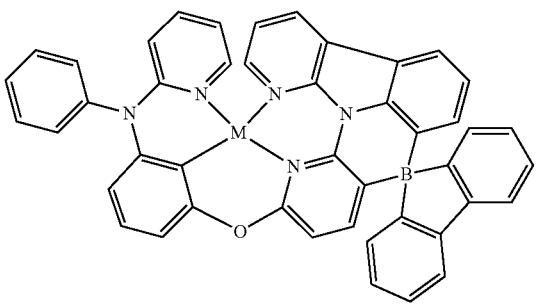
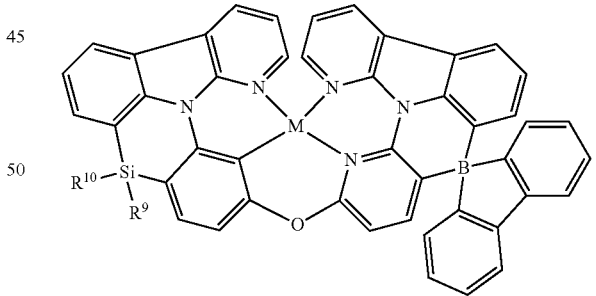
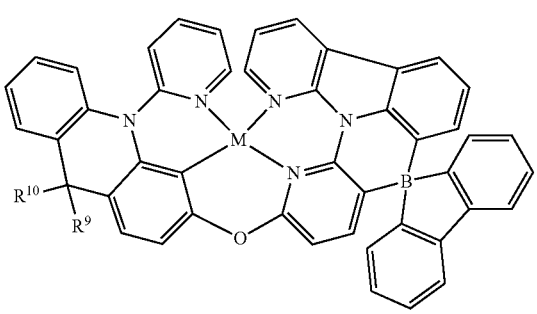
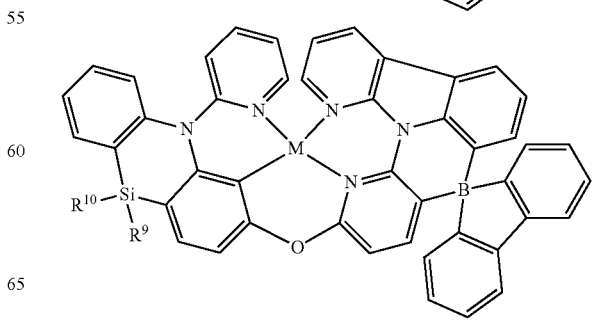

149
-continued
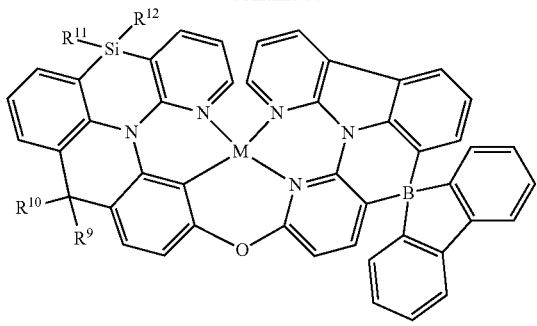
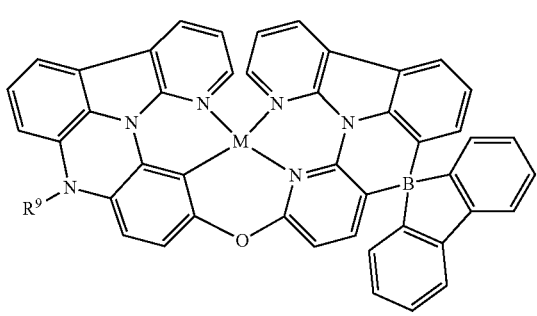
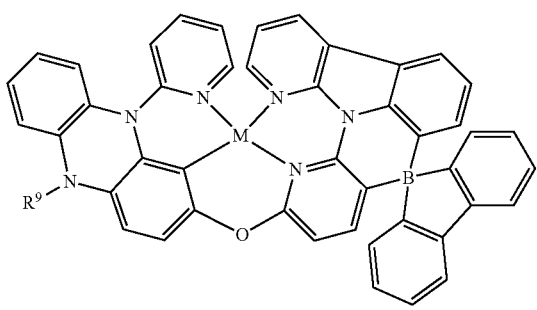
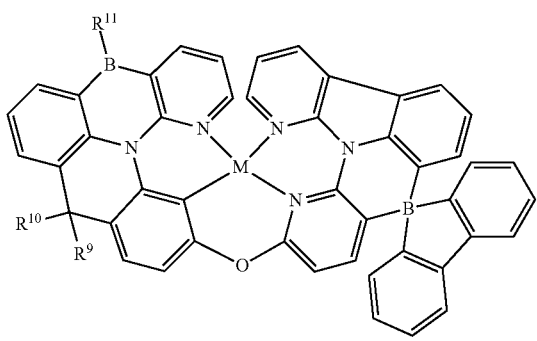
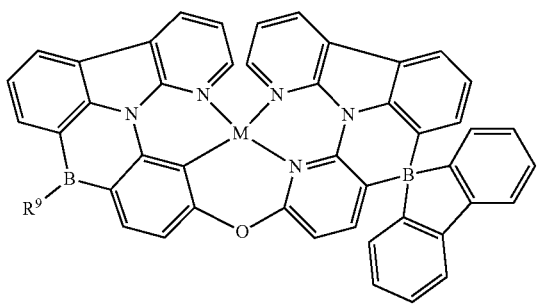
150
-continued
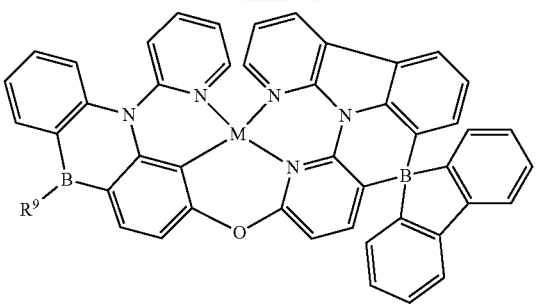
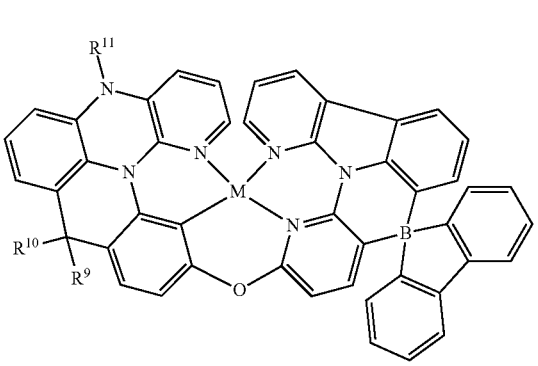
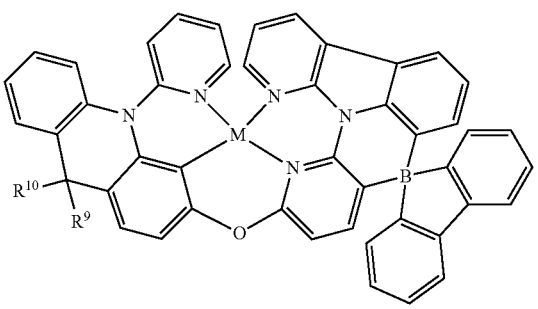
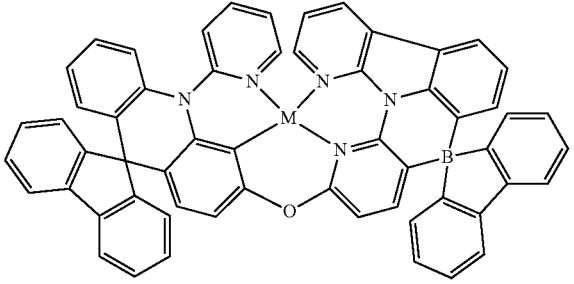
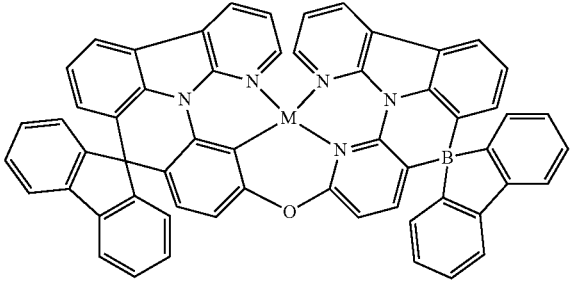

151
-continued
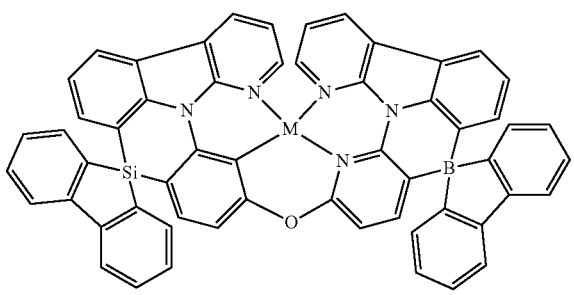
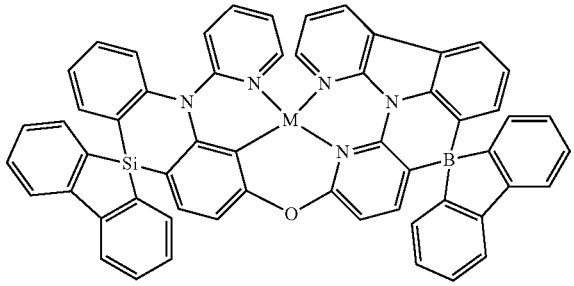
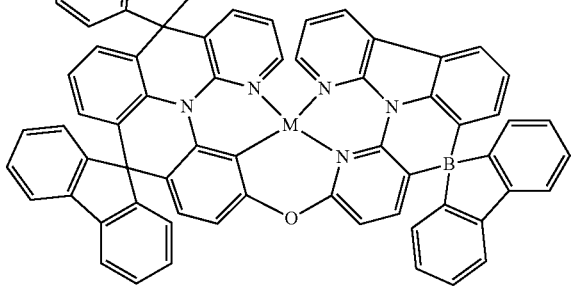
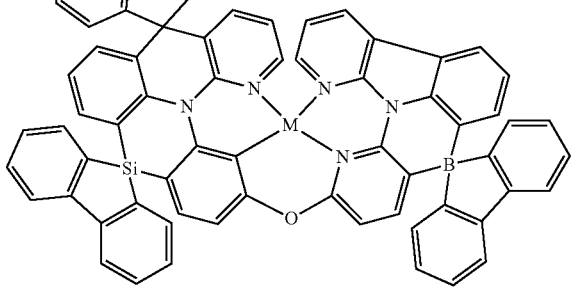
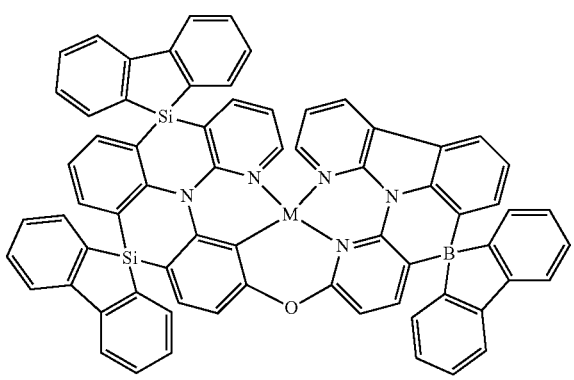
152
-continued
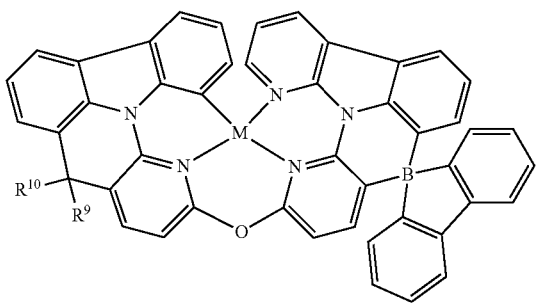
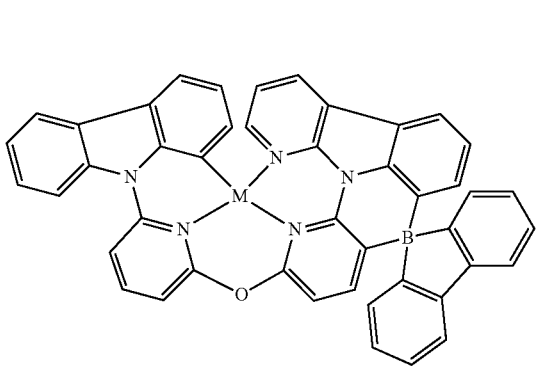
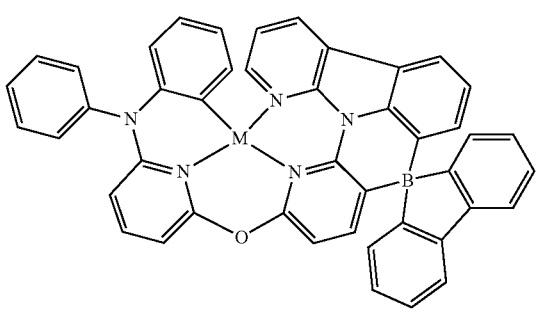
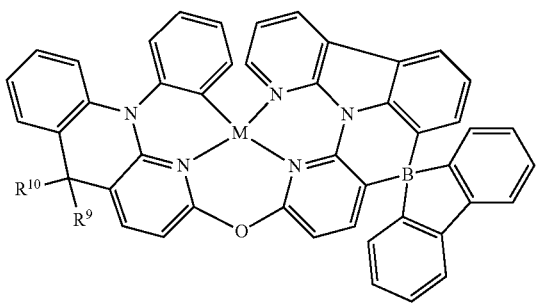
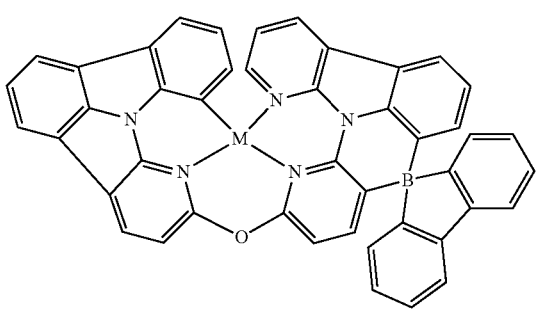

153
-continued
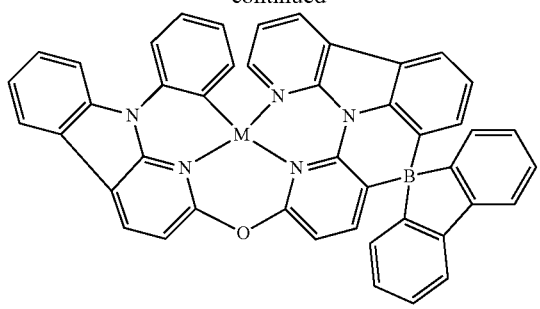
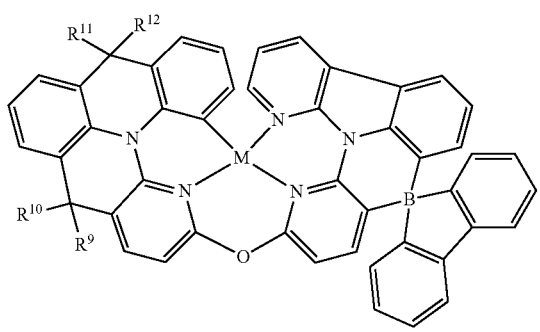
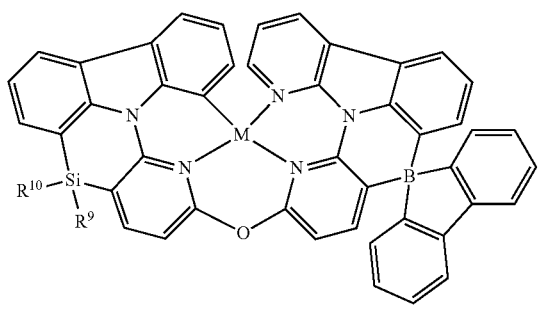
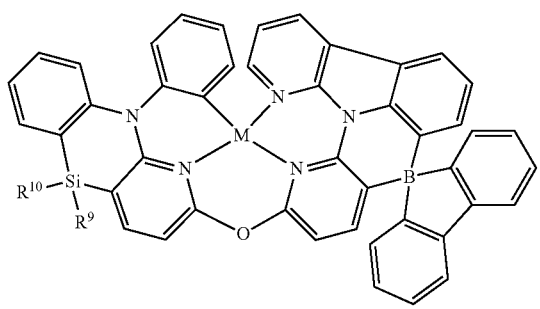
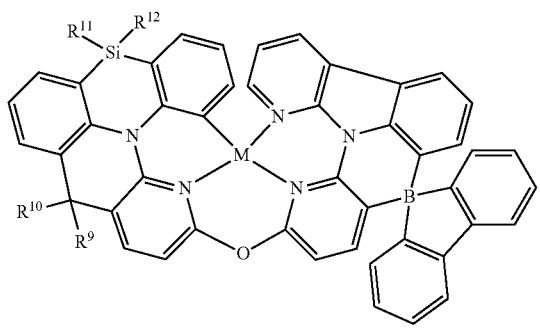
154
-continued
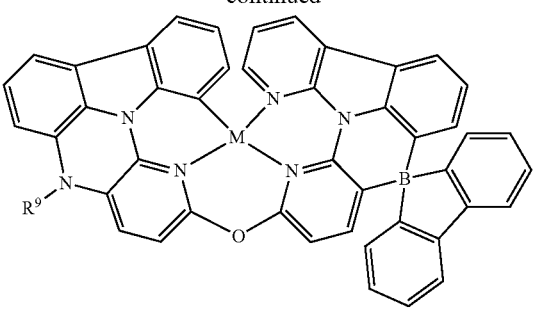
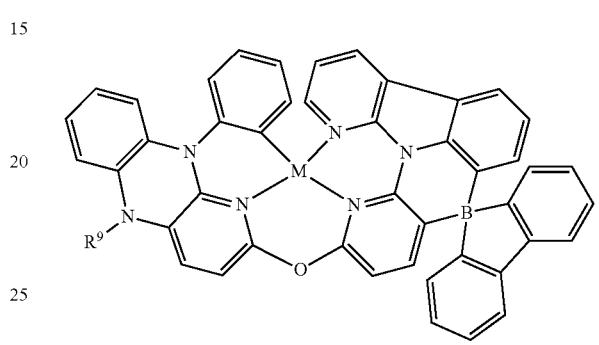
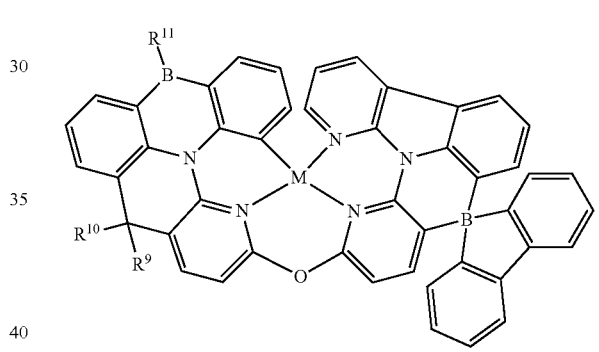
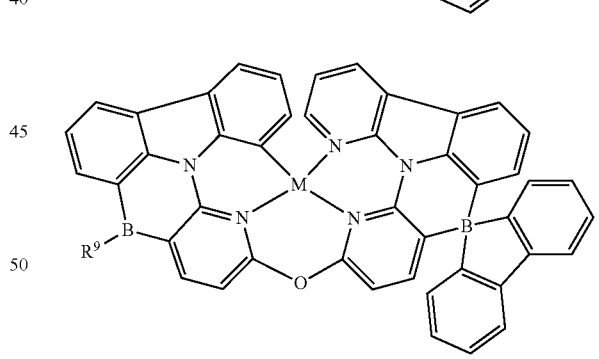
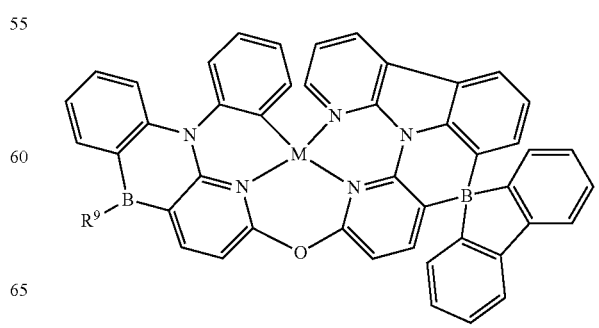

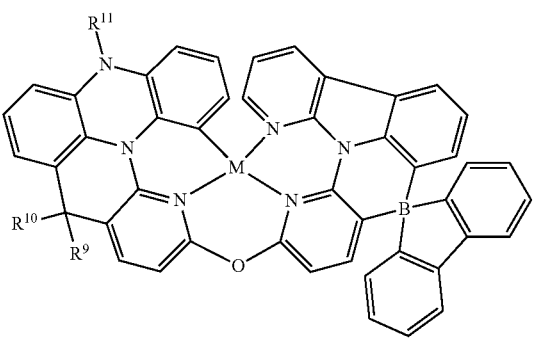
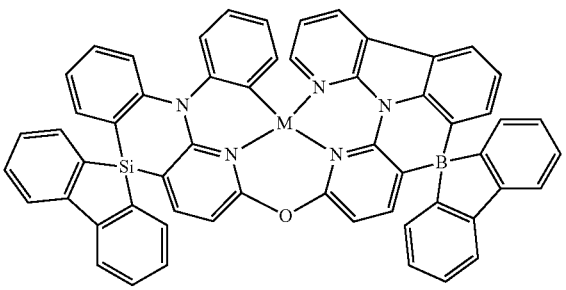
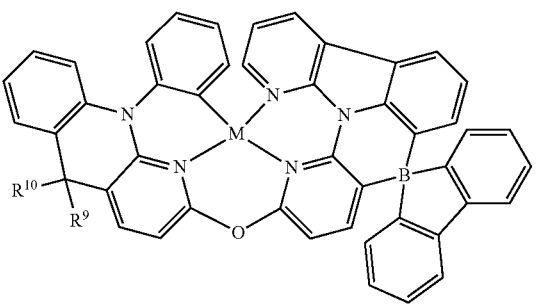
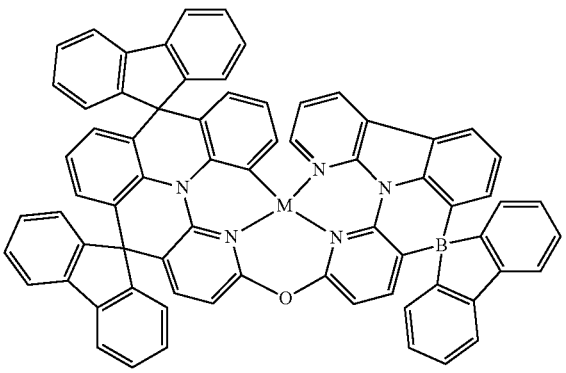
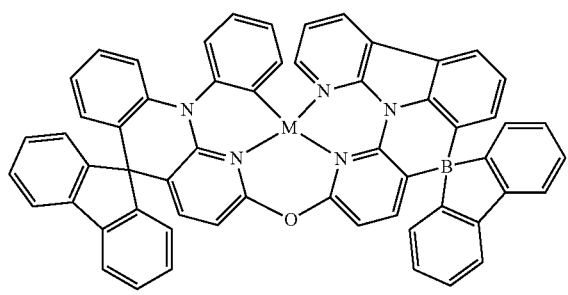
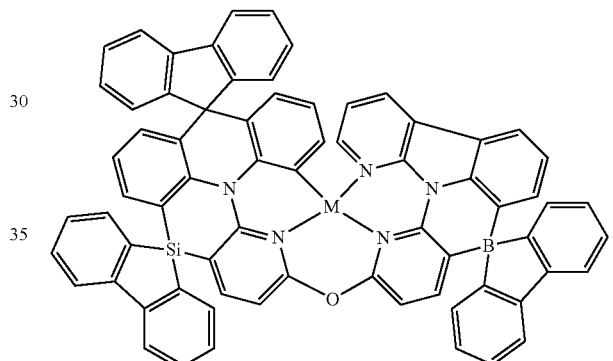
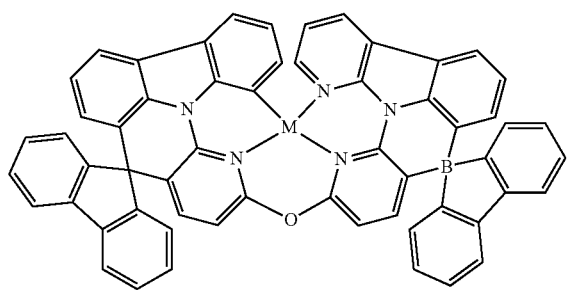
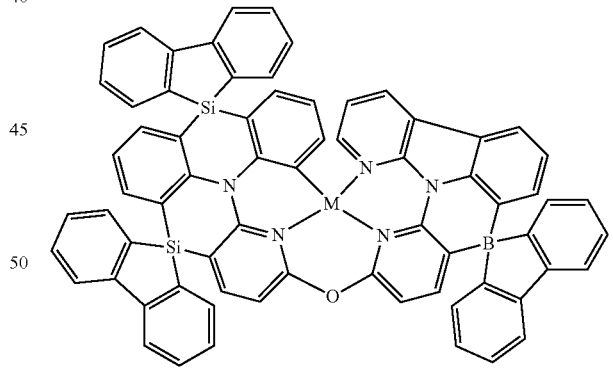
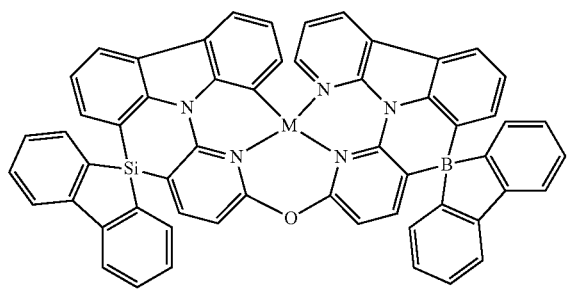
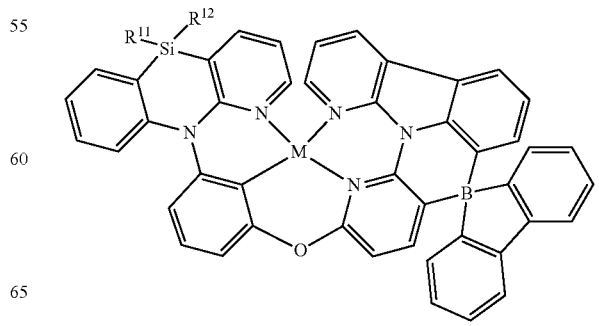

157
-continued
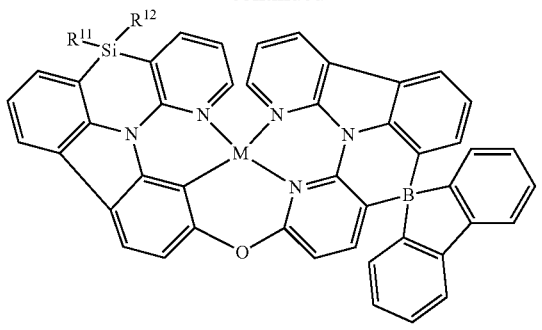
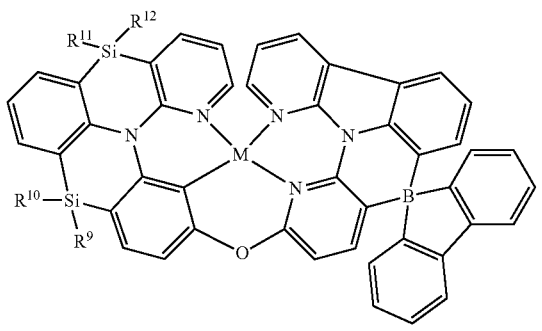
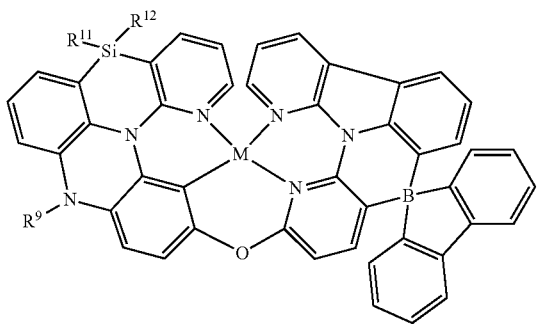
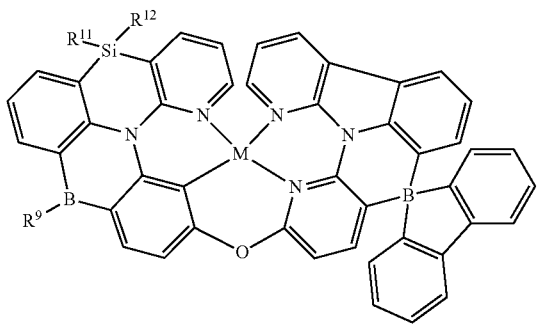
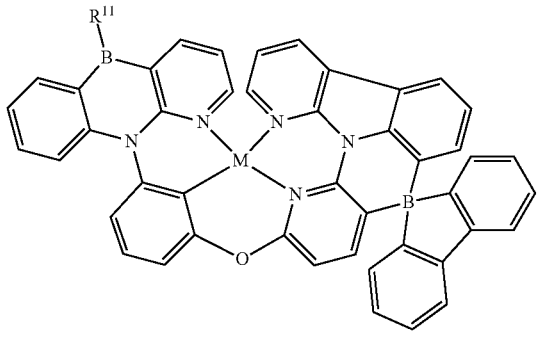
158
-continued
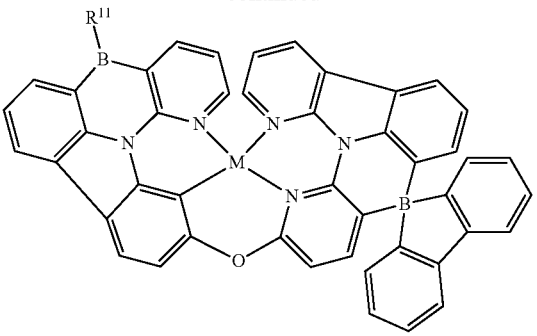
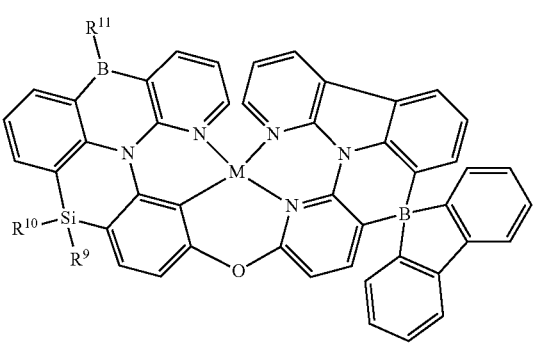
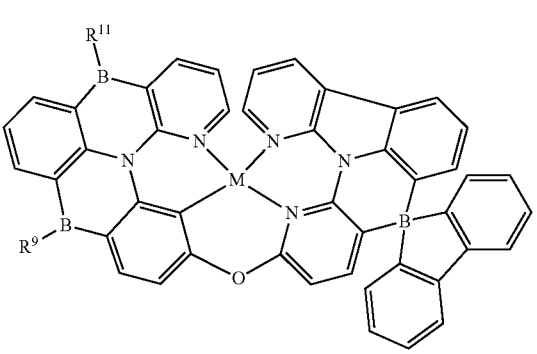

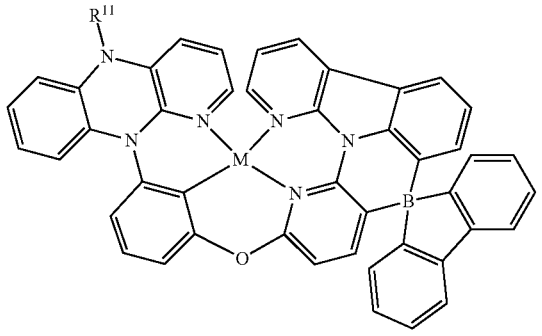
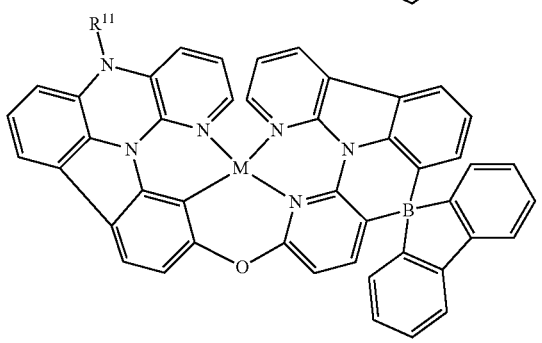
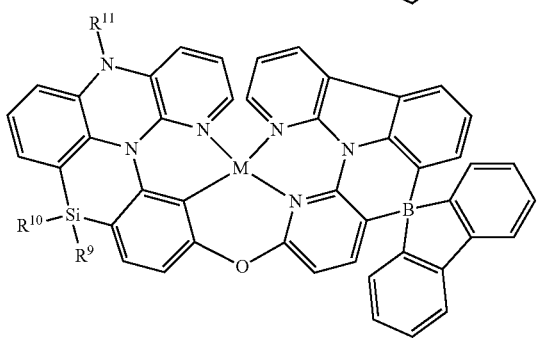
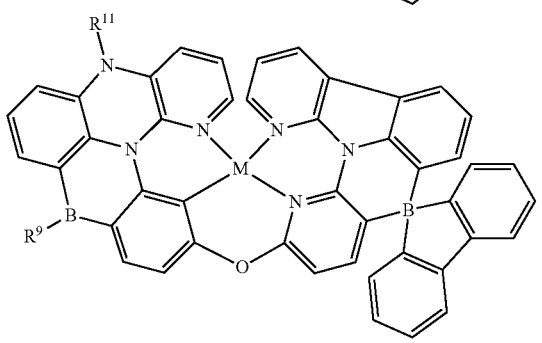
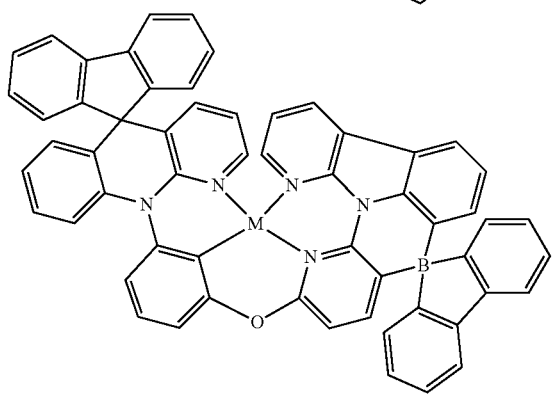
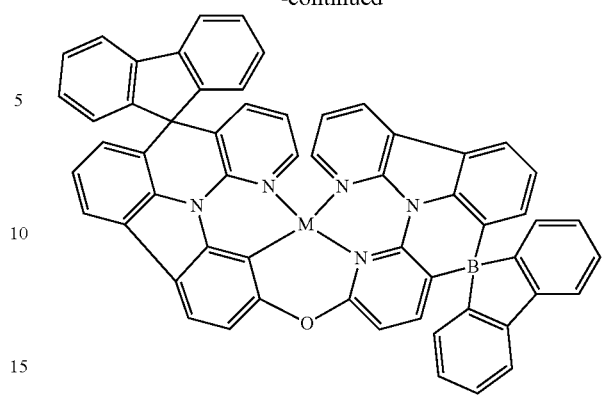
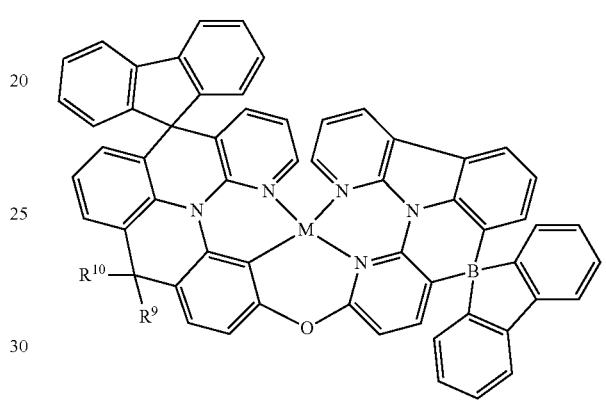
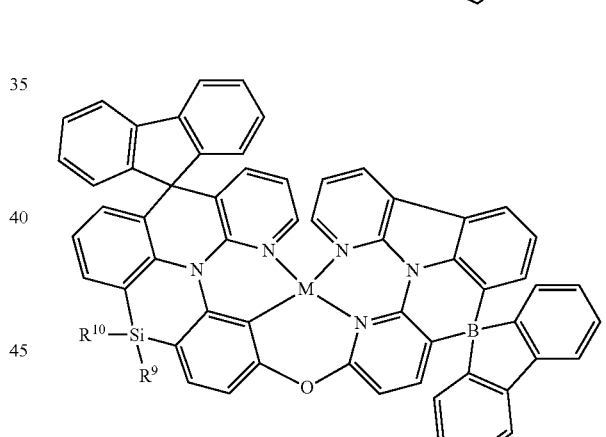
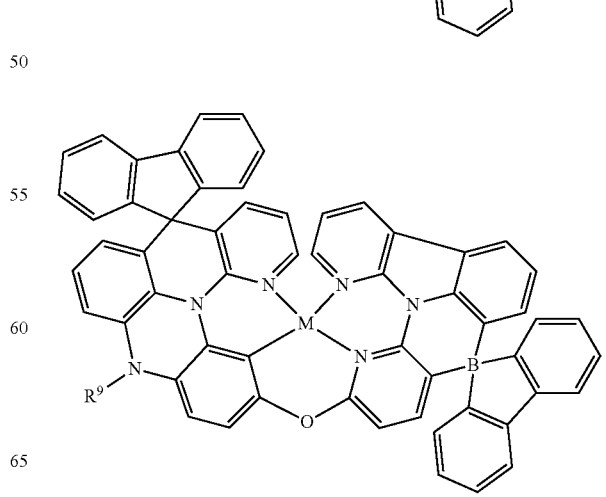

-continued
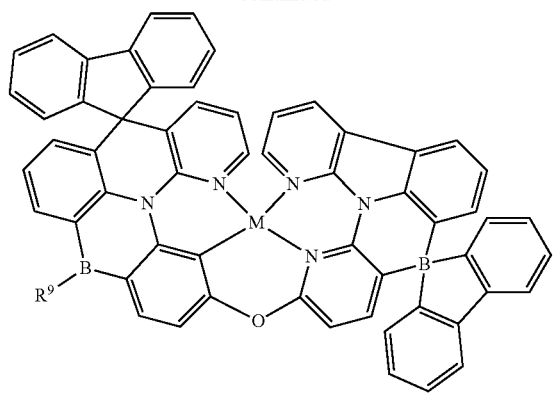
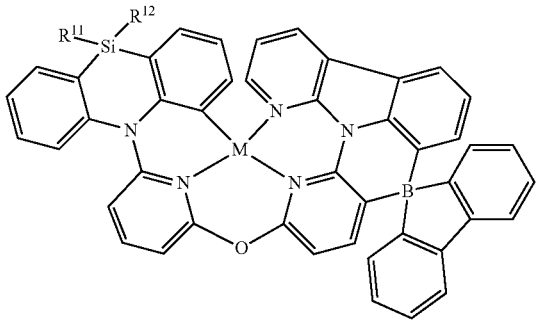
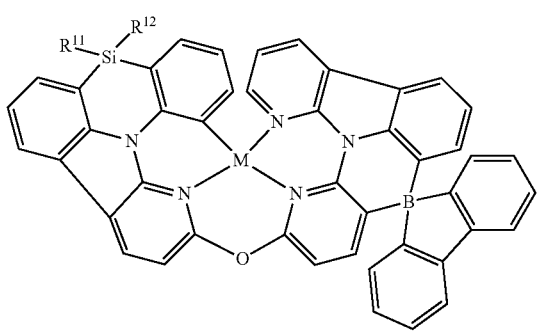
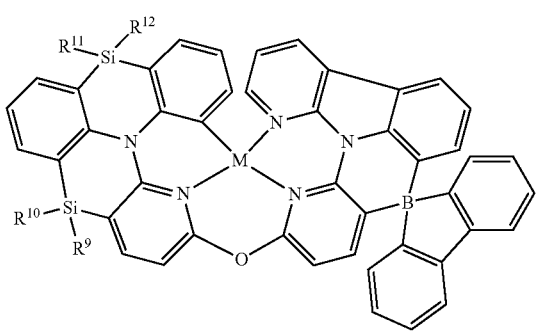
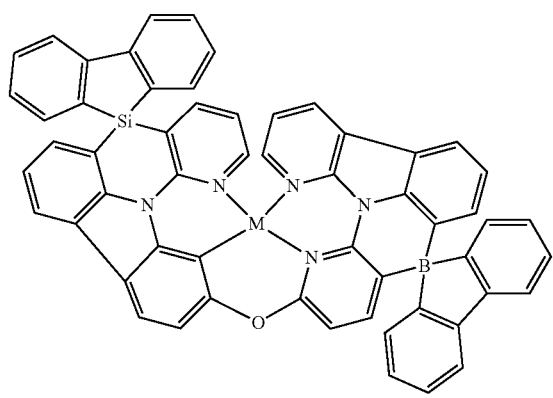
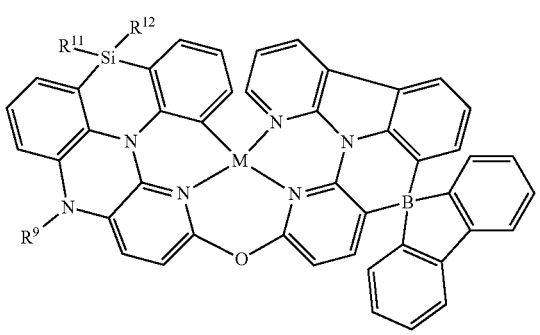
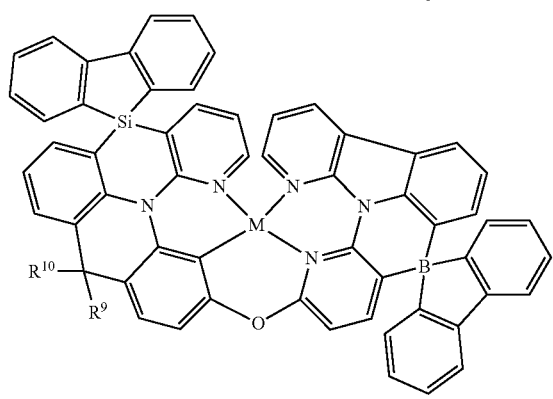
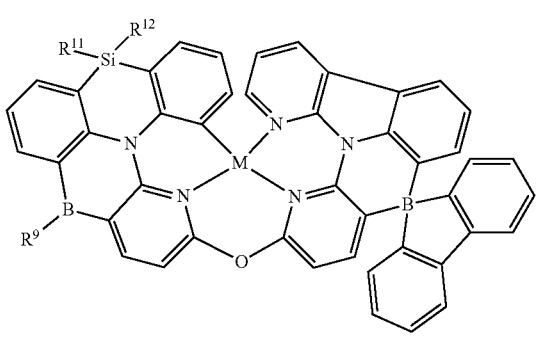

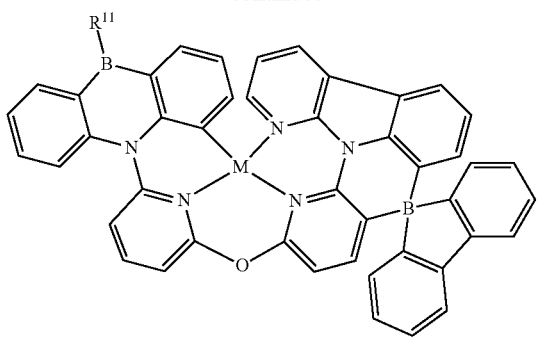
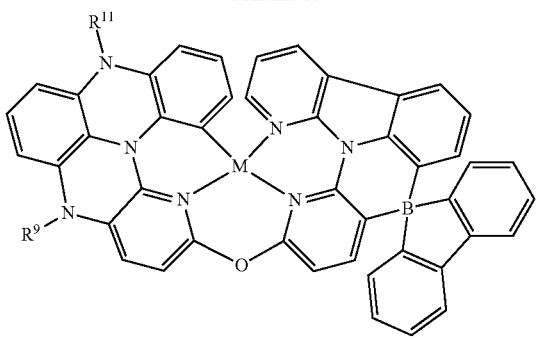
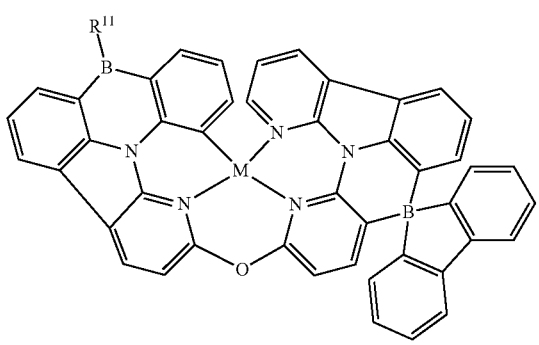
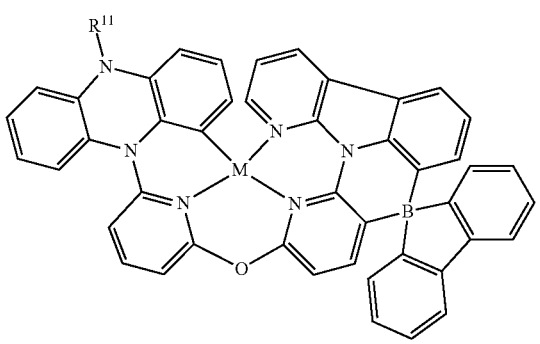
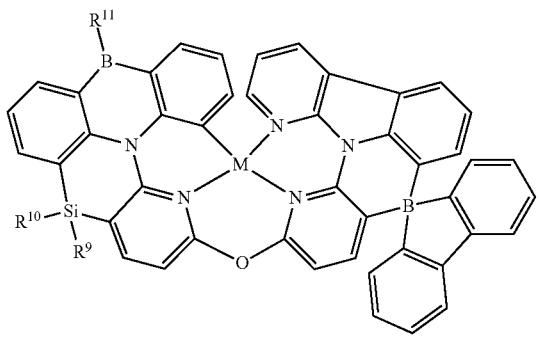
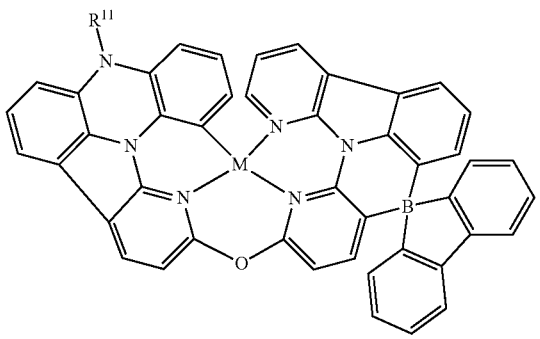
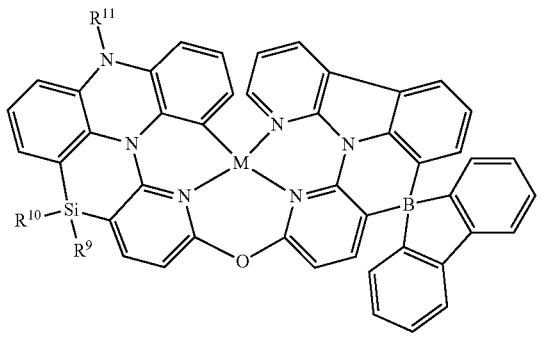

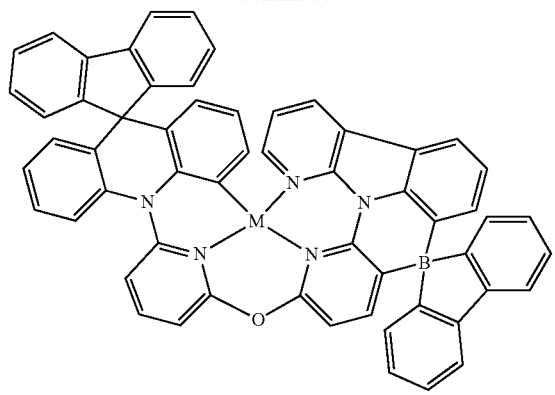
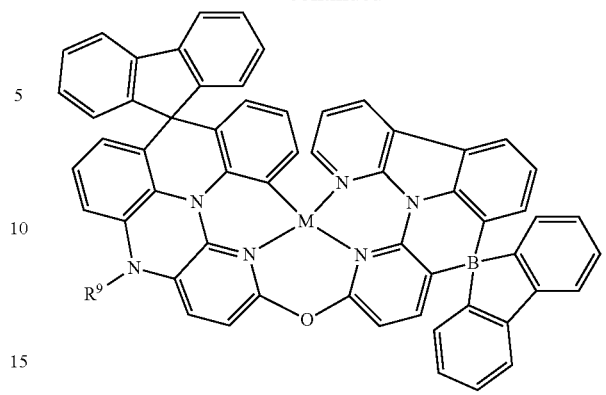
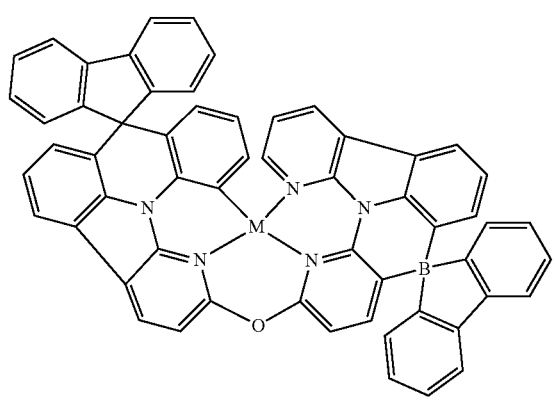
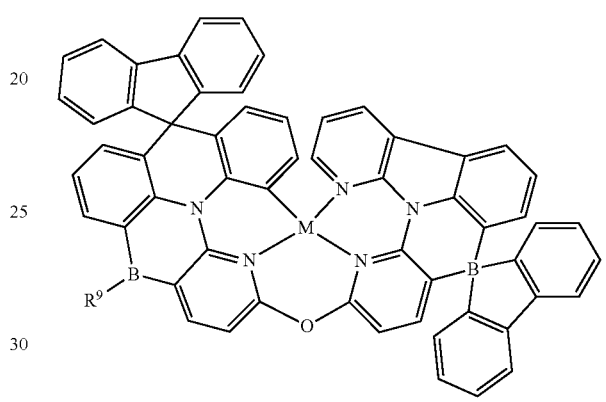
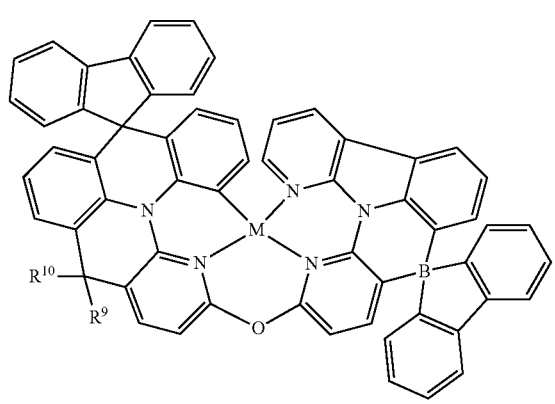
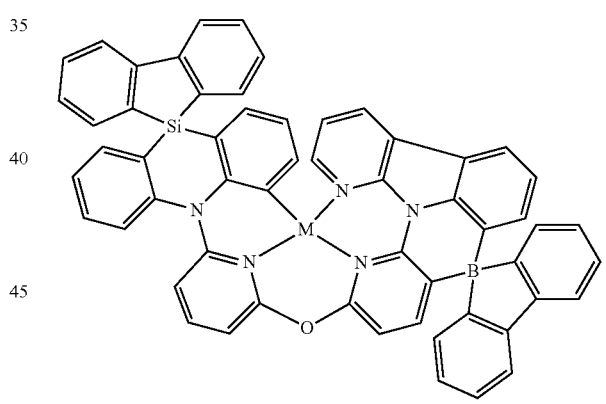
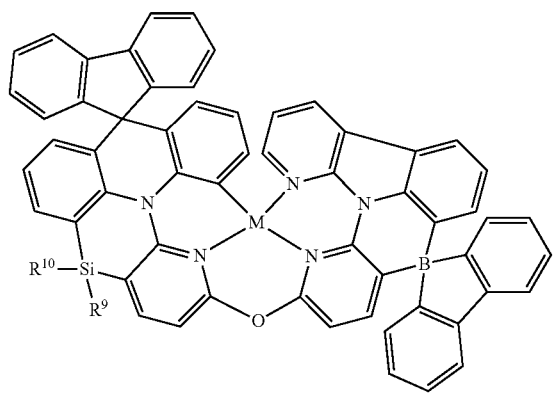
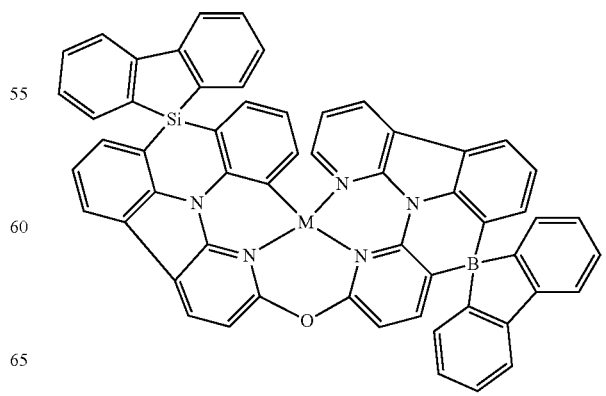

-continued
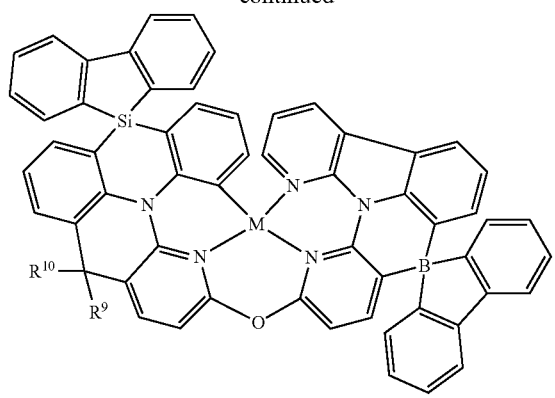
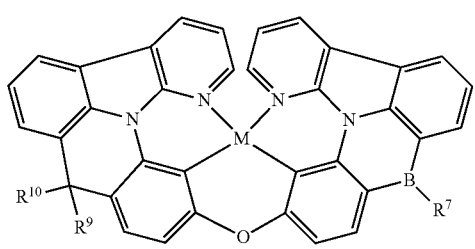
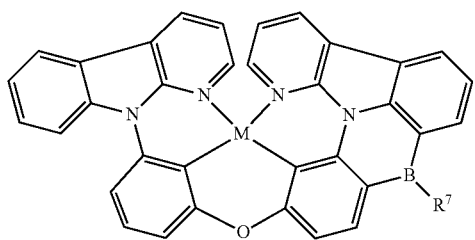
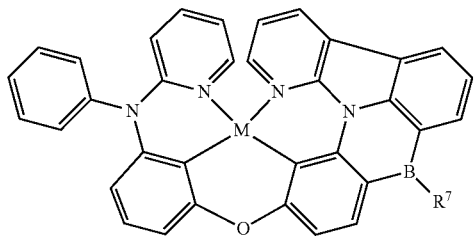
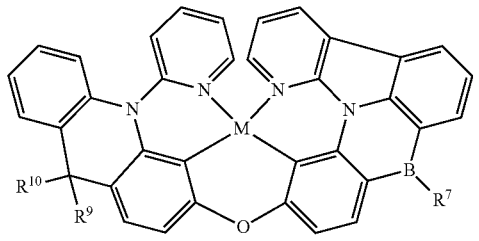
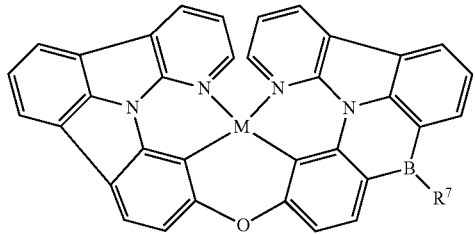
-continued
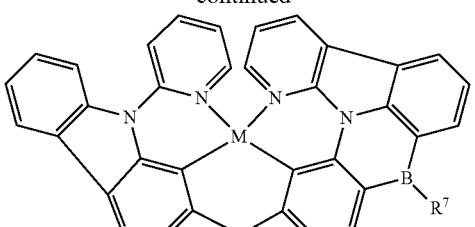
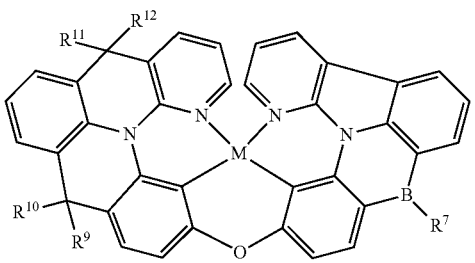
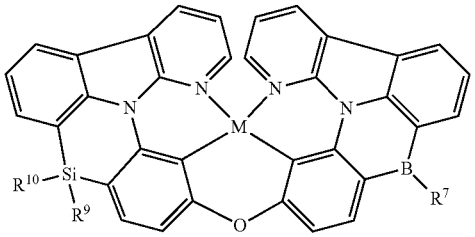
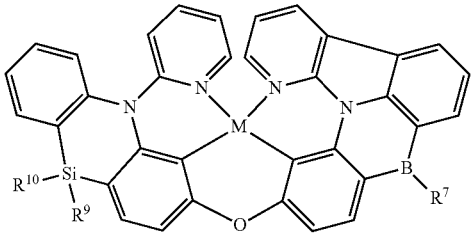

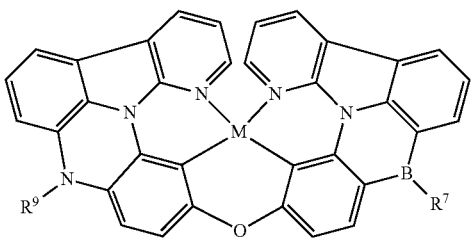

-continued
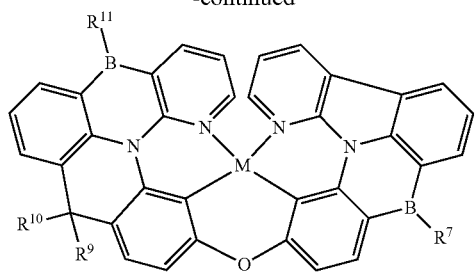
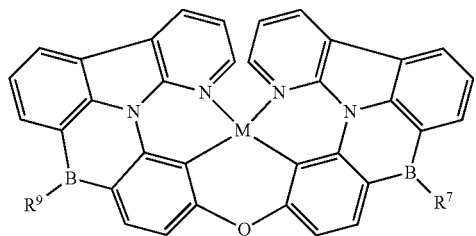
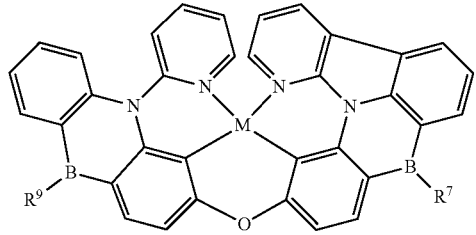
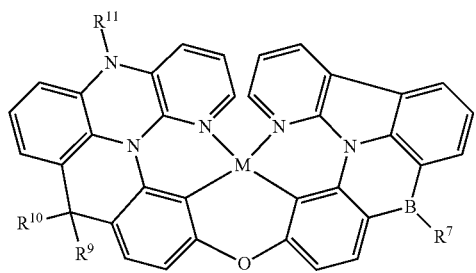
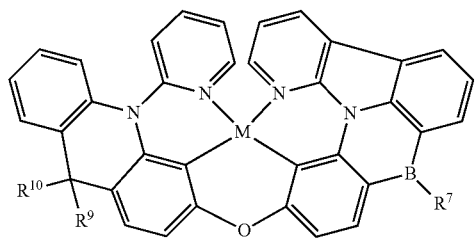
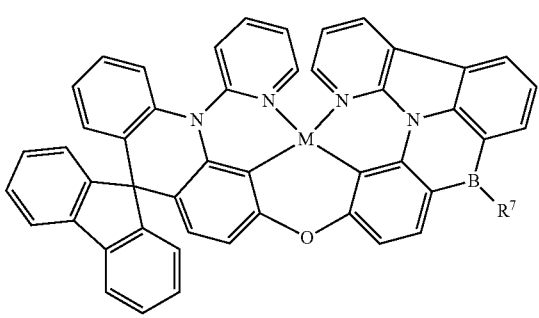
-continued
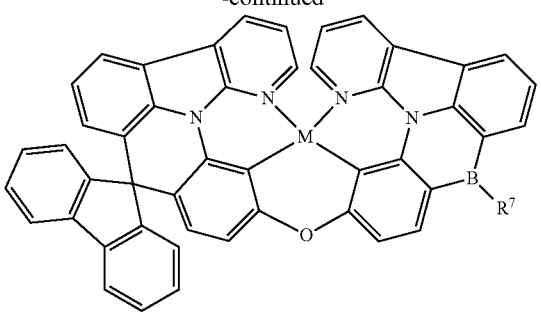
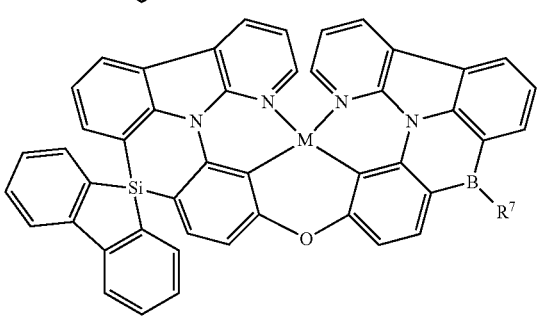
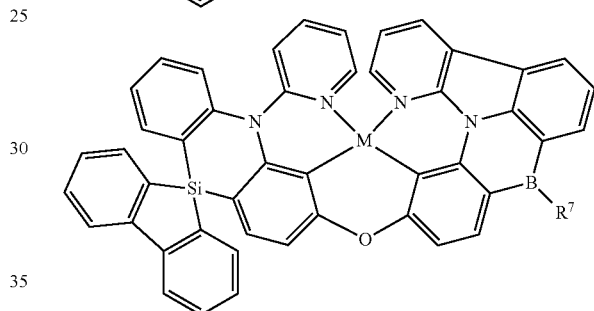
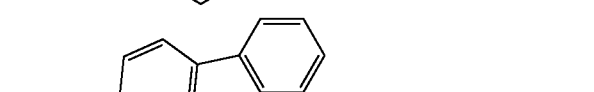
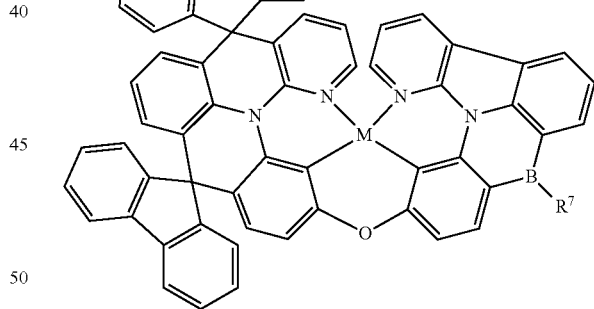
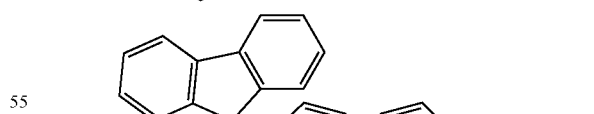
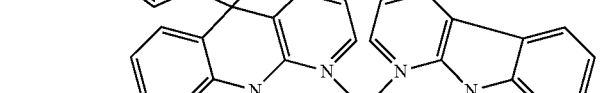
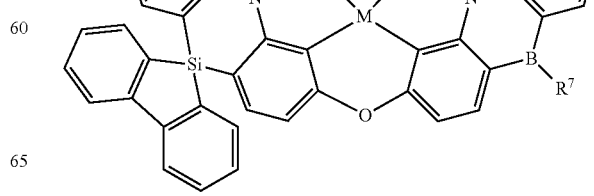

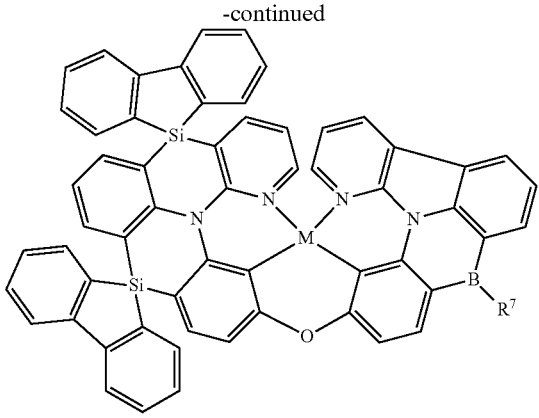
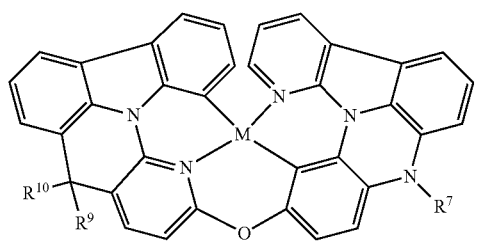
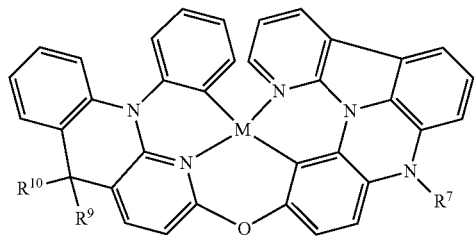
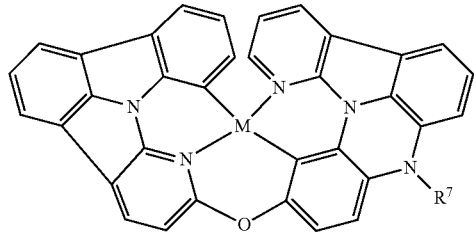
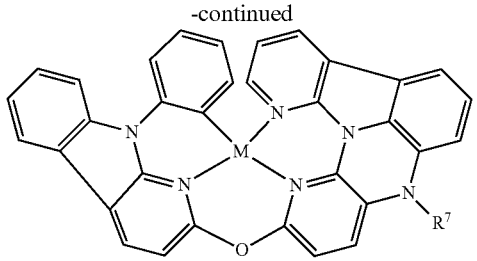
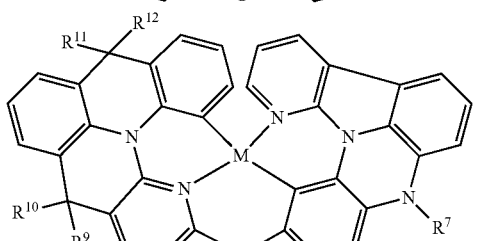
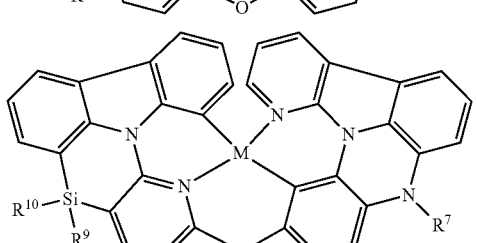
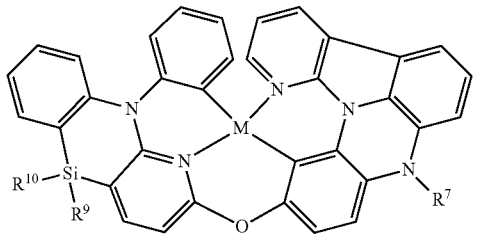
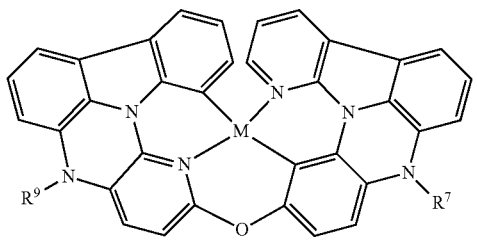
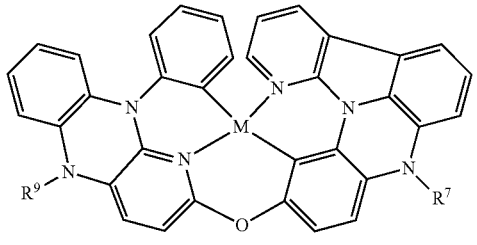

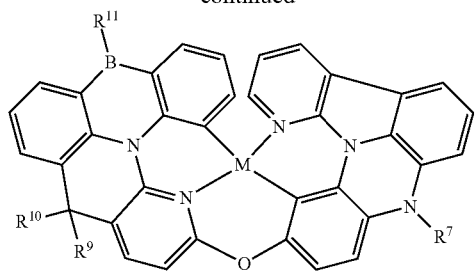
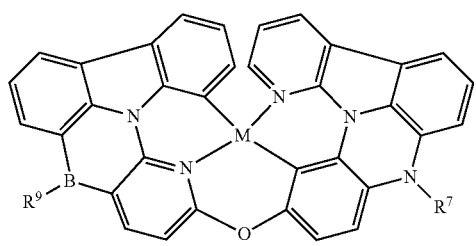
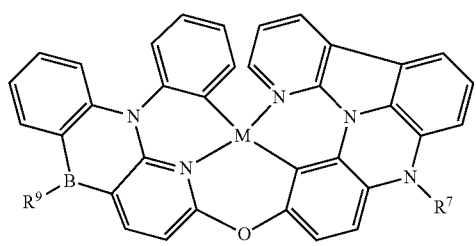
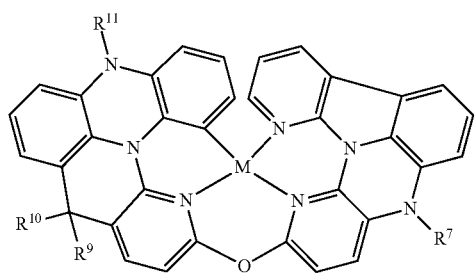
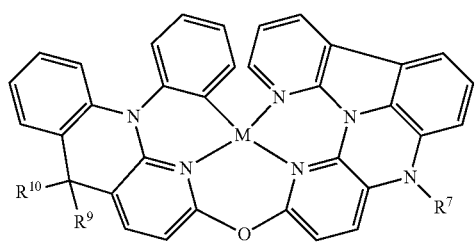
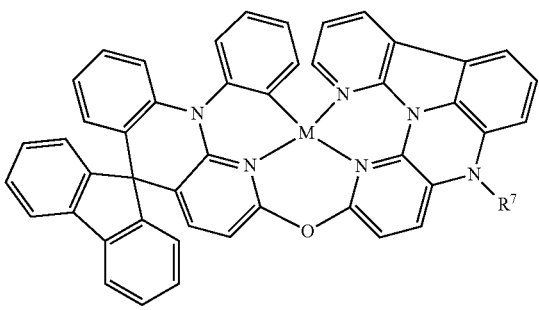
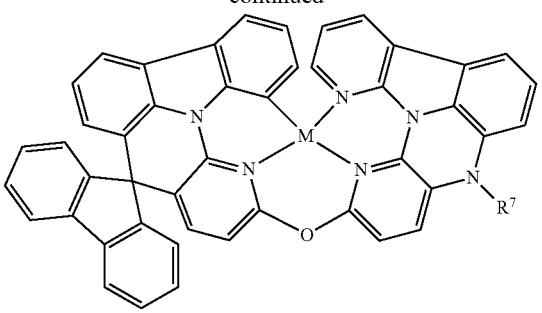
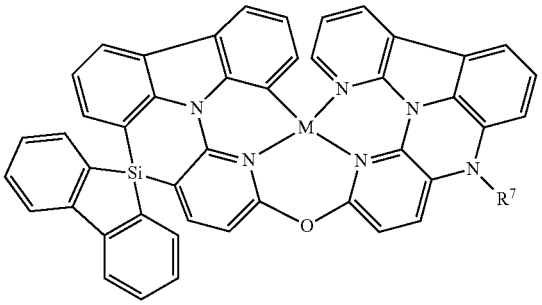
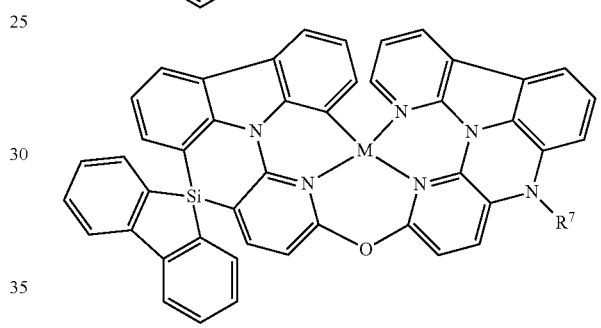
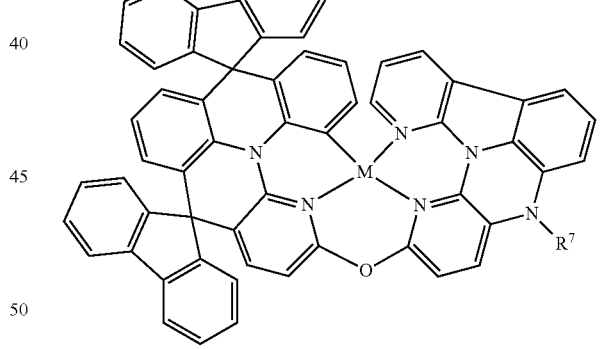
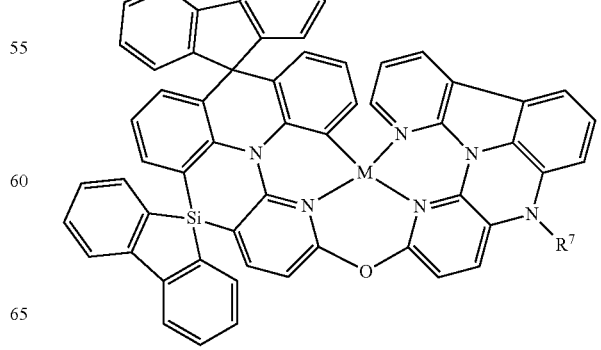

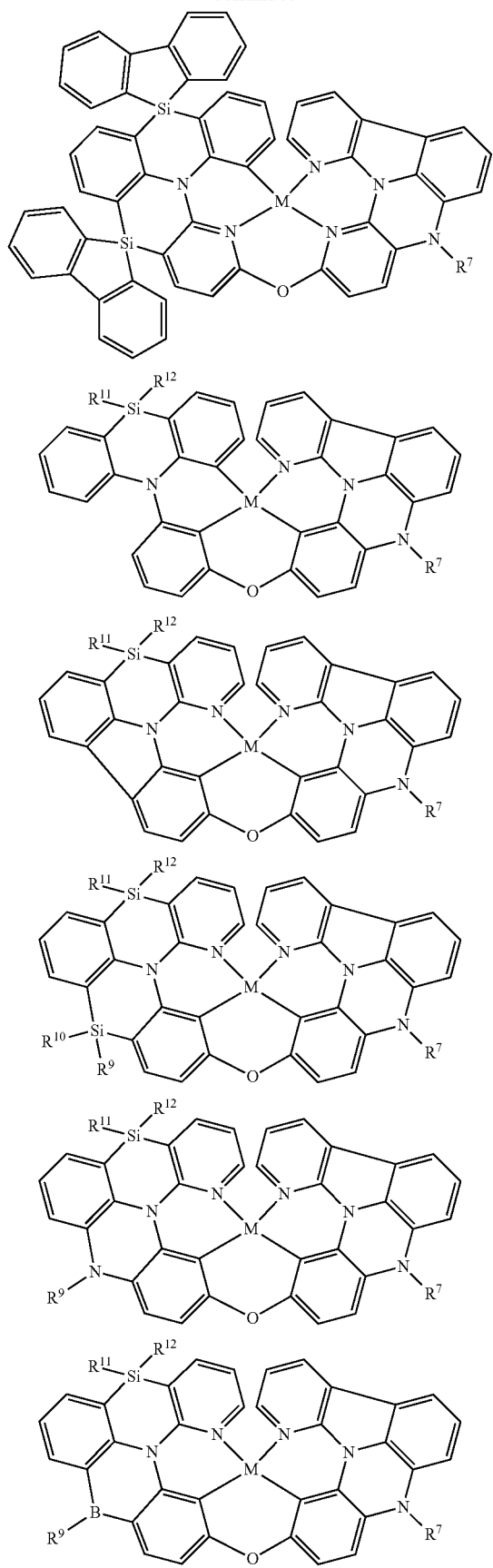
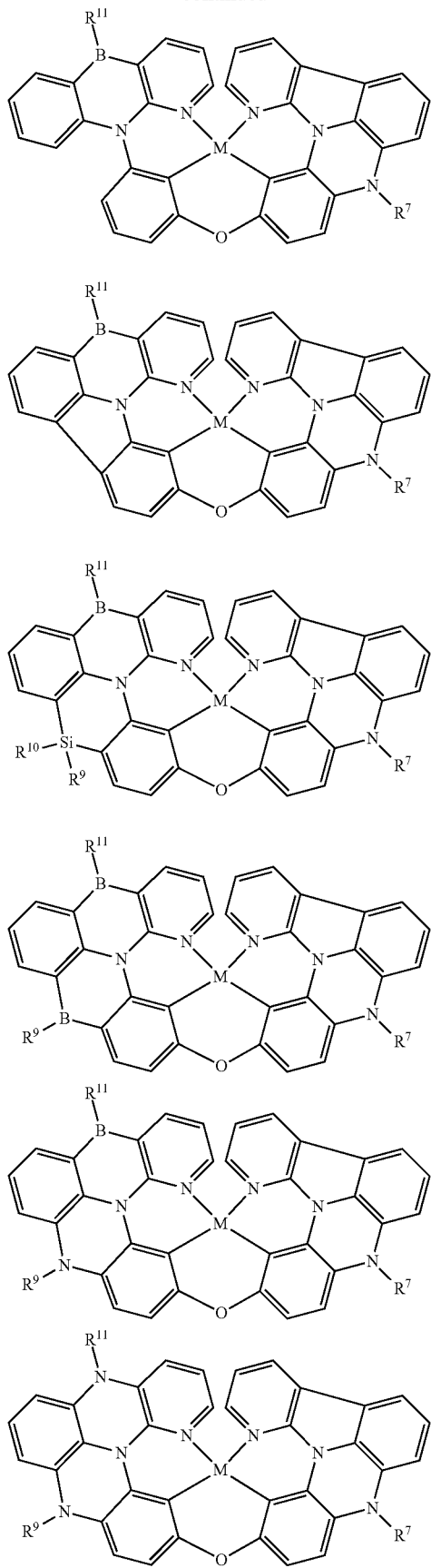

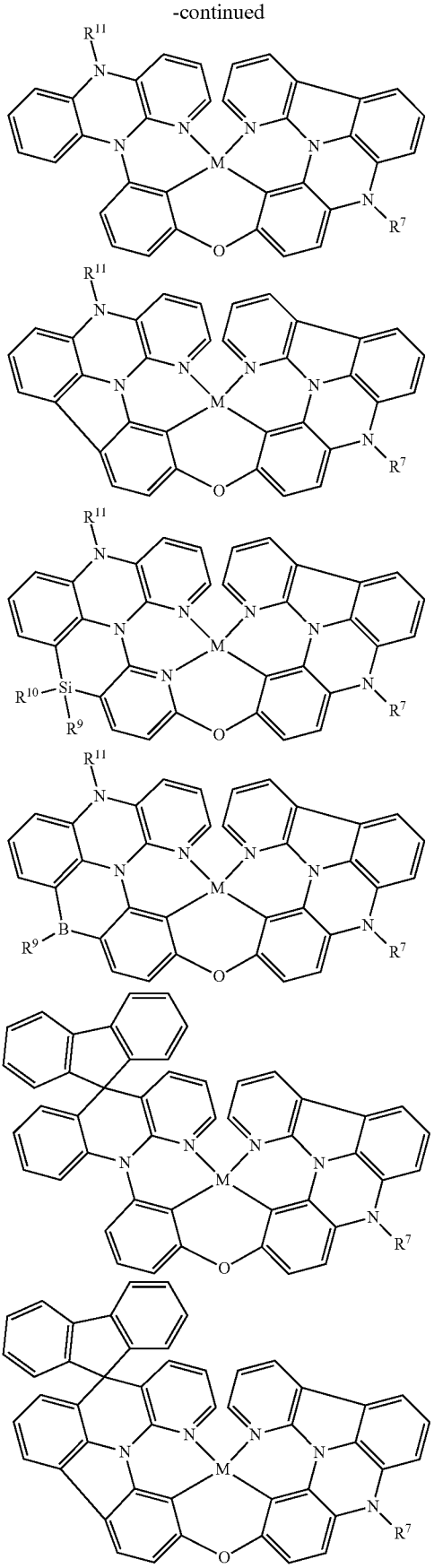
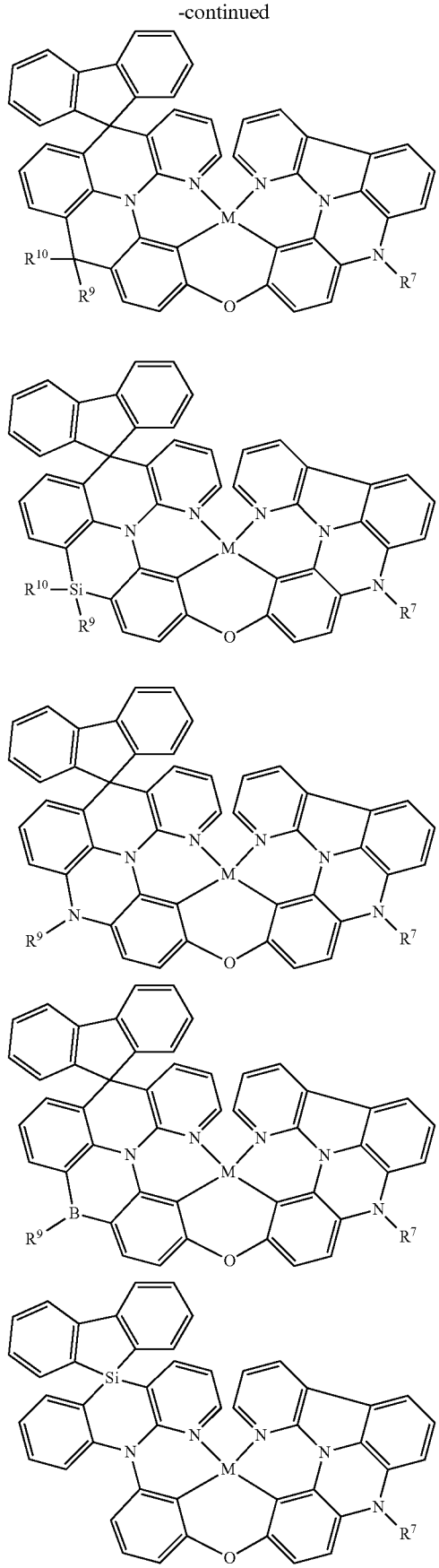

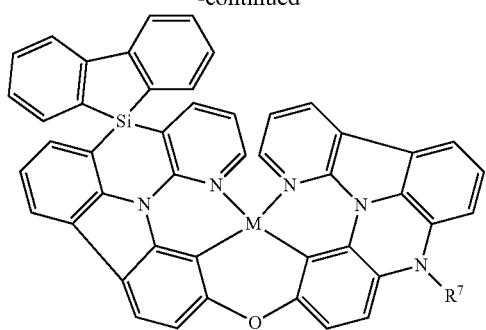
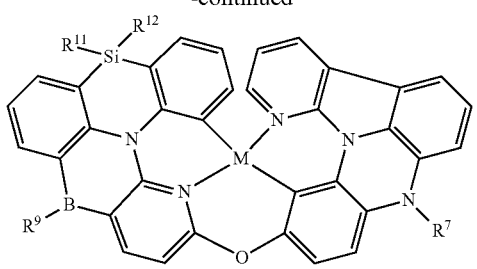
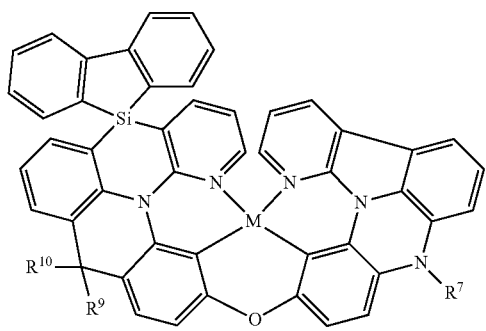
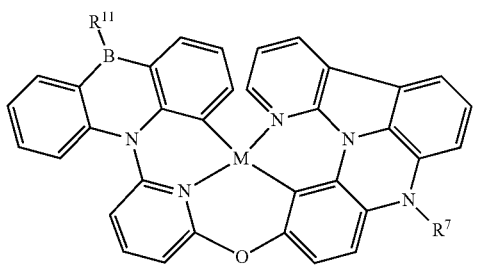
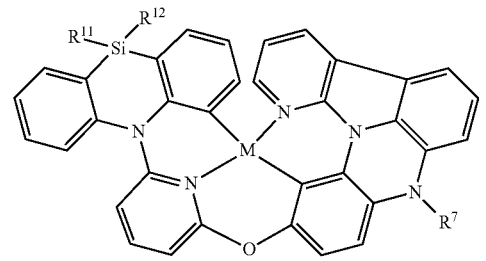
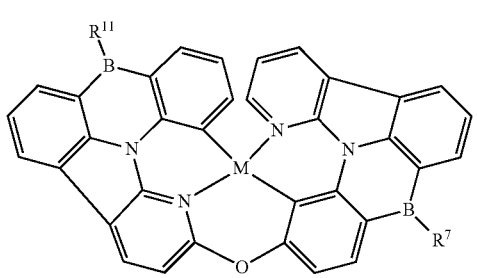
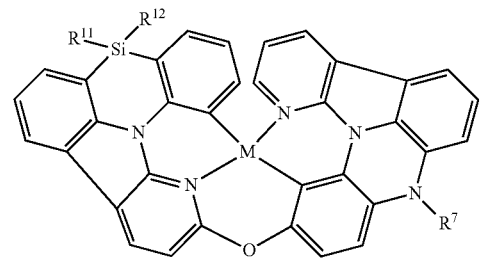
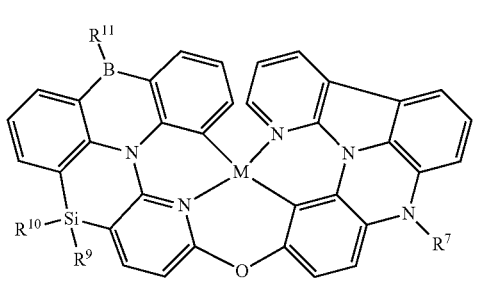
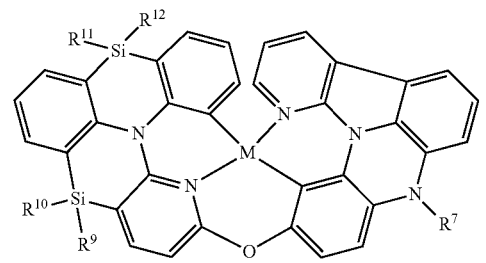
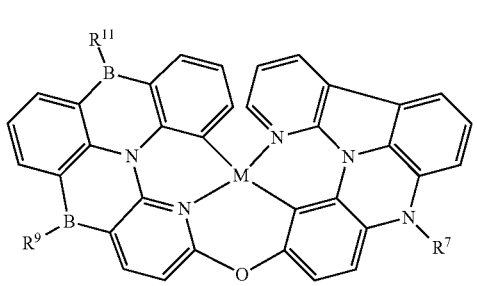
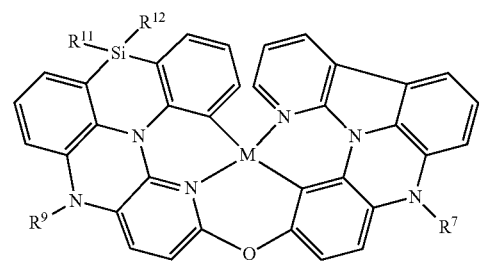
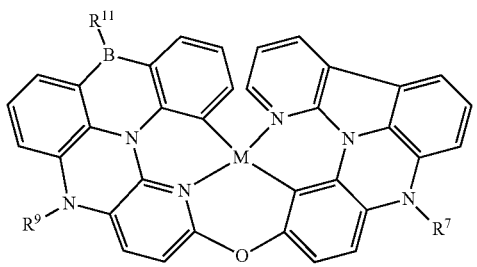

181
-continued
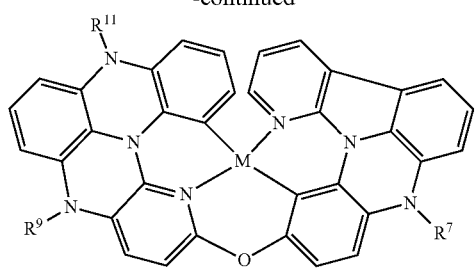
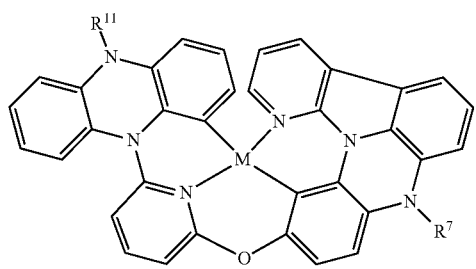
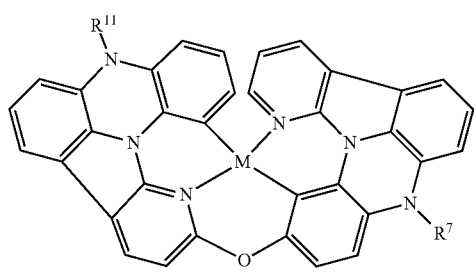
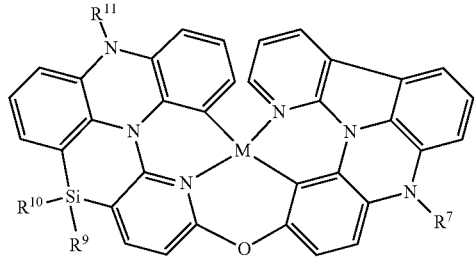
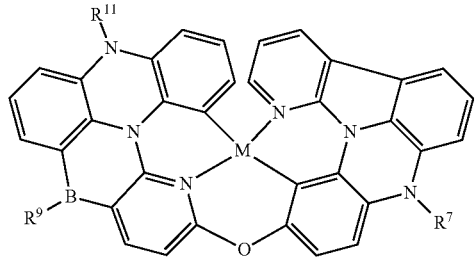
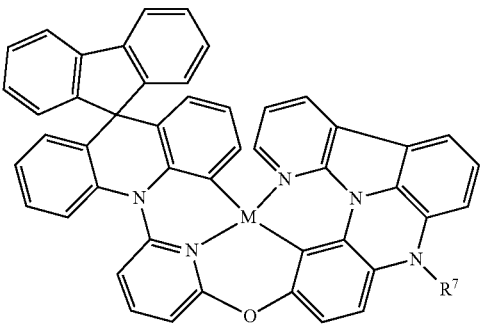
182
-continued
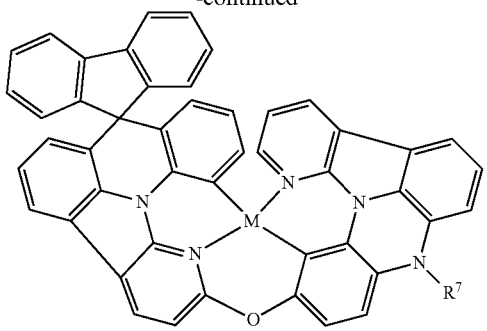
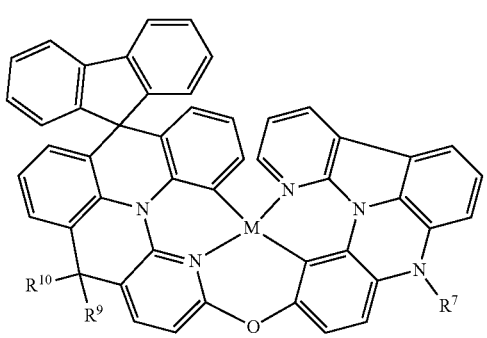
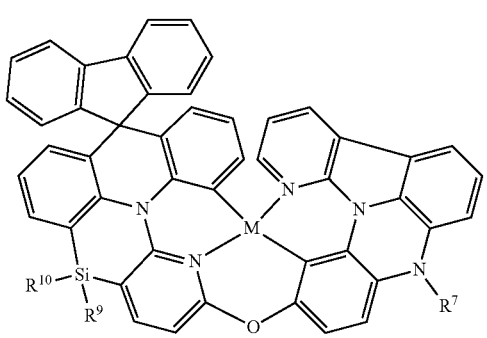
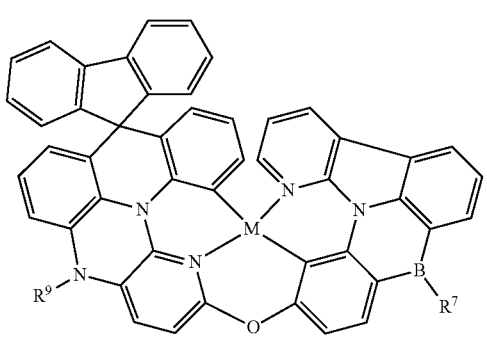
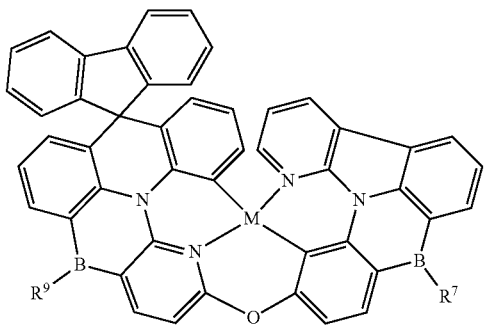

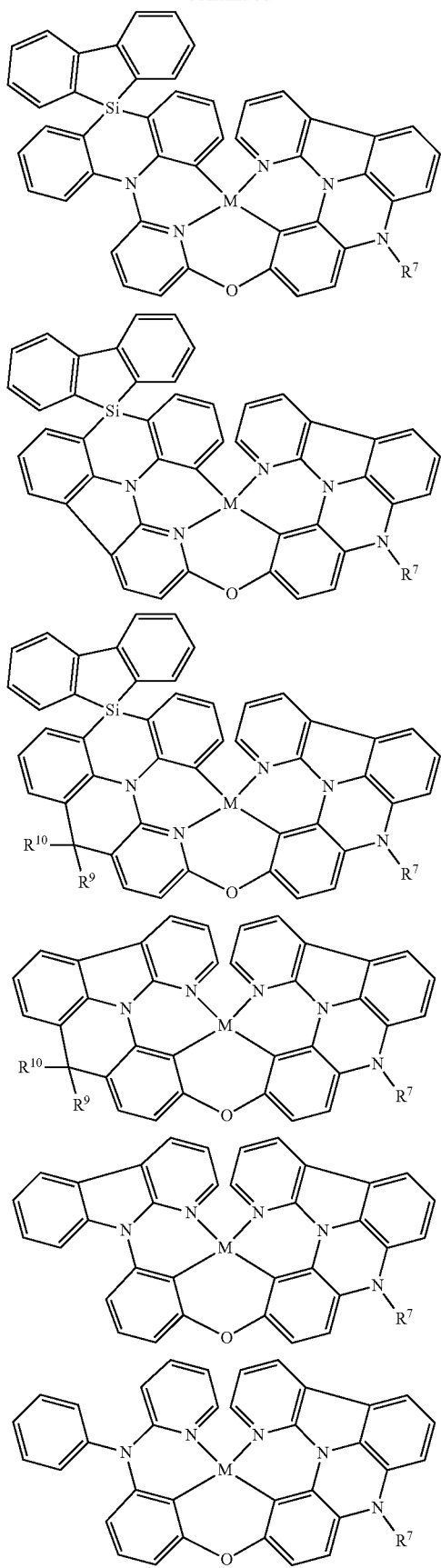
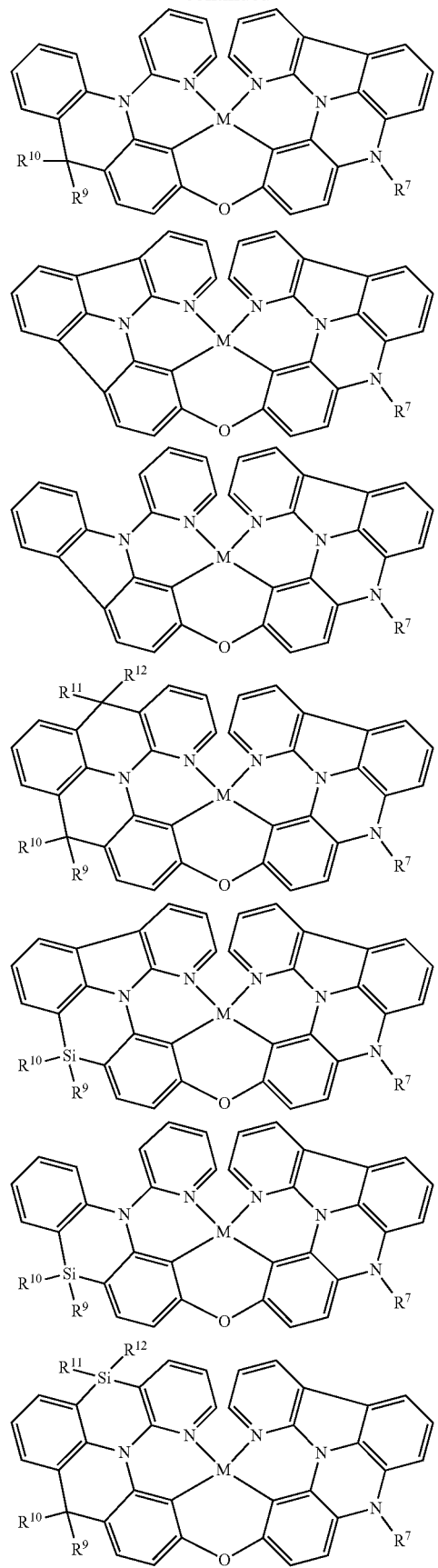

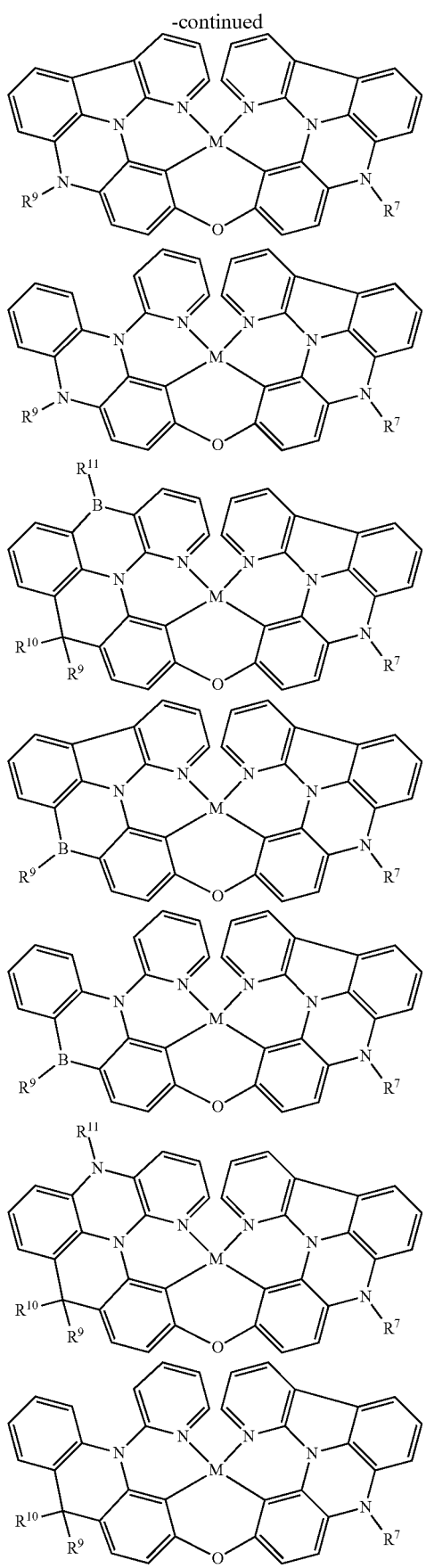
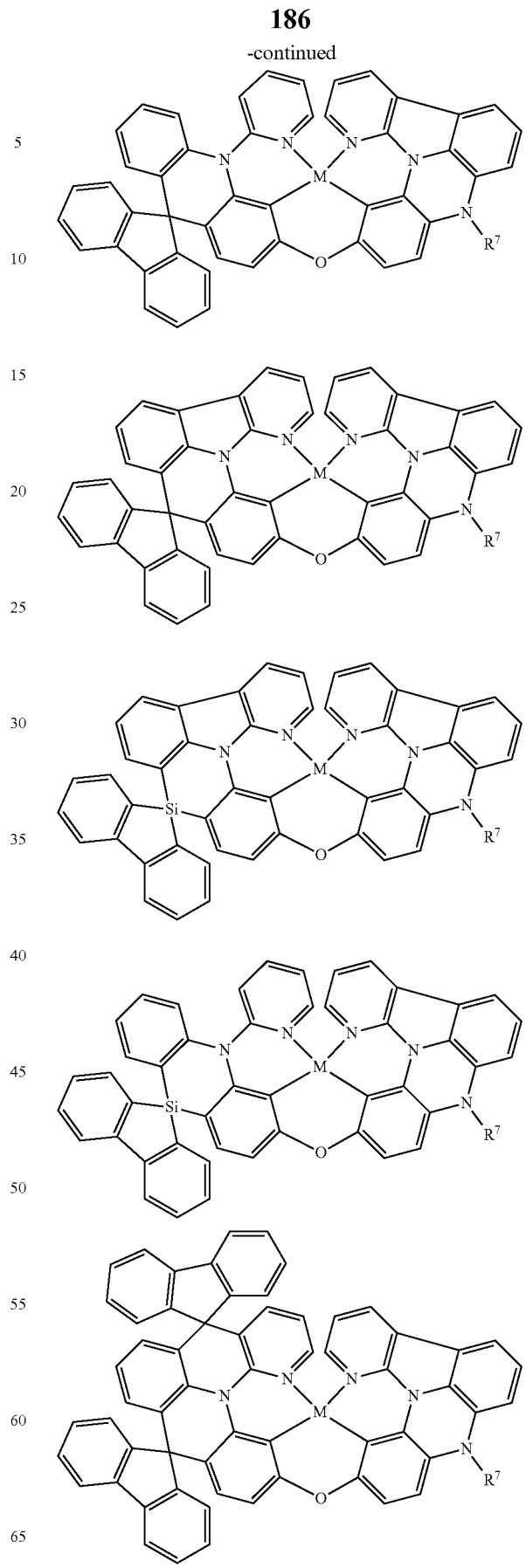

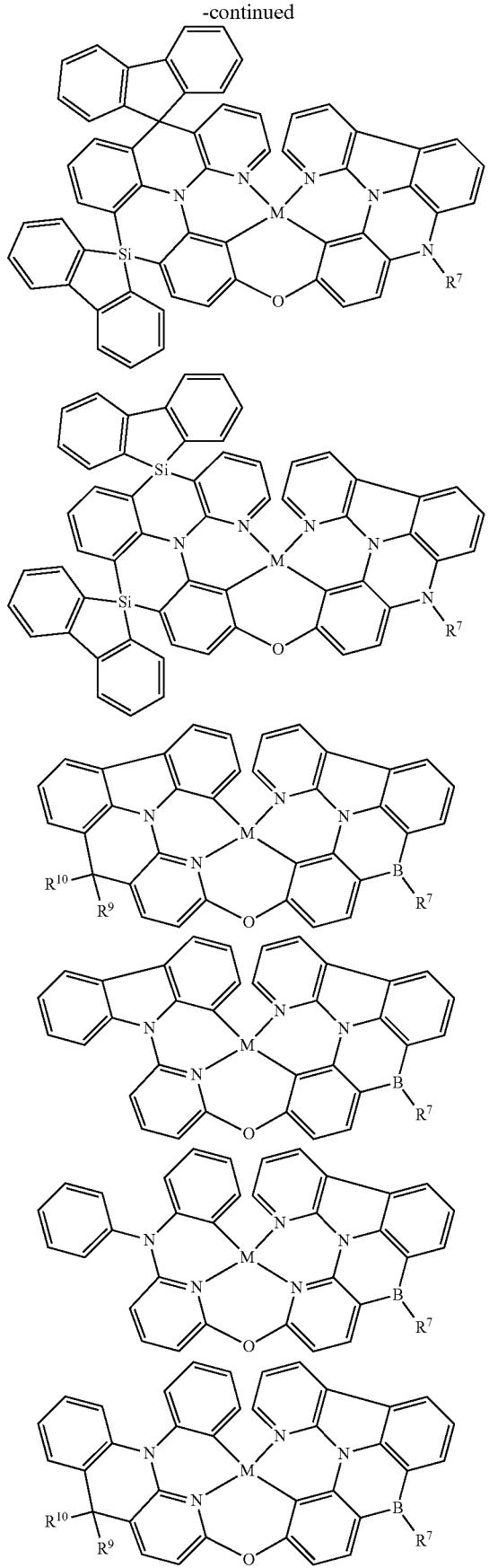
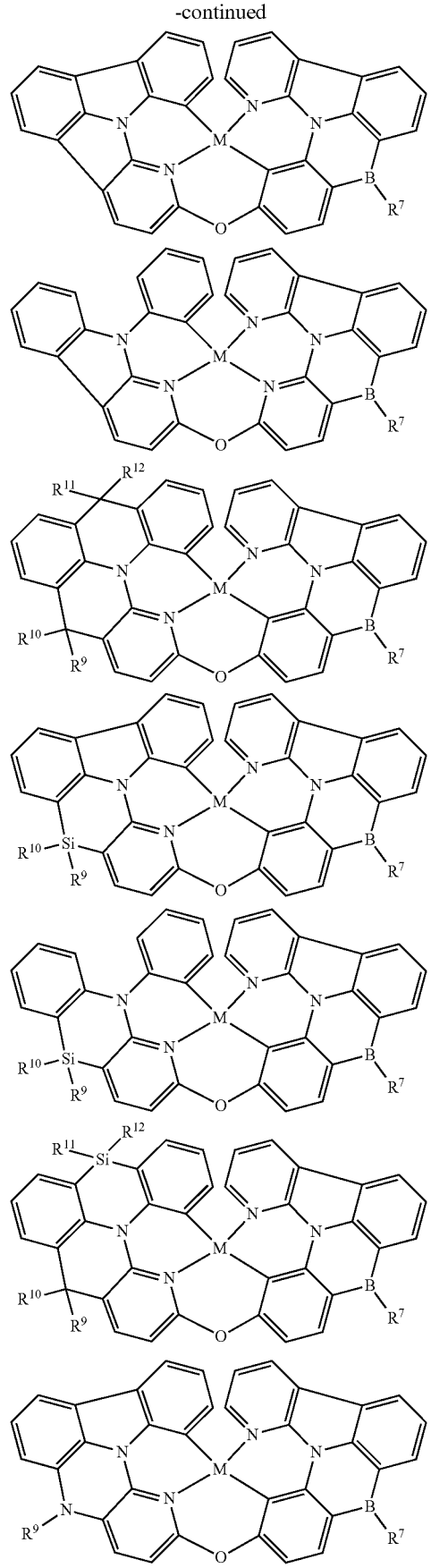

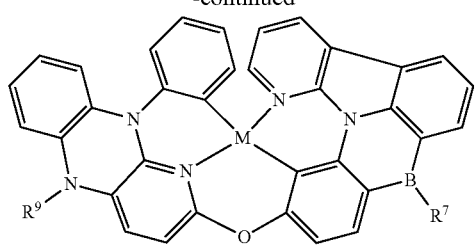
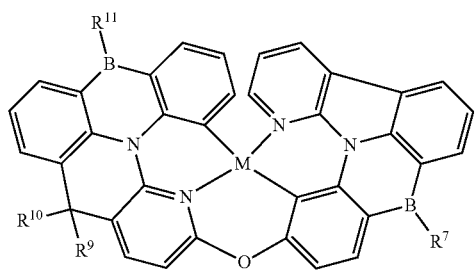
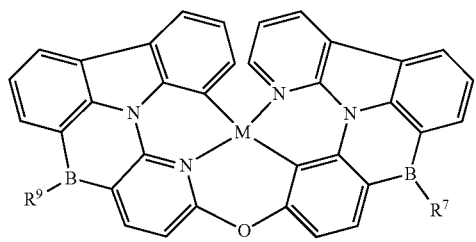
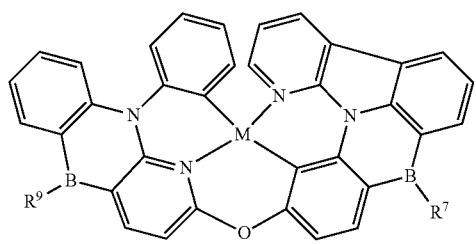
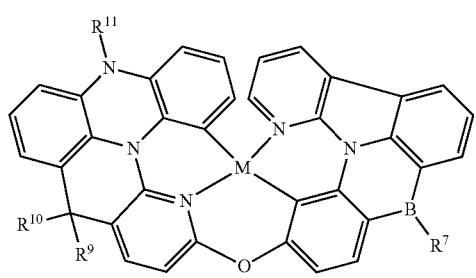
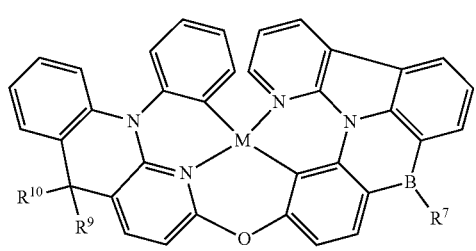
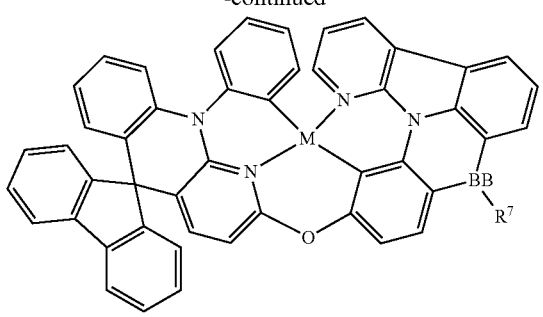
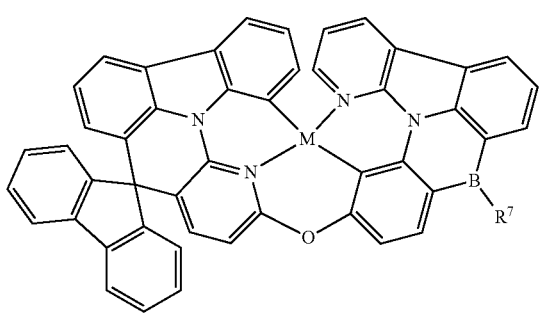
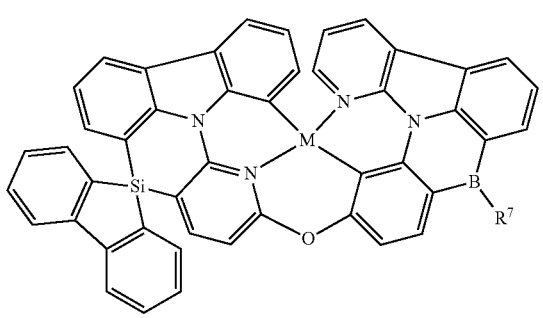
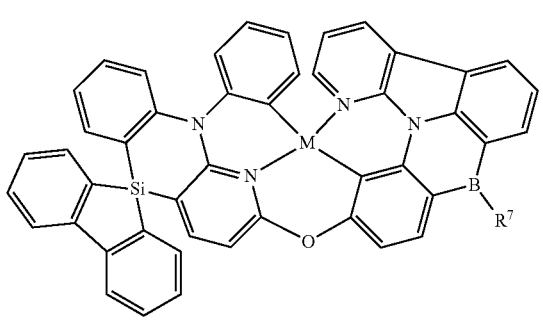
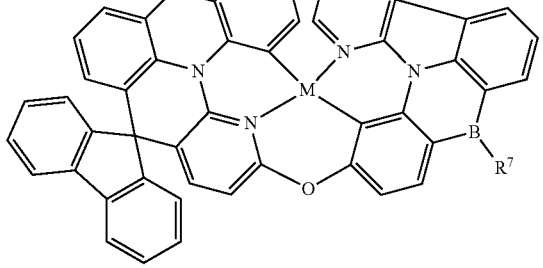

191
-continued
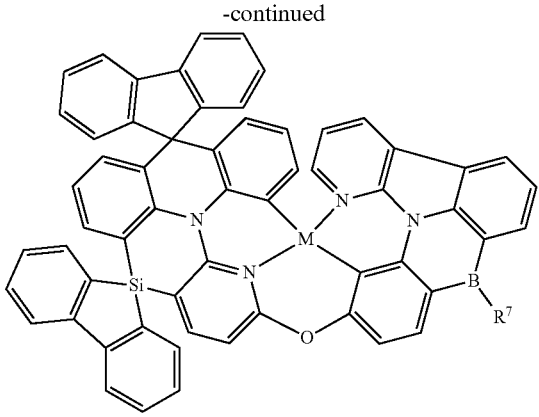
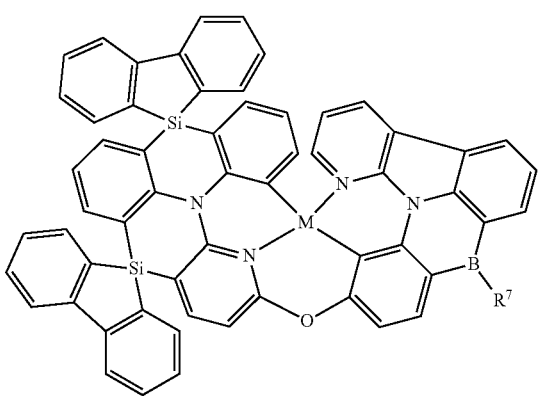
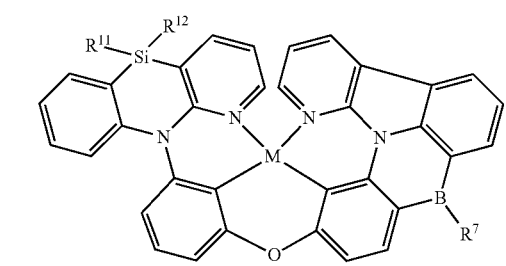
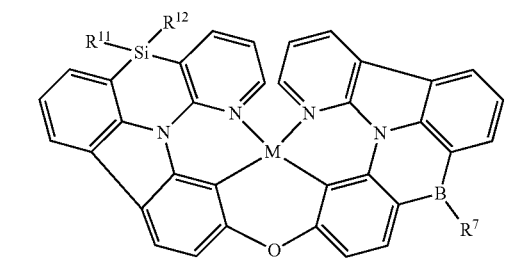
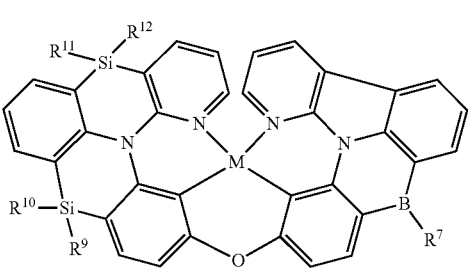
192
-continued
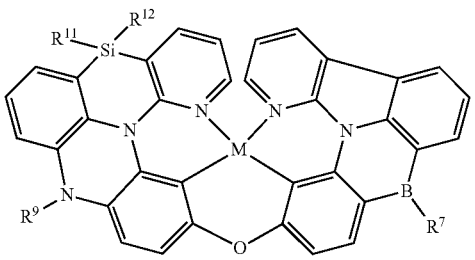
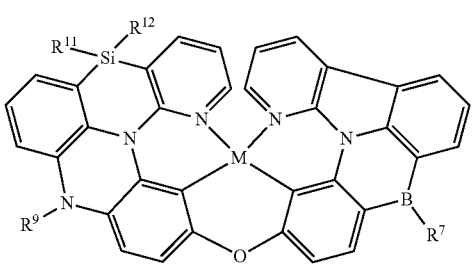
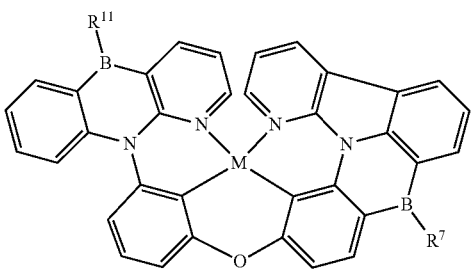
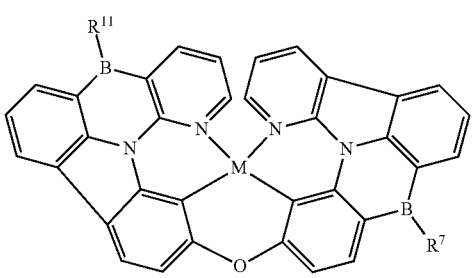
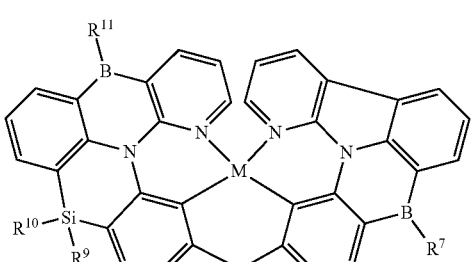
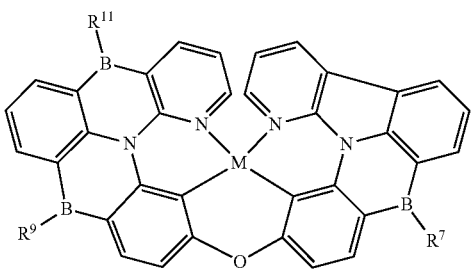

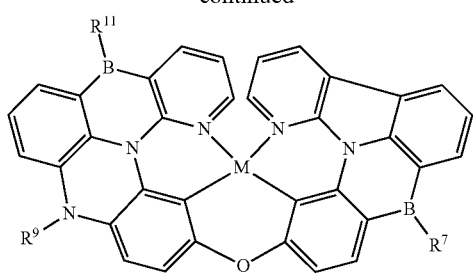
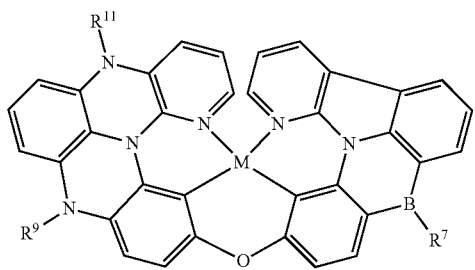
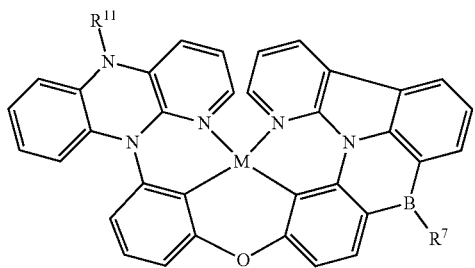
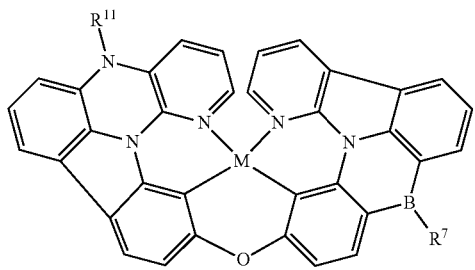
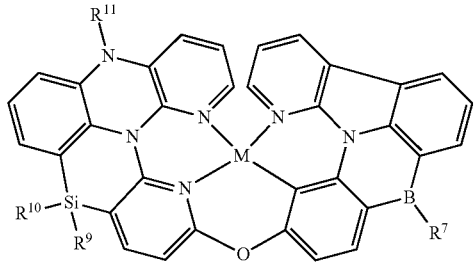
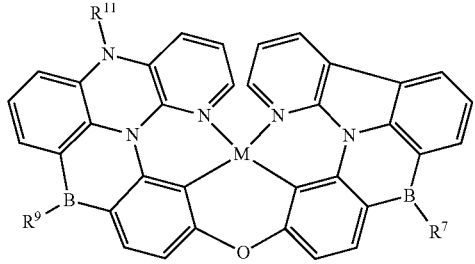
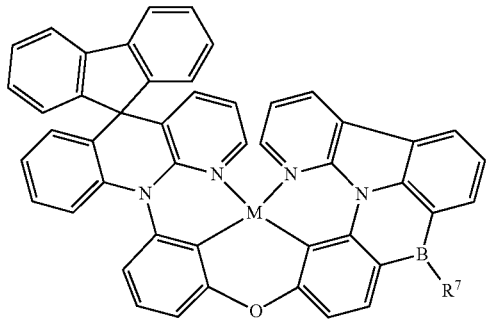
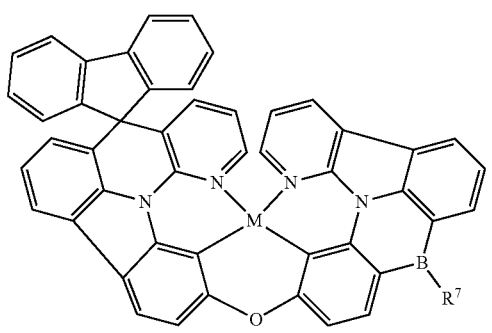
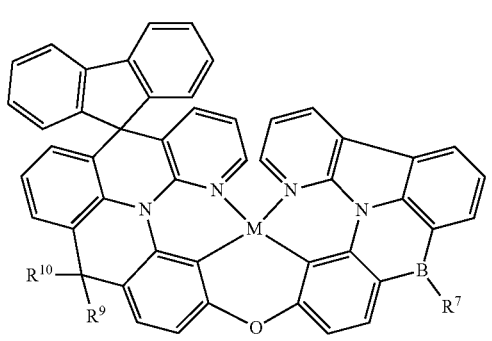
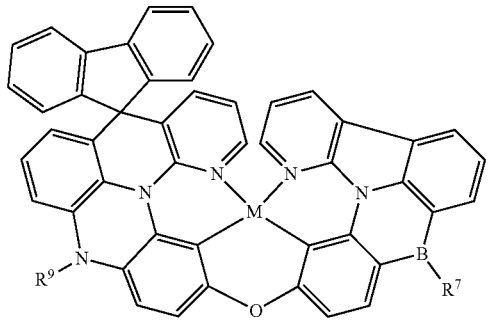

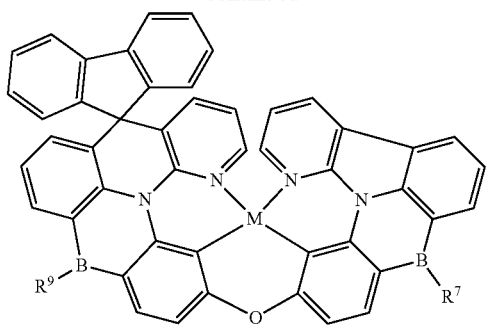
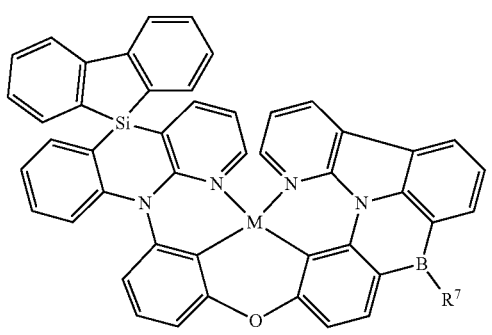
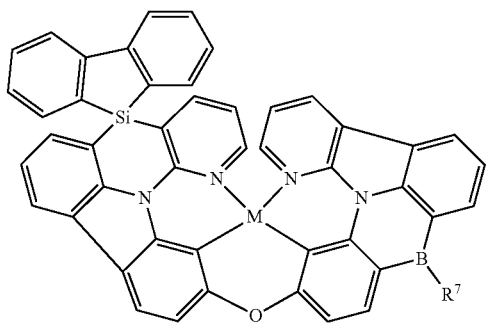
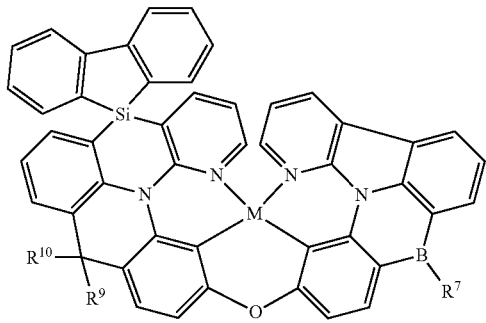
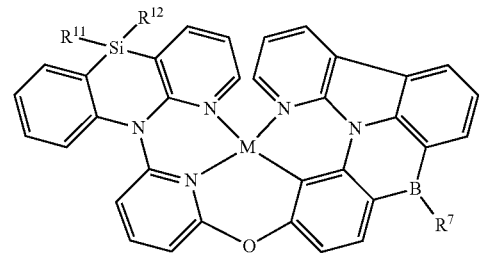
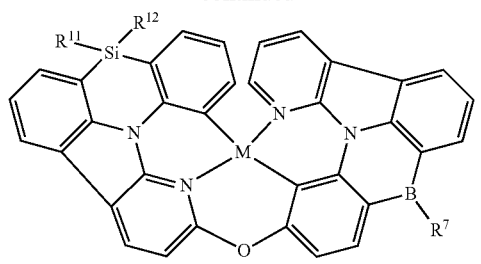
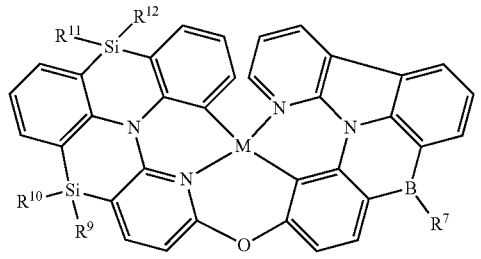
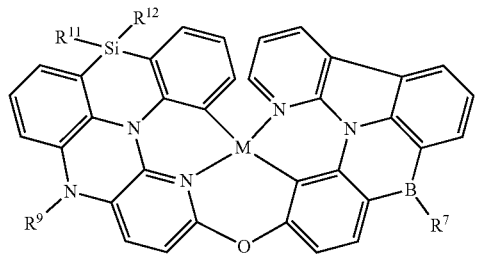
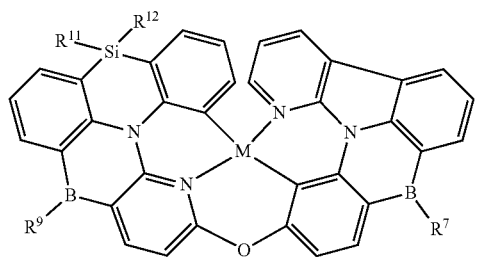
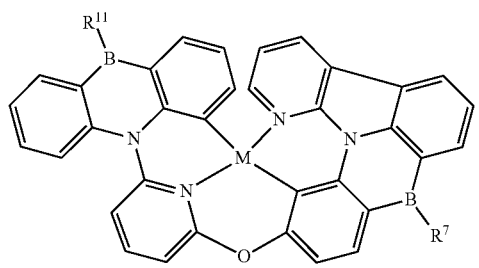
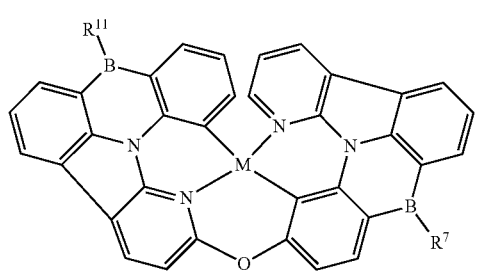

197
-continued
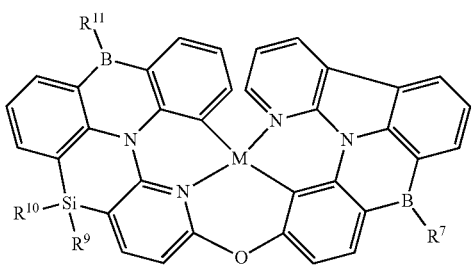
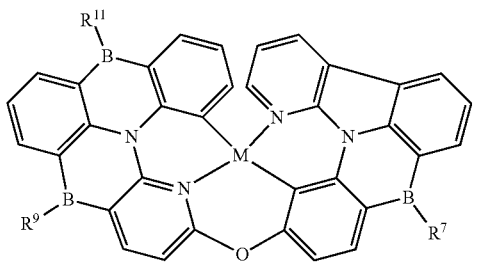
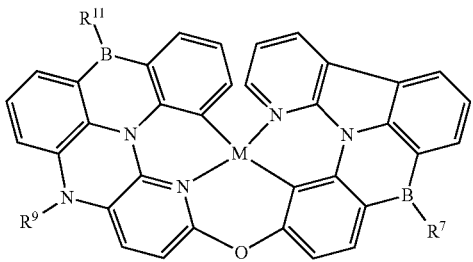
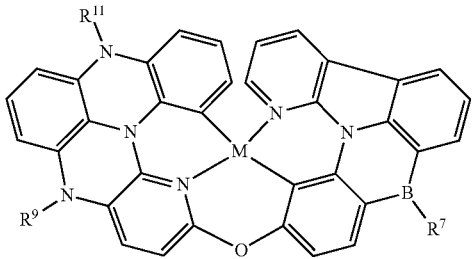
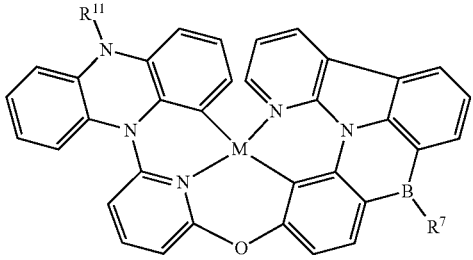
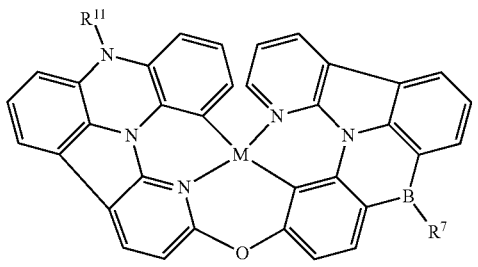
198
-continued
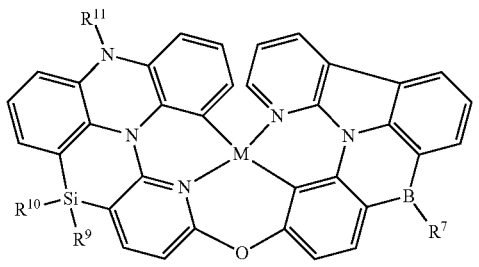
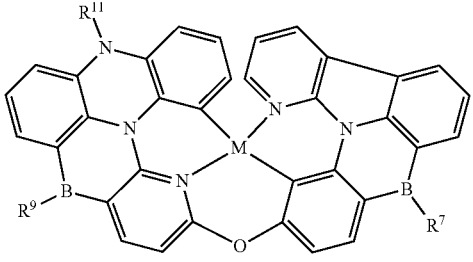
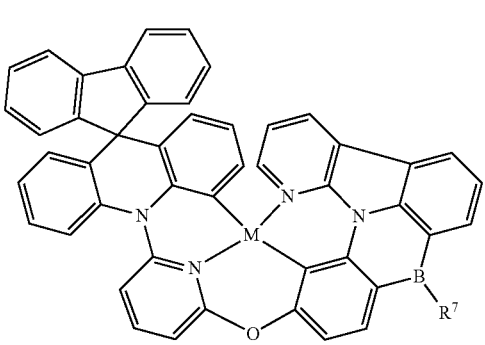
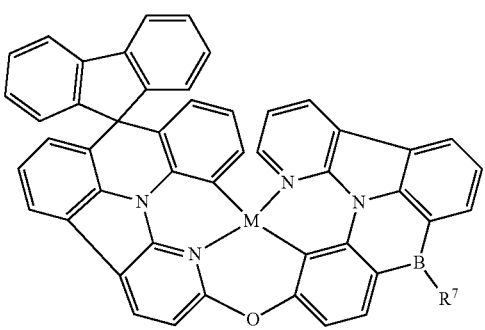
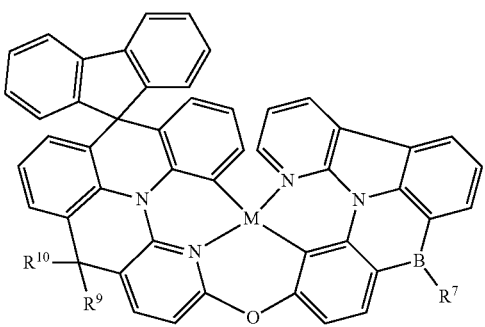

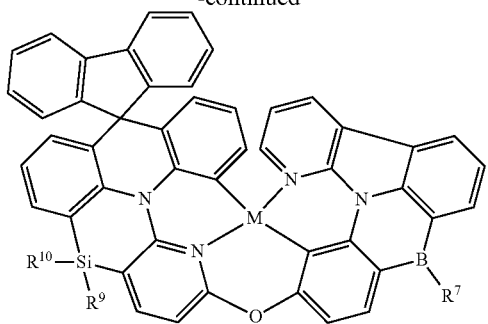
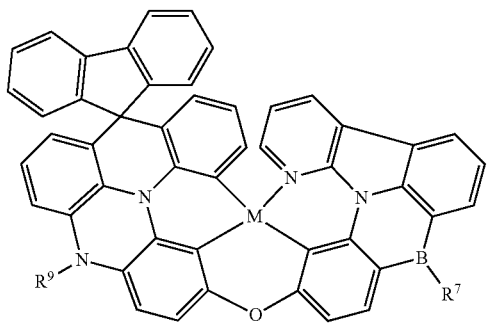
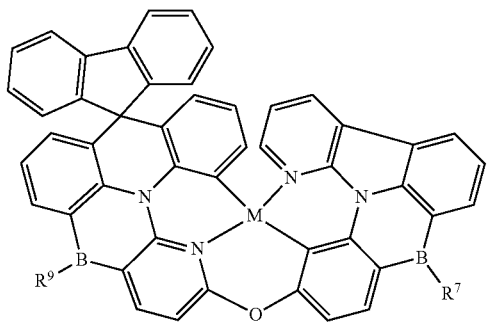
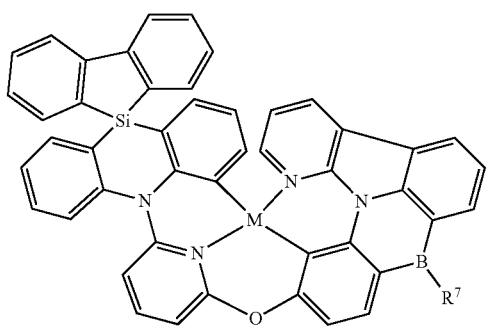
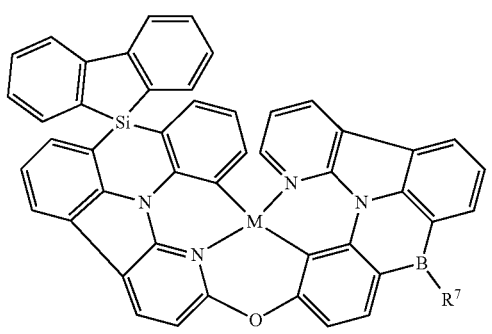
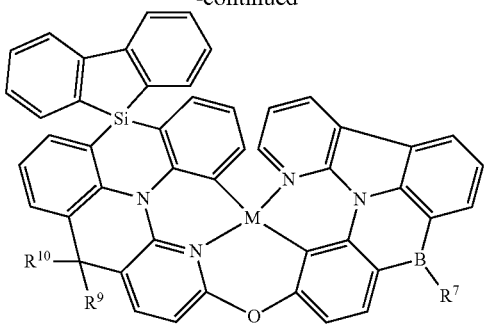

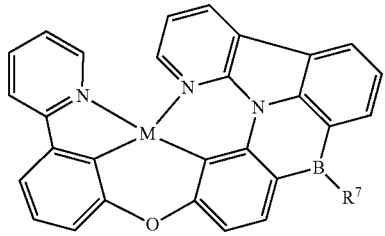
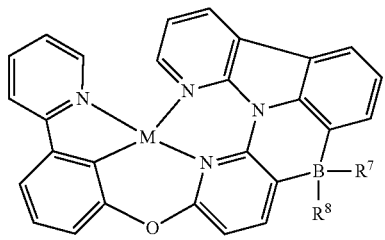
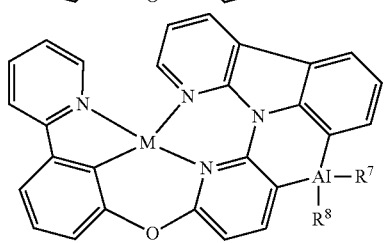

201
-continued
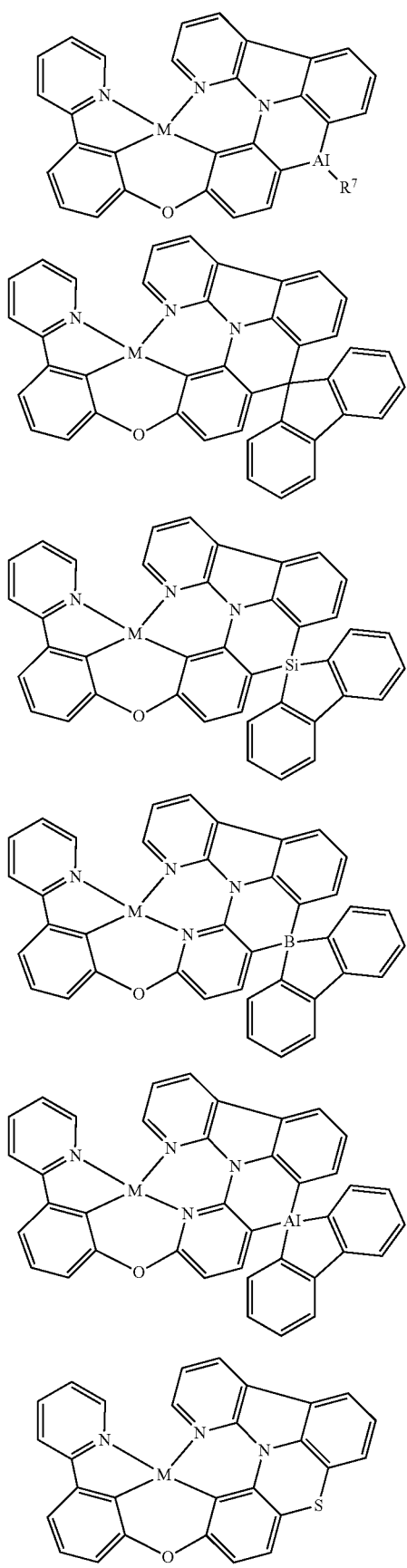
202
-continued
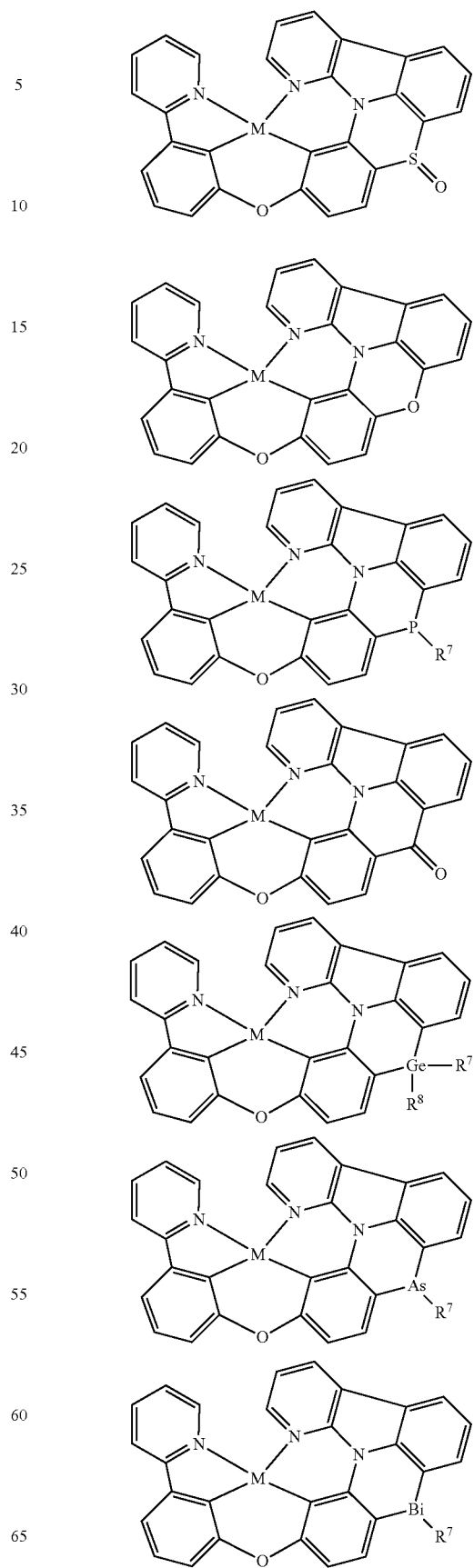

203
-continued
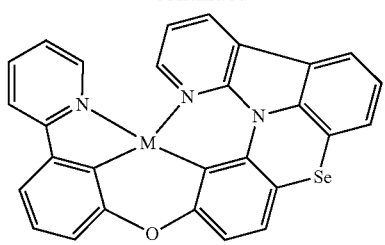
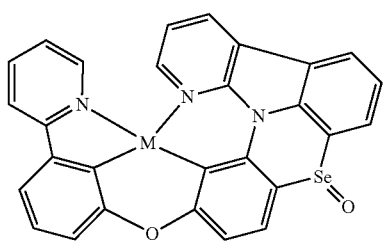
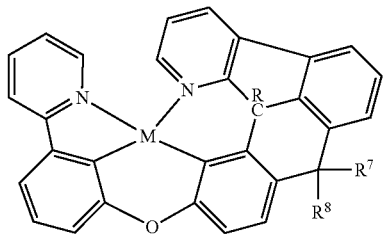
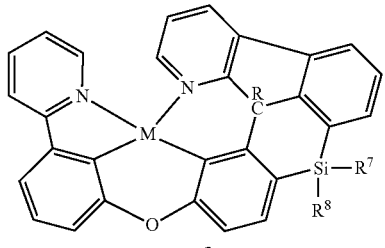
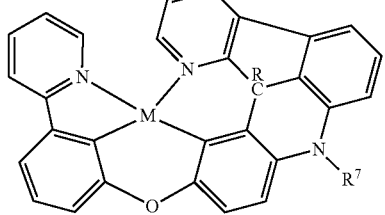
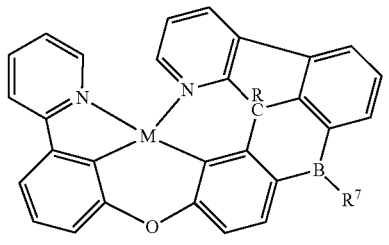
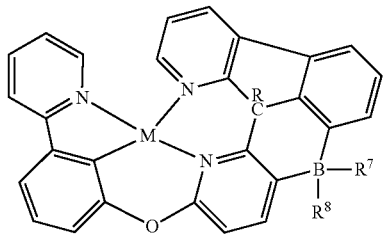
204
-continued
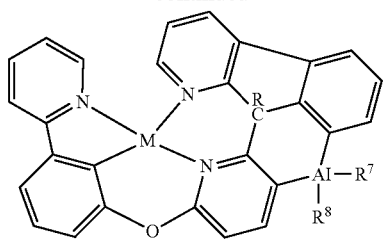
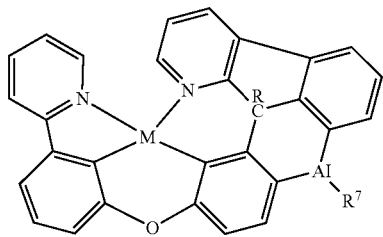
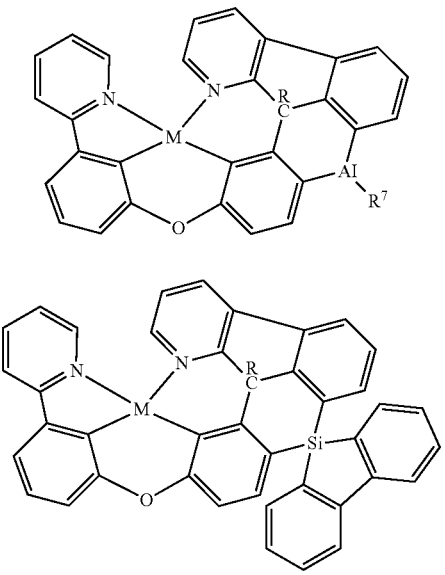
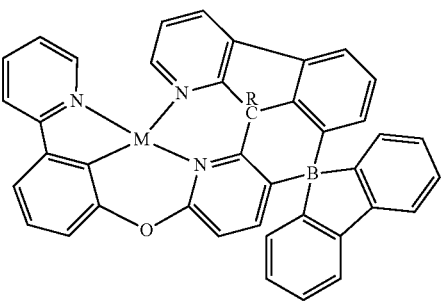
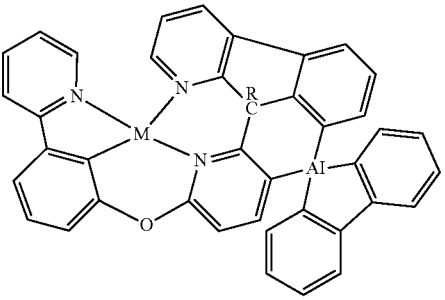
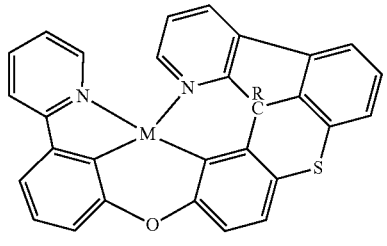

205
-continued
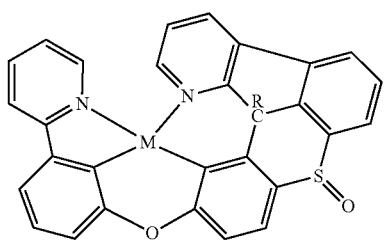
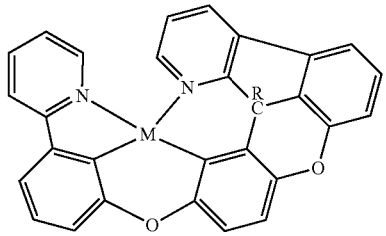
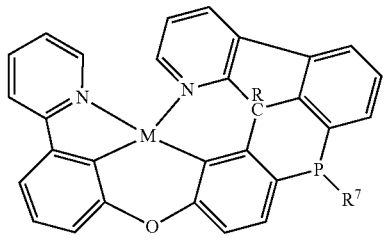
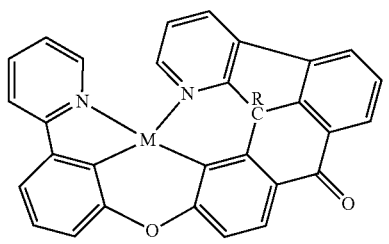
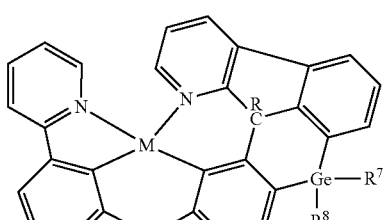
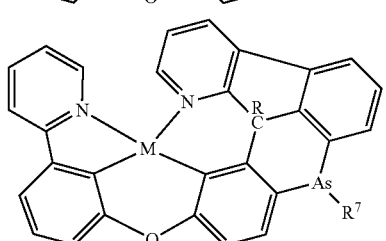
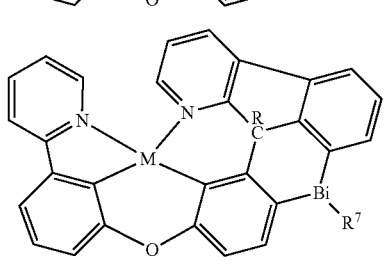
206
-continued
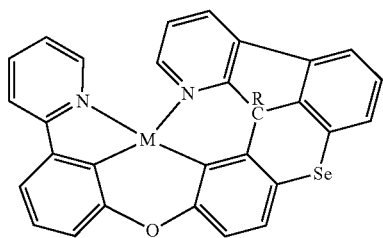
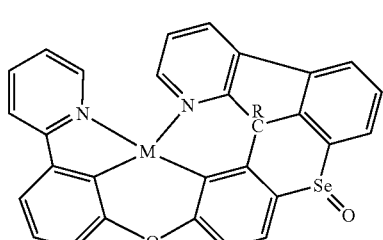
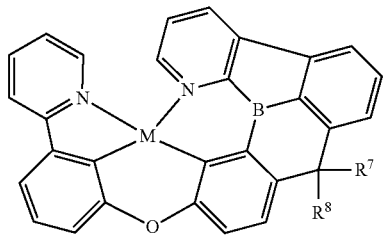
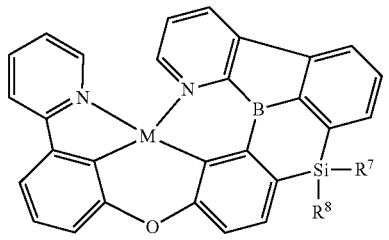
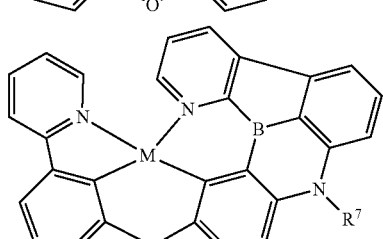
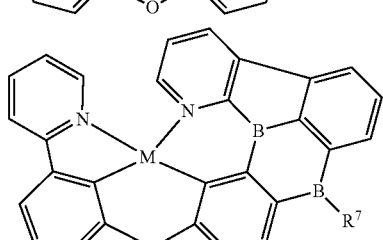
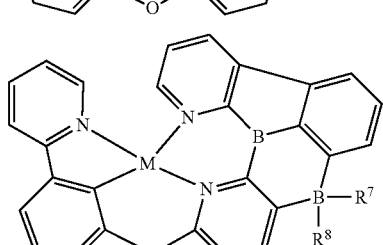

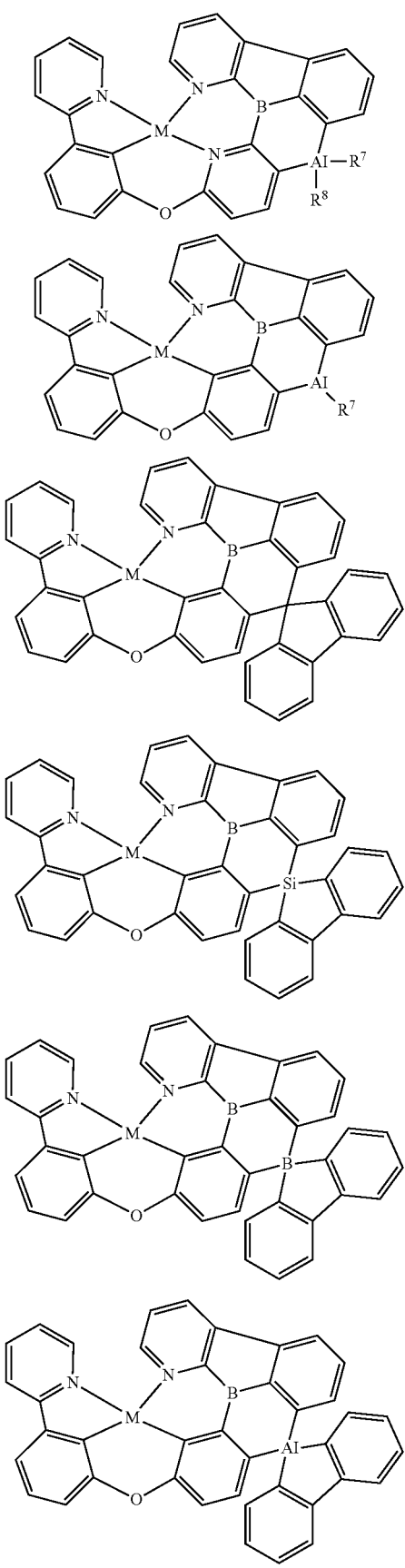
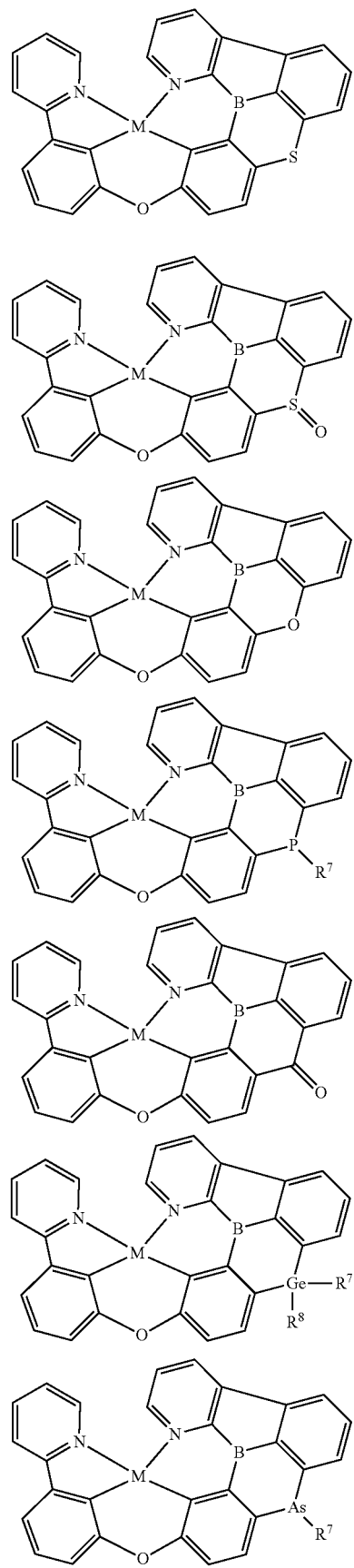

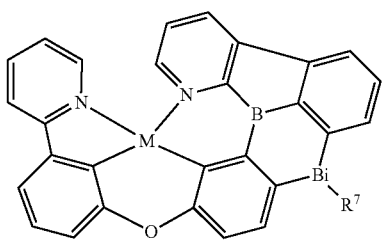
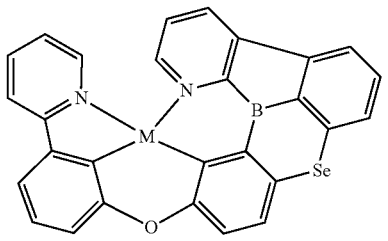
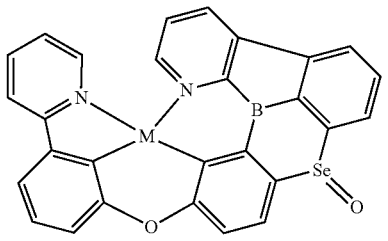
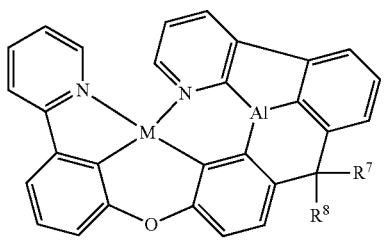
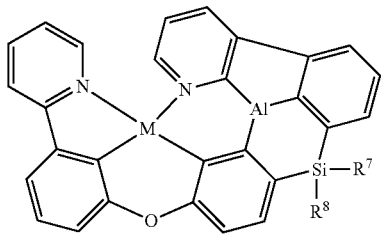
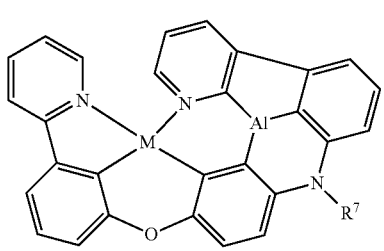
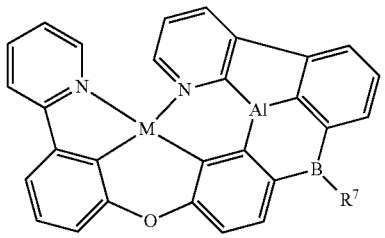
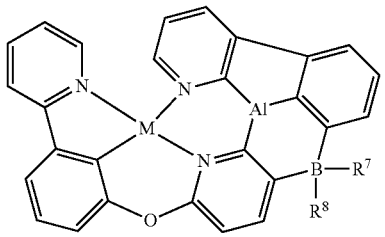
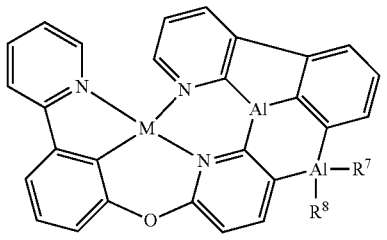
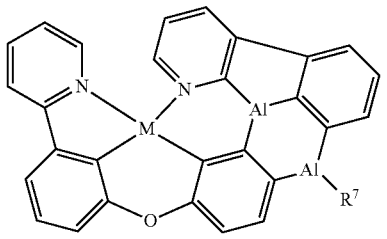
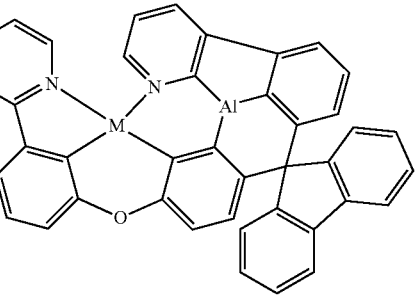
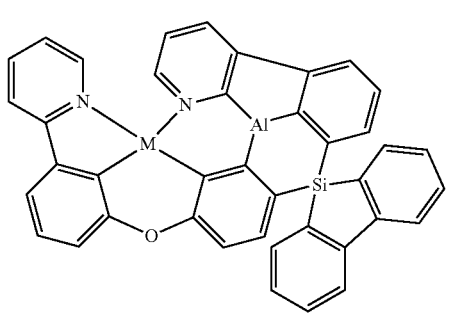

211
-continued
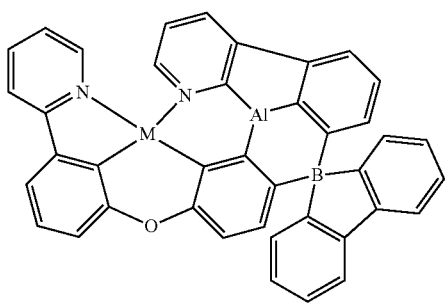
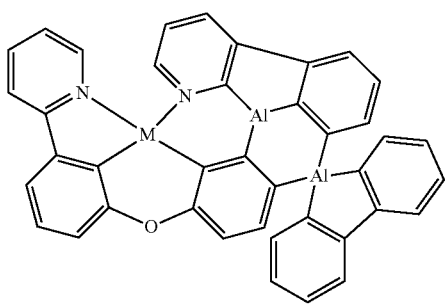
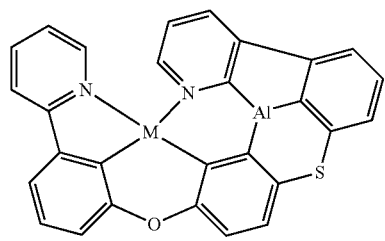
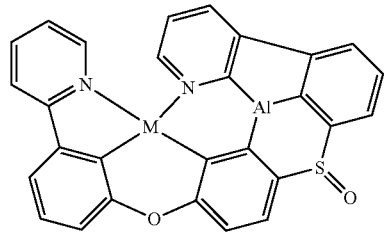
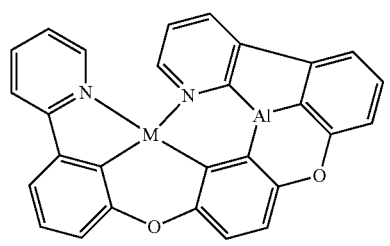
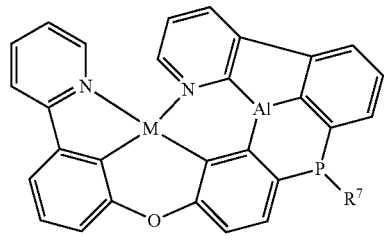
212
-continued
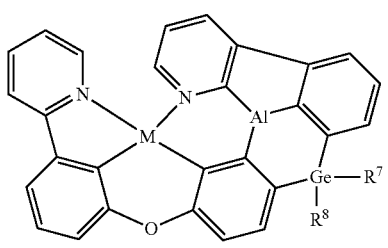
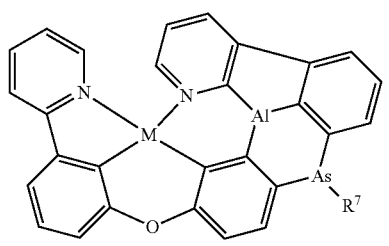
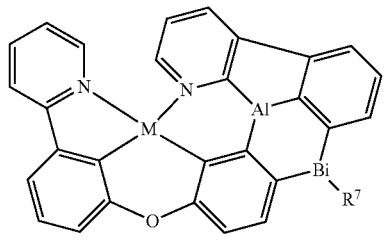
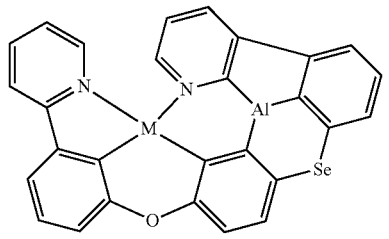
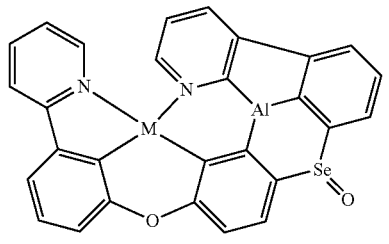
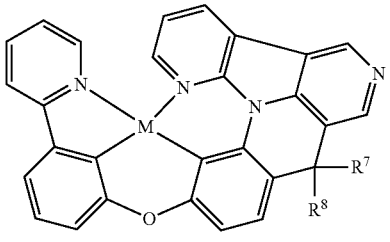

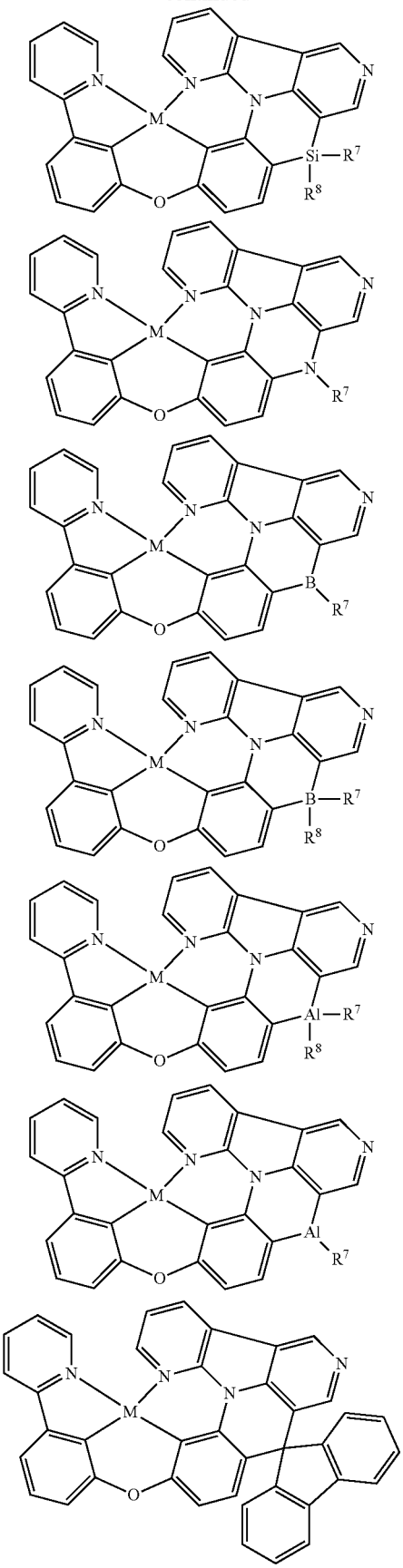
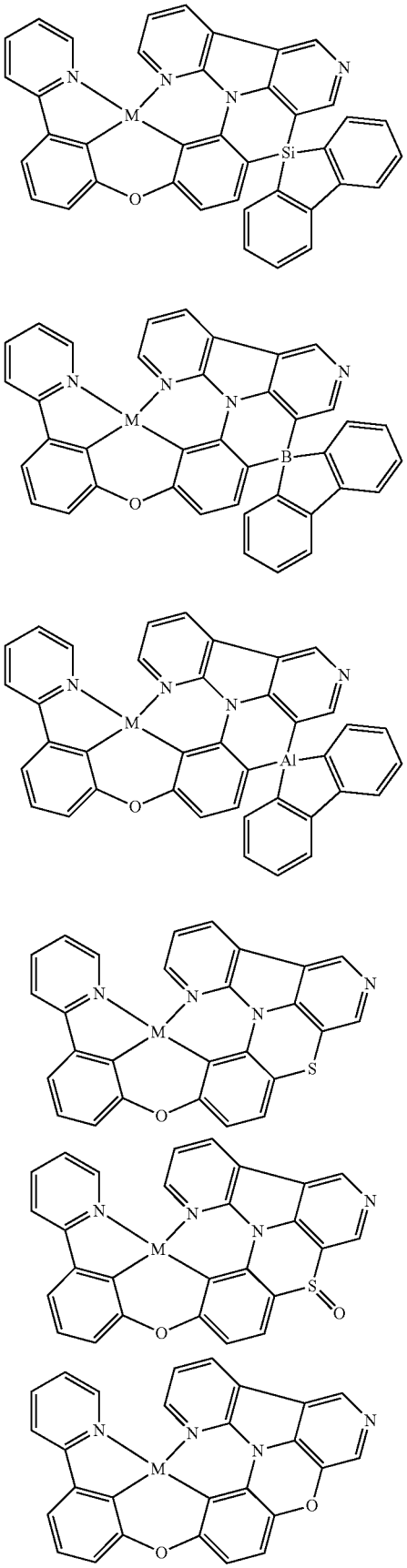

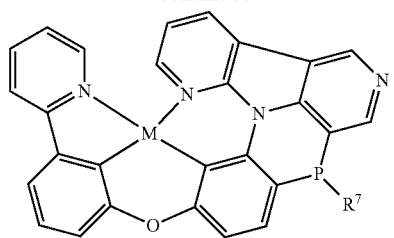
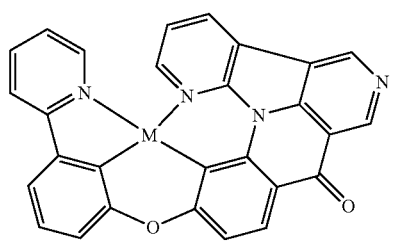
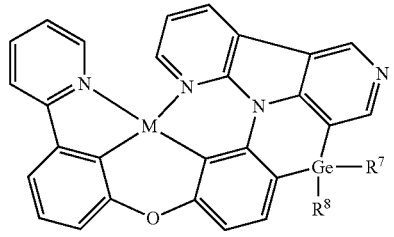
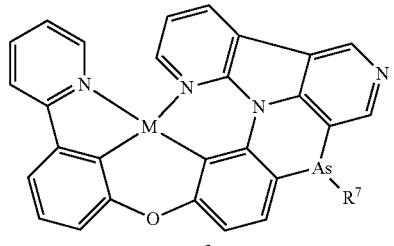
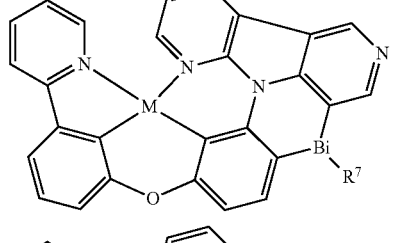
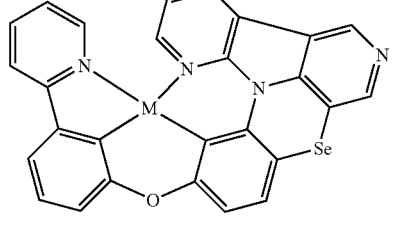
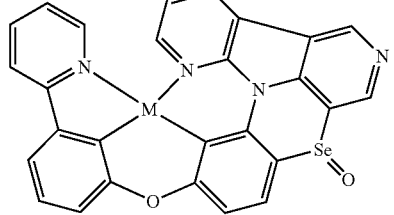
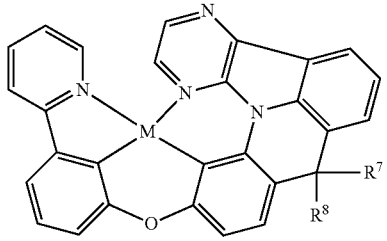
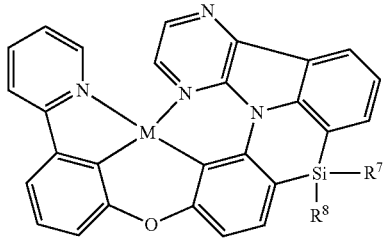
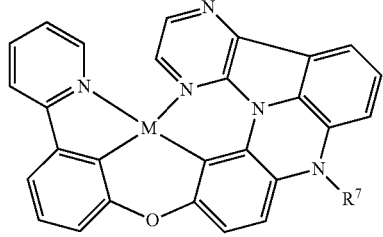
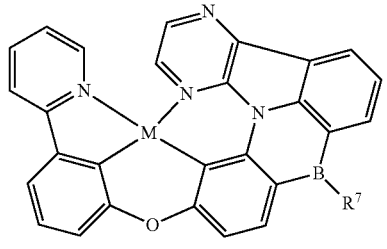
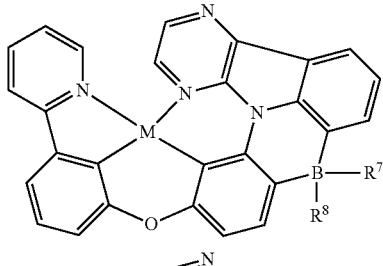
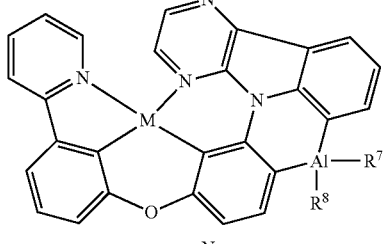
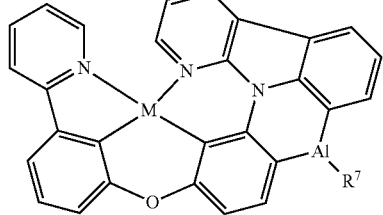

217
-continued

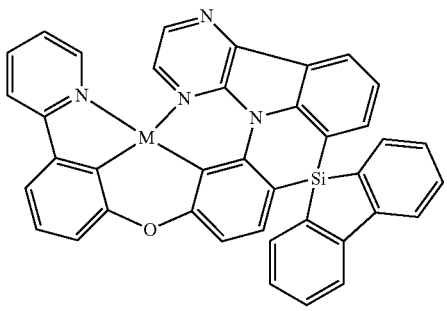
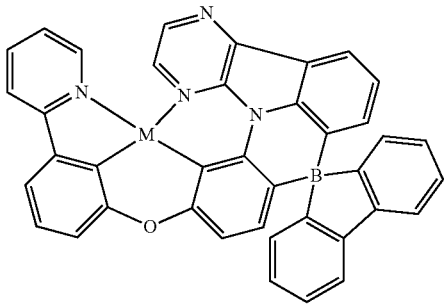
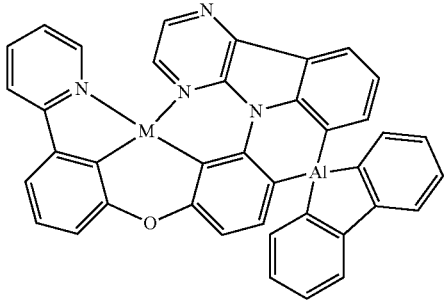
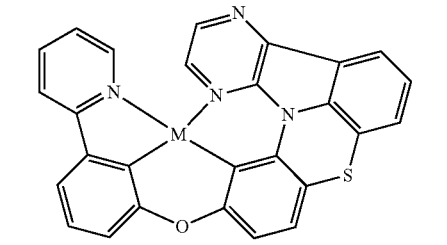
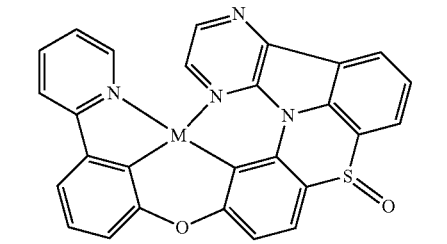
218
-continued
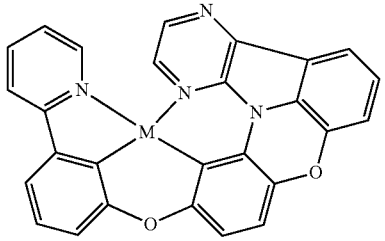
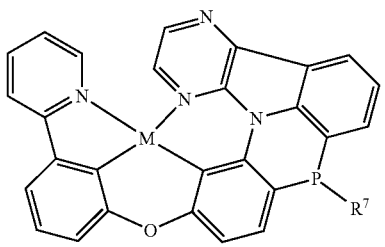
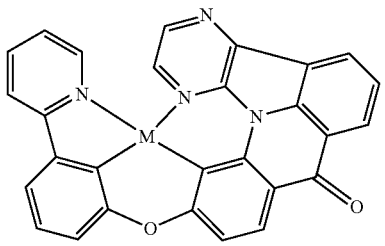
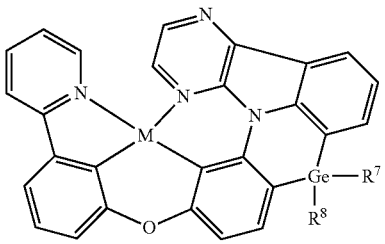
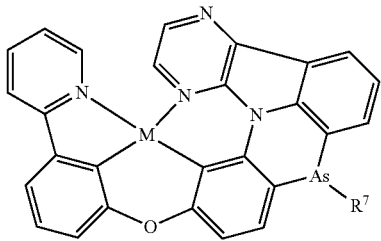
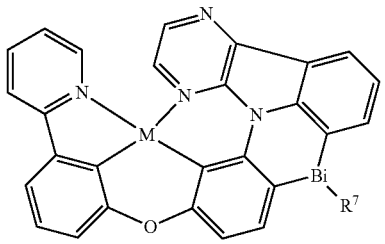
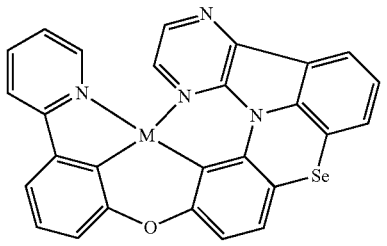

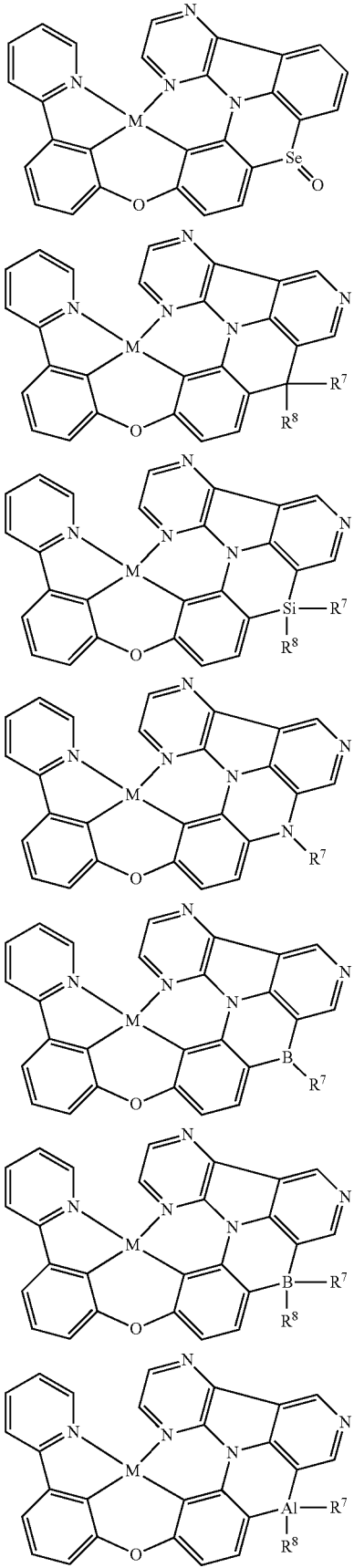
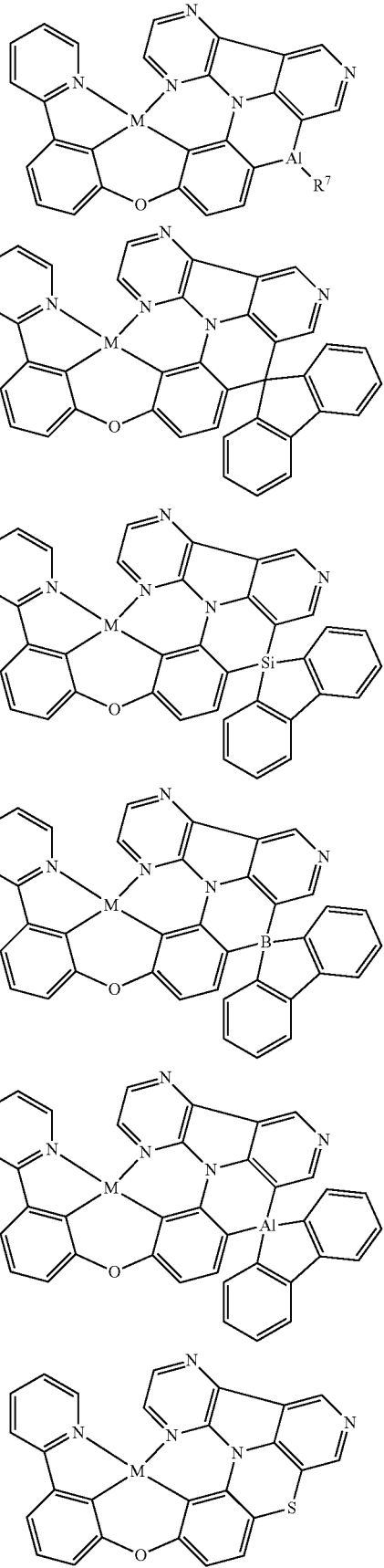

221
-continued
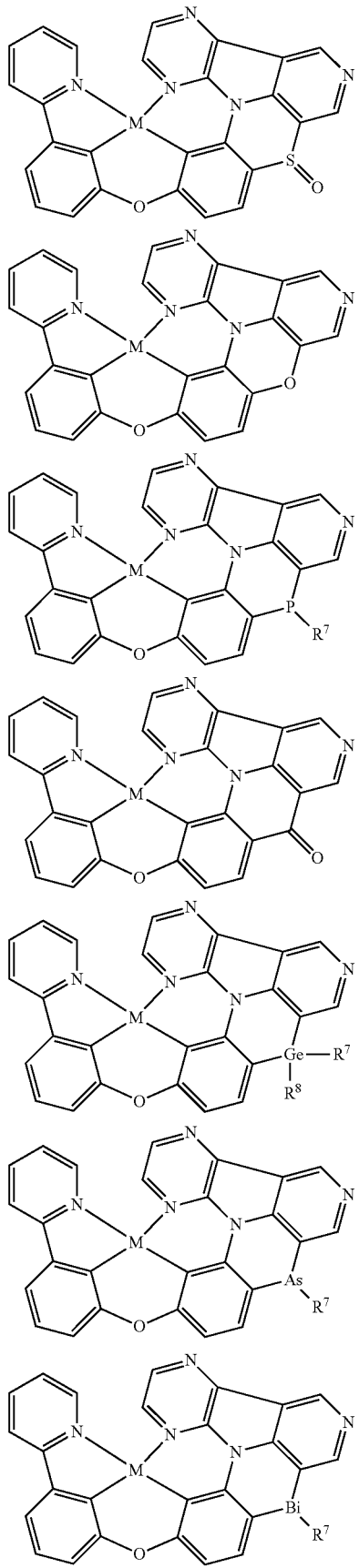
222
-continued
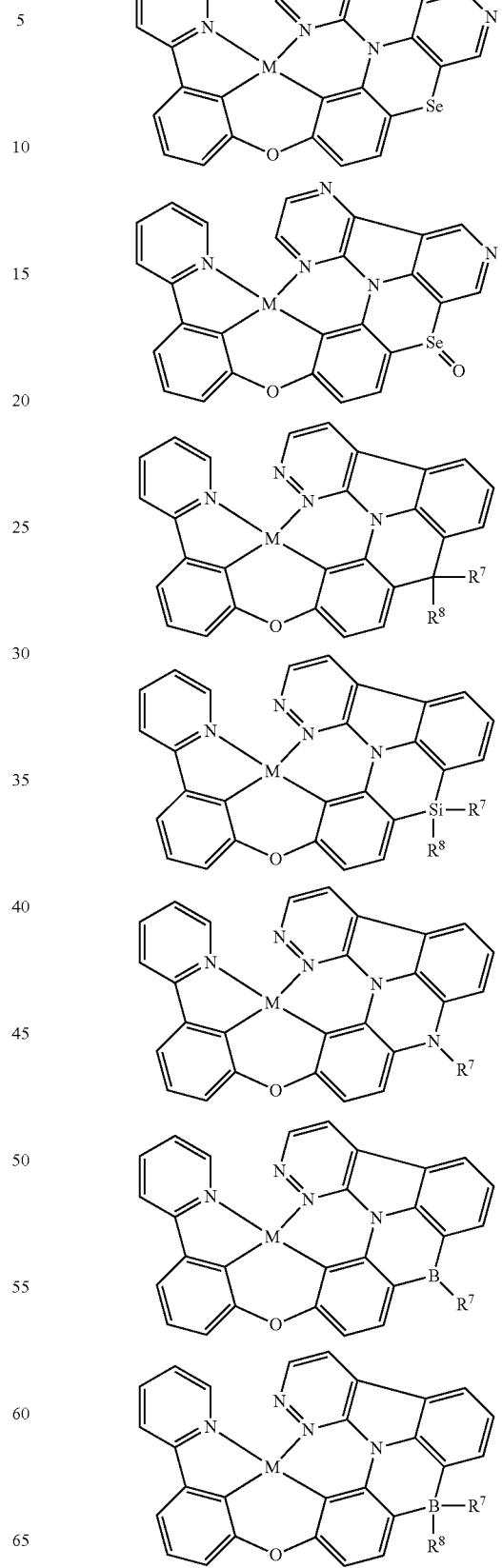

223
-continued
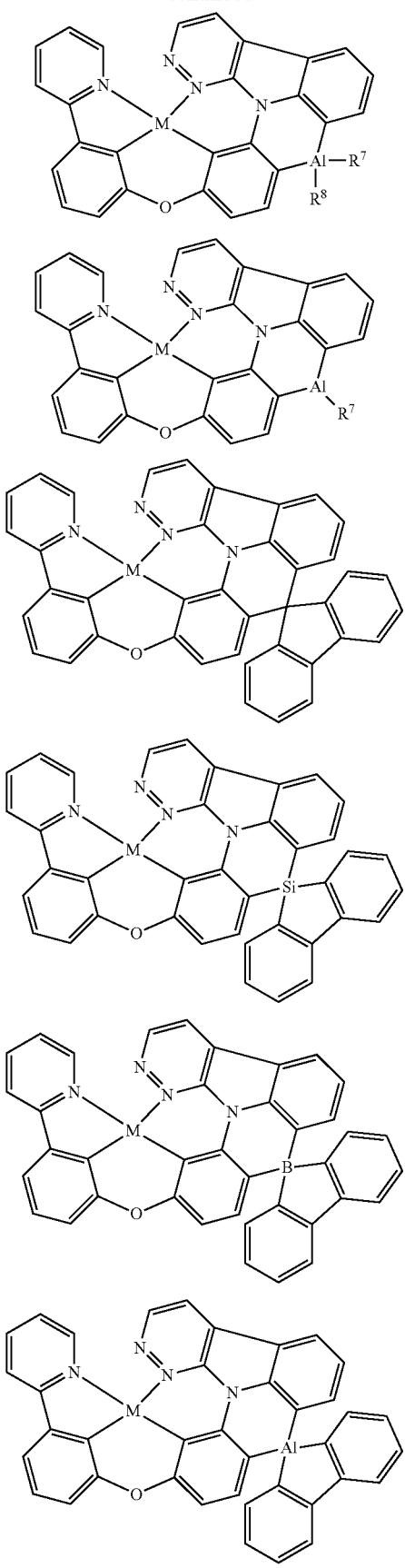
224
-continued
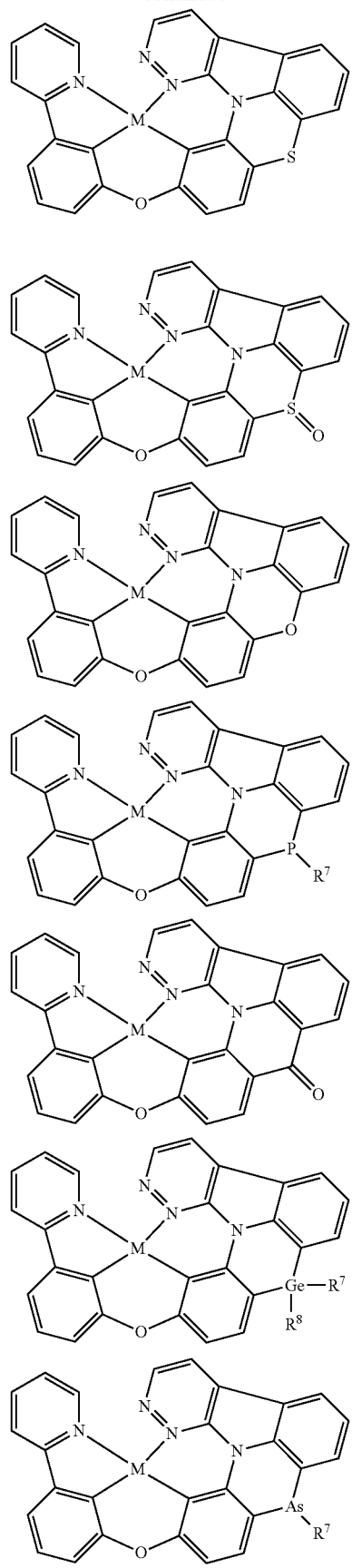

225
-continued
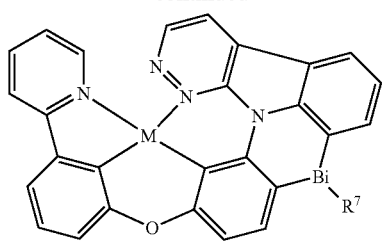
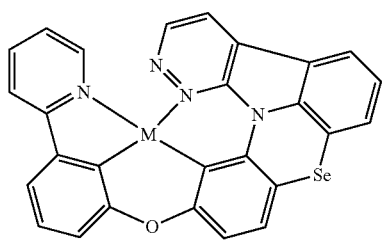
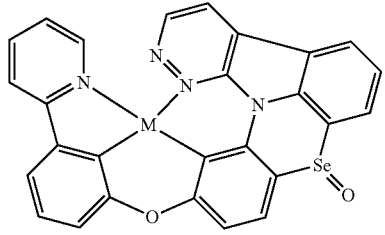
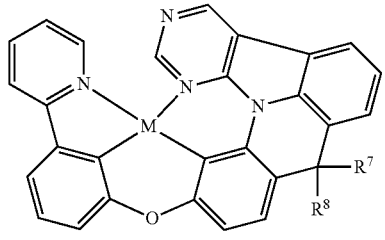
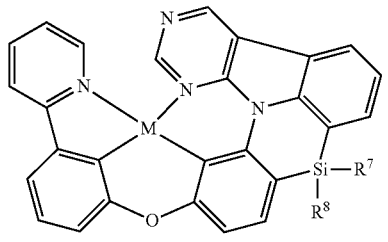
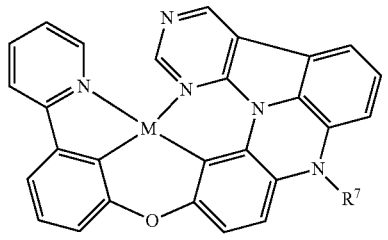
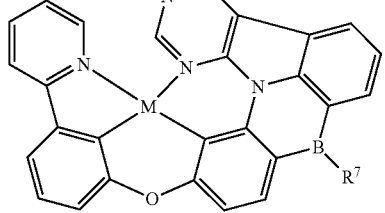
226
-continued
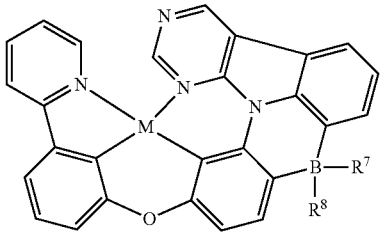
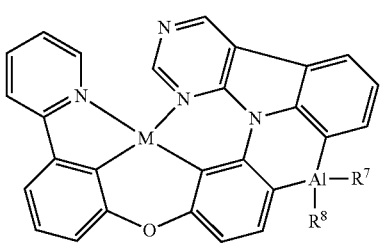
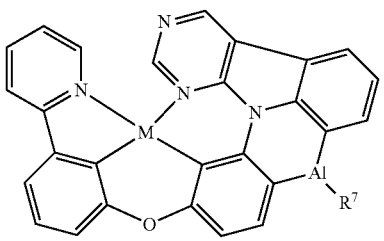
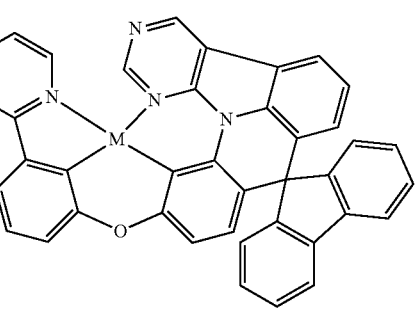
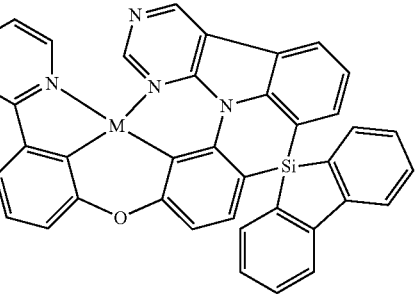
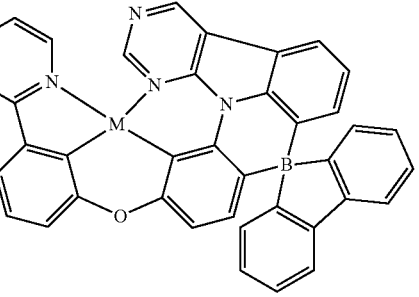

-continued
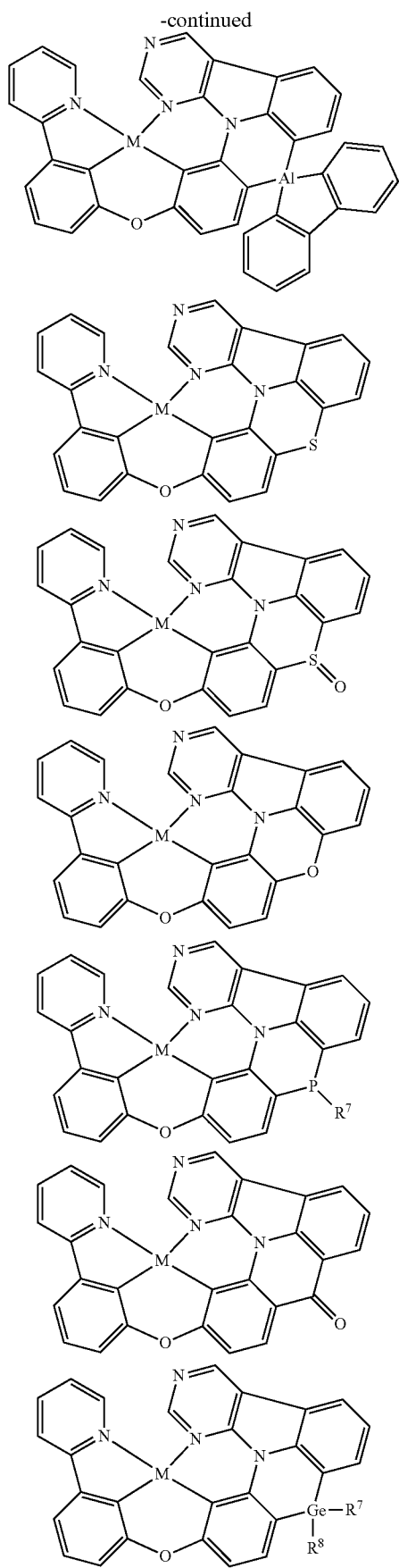
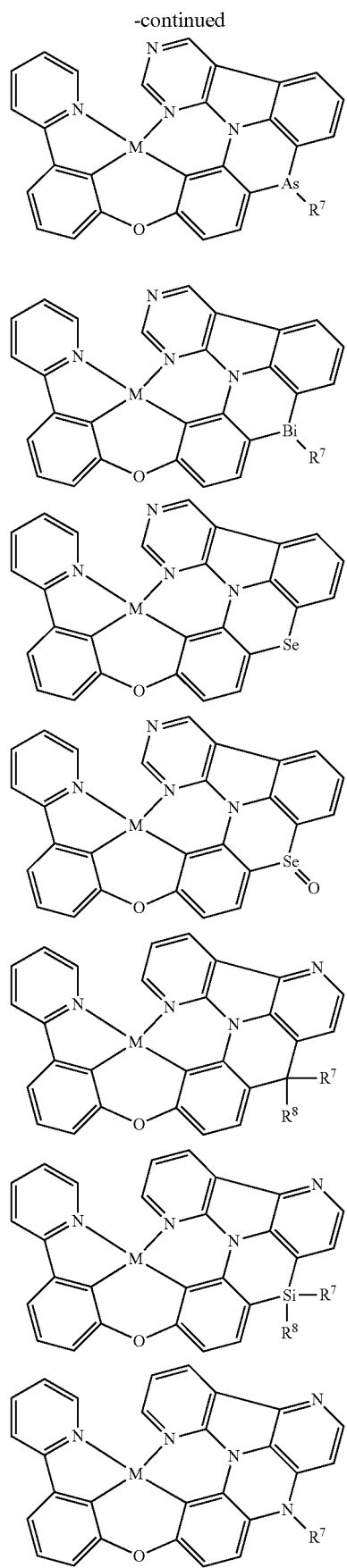

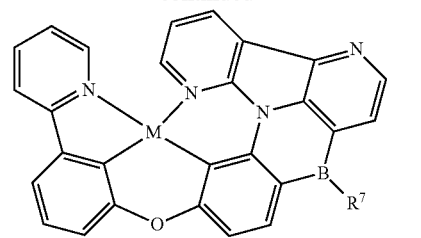
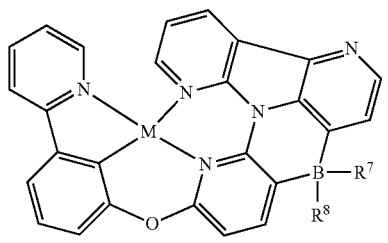
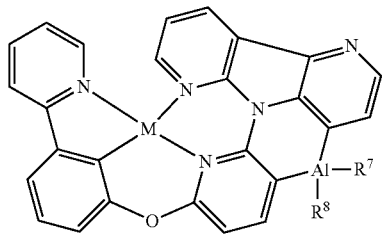
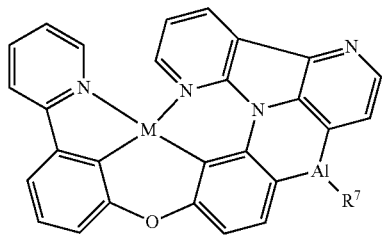
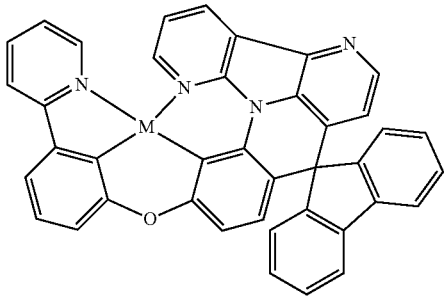
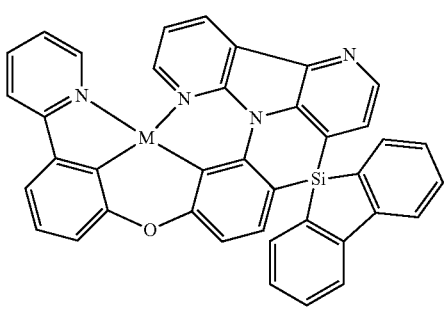
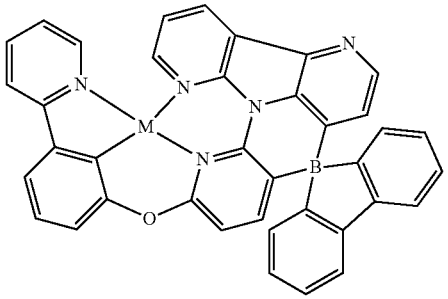
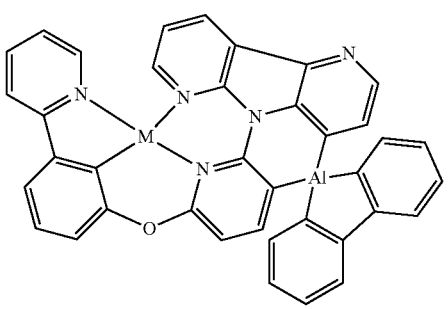
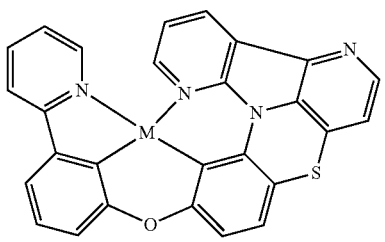
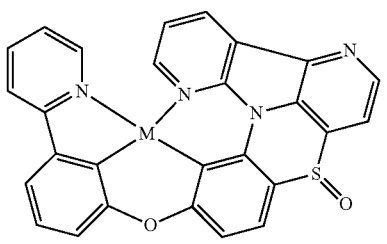
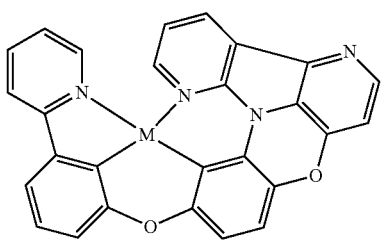
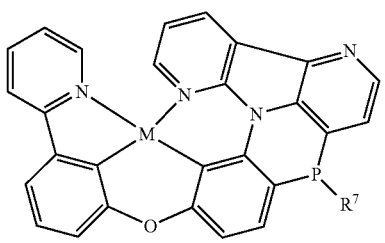

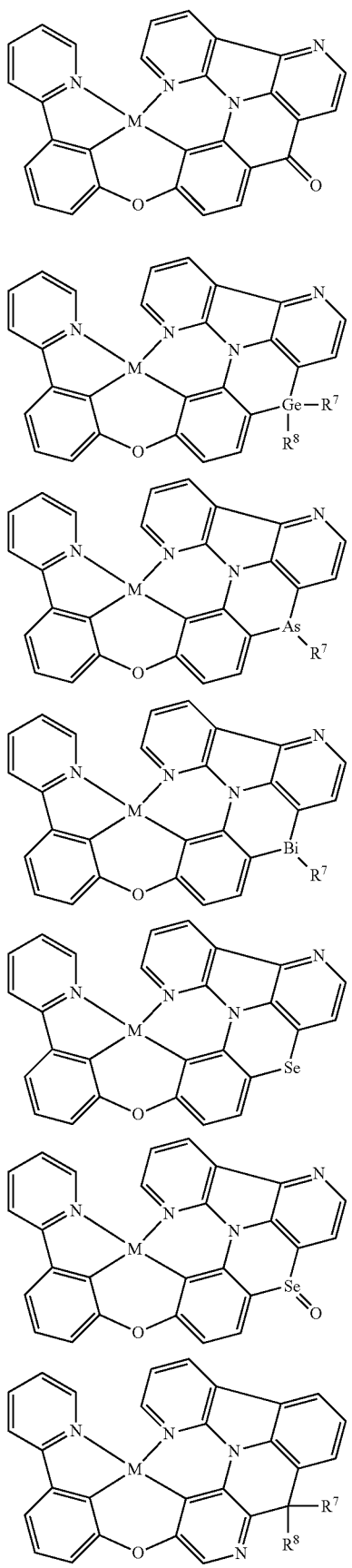
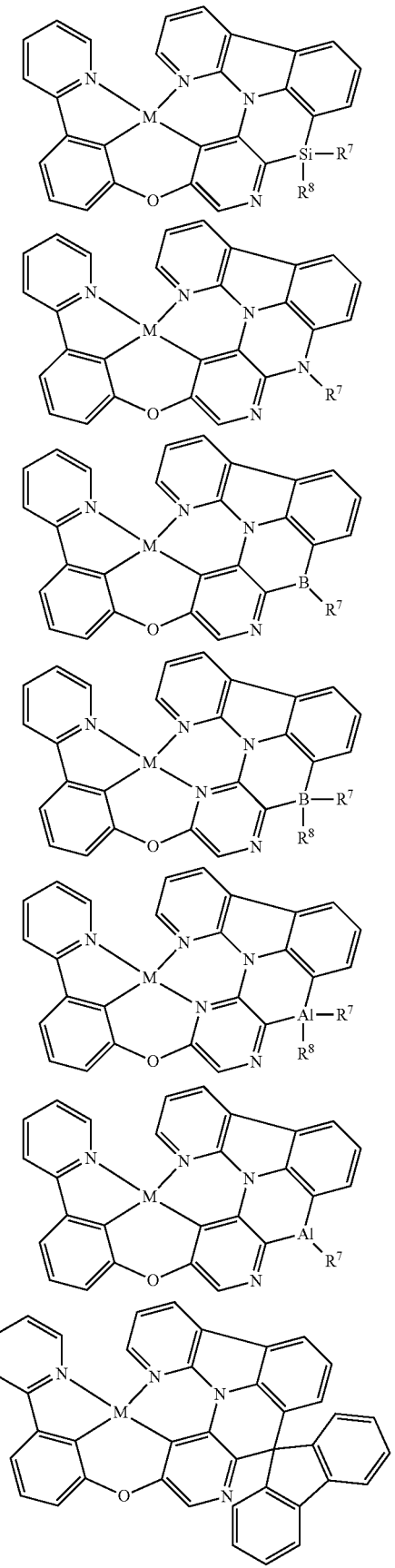

233
-continued
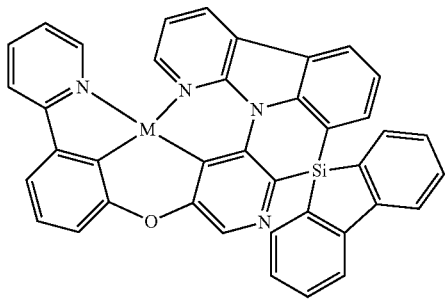
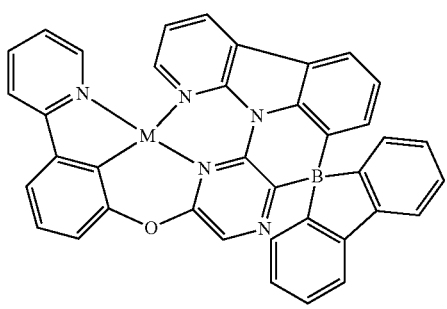
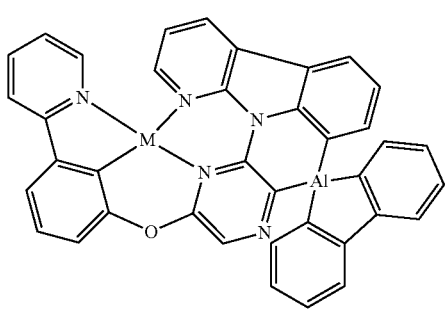
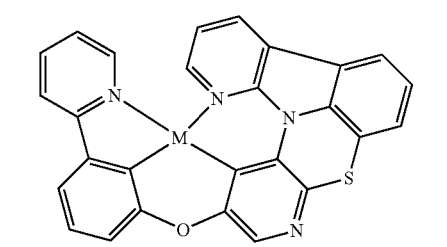
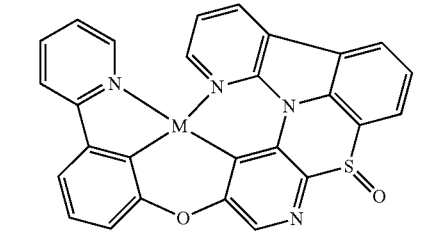
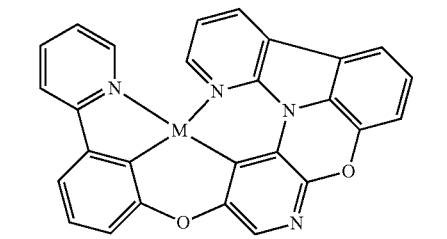
234
-continued
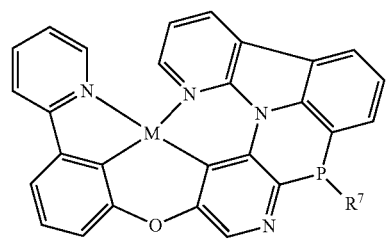
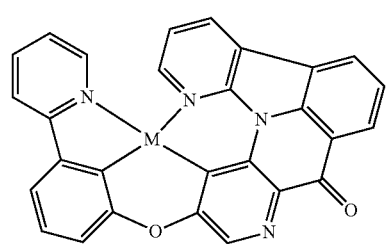
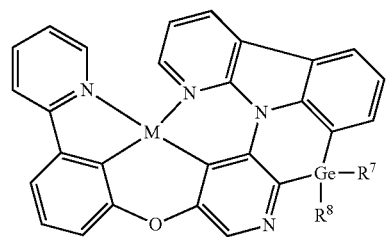
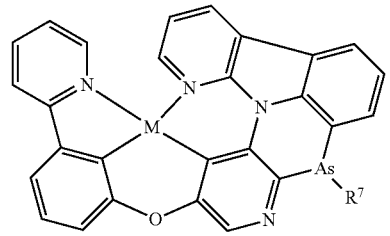
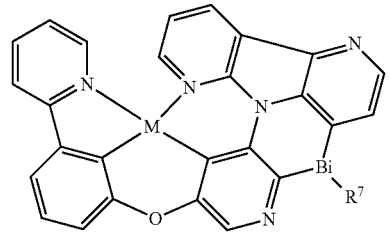
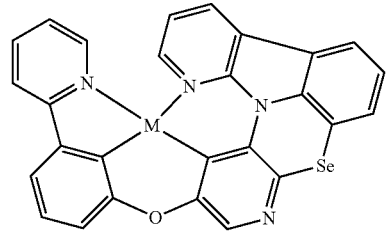
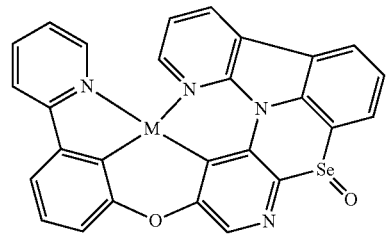

235
-continued
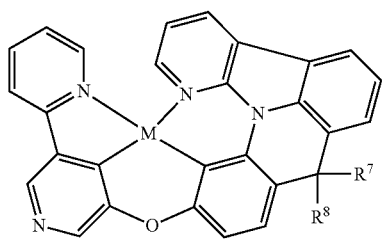
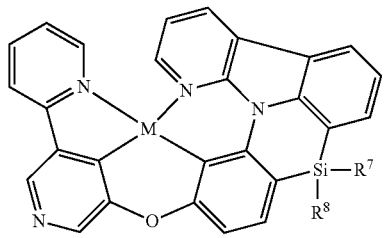
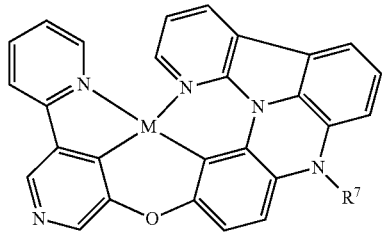
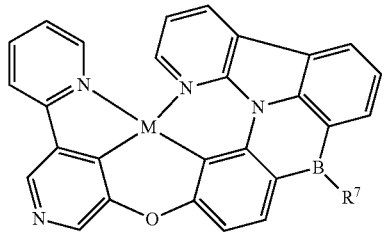
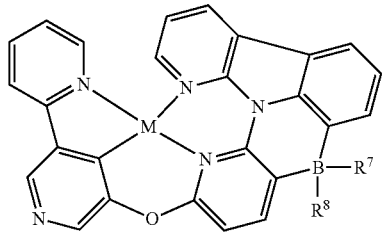
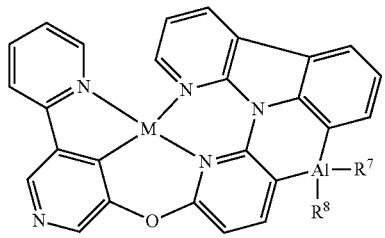
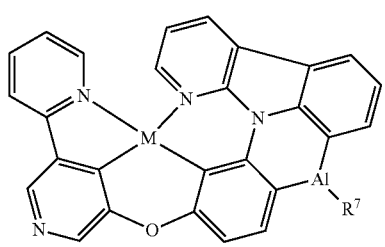
236
-continued
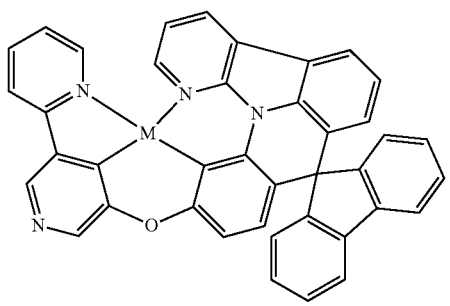
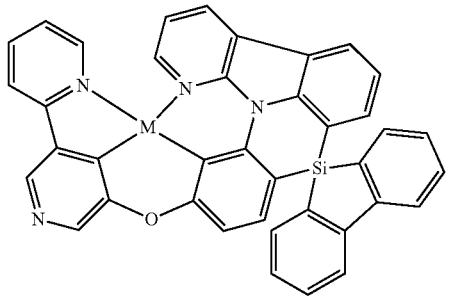
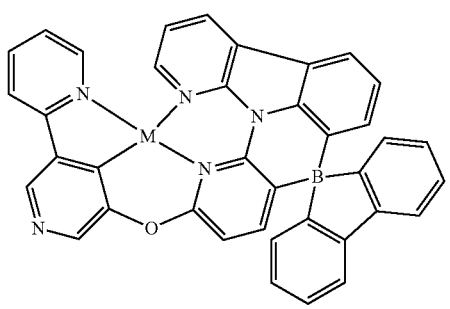
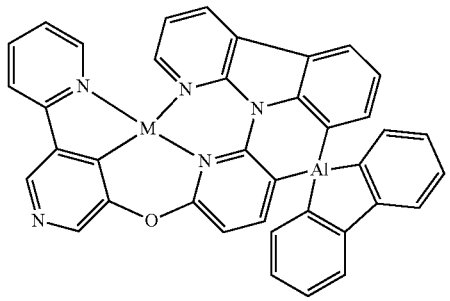
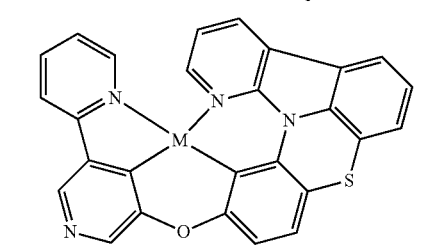
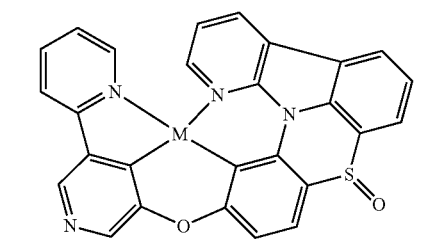

237
-continued
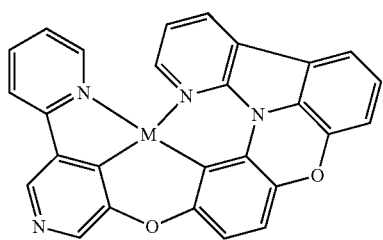
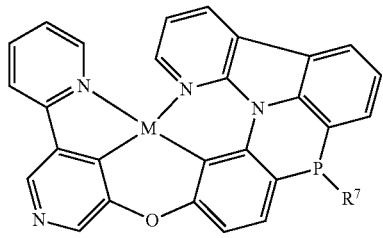
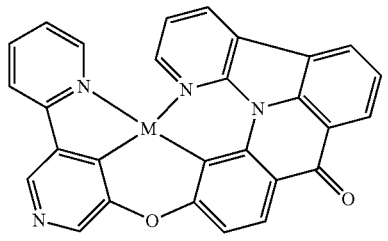
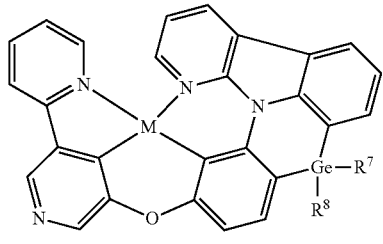
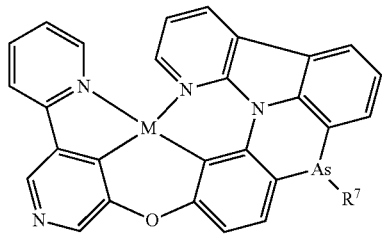
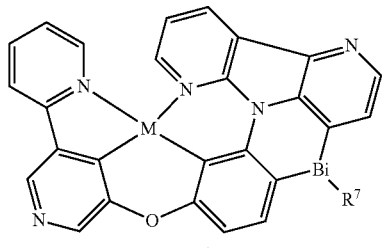
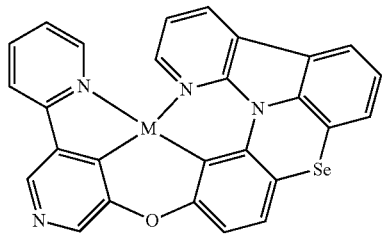
238
-continued
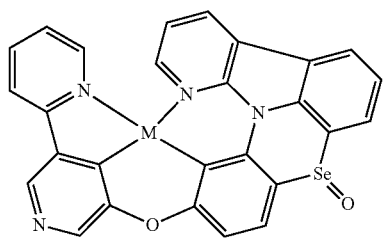
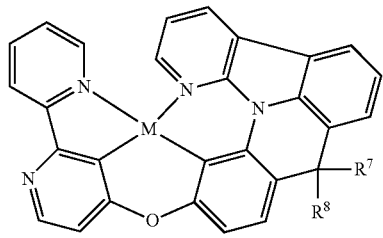
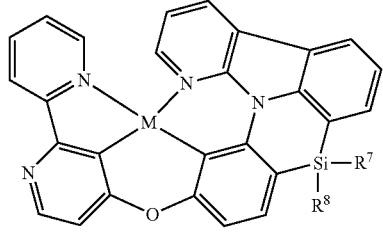
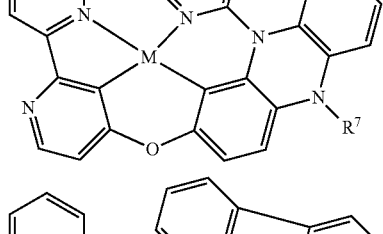
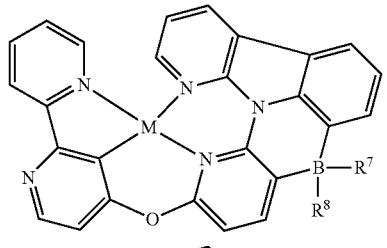
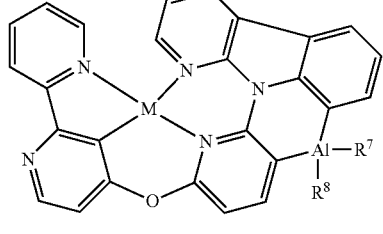

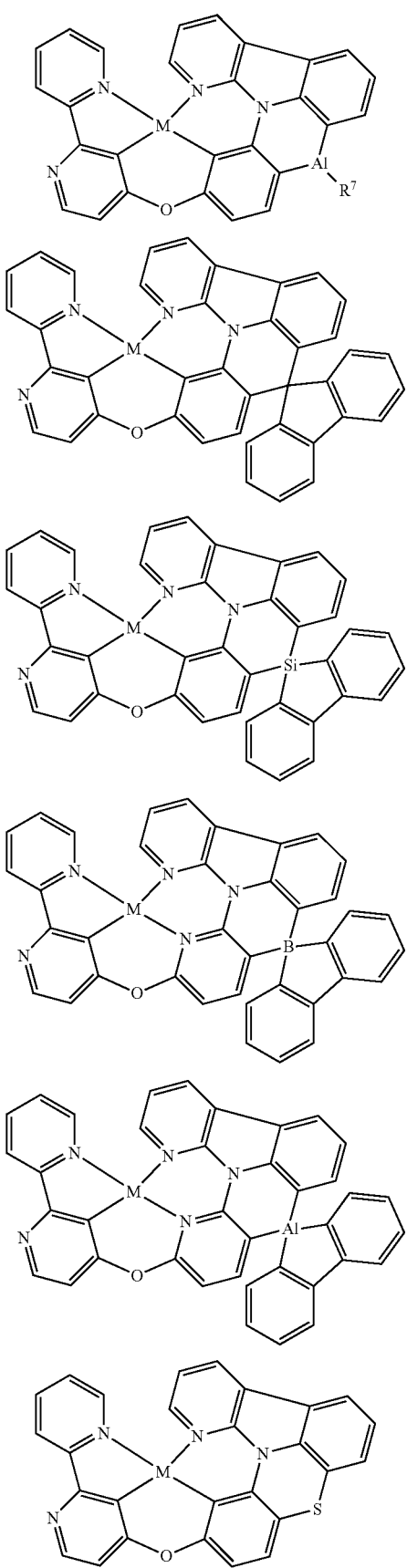
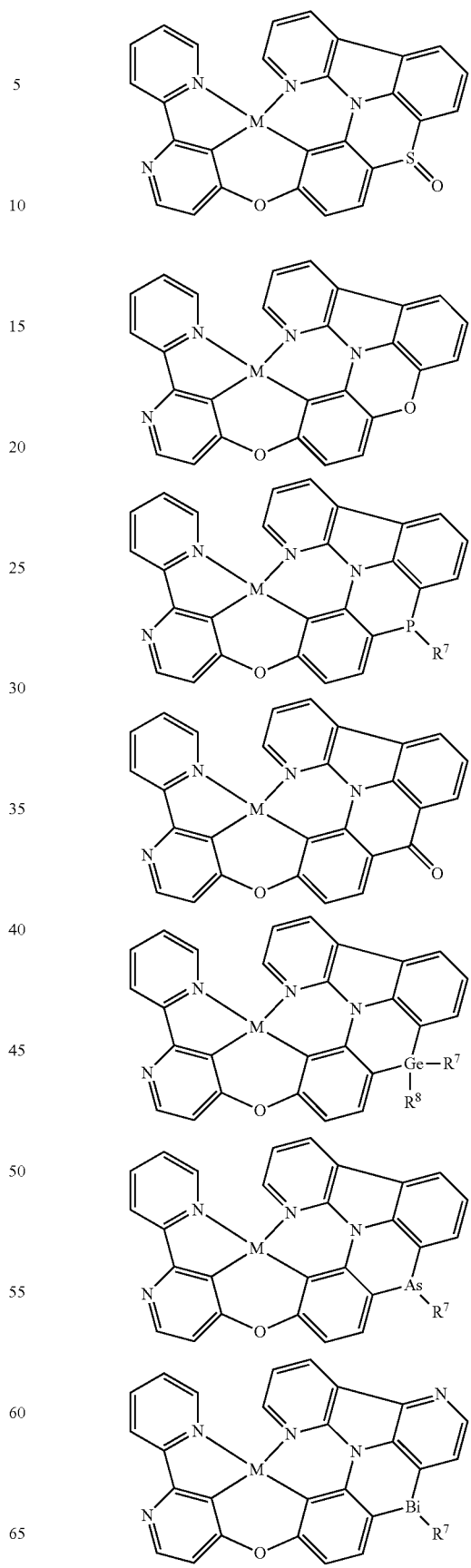

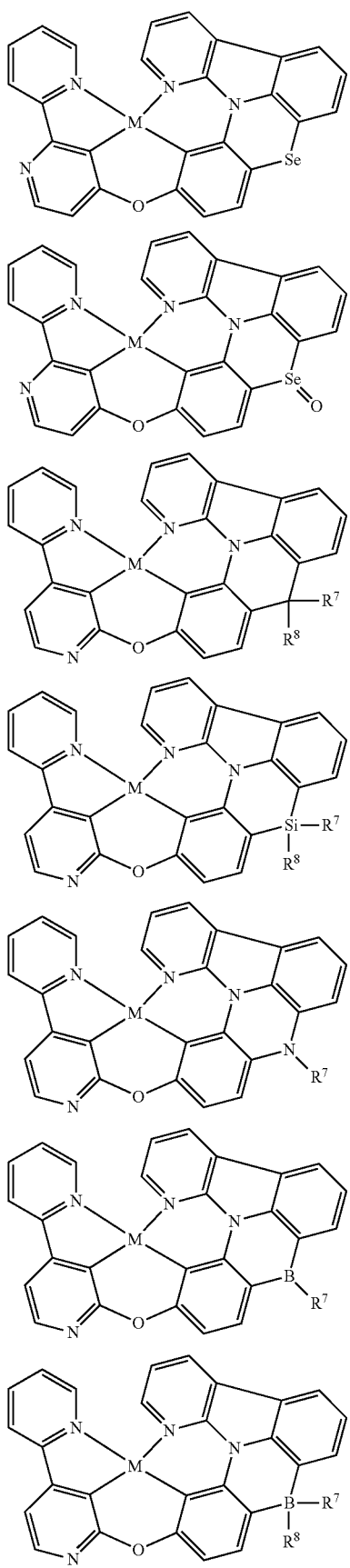
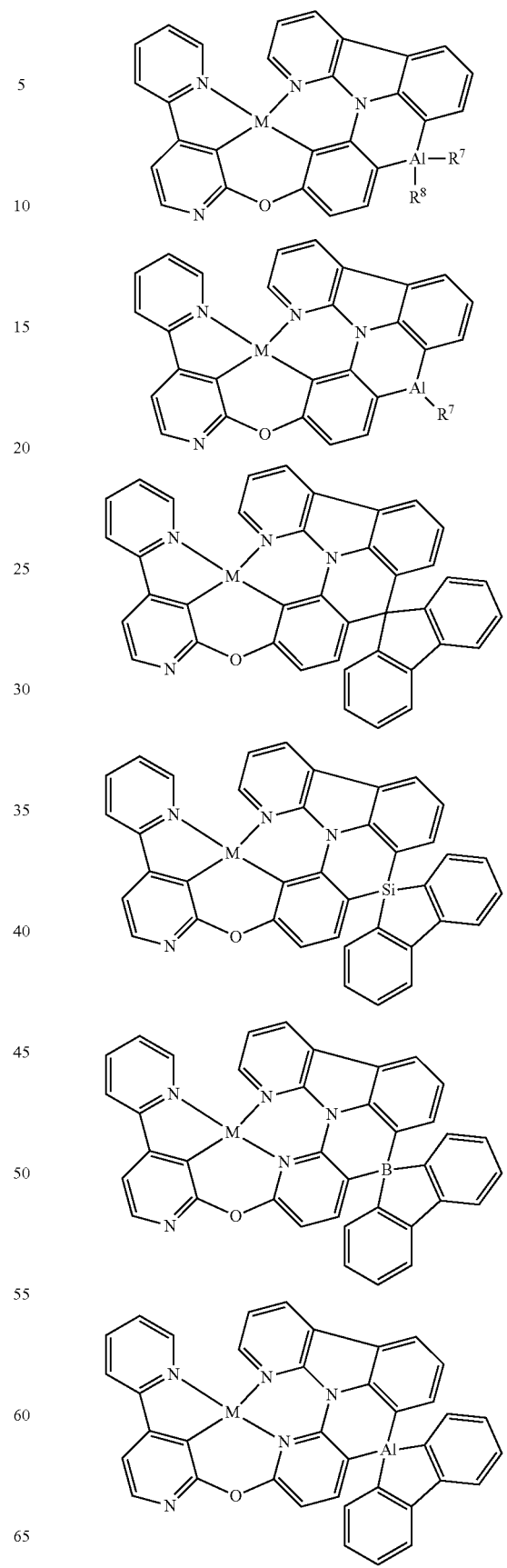

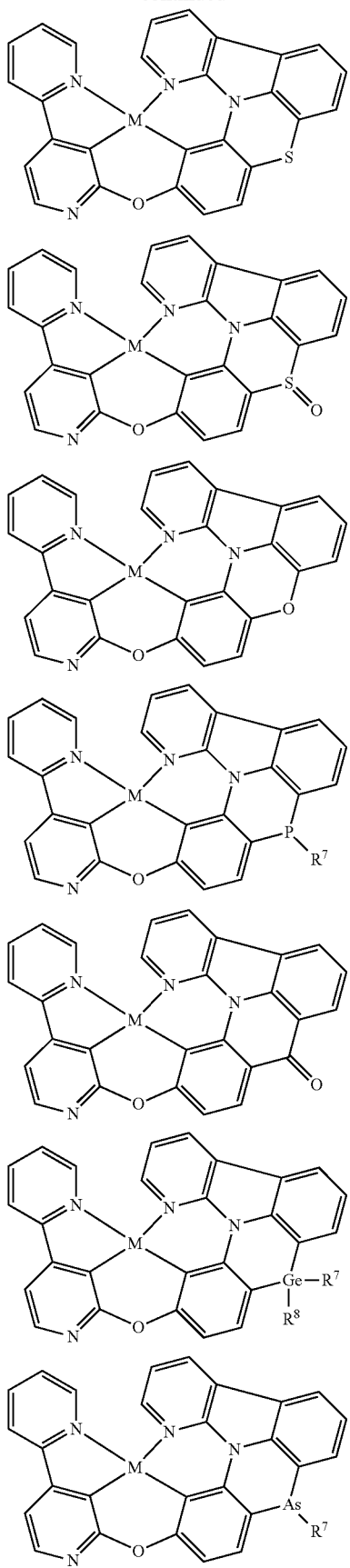
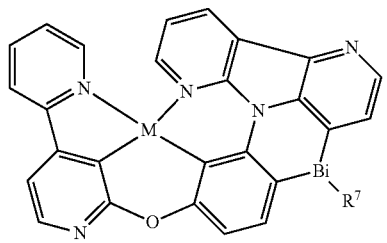
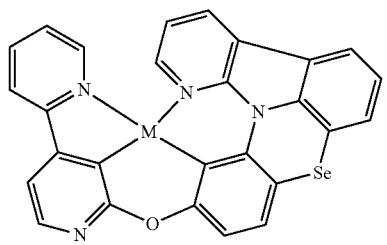
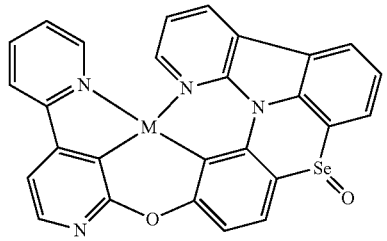
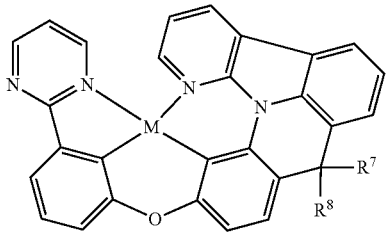
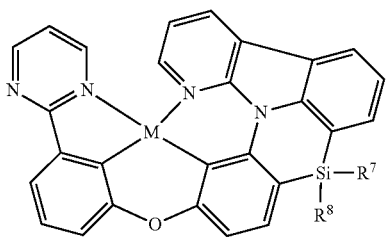
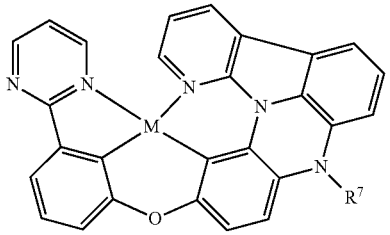
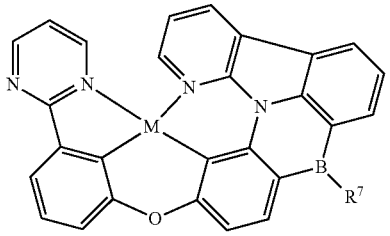

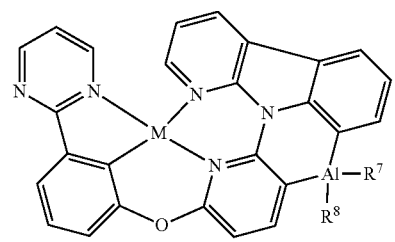
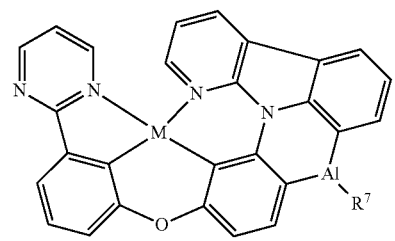
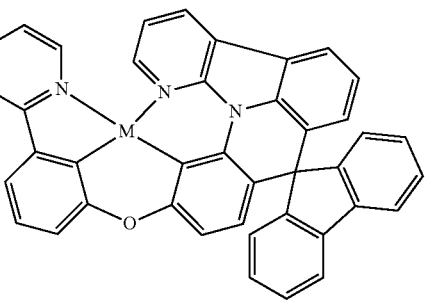
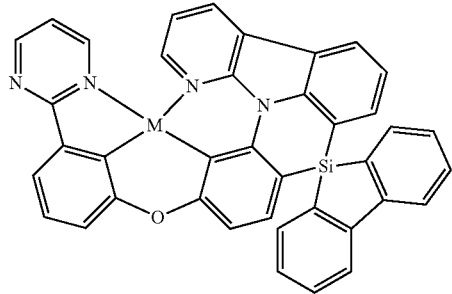
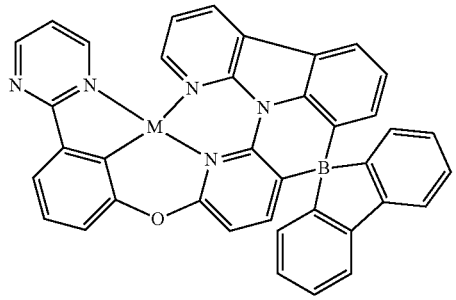
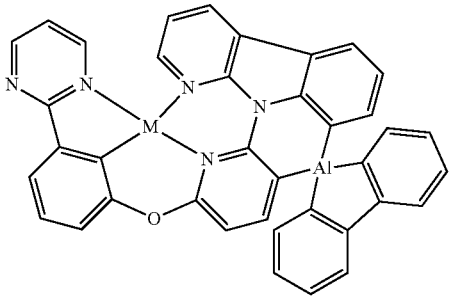
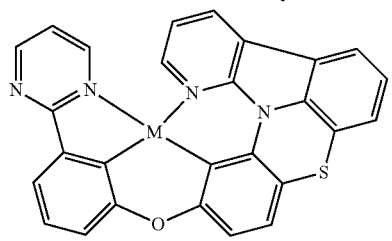
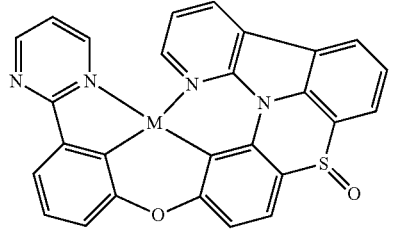
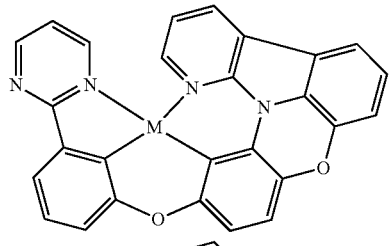
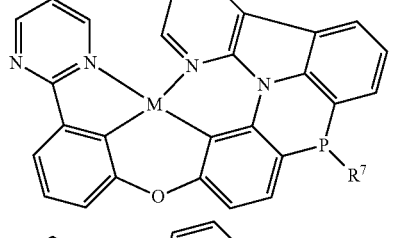
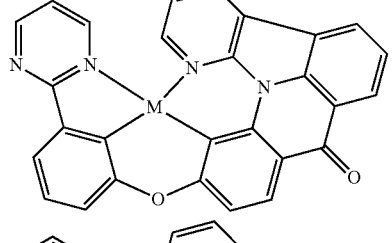
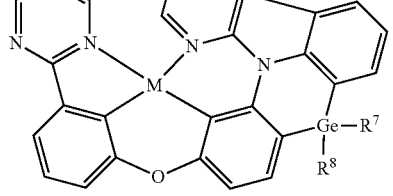

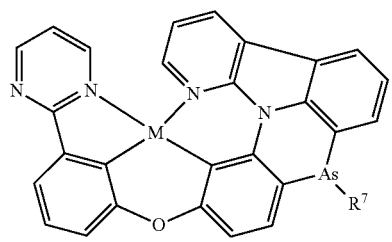
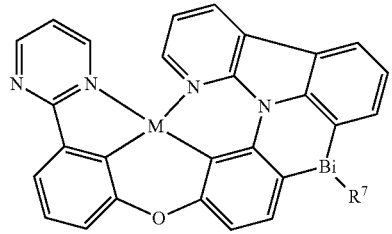
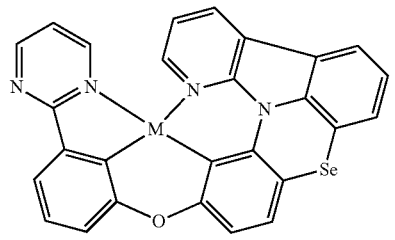
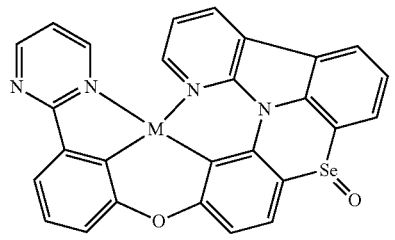
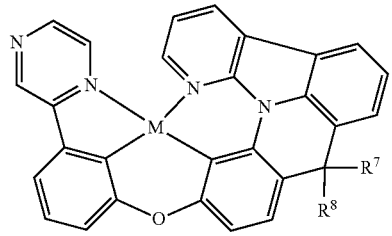
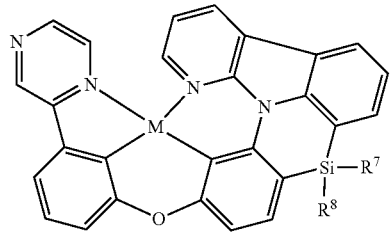
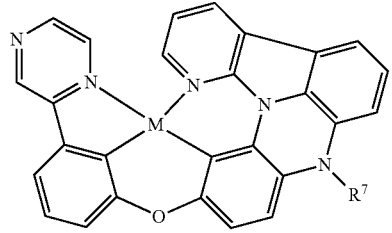
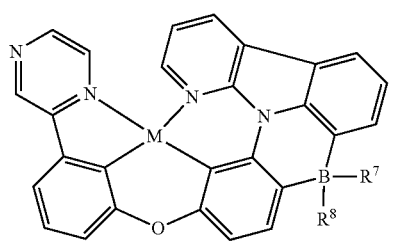
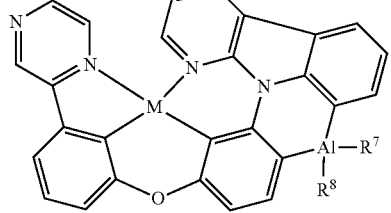
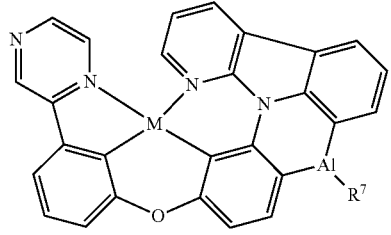
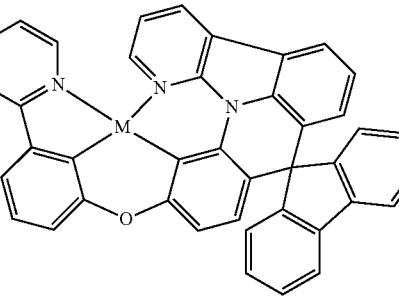
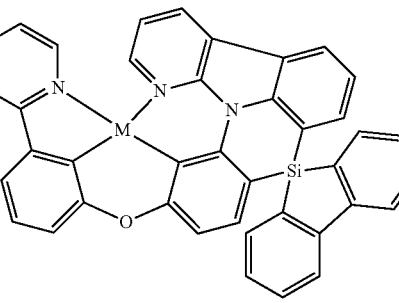

-continued
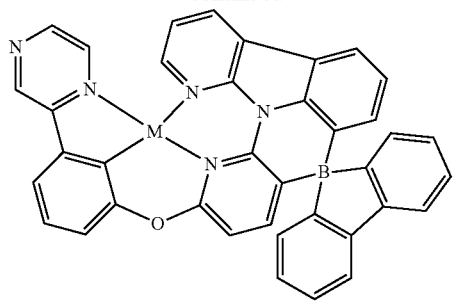
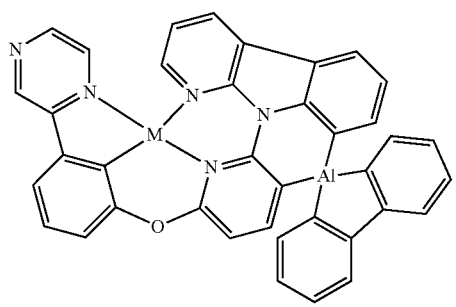
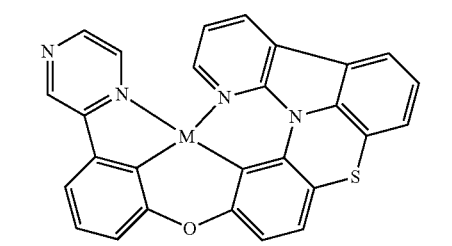
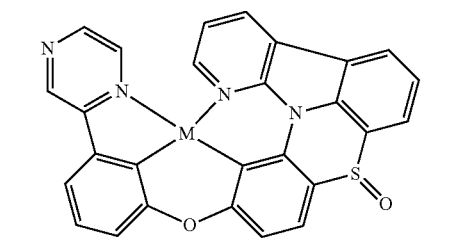
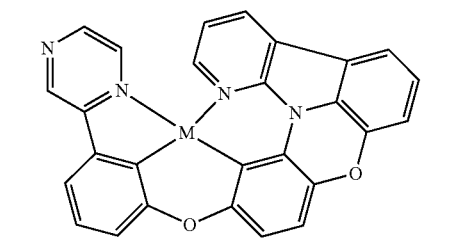
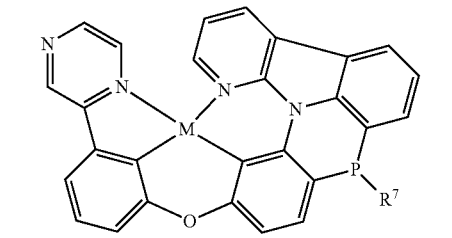
-continued
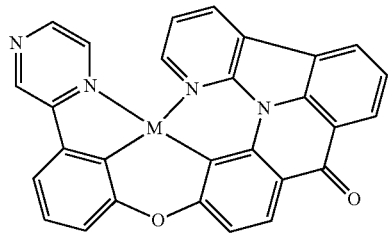
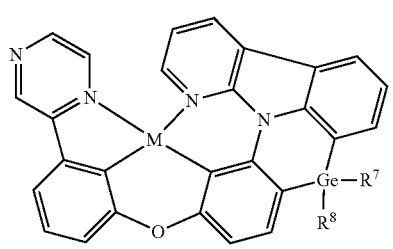
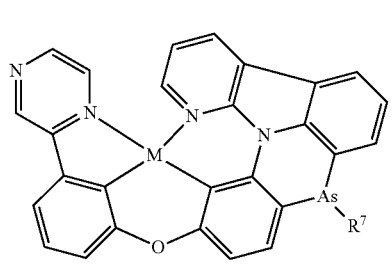
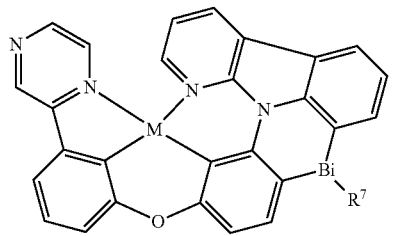
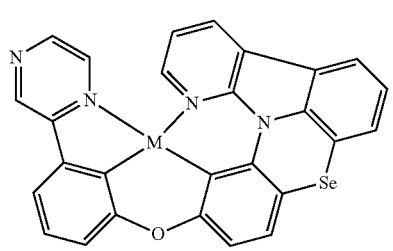
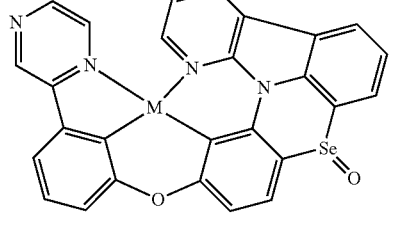

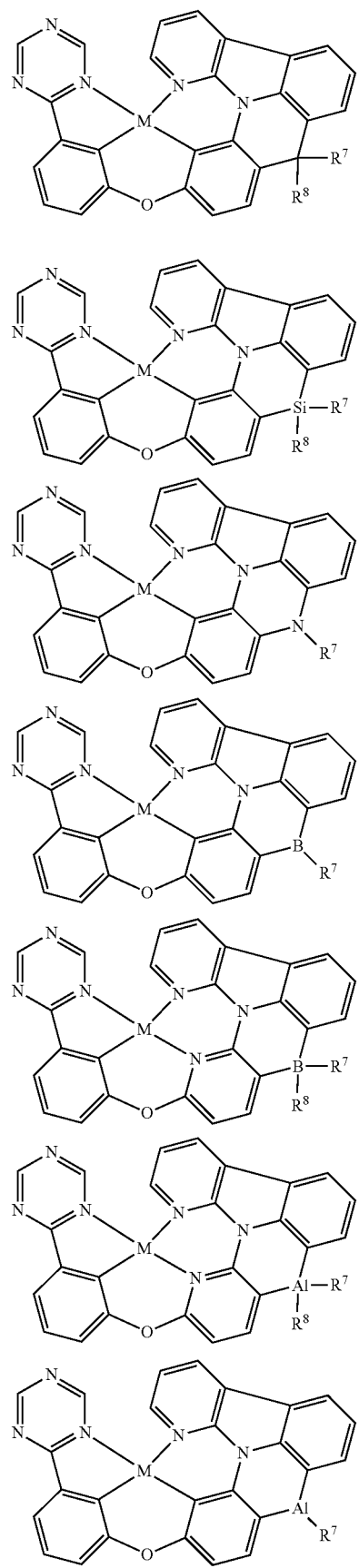
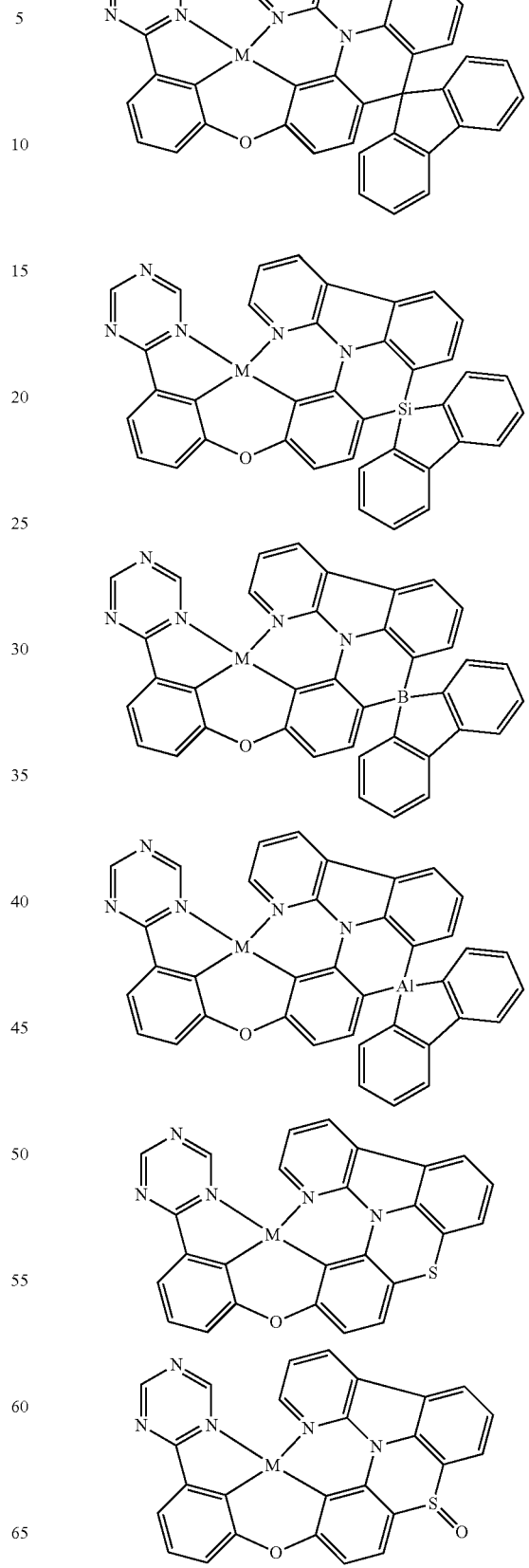

253
-continued
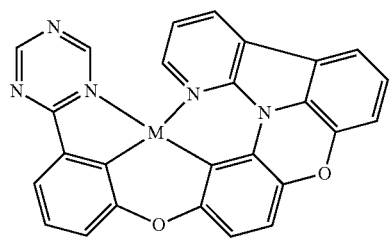
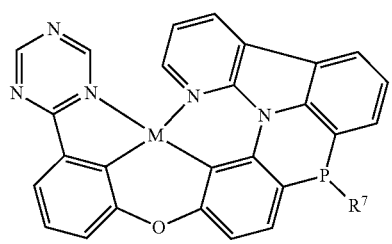
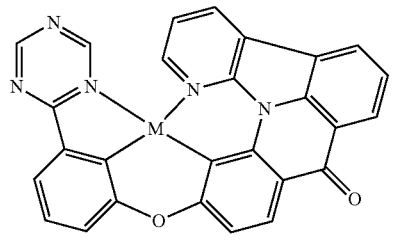
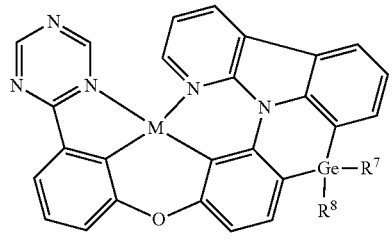
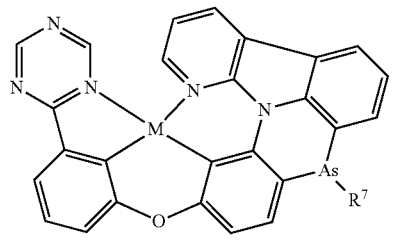
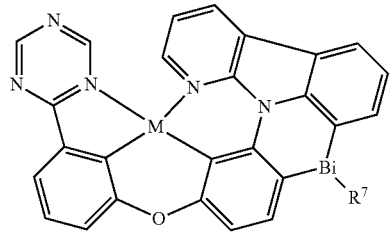
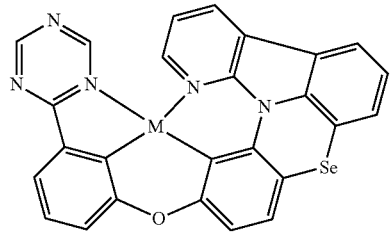
254
-continued
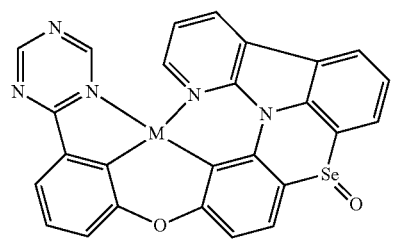
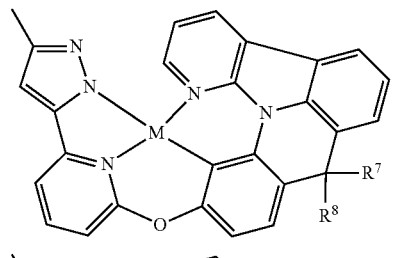
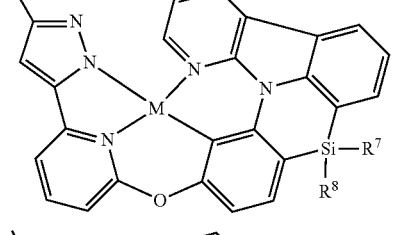
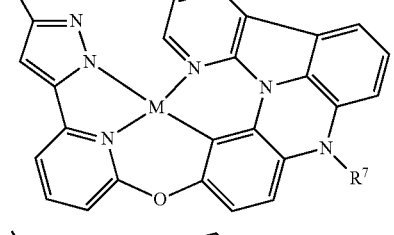
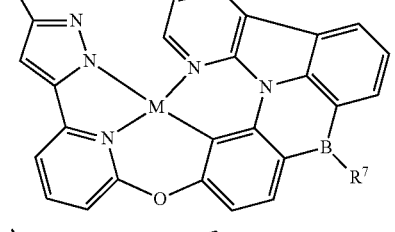
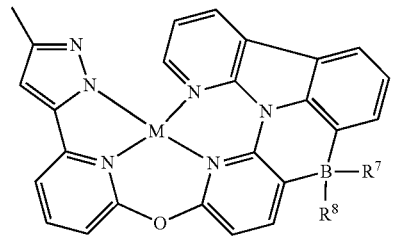
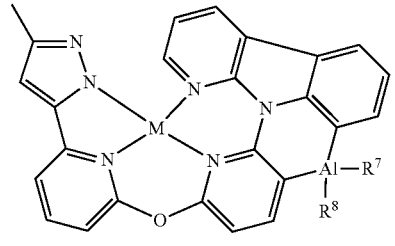

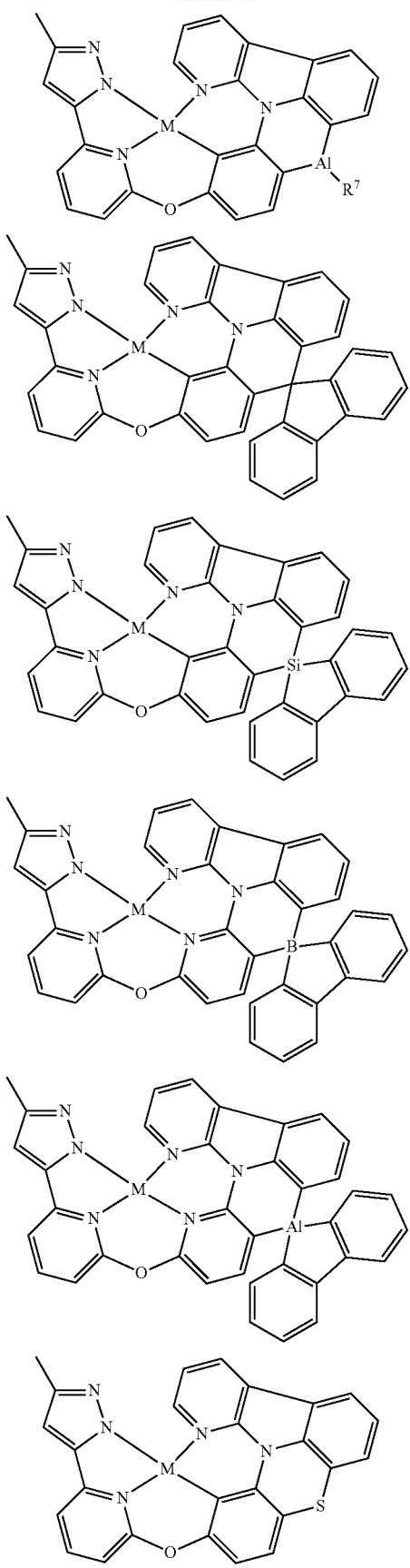
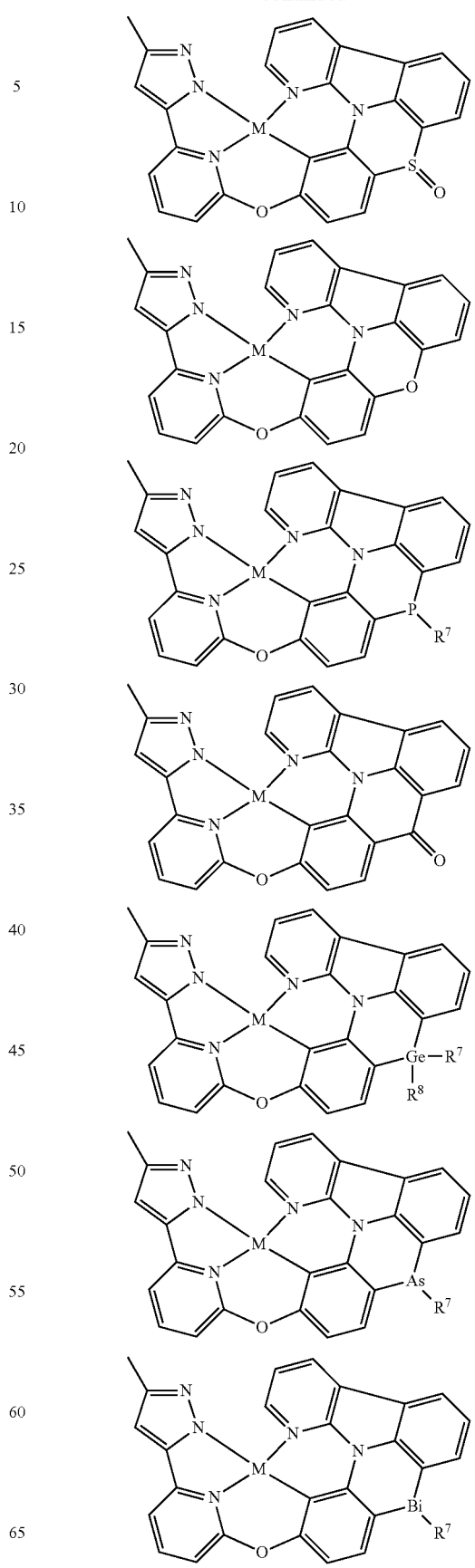

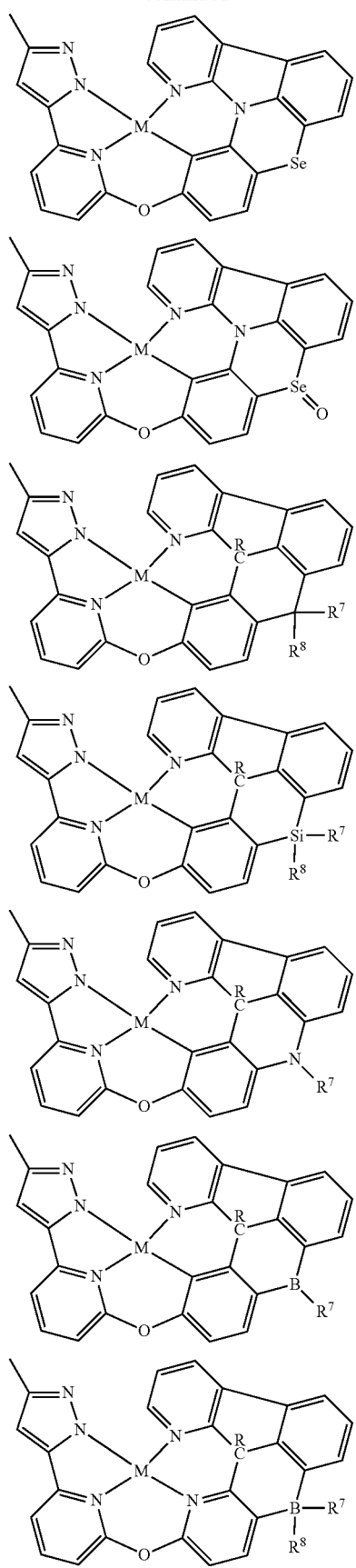
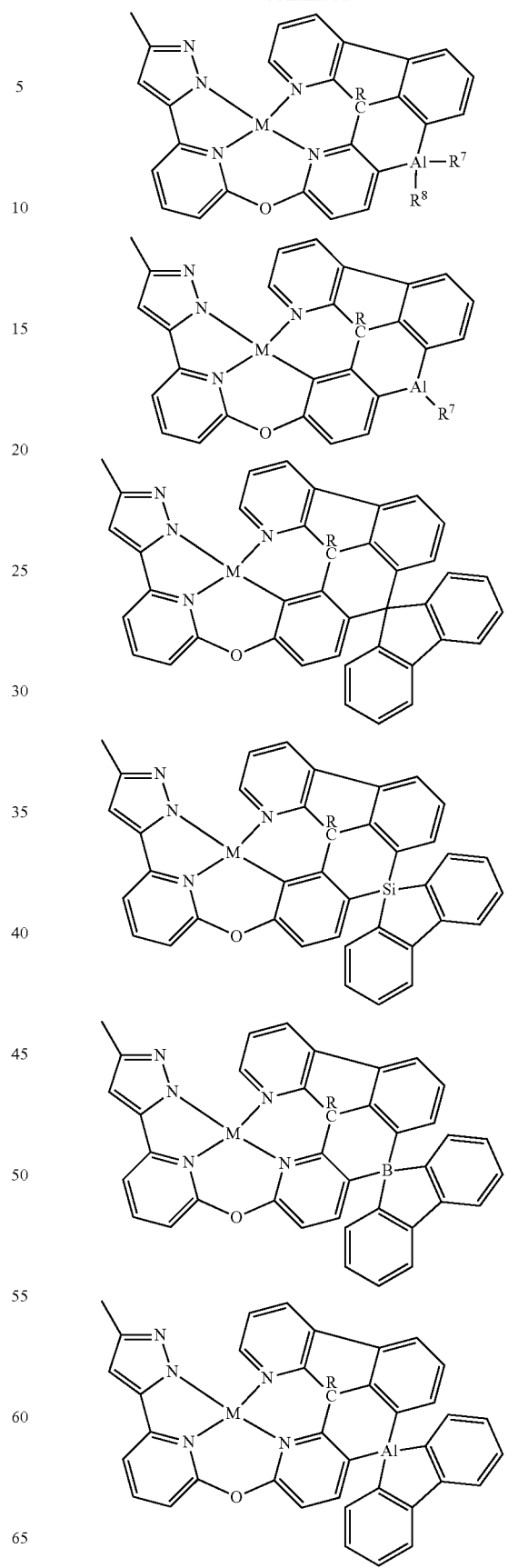

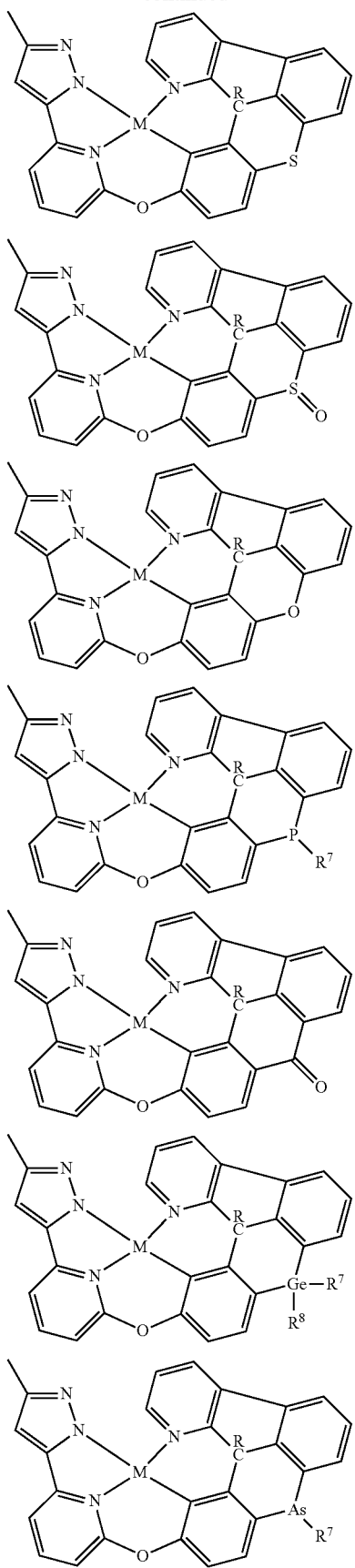
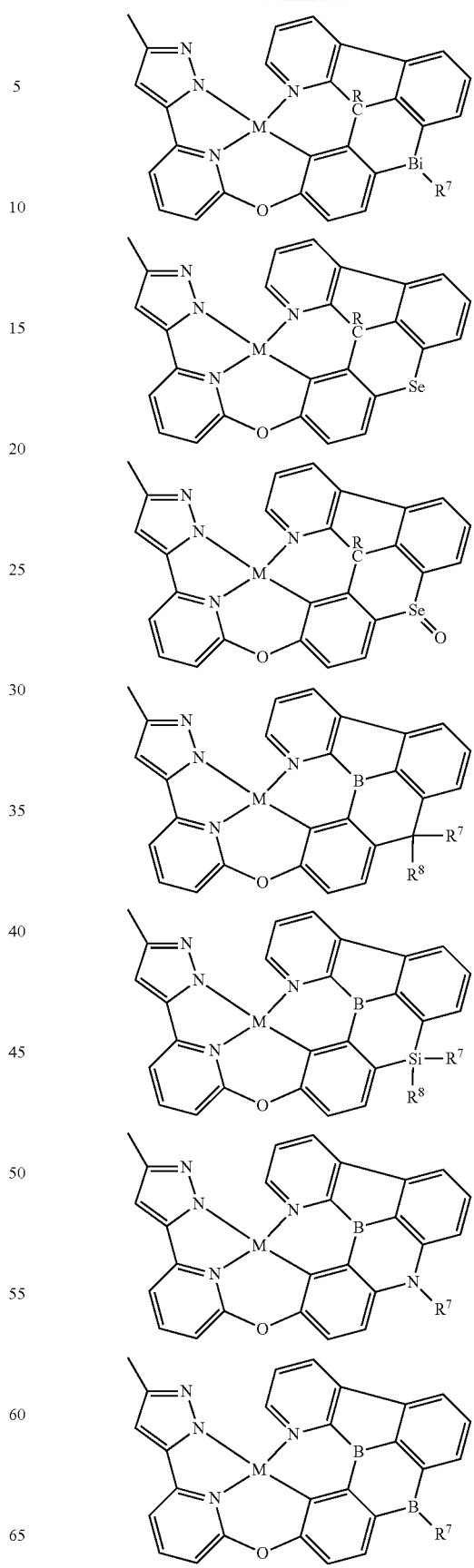

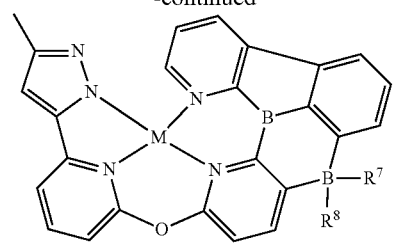
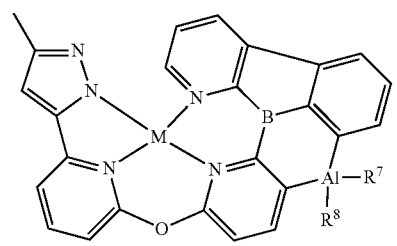
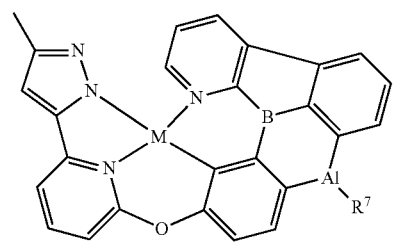
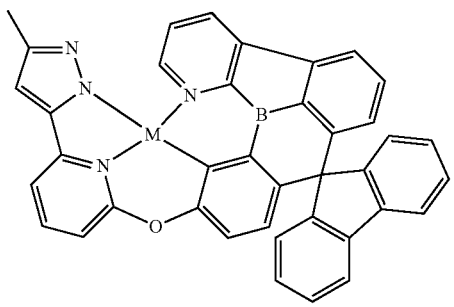
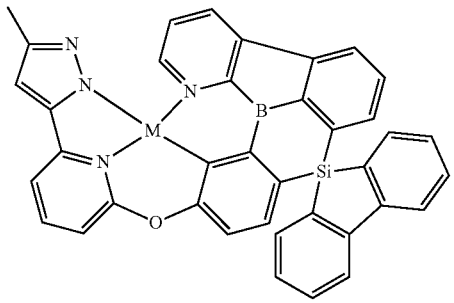
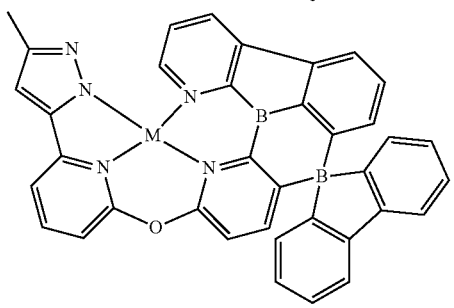
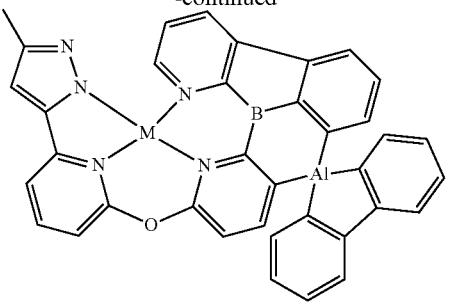
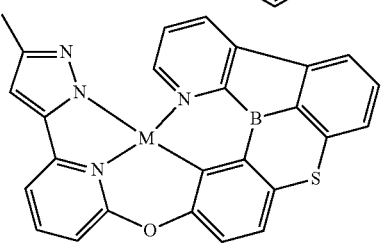
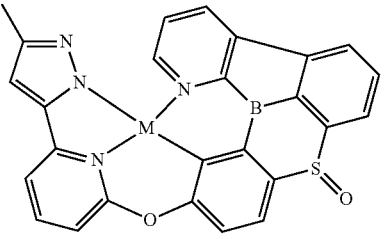
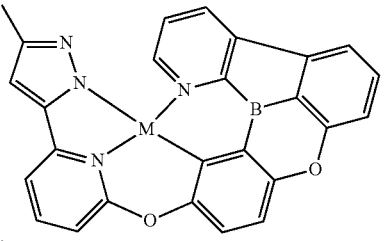
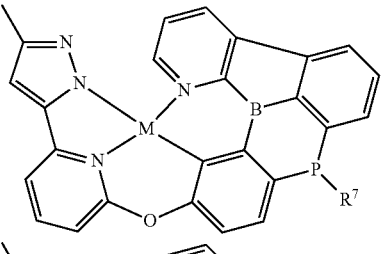
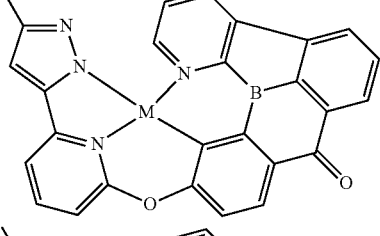
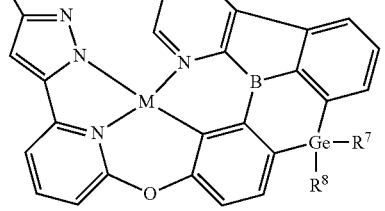

-continued
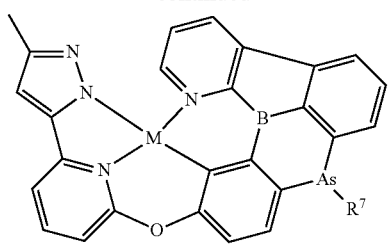
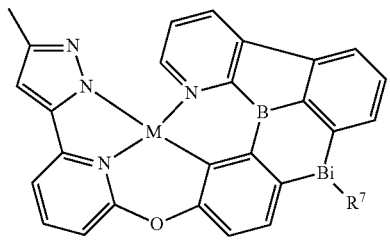
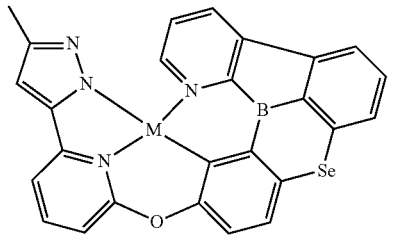
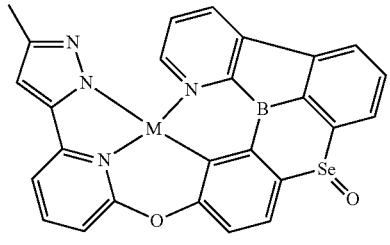
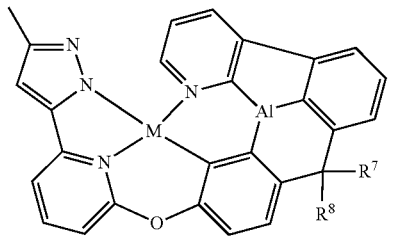
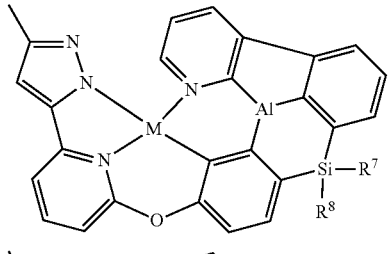
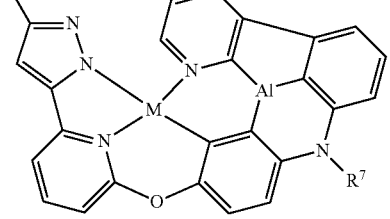
-continued
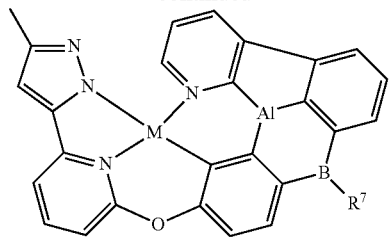
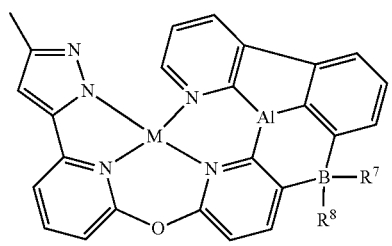
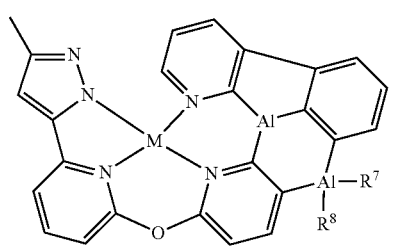
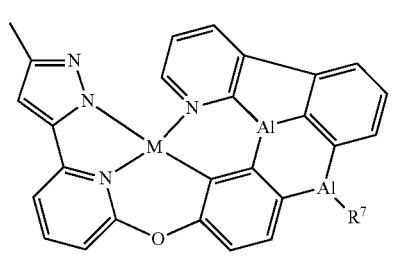
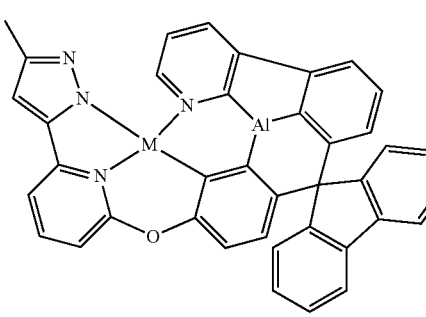
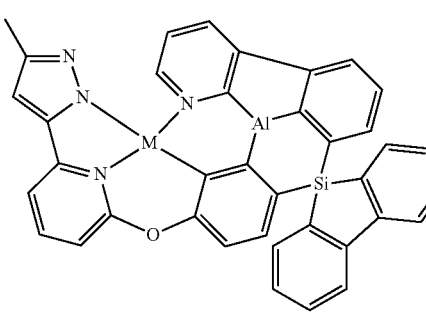

265
-continued
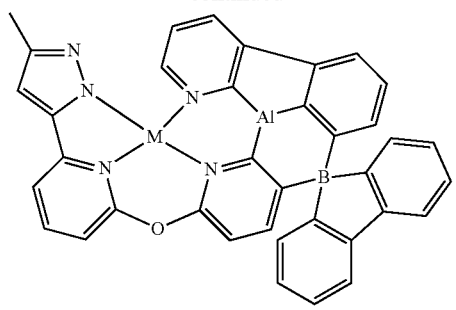
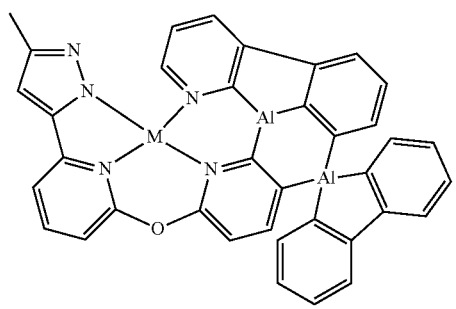
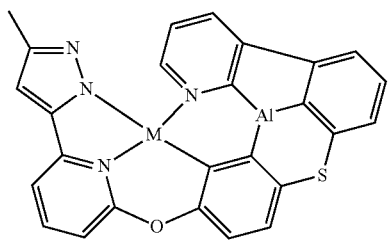
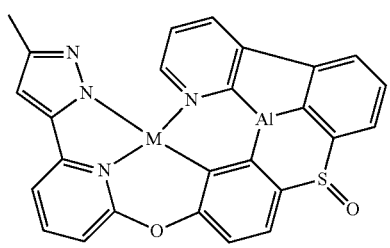
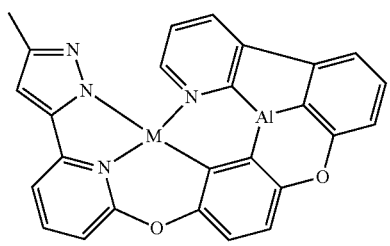
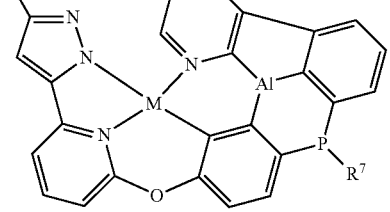
266
-continued
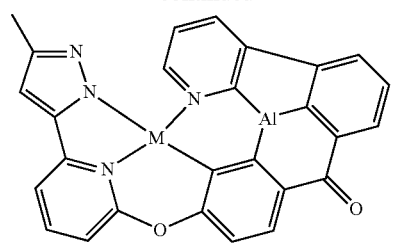
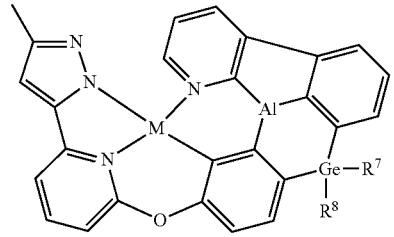
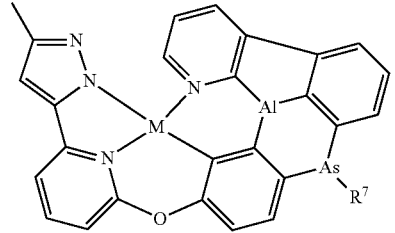
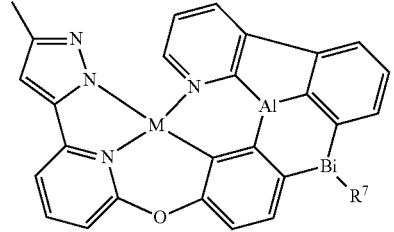
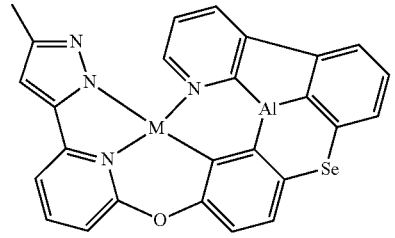
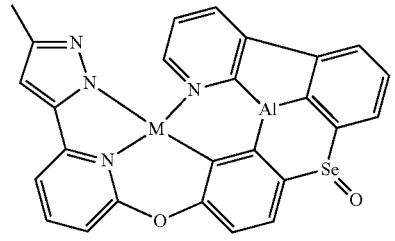
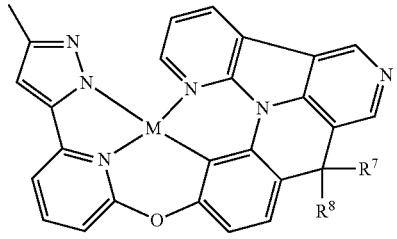

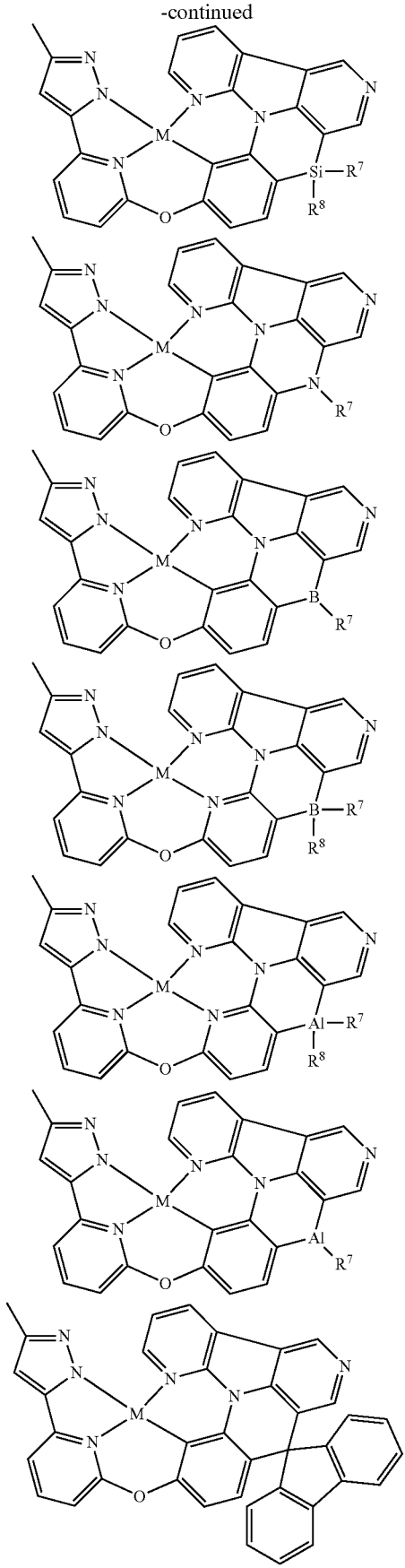
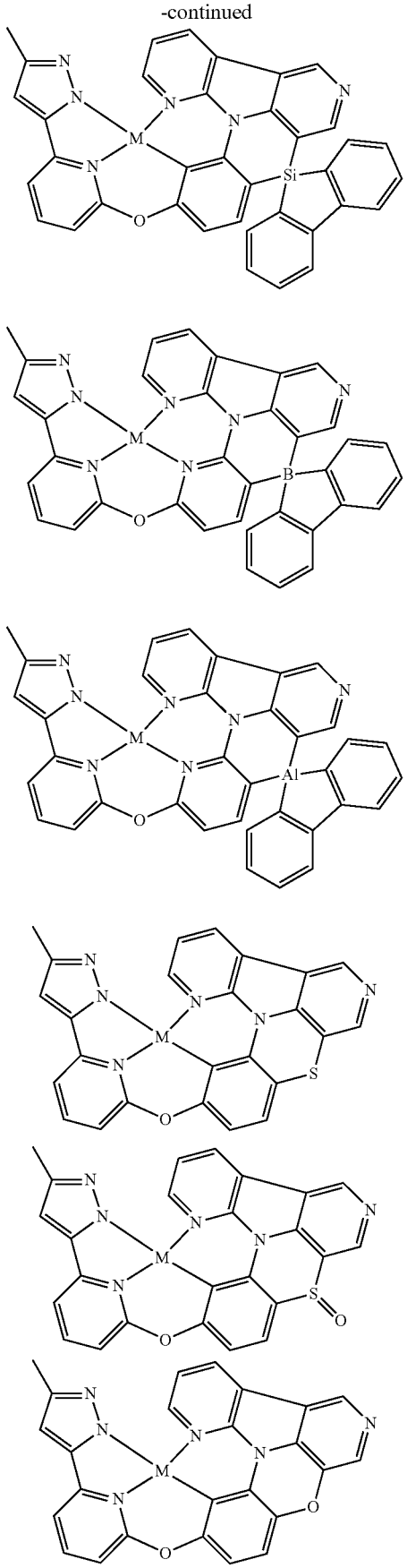

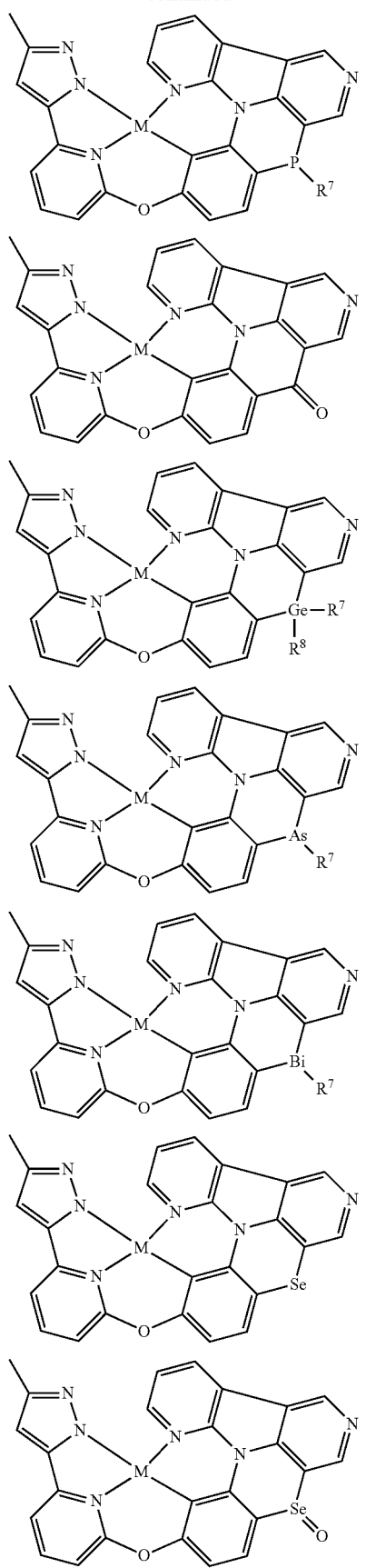
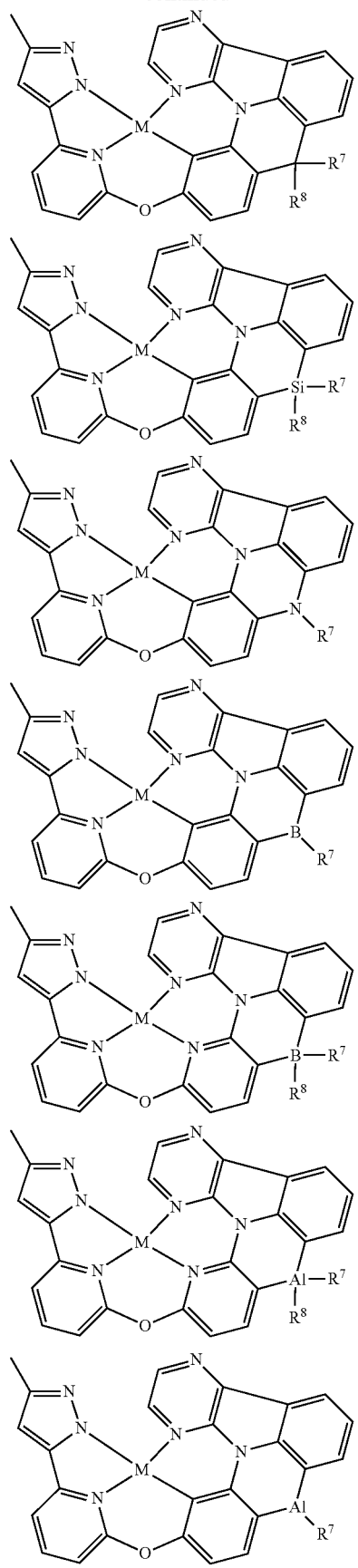

271
-continued
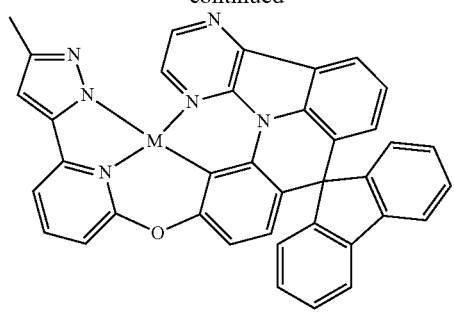
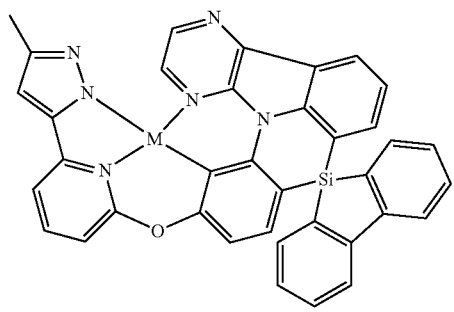
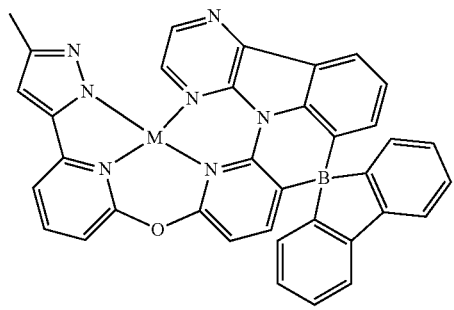
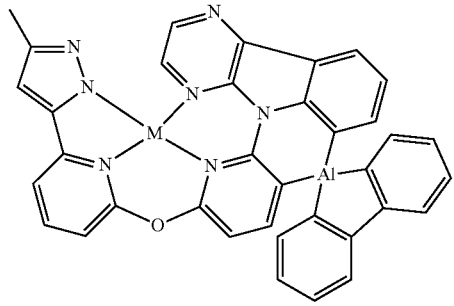
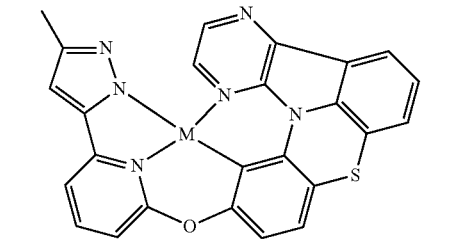
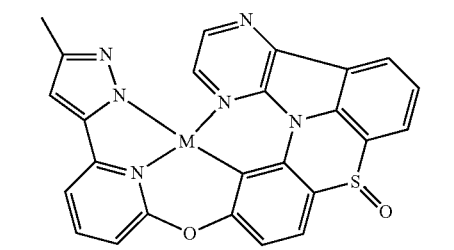
272
-continued
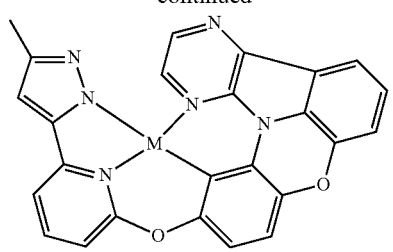
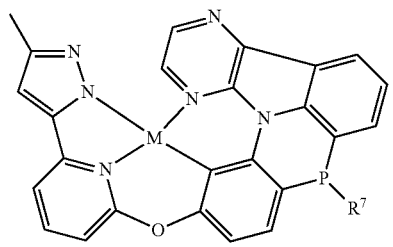
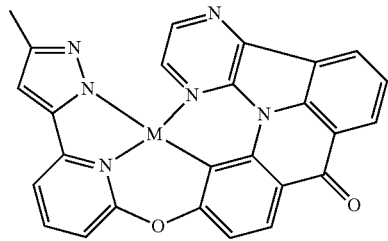
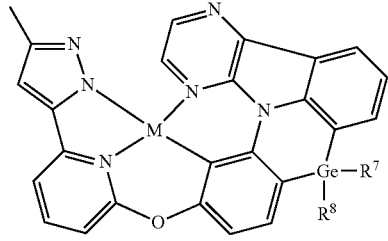
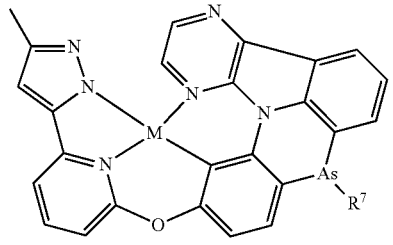
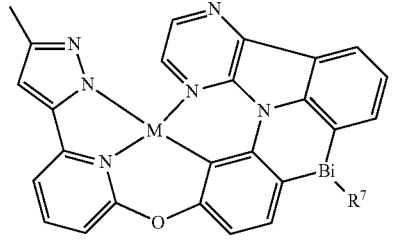
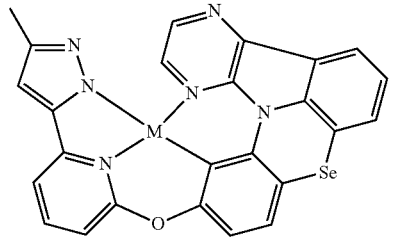

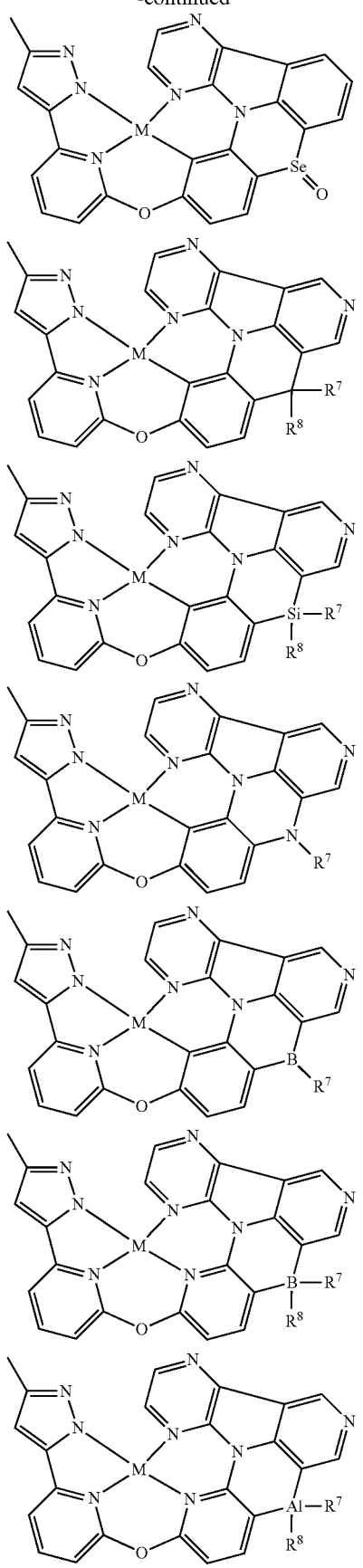
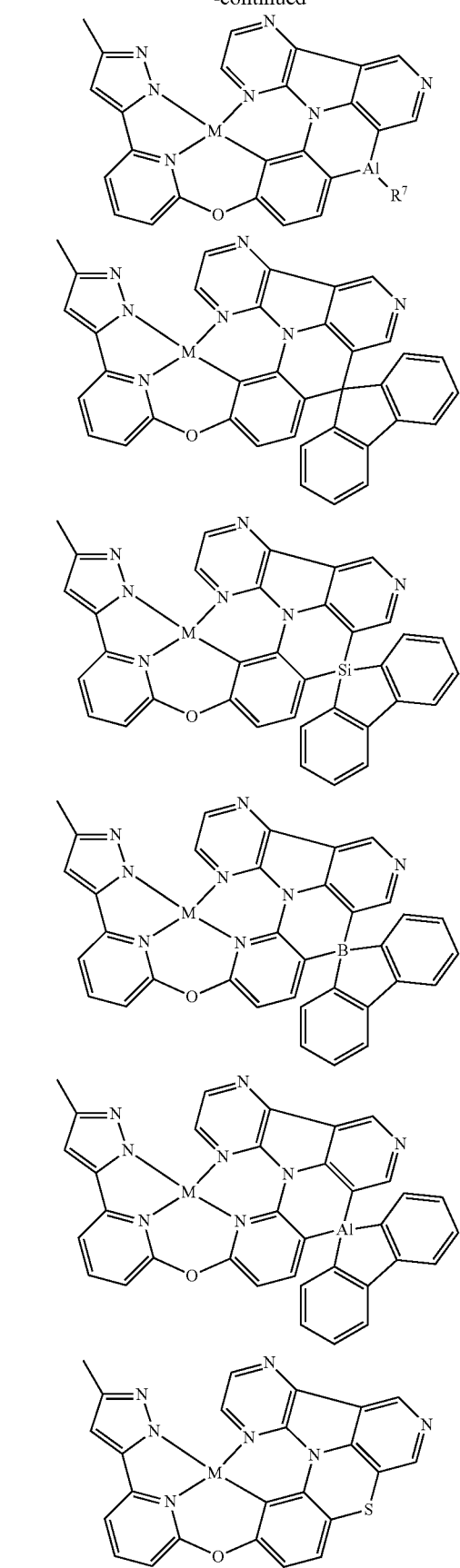

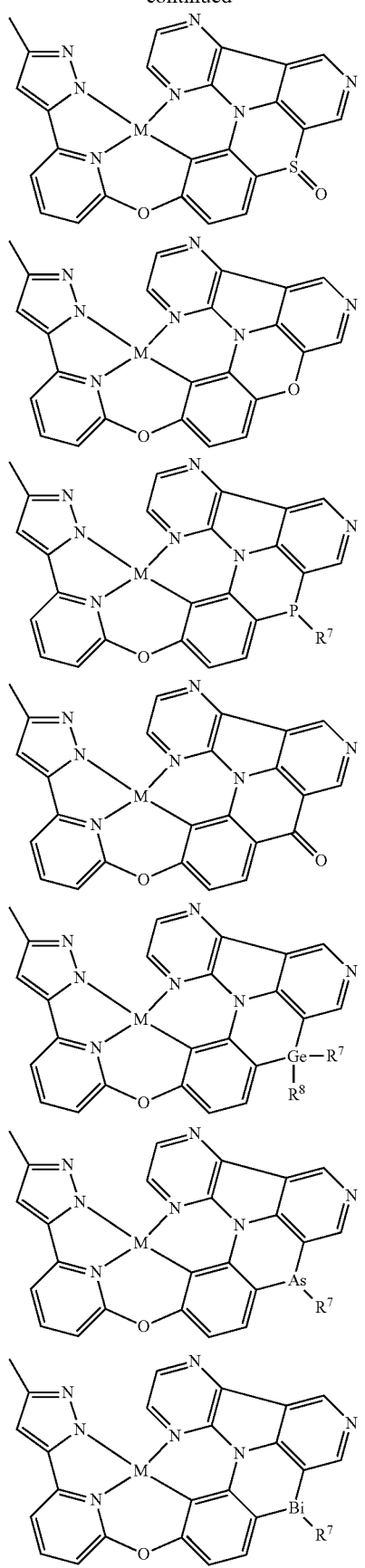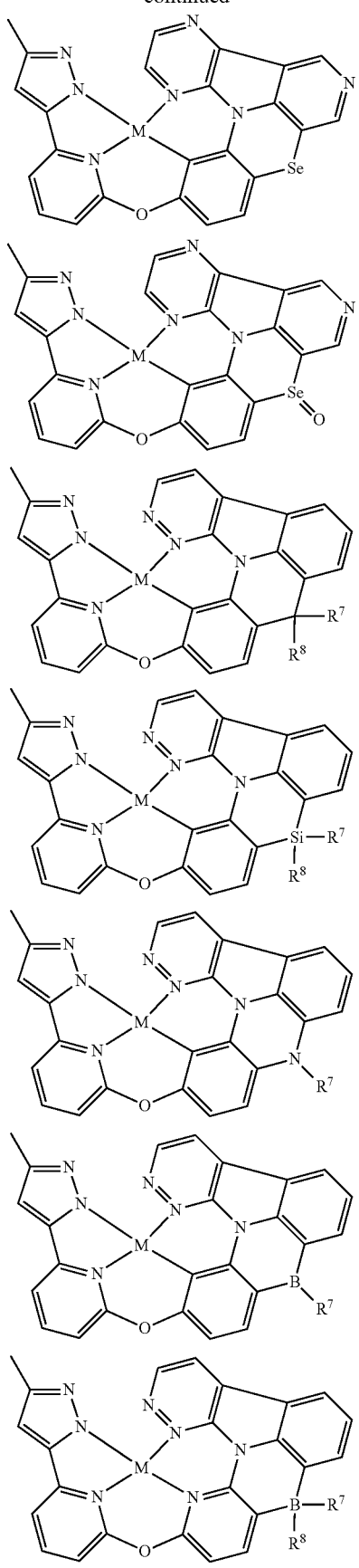

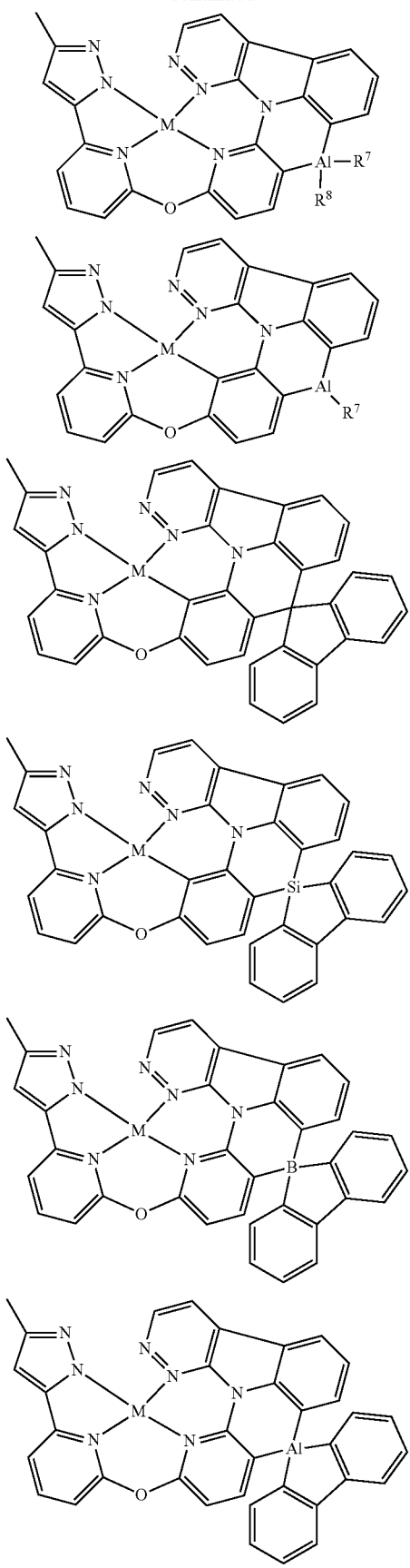
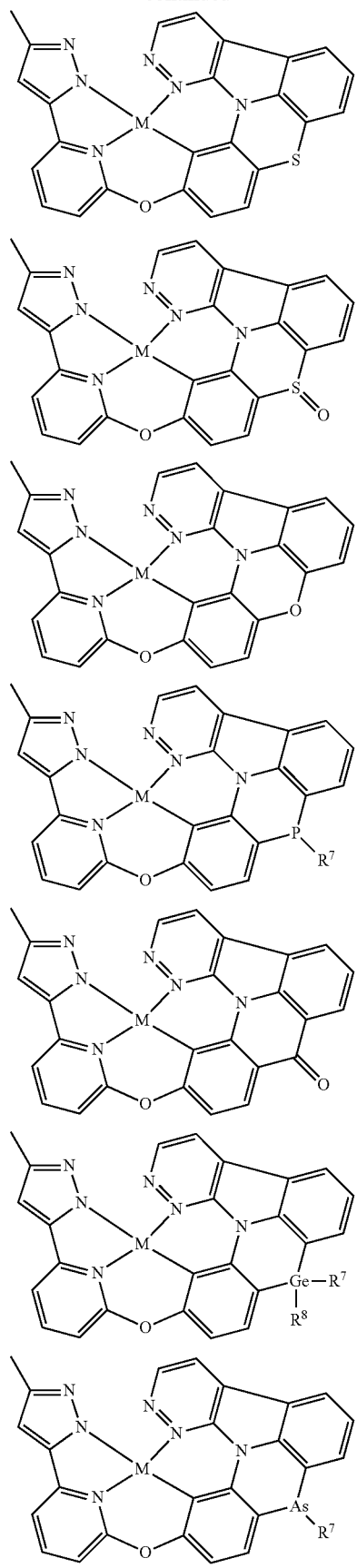

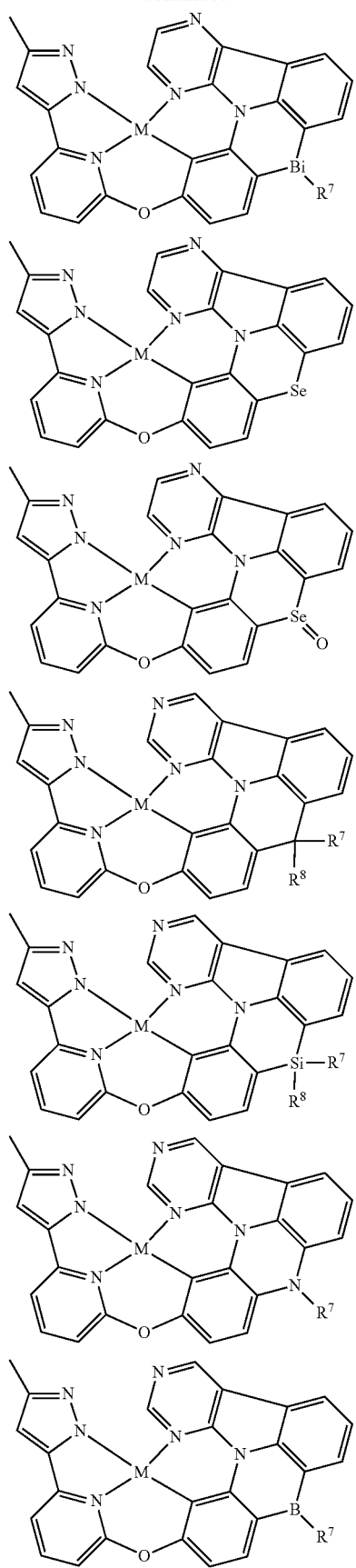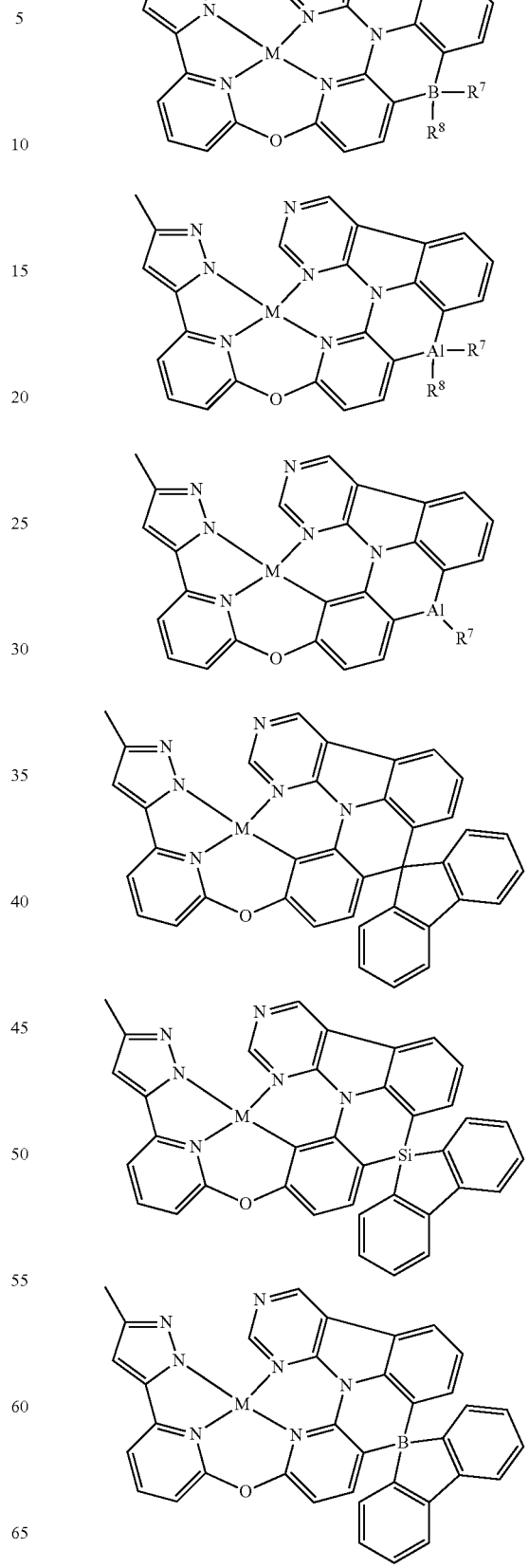

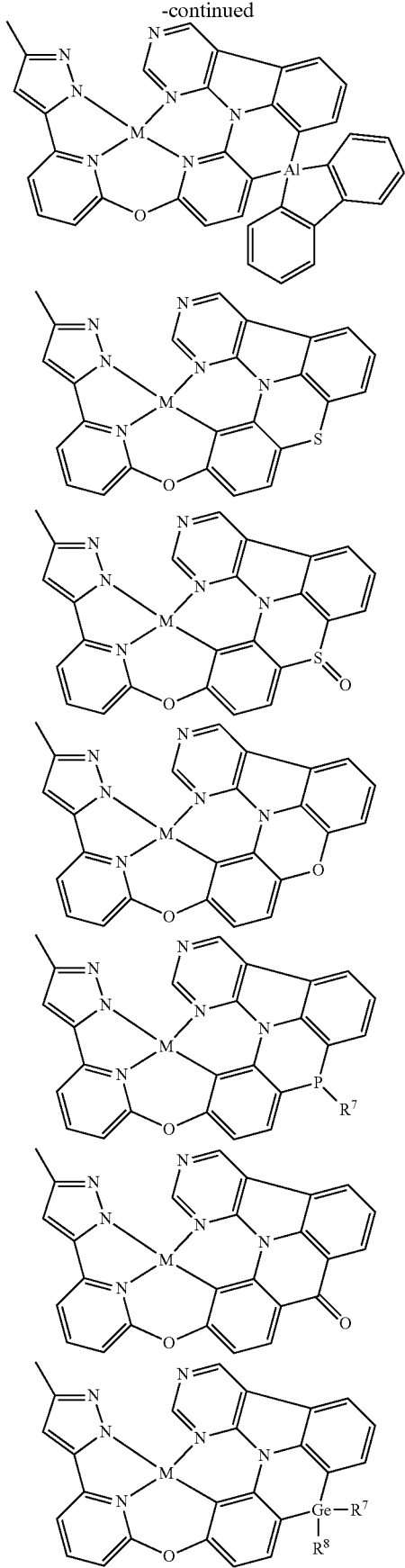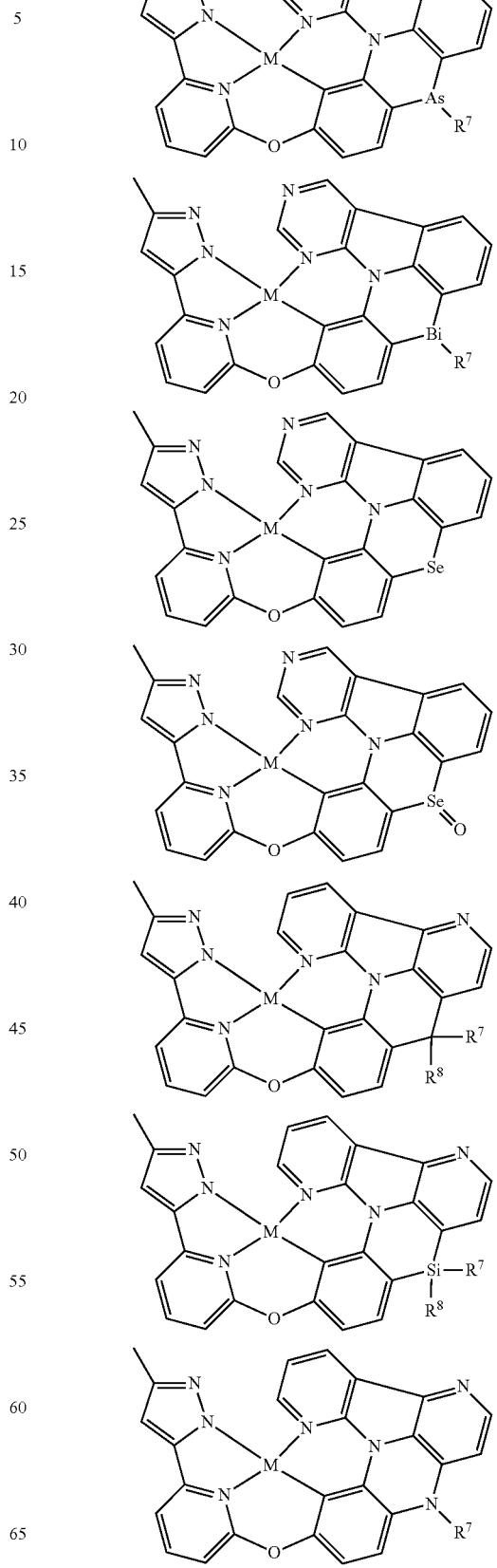

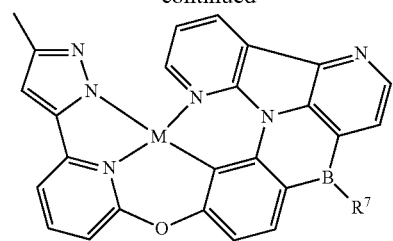
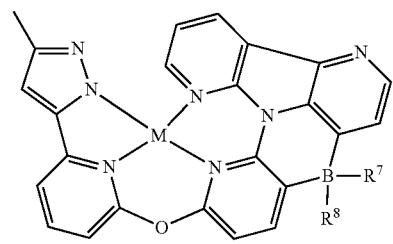
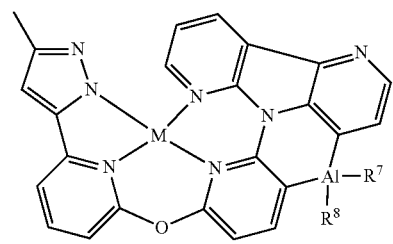
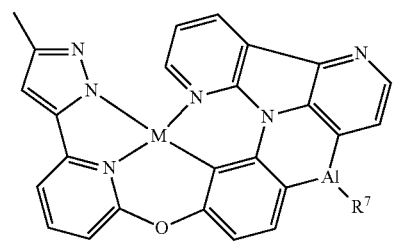
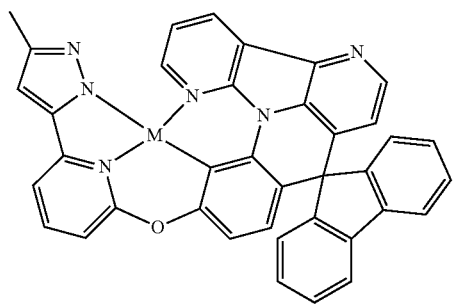
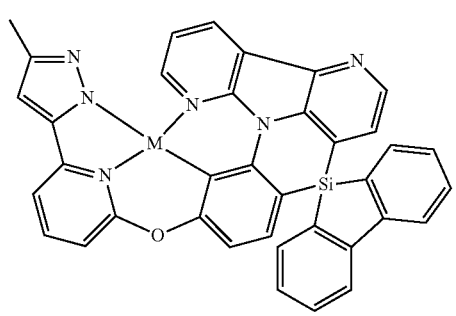
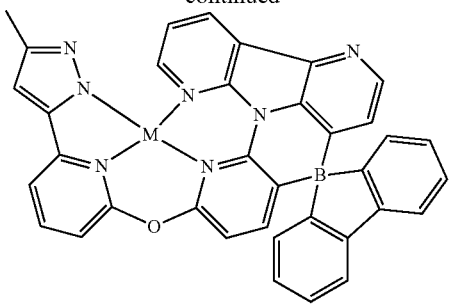
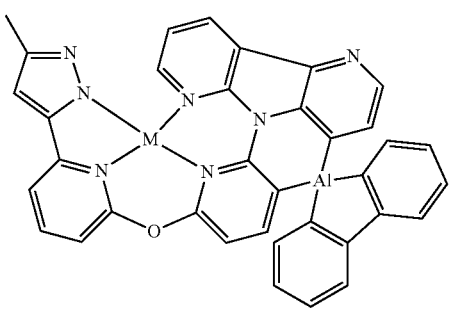
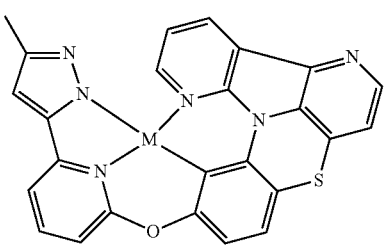
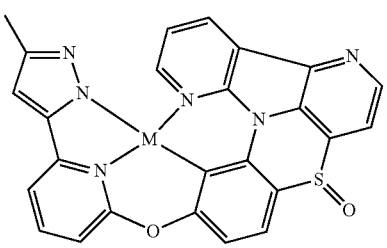
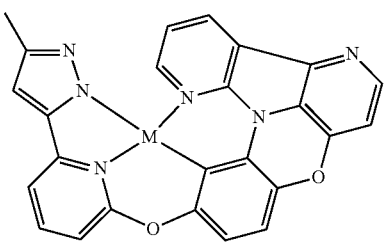
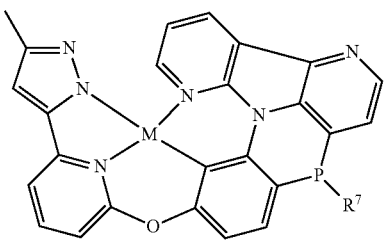

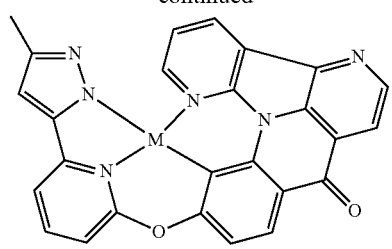
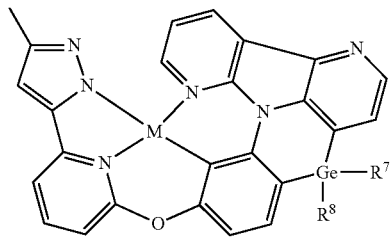
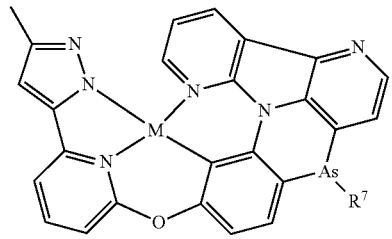
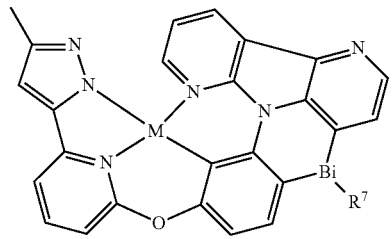
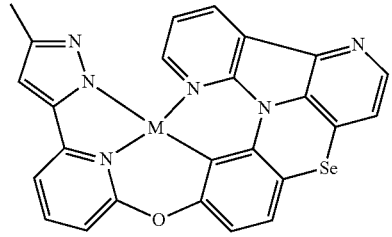
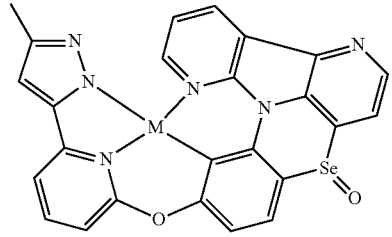
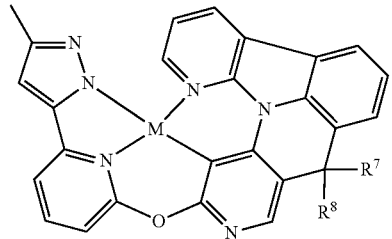
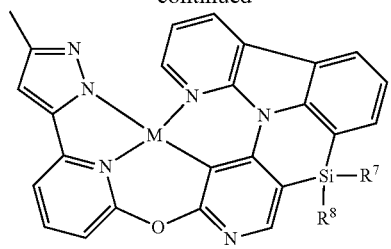
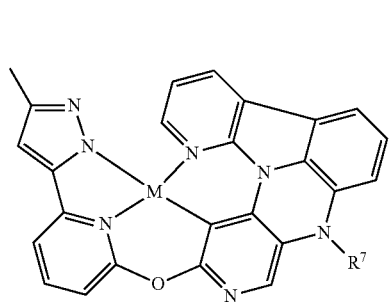
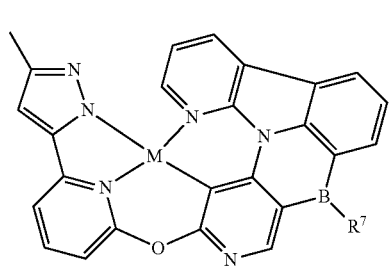
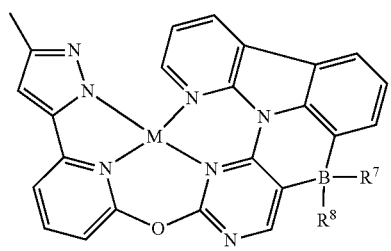
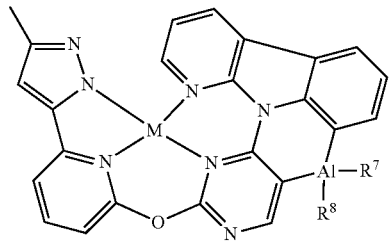
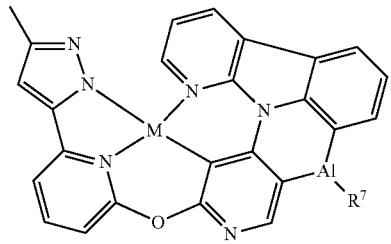

287
-continued
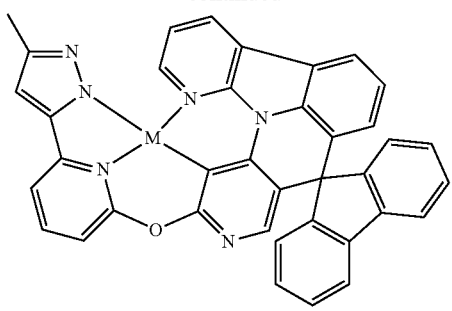
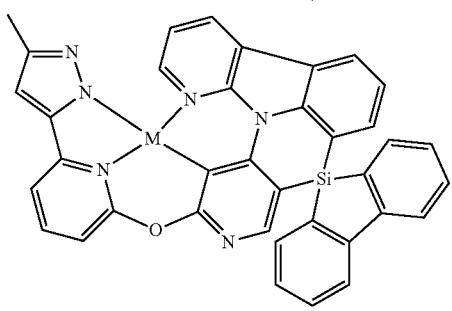
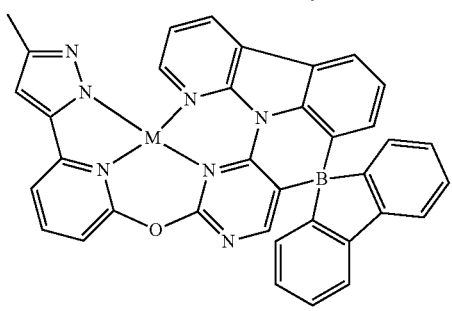
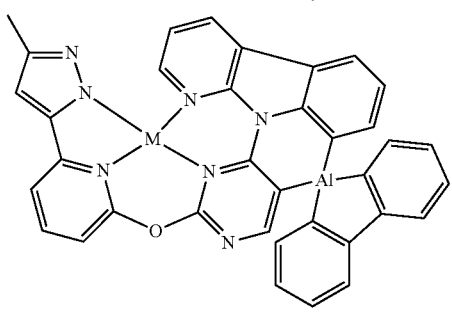
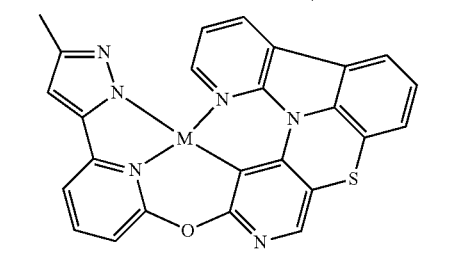
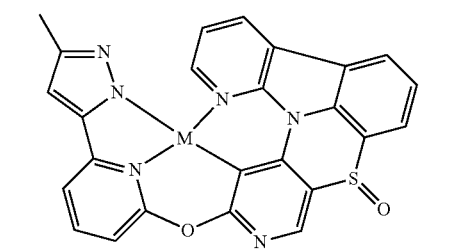
288
-continued
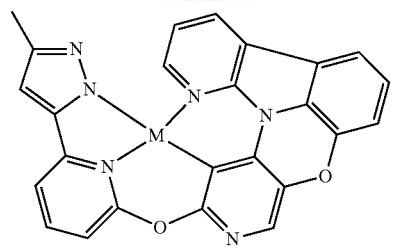
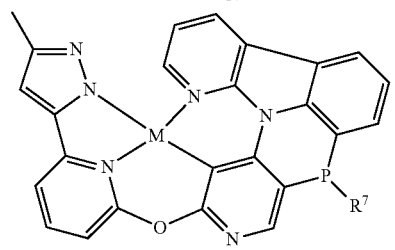
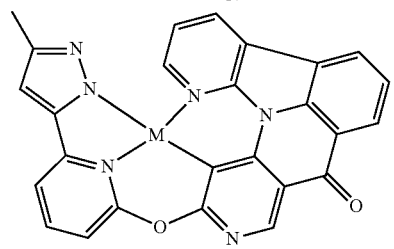
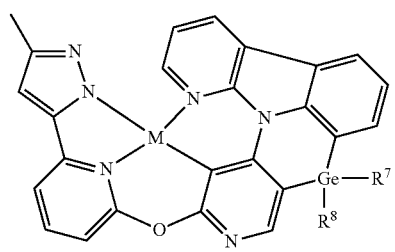
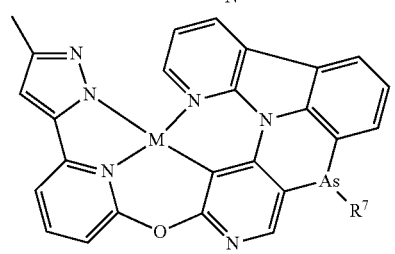
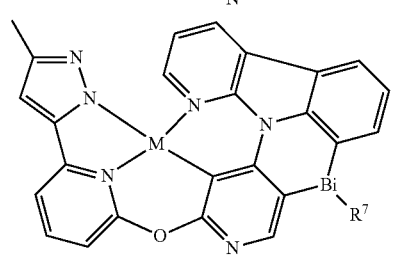
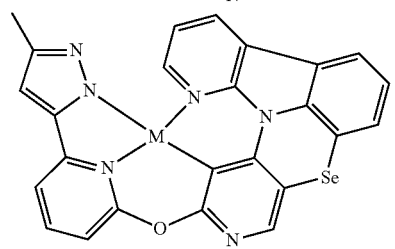

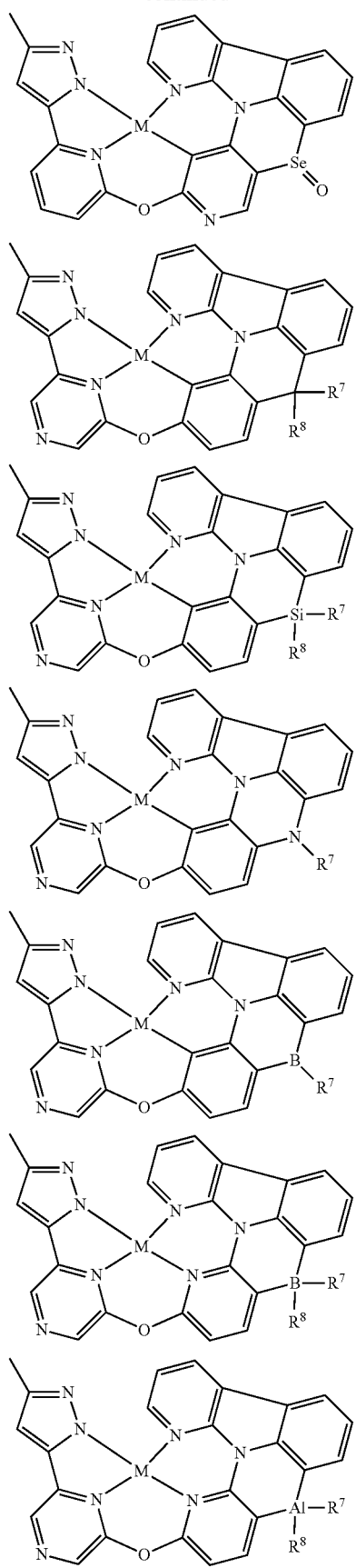
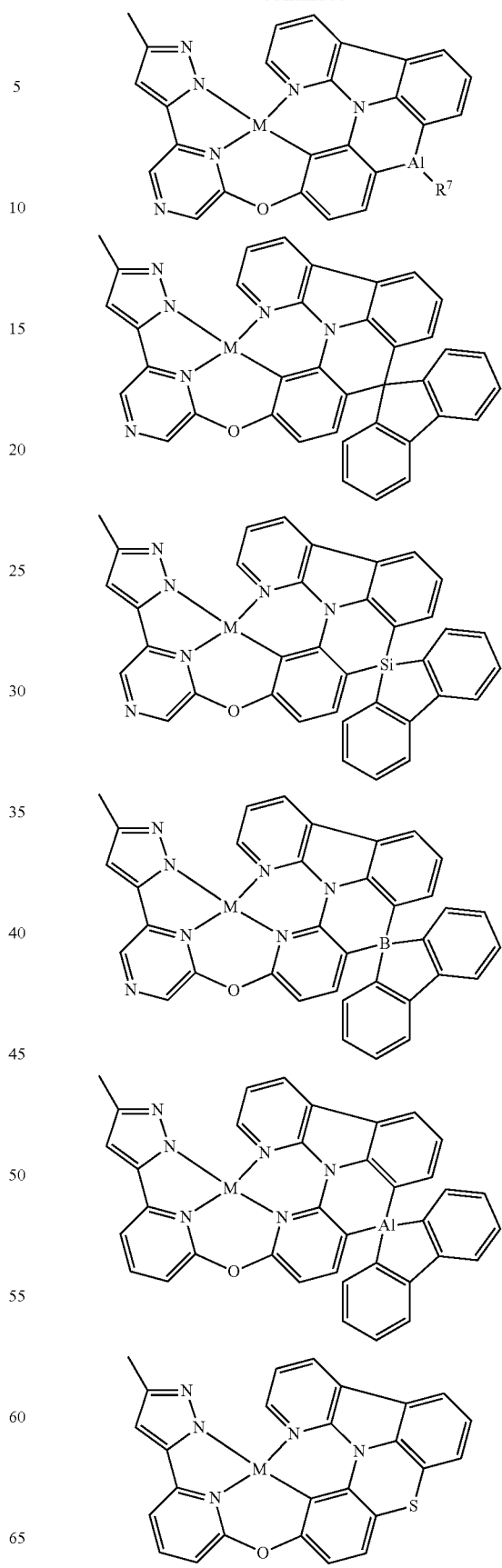

291
-continued
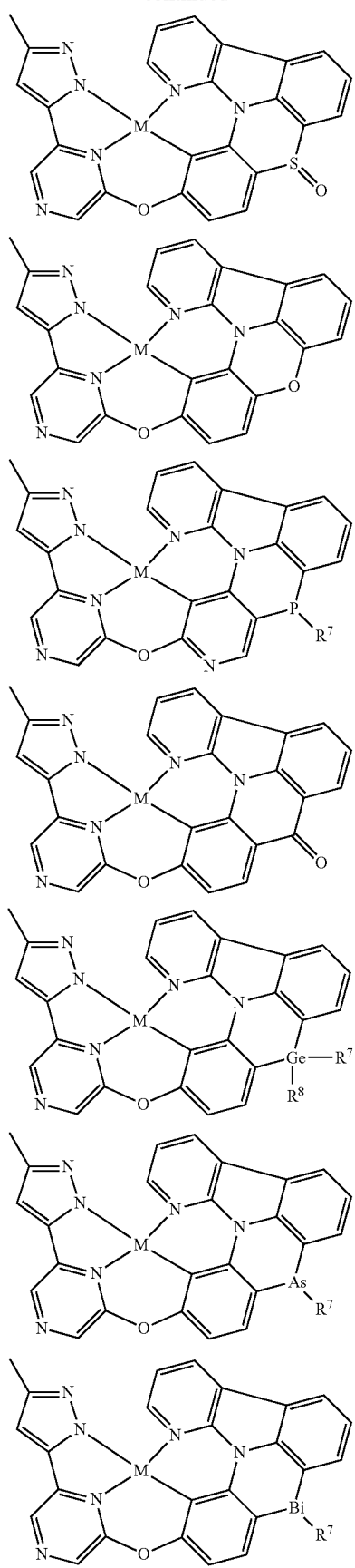
292
-continued
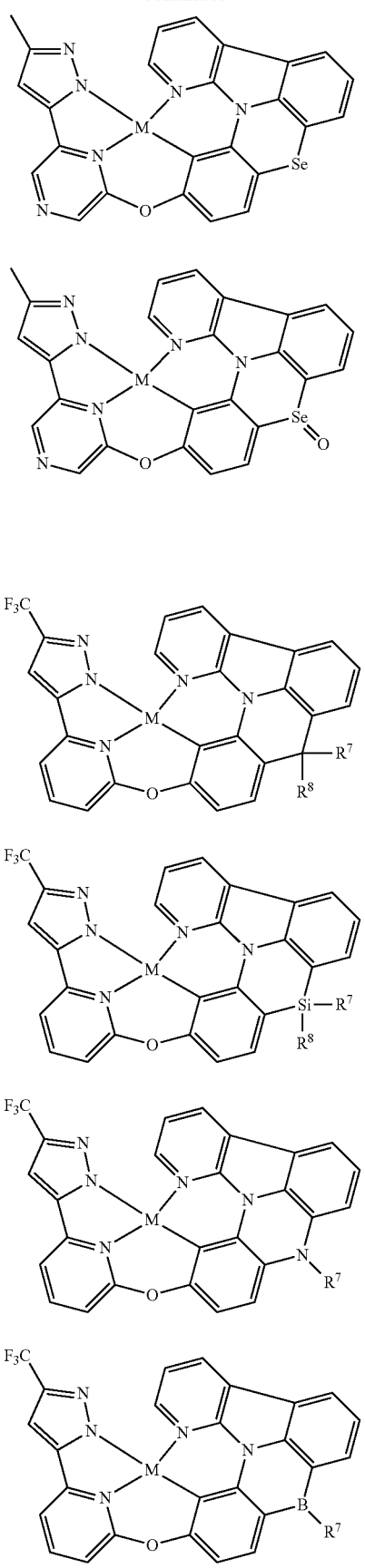

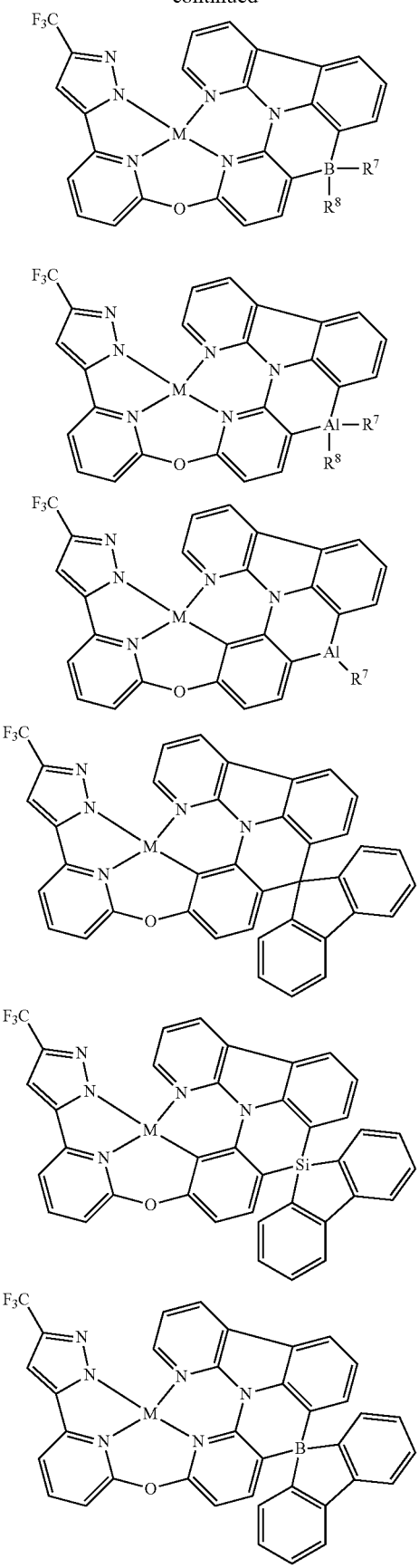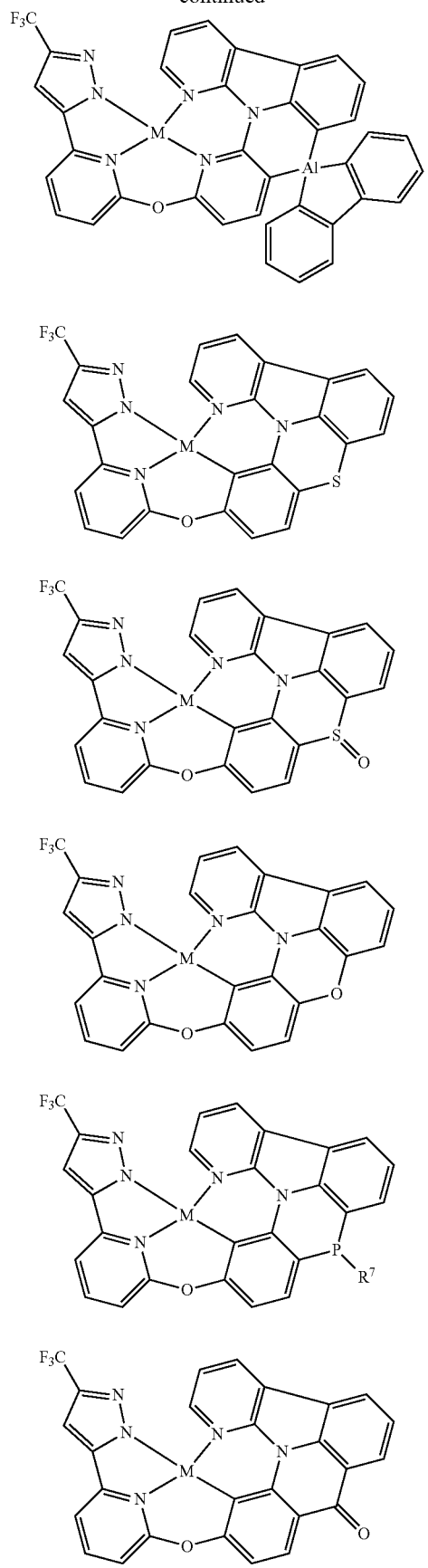

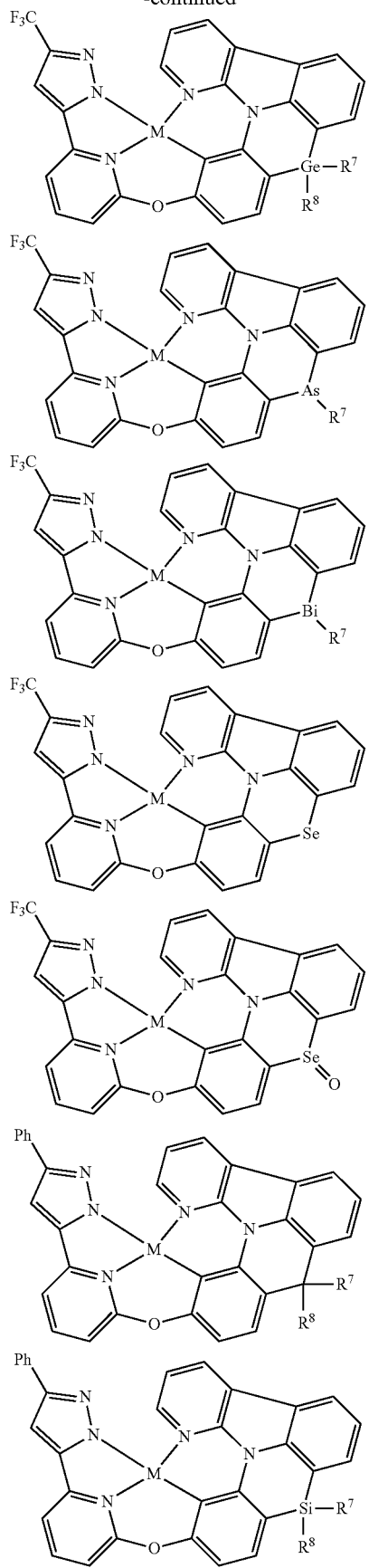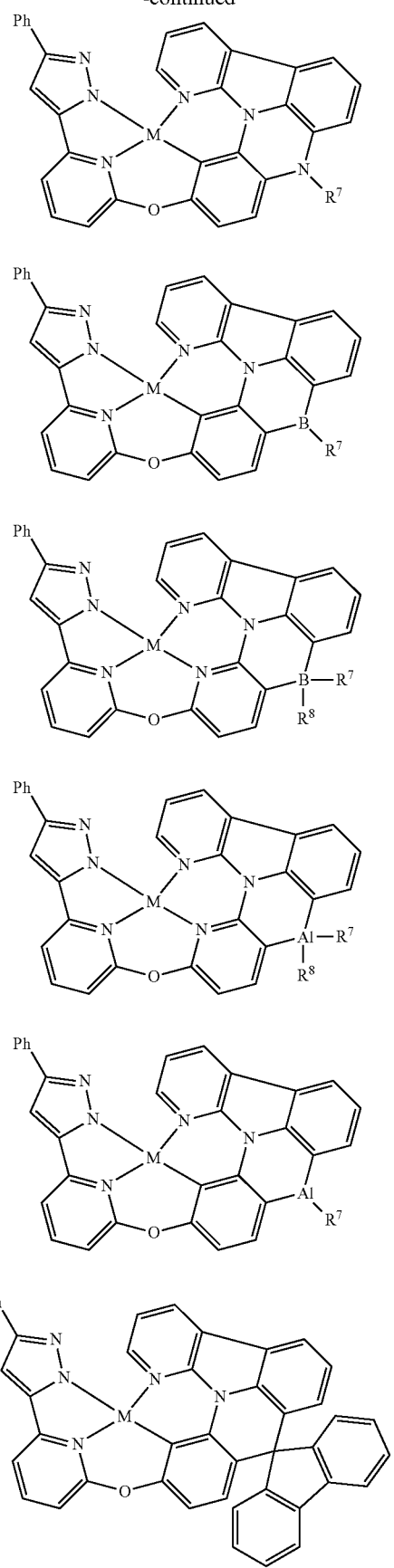

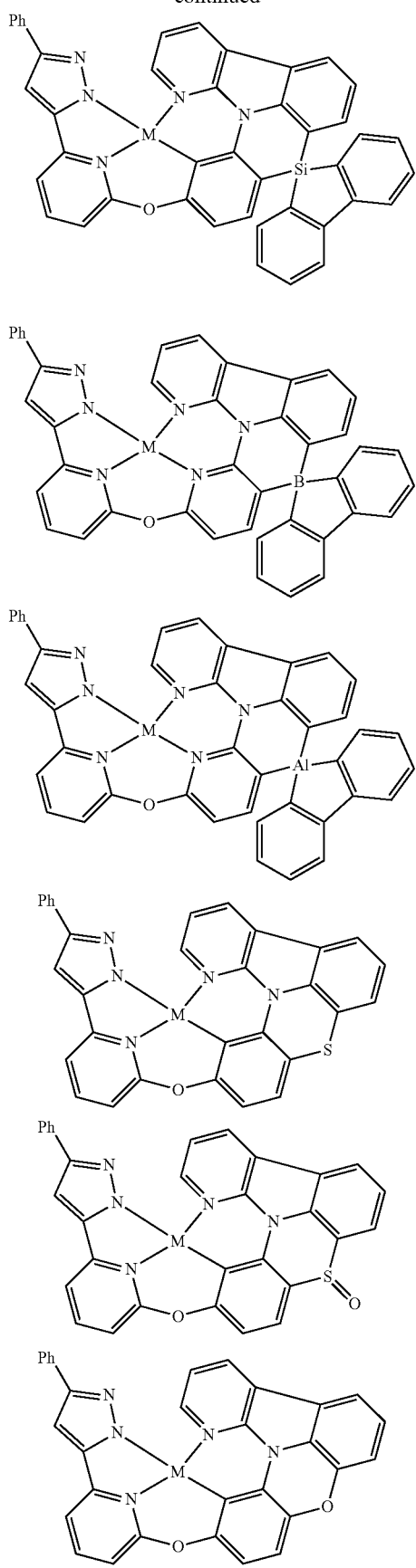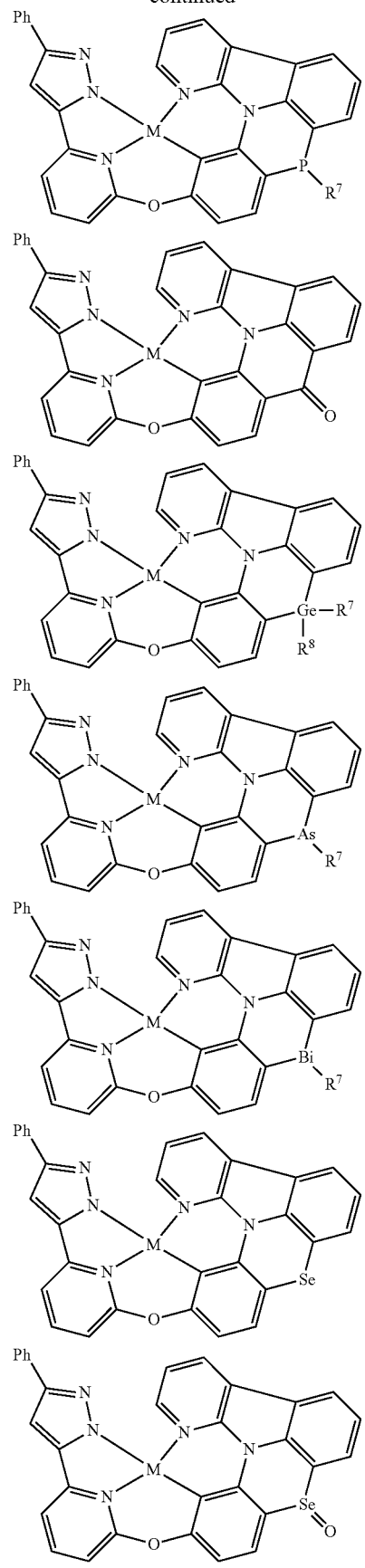

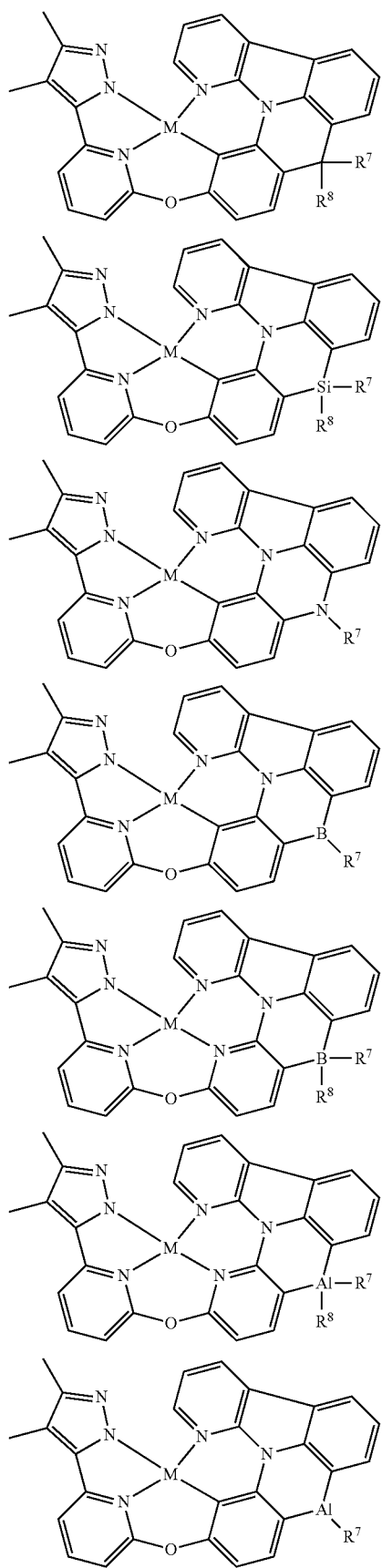
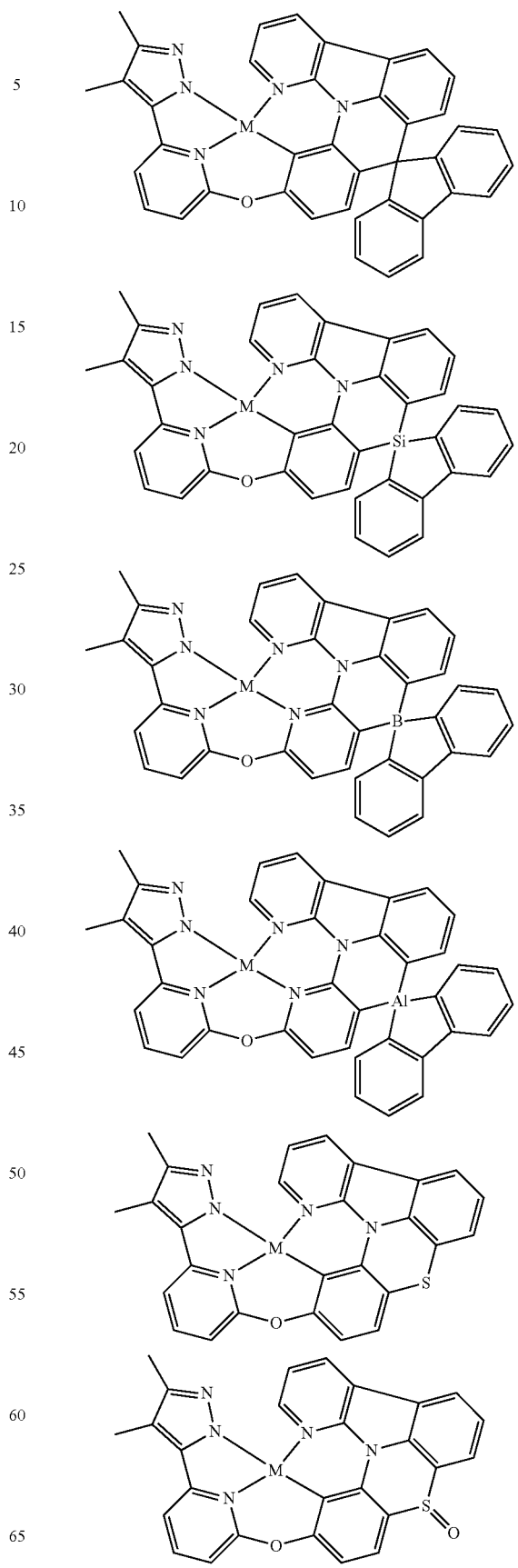

301
-continued
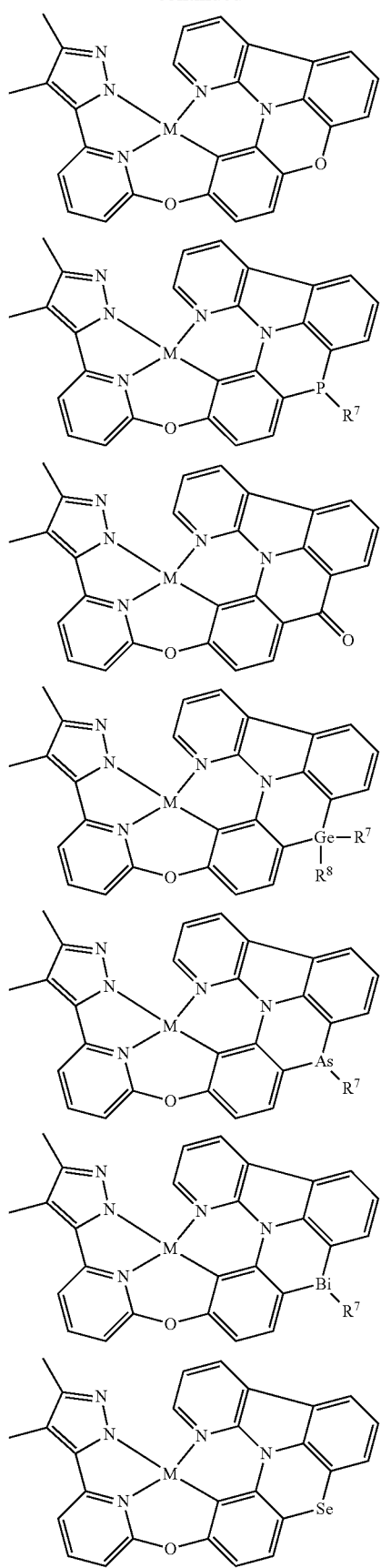
302
-continued
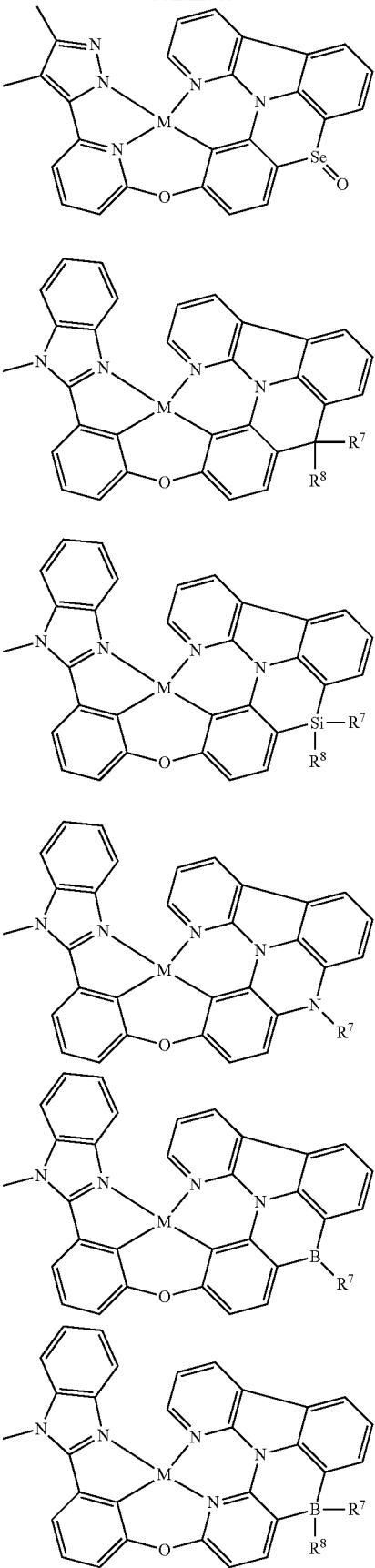

303
-continued
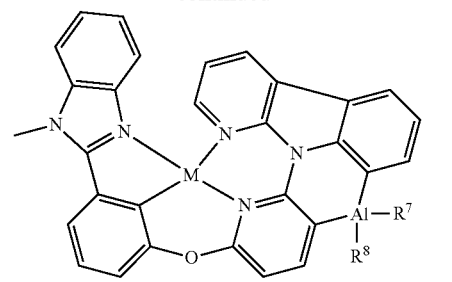
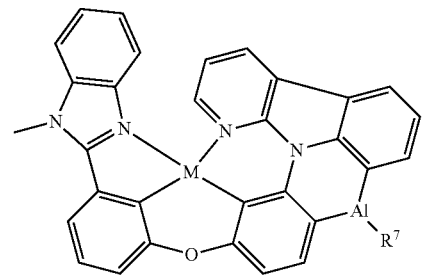
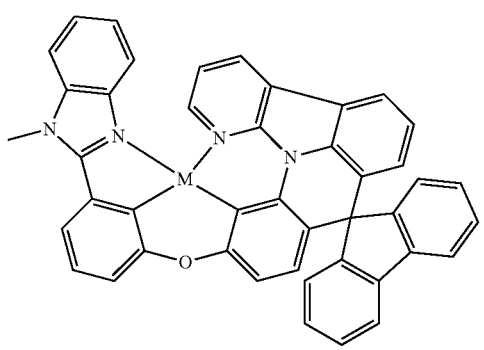
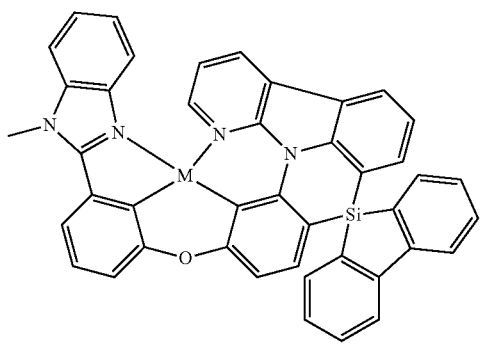
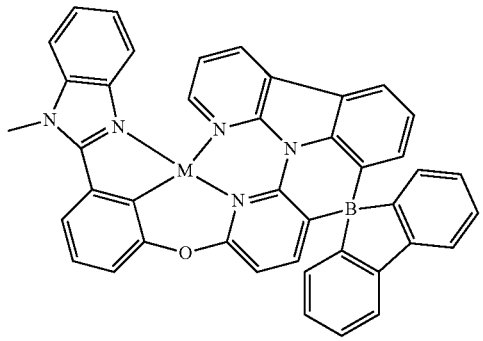
304
-continued
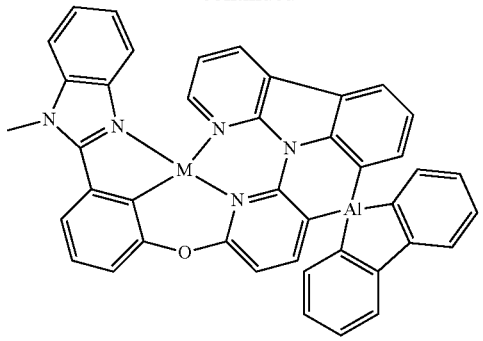
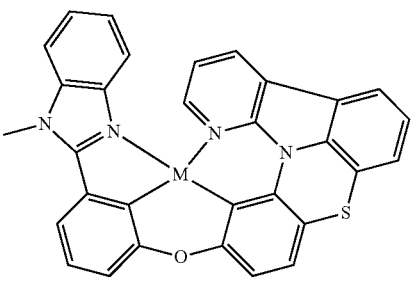
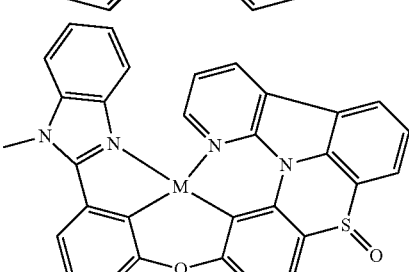
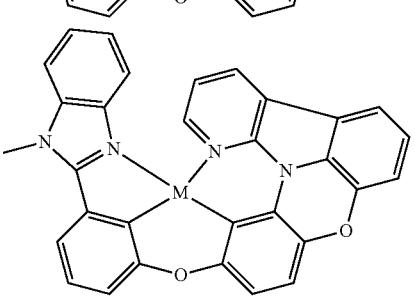
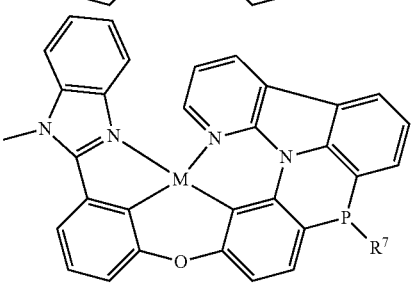
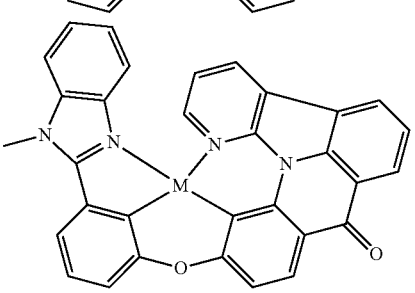

305
-continued
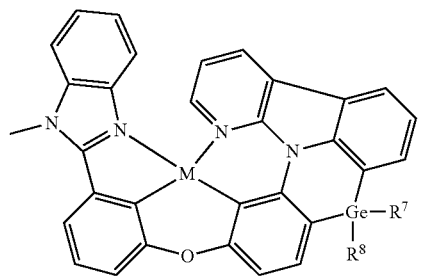
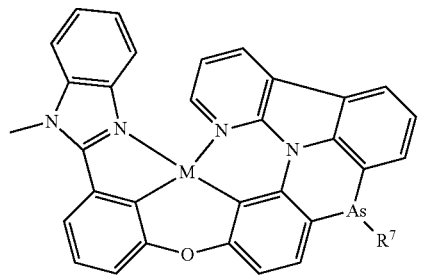
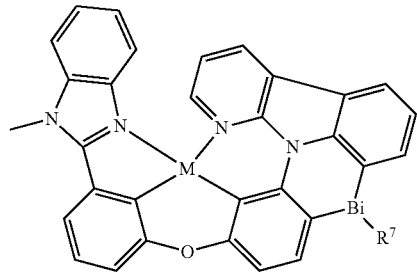
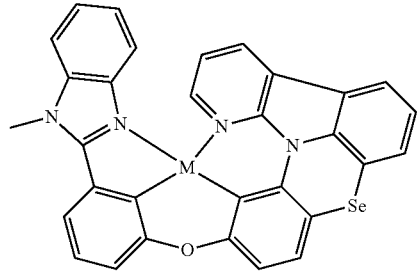
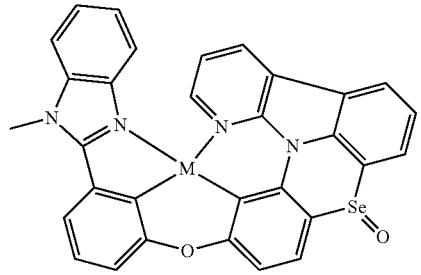
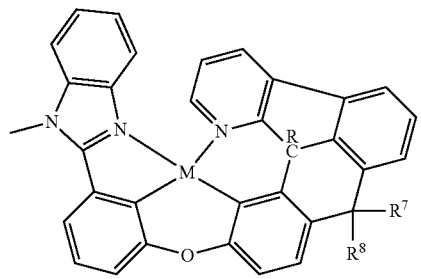
306
-continued
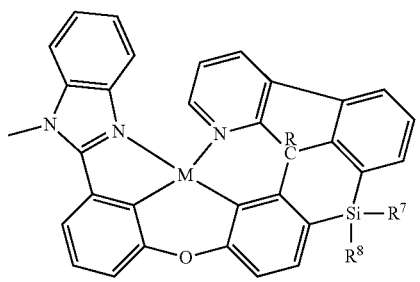
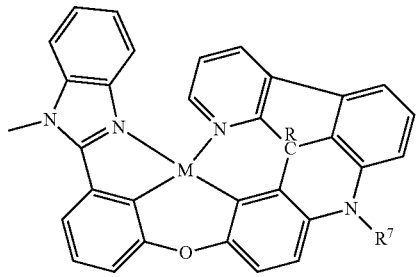
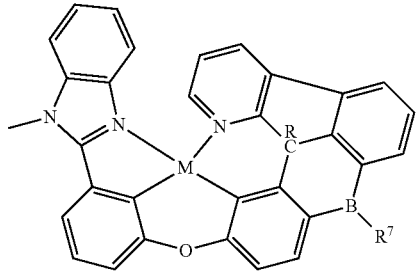
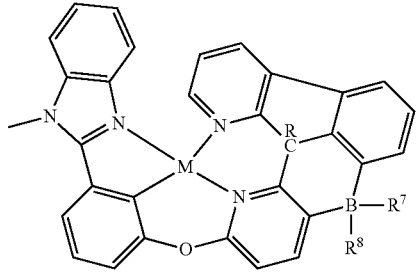
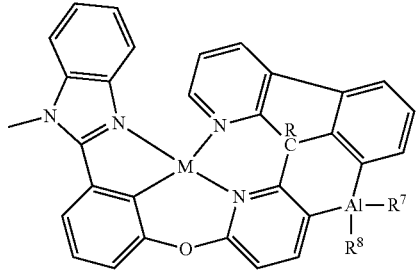
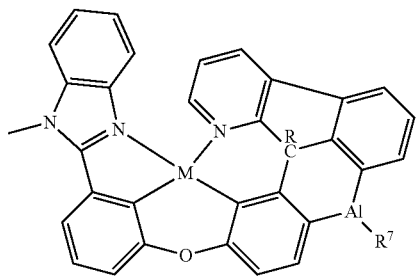

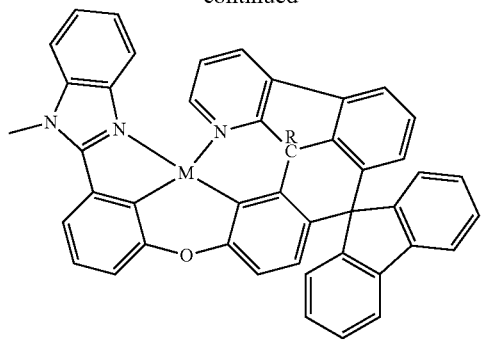
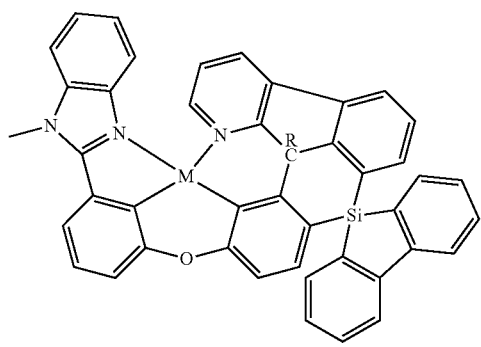
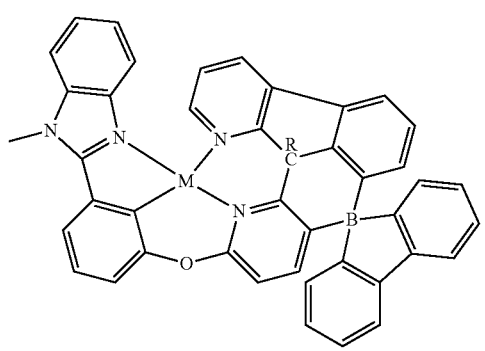
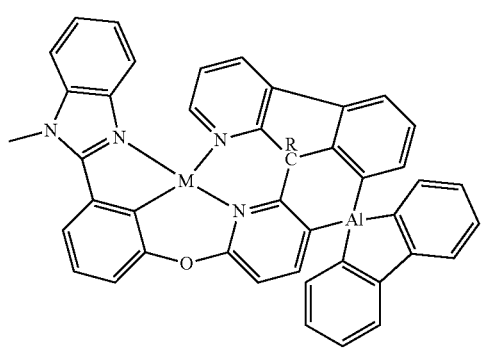
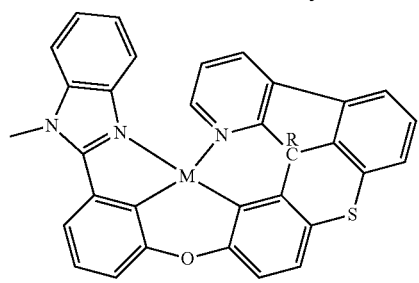
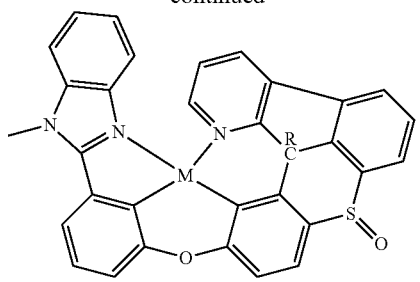
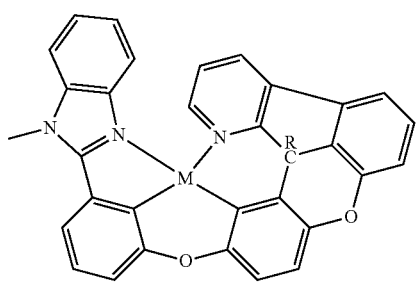
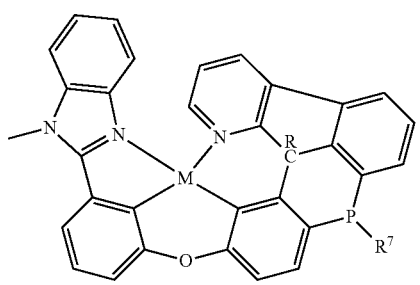
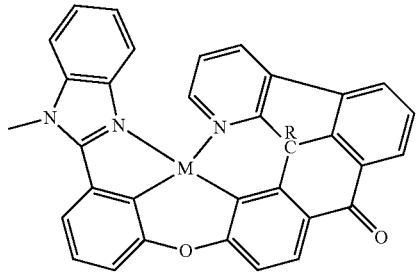
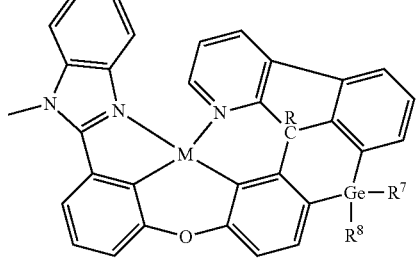

309
-continued
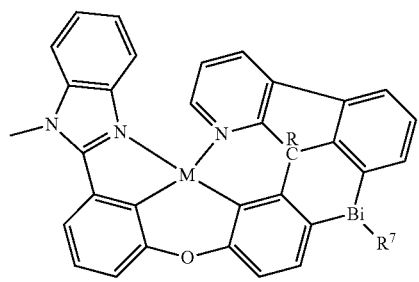
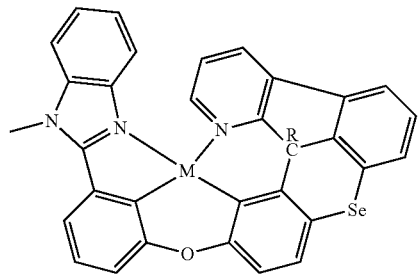
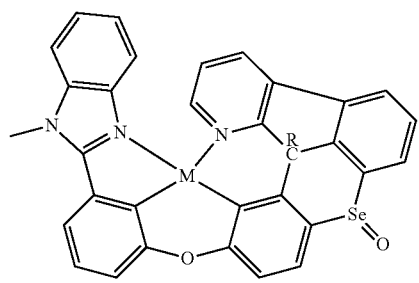
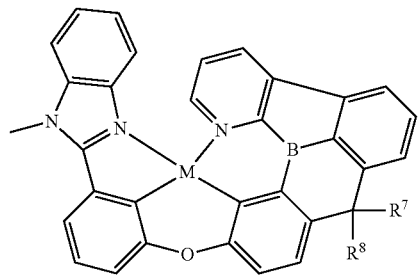
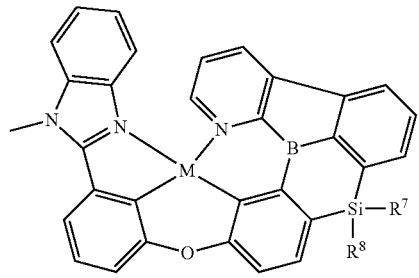
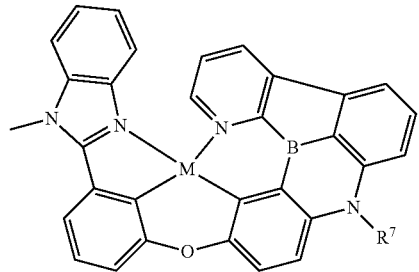
310
-continued
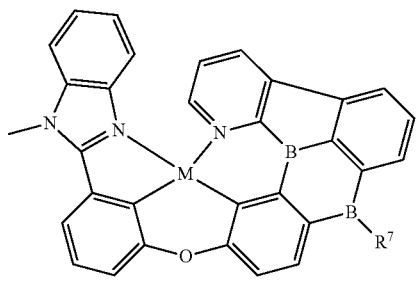
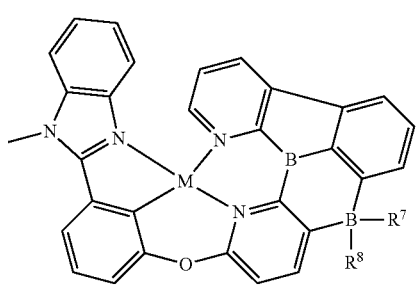
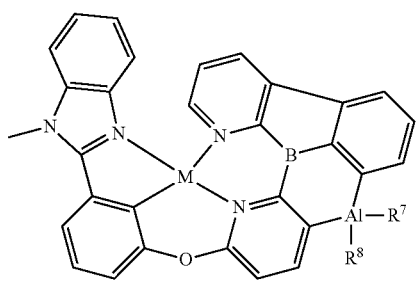
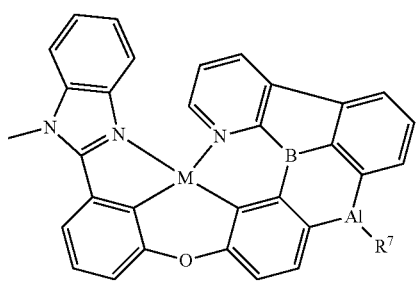
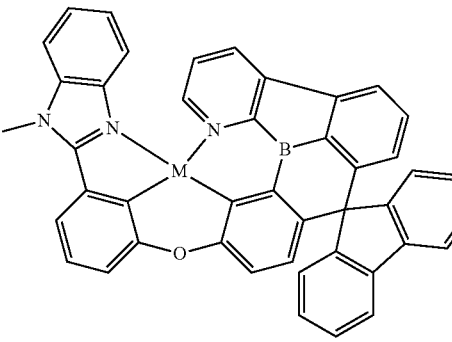

311
-continued
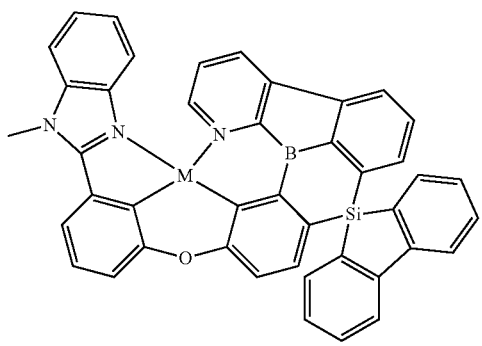
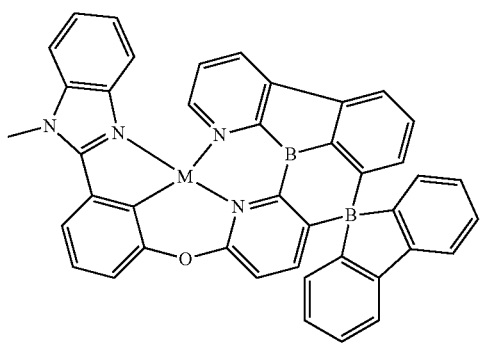
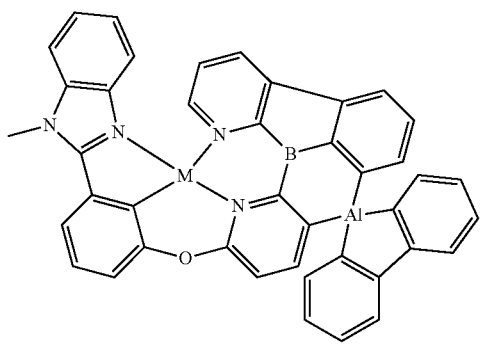
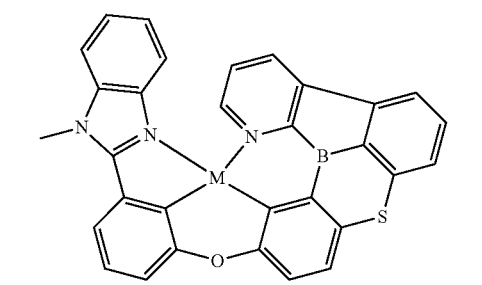
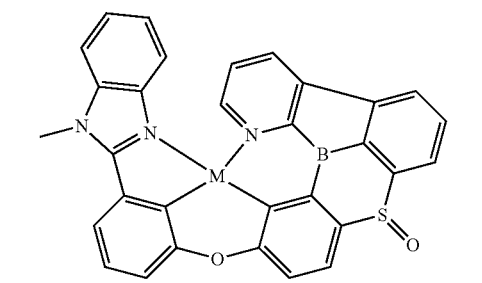
312
-continued
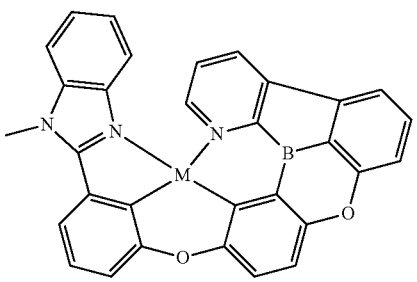
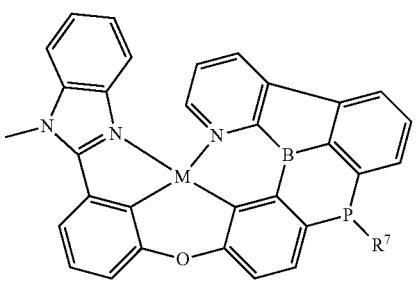
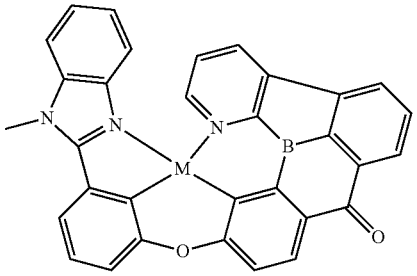
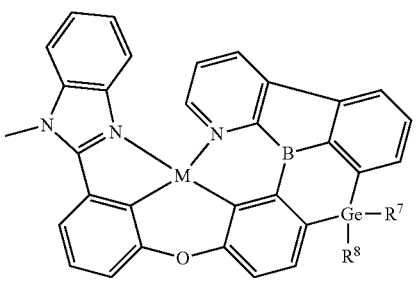
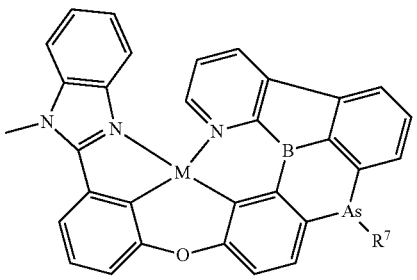
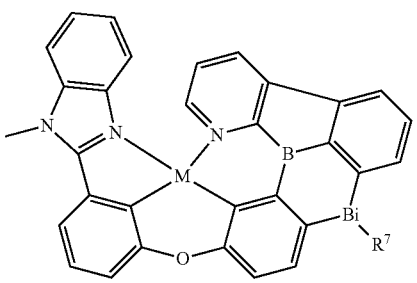

313
-continued
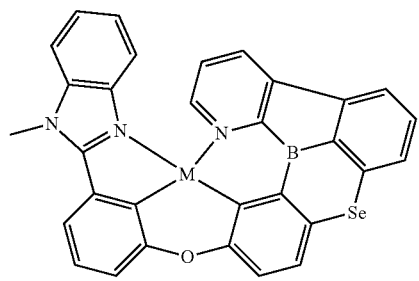
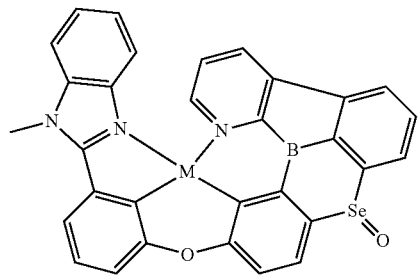
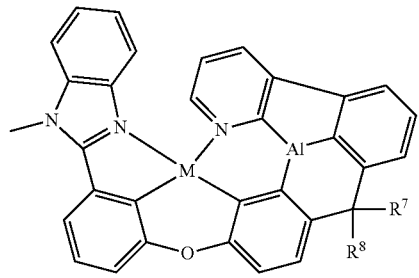
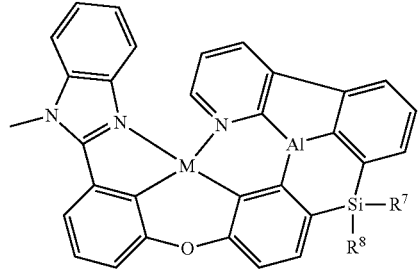
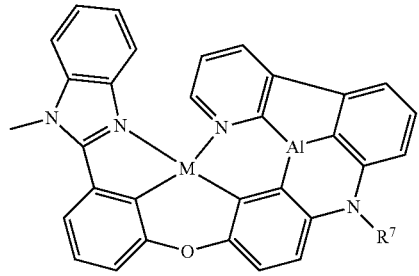
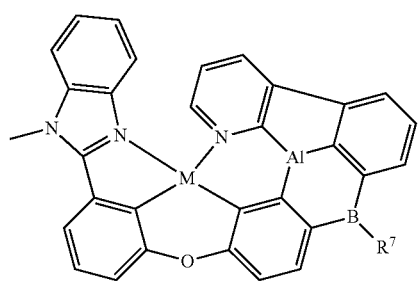
314
-continued
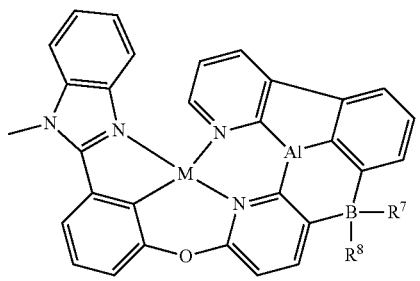
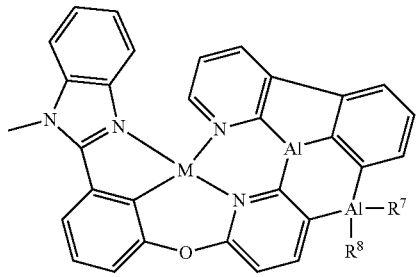
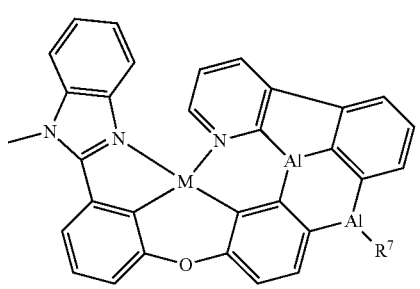
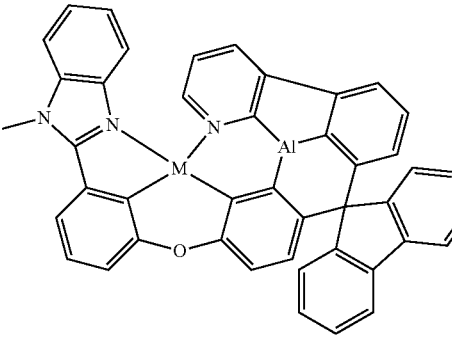
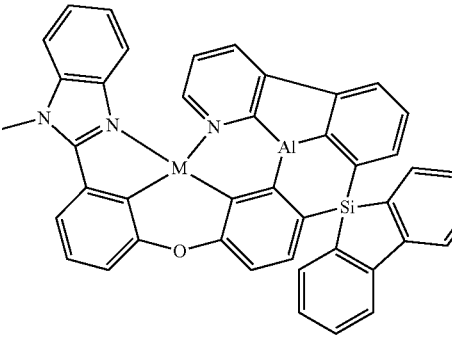

315
-continued
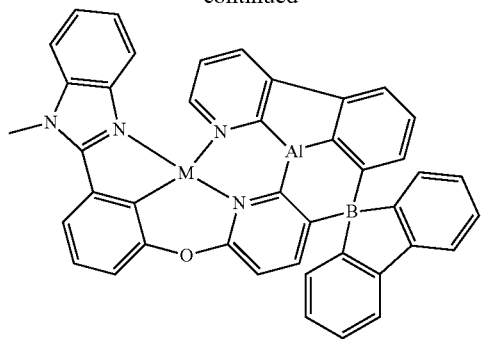
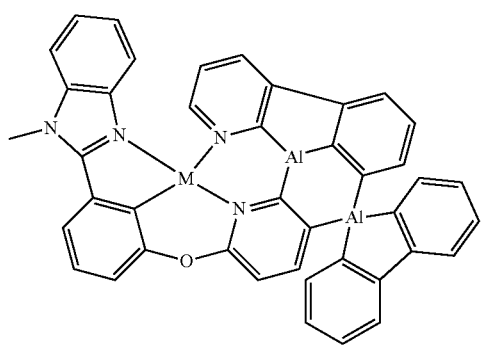
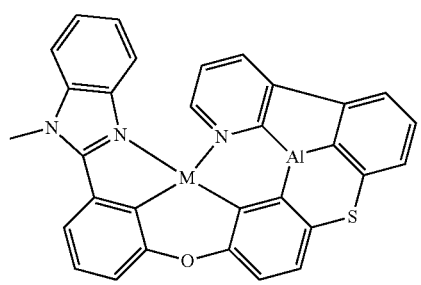
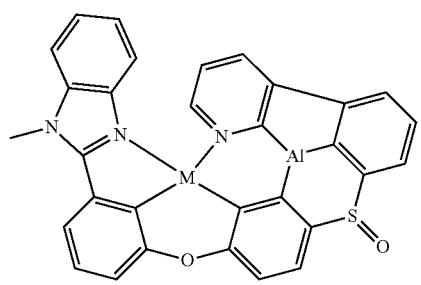
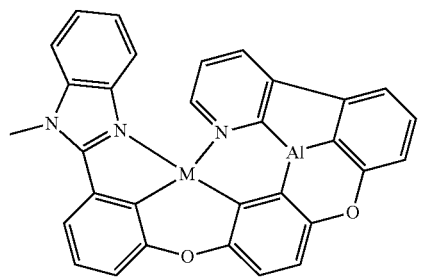
316
-continued
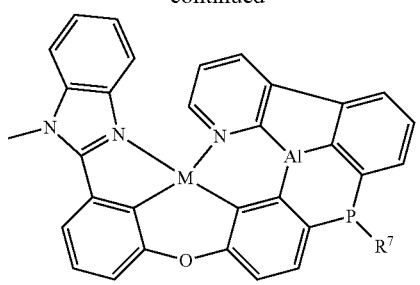
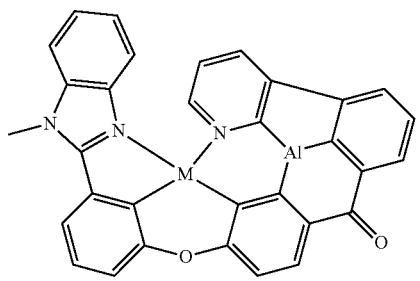
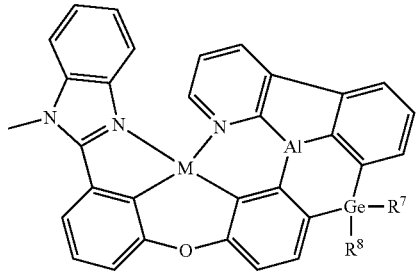
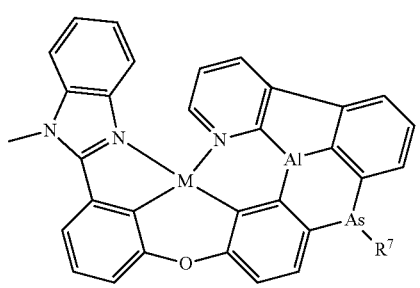
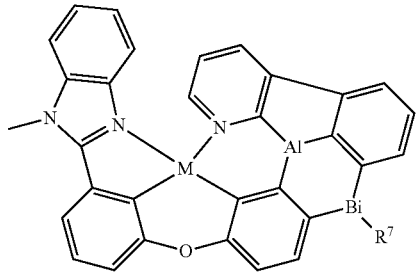
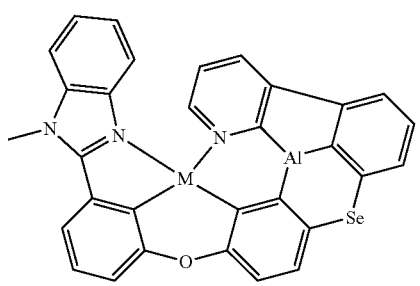

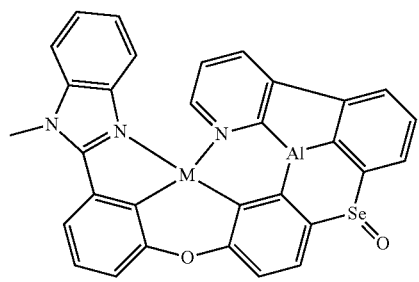
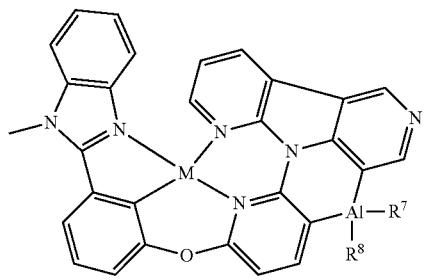
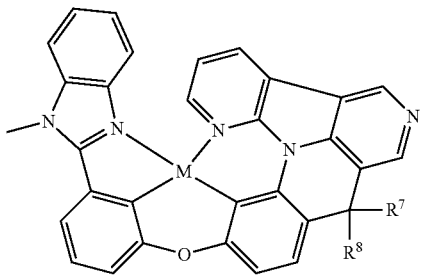
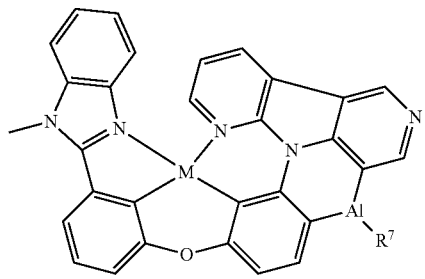
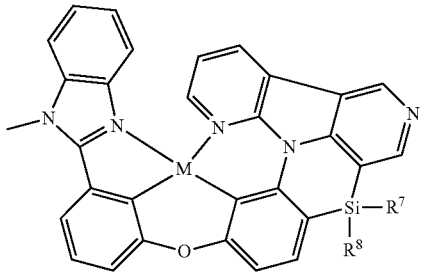
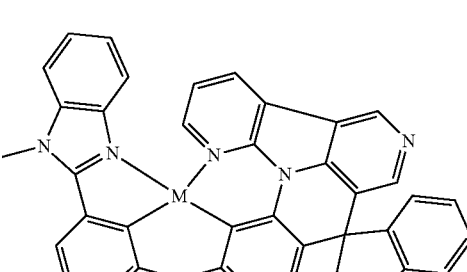
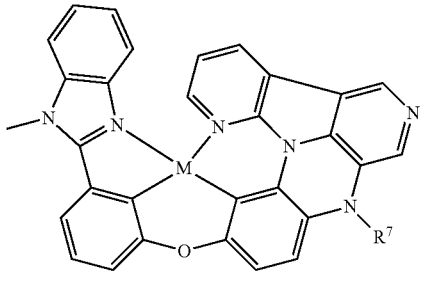
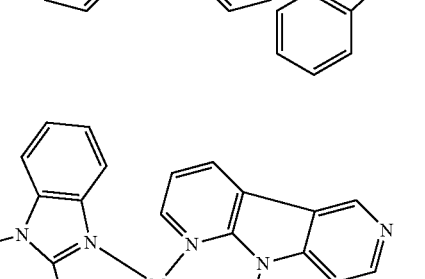
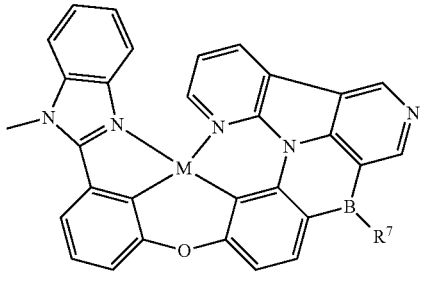
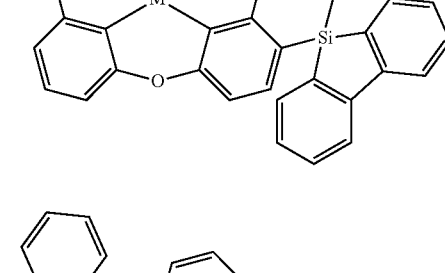
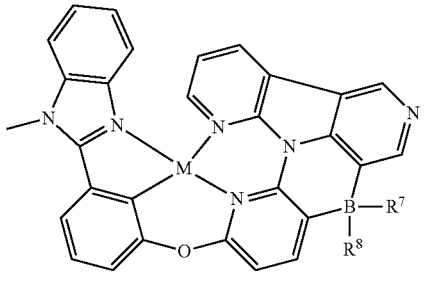
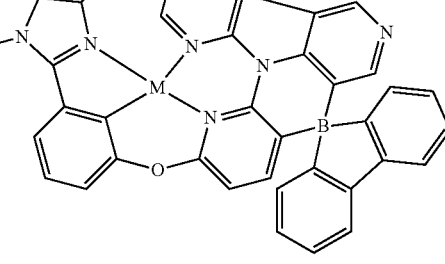

319
-continued
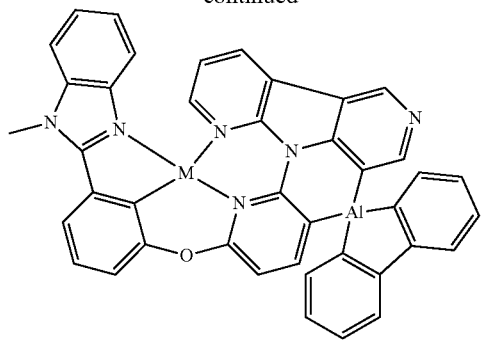
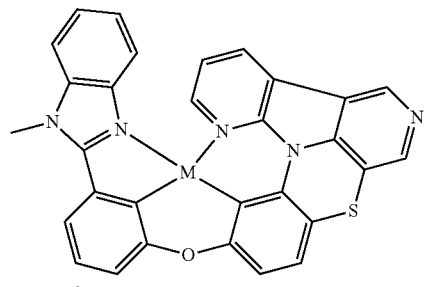
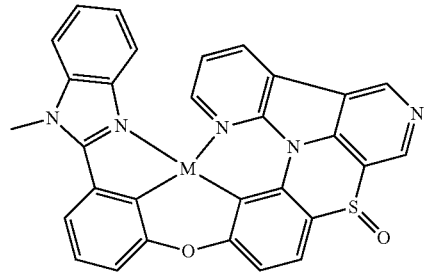
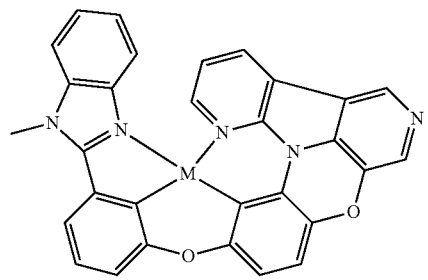
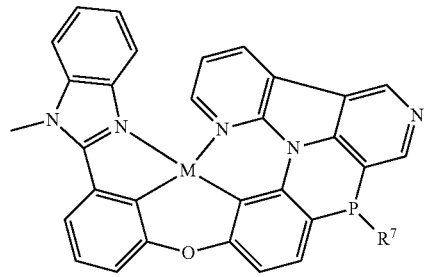
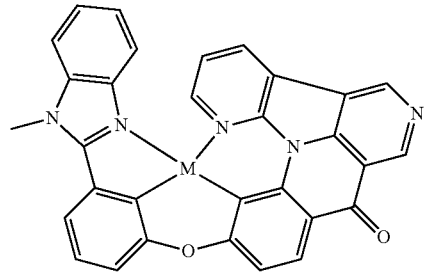
320
-continued
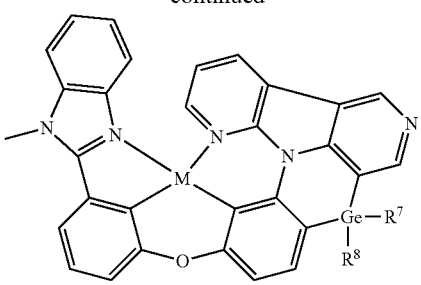
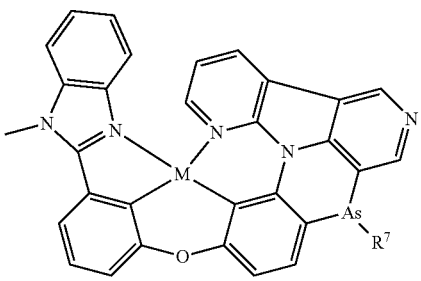
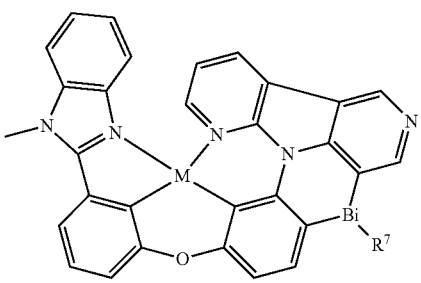
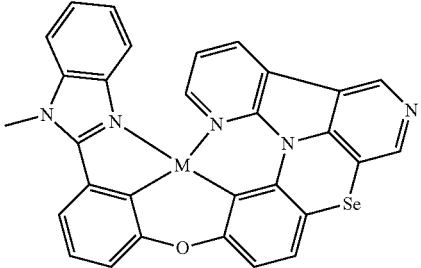
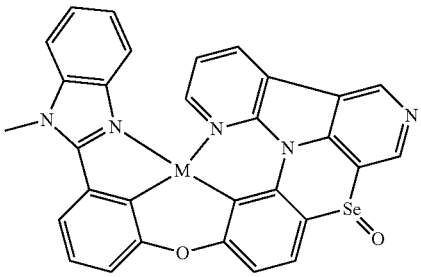
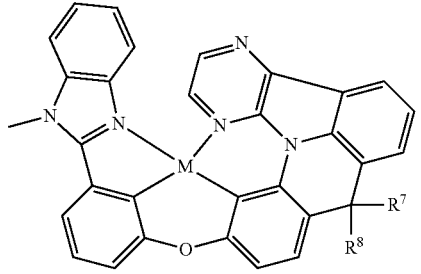

321
-continued
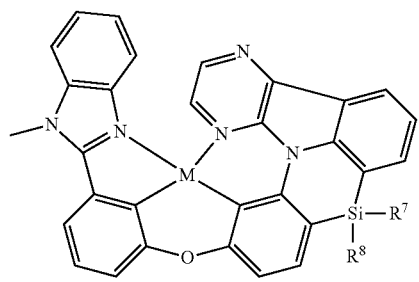
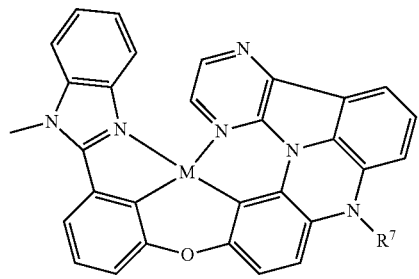
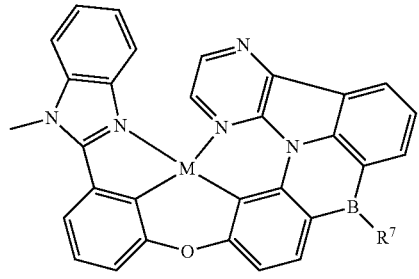
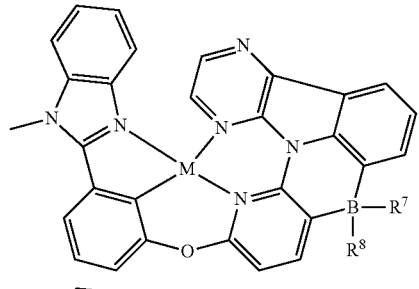
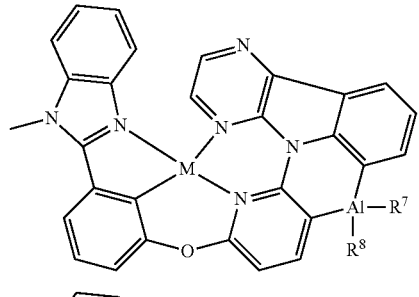
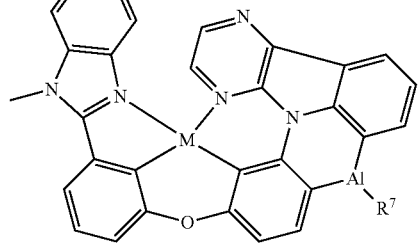
322
-continued
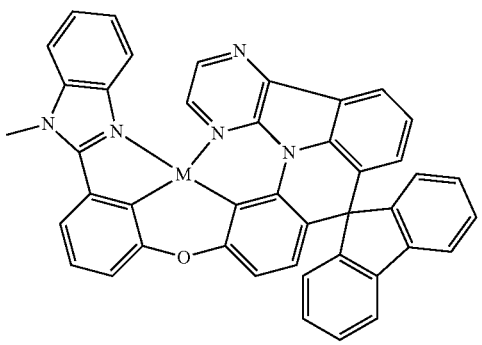
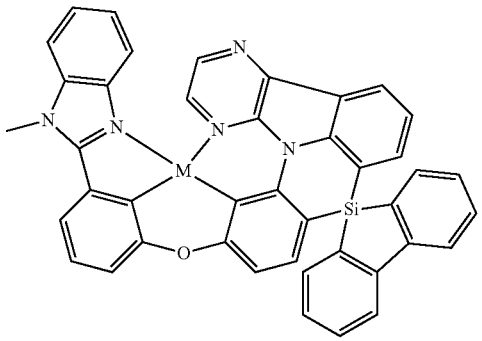
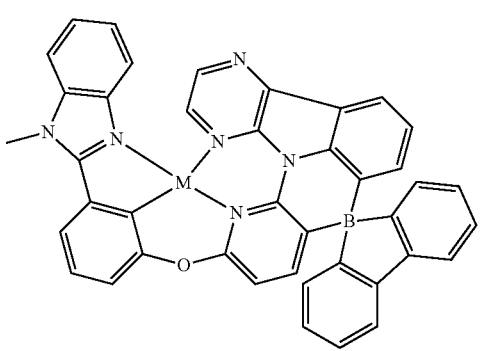
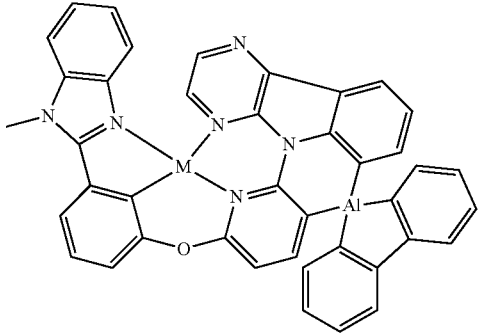
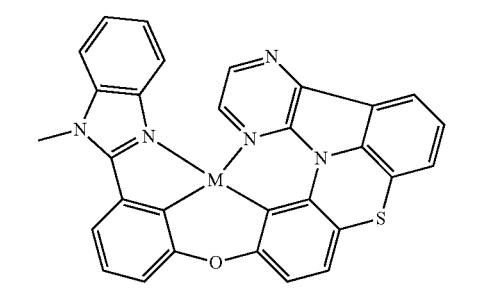

323
-continued
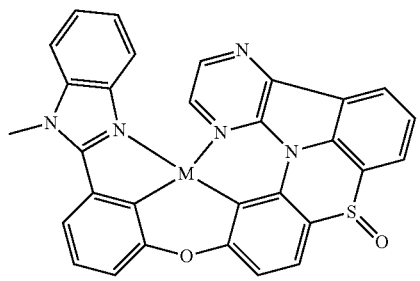
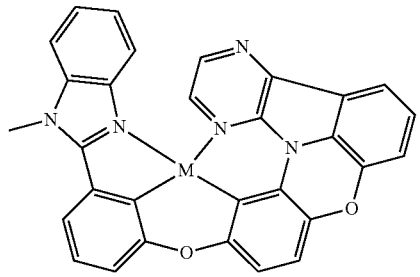
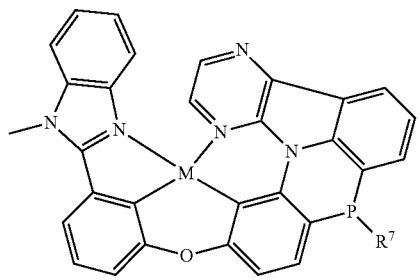
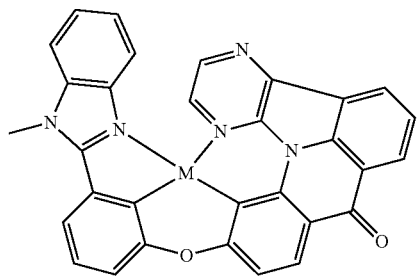
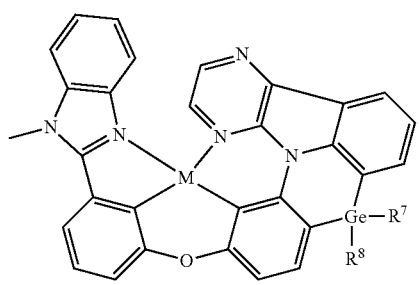
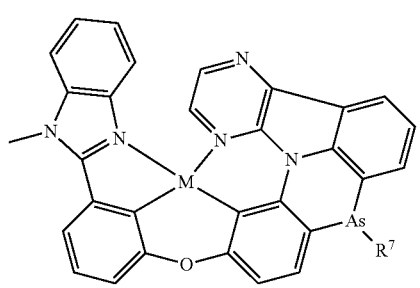
324
-continued
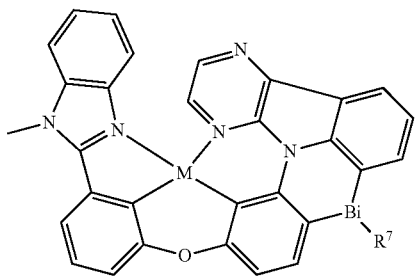
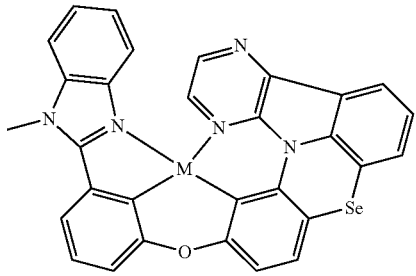
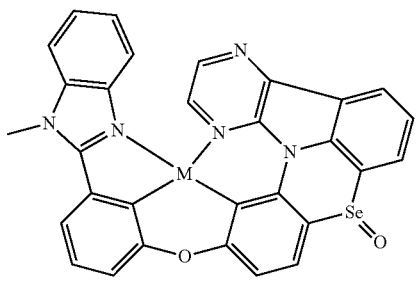
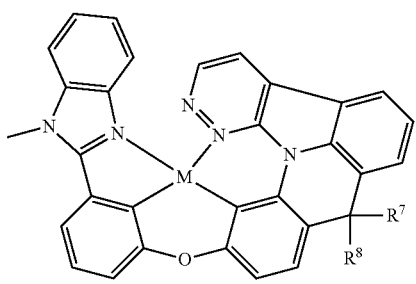
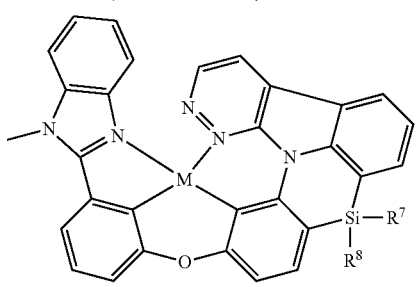
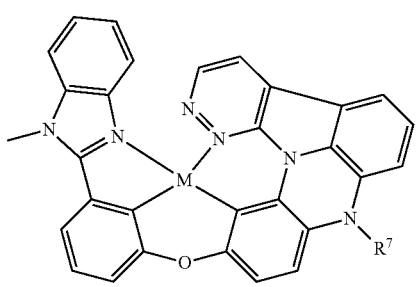

325
-continued
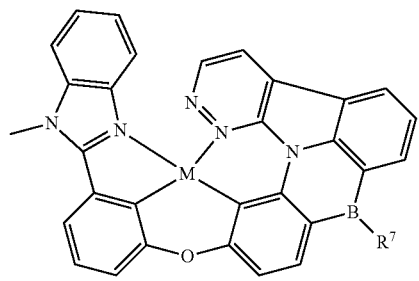
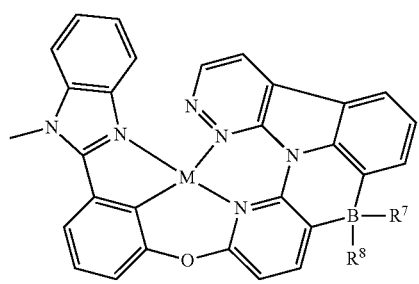
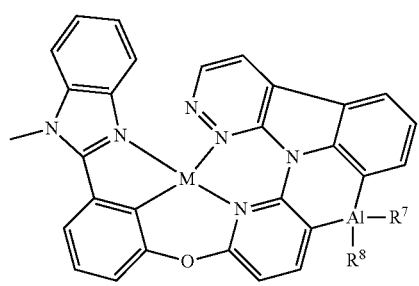
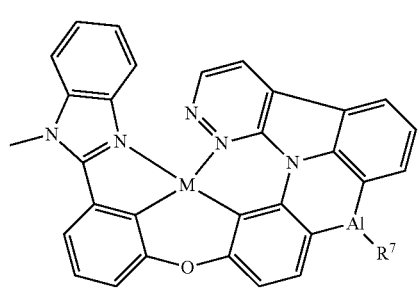
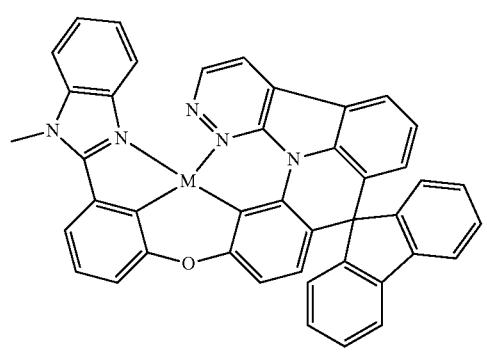
326
-continued
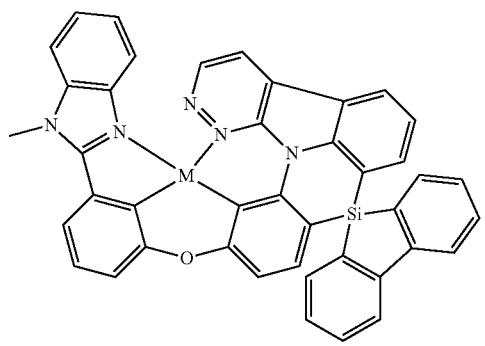
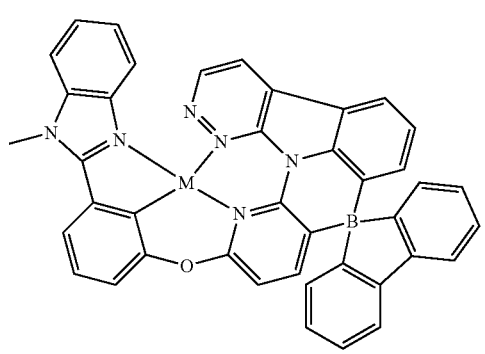
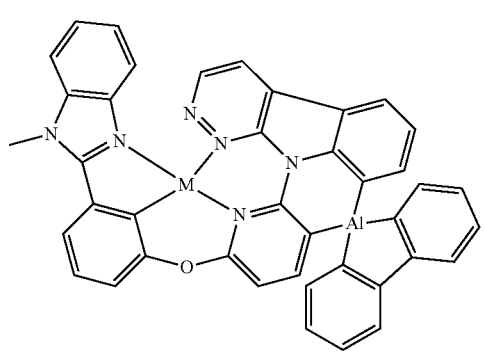
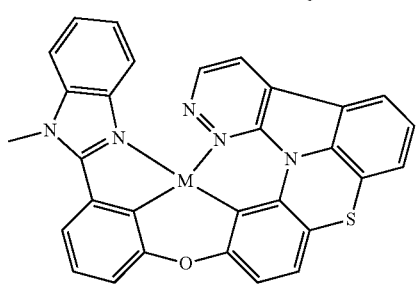
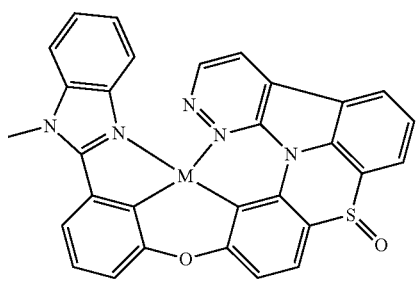

327
-continued
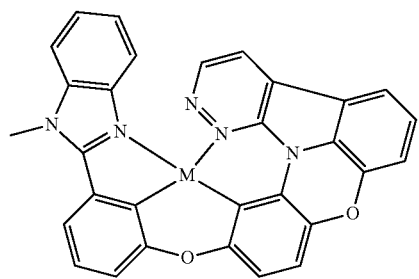
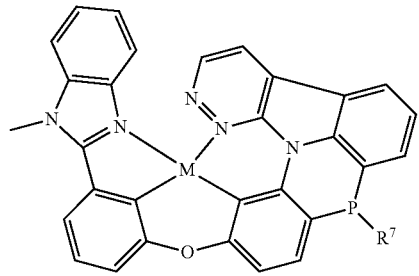
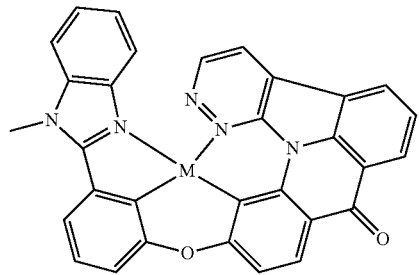
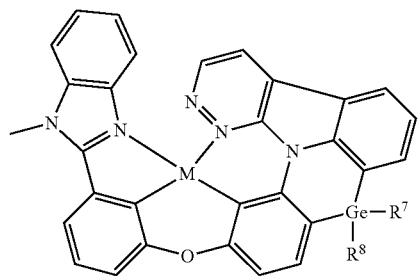
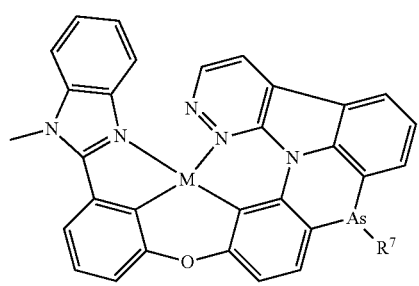
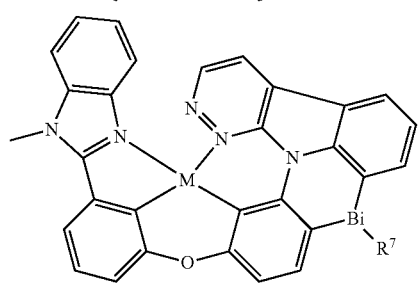
328
-continued
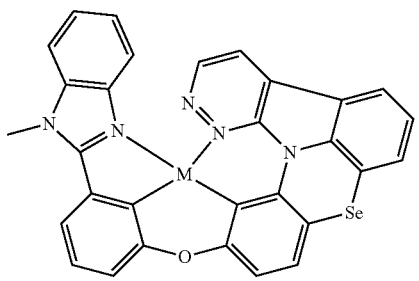
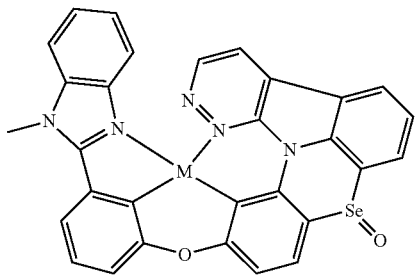
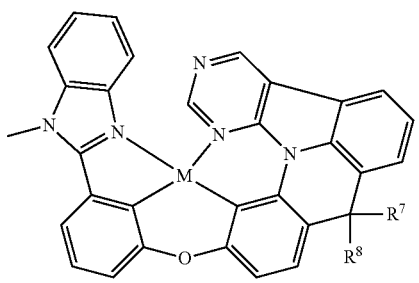
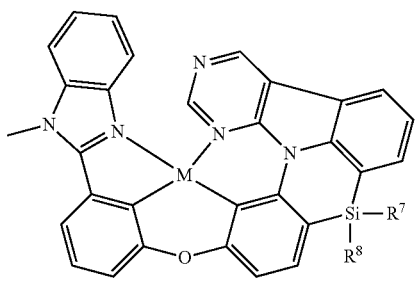
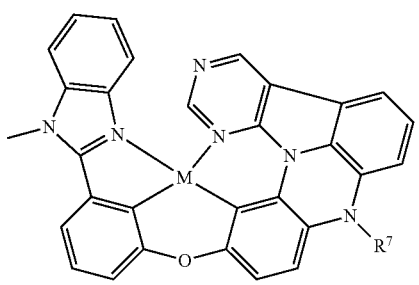
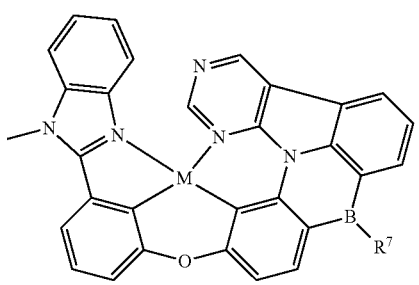

329
-continued
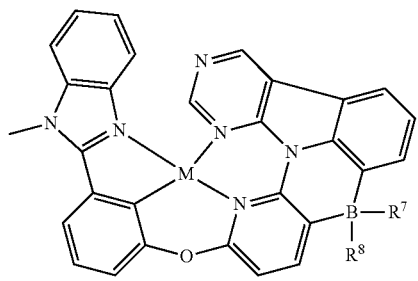
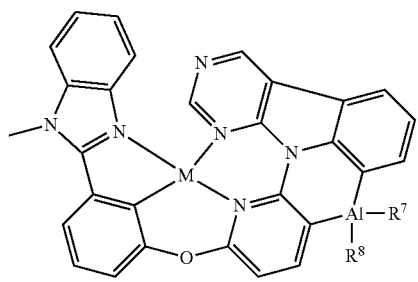
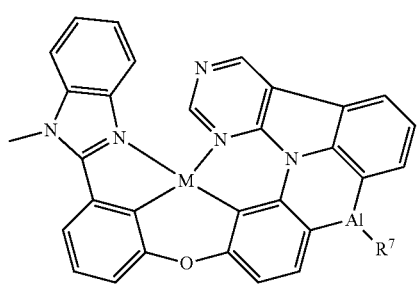
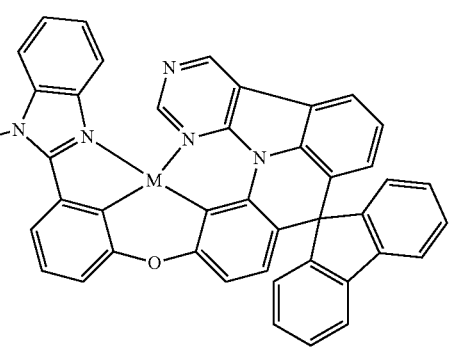
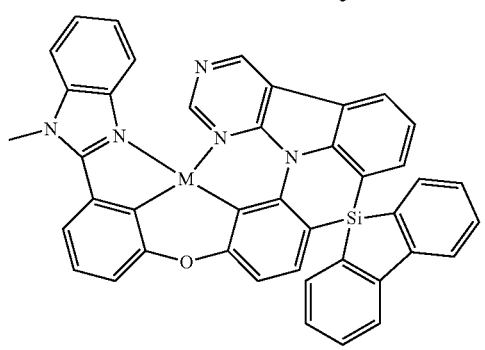
330
-continued
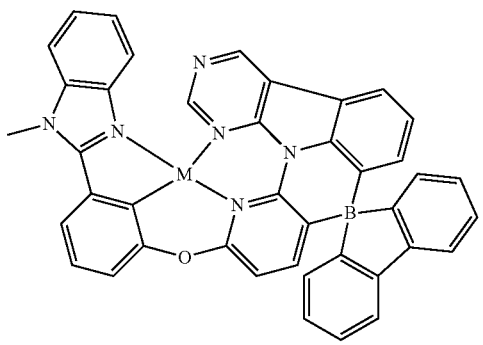
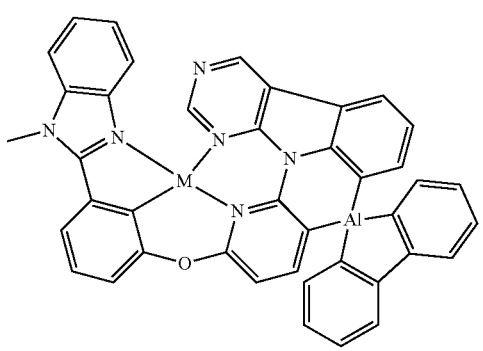
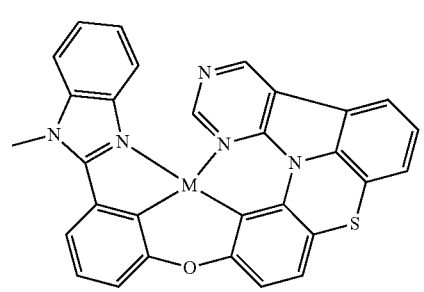
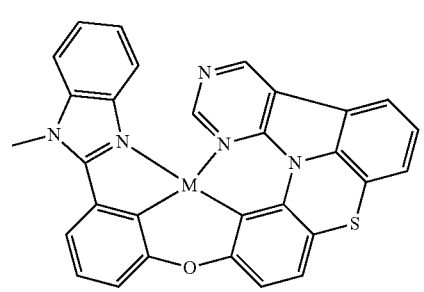
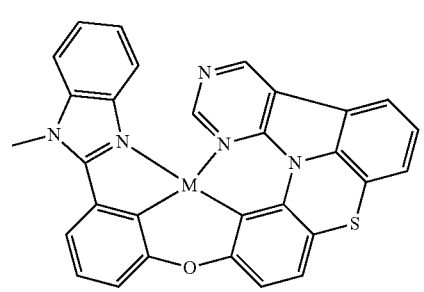

331
-continued
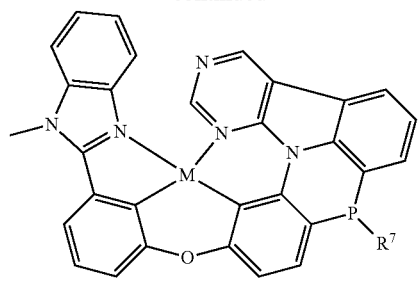
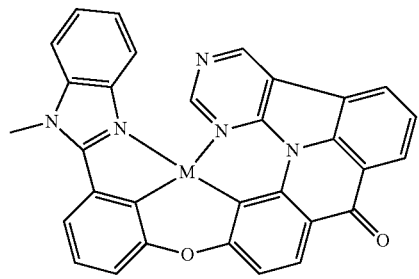
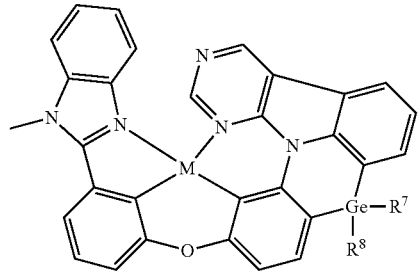
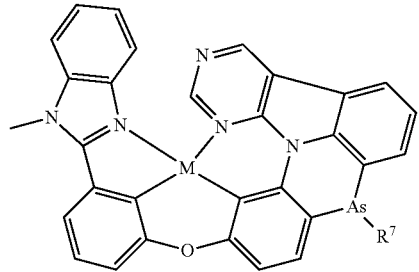
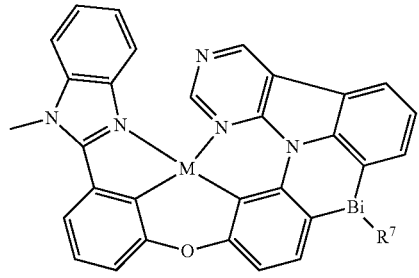
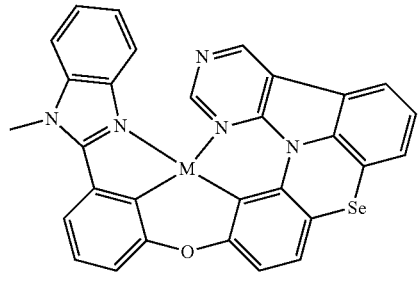
332
-continued
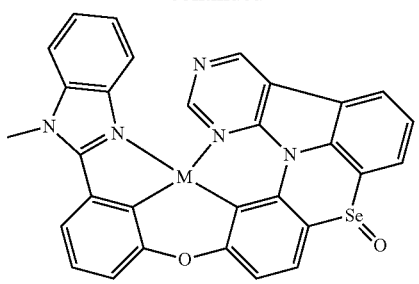
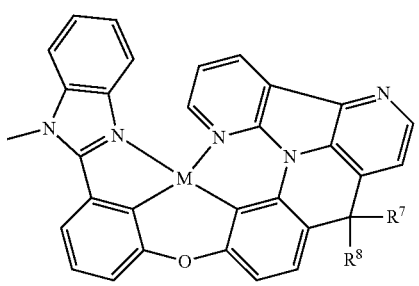
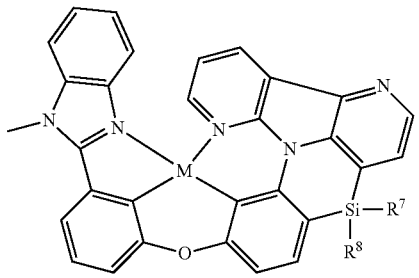
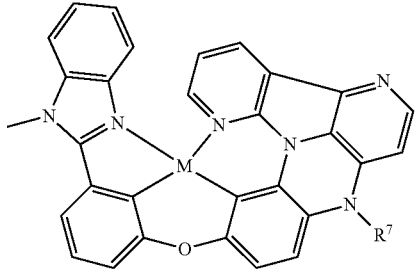
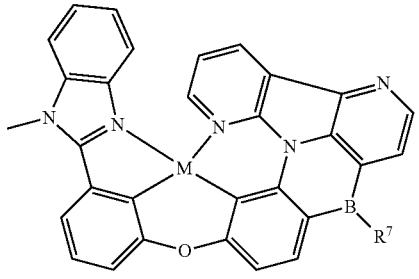
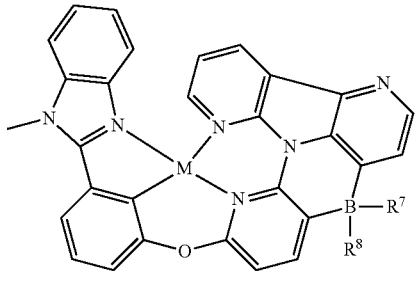

333
-continued
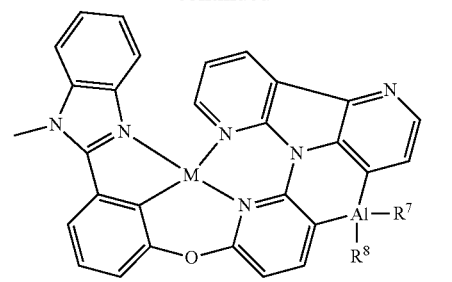
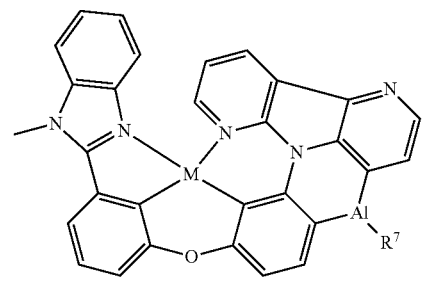
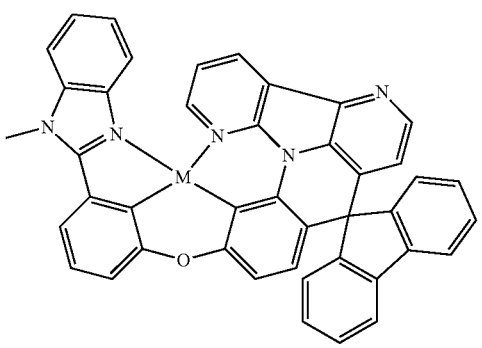
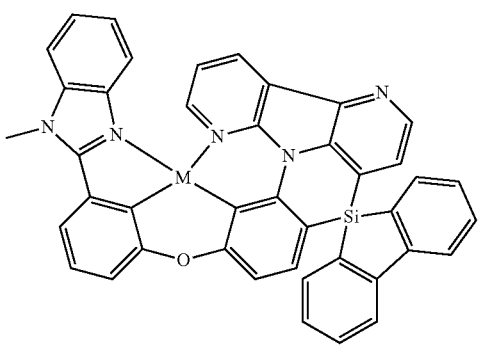
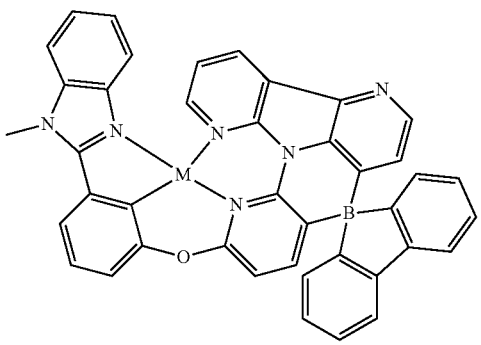
334
-continued
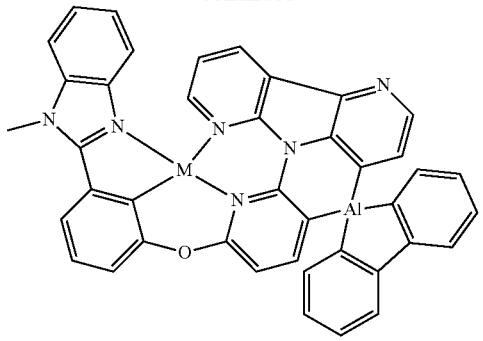
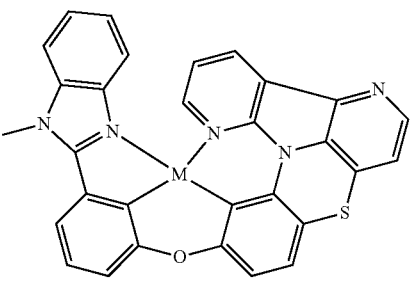
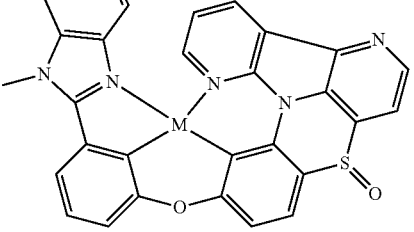
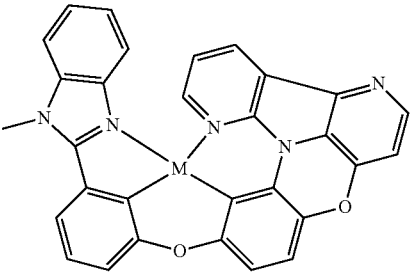
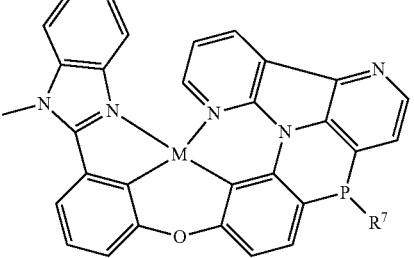
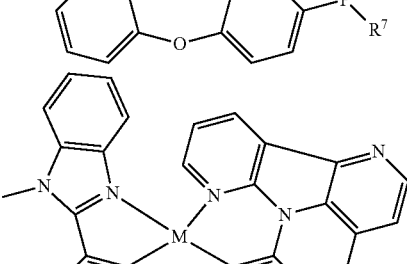
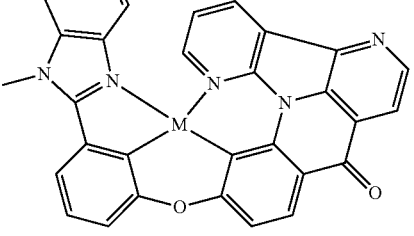

335
-continued
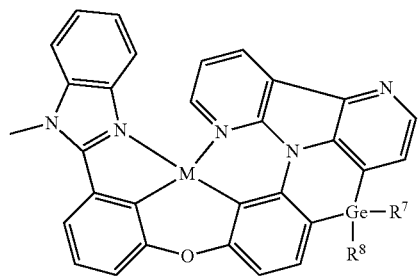
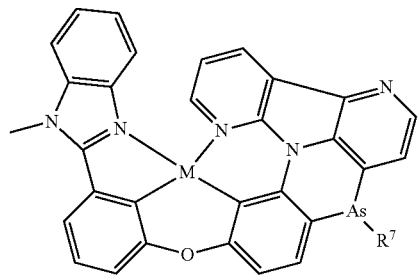
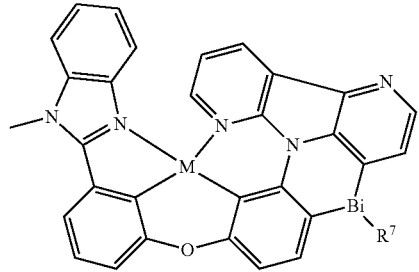
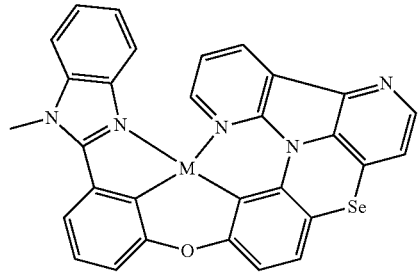
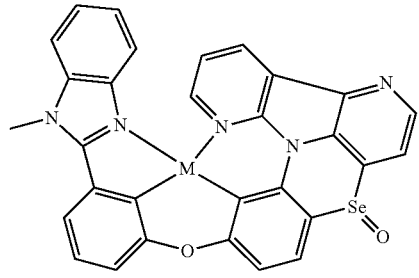
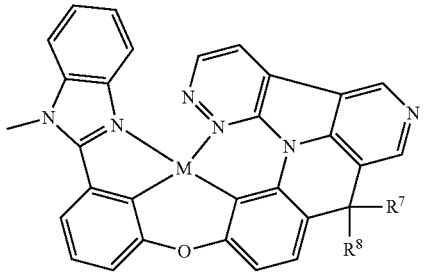
336
-continued
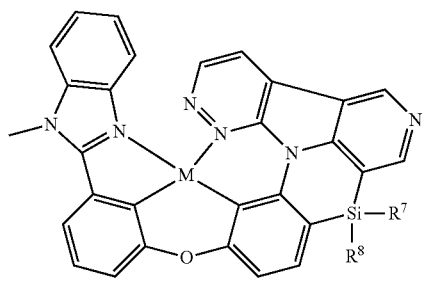
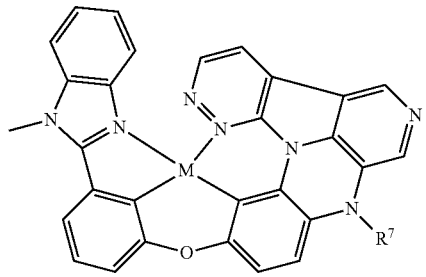
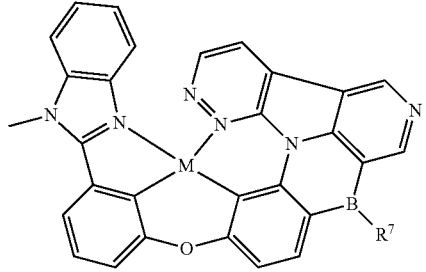
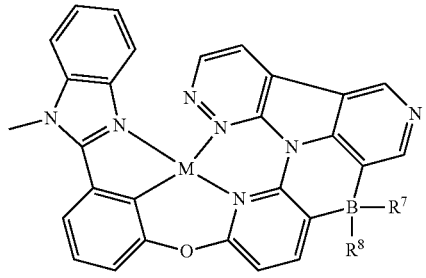
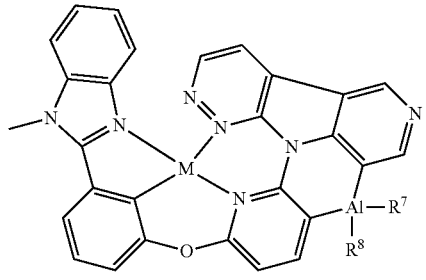
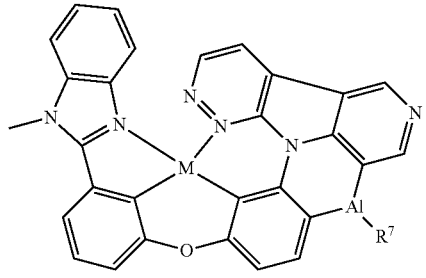

337
-continued
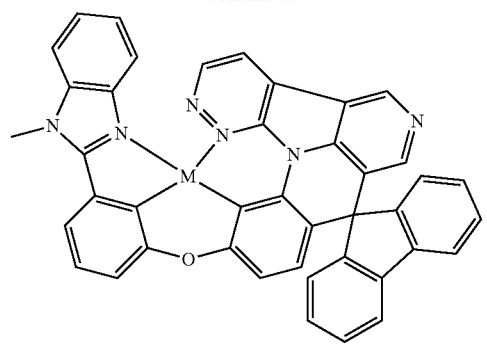
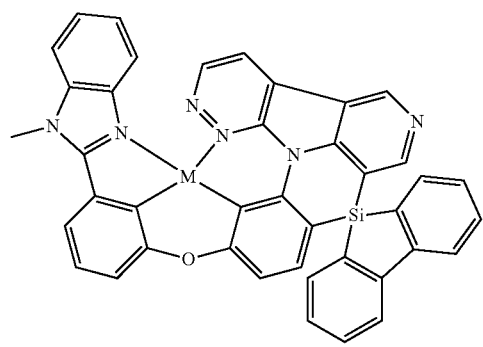
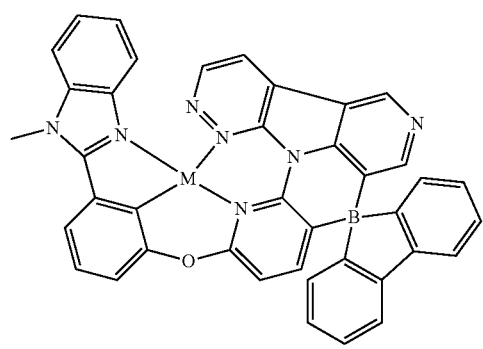
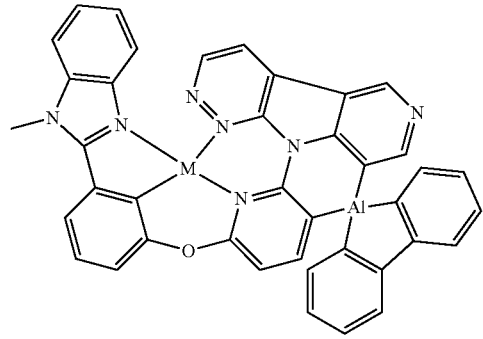
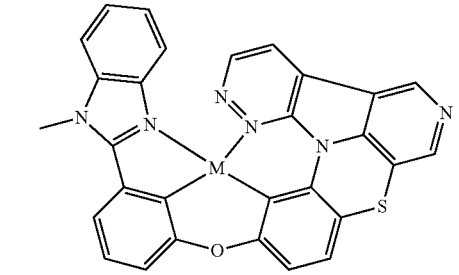
338
-continued
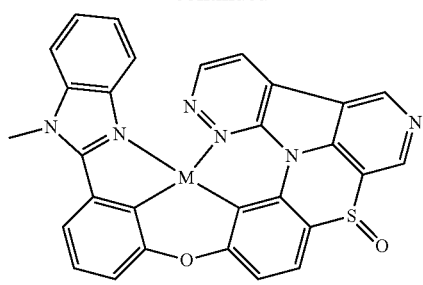
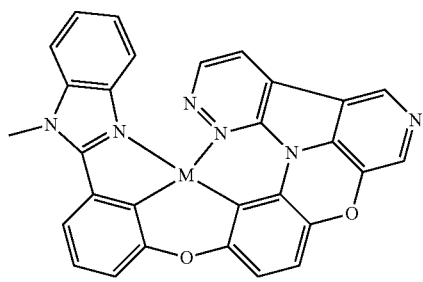
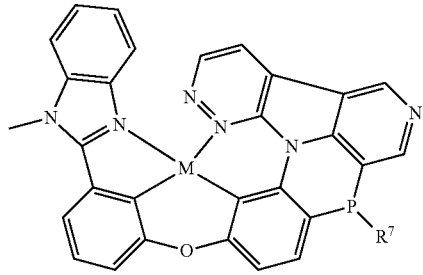
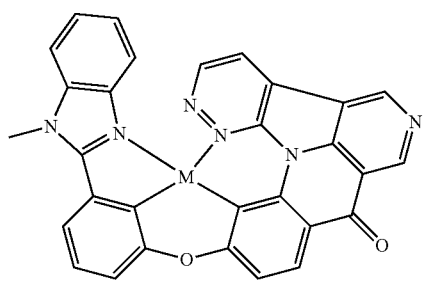
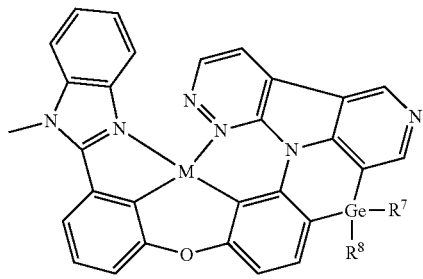
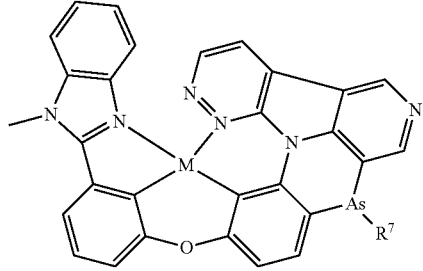

339
-continued
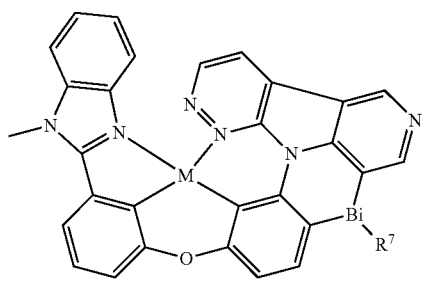
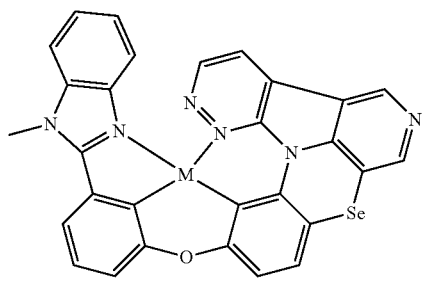
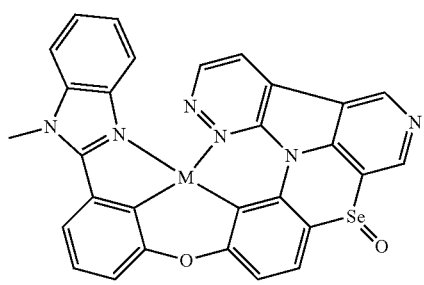
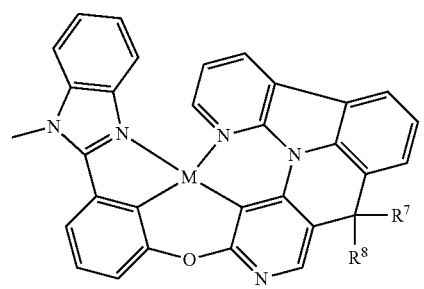
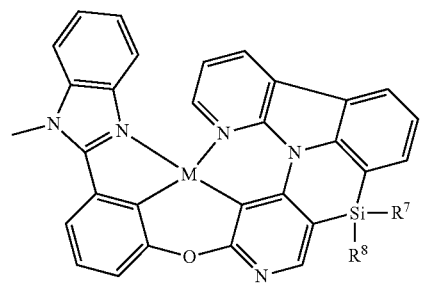
340
-continued
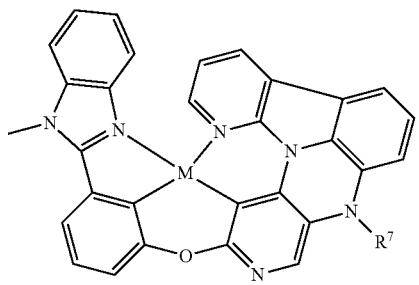
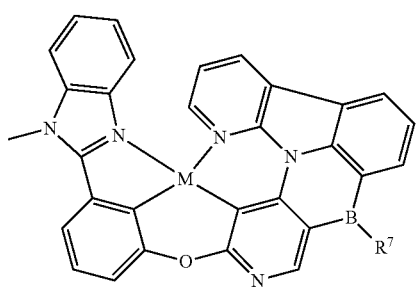
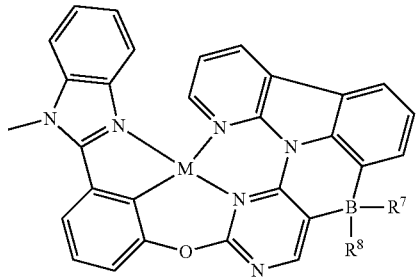
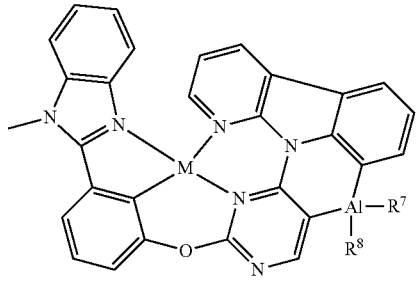
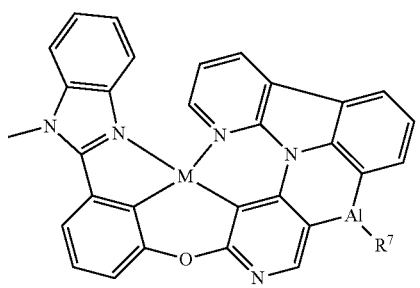

341
-continued
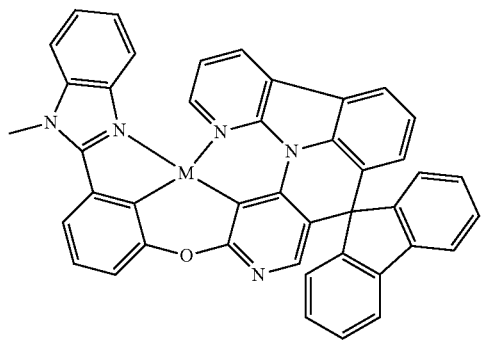
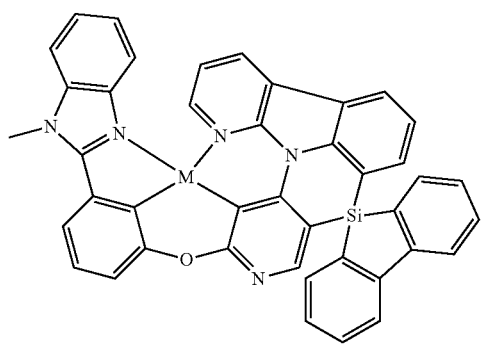
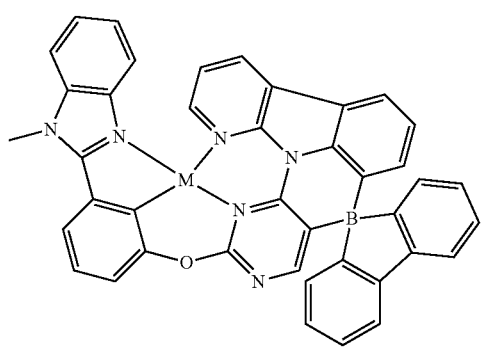
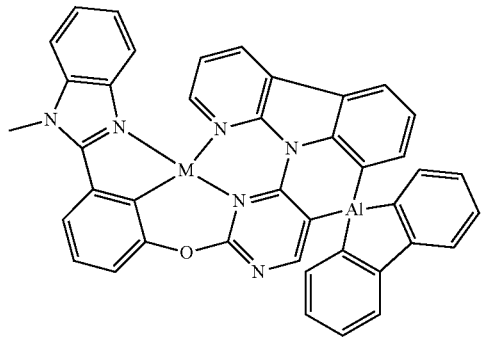
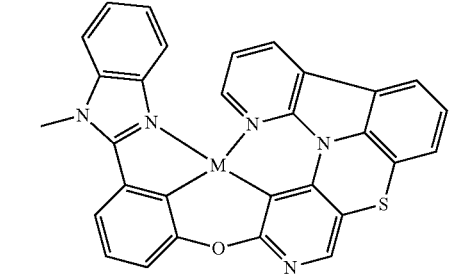
342
-continued
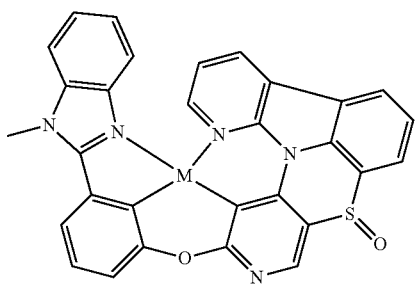
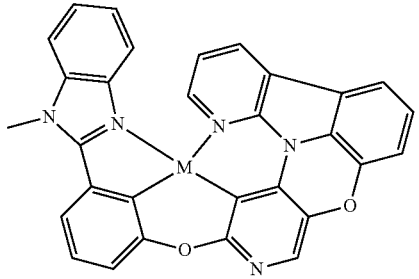
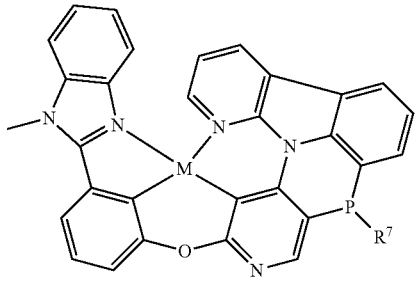
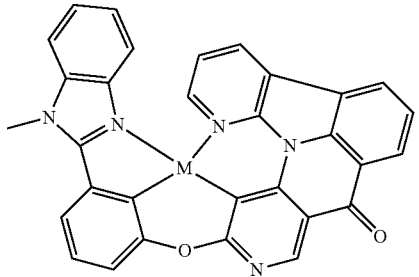
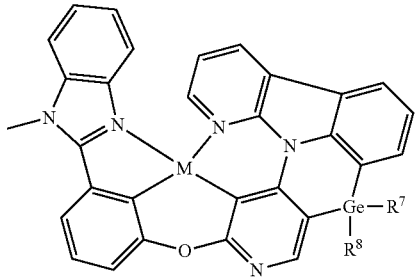
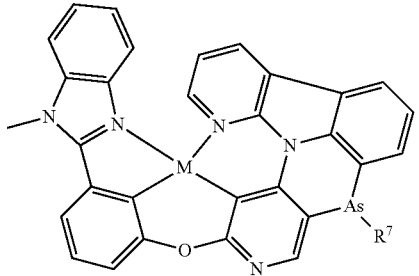

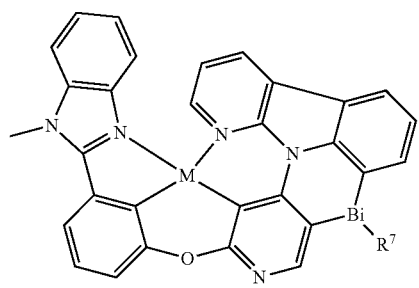
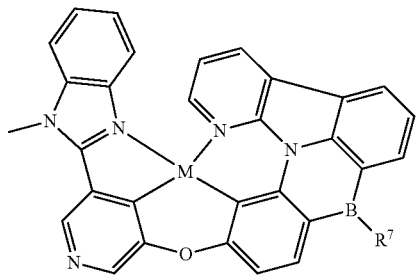
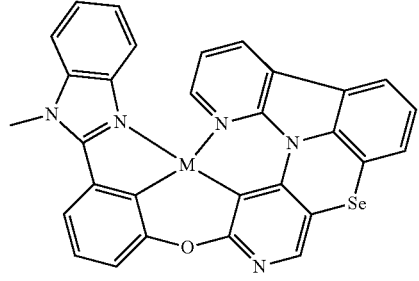
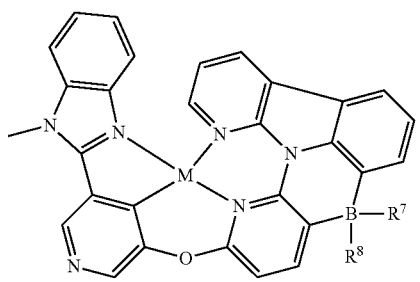
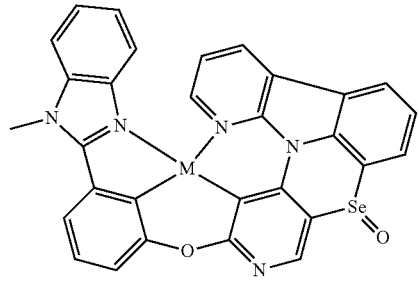
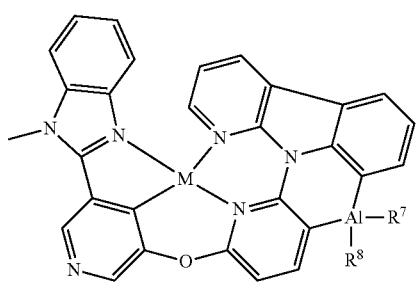
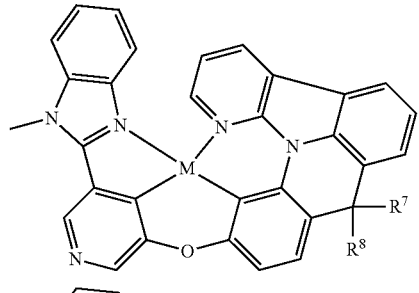
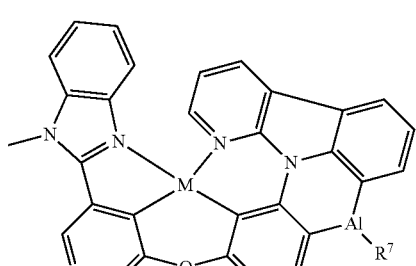
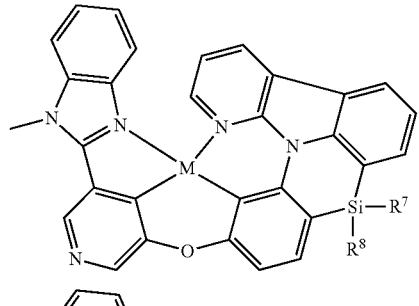
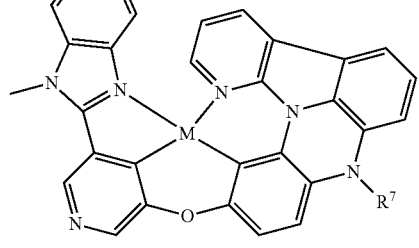
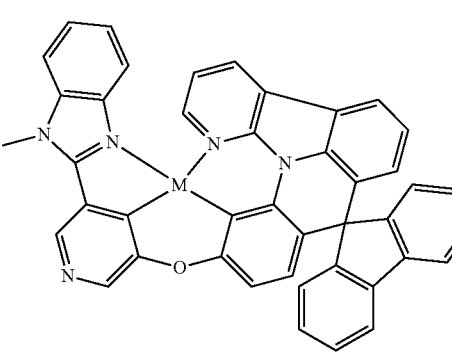

345
-continued
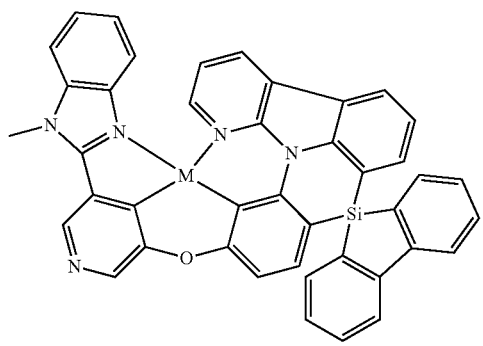
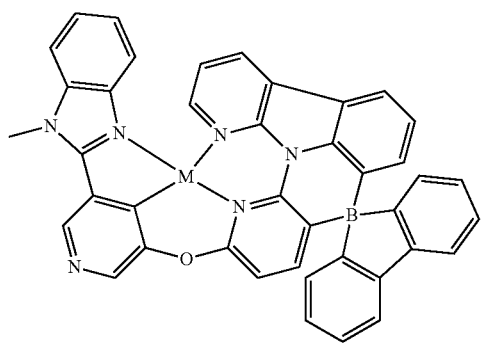
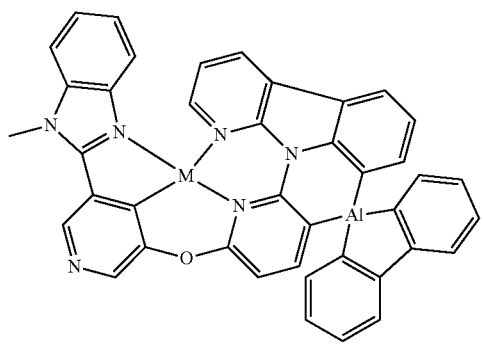
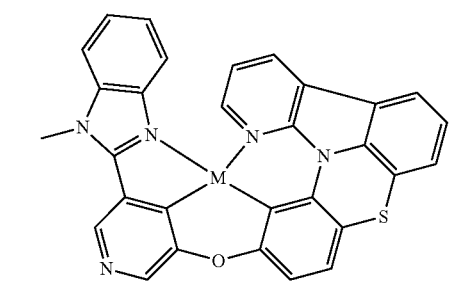
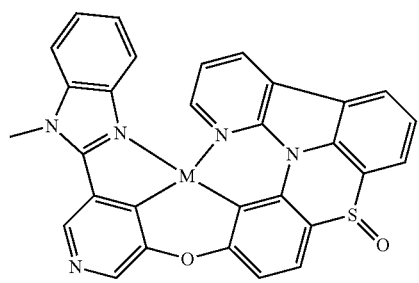
346
-continued
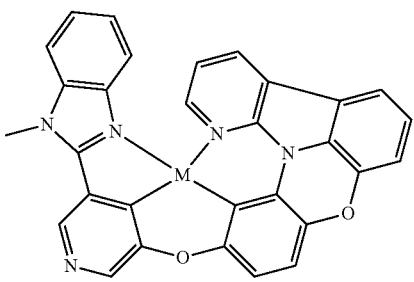
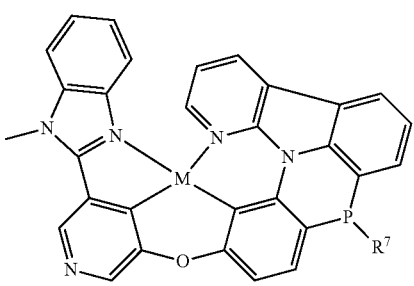
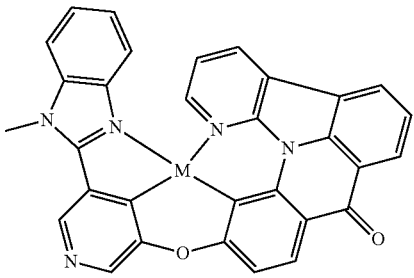
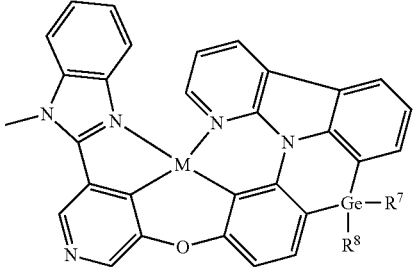
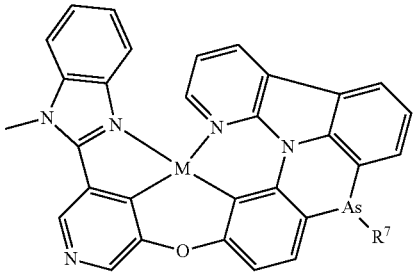
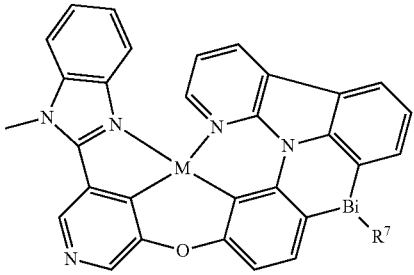

347
-continued
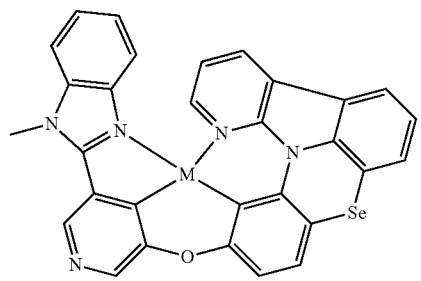
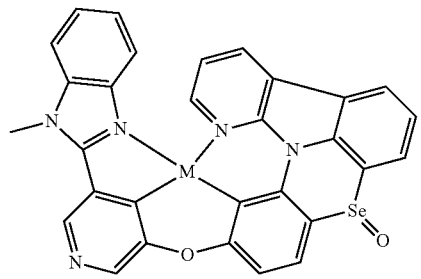
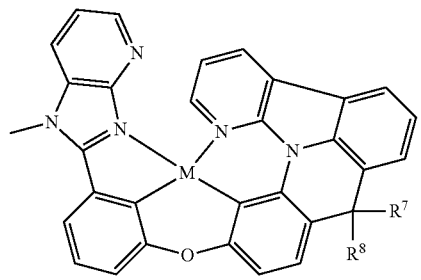
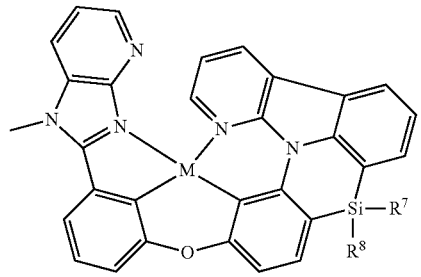
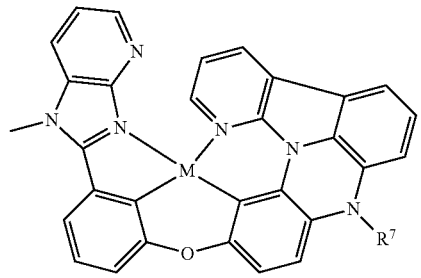
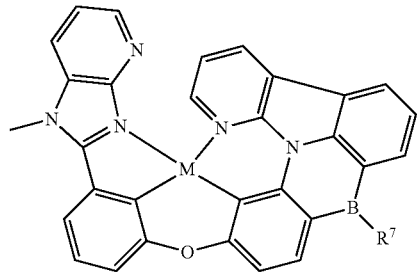
348
-continued
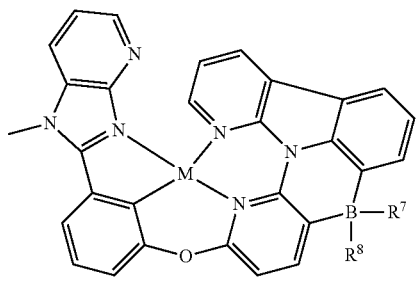
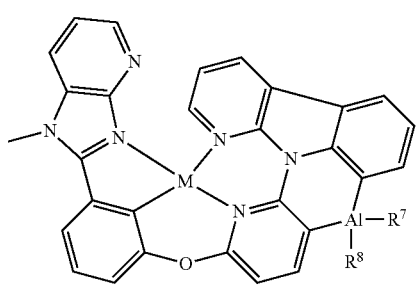
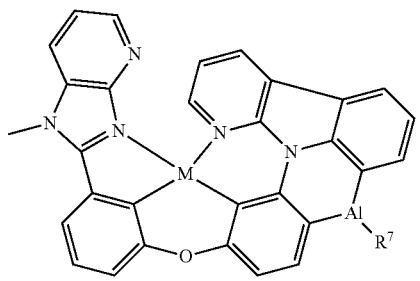
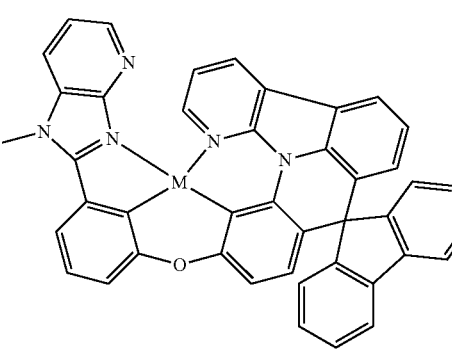
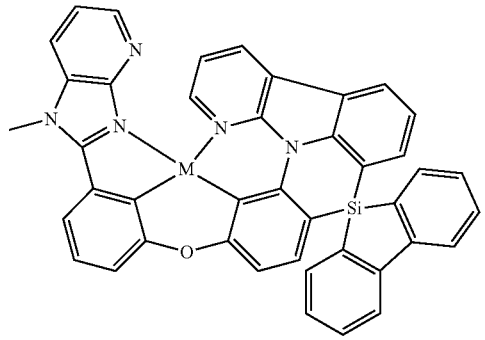

349
-continued
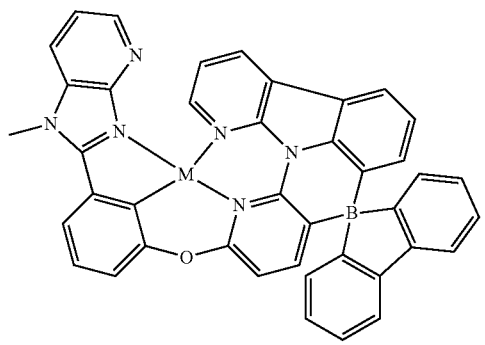
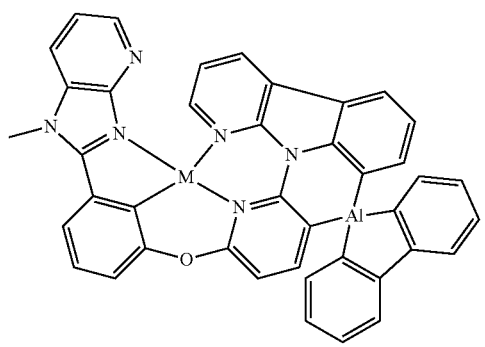
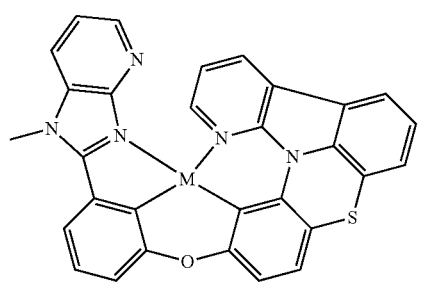
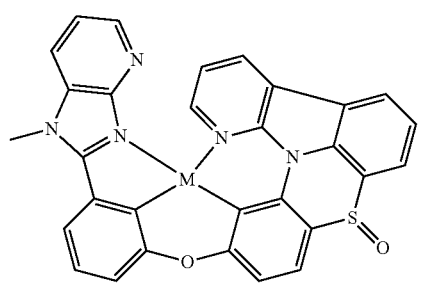
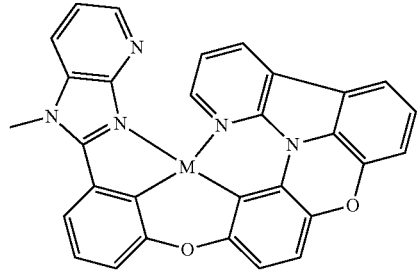
350
-continued
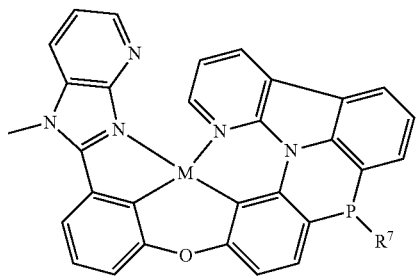
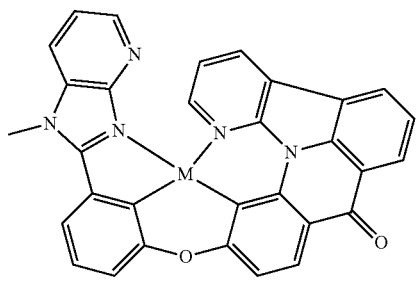
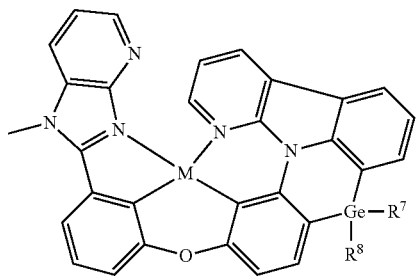
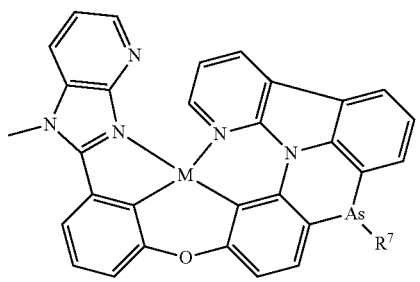
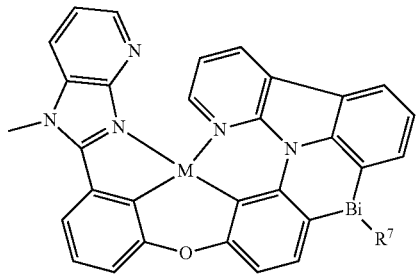
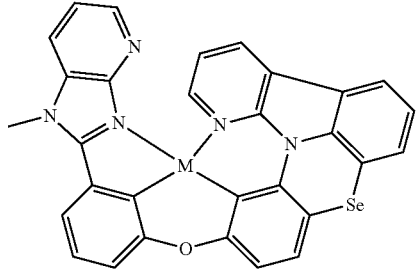

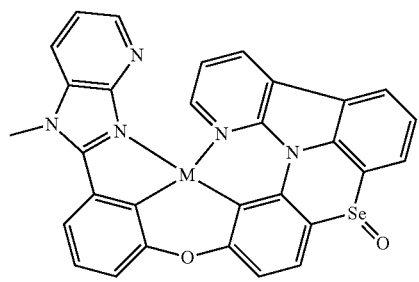
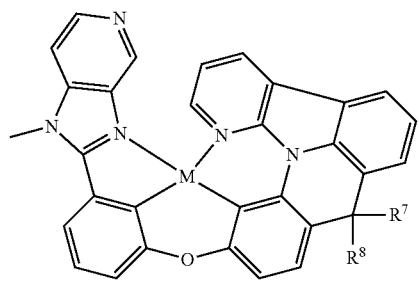
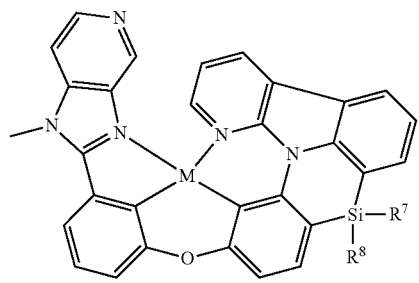
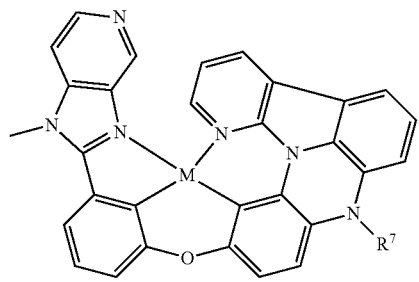
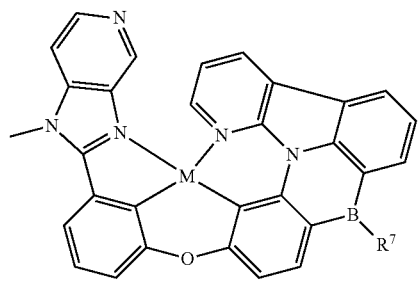
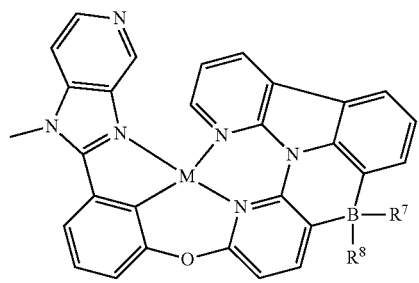
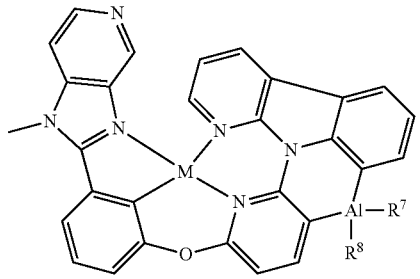
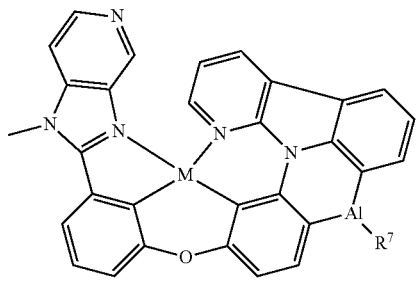
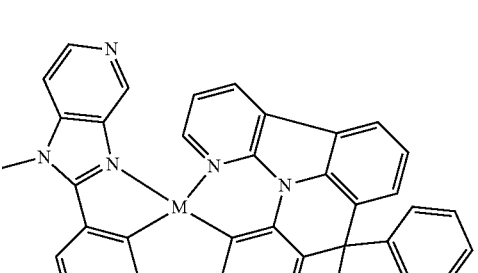
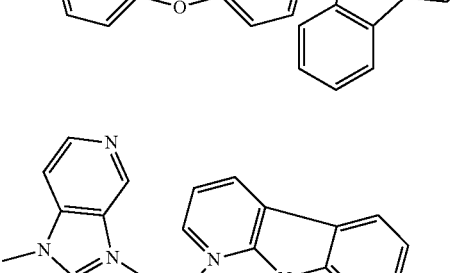
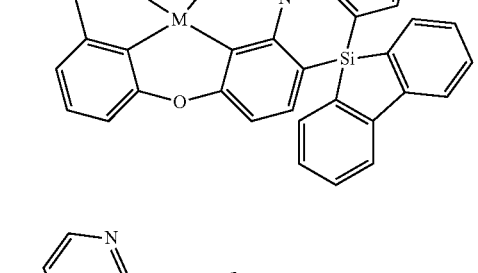
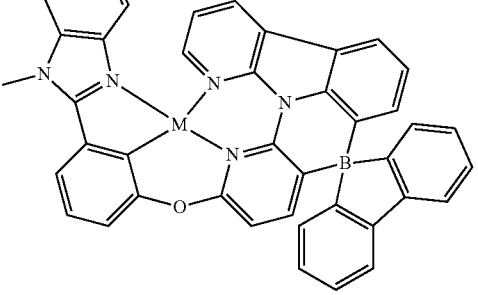

353
-continued
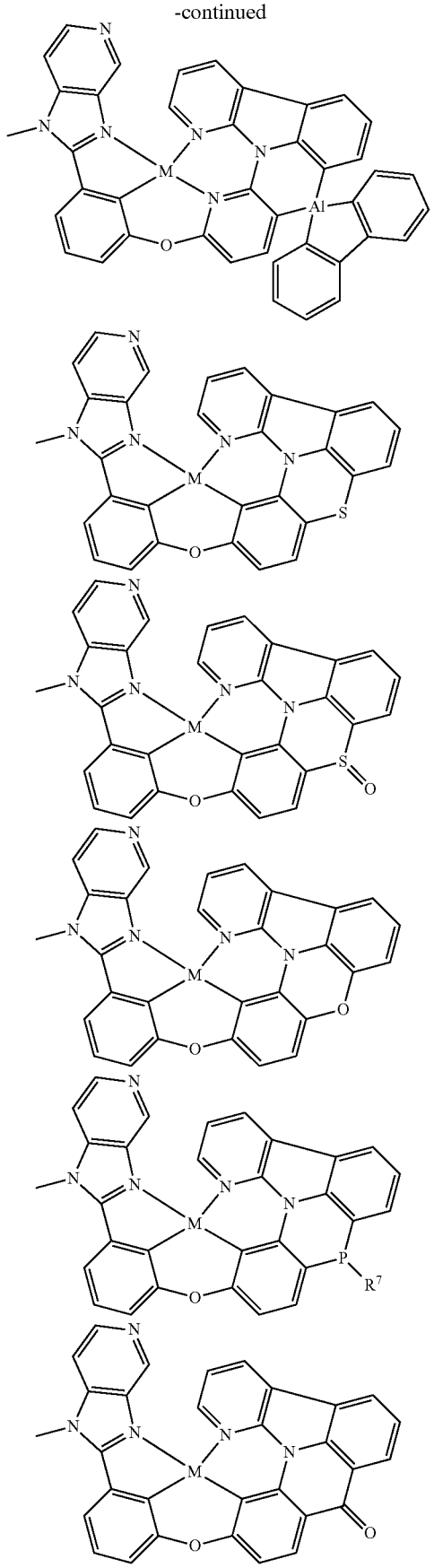
354
-continued
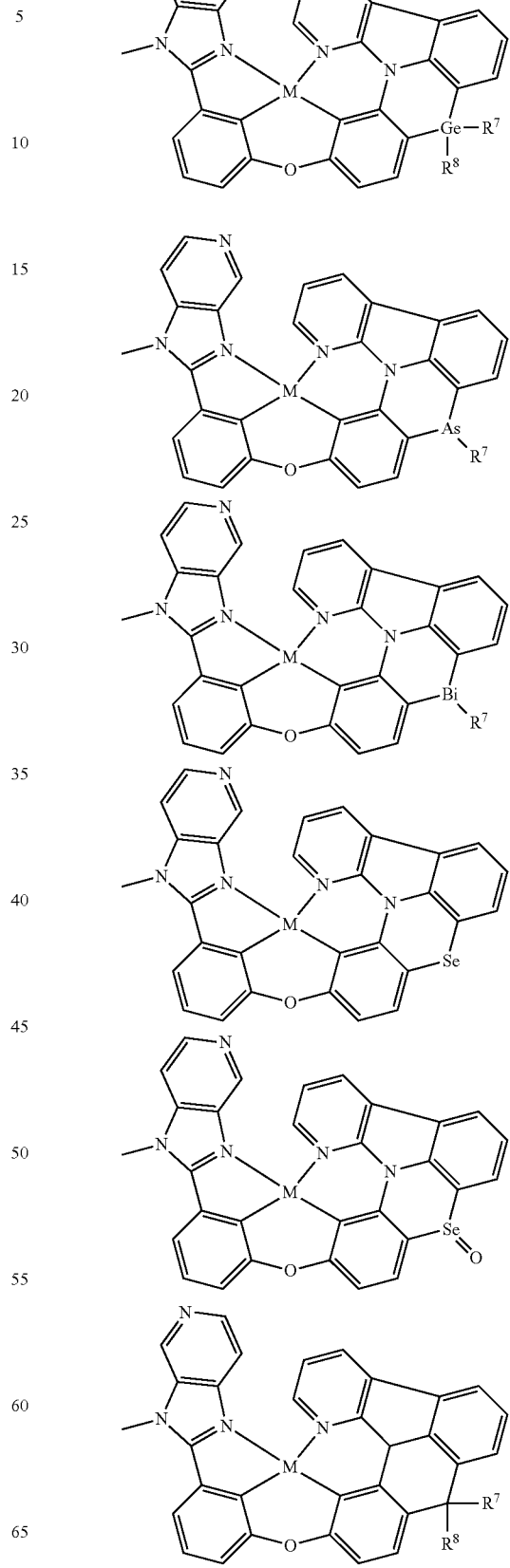

355
-continued
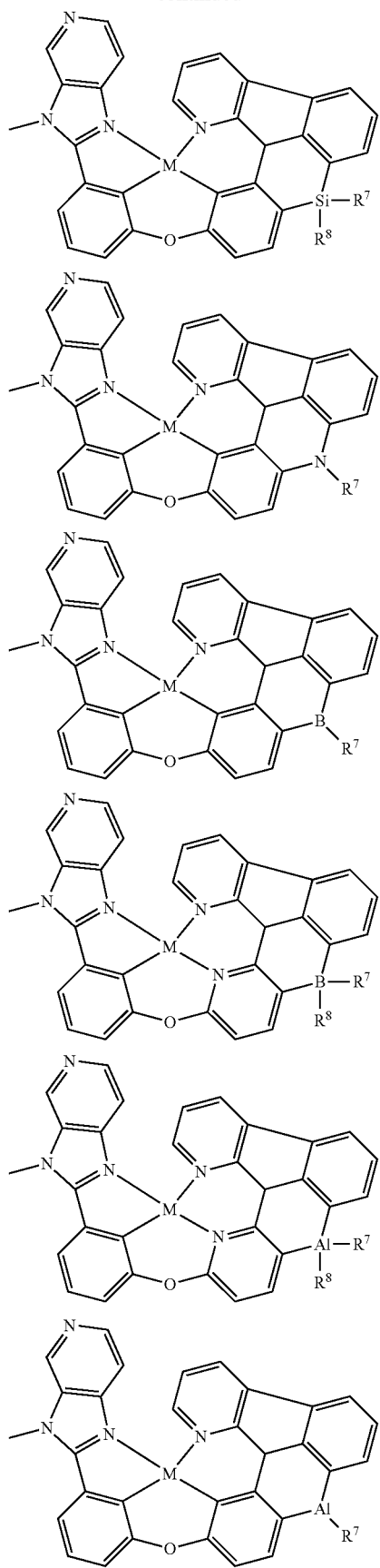
356
-continued
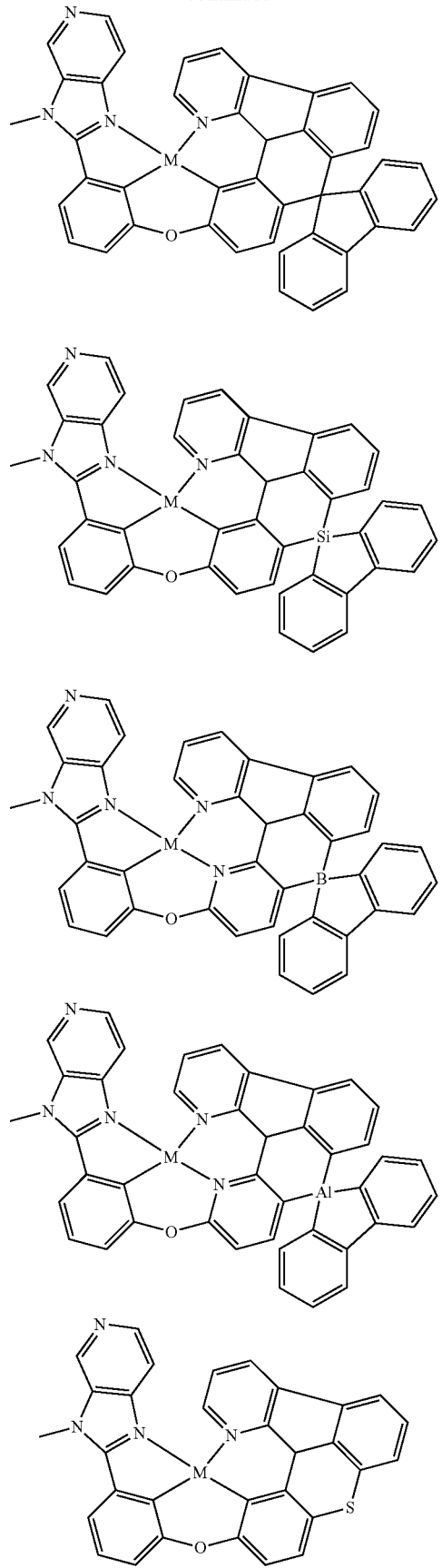

357
-continued
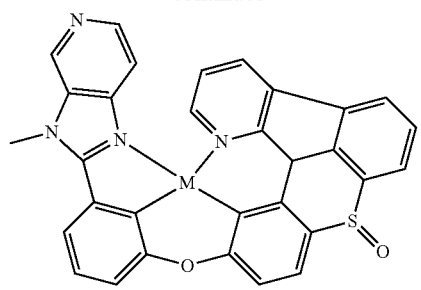
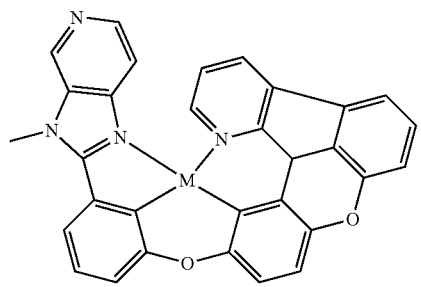
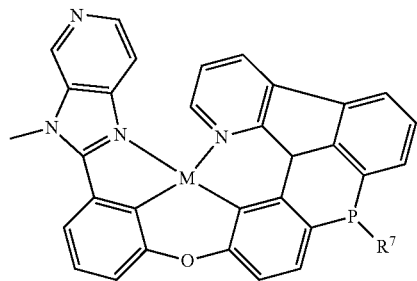
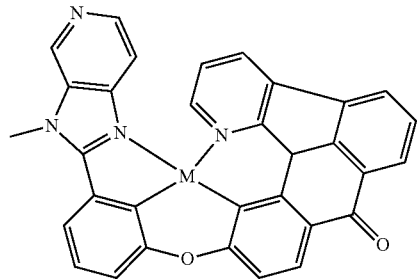
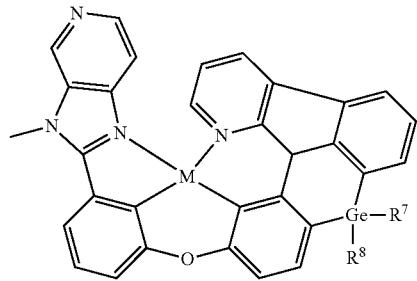
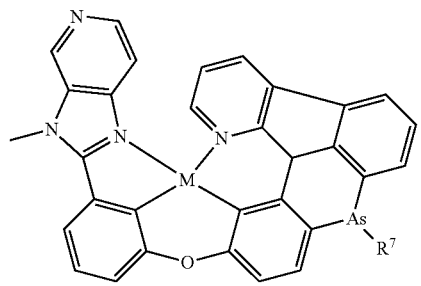
358
-continued
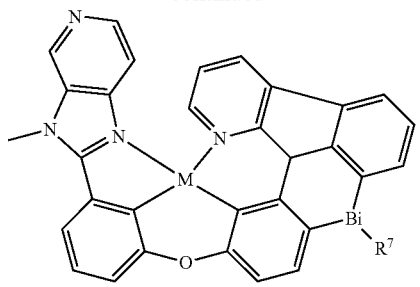
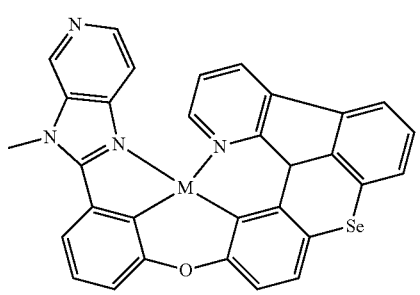
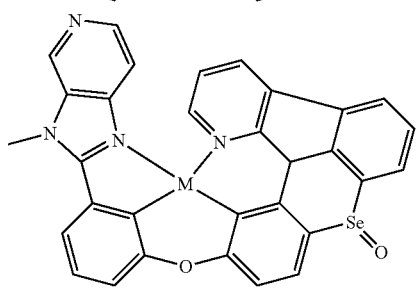
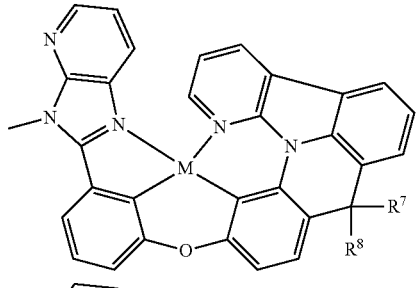
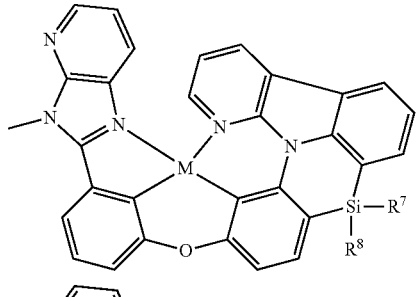
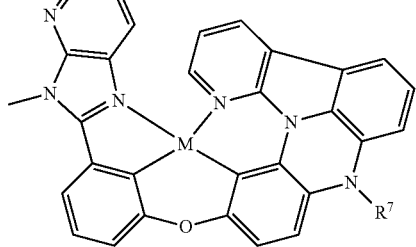

359
-continued
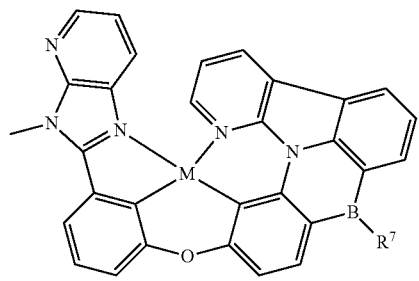
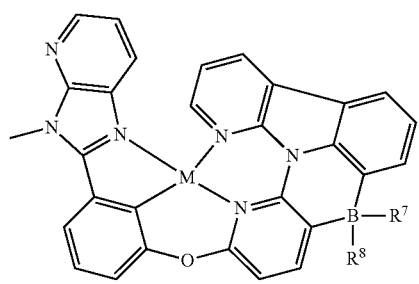
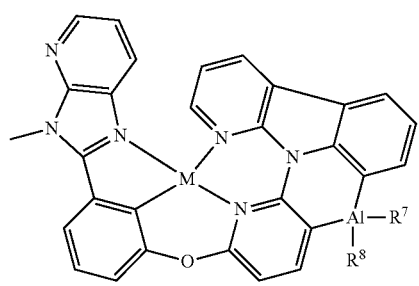
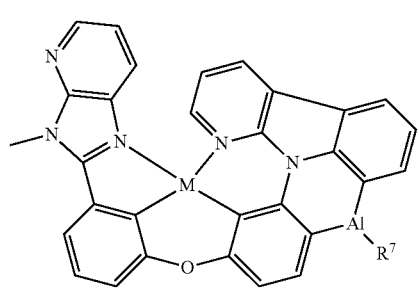
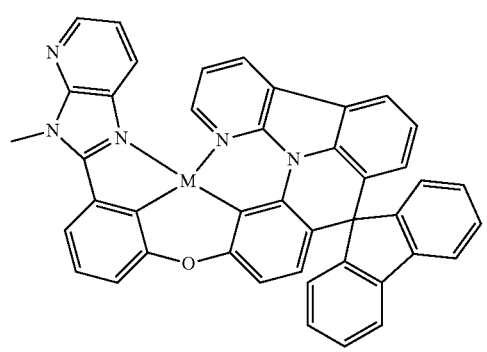
360
-continued
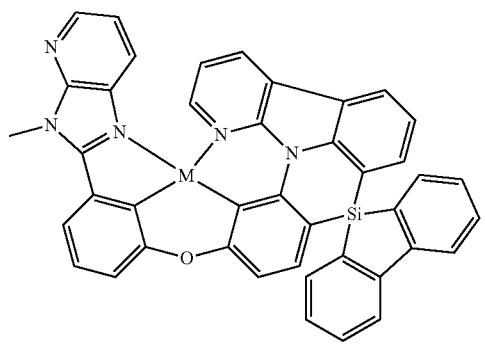
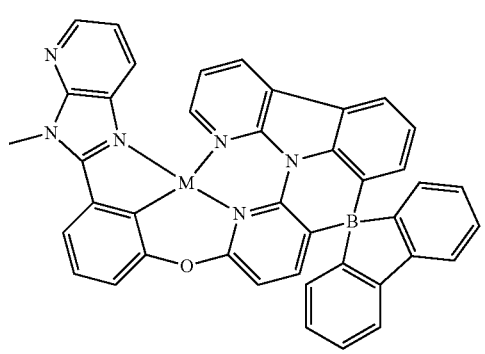
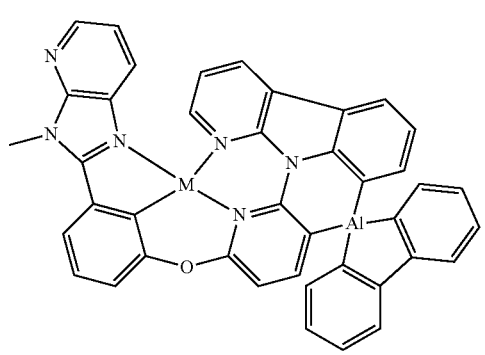
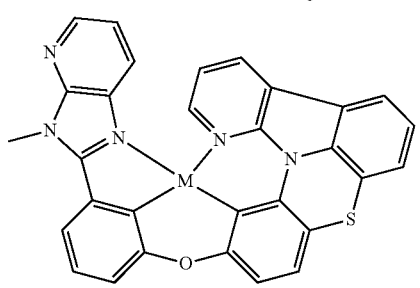
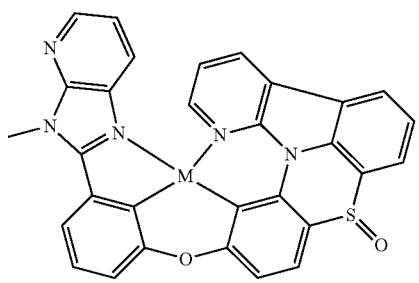

361
-continued
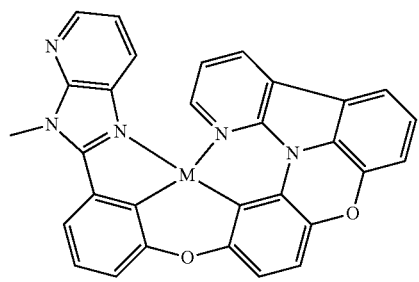
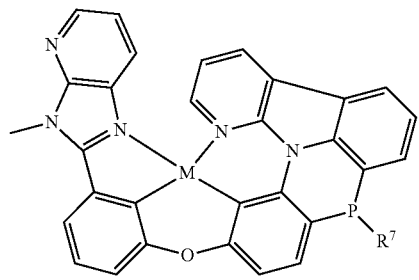
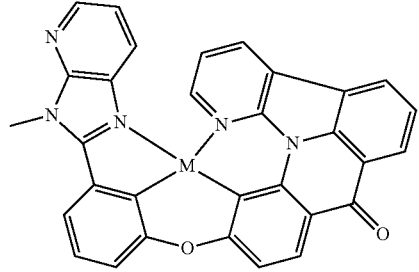
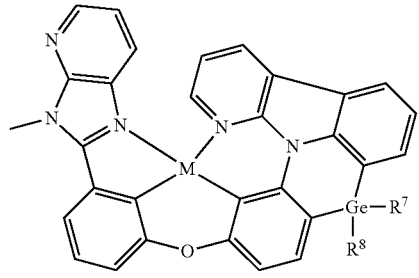
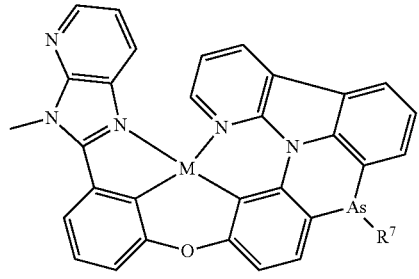
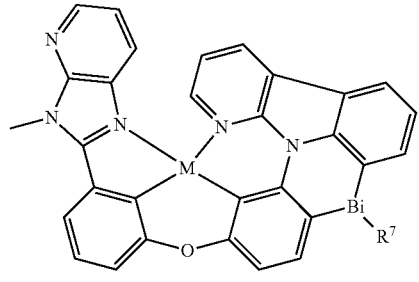
362
-continued
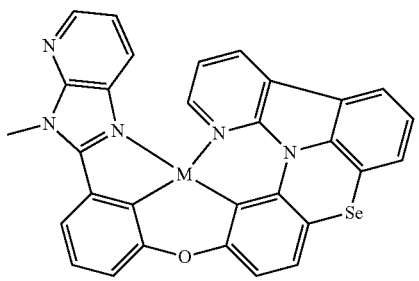
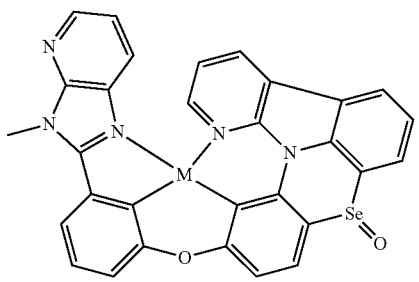
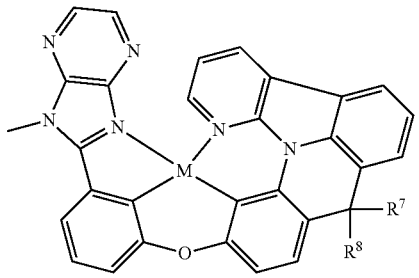
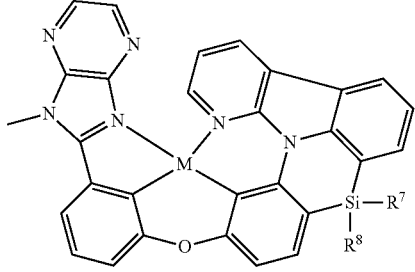
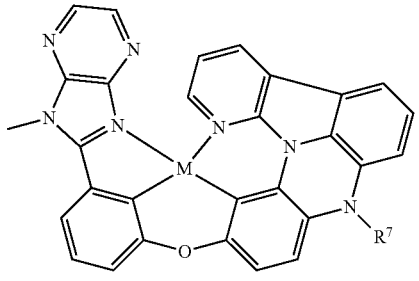
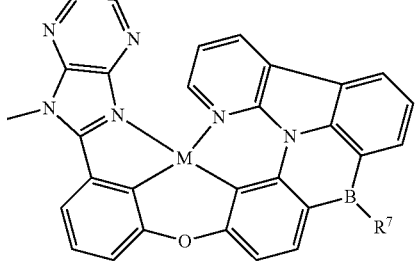

363
-continued
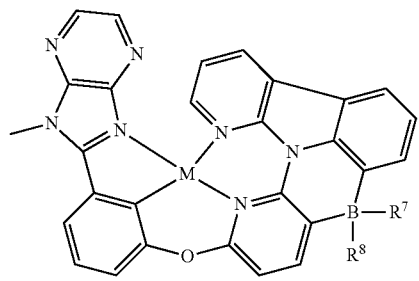
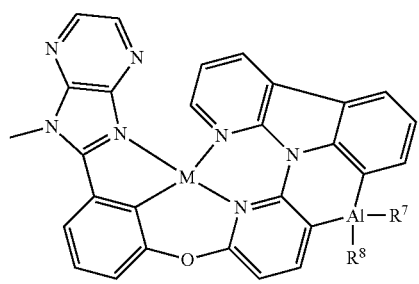
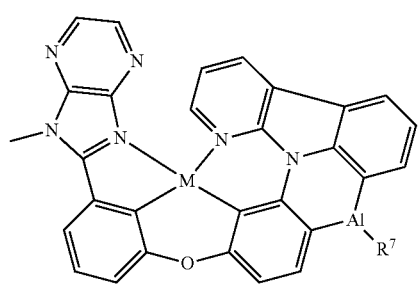
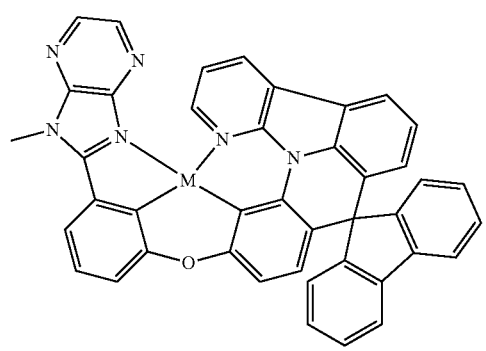
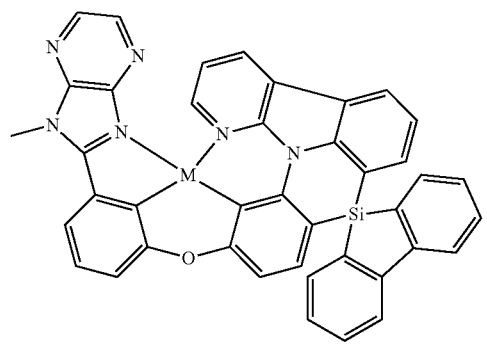
364
-continued
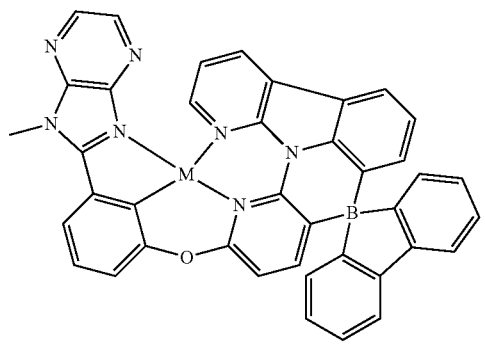
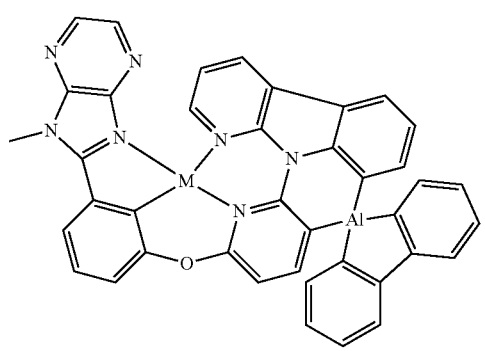
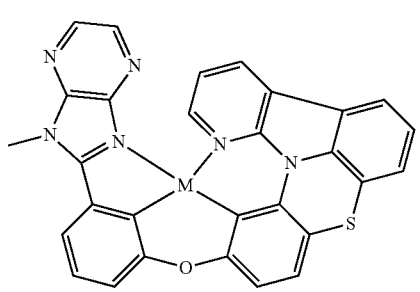
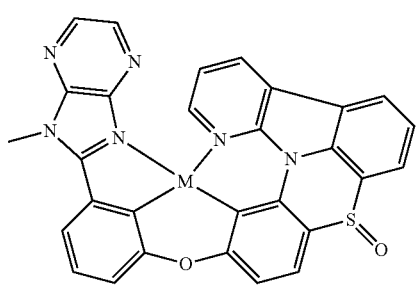
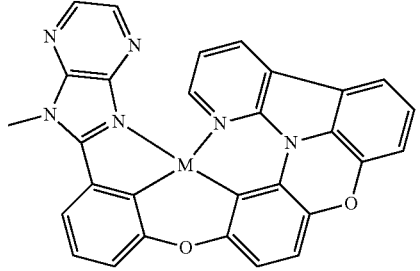

365
-continued
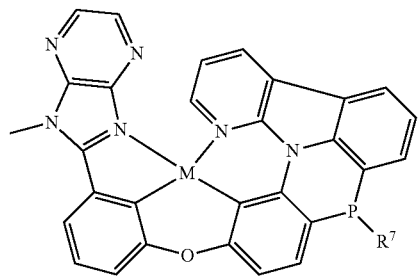
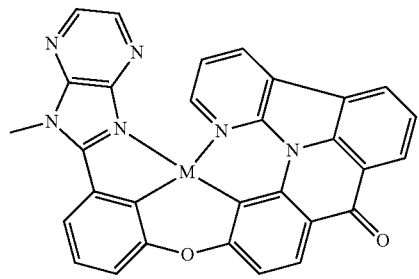
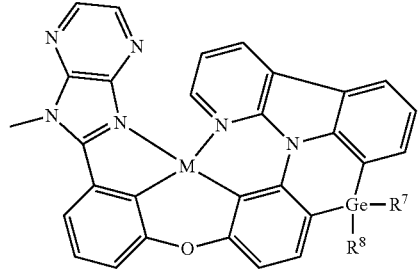
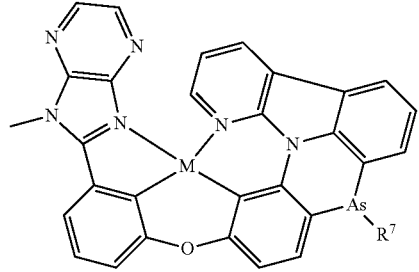
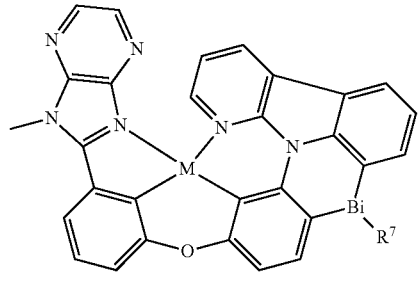
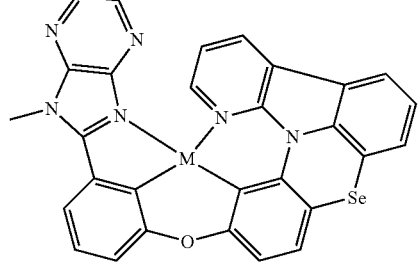
366
-continued
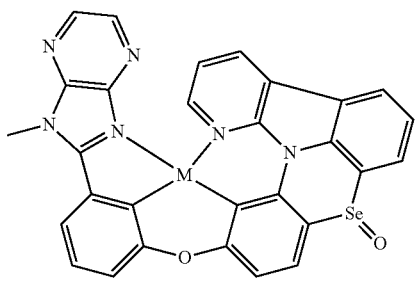
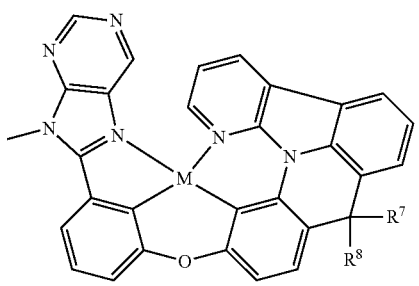
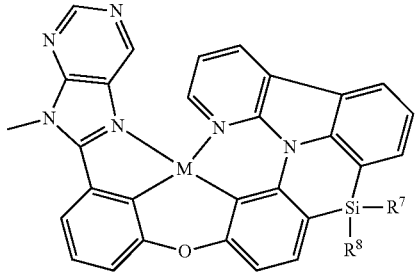
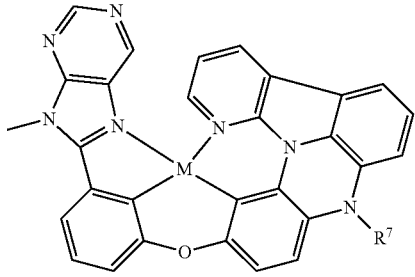
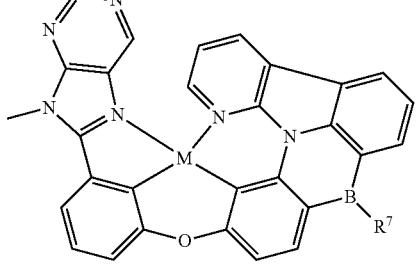
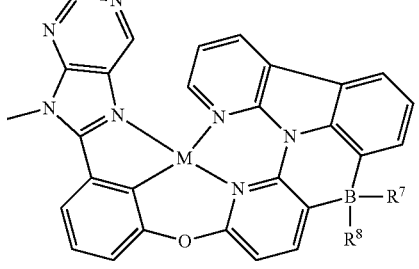

367
-continued
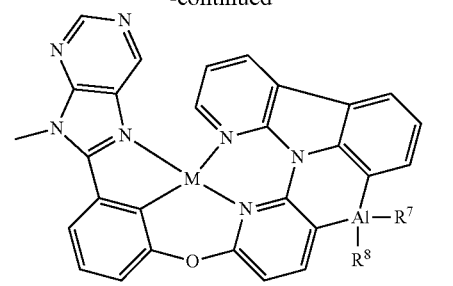
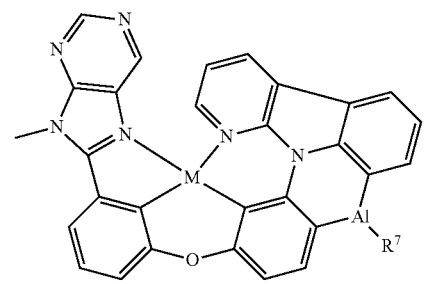
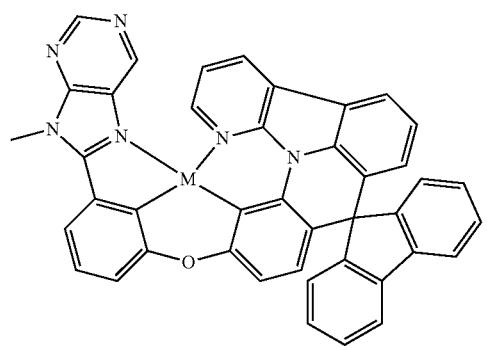
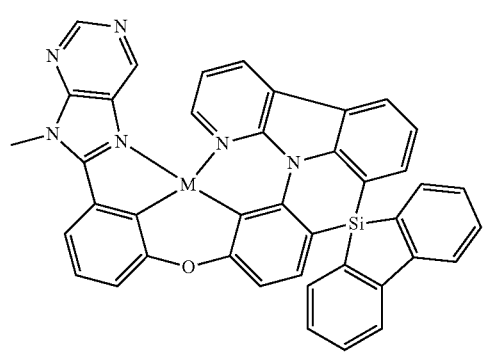
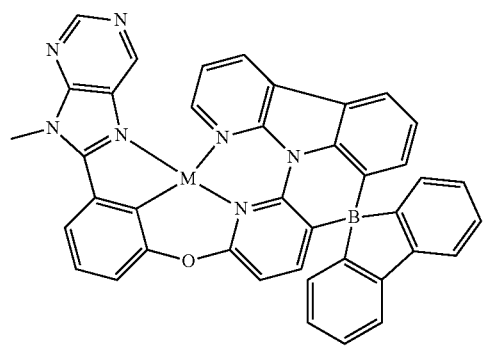
368
-continued
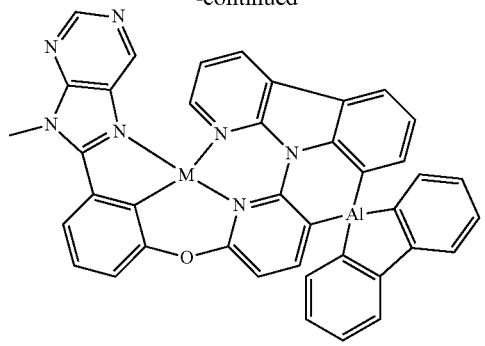
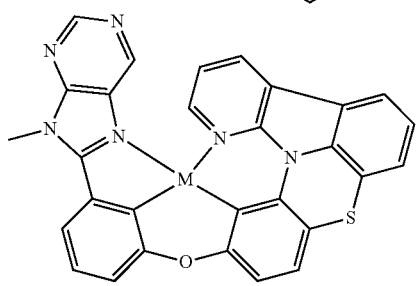
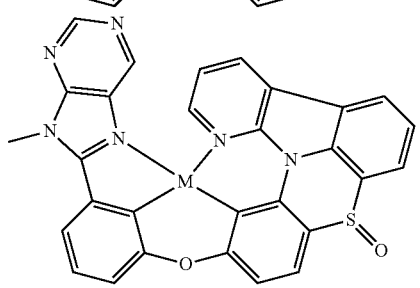
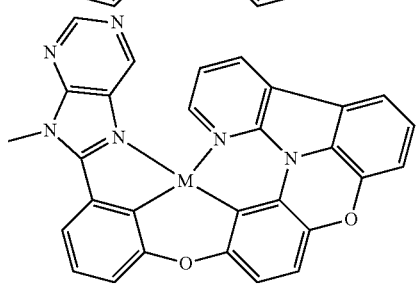
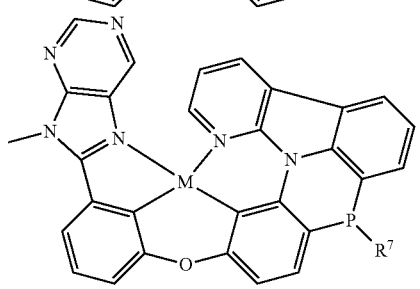
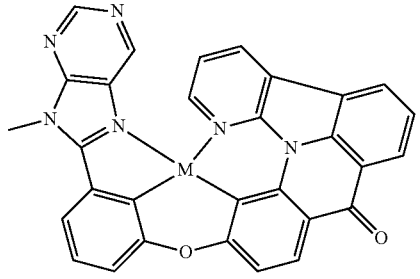

369
-continued
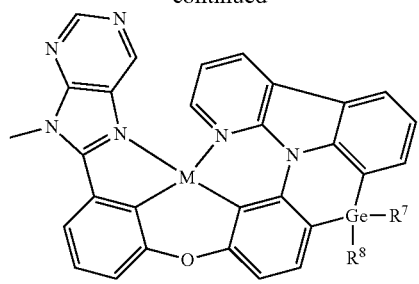
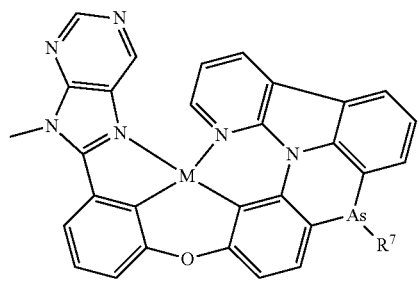
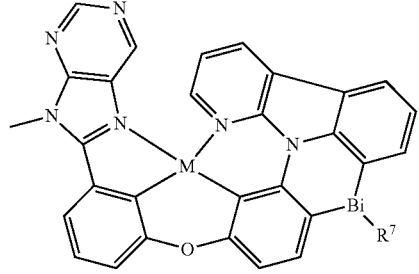
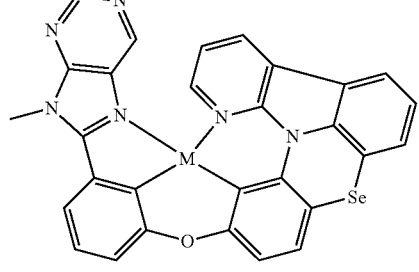
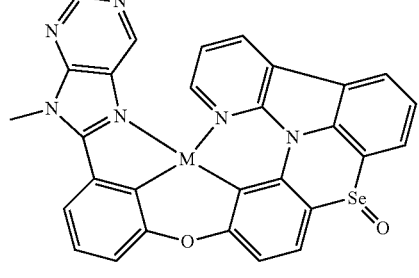
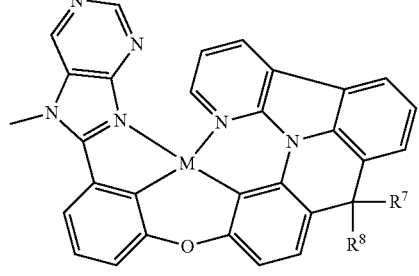
370
-continued
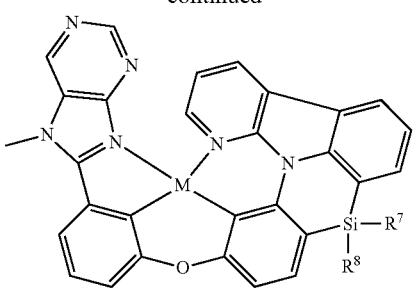
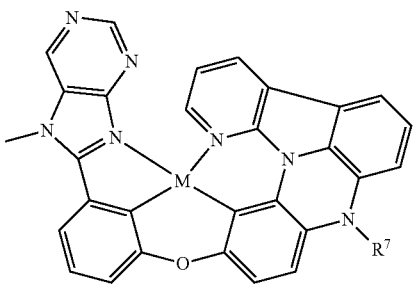
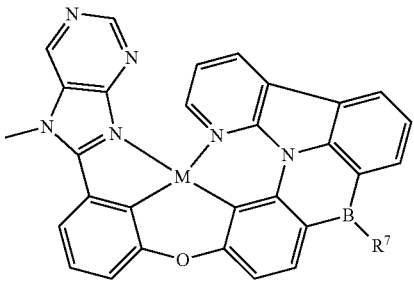
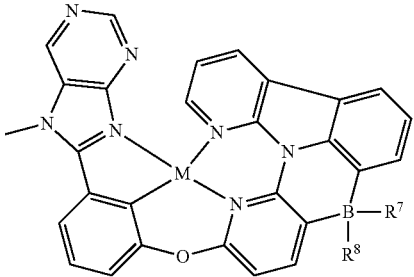
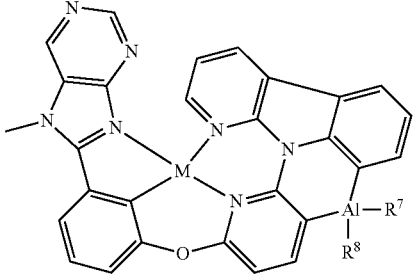
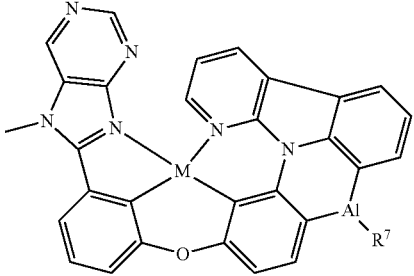

371
-continued
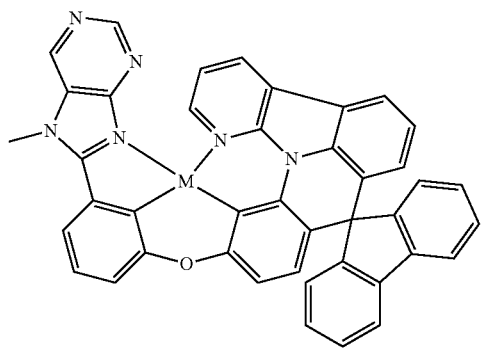
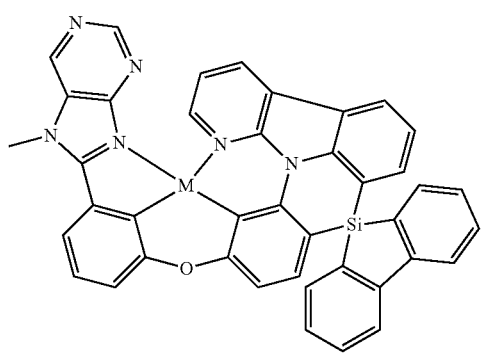
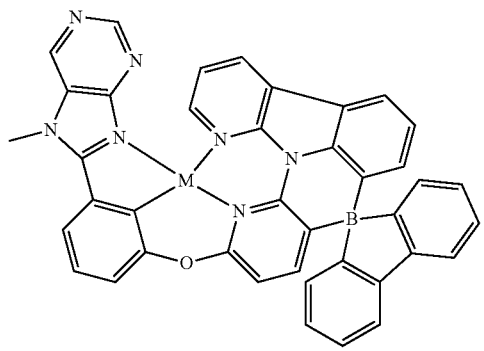
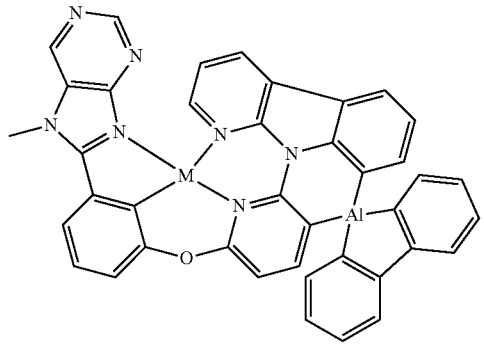
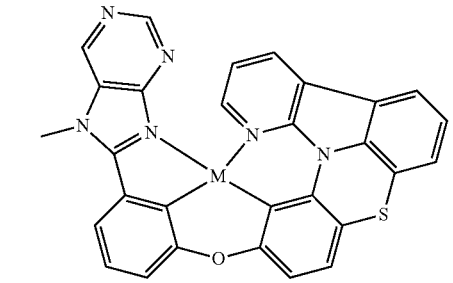
372
-continued
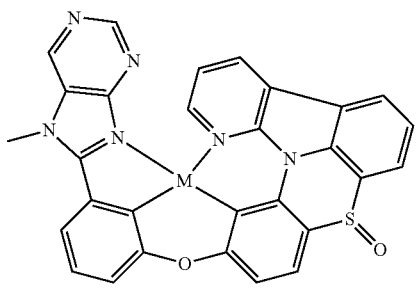
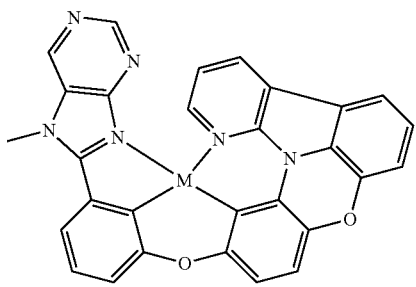
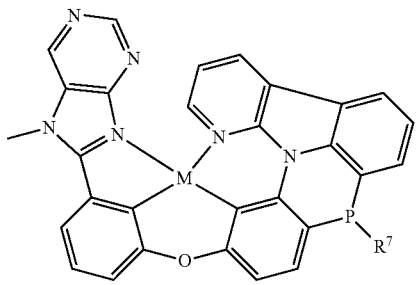
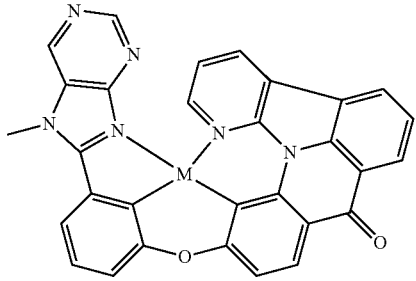
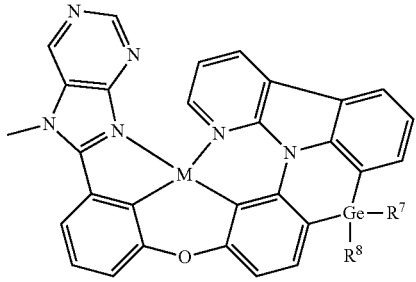
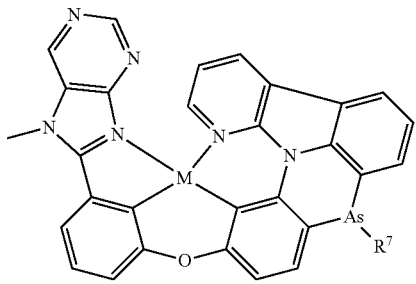

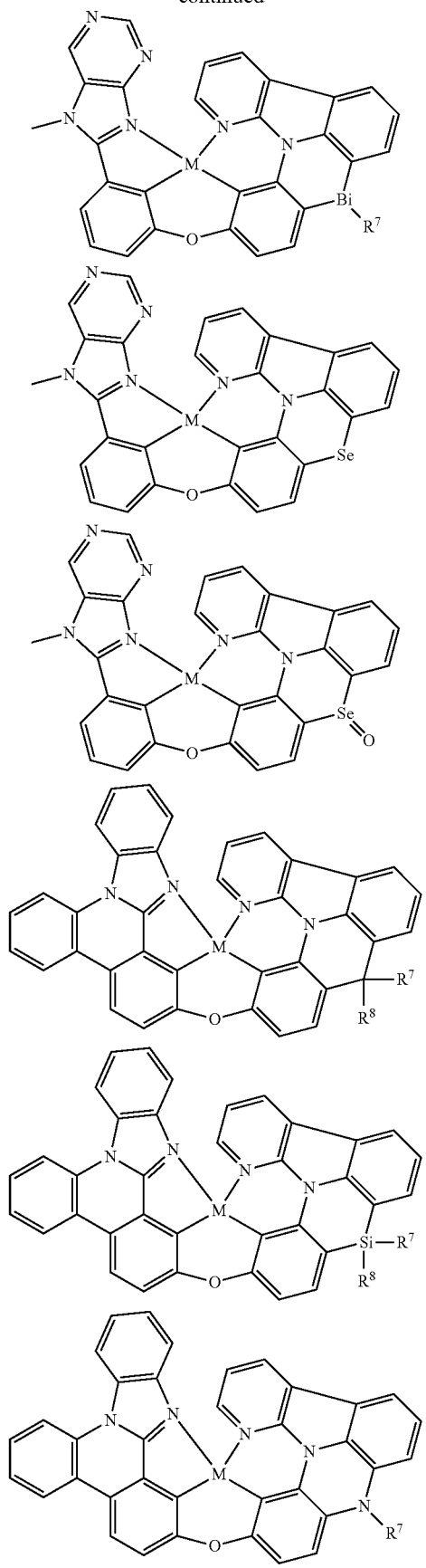
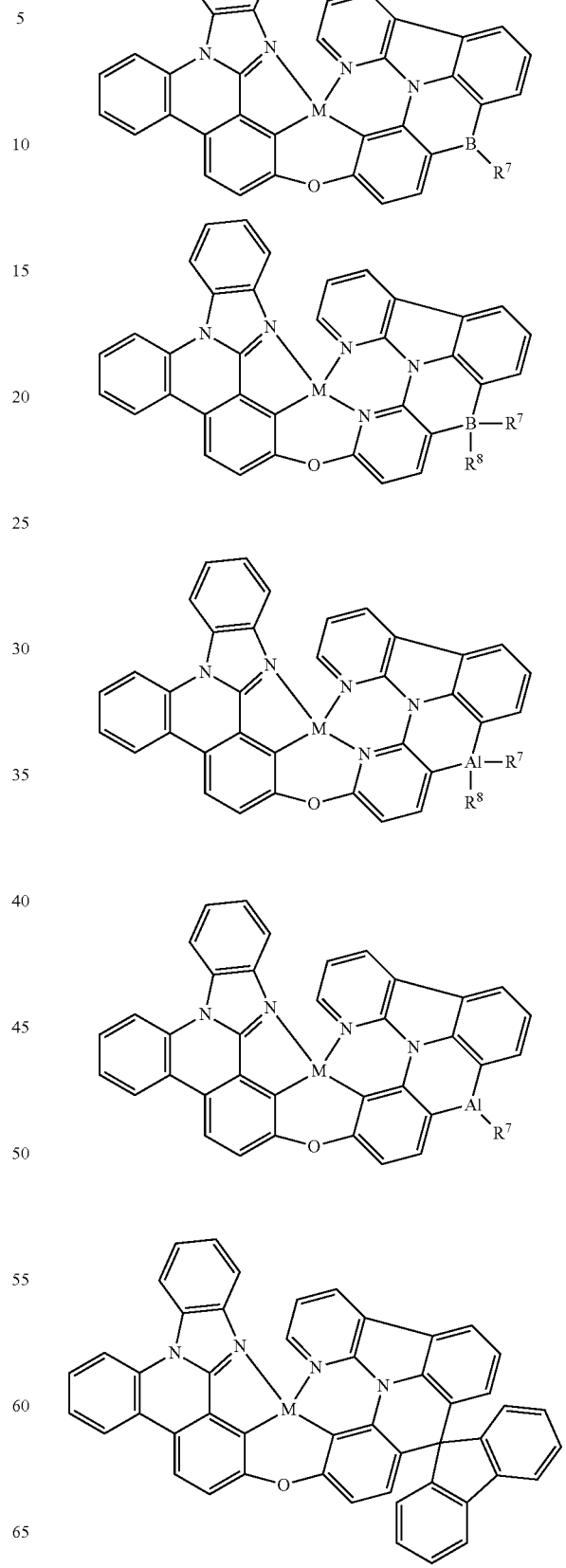

375
-continued
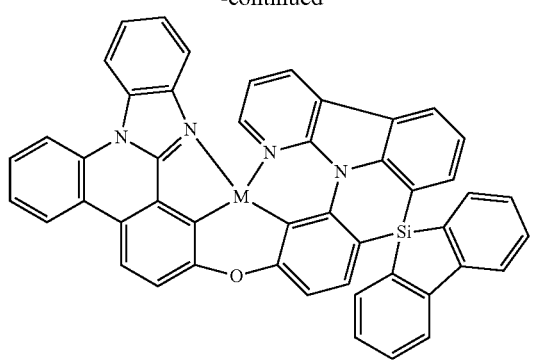
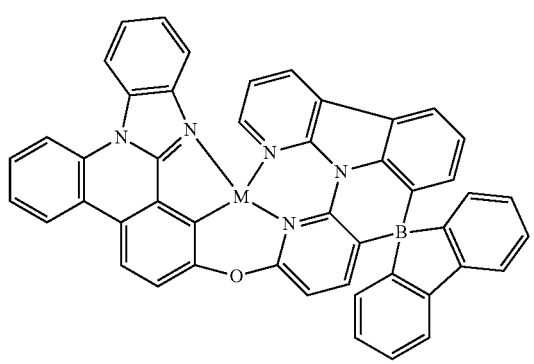
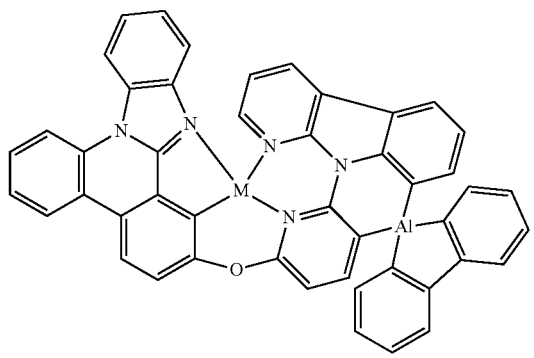
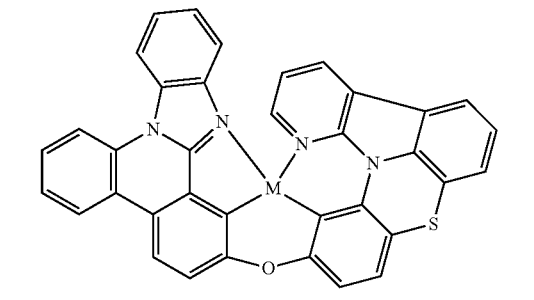
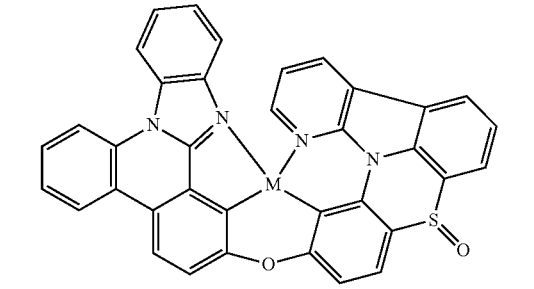
376
-continued
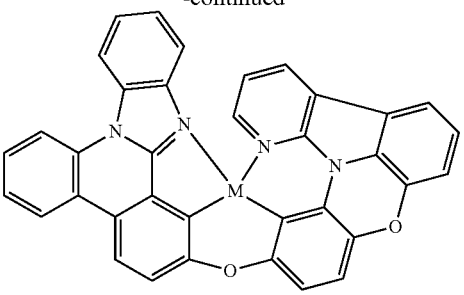
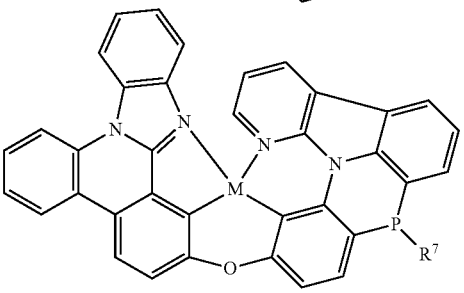
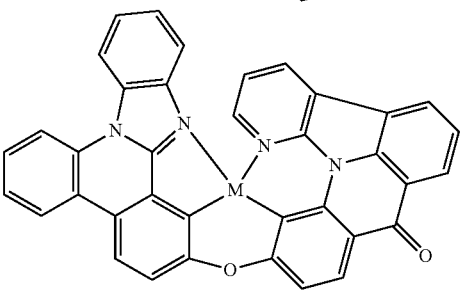
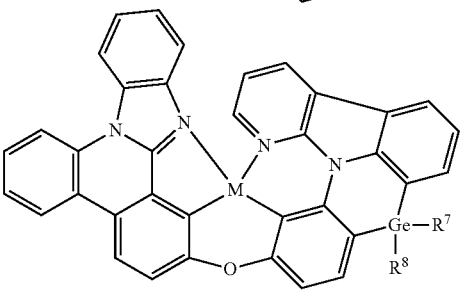
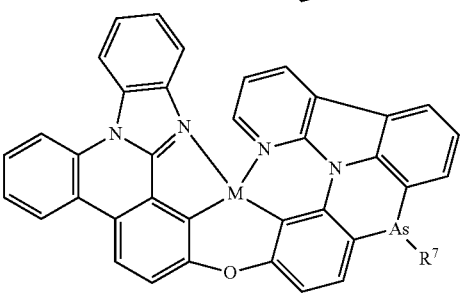
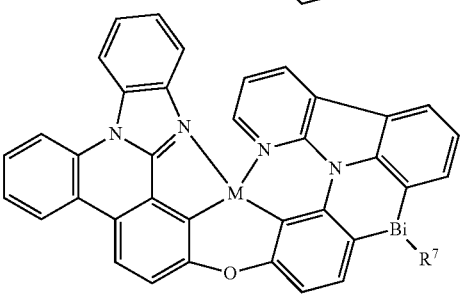

-continued

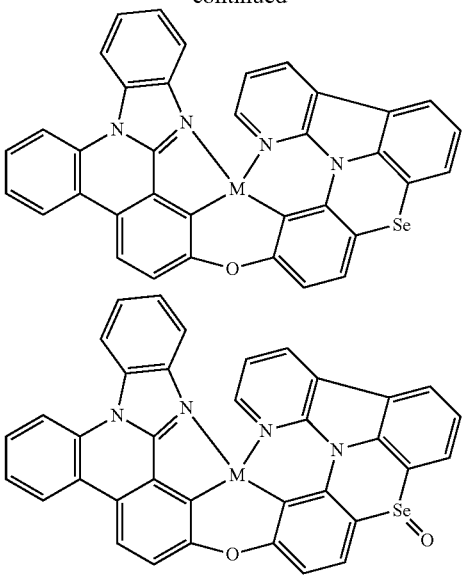

It is to be understood that the present complexes, devices, and/or methods are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of complexes of the present disclosure, example methods and materials are now described.

Disclosed are the components to be used to prepare the compositions of this disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C is disclosed as well as a class of molecules D, E, and F and an example of a combination molecule, A-D is disclosed, then even if each is not individually recited each is individually and collectively contemplated meaning combinations A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods described herein.

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3, 4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein.

Throughout this specification "S(O)" is a short hand notation for S=O. The term "sulfonyl" is used herein to refer to the sulfo-oxo group represented by the formula —S(O)$_2$A$^1$, where Al can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "R$^1$," "R$^2$," "R$^3$,", "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

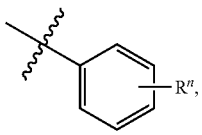

which is understood to be equivalent to a formula:

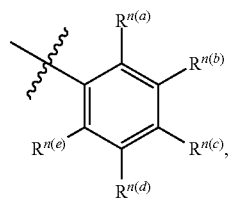

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^n(a)$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include OLEDs, organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Metal complexes of the present disclosure have improved the color purity, enhanced operational stability as well as elimination of the potential intermolecular interaction. The iridium (III) complexes described herein are useful for full color displays and lighting applications.

The complexes disclosed herein are suited for use in a wide variety of devices, including, for example, optical and electro-optical devices, including, for example, photo-absorbing devices such as solar- and photo-sensitive devices, OLEDs, photo-emitting devices, or devices capable of both photo-absorption and emission and as markers for bio-applications.

Also disclosed herein are compositions including one or more complexes disclosed herein. The present disclosure provides light emitting device that include one or more complexes or compositions described herein. The light emitting device can be an OLED (e.g., a phosphorescent OLED device). The present disclosure also provides a photovoltaic device comprising one or more complexes or compositions described herein. Further, the present disclosure also provides a luminescent display device comprising one or more complexes or compositions described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Figure 2:
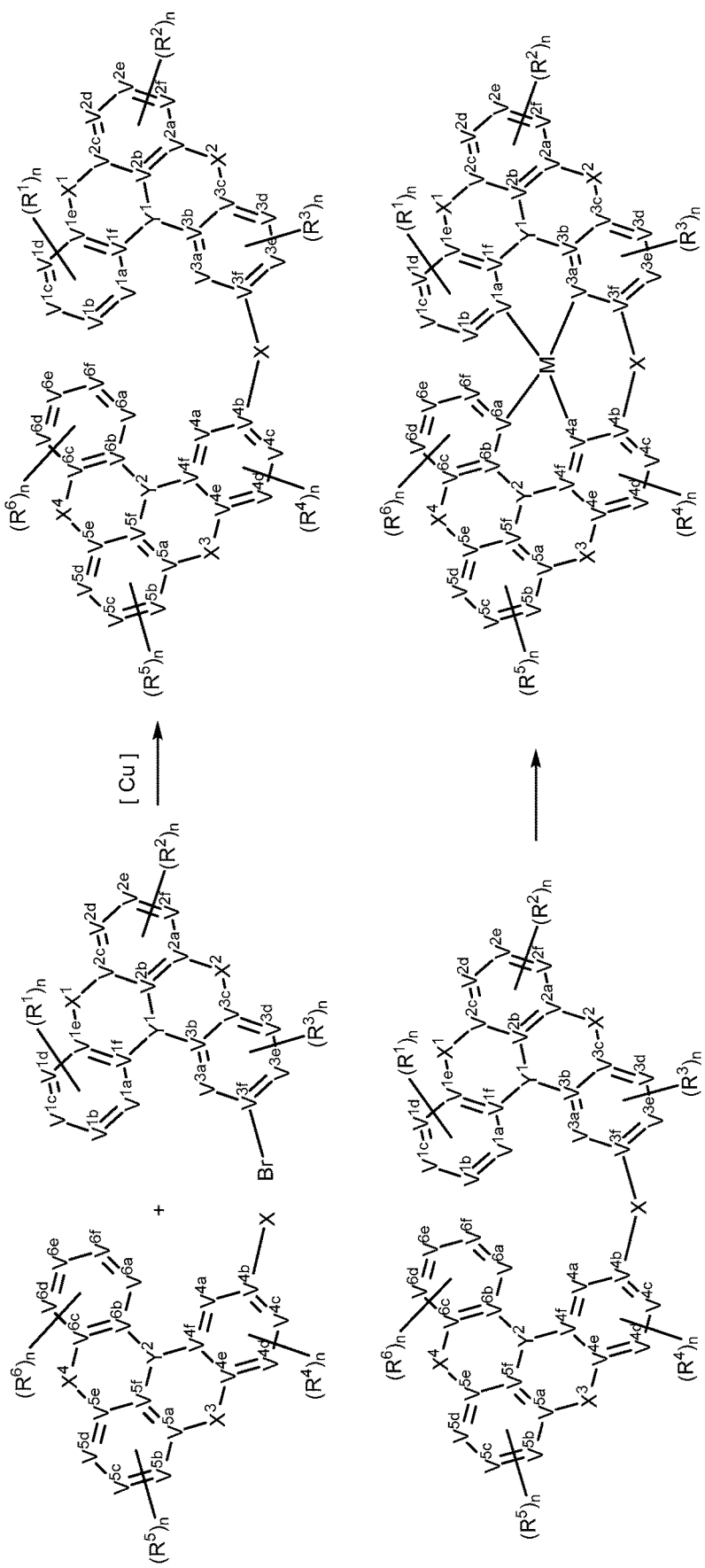
FIG. 2 shows a general synthetic procedure for complexes disclosed herein.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art. FIG. 2 shows a general synthetic procedure for complexes disclosed herein. As shown in FIG. 2, the relevant ligands are synthesized via a copper-catalyzed coupling reaction between brominated pyrido-pyrrolo-acridine and pyrido-pyrrolo-acridine with "X" as a substituent. Refluxing the corresponding ligand and selected metal salt (e.g., platinum or palladium metal salt) in acetic acid yields the desired pyrido-pyrrolo-acridine based complex.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz and 500 MHz on Varian Liquid-State NMR instruments in DMSO-d6 solutions and chemical shifts were referenced to residual protiated solvent. $^1$H NMR spectra were recorded with tetramethylsilane (δ=0.00 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Example 1. Synthesis of PdONac3

Synthesis of 8,8-dimethyl-11-(3-(pyridin-2-yl)phenoxy)-8H pyrido[3',2':4,5]pyrrolo[3,2,1-de]acridine (ONac3 Ligand)

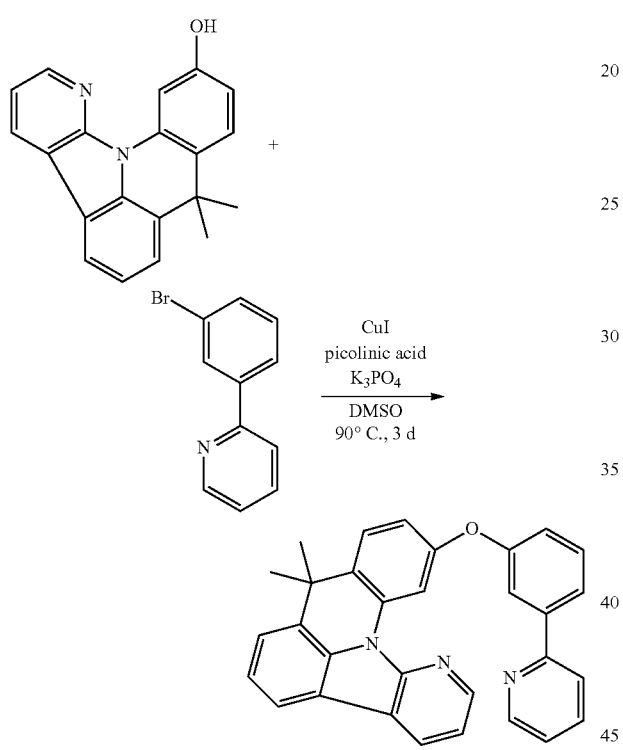

8,8-dimethyl-8H-pyrido[3',2'': 4,5]pyrrolo[3,2,1-de]acridin-11-ol (300.0 mg, 1 m ol, 1.0 eq), 2-(3-bromophenyl)pyridine (281 mg, 1.2 mmol, 1.2 eq), CuI (38 mg, 0.2 mmol, 0.2 eq), picolinic acid (49 mg, 0.4 mmol 0.4 eq) and K$_3$PO$_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (5:1) as and eluent to obtain the desired product Ligand ONac3 as a white solid 290 mg in 64% yield. $^1$H NMR (DMSO-d, 400 MHz) for the Ligand ONac3: δ 9.32 (d, J=2.6 Hz, 1H), 8.66-8.60 (nm, 2H), 8.49 (d, J=4.4 Hz, 1H), 8.06 (d, J=7.8 Hz, 1H), 8.00 (d, J=8.4 Hz, 1H), 7.92-7.82 (m, 3H), 7.75 (d, J=8.5 Hz, 1H), 768 (d, J=8.1 Hz, 1H), 7.54 (t, J=7.9 Hz, 1H), 7.43 (t, J=7.7 Hz, 1H), 7.36 (dd, J=12.3, 7.3 Hz, 2H), 7.19 (dd, J=7.6, 1.6 Hz, 1H), 6.88 (dd, J=8.5, 2.4 Hz, 1H), 1.73 (s, 5H).

Synthesis of PdONac3

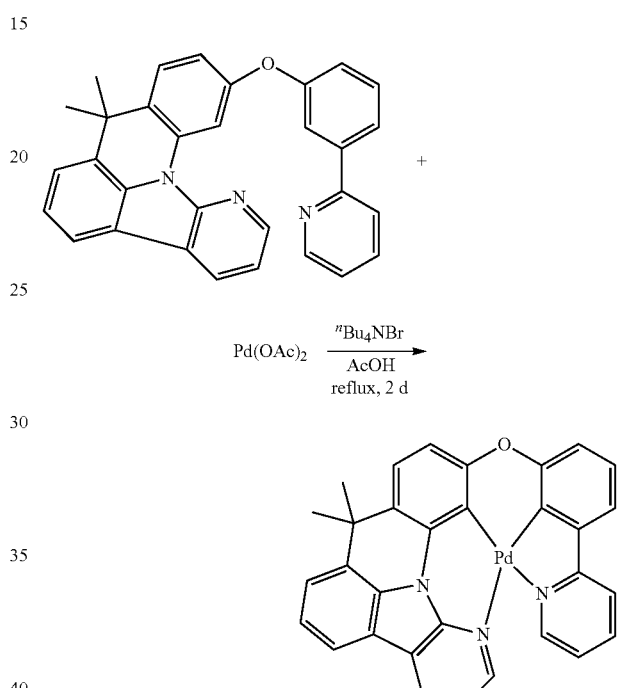

Figure 3:
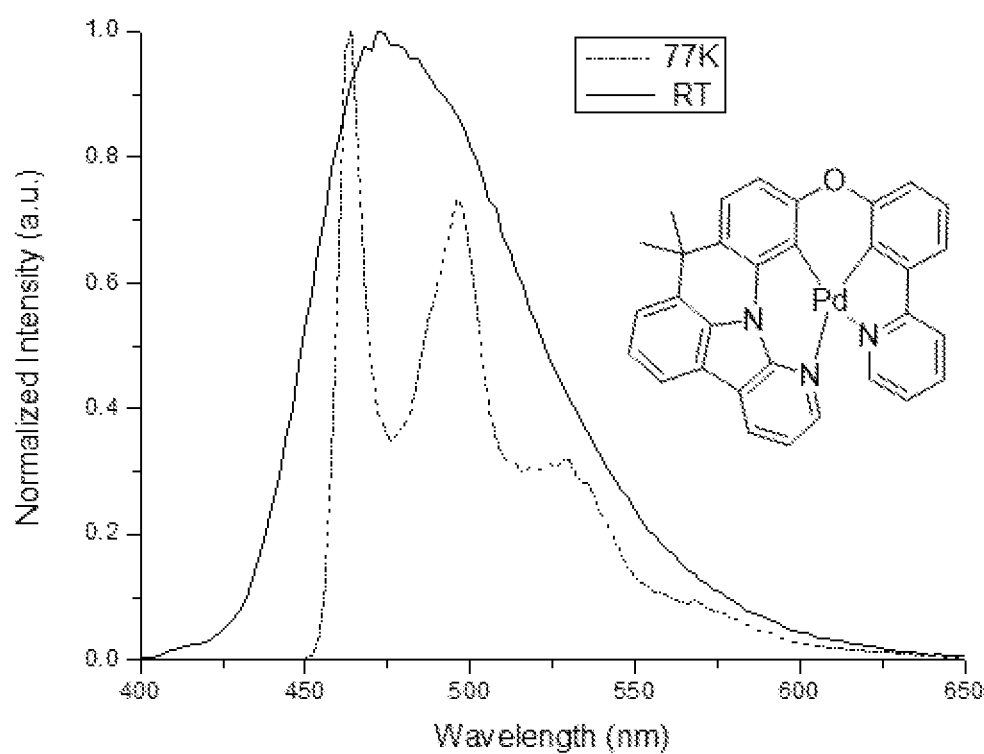
FIG. 3 shows emission spectra of PdONac3 in CH₂Cl₂ at room temperature and in tetrahydro-2-methylfuran at 77K.

8,8-dimethyl-1-(3-(pyridin-2-yl)phenoxy)-8H-pyrido[3',2':4,5]pyrrolo[3,2,1-de]acridine (91 mg, 0.20 mmol, 1.0 eq), Pd(OAc)$_2$ (54 mg, 0.24 mmol, 1.2 eq) and n-Bu$_4$NBr (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product, PdONac3 as a white solid 46 mg in 40% yield. $^1$H NMR (400 MHz, d6-DMSO): δ 8.90 (dd, J=7.5, 1.2 Hz, 1H), 8.76 (dd, J=5.6, 1.4 Hz, 1H), 8.45 (dd, J=5.2, 1.3 Hz, 1H), 8.24-8.14 (m, 2H), 8.06 (td, J=7.9, 1.5 Hz, 1H), 7.74 (d, J=7.6 Hz, 1H), 7.67 (d, J=6.7 Hz, 1H), 7.62 (dd, J=7.5, 5.6 Hz, 1H), 7.55-7.39 (m, 3H), 7.22 (t, J=7.6 Hz, 1H), 7.05 (d, J=8.3 Hz, 2H), 1.69 (s, 6H). FIG. 3 shows an emission spectrum of PdONac3 in CH$_2$Cl$_2$ at room temperature and in tetrahydro-2-methylfuran at 77K.

Example 2. Synthesis of PtNacONac

Synthesis of 11,11'-oxybis(8,8-dimethyl-8H-pyrido[3',2':4,5]pyrrolo[3,2,1-de]acridine) (NacONac Ligand)

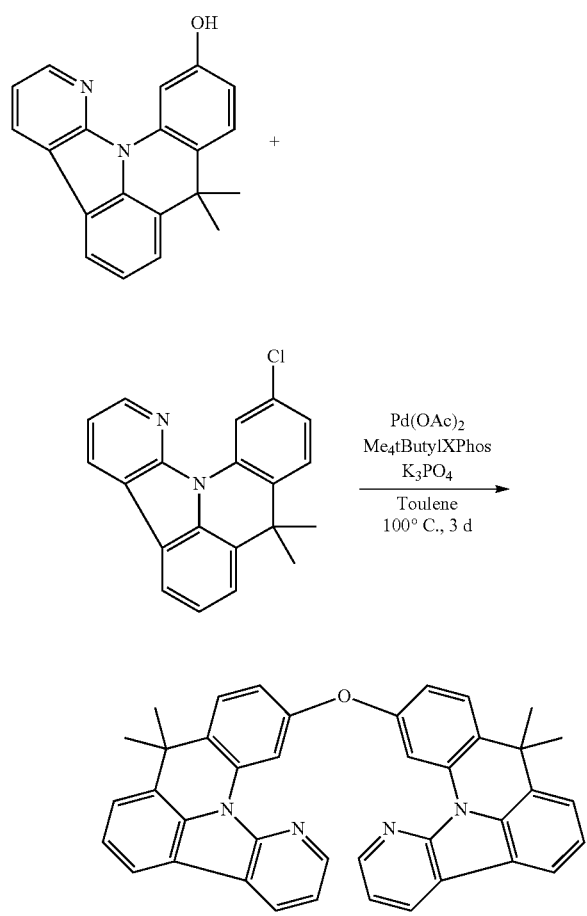

8,8-dimethyl-8H-pyrido[3',2':4,5]pyrrolo[3,2,1-de]acridin-11-ol (300 mg, 1 mmol, 1.0 eq), 11-chloro-8,8-dimethyl-8H-pyrido[3',2':4,5]pyrrolo[3,2,1-de]acridine (351 mg, 1.1 mmol, 1.1 eq), Pd(OAc)$_2$ (45 mg, 0.2 mmol, 0.2 eq), 2-Di-t-butylphosphino-3,4,5,6-tetramethyl-2',4',6'-triisopropylbiphenyl (144 mg, 0.3 mmol, 0.3 eq) and K$_3$PO$_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent toulene (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (5:1) as and eluent to obtain the desired product Ligand NacONac as a white solid 239 mg in 41% yield. $^1$H NMR (DMSO-d6, 400 MHz) for the Ligand NacONac: δ 9.30 (d, J=2.6 Hz, 2H), 8.59 (dd, J=7.7, 1.6 Hz, 2H), 8.42 (dd, J=4.8, 1.7 Hz, 2H), 8.03 (d, J=7.7 Hz, 2H), 7.74 (d, J=8.7 Hz, 2H), 7.65 (d, J=7.6 Hz, 2H), 7.42-7.37 (m, 2H), 7.31 (dd, J=7.8, 4.9 Hz, 2H). 6.91 (dd, J=8.6, 2.6 Hz, 2H), 1.71 (s, 12H).

Synthesis of PtNacONac

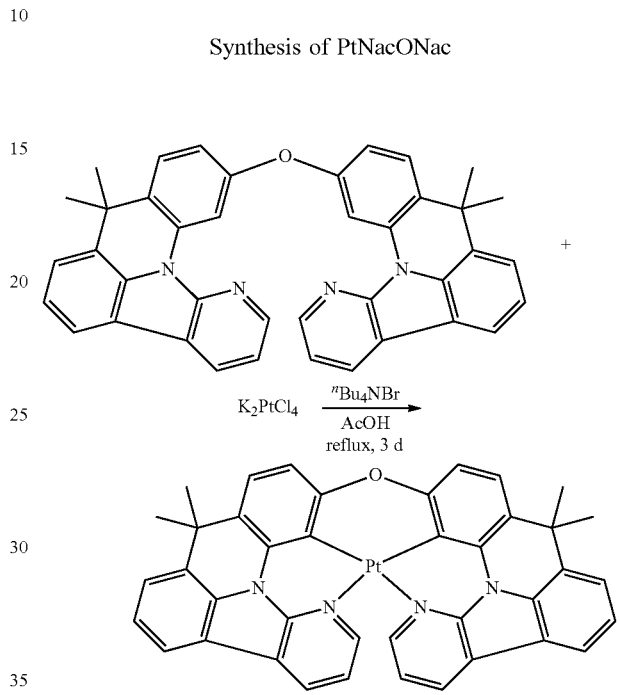

Figure 4:
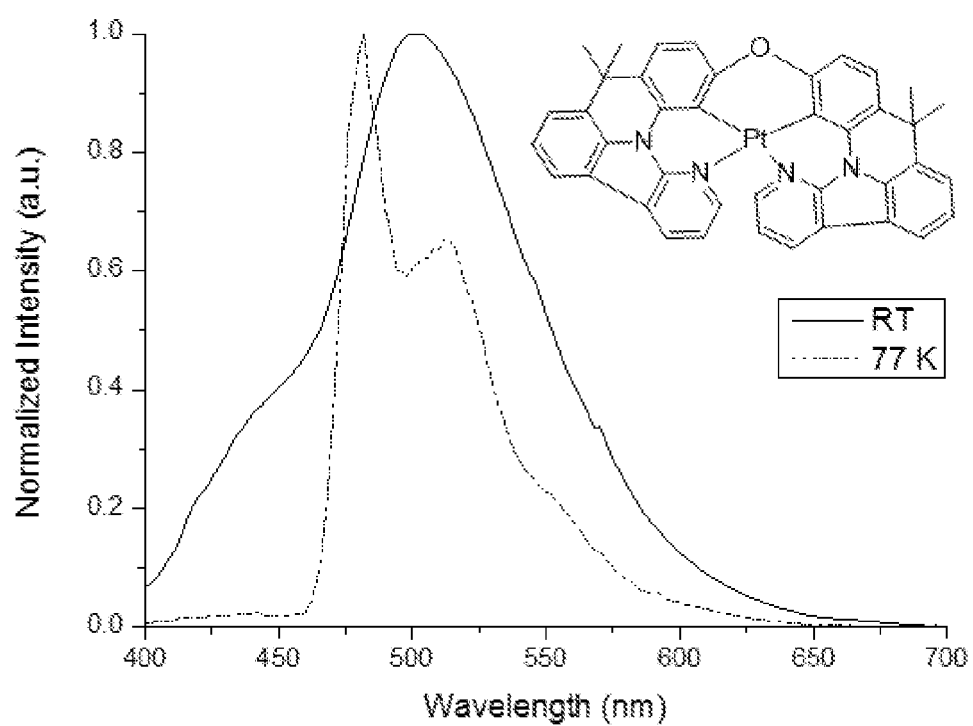
FIG. 4 shows emission spectra of PtNacONac in CH₂Cl₂ at room temperature and in tetrahydro-2-methylfuran at 77K.

11,11'-oxybis(8,8-dimethyl-8H-pyrido[3',2':4,5]pyrrolo[3,2,1-de]acridine) (58 mg, 0.1 mmol, 1.0 eq), K$_2$PtCl$_4$ (50 mg, 0.12 mmol, 1.2 eq) and n-Bu$_4$NBr (3.2 mg, 0.01 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 3 days, cooled to ambient temperature and removed the solvent. Then the solid was purified through column chromatography on silica gel using dichloromethane as eluent to obtain to obtain the desired product, PtNacONac as a yellow solid 46 mg in 59% yield. $^1$H NMR (500 MHz, d6-DMSO): δ 8.92 (dd, J=7.6, 0.9 Hz, 2H), 8.26 (dd, J=6.0, 1.0 Hz, 2H), 8.20 (dd, J=7.9, 0.7 Hz, 2H), 7.79 (dd, J=7.8, 0.6 Hz, 2H), 7.58-7.52 (m, 2H), 7.47 (d, J=8.6 Hz, 2H), 7.37 (dd, J=7.6, 5.6 Hz, 2H), 6.98 (d, J=8.5 Hz, 2H), 1.76 (s, 12H). FIG. 4 shows an emission spectrum of PtNacONac in CH$_2$Cl$_2$ at room temperature and in tetrahydro-2-methylfuran at 77K.

A number of embodiments have been described. Nevertheless, it will be understood that various modifications may be made without departing from the spirit and scope of disclosure. Accordingly, other embodiments are within the scope of the following claims.

What is claimed is:

1. A complex of General Formula IV:

General Formula IV

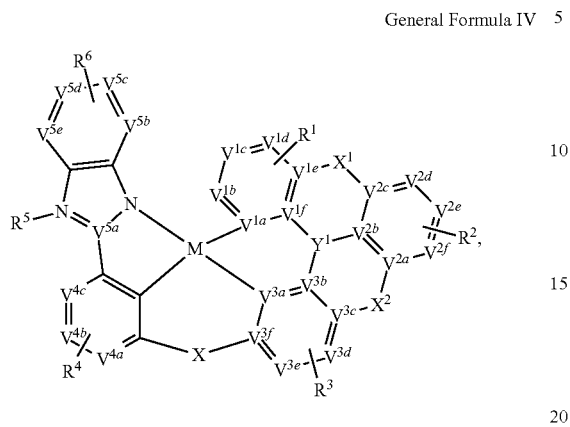

wherein:

M is Pt (II) or Pd (II);

each of $V^{1a}$-$V^{1f}$, $V^{2a}$-$V^{2f}$, $V^{3a}$-$V^{3f}$, $V^{4a}$-$V^{4c}$, and $V^{5a}$-$V^{5e}$ is independently N, C, P, O, S or Si;

each of X, $X^1$, and $X^2$ is independently present or absent, and each X, $X^1$, and $X^2$ present independently represents a single bond, $CR^7R^8$, C=O, $SiR^7R^8$, $GeR^7R^8$, $NR^7$, $PR^7$, $PR^7R^8$, $R^7P$=O, $AsR^7$, $R^7As$=O, O, S, S=O, $SO_2$, Se, Se=O, $SeO_2$, $BR^7$, $BR^7R^8$, $AlR^7$, $AlR^7R^8$, $R^7Bi$=O, or $BiR^7$;

$Y^1$ is CR, SiR, GeR, N, NR, P, P=O, As, As=O, B, BR, Al, AlR, Bi=O, or Bi; and each of R, $R^1$, $R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

2. A light emitting device comprising a complex of claim 1.

3. An OLED device comprising a complex of claim 1.

4. A luminescent label comprising a complex of claim 1.

5. A compound having one of the following structural formulas, wherein M is Pt (II) or Pd (II) and wherein each of $R^7$ and $R^8$, if present, independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof:

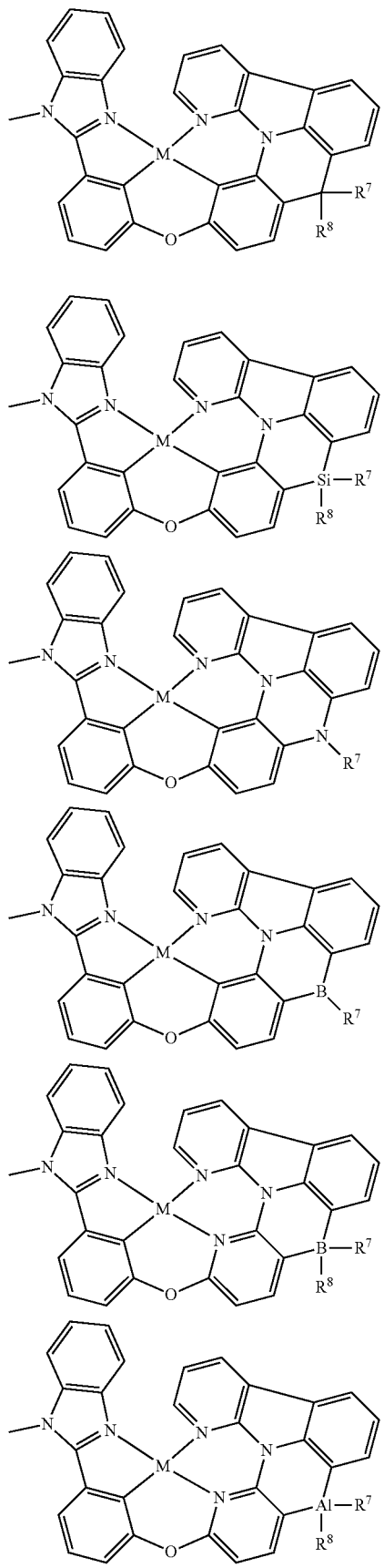

391
-continued
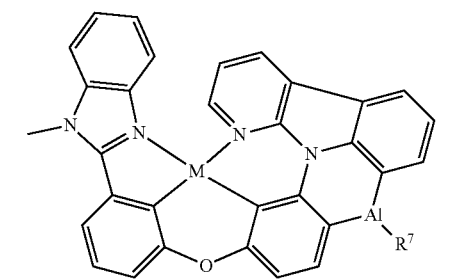
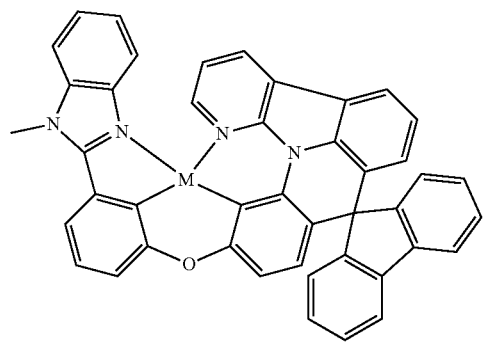
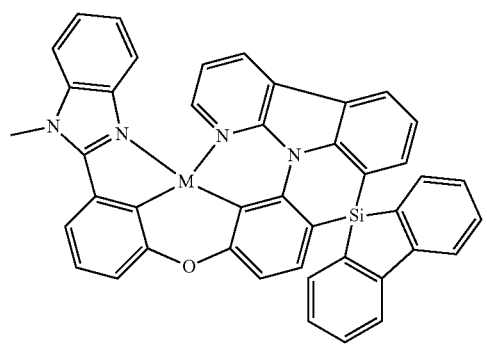
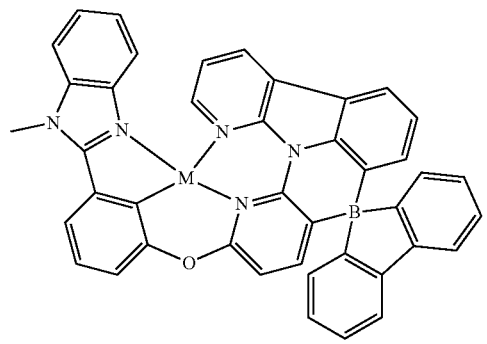
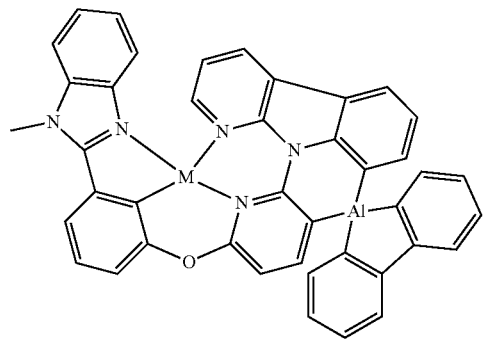
392
-continued
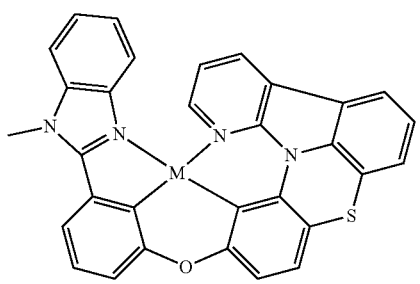
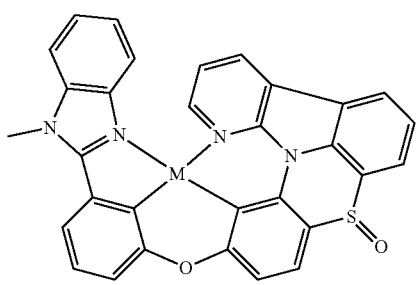
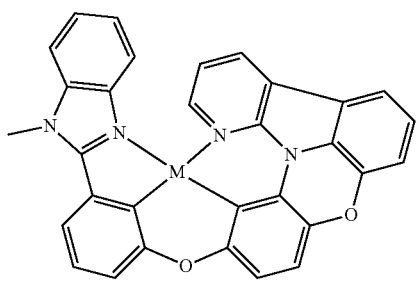
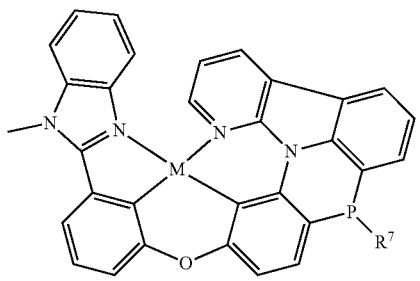
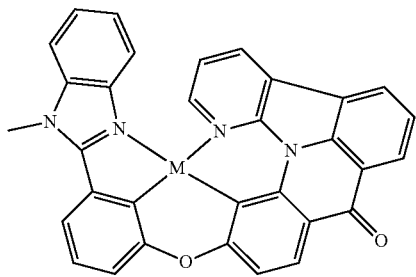

393
-continued
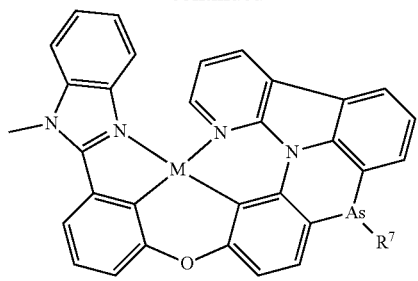
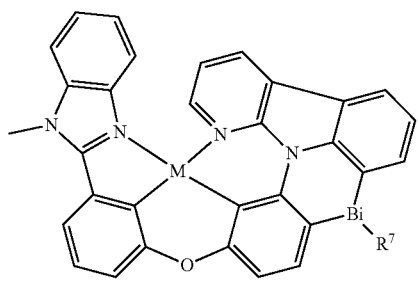
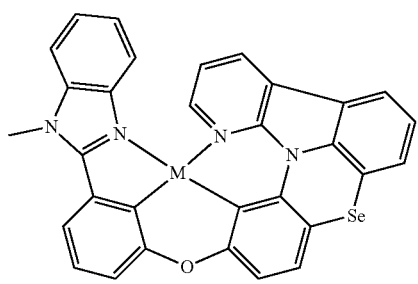
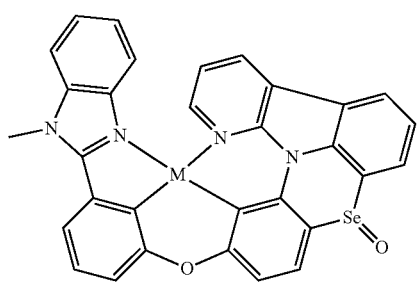
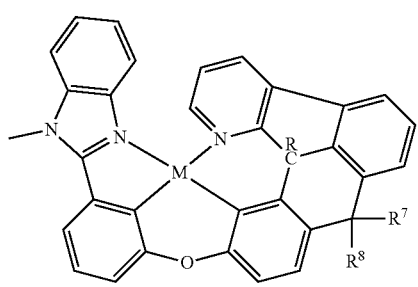
394
-continued
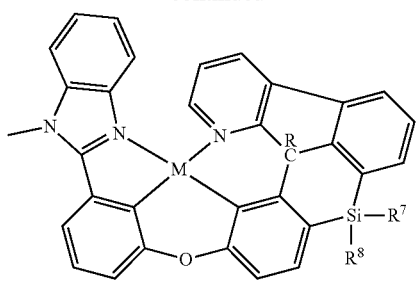
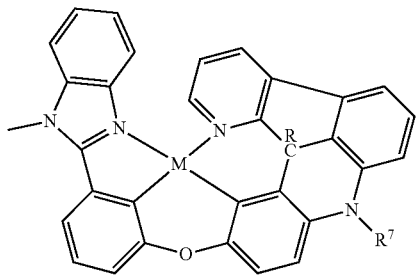
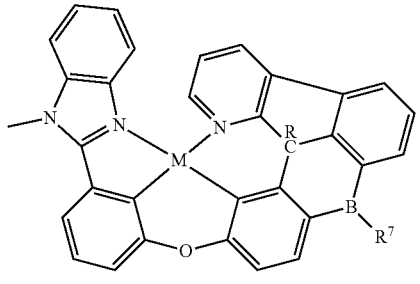
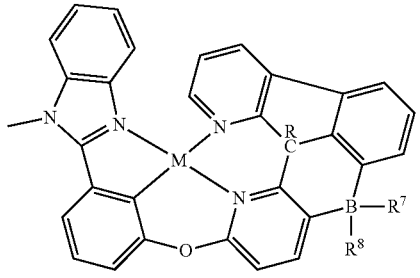
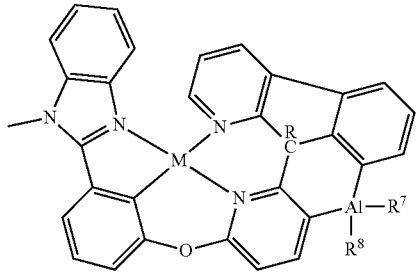
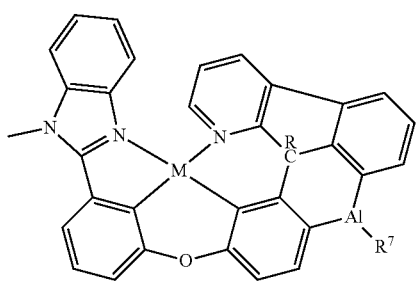

395
-continued
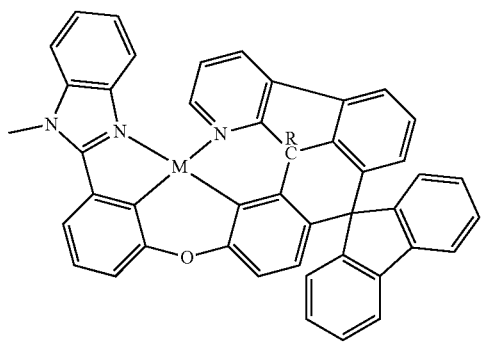
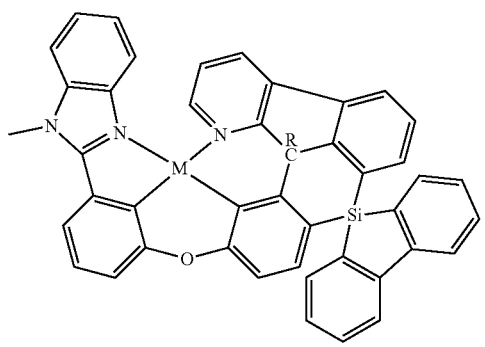
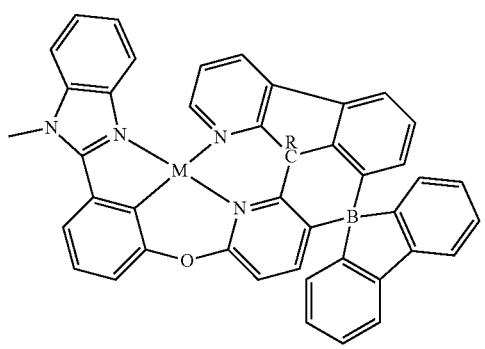
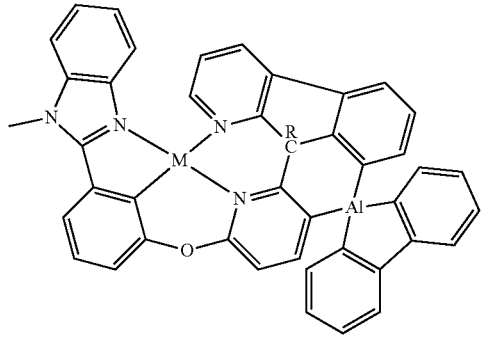
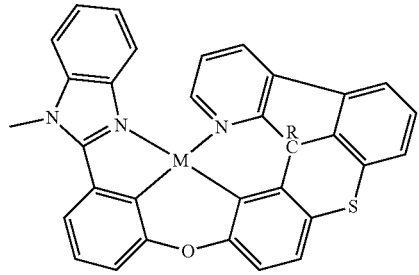
396
-continued
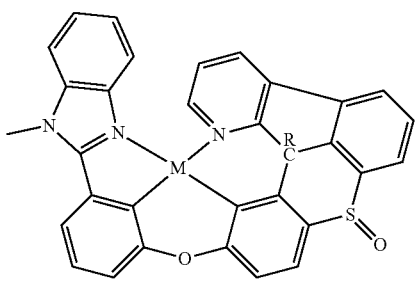
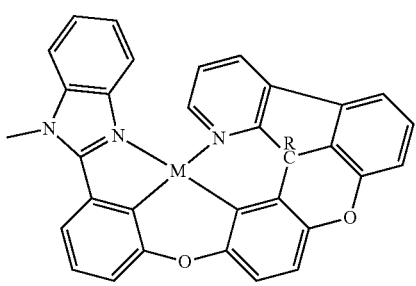
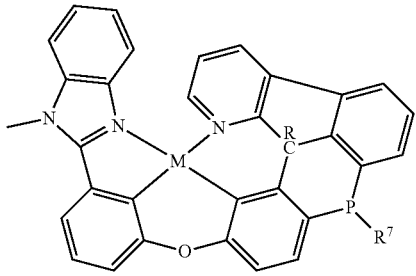
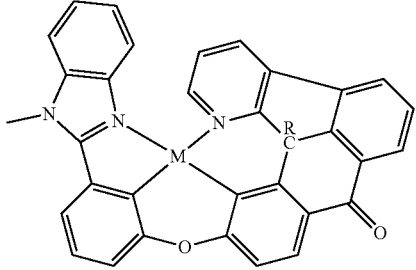
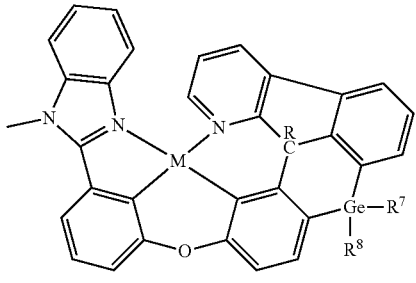
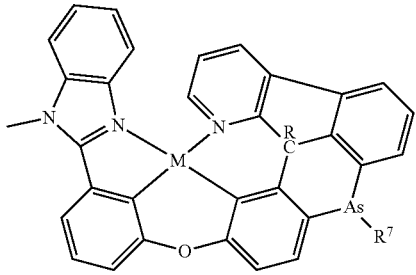

397
-continued
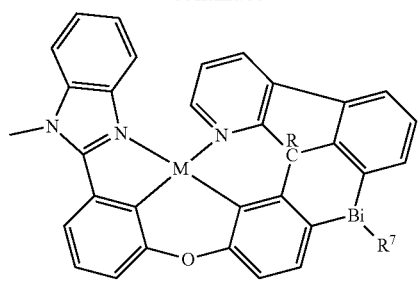
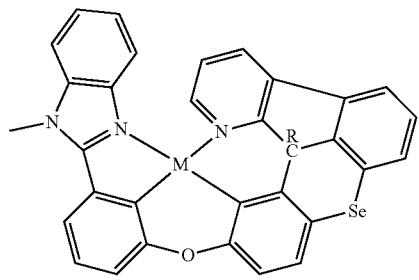
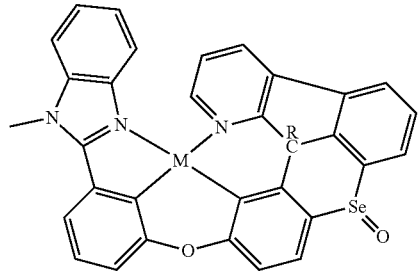
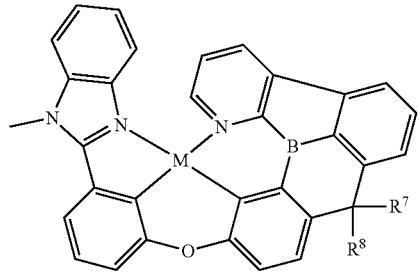
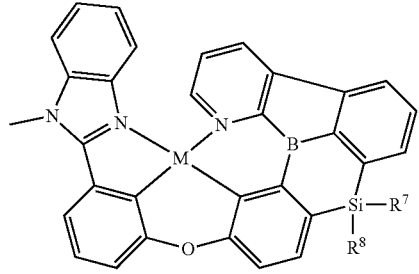
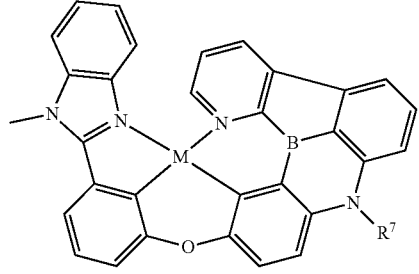
398
-continued
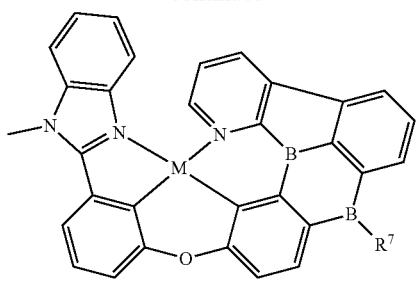
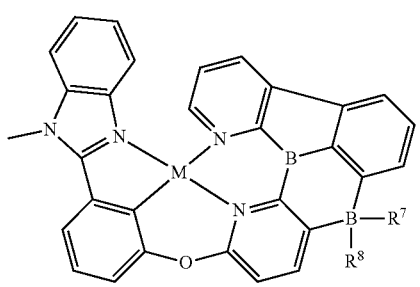
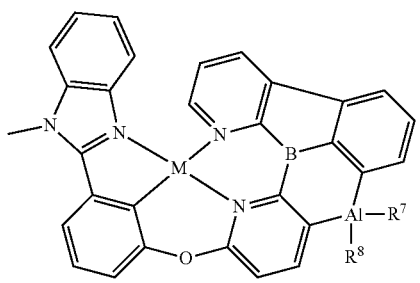
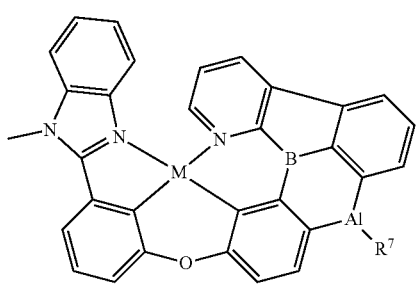
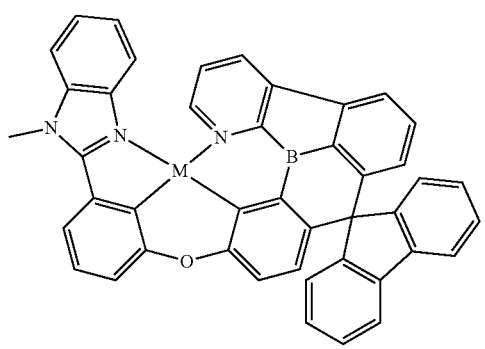

399
-continued
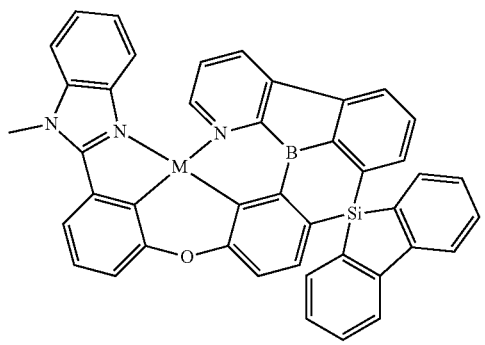
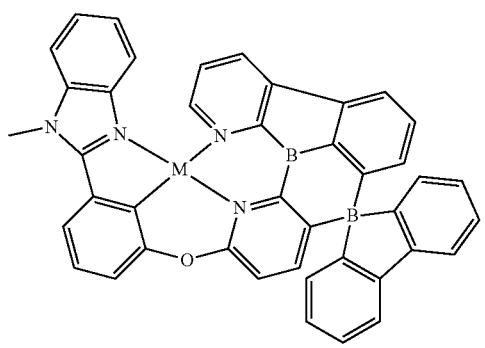
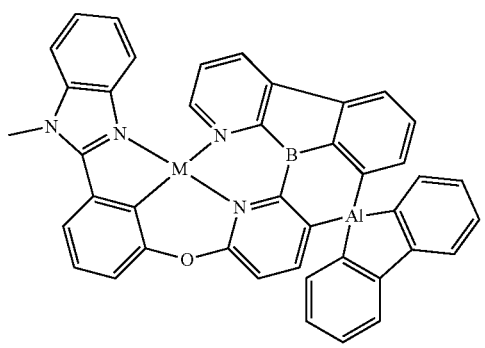
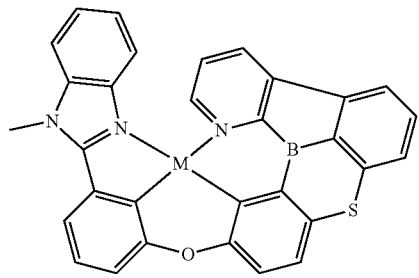
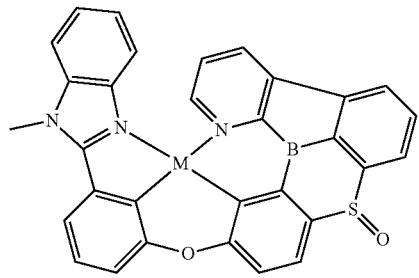
400
-continued
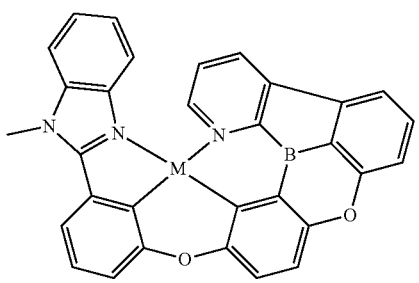
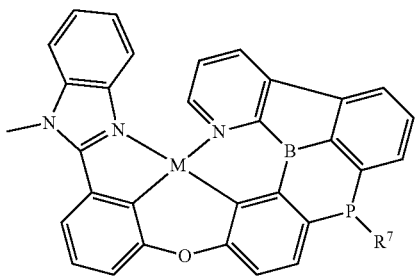
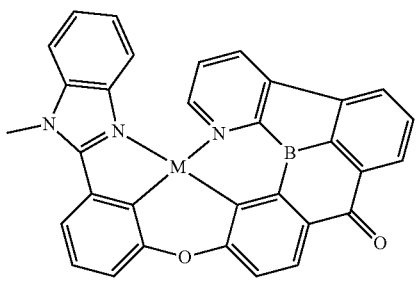
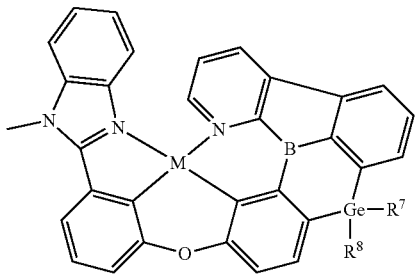
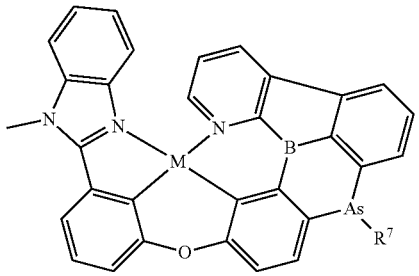
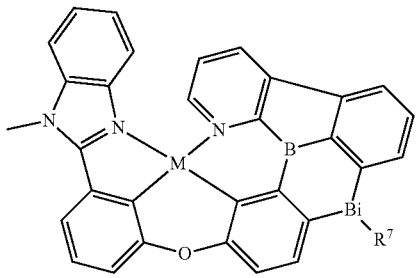

401
-continued
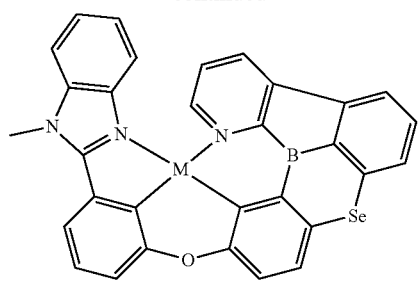
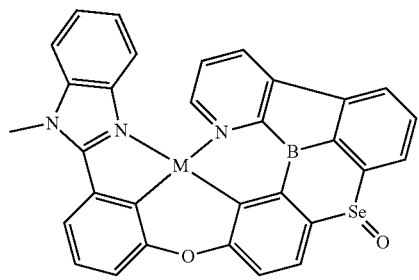
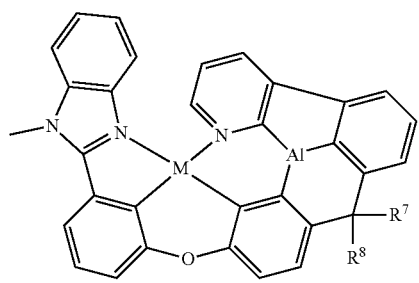
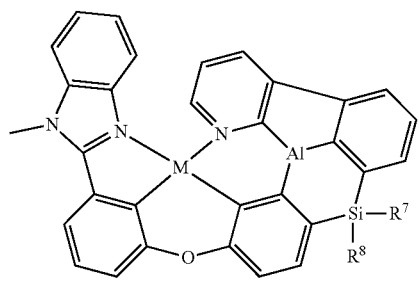
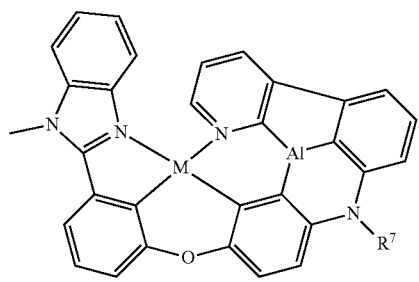
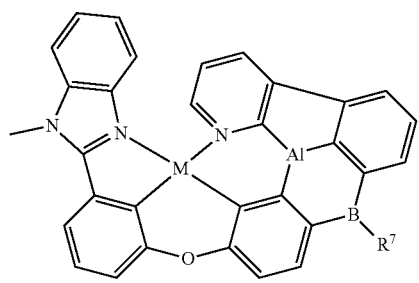
402
-continued
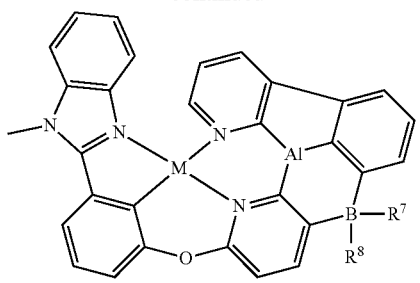
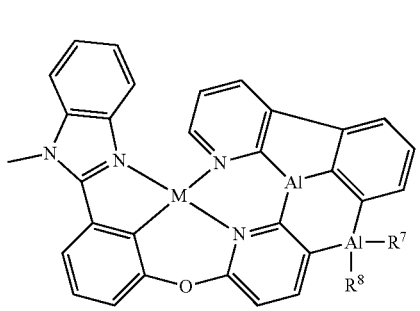
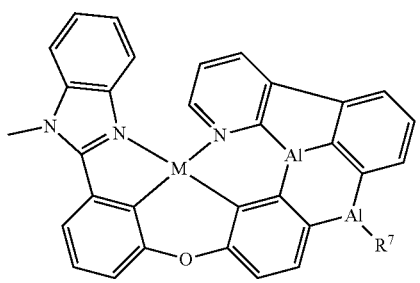
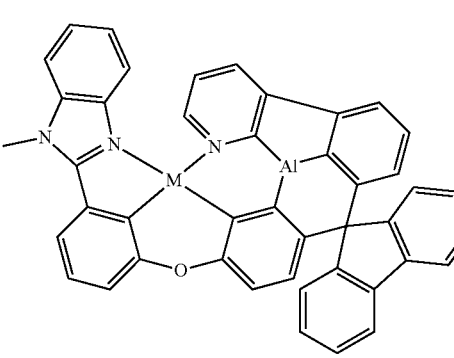
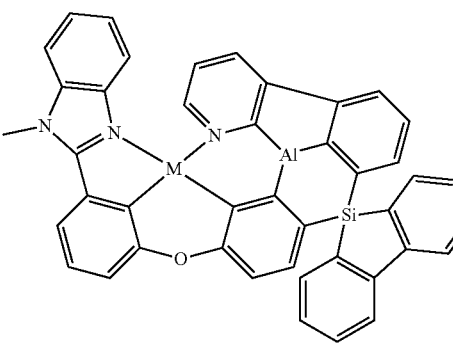

403
-continued
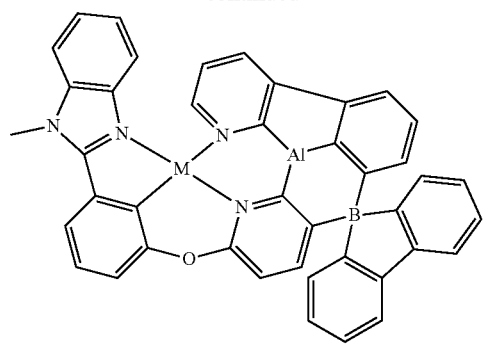
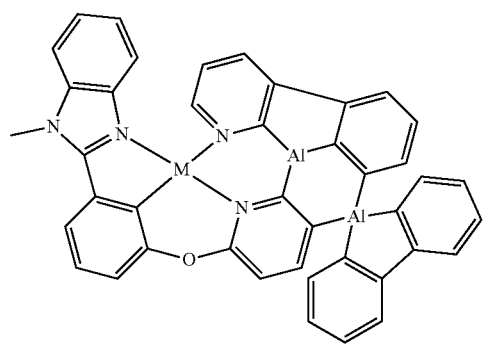
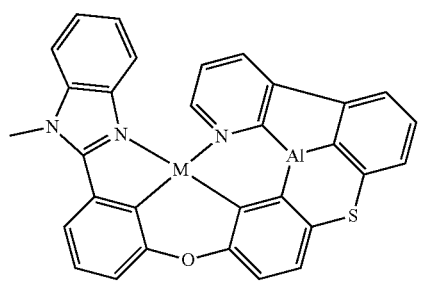
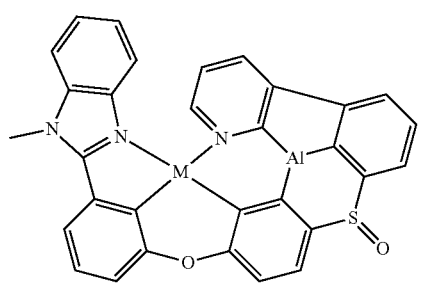
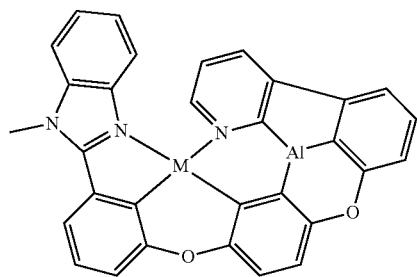
404
-continued
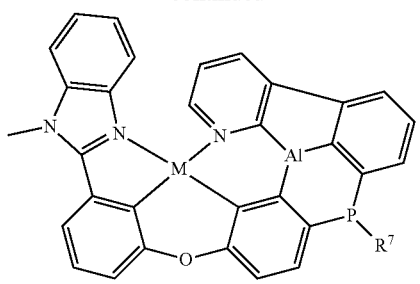
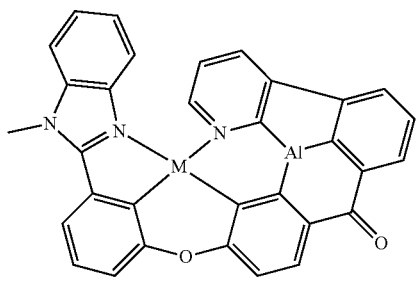
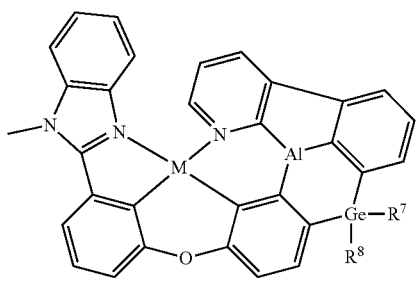
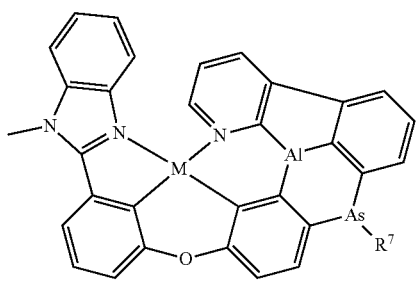
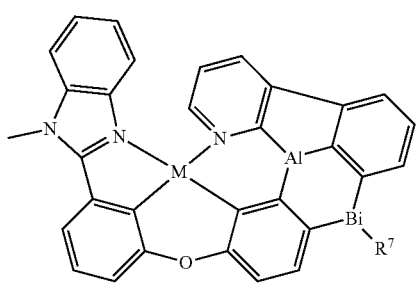
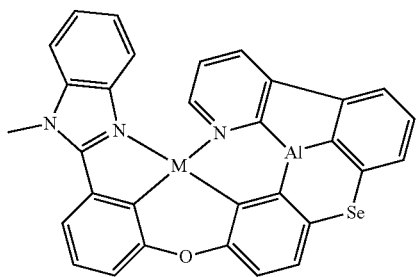

405
-continued
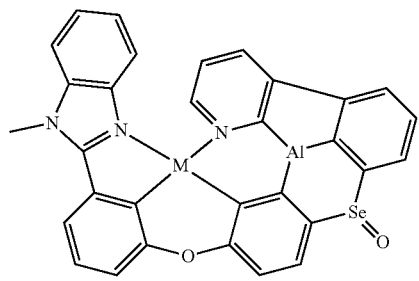
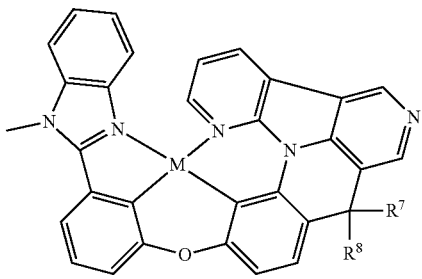
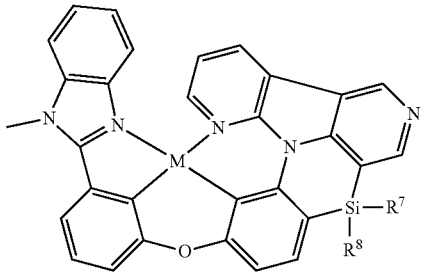
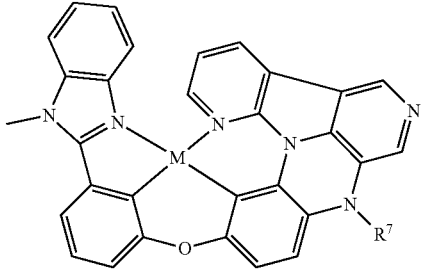
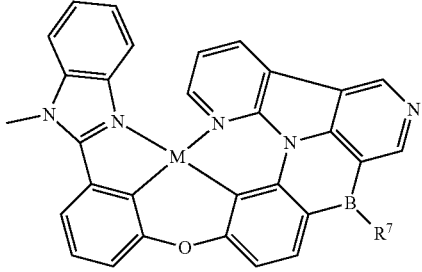
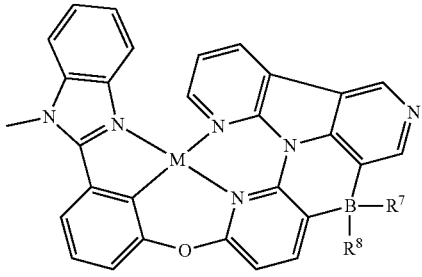
406
-continued
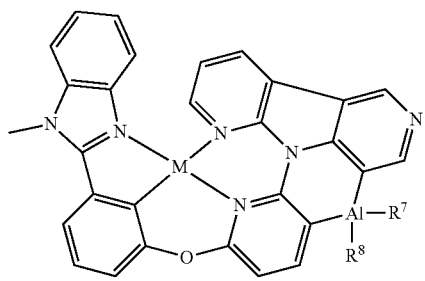
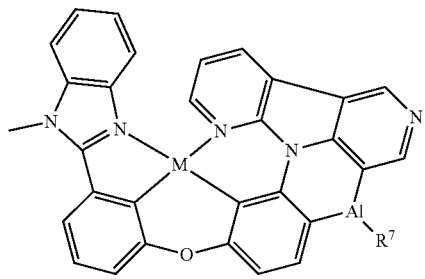
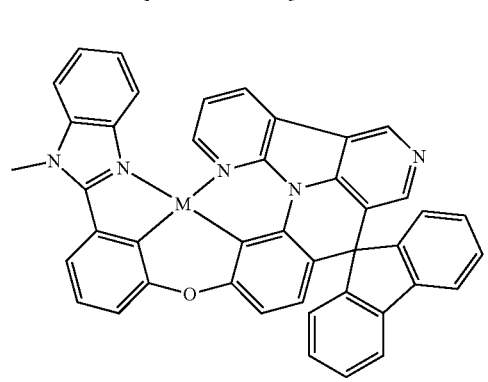
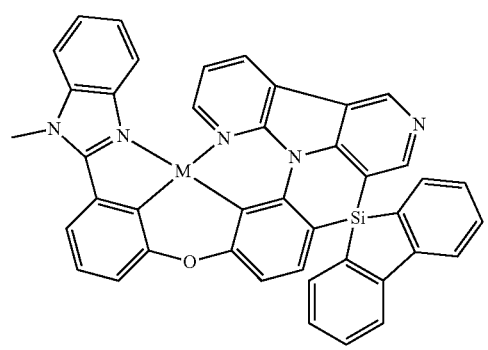
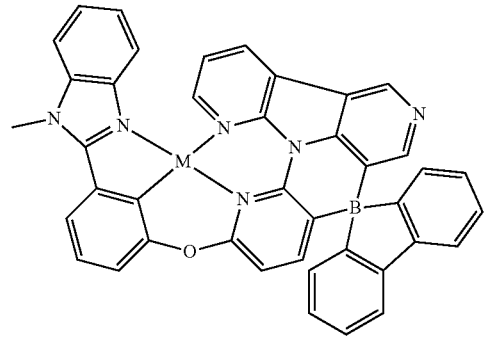

407
-continued
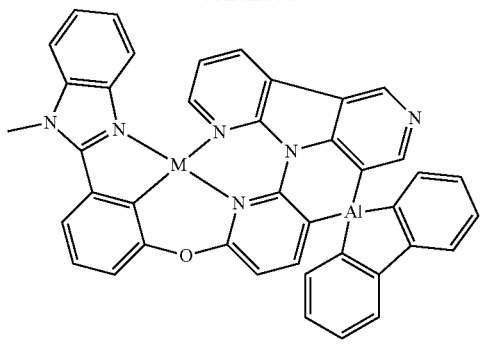
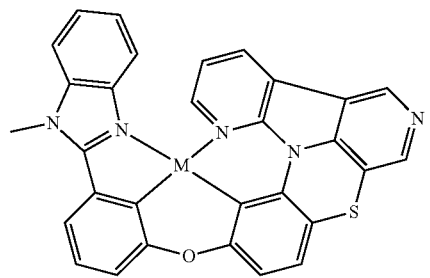
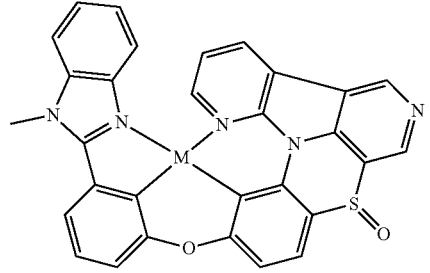
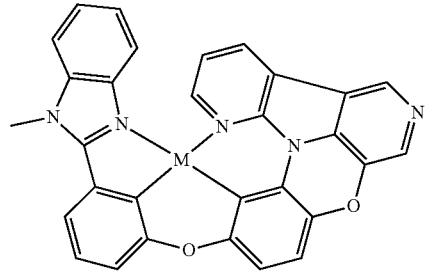
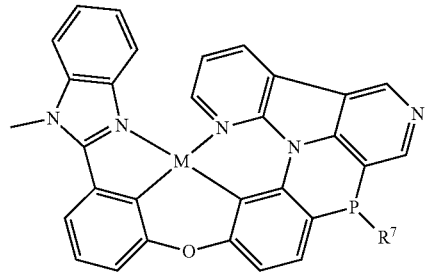
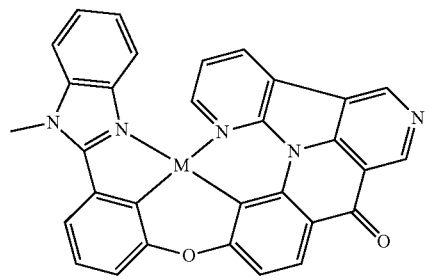
408
-continued
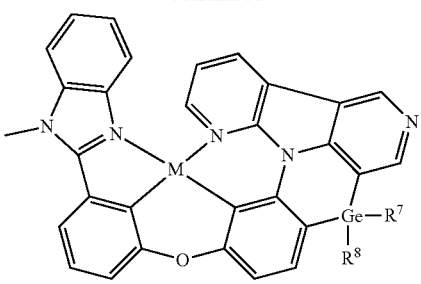
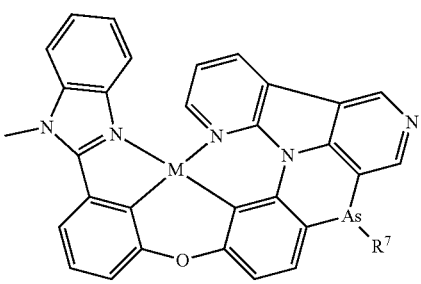
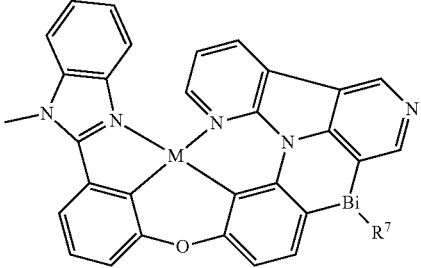
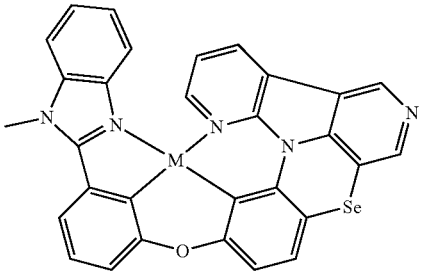
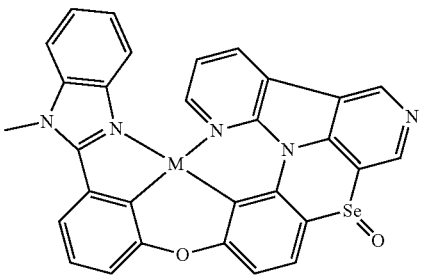
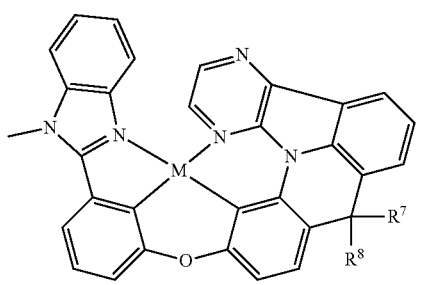

409-continued
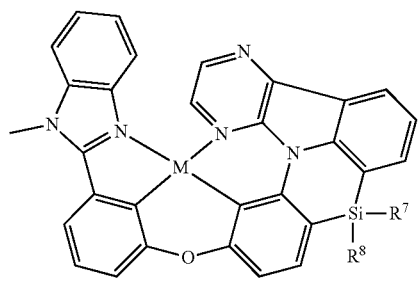
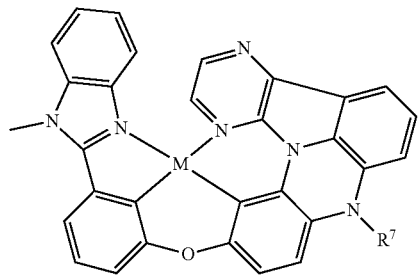
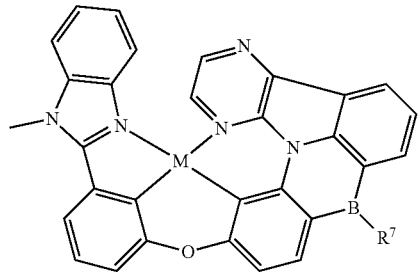
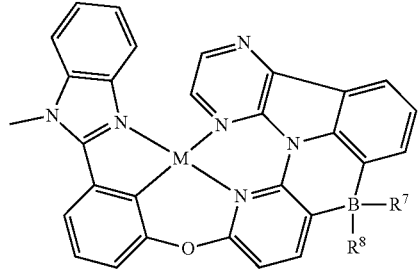
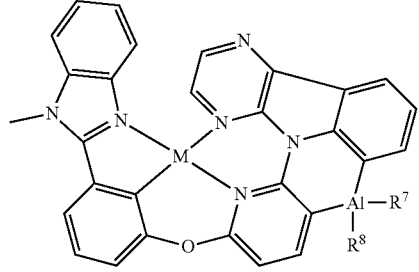
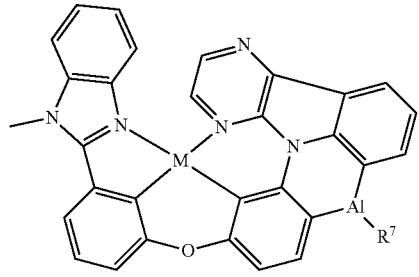
410-continued
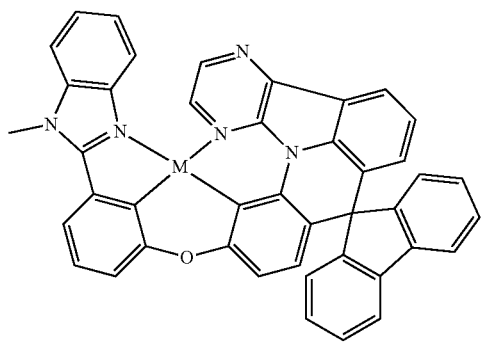
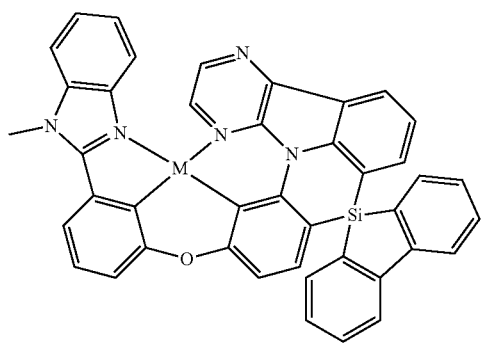
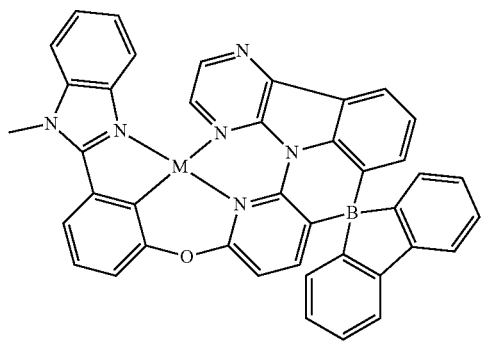
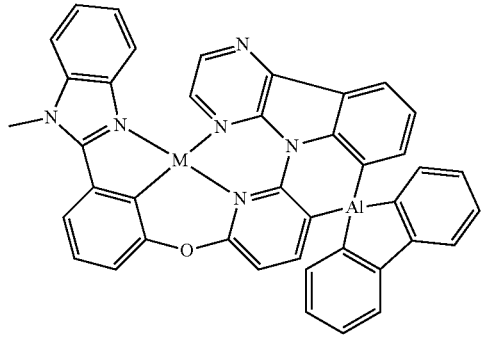
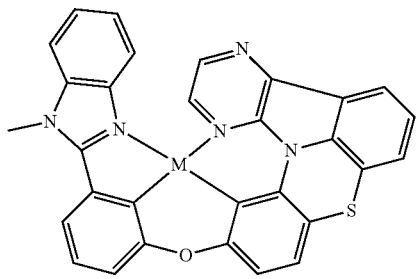

| 411 -continued | 412 -continued |
|---|---|
| 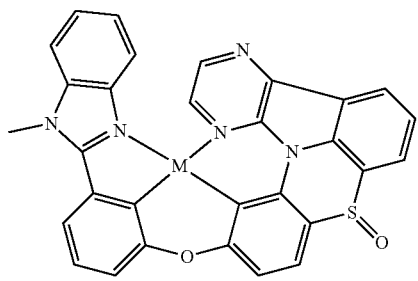 | 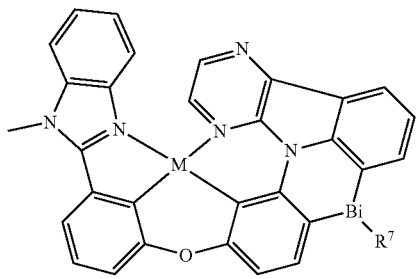 |
| 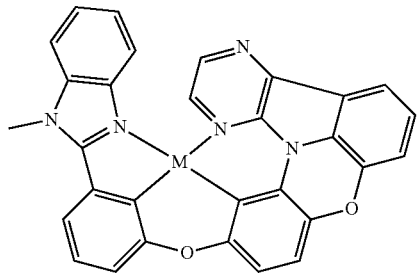 | 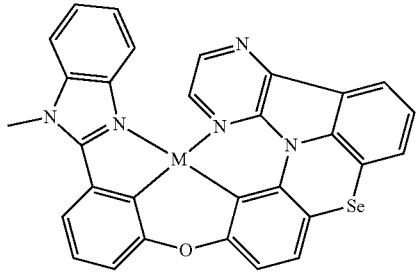 |
| 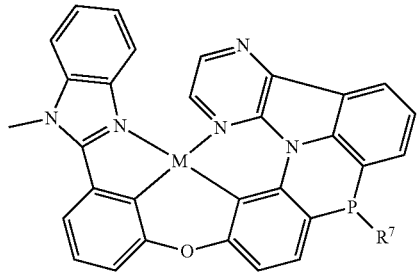 | 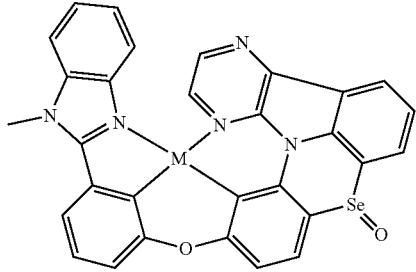 |
| 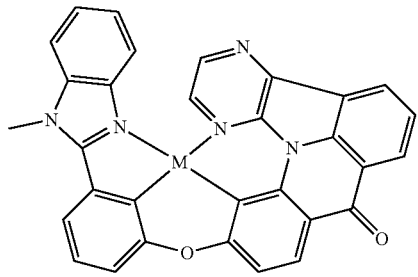 | 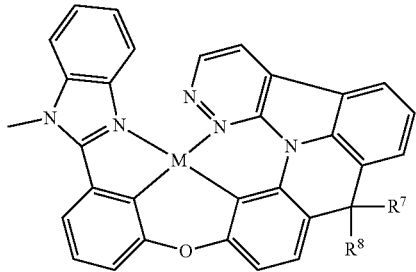 |
| 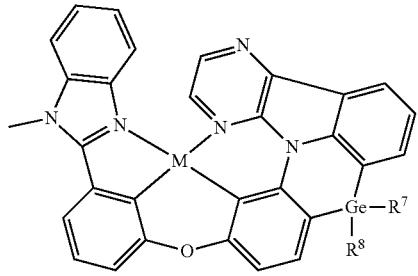 | 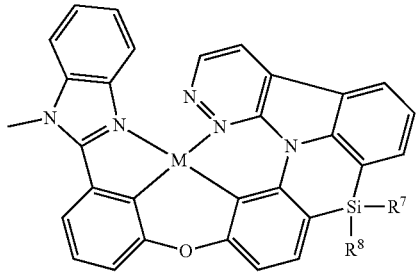 |
| 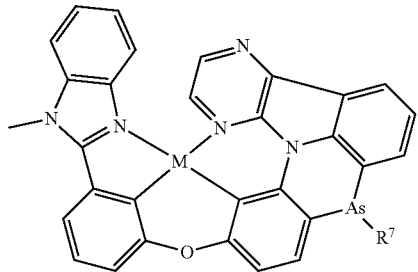 | 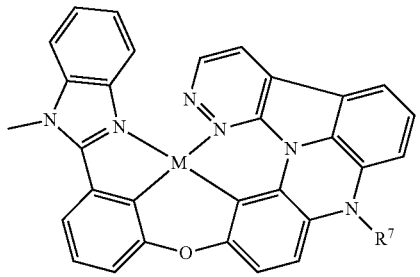 |

413
-continued
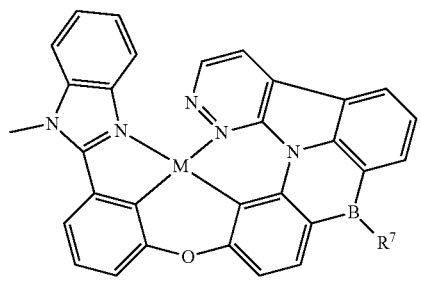
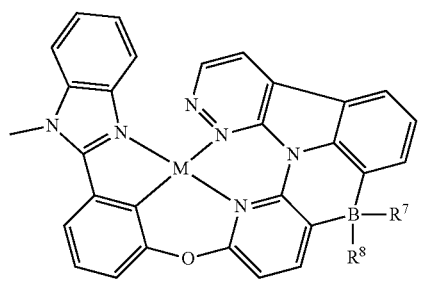
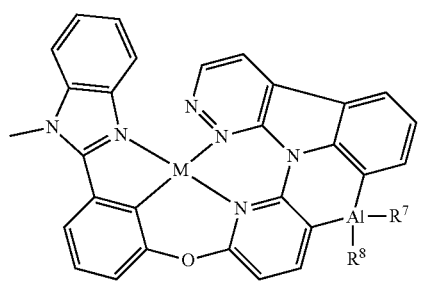
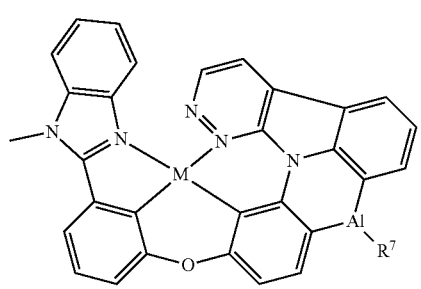
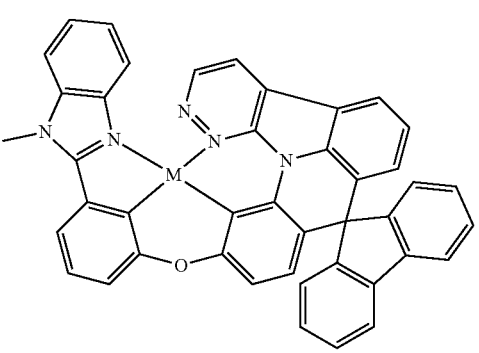
414
-continued
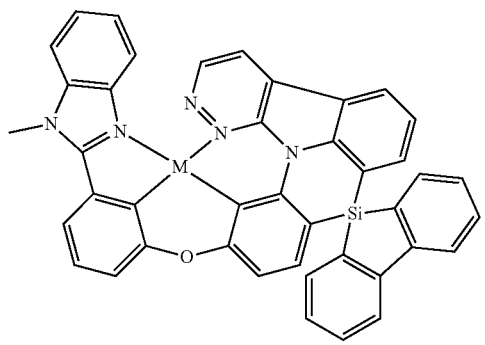
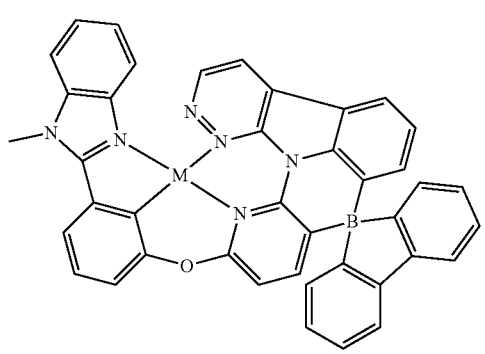
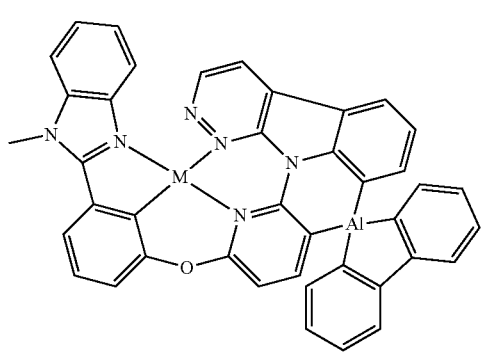
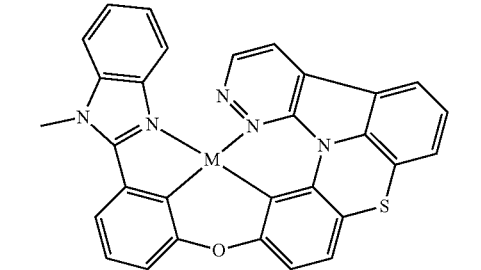
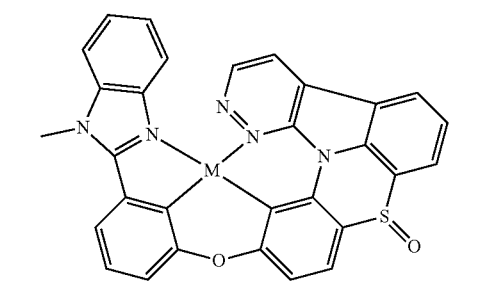

415
-continued
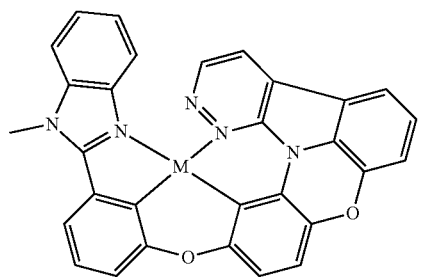
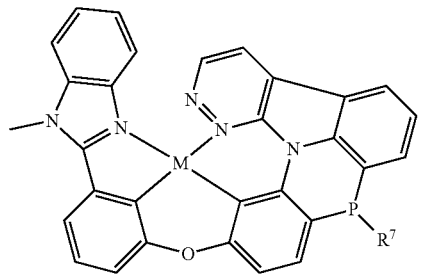
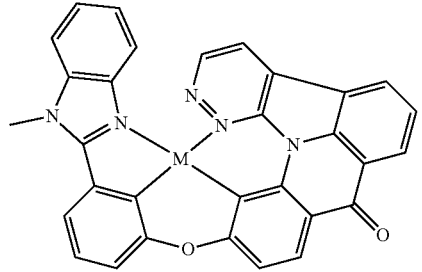
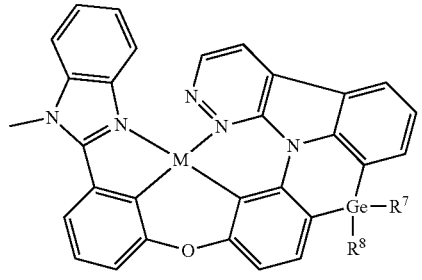
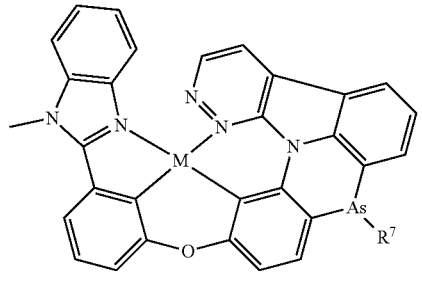
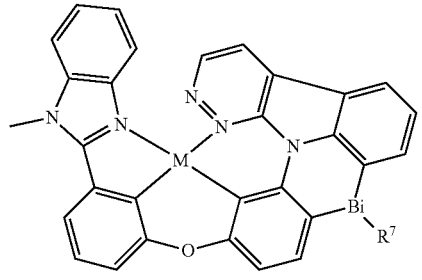
416
-continued
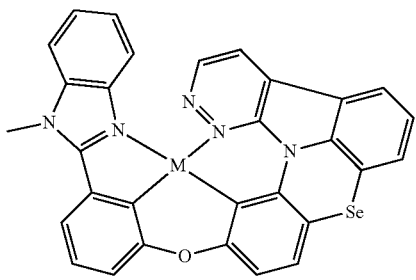
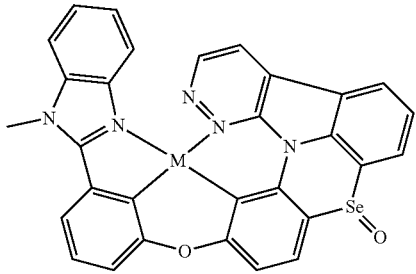
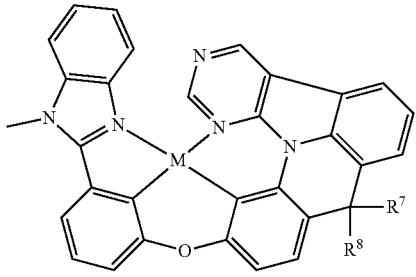
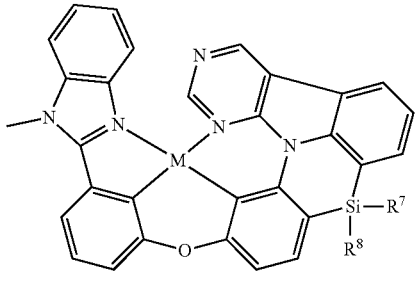
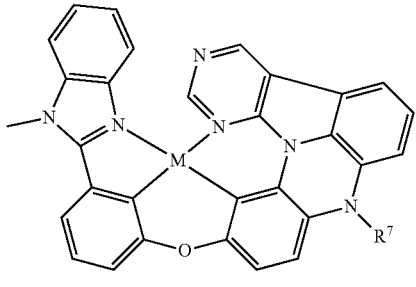
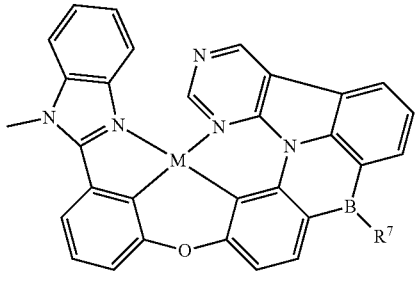

417
-continued
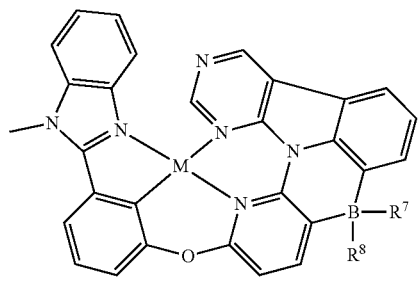
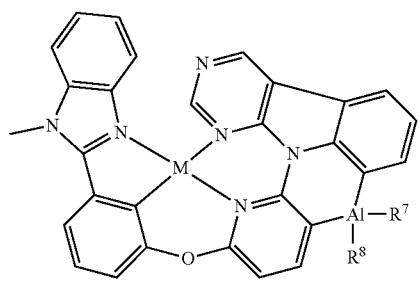
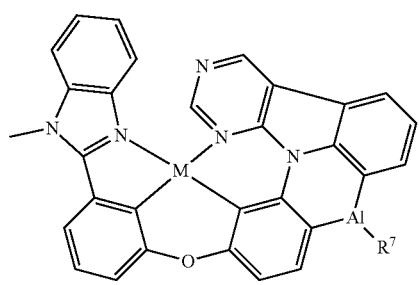
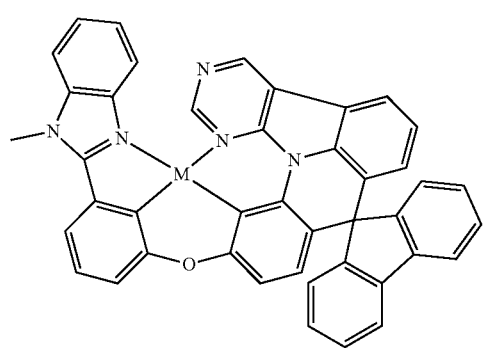
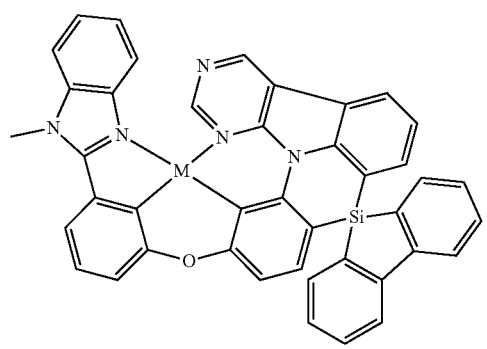
418
-continued
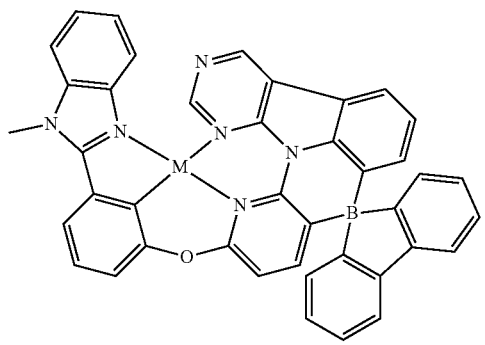
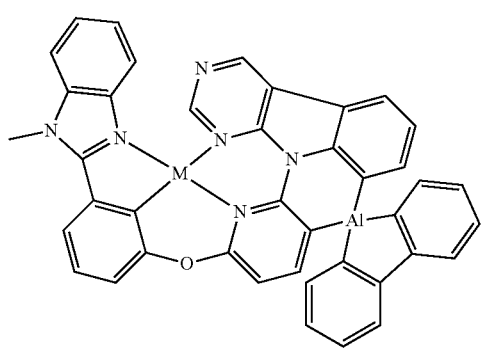
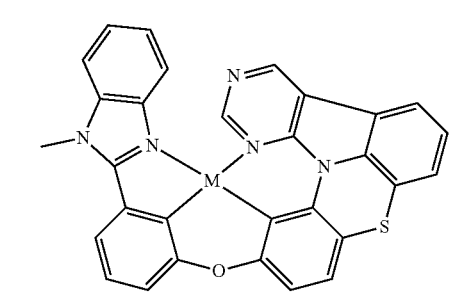
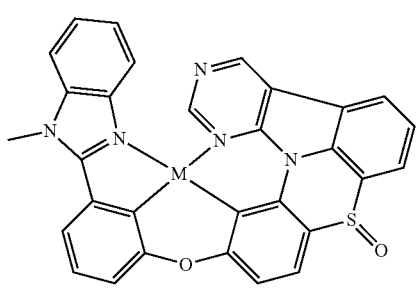
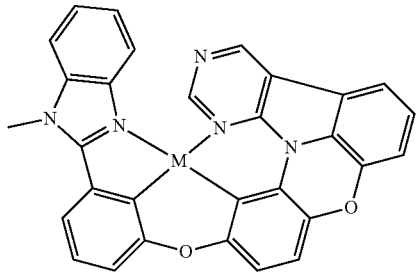

419
-continued
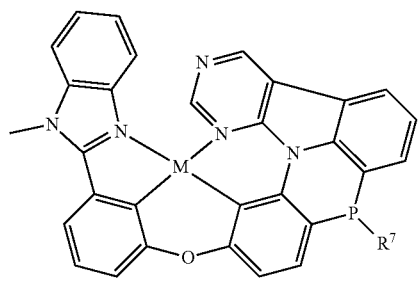
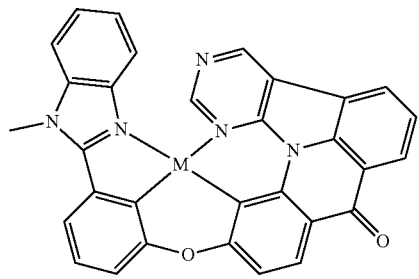
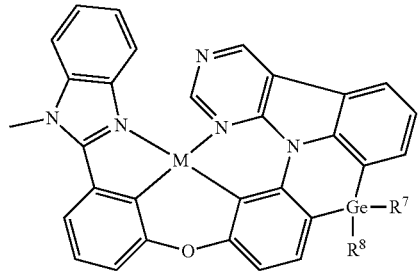
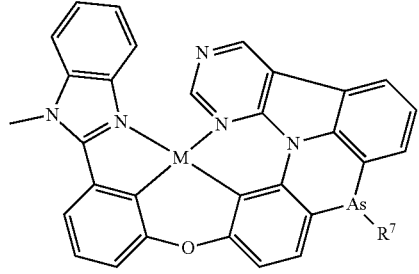
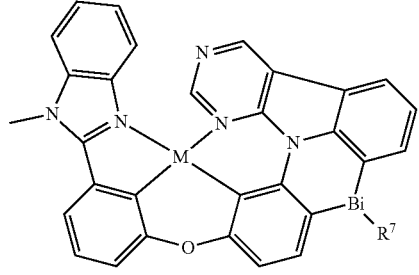
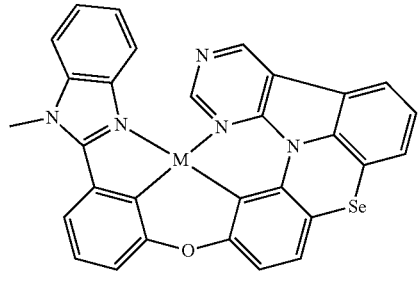
420
-continued
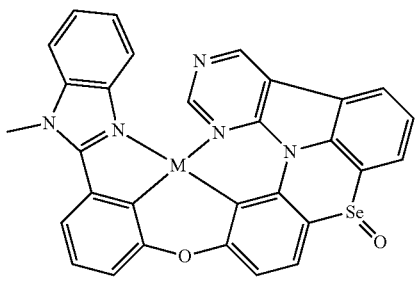
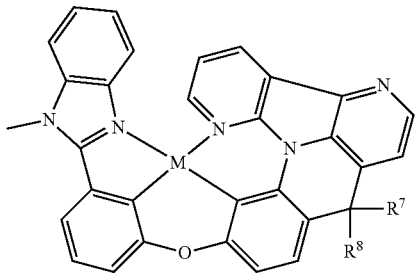
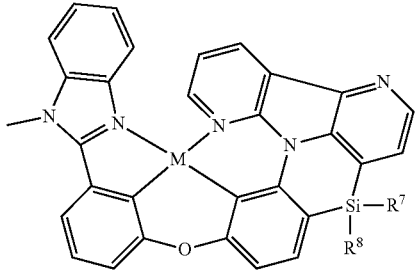
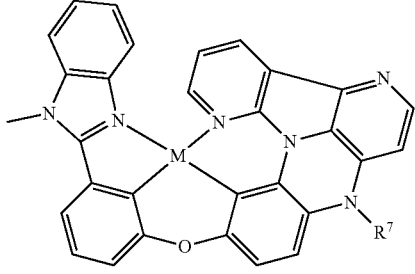
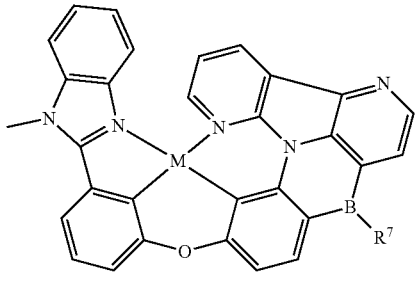
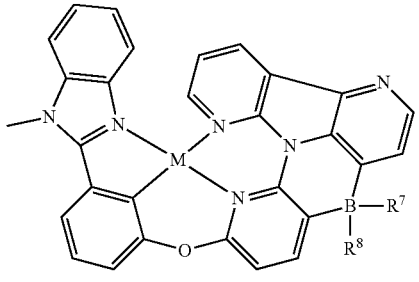

421
-continued
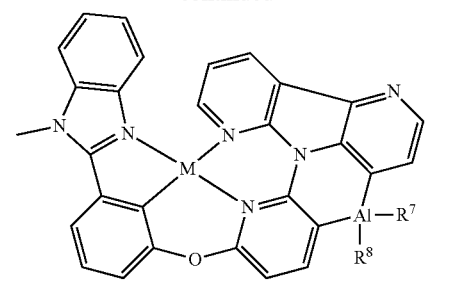
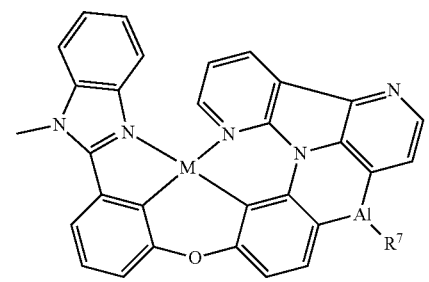
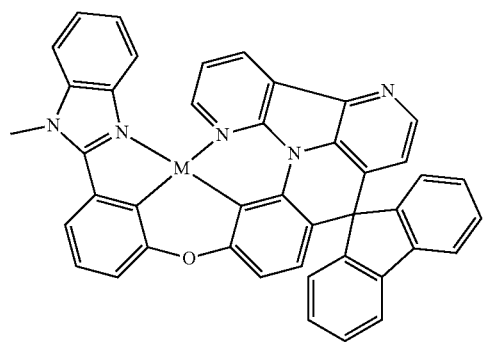
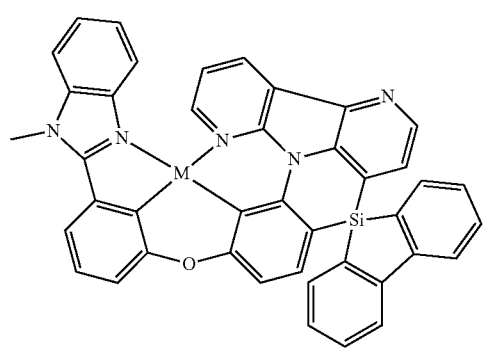
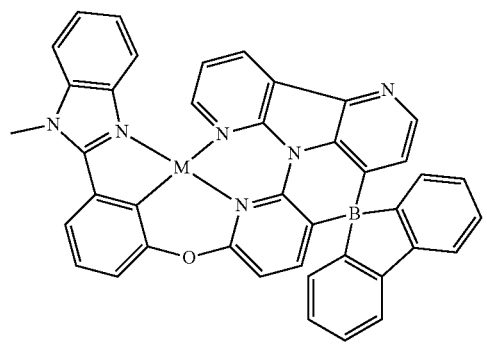
422
-continued
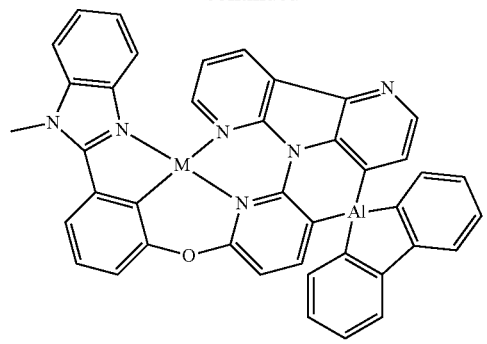
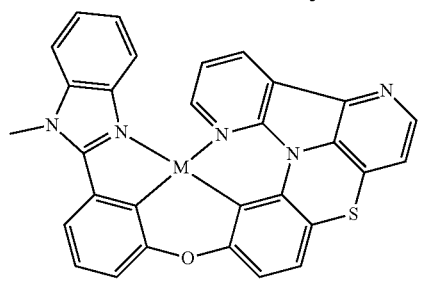
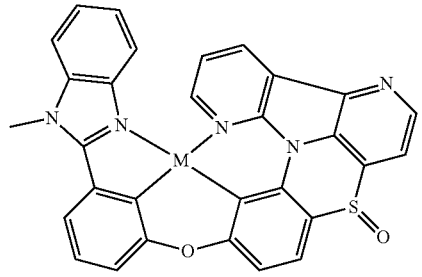
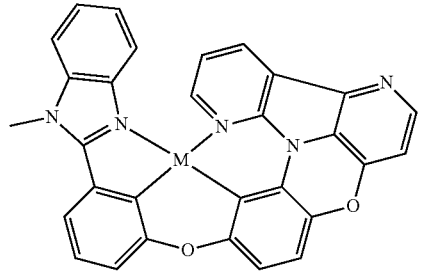
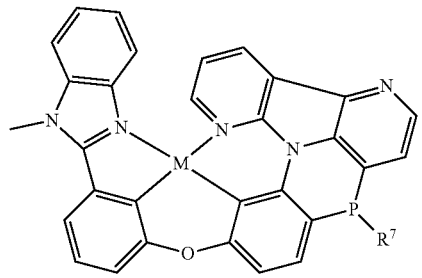
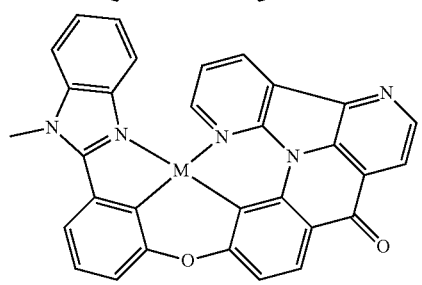

423
-continued
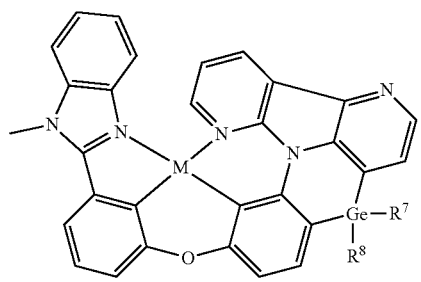
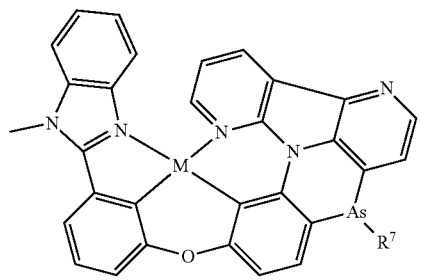
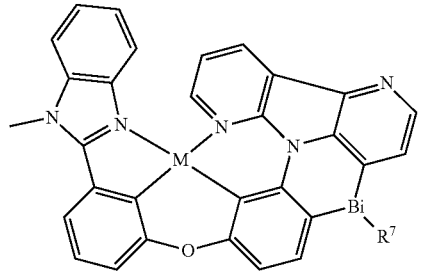
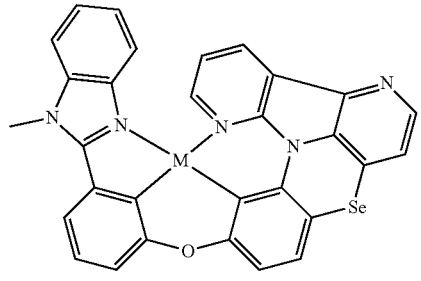
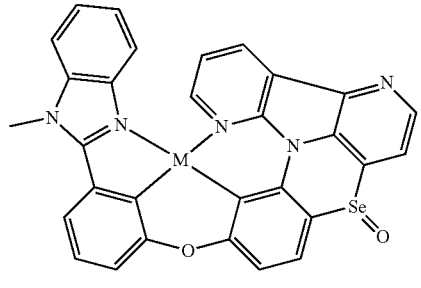
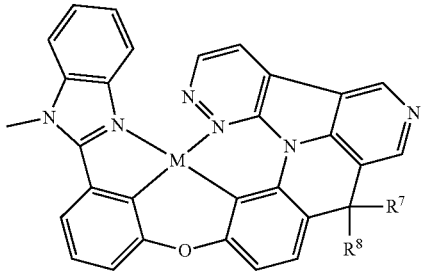
424
-continued
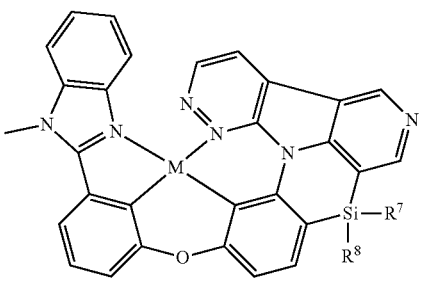
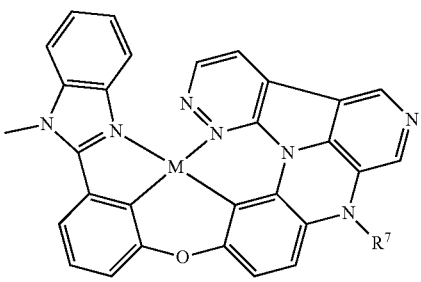
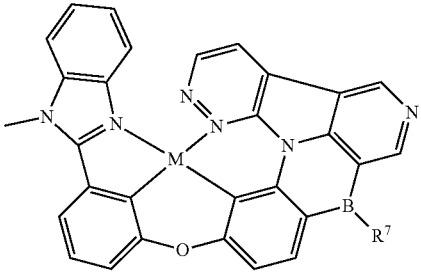
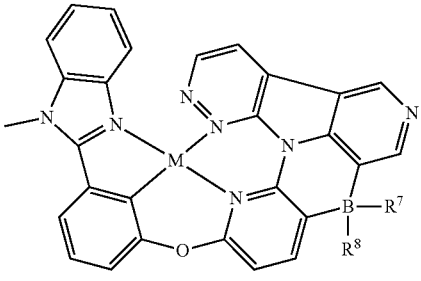
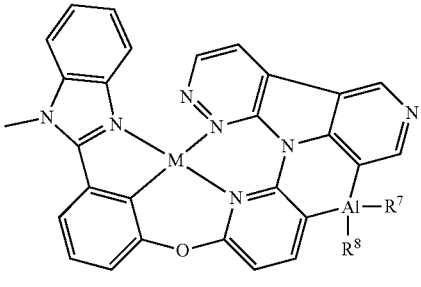
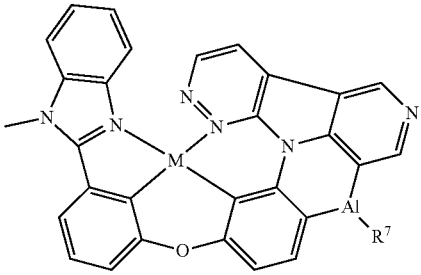

425
-continued
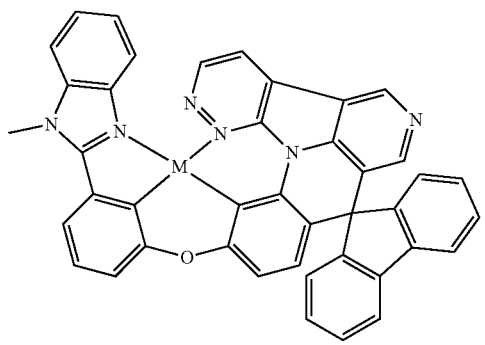
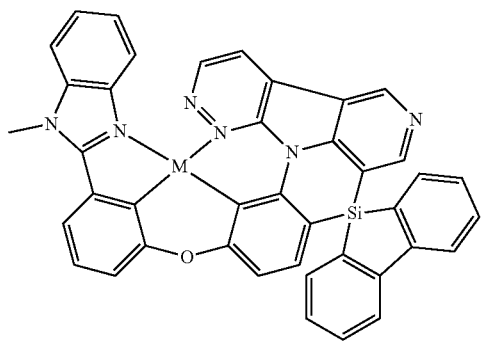
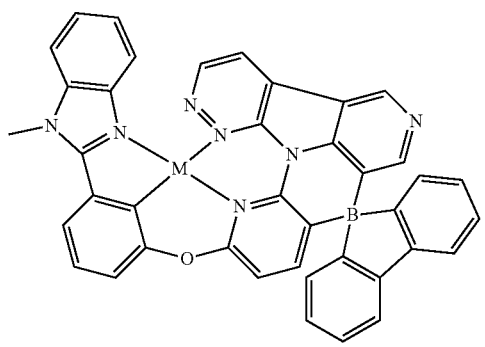
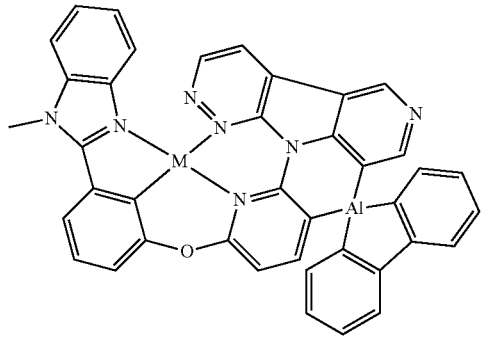
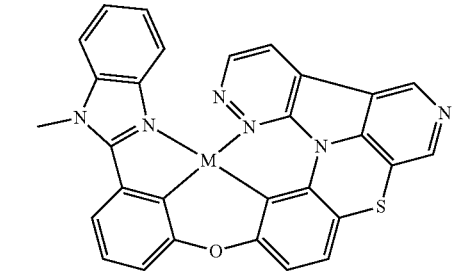
426
-continued
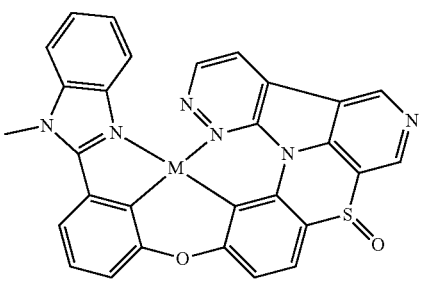
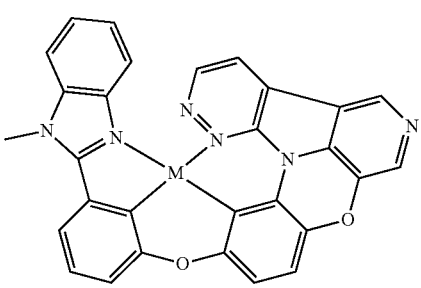
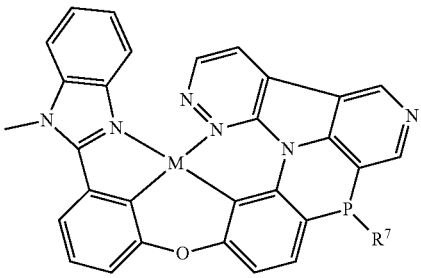
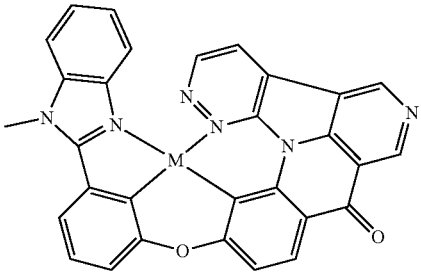
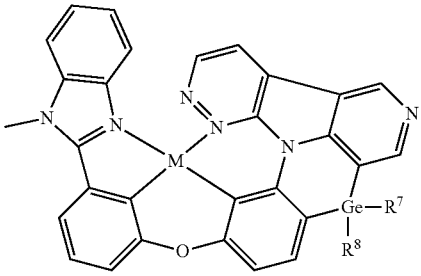
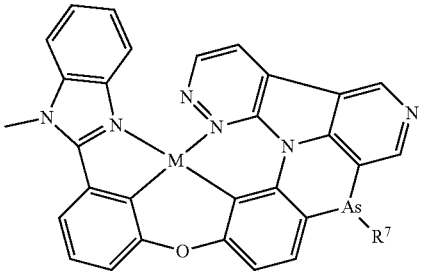

427
-continued
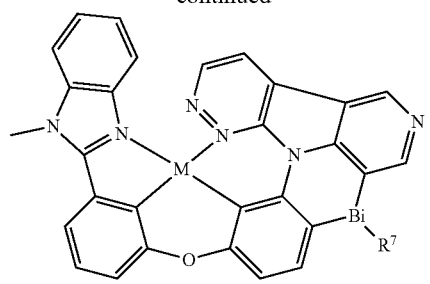
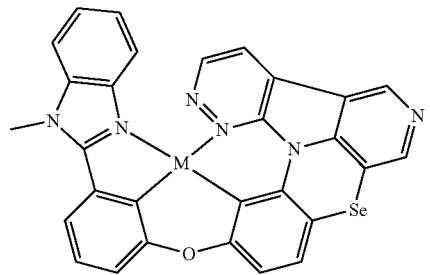
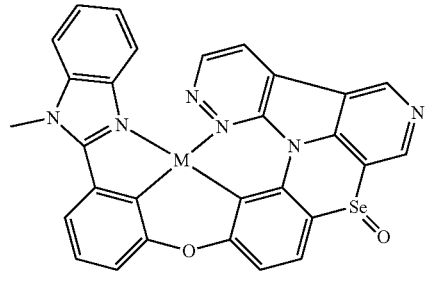
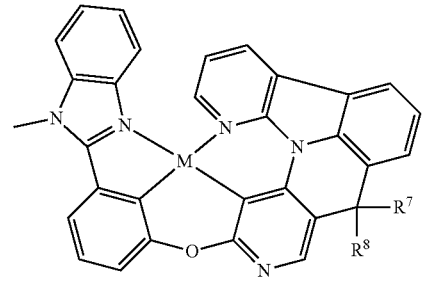
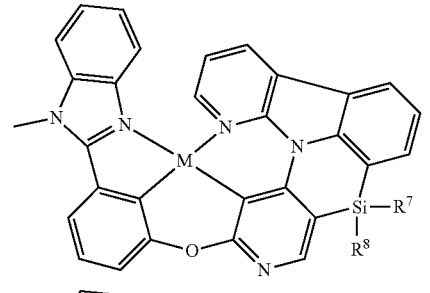
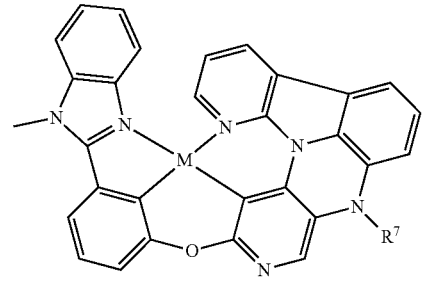
428
-continued
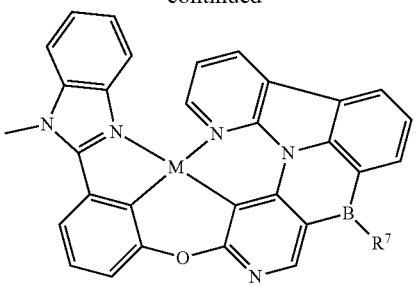
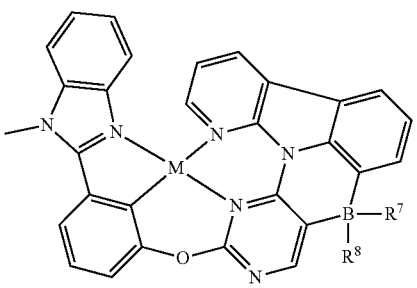
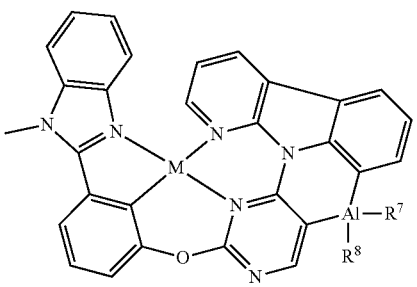
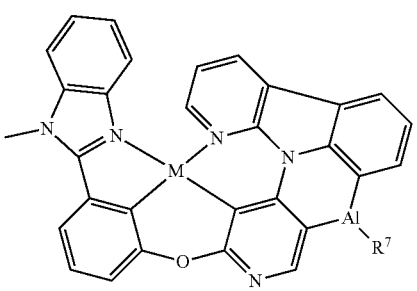
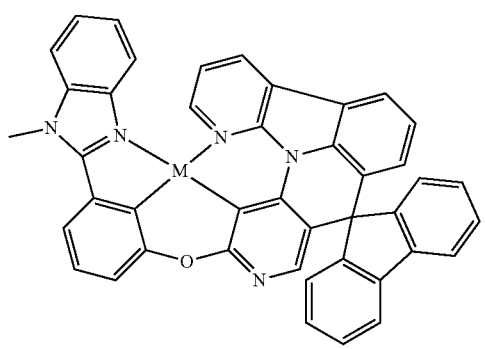

429
-continued
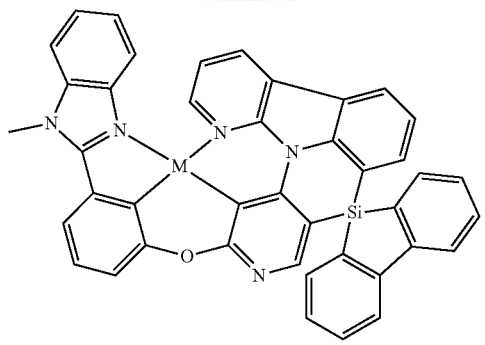
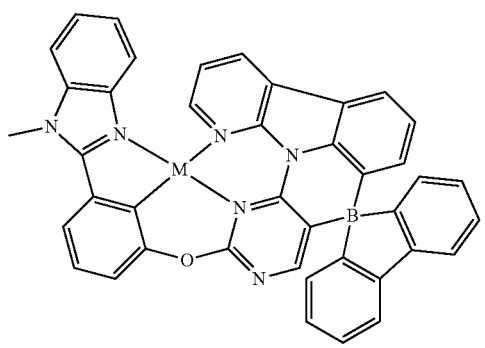
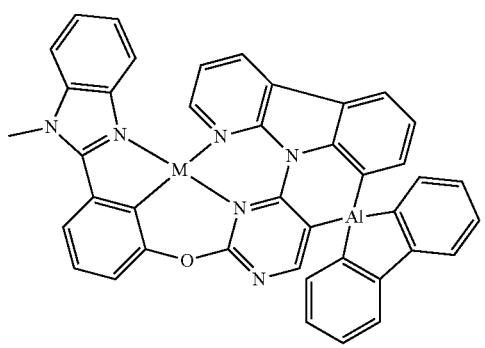
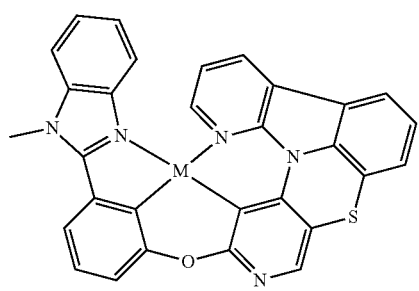
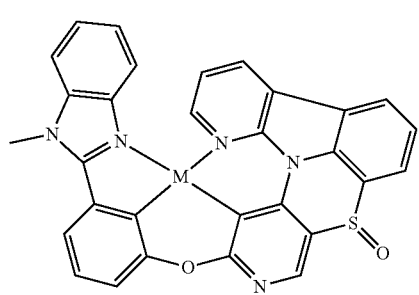
430
-continued
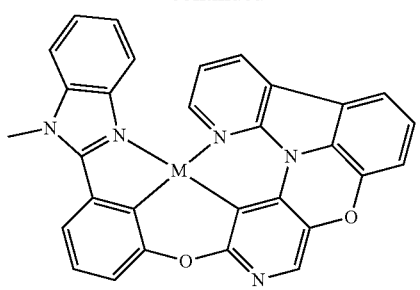
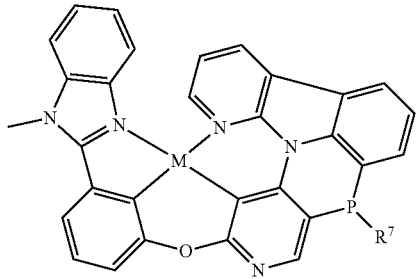
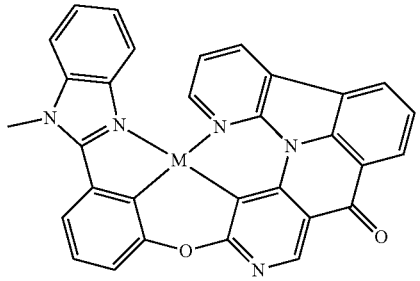
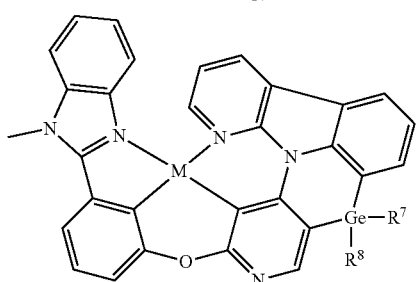
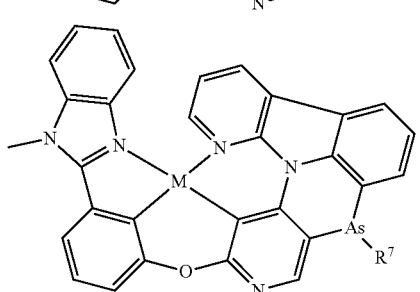
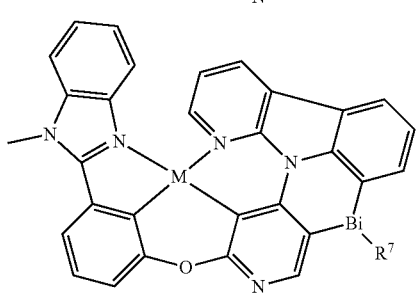

431
-continued
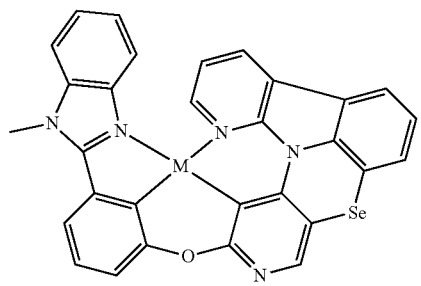
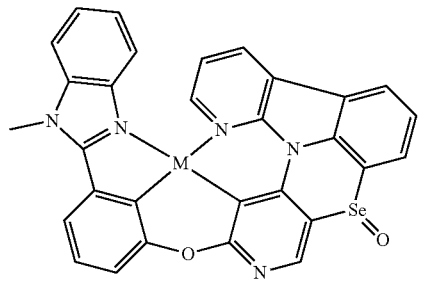
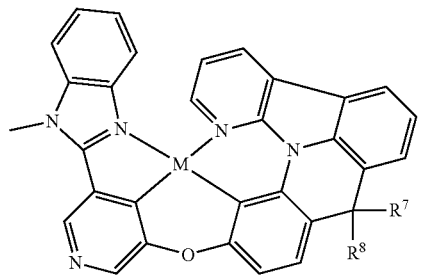
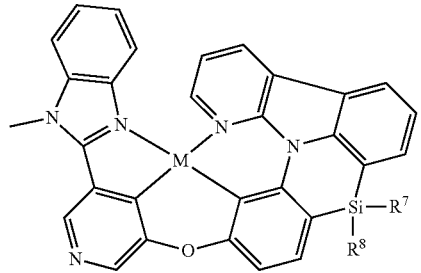
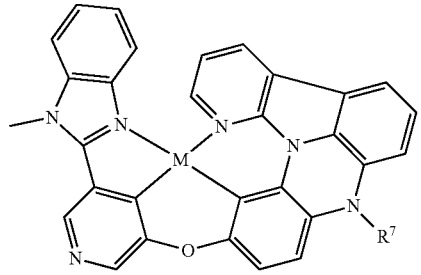
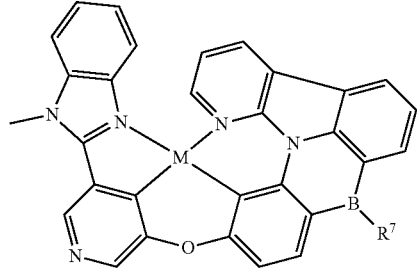
432
-continued
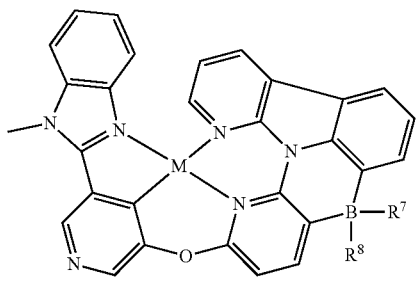
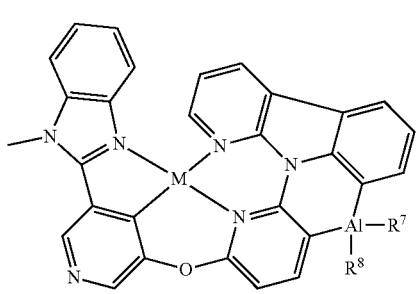
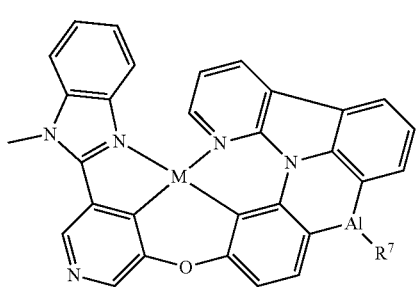
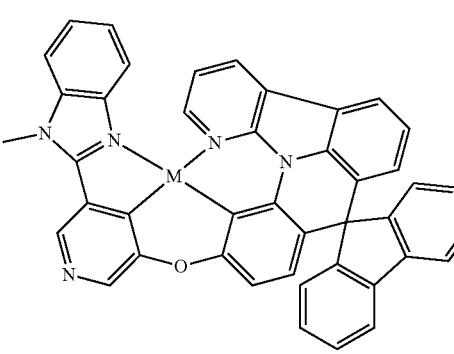
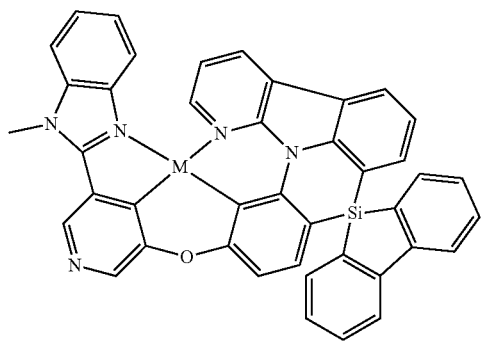

433
-continued
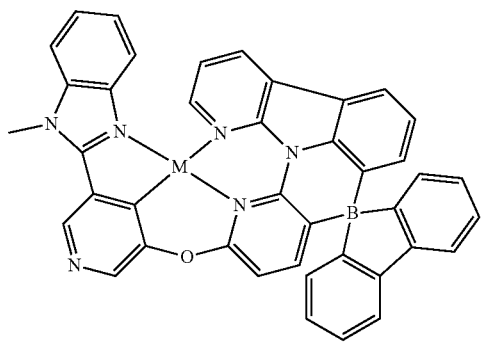
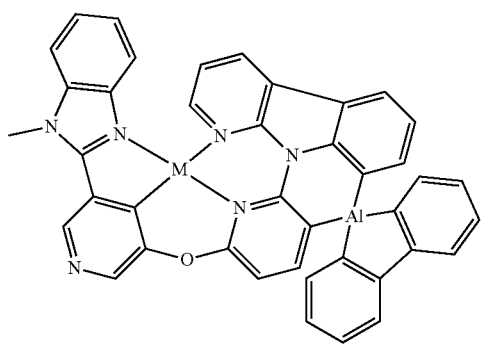
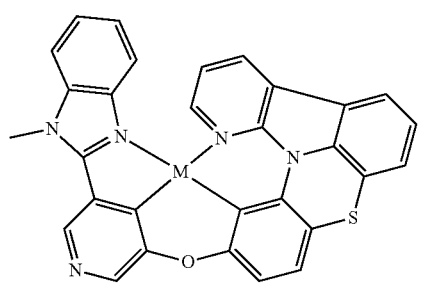
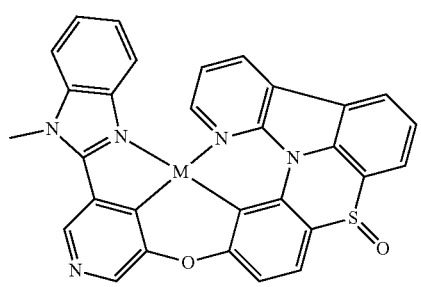
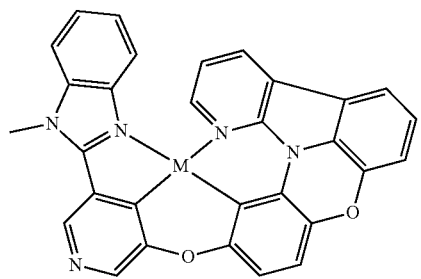
434
-continued
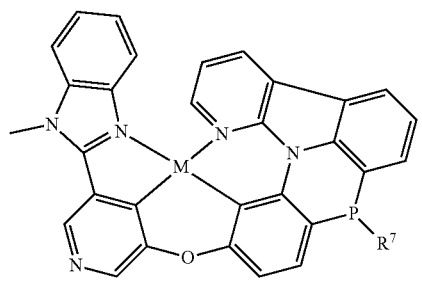
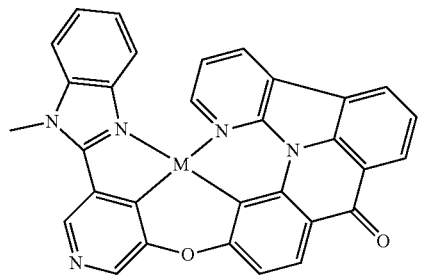
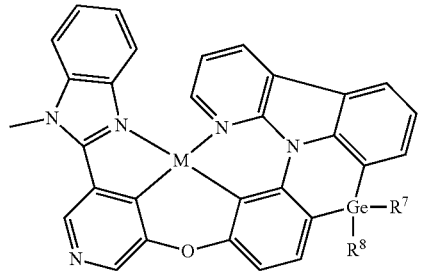
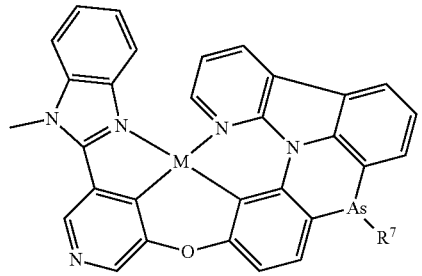
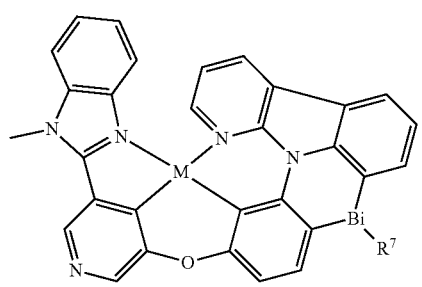
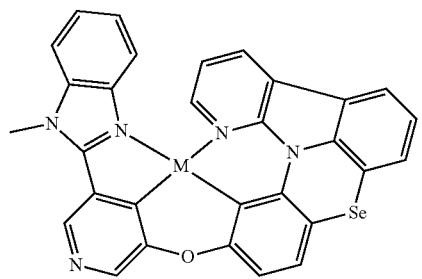

435
-continued
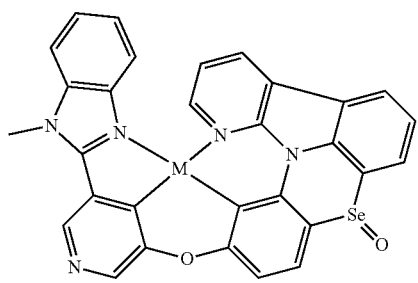
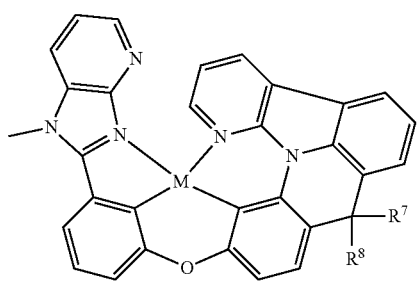
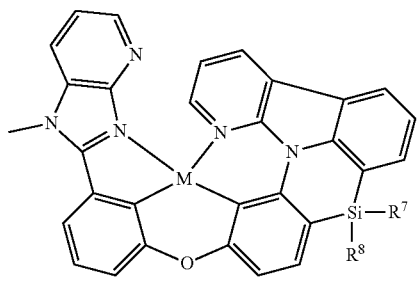
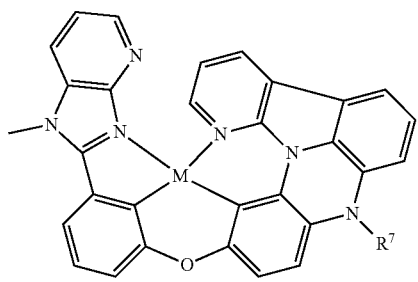
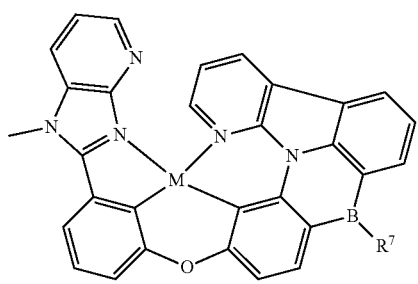
436
-continued
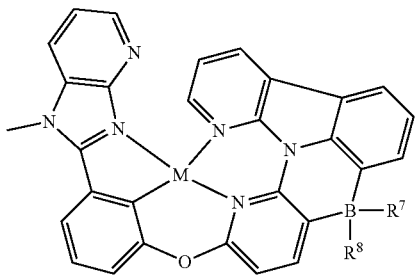
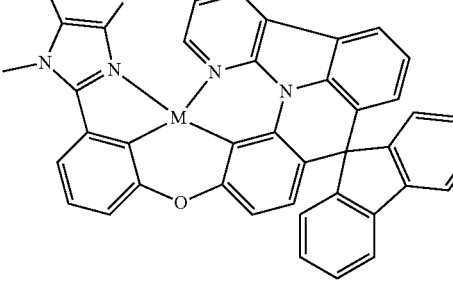
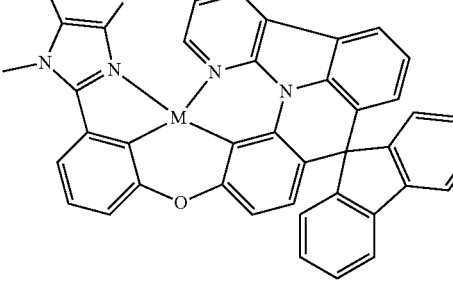
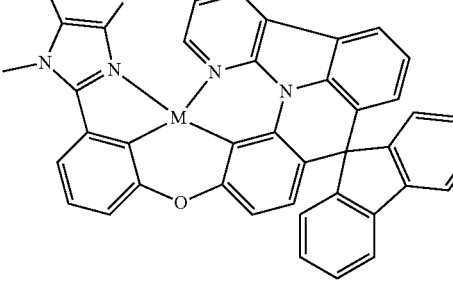
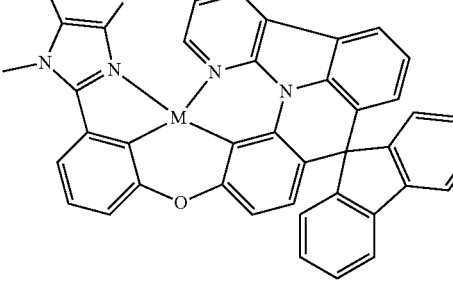

437
-continued
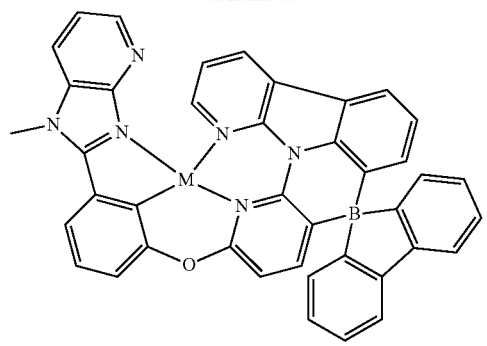
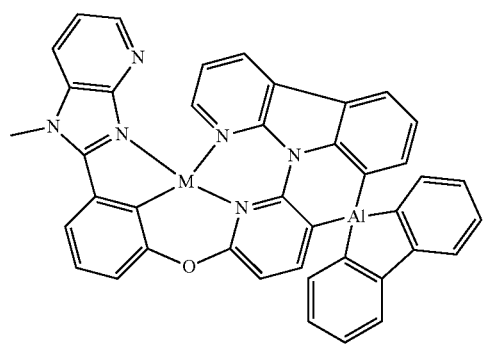
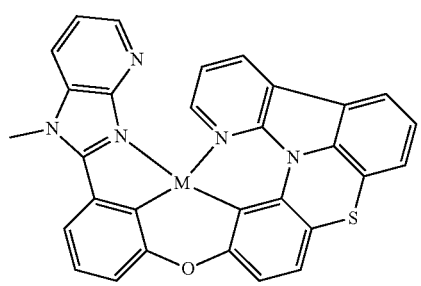
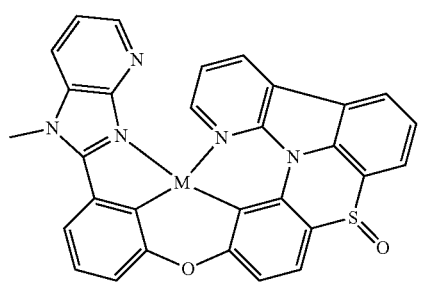
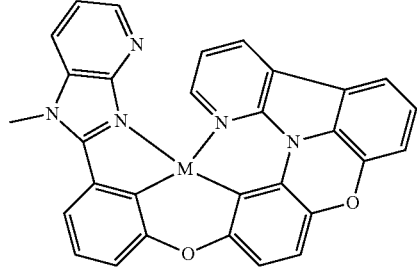
438
-continued
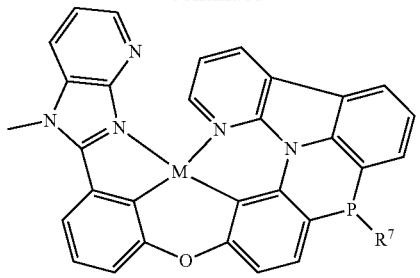
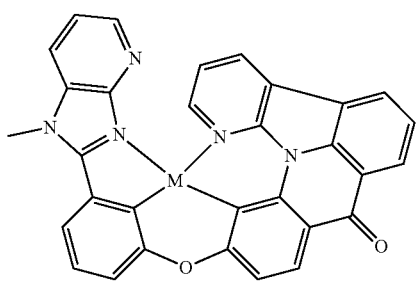
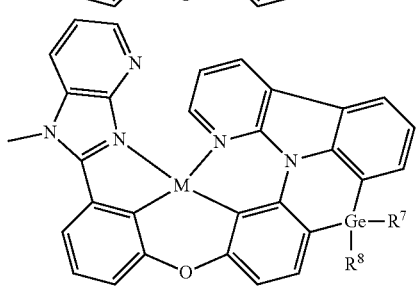
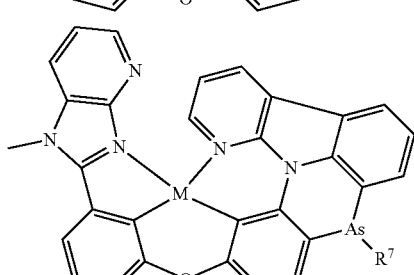
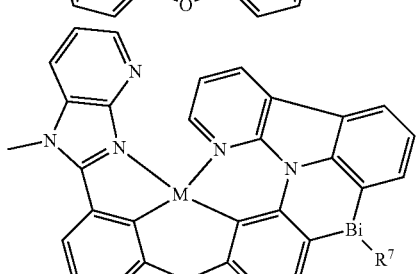
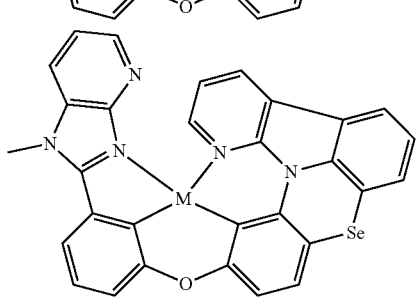

439
-continued
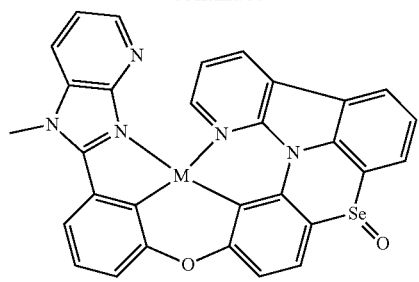
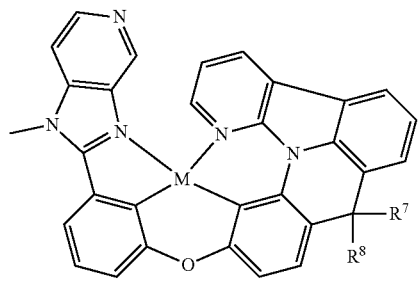
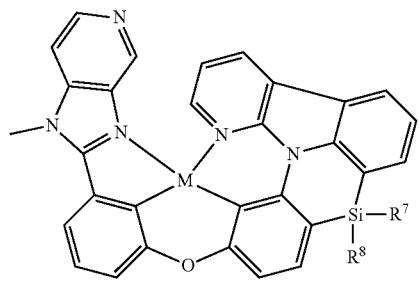
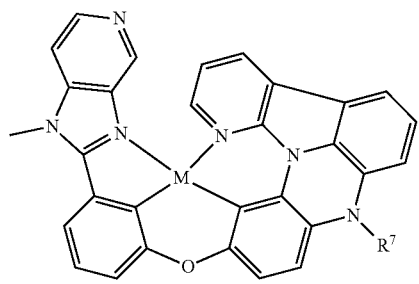
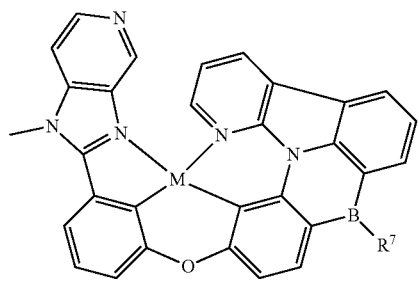
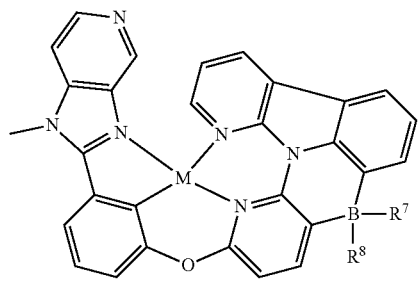
440
-continued
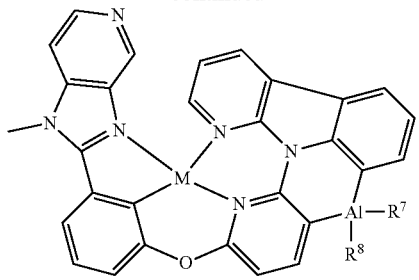
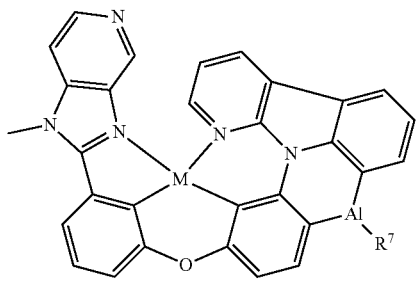
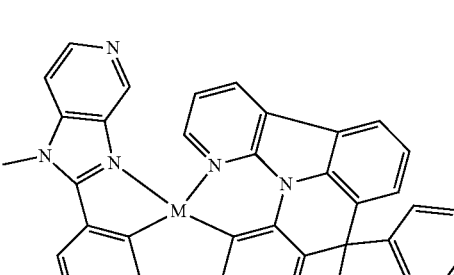
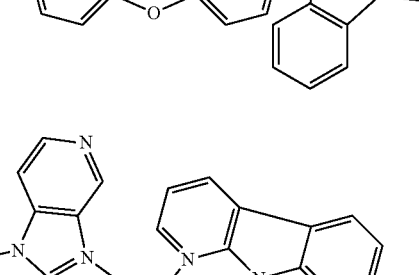
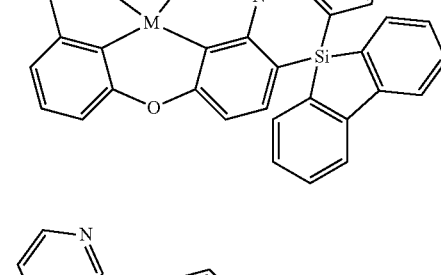
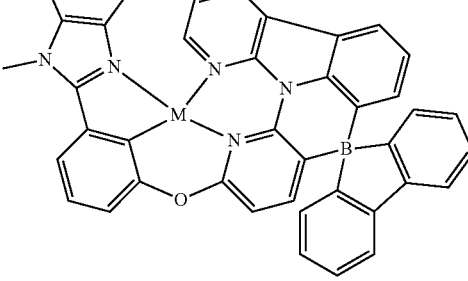

441
-continued
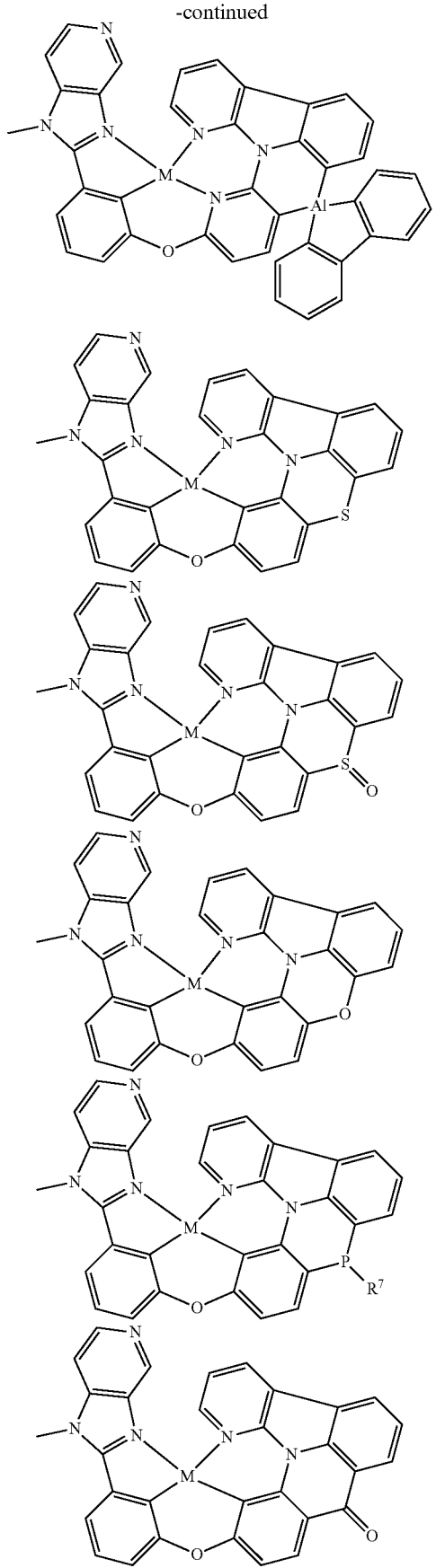
442
-continued
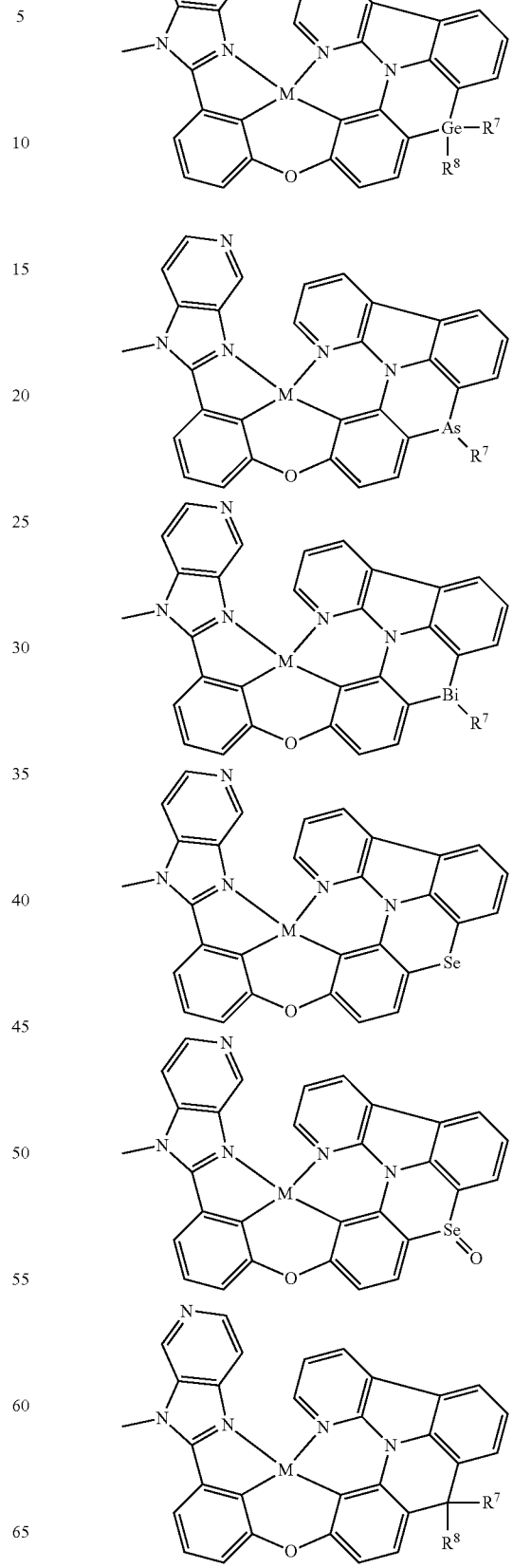

443
-continued
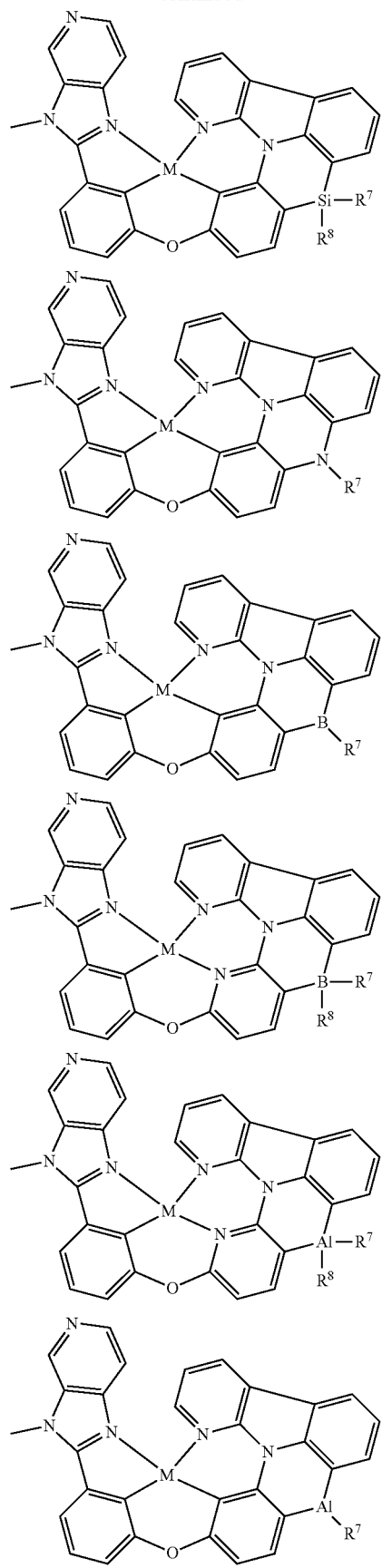
444
-continued
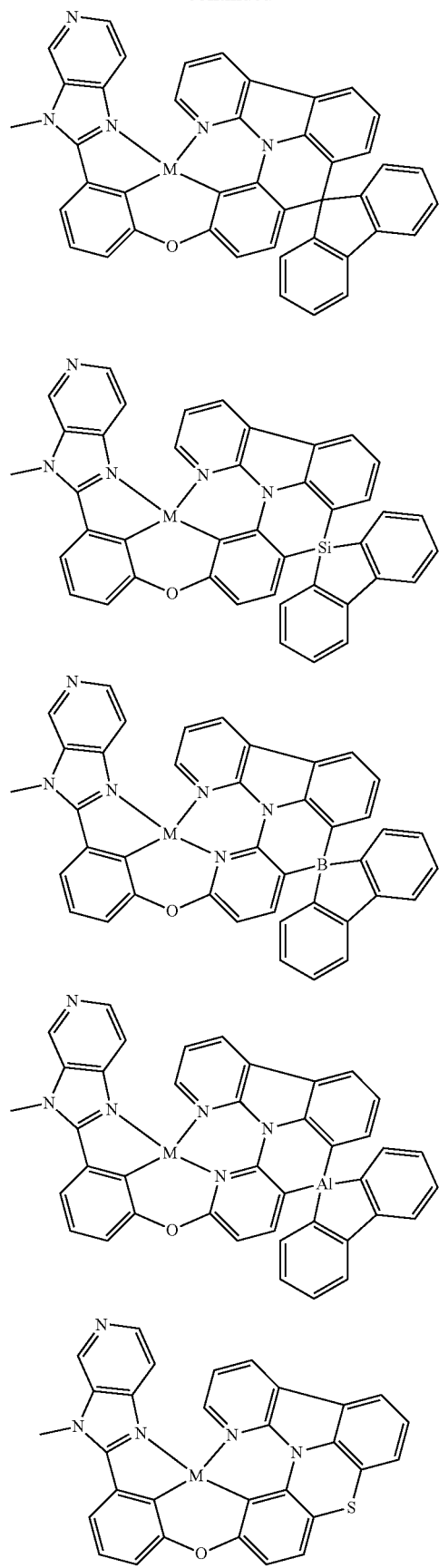

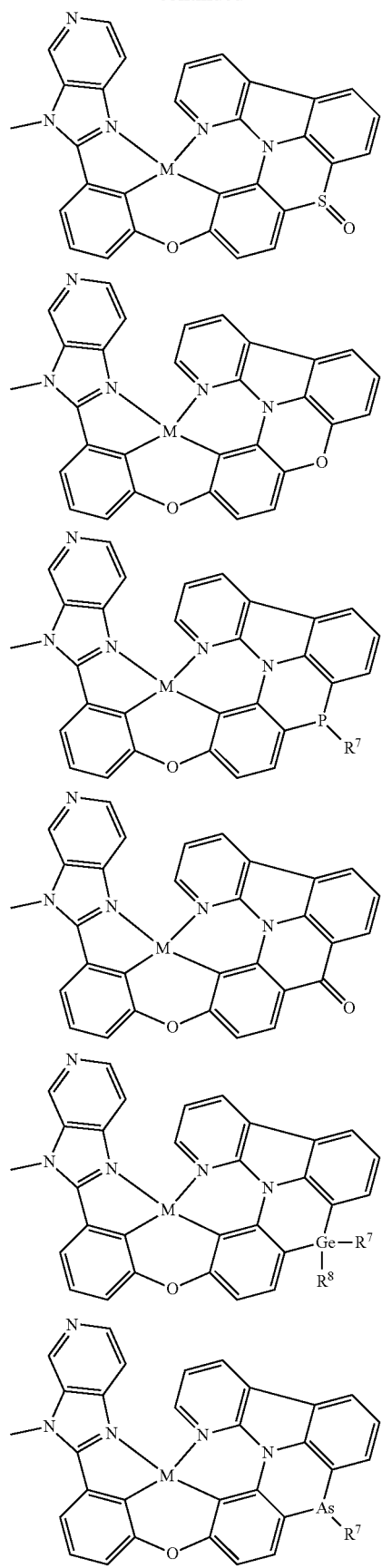
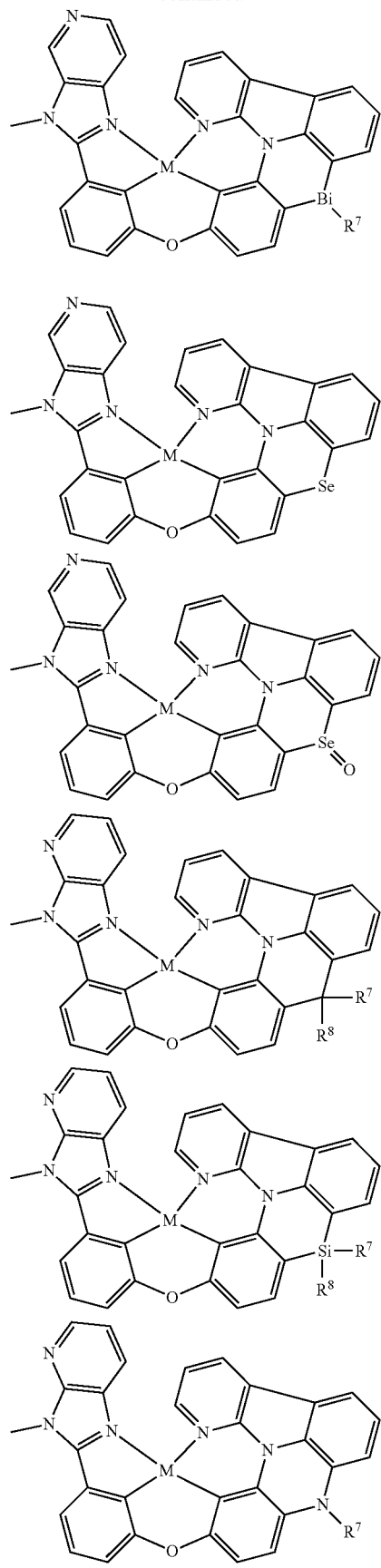

447
-continued
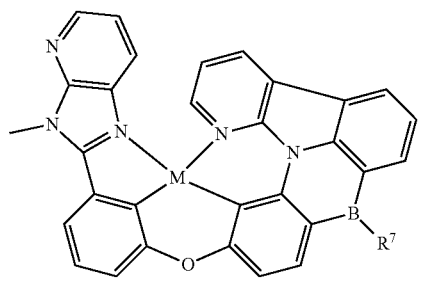
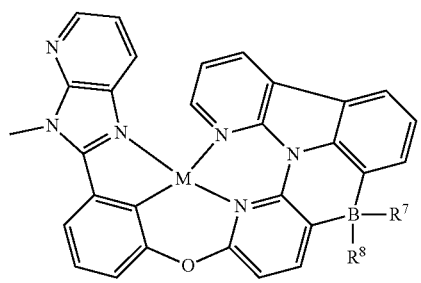
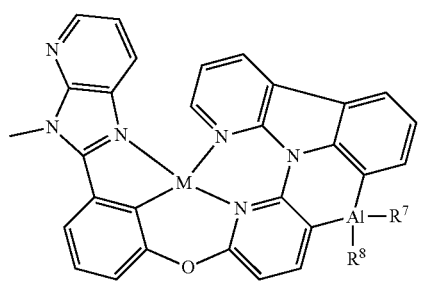
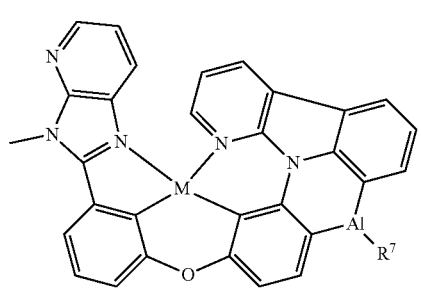
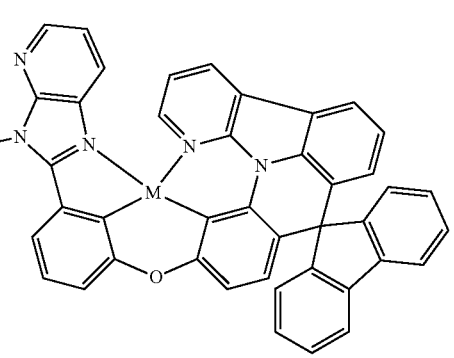
448
-continued
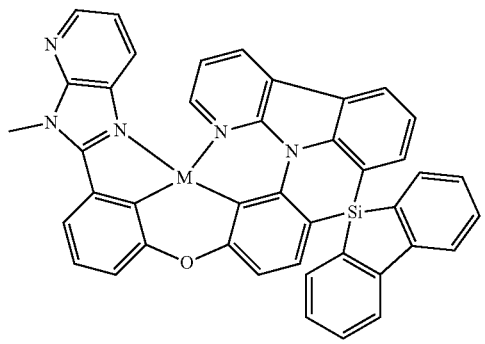
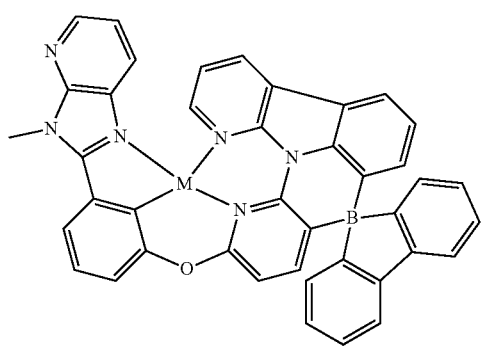
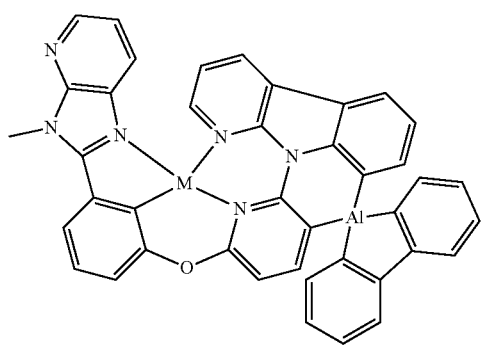
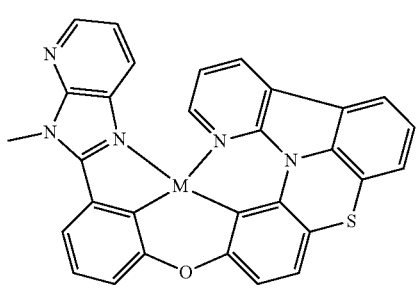
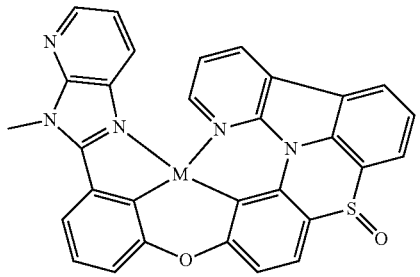

449
-continued
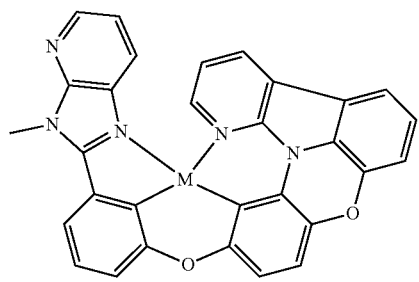
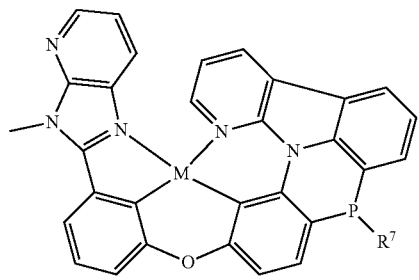
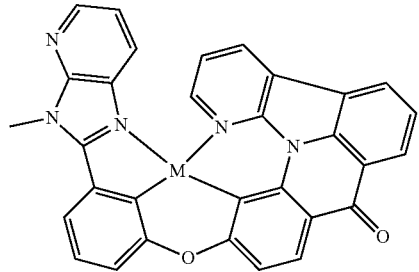
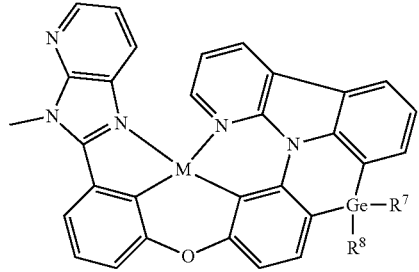
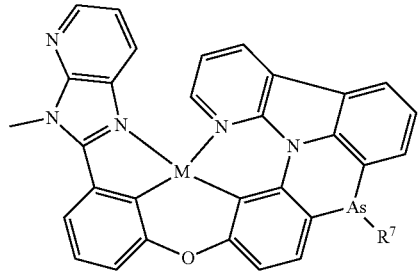
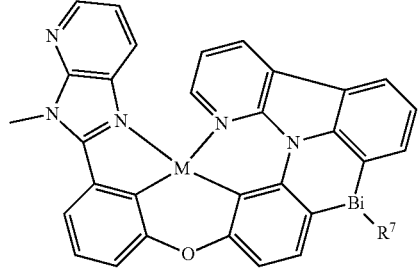
450
-continued
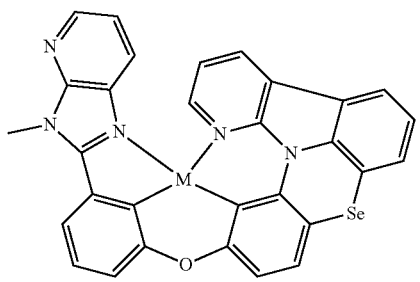
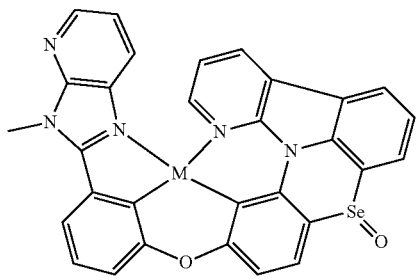
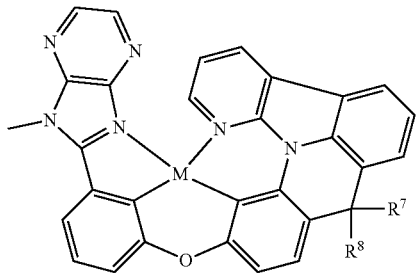
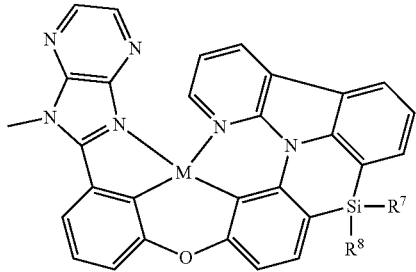
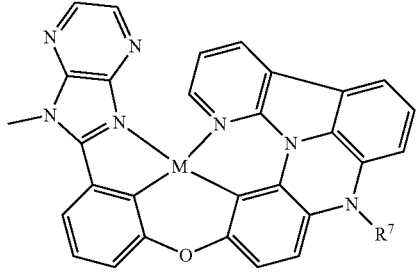
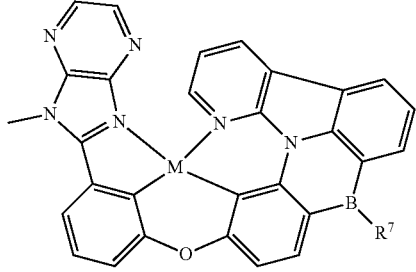

451
-continued
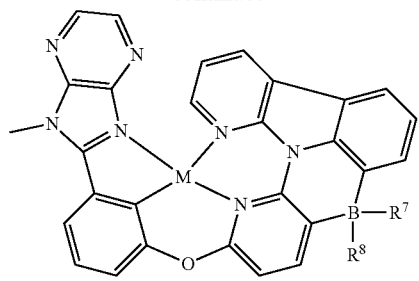
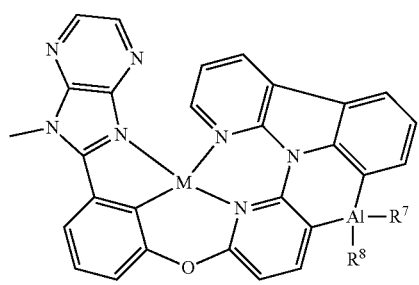
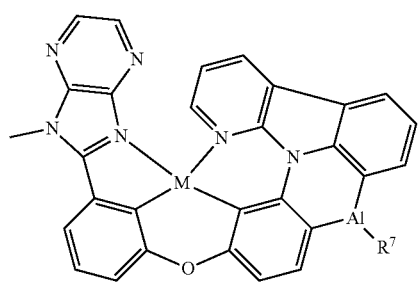
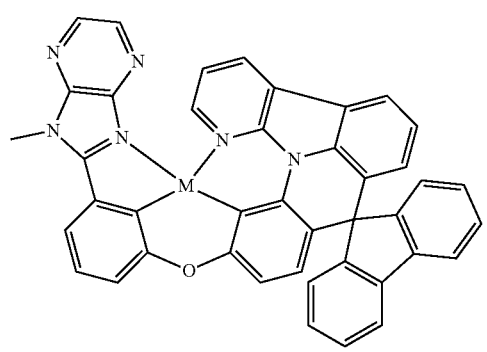
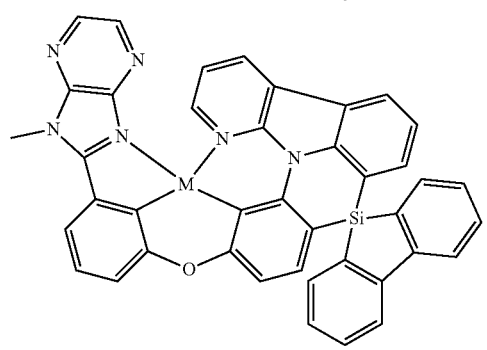
452
-continued
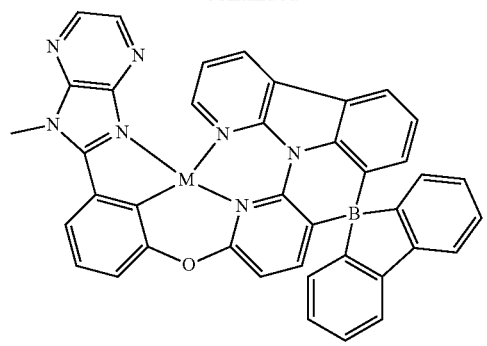
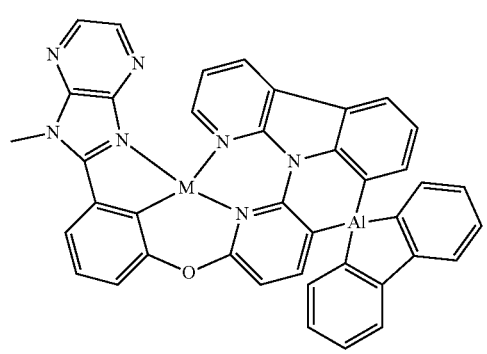
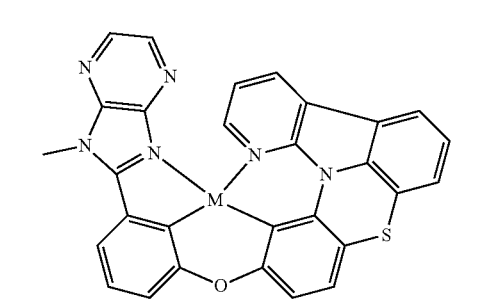
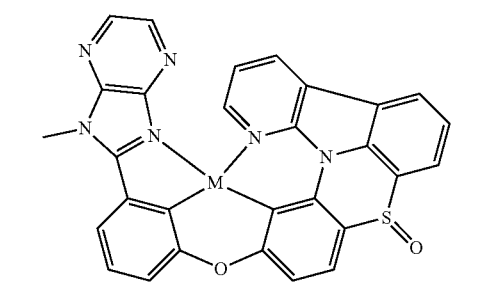
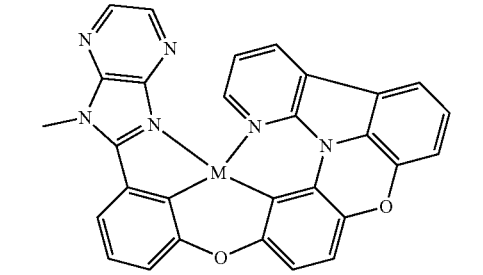

453
-continued
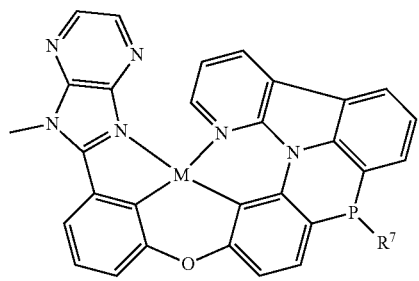
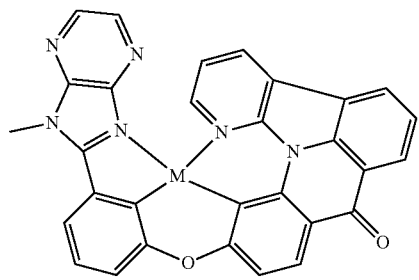
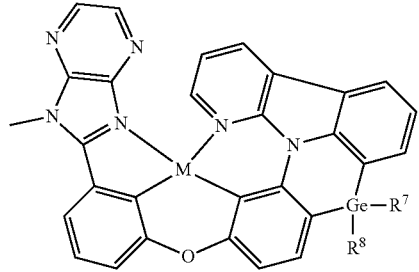
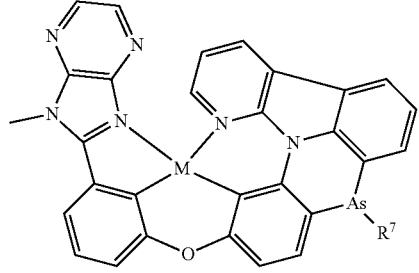
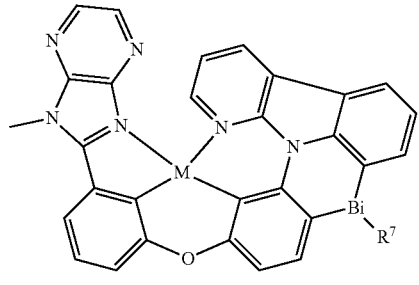
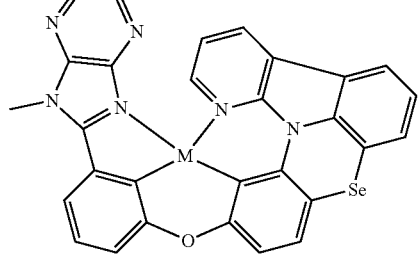
454
-continued
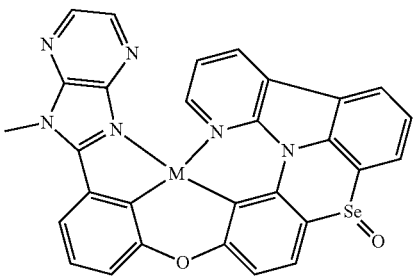
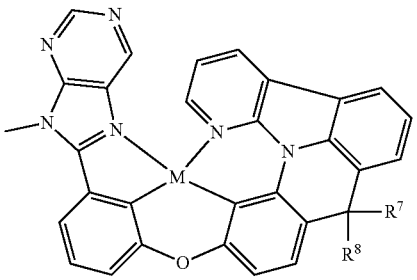
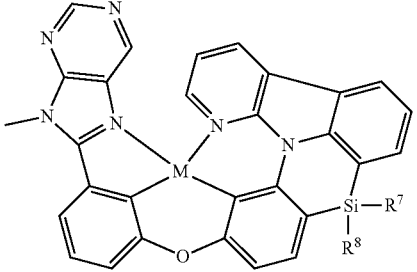
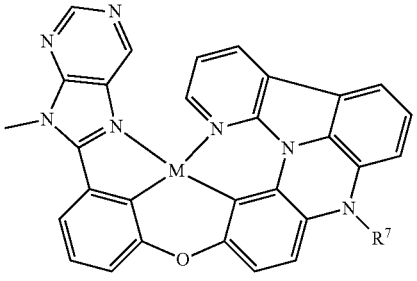
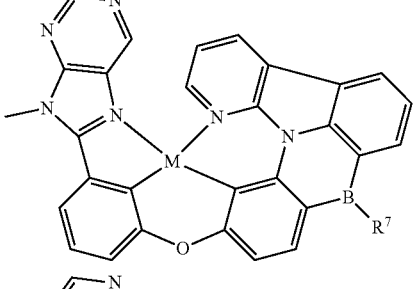
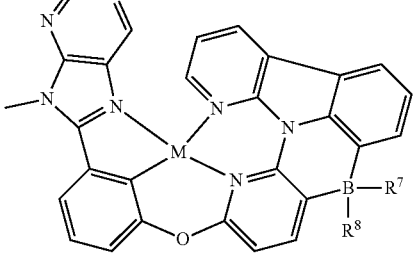

455
-continued
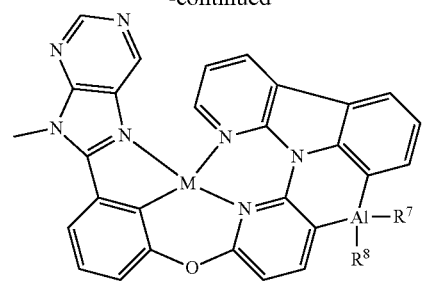
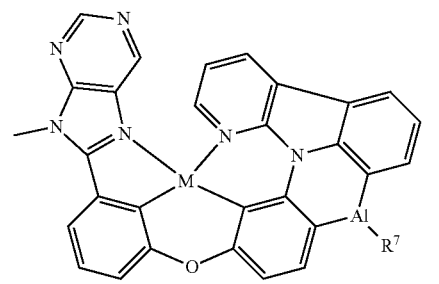
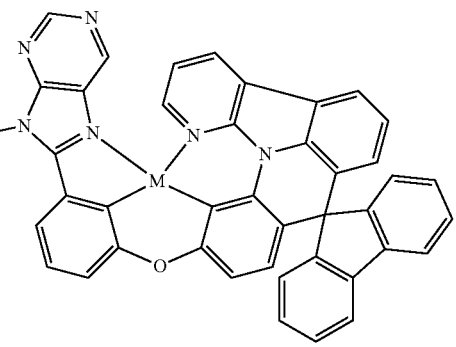
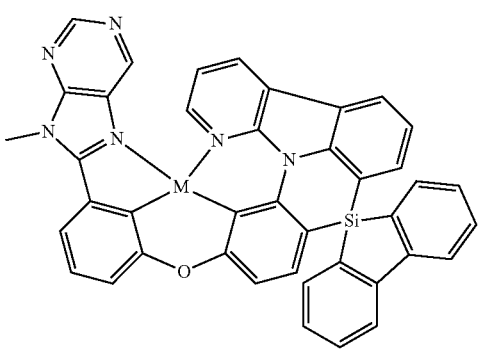
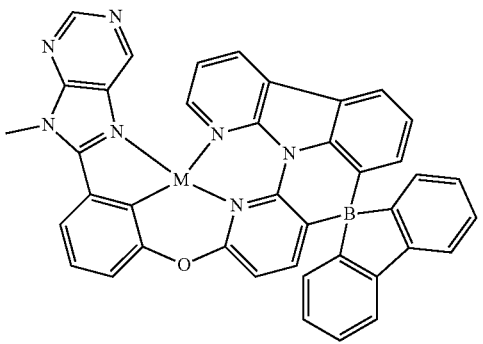
456
-continued
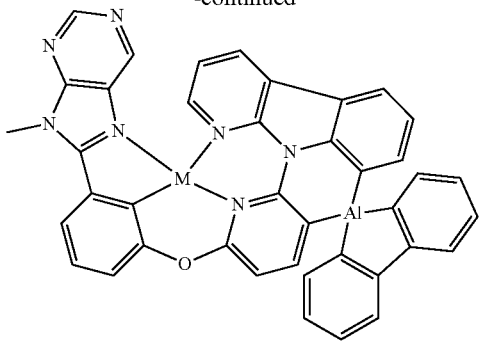
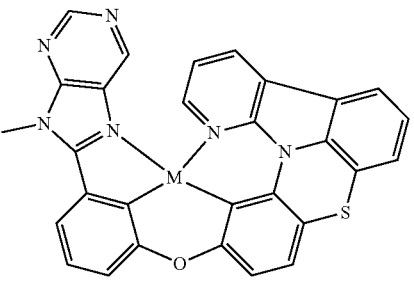
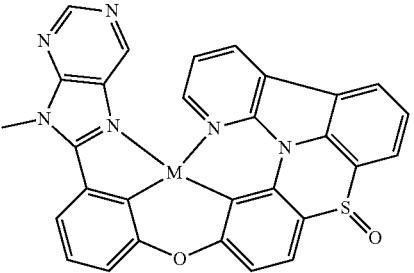
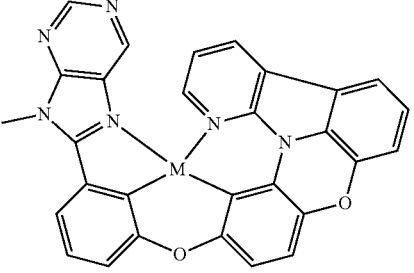
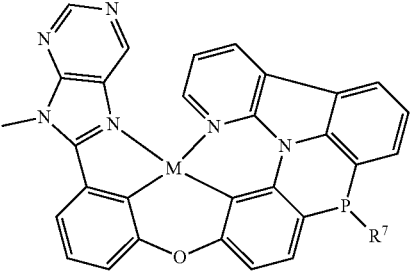
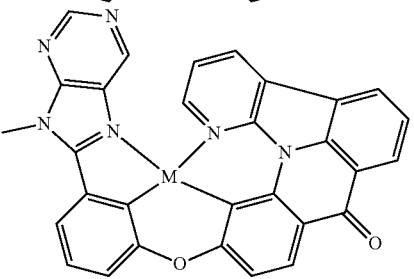

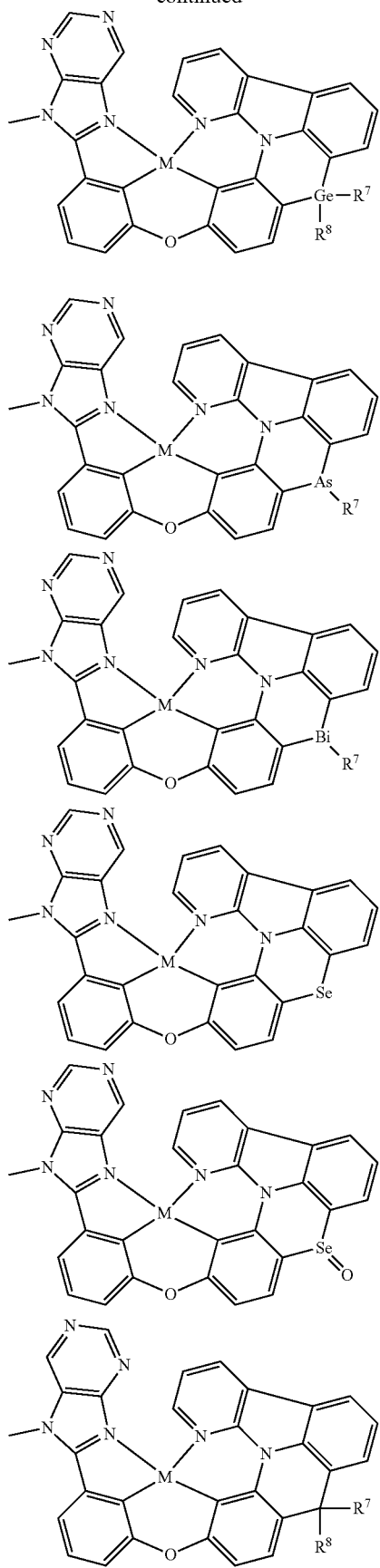
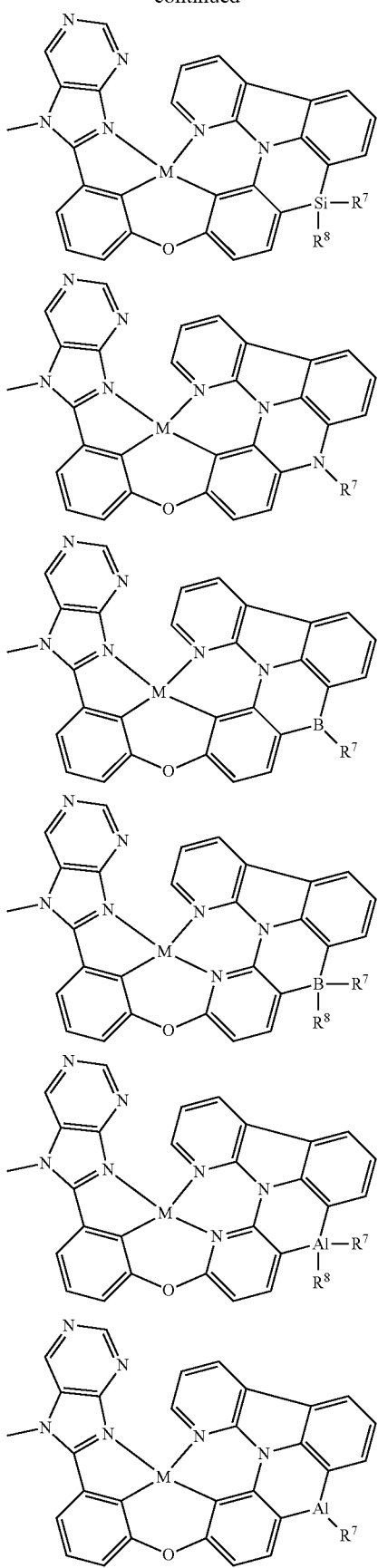

459
-continued
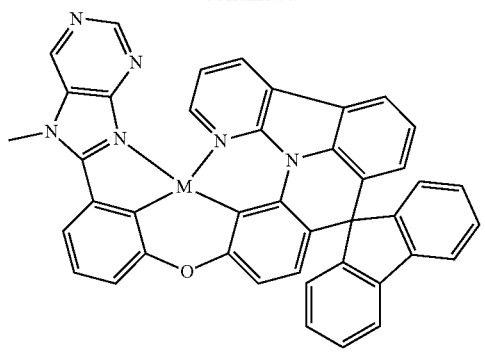
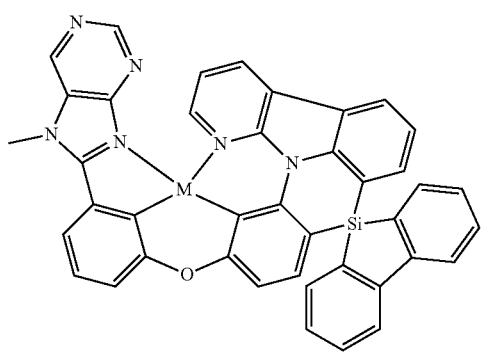
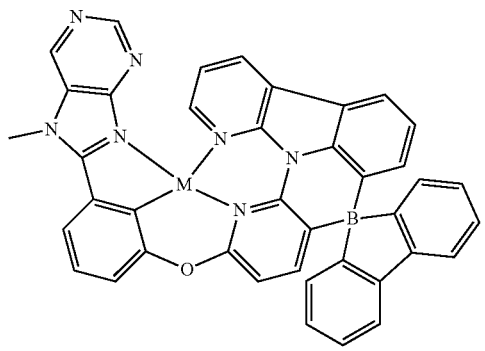
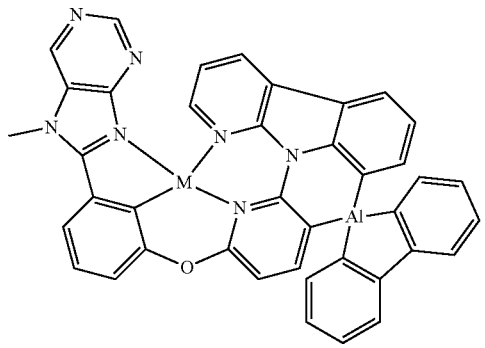
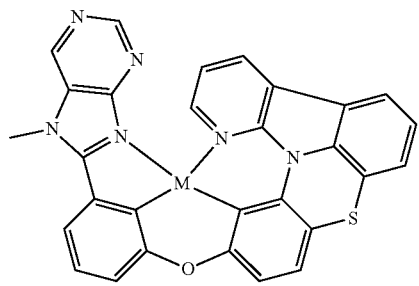
460
-continued
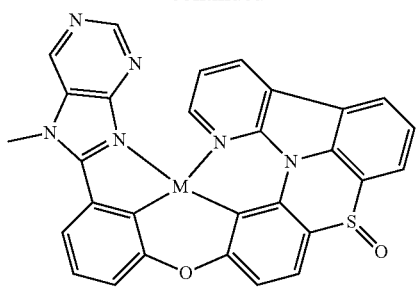
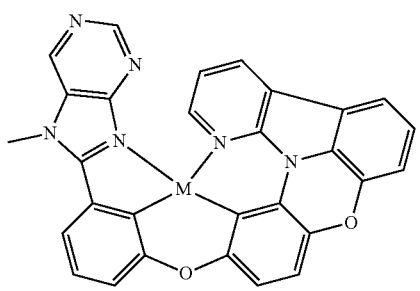
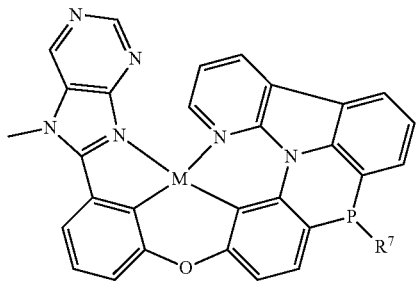
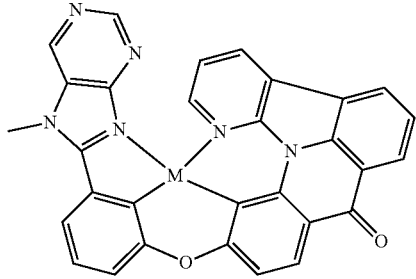
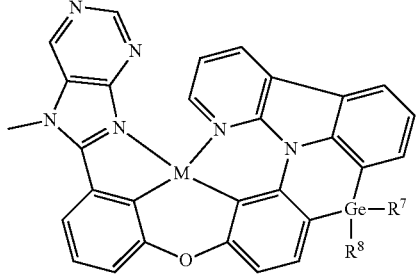
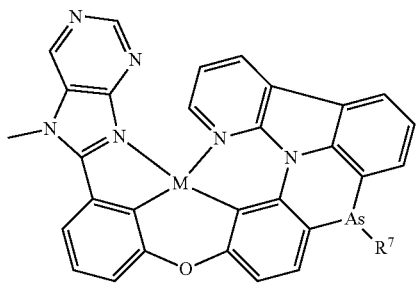

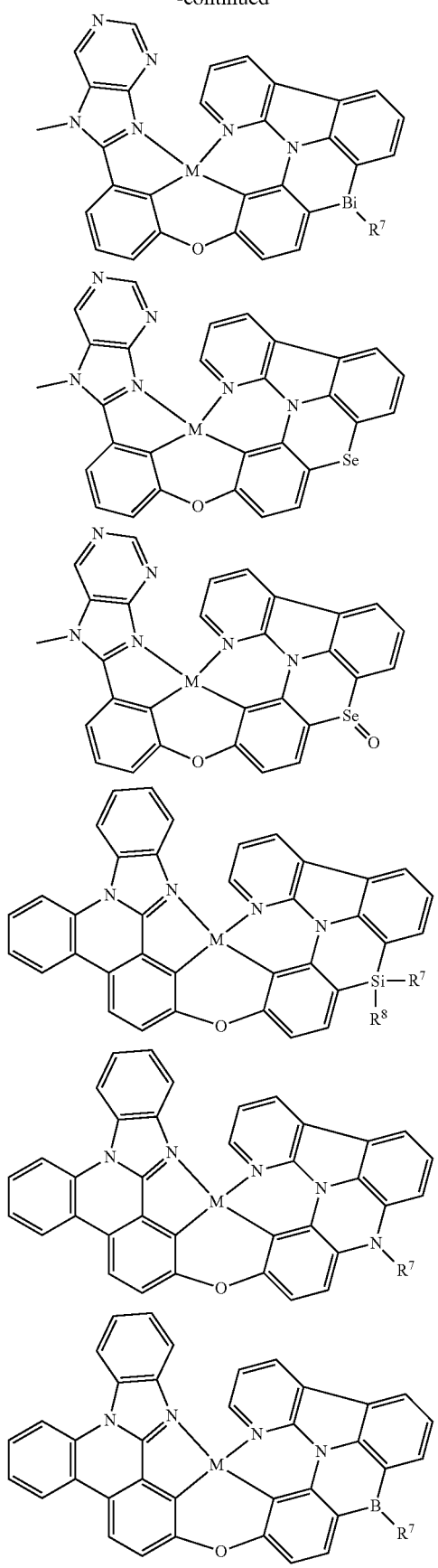
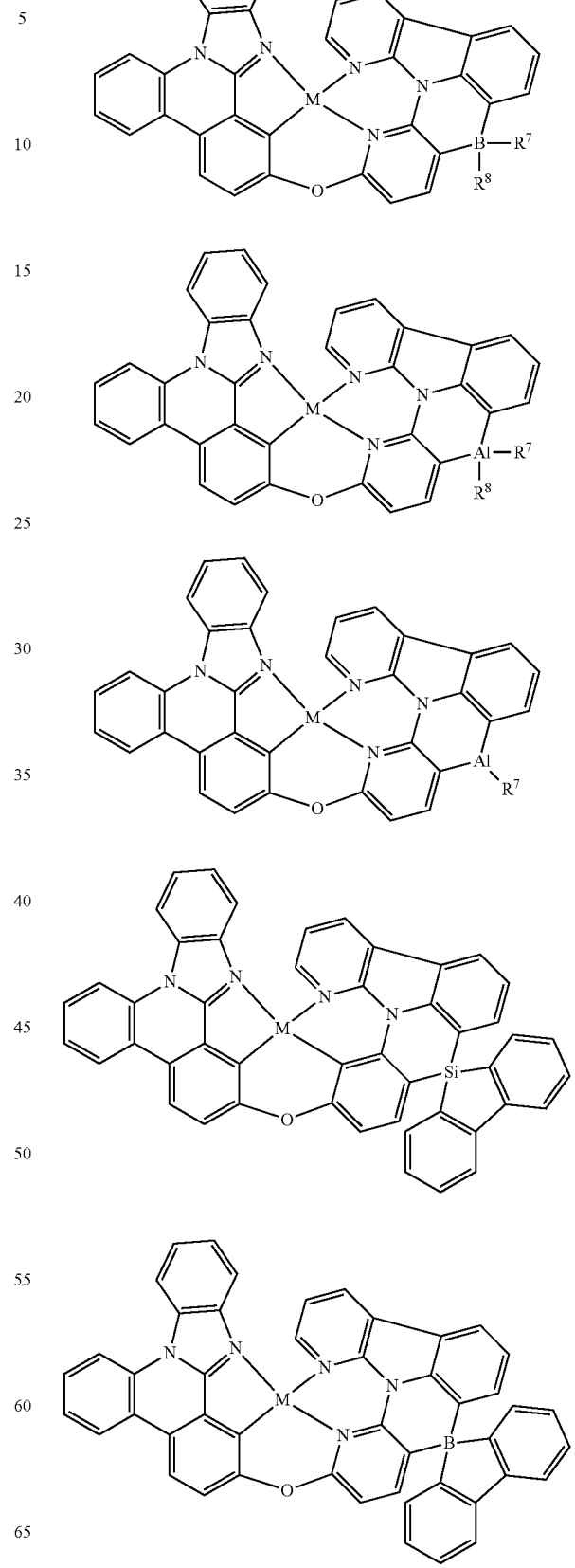

463
-continued
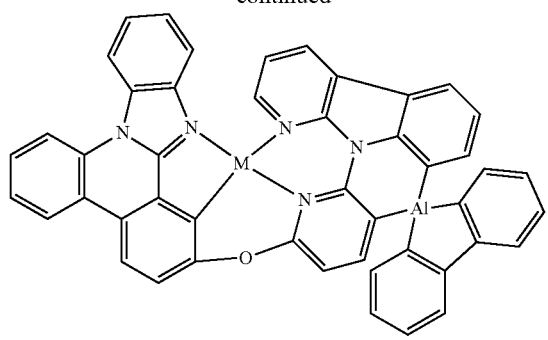
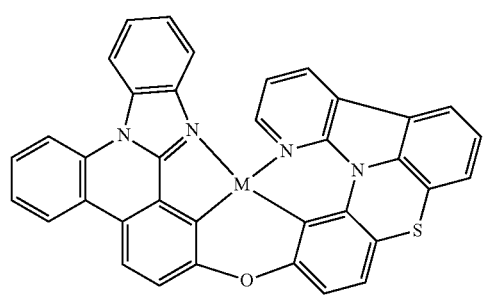
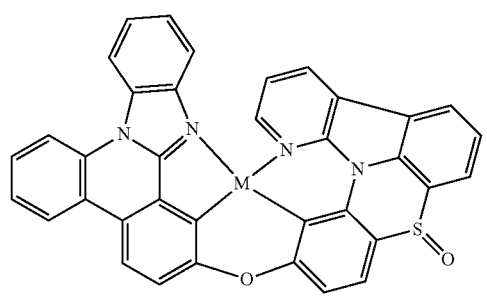
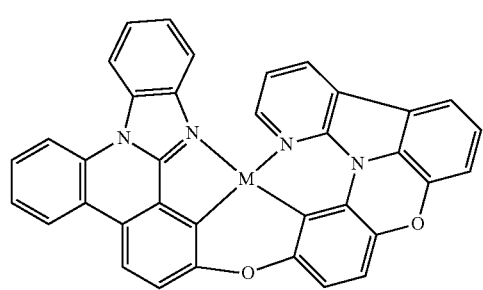
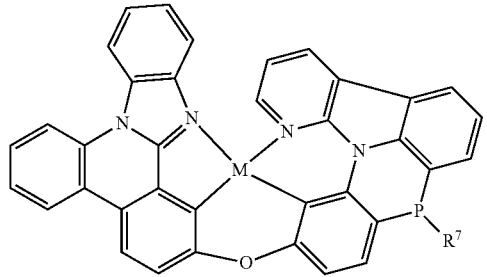
464
-continued
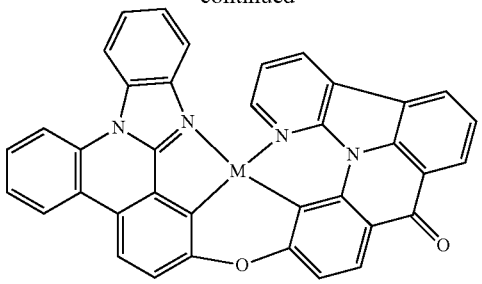
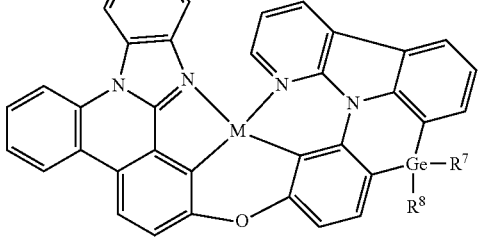
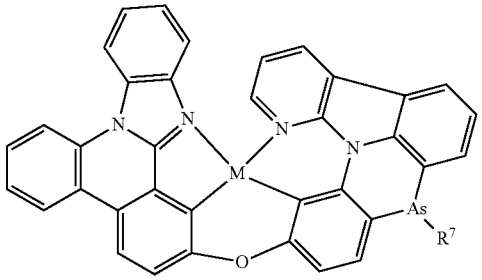
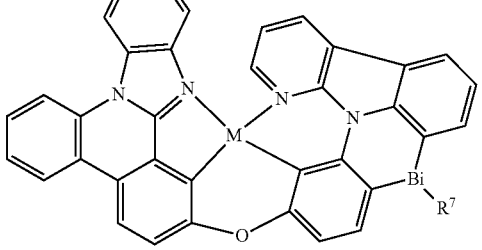
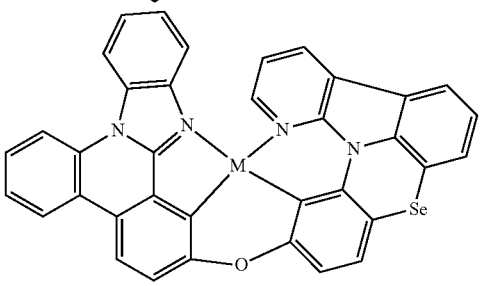
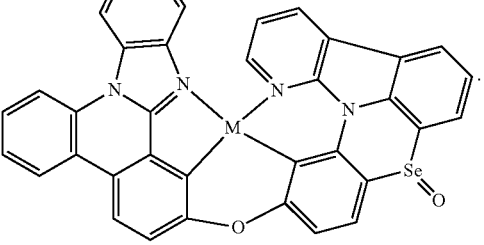
* * * * *